United States Patent
Terauchi et al.

(10) Patent No.: US 9,212,149 B2
(45) Date of Patent: Dec. 15, 2015

(54) SUBSTITUTED 2-AMIDOQUINAZOL-4-ONES AS MATRIX METALLOPROTEINASE-13 INHIBITORS

(75) Inventors: Jun Terauchi, Osaka (JP); Hiroshi Nara, Kanagawa (JP); Hideyuki Oki, Kanagawa (JP); Kenjiro Sato, Kanagawa (JP)

(73) Assignee: Takeda Pharmaceutical Company Limited, Osaka-Shi (JP)

( * ) Notice: Subject to any disclaimer, the term of this patent is extended or adjusted under 35 U.S.C. 154(b) by 954 days.

(21) Appl. No.: 11/579,298

(22) PCT Filed: Apr. 28, 2005

(86) PCT No.: PCT/JP2005/008549
§ 371 (c)(1),
(2), (4) Date: Oct. 30, 2006

(87) PCT Pub. No.: WO2005/105760
PCT Pub. Date: Nov. 10, 2005

(65) Prior Publication Data
US 2008/0027050 A1   Jan. 31, 2008

(30) Foreign Application Priority Data

Apr. 30, 2004   (JP) .................................. 2004-135596

(51) Int. Cl.
| | |
|---|---|
| *C07D 239/90* | (2006.01) |
| *C07D 487/04* | (2006.01) |
| *C07D 491/04* | (2006.01) |
| *C07D 495/04* | (2006.01) |
| *C07D 471/04* | (2006.01) |
| *C07D 217/26* | (2006.01) |
| *C07D 401/12* | (2006.01) |
| *C07D 405/12* | (2006.01) |
| *C07D 405/14* | (2006.01) |
| *C07D 409/14* | (2006.01) |
| *C07D 413/14* | (2006.01) |

(52) U.S. Cl.
CPC ............ *C07D 239/90* (2013.01); *C07D 217/26* (2013.01); *C07D 401/12* (2013.01); *C07D 405/12* (2013.01); *C07D 405/14* (2013.01); *C07D 409/14* (2013.01); *C07D 413/14* (2013.01); *C07D 471/04* (2013.01); *C07D 487/04* (2013.01); *C07D 491/04* (2013.01); *C07D 495/04* (2013.01)

(58) Field of Classification Search
CPC ... A61K 31/517; C07D 239/88; C07D 239/90
USPC ........................................ 544/283; 514/266.1
See application file for complete search history.

(56) References Cited

U.S. PATENT DOCUMENTS

| 4,011,324 A | 3/1977 | Althuis |
|---|---|---|
| 4,563,306 A | 1/1986 | Sugano et al. |

(Continued)

FOREIGN PATENT DOCUMENTS

| EP | 0304158 A1 | 2/1989 |
|---|---|---|
| JP | 11-43489 | 2/1999 |

(Continued)

OTHER PUBLICATIONS

STN databse structure search, downloaded Dec. 4, 2008, pp. 1-3.*
Wolff, Manfred E. "Burger's Medicinal Chemistry, 5rd, Part I", John Wiley & Sons, 1995, pp. 975-977.*
Banker, G.S. et al, "Modern Pharmaceutics, 3rd.", Marcel Dekker, New York, 1996, pp. 451 and 596.*
Breuer et. al. (Expert Opin. Ther. Patents, 2005, 15(3), 253-269).*
Reddy et al. (Indian Journal of Chemistry, Section B: Organic Chemistry Including Medicinal Chemistry, 1990, 29B(6), pp. 564-565).*
Mekuskiene et al. (Khimiko-Farmatsevticheskii Zhurnal, 1998, 32(10), pp. 10-12).*
American Chemical Society, 113:132122 (1997).
American Chemical Society, 130:223234 (2002).
American Chemical Society, 136:102347 (2003).

(Continued)

*Primary Examiner* — Susanna Moore
(74) *Attorney, Agent, or Firm* — Mintz Levin Cohn Ferris Glovsky and Popeo, P.C.; David G. Conlin

(57) ABSTRACT

The present invention provides a novel amide derivative having a matrix metalloproteinase inhibitory activity, and useful as a pharmaceutical agent, which is a compound represented by the formula (I) wherein ring A is an optionally substituted, nitrogen-containing heterocycle, ring B is an optionally substituted monocyclic homocycle or an optionally substituted monocyclic heterocycle, Z is N or $NR^1$ ($R^1$ is a hydrogen atom or an optionally substituted hydrocarbon group), $=\!=\!=$ is a single bond or a double bond, $R^2$ is a hydrogen atom or an optionally substituted hydrocarbon group, X is an optionally substituted spacer having 1 to 6 atoms, ring C is (1) an optionally substituted homocycle or (2) an optionally substituted heterocycle other than a ring represented by (II) (X' is S, O, SO, or $CH_2$), and at least one of ring B and ring C has substituent(s), provided that N-{(1S,2R)-1-(3,5-difluorobenzyl)-3-[(3-ethylbenzyl)amino]-2-hydroxypropyl}-5,6-dimethyl-4-oxo-1,4-dihydrothieno[2,3-d]pyrimidine-2-carboxamide is excluded, or a salt thereof.

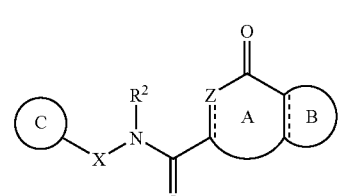

[I]

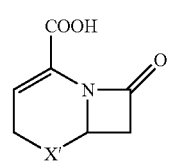

[II]

2 Claims, No Drawings

(56) References Cited

U.S. PATENT DOCUMENTS

| | | | |
|---|---|---|---|
| 5,098,888 A | | 3/1992 | Vincent et al. |
| 6,008,208 A | * | 12/1999 | Petrie et al. .................. 514/150 |
| 6,486,155 B1 | | 11/2002 | Pamukcu et al. |

FOREIGN PATENT DOCUMENTS

| | | | |
|---|---|---|---|
| WO | 96/28444 A1 | | 9/1996 |
| WO | WO 96/28444 | | 9/1996 |
| WO | 97/15308 A1 | | 5/1997 |
| WO | WO 97/15308 | | 5/1997 |
| WO | 98/17267 A1 | | 4/1998 |
| WO | WO 98/17267 | | 4/1998 |
| WO | 98/26664 A1 | | 6/1998 |
| WO | WO 98/26664 A1 | | 6/1998 |
| WO | WO-01/25212 | | 4/2001 |
| WO | WO 03/032916 | * | 4/2003 |
| WO | 03/040096 A2 | | 5/2003 |
| WO | WO 03/040096 A2 | | 5/2003 |
| WO | WO 03/040096 A3 | | 5/2003 |
| WO | 2004/058715 A1 | | 7/2004 |
| WO | WO 2004/058715 A1 | | 7/2004 |

OTHER PUBLICATIONS

Pariah et al. "Syntheses and Diuretic Activity of 1,2-Dihydro-2-(3-pyridul)-3H-pyrido[2,3-d]pyrimidin-4-one and Related Compounds." J. Med. Chem., 25, pp. 98-102, (1982).

Ikeura et al. "Axially Chiral N-Benzyl-N,7-dimethyl-5-phenyl-1,7-napthyridine-6-carboxamide Derivatices as Tachykinin NK1 Receptor Antagonists: Determination of the Absolute Stereochemical Requirements." J. Med. Chem., 41, pp. 4232-4239 (1998).

Hassanein et al., "Synthesis of some non-antimonial compounds bioisoteric to praziquantel." Eur. J. Med. Chem., 30, pp. 525-529 (1995).

Ikeura et al. "Potent NK1 Receptor Antagonists: Synthesis and Antagonistic Activity of Various Heterocycles with an N-[3,5-Bis(trifluoromethyl)benzyl]-N-methylcarbonyl Substituent." Chem. Pharm. Bullm, 45(10) pp. 1642-1652 (1997).

Natsugari et al., "Novel, Potent, and Orally Active Substance p. Antagonists: Synthesis and Antagonist Activity of N-Bezylcarboxamide Derivatives of Pyrido[3,4-b]pyridine." J. Med. Chem., 38, pp. 3106-3120 (1995).

Joshi et al., "Synthesis of Some New 4-Quinazolinone-2-carboxy Esters, 2-Carboxyamides, 2-Carboxyhydrazeds & Their Tosyl Derivatives Having Potential Biological Activity." Indian Journal of Chemistry, 26B, pp. 602-604 (1987).

Reddy et al. "Synthesis of some new 2-azaheteryl and 2,3-azahetero-annelated quinazolinones." Indian Journal of Chemistry, 31B, pp. 764-767 (1992).

Lazer et al. "Effect of Structural Modification of Enol-Carboxamide-Type Nonsteroidal Antiinflammatory Drugs on COX-2/COX-1 Selectivity." J. Med. Chem. 40, pp. 980-989 (1997).

Wang et al. "Novel Inhibitors of Plasminogen Activator Inhibitor-1: Development of New Templates From Diketopiperazines." Bioorganic & Medicinal Chemistry Letters 12, pp. 2367-2370 (2002).

George et al., "Synthesis of Substituted Quinazolines: Part II—Use of Diethyl Oxalate in Quinazoline Synthesis." Indian J. Chem., 9, pp. 1077-1080 (1971).

Myakushkene et al., "Synthesis and Antimonamineoxidase Activity of 1-(2-Quinazolonecarbonyl)-2-Arylmethyl-and (1-Arylethyl)hydrazines." Pharm. Chem. J., 32:10, pp. 521-523 (1998).

Reddy et al., "Bisazaheterocycles: Part VIII—A new synthesis of 2,2'-bisquinazolinones." Indian J. Chem., 41B, pp. 1950-1952 (2002).

Singh, "Nitriles in Heterocyclic Synthesis: 1-Cyanoformanilide as Precursor for a Variety of Heterocyclic Ring Systems." Heterocycle 27:7 pp. 1579-1583 (1988).

Fuwa et al., "Intramolecular Nucleophilic Aromatic Substitution Reaction of 2-Carboxamido-3-arylquinazolin-4-ones and its Application to the Synthesis of Secondary Aryl Amines." Synlett 2004, 14, pp. 2497-2500 (2004).

Maeda, H. et al.; "Synthesis and Central Nervous System Actions of Thyrotropin-Releasing Hormone Analogs Containing a 1-Oxo-1,2,3,4-tetrahydroisoquinoline Moiety1)"; Chem. Pharm Bull, vol. 36; 1998.

* cited by examiner

SUBSTITUTED 2-AMIDOQUINAZOL-4-ONES AS MATRIX METALLOPROTEINASE-13 INHIBITORS

TECHNICAL FIELD

The present invention relates to a heterocyclic amide derivative having a superior matrix metalloproteinase inhibitory activity and useful as a drug for the prophylaxis or treatment of osteoarthritis, rheumatoid arthritis and the like.

BACKGROUND ART

Matrix metalloproteinase (MMP) is an endopeptidase that physiologically plays a key role in the tissue remodeling, wherein its protease activity is strictly controlled. In the diseased state, however, the control is disrupted, and the disruption induces excess degradation of extracellular matrix, which in turn is deeply involved in the etiology of many diseases including joint diseases such as osteoarthritis, rheumatoid arthritis and the like, bone diseases such as osteoporosis and the like, periodontal disease, infiltration and metastasis of tumor, corneal ulcer formation and the like (Expert Opinion on Therapeutic Patents, vol. 12, pp. 665-705 (2002)).

At present, MMP is known to include at least 26 different enzymes, which are divided into five groups based on the variation in the primary structure and substrate specificity: collagenase group (MMP-1, 8, 13, 18), gelatinase group (MMP-2, 9), stromelysin group (MMP-3, 10, 11), membrane MMP group (MMP-14, 15, 16, 17), and other group (MMP-7, 12). Of these, MMP-13 belonging to the collagenase group has been reported to almost always express in cartilage and bone tissue, and to show increased production amount in joint disease and the like.

Moreover, since MMP-13 shows a potent collagen degradation activity as compared to other collagenases, it is considered to be deeply involved in the bone and joint diseases.

There are many MMP inhibitors so far reported (e.g., *Chemical Reviews*, vol. 99, pp. 2735-2776 (1999), *Current Medicinal Chemistry*, vol. 8, pp. 425-474 (2001)), and a number of reports have also been documented on the compounds showing MMP-13 inhibitory activity. They are largely divided into (i) hydroxamic acid derivatives (e.g., *Journal of Medicinal Chemistry*, vol. 46, pp. 2361-2375 (2003), *Journal of Medicinal Chemistry*, vol. 46, pp. 2376-2396 (2003), WO2004/811, WO2003/91247, WO2003/55851), (ii) carboxylic acid derivatives (e.g., *Bioorganic & Medicinal Chemistry*, vol. 10, pp. 3529-3534 (2002), WO2003/35610) and (iii) thiol derivatives (e.g., *Bioorganic & Medicinal Chemistry Letters*, vol. 9, pp. 1757-1760 (1999), WO2063/91242) and (iv) others (e.g., *Bioorganic & Medicinal Chemistry Letters*, vol. 11, pp. 969-972 (2001), WO2003/91252, WO2004/14909), based on the contents thereof.

Meanwhile, as a compound having a heterocyclic amide skeleton, Bulletin of The Chemical Society of Japan, 1990, pp. 72-83 describes a compound represented by the formula

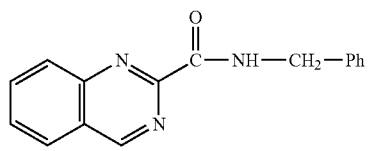

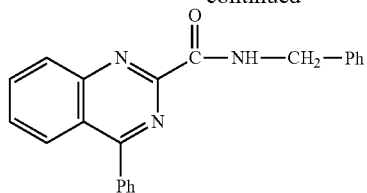

In addition, WO2003/91224 describes a compound represented by

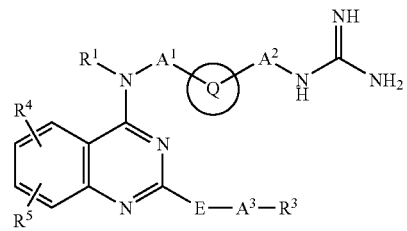

wherein $R^1$ is a hydrogen atom or alkyl; ring Q is a cyclohexylene group or a phenylene group; $A^1$ and $A^2$ are the same or different and each is a single bond or an alkylene group; E is —NHCO— or —CON($R^2$)— wherein $R^2$ is a hydrogen atom or alkyl; $A^3$ is $A^{31}$-$A^{32}$-$A^{33}$, $A^{31}$ and $A^{33}$ are the same or different and each is a single bond, or the same or different 1 or 2 saturated or unsaturated aliphatic hydrocarbon groups at substitutable position(s), which, when one carbon atom has two branched chains, may form a divalent cycloalkyl together with the carbon atom, $A^{32}$ is a single bond, an oxygen atom, a sulfur atom or —N($R^{32}$)— wherein $R^{32}$ is a hydrogen atom or alkyl; $R^3$ is an optionally substituted acyclic aliphatic hydrocarbon group having 1 to 8 carbon atoms, an optionally substituted mono- to tricyclic cyclic aliphatic hydrocarbon group having 3 to 10 carbon atoms, an optionally substituted mono- or bicyclic aromatic hydrocarbon group having 6 to 12 carbon atoms, or an optionally substituted mono- to tricyclic heterocyclic group; when E is —CON($R^2$)—, this —N($R^2$)— and -$A^3$-$R^3$ may form a cyclic amino group; and $R^4$ and $R^5$ are the same or different and each is a hydrogen atom, alkyl, alkoxy, or halogen.

DISCLOSURE OF THE INVENTION

There is a demand for the development of a novel compound superior in action effect, durability, safety, oral absorbability, selectivity and the like as compared to conventional MMP inhibitors and the like, and useful as a drug for the prophylaxis or treatment of joint diseases (osteoarthritis, rheumatoid arthritis and the like), osteoporosis, periodontal diseases, corneal ulcer and other MMP associated diseases.

The present inventors have conducted intensive studies and first succeeded in the creation of a novel compound represented by the formula

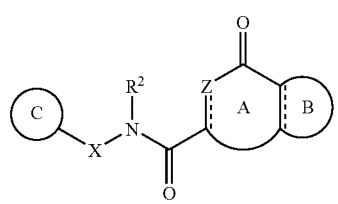

[I]

wherein ring A is an optionally substituted, nitrogen-containing heterocycle, ring B is an optionally substituted monocyclic homocycle or optionally substituted monocyclic heterocycle, Z is N or NR¹ (R¹ is a hydrogen atom or an optionally substituted hydrocarbon group), ─── is a single bond or a double bond, R² is a hydrogen atom or an optionally substituted hydrocarbon group, X is an optionally substituted spacer having 1 to 6 atoms, ring C is (1) an optionally substituted homocycle or (2) an optionally substituted heterocycle other than a ring represented by the formula

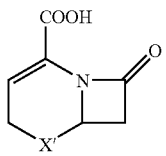

(X' is S, O, SO or CH₂), and at least one of ring B and ring C has substituent(s), provided that N-{(1S,2R)-1-(3,5-difluorobenzyl)-3-[(3-ethylbenzyl)amino]-2-hydroxypropyl}-5,6-dimethyl-4-oxo-1,4-dihydrothieno[2,3-d]pyrimidine-2-carboxamide and 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinazoline-2-carboxamide are excluded, or a salt thereof [hereinafter to be abbreviated as compound [I]], and found that this compound [I] unexpectedly has superior properties as an MMP inhibitor and is highly satisfactory as a pharmaceutical agent, which resulted in the completion of the present invention.

Accordingly, the present invention relates to
(1) a compound represented by the formula

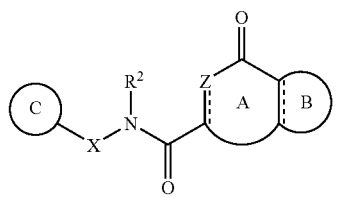

[I]

wherein ring A is an optionally substituted, nitrogen-containing heterocycle, ring B is an optionally substituted monocyclic homocycle or an optionally substituted monocyclic heterocycle, Z is N or NR¹ (R¹ is a hydrogen atom or an optionally substituted hydrocarbon group), ─── is a single bond or a double bond, R² is a hydrogen atom or an optionally substituted hydrocarbon group, X is an optionally substituted spacer having 1 to 6 atoms, ring C is (1) an optionally substituted homocycle or (2) an optionally substituted heterocycle other than a ring represented by the formula

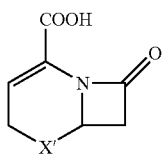

(X' is S, O, SO or CH₂), and at least one of ring B and ring C has substituent(s), provided that N-{(1S,2R)-1-(3,5-difluorobenzyl)-3-[(3-ethylbenzyl)amino]-2-hydroxypropyl}-5,6-dimethyl-4-oxo-1,4-dihydrothieno[2,3-d]pyrimidine-2-carboxamide and 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl]amino}cyclohexyl)-4-oxo-1,4-dihydroquinazoline-2-carboxamide are excluded, or a salt thereof, (2) the compound of the above-mentioned (1), wherein, when the partial structure represented by the formula

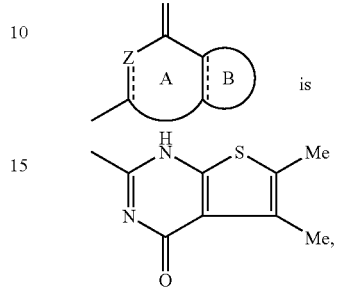

[II]

is

X is an optionally substituted spacer having 1, 3 or 4 carbon atoms or a salt thereof, (3) the compound of the above-mentioned (1), wherein ring A is

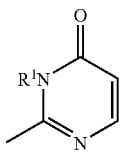

wherein R¹ is a hydrogen atom or an optionally substituted hydrocarbon group or a salt thereof, (4) the compound of the above-mentioned (1), wherein ring A is

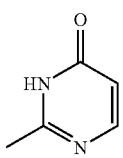

or a salt thereof, (5) the compound of the above-mentioned (1), wherein ring B is an optionally substituted 5- or 6-membered monocyclic heterocycle containing, besides carbon atom, 1 to 3 hetero atoms selected from the group consisting of nitrogen atom, oxygen atom and sulfur atom or a salt thereof, (6) the compound of the above-mentioned (1), wherein ring B is an optionally substituted benzene ring or a salt thereof, (7) the compound of the above-mentioned (1), wherein the partial structure represented by the formula

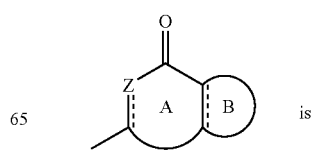

[II]

is

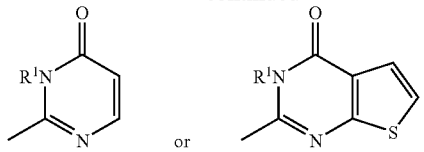

wherein R¹ is a hydrogen atom or an optionally substituted hydrocarbon group or a salt thereof,
(8) the compound of the above-mentioned (1), wherein the partial structure represented by the formula

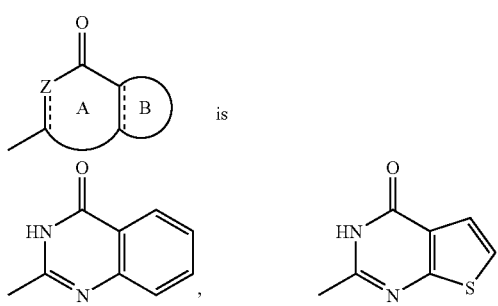

or a salt thereof,
(9) the compound of the above-mentioned (1), wherein the partial structure represented by the formula

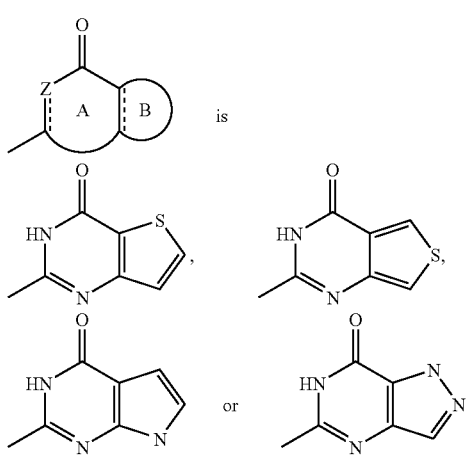

or a salt thereof,
(10) the compound of the above-mentioned (1), wherein the substituent of ring B is selected from (1) a $C_{1-6}$ alkyl group, (2) a $C_{1-6}$ alkyl group substituted by a $C_{7-16}$ aralkyloxy optionally substituted by a carboxyl group, (3) a $C_{1-6}$ alkyl group substituted by a $C_{6-14}$ aryl-aminocarbonyl optionally substituted by a carboxyl group, (4) a $C_{1-6}$ alkyl group substituted by a $C_{6-14}$ aryl-carbonylamino optionally substituted by a carboxyl group, (5) a $C_{1-6}$ alkyl group substituted by a $C_{6-14}$ aryloxy optionally substituted by a carboxyl group, (6) a $C_{6-14}$ aryloxy group optionally substituted by a carboxyl group, (7) a $C_{7-16}$ aralkyloxy group optionally substituted by a carboxyl group, (8) a $C_{6-14}$ aryl group optionally substituted by a carboxyl group, (9) a carbamoyl group optionally substituted by a $C_{7-16}$ aralkyl optionally substituted by a carboxyl group, (10) an amino group optionally substituted by $C_{7-16}$ aralkyl-carbonyl and (11) halogen atoms, or a salt thereof,
(11) the compound of the above-mentioned (1), wherein the partial structure represented by the formula

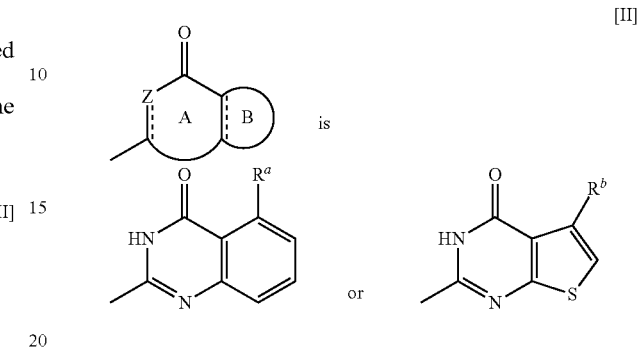

wherein $R^a$ and $R^b$ are each (1) a $C_{1-6}$ alkyl group, (2) a $C_{1-6}$ alkyl group substituted by a $C_{7-16}$ aralkyloxy optionally substituted by a carboxyl group, (3) a $C_{1-6}$ alkyl group substituted by a $C_{6-14}$ aryl-aminocarbonyl optionally substituted by a carboxyl group, (4) a $C_{1-6}$ alkyl group substituted by a $C_{6-14}$ aryl-carbonylamino optionally substituted by a carboxyl group, (5) a $C_{1-6}$ alkyl group substituted by a $C_{6-14}$ aryloxy optionally substituted by a carboxyl group, (6) a $C_{6-14}$ aryloxy group optionally substituted by a carboxyl group, (7) a $C_{7-16}$ aralkyloxy group optionally substituted by a carboxyl group, (8) a $C_{6-14}$ aryl group optionally substituted by a carboxyl group, (9) a carbamoyl group optionally substituted by a $C_{7-16}$ aralkyl optionally substituted by a carboxyl group or (10) an amino group optionally substituted by a $C_{7-16}$ aralkyl-carbonyl or a salt thereof,
(12) the compound of the above-mentioned (1), wherein X is an optionally substituted group represented by the formula —$(CH_2)_n$—$X^1$—$(CH_2)_m$— wherein $X^1$ is O, $NR^3$ ($R^3$ is a hydrogen atom or an optionally substituted lower alkyl group), $SO_2$ or $CH_2$, n and m are each an integer of 0 to 3 and n+m≤6 or a salt thereof,
(13) the compound of the above-mentioned (1), wherein X is an optionally substituted methylene group or a salt thereof,
(14) the compound of the above-mentioned (1), wherein ring C is an optionally substituted benzene ring or an optionally substituted pyridine ring or a salt thereof,
(15) 4-[2-({6-fluoro-2-[({[3-(methoxy)phenyl]methyl}amino)carbonyl]-4-oxo-3,4-dihydroquinazolin-5-yl}oxy)ethyl]benzoic acid, 4-[({2-({[(3-chloro-4-fluorophenyl)methyl]amino}carbonyl)-4-oxo-3,4-dihydrothieno[2,3-d]pyrimidin-5-yl]methyl}oxy)methyl]benzoic acid, 4-[({2-({[(4-fluoro-3-methylphenyl)methyl]amino}carbonyl)-4-oxo-3,4-dihydrothieno[2,3-d]pyrimidin-5-yl]methyl}oxy)methyl]benzoic acid, 4-{[({2-[({[3-(methoxy)phenyl]methyl}amino)carbonyl]-4-oxo-3,4-dihydrothieno[2,3-d]pyrimidin-5-yl}methyl)oxy]methyl}benzoic acid or a salt thereof,
(16) a prodrug of the compound of the above-mentioned (1) or a salt thereof,
(17) a pharmaceutical agent comprising the compound of the above-mentioned (1) or a salt thereof or a prodrug thereof,
(18) a pharmaceutical agent of the above-mentioned (17), which is an agent for the prophylaxis or treatment of osteoarthritis or rheumatoid arthritis,
(19) a production method of the compound of the above-mentioned (1) or a salt thereof, which comprises [1] reacting a compound represented by the formula

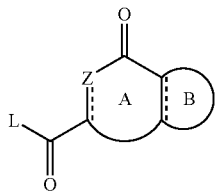

wherein L is a leaving group, and other symbols are as defined in the above-mentioned (1), or a salt thereof, with a compound represented by the formula

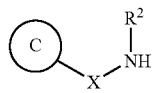

wherein each symbol is as defined in the above-mentioned (1), or a salt thereof, or

[2] reacting a compound represented by the formula

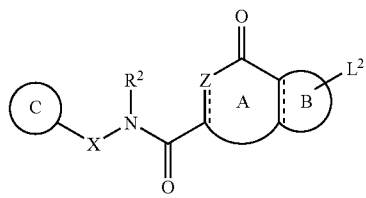

wherein $L^2$ is a leaving group, and other symbols are as defined in the above-mentioned (1), or a salt thereof, with a compound represented by the formula R—H wherein R is a substituent of ring B, or a salt thereof,

(20) a matrix metalloproteinase inhibitor comprising a compound represented by the formula

[I']

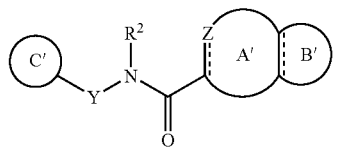

wherein Z is N or $NR^1$ ($R^1$ is a hydrogen atom or an optionally substituted hydrocarbon group), ring A' is an optionally substituted, nitrogen-containing heterocycle, ring B' and ring C' are each an optionally substituted homocycle or an optionally substituted heterocycle, ═══ is a single bond or a double bond, $R^2$ is a hydrogen atom or an optionally substituted hydrocarbon group, and Y is a bond or an optionally substituted spacer having 1 to 6 atoms, or a salt thereof or a prodrug thereof,

(21) the inhibitor of the above-mentioned (20), wherein the matrix metalloproteinase is matrix metalloproteinase-13 (MMP-13),

(22) a method of inhibiting a matrix metalloproteinase, which comprises administering, to a mammal, an effective amount of a compound represented the formula

[I']

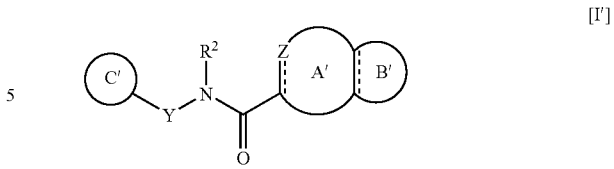

wherein Z is N or $NR^1$ ($R^1$ is a hydrogen atom or an optionally substituted hydrocarbon group), ring A' is an optionally substituted, nitrogen-containing heterocycle, ring B' and ring C' are an optionally substituted homocycle or an optionally substituted heterocycle, ═══ is a single bond or a double bond, $R^2$ is a hydrogen atom or an optionally substituted hydrocarbon group, and Y is a bond or an optionally substituted spacer having 1 to 6 atoms, or a salt thereof or a prodrug thereof, and

(23) use of a compound represented by the formula

[I']

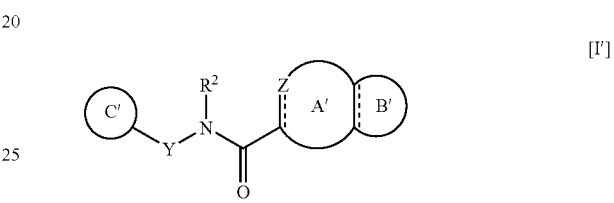

wherein Z is N or $NR^1$ ($R^1$ is a hydrogen atom or an optionally substituted hydrocarbon group), ring A' is an optionally substituted, nitrogen-containing heterocycle, ring B' and ring C' are an optionally substituted homocycle or an optionally substituted heterocycle, ═══ is a single bond or a double bond, $R^2$ is a hydrogen atom or an optionally substituted hydrocarbon group, and Y is a bond or an optionally substituted spacer having 1 to 6 atoms, or a salt thereof or a prodrug thereof, for the production of a matrix metalloproteinase inhibitor, and the like.

Furthermore, while a compound represented by the formula [I] and a salt thereof produce tautomers, any tautomer is encompassed in the present invention, and a compound represented by the formula [I] and a salt thereof may be any of solvates, hydrates, non-solvates and non-hydrates.

BEST MODE FOR CARRYING OUT THE INVENTION

The present invention is described in detail in the following.

(1) "Ring A (Ring A')"

The ring A (ring A') is an optionally substituted, nitrogen-containing heterocycle, and Z is N or $NR^1$ ($R^1$ is a hydrogen atom or an optionally substituted hydrocarbon group to be described in (3) below).

As the combination of Z and ═══ (1) Z is N and ═══ is a double bond, and (2) Z is $NR^1$ and ═══ is a single bond can be mentioned, with preference given to Z is $NR^1$ and ═══ is a single bond.

As the "nitrogen-containing heterocycle" represented by ring A, for example, a 4- to 9-membered, preferably 5- to 9-membered, more preferably 5- or 6-membered, nitrogen-containing heterocycle, containing, besides carbon atom and one nitrogen atom, 1 to 3 hetero atoms selected from nitrogen atom, oxygen atom, sulfur atom and the like (e.g., pyridine, pyrazine, pyrimidine, pyridazine, pyrrole, imidazole, pyrazole, triazole, pyrrolidine, imidazoline, imidazolidine, piperidine, piperazine, triazine, tetrahydropyridine, dihydropyridine, tetrahydropyrazine, dihydropyridine, tetrahydropyrimidine, tetrahydropyridazine, dihydropyrimidine, pyrroline, imidazoline, pyrazoline, hexahydropyrimidine, hexahydropyridazine, dihydrothiazine, tetrahydrothiazine, dihydrooxazine, tetrahydrooxazine, and the like) can be mentioned, with preference given to a 6-membered nitrogen-containing non-aromatic heterocycle containing, besides carbon atom, 1 or 2 nitrogen atoms and the like. Of these, a dihydropyrimidine ring is most preferable.

As the "nitrogen-containing heterocycle" represented by ring A', for example, a 4- to 9-membered, preferably 5- to 9-membered, more preferably 5- or 6-membered nitrogen-containing heterocycle containing, besides carbon atom and one nitrogen atom, 1 to 3 hetero atoms selected from nitrogen atom, oxygen atom, sulfur atom and the like (e.g., pyridine, pyrimidine, pyridazine, pyrrole, pyrazole, pyrrolidine, imidazoline, imidazolidine, piperidine, piperazine, triazine, tetrahydropyridine, dihydropyridine, tetrahydropyrazine, dihydropyrimidine, tetrahydropyrimidine, dihydropyridazine, tetrahydropyridazine, pyrroline, imidazoline, pyrazoline, hexahydropyrimidine, hexahydropyridazine, thiazole, isothiazole, oxazole, isoxazole, oxazoline, oxazolidine, thiazine, oxazine, morpholine, thiazoline, isooxazoline, thiazolidine, isothiazolidine, oxazoline, isooxazolidine and the like) can be mentioned, with preference given to a 6-membered nitrogen-containing aromatic heterocycle containing, besides carbon atom, 1 or 2 nitrogen atoms (e.g., pyridine, pyrazine, pyrimidine and the like) and a 6-membered nitrogen-containing non-aromatic heterocycle containing, besides carbon atom, 1 or 2 nitrogen atoms (e.g., dihydropyridine, dihydropyrazine, dihydropyrimidine and the like) and the like can be mentioned. Of these, a dihydropyrimidine ring is most preferable.

As the substituent that the "optionally substituted, nitrogen-containing heterocycle" represented by ring A (ring A') may have, for example, (i) a halogen atom,
(ii) a cyano group,
(iii) a hydroxy group,
(iv) a nitro group,
(v) a formyl group,
(vi) an optionally substituted amino group (e.g., an amino group, an cyclic amino group and the like, which are optionally substituted by an optionally substituted alkyl group to be mentioned in (vii) below, an optionally substituted aryl group to be mentioned in (viii) below, an optionally substituted alkoxy group to be mentioned in (ix) below, an optionally substituted carbonyl group to be mentioned in (xii) below, an optionally substituted sulfonyl group to be mentioned in (xvi) below, an optionally substituted 5- to 8-membered non-aromatic heterocyclic group containing, besides carbon atom, 1 to 3 hetero atoms selected from nitrogen atom, sulfur atom and oxygen atom to be mentioned in (xvii) below, an optionally substituted 5- to 8-membered aromatic heterocyclic group containing, besides carbon atom, 1 to 3 hetero atoms selected from nitrogen atom, sulfur atom and oxygen atom, to be mentioned in (xviii) below, a formyl group and the like, specifically, a $C_{7-16}$ aralkylamino group optionally substituted by a $C_{1-6}$ alkoxy group, a formylamino group, a $C_{1-6}$ alkyl-carbonylamino group optionally substituted by a $C_{6-14}$ aryloxy group, a $C_{1-6}$ alkylsulfonylamino group or an amino group mono- or di-substituted by an optionally substituted alkyl group (specifically, mono- or di-$C_{1-6}$ alkylamino group such as methylamino, ethylamino, propylamino, dimethylamino, diethylamino group and the like (particularly, a mono- or di-$C_{1-4}$ alkylamino group), a pyrimidinylmethylamino group), a cyclic amino group (e.g., a 5- to 8-membered cyclic amino group optionally containing, besides nitrogen atom, 1 to 3 hetero atoms from oxygen atom, sulfur atom and the like (e.g., pyrrolidino, piperidino, piperazino, morpholino group and the like), an alkoxy-carbonylamino group (e.g., a $C_{1-6}$ alkoxycarbonylamino group such as an ethoxycarbonylamino group etc., and the like), an aryl-carbonylamino group (e.g., a $C_{6-14}$ aryl-carbonylamino group such as a benzoylamino group etc., and the like), a $C_{1-6}$ alkoxy-carbonyl-carbonylamino group, a $C_{1-6}$ alkoxy-carbonyl-$C_{1-6}$ alkyl-carbonylamino group, a 5- to 8-membered non-aromatic heterocycle having, besides carbon atom, 1 to 3 hetero atoms selected from nitrogen atom and oxygen atom-carbonylamino group), (vii) an optionally substituted alkyl group (e.g., an alkyl group, a cycloalkyl group and the like, which is optionally substituted by a halogen atom, an amino group, an alkylamino group, a carboxyl group, an alkoxycarbonyl group, a hydroxy group, an optionally substituted aryl group, an alkoxy group, an optionally substituted aralkyloxy group, an alkylcarbonylamino group, an alkylsulfonylamino group, an alkoxycarbonylamino group, an alkoxycarbonylcarbonylamino group, an alkylcarbonyloxy group, a heterocyclic group, a heterocycle-carbonylamino group, an optionally substituted ureido group, a nitro group, a cyano group, a $C_{1-6}$ alkylcarbonyl group, an alkylthio group, an optionally substituted arylaminocarbonyl group, an optionally substituted arylcarbonylamino group, an optionally substituted aryloxy group, an arylcarbonyloxy group, an N-alkyl-N-aralkylamino group, an aralkylthio group, an azide group and the like), More specifically
(a) a linear or branched alkyl group having 1 to 6 carbon atoms such as methyl, ethyl, propyl, isopropyl, butyl, isobutyl, sec-butyl, tert-butyl and the like, cycloalkyl group (e.g., a $C_{3-8}$ cycloalkyl group such as cyclopropyl, cyclobutyl, cyclopentyl, cyclohexyl etc., and the like),
(b) a halogenated $C_{1-6}$ alkyl group or halogenated $C_{3-8}$ cycloalkyl group (e.g., chloromethyl, difluoromethyl, trichloromethyl, trifluoromethyl, 2-bromoethyl, 2,2,2-trifluoroethyl, 3,3,3-trifluoropropyl and the like),
(c) a $C_{1-6}$ alkyl group or a $C_{3-8}$ cycloalkyl group each substituted by an amino group (e.g., aminomethyl, 2-aminoethyl group and the like),
(d) a $C_{1-6}$ alkyl group or a $C_{3-8}$ cycloalkyl group each substituted by mono- or di-$C_{1-6}$ alkylamino group (e.g., methylaminomethyl, dimethylaminomethyl, 2-methylaminoethyl, 2-dimethylaminoethyl group and the like),
(e) a $C_{1-6}$ alkyl group or a $C_{3-8}$ cycloalkyl group each substituted by a carboxyl group (e.g., carboxymethyl, carboxyethyl group and the like),
(f) a $C_{1-6}$ alkyl group or a $C_{3-8}$ cycloalkyl group each substituted by a $C_{1-6}$ alkoxy-carbonyl group (e.g., methoxycarbonylethyl, ethoxycarbonylethyl, tert-butoxycarbonylmethyl group and the like),
(g) a $C_{1-6}$ alkyl group or $C_{3-8}$ cycloalkyl group each substituted by a hydroxy group (e.g., hydroxymethyl, hydroxyethyl group and the like),
(h) a $C_{1-6}$ alkyl group or a $C_{3-8}$ cycloalkyl group each substituted by a $C_{6-14}$ aryl group, which may have a halogen atom, a cyano group, a hydroxy group, a nitro group, a carboxyl group, a $C_{1-6}$ alkoxy group, a formyl group, a $C_{1-6}$ alkyl-carbonyl group, a $C_{1-6}$ alkoxycarbonyl group, an amino group, a mono or di-$C_{1-6}$ alkylamino group and the like (e.g., benzyl and the like), (i) a $C_{1-6}$ alkyl group or a $C_{3-8}$ cycloalkyl group each substituted by a $C_{1-6}$ alkoxy group (e.g., methoxymethyl, methoxyethyl and the like), (j) a $C_{1-6}$ alkyl group or a $C_{3-8}$ cycloalkyl group each substituted by a $C_{7-16}$ aralkyloxy group, which may have a halogen atom, a cyano group, a hydroxy group, a nitro group, a carboxyl group, a $C_{1-6}$ alkoxy group, a formyl group, a $C_{1-6}$ alkyl-carbonyl group, a $C_{1-6}$ alkoxycarbonyl group, an amino group, a mono or di-$C_{1-6}$ alkylamino group and the like (e.g., benzyloxymethyl and the like), (k) a $C_{1-6}$ alkyl group or a $C_{3-8}$ cycloalkyl group each substituted by a $C_{1-6}$ alkyl-carbonylamino group (e.g., acetylaminomethyl, acetylaminoethyl and the like), (l) a $C_{1-6}$ alkyl group or a $C_{3-8}$ cycloalkyl group each substituted by a $C_{1-6}$ alkylsulfonylamino group (e.g., methylsulfonylaminomethyl and the like), (m) a $C_{1-6}$ alkyl group or a $C_{3-8}$ cycloalkyl group each substituted by a $C_{1-6}$ alkoxy-carbonylamino group (e.g., ethoxycarbonylaminoethyl, tert-butoxycarbonylaminoethyl group and the like), (n) a $C_{1-6}$ alkyl group or a $C_{3-8}$ cycloalkyl group each substituted by a $C_{1-6}$ alkoxy-carbonyl-carbonylamino group (e.g., methoxycarbonylcarbonylaminomethyl group and the like), (o) a $C_{1-6}$ alkyl group or a $C_{3-8}$ cycloalkyl group each substituted by a $C_{1-6}$ alkyl-carbonyloxy group (e.g., acetyloxymethyl group and the like), (p) a $C_{1-6}$ alkyl group or a $C_{3-8}$ cycloalkyl group each substituted by a heterocyclic group (e.g., a 3- to 12-membered, preferably 5- or 6-membered, aromatic heterocyclic group containing, besides carbon atom, 1 to 3 hetero atoms selected from the group consisting of nitrogen atom, oxygen atom and sulfur atom, such as furyl, thienyl, pyrrolyl and the like, a 5- to 8-membered non-aromatic heterocyclic group containing, besides carbon atom, 1 to 3 hetero atoms selected from the group consisting of nitrogen atom, oxygen atom and sulfur atom) (e.g., 2-furylmethyl group and the like)

(q) a $C_{1-6}$ alkyl group or a $C_{3-8}$ cycloalkyl group each substituted by a heterocyclic group (e.g., a 3- to 12-membered, preferably 5- or 6-membered, aromatic heterocyclic group containing, besides carbon atom, 1 to 3 hetero atoms selected from the group consisting of nitrogen atom, oxygen atom and sulfur atom, such as furyl, thienyl, pyrrolyl and the like, a 5- to 8-membered non-aromatic heterocyclic group containing, besides carbon atom, 1 to 3 hetero atoms selected from the group consisting of nitrogen atom, oxygen atom and sulfur atom)-carbonylamino group, (r) a $C_{1-6}$ alkyl group or a $C_{3-8}$ cycloalkyl group each substituted by (1) optionally halogenated $C_{1-6}$ alkyl, (2) optionally halogenated $C_{3-8}$ cycloalkyl, (3) a ureido group optionally substituted by an optionally substituted $C_{6-14}$ aryl group (e.g., optionally substituted $C_{6-14}$ aryl group to be mentioned in (viii) below), (s) a $C_{1-6}$ alkyl group or a $C_{3-8}$ cycloalkyl group substituted by a nitro group (e.g., nitromethyl, 2-nitroethyl etc.), (t) a $C_{1-6}$ alkyl group or a $C_{3-8}$ cycloalkyl group substituted by a cyano group (e.g., cyanomethyl, 2-cyanoethyl etc.), (u) a $C_{1-6}$ alkyl group or a $C_{3-8}$ cycloalkyl group substituted by a $C_{1-6}$ alkyl-carbonyl (e.g., acetylmethyl etc.), (v) a $C_{1-6}$ alkyl group or a $C_{3-8}$ cycloalkyl group substituted by a $C_{1-6}$ alkylthio (e.g., methylthio etc.), (w) a $C_{1-6}$ alkyl group or a $C_{3-8}$ cycloalkyl group substituted by a $C_{6-14}$ aryl-aminocarbonyl optionally substituted by a carboxyl group (e.g., phenylaminocarbonylmethyl etc.), (x) a $C_{1-6}$ alkyl group or a $C_{3-8}$ cycloalkyl group substituted by a $C_{6-14}$ aryl-carbonylamino group optionally substituted by a carboxyl group or $C_{1-6}$ alkoxy-carbonyl (e.g., benzoylaminomethyl etc.), (y) a $C_{1-6}$ alkyl group or a $C_{3-8}$ cycloalkyl group substituted by a $C_{6-14}$ aryloxy group optionally substituted by a carboxyl group (e.g., phenoxymethyl etc.), (z) a $C_{1-6}$ alkyl group or a $C_{3-8}$ cycloalkyl group substituted by a $C_{6-14}$ aryl-carbonyloxy group optionally substituted by hydroxy-$C_{1-6}$ alkyl (e.g., benzoyloxymethyl etc.), (aa) a $C_{1-6}$ alkyl group or a $C_{3-8}$ cycloalkyl group substituted by an N—$C_{1-6}$ alkyl-N—$C_{7-14}$ aralkylamino group (e.g., N-benzyl-N-methylaminomethyl etc.), (bb) a $C_{1-6}$ alkyl group or a $C_{3-8}$ cycloalkyl group substituted by a $C_{7-16}$ aralkylthio group (e.g., benzylthiomethyl etc.), (ee) a $C_{1-6}$ alkyl group or a $C_{3-8}$ cycloalkyl group substituted by an azide group (e.g., azidemethyl etc.), and the like, (viii) an optionally substituted $C_{6-14}$ aryl group (e.g., a $C_{6-14}$ aryl group optionally substituted by a substituent selected from a halogen atom, a cyano group, a hydroxy group, a nitro group, a carboxyl group, a $C_{1-6}$ alkoxy group, a 5- to 8-membered non-aromatic heterocyclic group containing, besides carbon atom, 1 to 3 hetero atoms selected from the group consisting of nitrogen atom, oxygen atom and sulfur atom, optionally halogenated $C_{1-6}$ alkyl group such as methyl, ethyl, trifluoromethyl and the like, a formyl group, a $C_{1-6}$ alkyl-carbonyl group, a $C_{1-6}$ alkoxy-carbonyl group, an amino group, a mono or di-$C_{1-6}$ alkylamino group, a $C_{1-6}$ alkoxy-carbonylamino group, a carbamoyl group, a $C_{1-6}$ alkylcarbamoyl group, a $C_{6-14}$ aryl group, a $C_{1-3}$ alkylenedioxy group, a $C_{1-6}$ alkyl-ureido group and the like, and the like), (ix) an optionally substituted $C_{1-6}$ alkoxy group (e.g., a $C_{1-6}$ alkoxy group optionally substituted by a substituent selected from a halogen atom; a hydroxy group; a cyano group; a nitro group; a carboxyl group; a formyl group; a $C_{1-6}$ alkyl-carbonyl group; a $C_{1-6}$ alkoxy-carbonyl group; amino; mono or di-$C_{1-6}$ alkylamino group; a $C_{1-6}$ alkoxy-carbonylamino group; a carbamoyl group; a $C_{1-6}$ alkylcarbamoyl group; a $C_{6-14}$ aryl group; a $C_{3-7}$ cycloalkyl group; a $C_{7-16}$ aralkyloxy group; a 5- to 8-membered aromatic heterocyclic group containing, besides carbon atom, 1 to 3 hetero atoms selected from nitrogen atom, oxygen atom and sulfur atom, which may be substituted by a $C_{1-6}$ alkoxy group or a $C_{1-6}$ alkyl group; a 5- to 8-membered non-aromatic heterocyclic group containing, besides carbon atom, 1 to 3 hetero atoms selected from the group consisting of nitrogen atom and oxygen atom, which may have a carboxy group or a carbonyl group; and a $C_{6-14}$ arylcarbonyl group and the like), (x) a substituted oxy group (e.g., an optionally substituted aralkyloxy group (e.g., a $C_{7-16}$ aralkyloxy group optionally substituted by a substituent selected from a halogen atom, a cyano group, a hydroxy group, a nitro group, a carboxyl group, a $C_{1-6}$ alkyl group optionally having a carboxyl group, a $C_{1-6}$ alkoxy group optionally having a carboxyl group, a formyl group, a $C_{1-6}$ alkyl-carbonyl group, an amino group, a mono or di-$C_{1-6}$ alkylamino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, an amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom, $C_{1-3}$ alkylenedioxy and $C_{6-14}$ aryl, and the like), an optionally substituted aryloxy group (e.g., a $C_{6-14}$ aryloxy group optionally substituted by a substituent selected from a halogen atom; a cyano group; a hydroxy group; a nitro group; a carboxyl group; a $C_{1-6}$ alkyl group optionally having a carboxyl group; a $C_{1-6}$ alkoxy group optionally having a carboxyl group; a formyl group; a $C_{1-6}$ alkyl-carbonyl group; an amino group; a mono or di-$C_{1-6}$ alkylamino group; a $C_{1-6}$ alkoxycarbonyl group; a carbamoyl group; a 5- to 8-membered aromatic heterocyclic group containing, besides carbon atom, 1 to 3 hetero atoms selected from the group consisting of nitrogen atom, oxygen atom and sulfur atom, which may have hydroxy or $C_{1-6}$ alkoxy; an amino-sulfonylamino group optionally having a $C_{1-6}$ alkoxycarbonyl group; and a 5- to 8-membered non-aromatic heterocyclic group containing, besides carbon atom, 1 to 3 hetero atoms selected from the group consisting of nitrogen atom, oxygen atom and sulfur atom, and the like, such as phenoxy, naphthyloxy group and the like, and the like), an aminocarbonyloxy group, a mono- or di-alkylamino-carbonyloxy group (e.g., a mono- or di-$C_{1-6}$ alkylamino-carbonyloxy group such as methylaminocarbonyloxy, ethylaminocarbonyloxy, dimethylaminocarbonyloxy, a diethylamino-carbonyloxy group etc., and the like), a formyloxy group, an alkylcarbonyloxy group (e.g., a $C_{1-6}$ alkyl-carbonyloxy group such as acetyloxy, propionyloxy, butyryloxy etc., and the like), a mono- or di-$C_{1-6}$ alkylamino-thiocarbonyloxy group, a heterocyclic group-oxy group (heterocyclic group is, for example, a 3- to 12-membered, preferably 5- or 6-membered, aromatic heterocyclic group containing, besides carbon atom, 1 to 3 hetero atoms selected from the group consisting of nitrogen atom, oxygen atom and sulfur atom, such as furyl, thienyl, pyrrolyl and the like, a 5- to 8-membered non-aromatic heterocyclic group containing, besides carbon atom, 1 to 3 hetero atoms selected from the group consisting of nitrogen atom, oxygen atom and sulfur atom and the like), (xi) a carboxyl group, (xii) an optionally substituted carbonyl group (e.g., alkoxy-carbonyl group (e.g., a $C_{1-6}$ alkoxy-carbonyl group such as methoxycarbonyl, ethoxycarbonyl, propoxycarbonyl, butoxycarbonyl, isobutoxycarbonyl group etc., and the like), an aralkyloxy-carbonyl group (e.g., a $C_{7-16}$ aralkyloxy-carbonyl group such as benzyloxycarbonyl group etc., and the like), an aryloxy-carbonyl group (e.g., a $C_{6-14}$ aryloxy-carbonyl group such as phenoxycarbonyl group etc., and the like), an alkylcarbonyl group optionally substituted by a $C_{6-14}$ aryloxy group (e.g., a $C_{1-6}$ alkyl-carbonyl group such as methylcarbonyl, ethylcarbonyl, butylcarbonyl and the like, and the like), a cycloalkylcarbonyl group (e.g., a $C_{3-8}$ cycloalkyl-carbonyl group such as cyclopentylcarbonyl, cyclohexylcarbonyl group and the like, and the like), an aryl-carbonyl group (e.g., a $C_{6-14}$ aryl-carbonyl group such as benzoyl and the like, and the like), an aralkyl-carbonyl group (e.g., a $C_{7-16}$ aralkyl-carbonyl group such as benzylcarbonyl and the like, and the like), a $C_{1-6}$ alkoxy-carbonyl-carbonyl group, a $C_{1-6}$ alkoxy-carbonyl-$C_{1-6}$ alkyl-carbonyl group, a 5- or 6-membered aromatic heterocyclic group containing, esides carbon atom, 1 to 3 hetero atoms selected from the group consisting of nitrogen atom, oxygen atom and sulfur atom-carbonyl group, a 5- to 8-membered non-aromatic heterocyclic group containing, besides carbon atom, 1 to 3 hetero atoms selected from the group consisting of nitrogen atom, oxygen atom and sulfur atom-carbonyl group, a $C_{1-6}$ alkoxy-5- or 6-membered aromatic heterocycle containing, besides carbon atom, 1 to 3 etero atoms selected from the group consisting of nitrogen atom, oxygen atom and sulfur atom-carbonyl group, $C_{1-6}$ alkoxy-5- to 8-membered non-aromatic heterocycle containing, besides carbon atom, 1 to 3 hetero atoms selected from the group consisting of nitrogen atom, oxygen atom and sulfur atom-carbonyl group), (xiii) an optionally substituted carbamoyl group (e.g., a carbamoyl group, a thiocarbamoyl group, a mono- or di-alkyl-carbamoyl group (e.g., a mono- or di-$C_{1-6}$ alkyl-carbamoyl group such as methylcarbamoyl, ethylcarbamoyl, propylcarbamoyl, utylcarbamoyl, diethylcarbamoyl, dibutylcarbamoyl group and the like), a mono- or di-aralkyl-carbamoyl group optionally substituted by a carboxyl group or $C_{1-6}$ alkoxy-carbonyl (e.g., a mono- or di-$C_{7-16}$ aralkyl-carbamoyl group such as benzylcarbamoyl and the like) and the like), (xiv) a thiol group, (xv) a thiol group having a substituent (e.g., an optionally halogenated $C_{1-6}$ alkylthio group, a $C_{7-16}$ aralkylthio group, a 5- to 8-membered aromatic heterocycle-thio group containing, besides carbon atom, 1 to 3 hetero atoms selected from the group consisting of nitrogen atom, oxygen atom and sulfur atom, a mono- or di-$C_{1-6}$ alkylcarbamoyl-thio group), (xvi) an optionally substituted sulfonyl group (e.g., a $C_{1-6}$ alkylsulfonyl group (e.g., a $C_{1-6}$ alkylsulfonyl group such as methylsulfonyl, ethylsulfonyl, propylsulfonyl and the like, and the like), a cycloalkylsulfonyl group (e.g., a $C_{3-8}$ cycloalkylsulfonyl group such as cyclopentylsulfonyl, cyclohexylsulfonyl and the like, and the like), an arylsulfonyl group (e.g., a $C_{6-14}$ arylsulfonyl group such as phenylsulfonyl, naphthylsulfonyl and the like, and the like), an aralkylsulfonyl group (e.g., a $C_{7-15}$ aralkylsulfonyl group such as benzylsulfonyl and the like, and the like)), (xvii) an optionally substituted (e.g., optionally substituted by a substituent selected from a halogen atom, a cyano group, a hydroxy group, a nitro group, a carboxyl group, a $C_{1-6}$ alkoxy group, a 5- to 8-membered non-aromatic heterocyclic group containing, besides carbon atom, 1 to 3 hetero atoms selected from the group consisting of nitrogen atom, oxygen atom and sulfur atom, optionally halogenated $C_{1-6}$ alkyl group such as methyl, ethyl, trifluoromethyl and the like, a formyl group, a $C_{1-6}$ alkyl-carbonyl group, a $C_{1-6}$ alkoxy-carbonyl group, an amino group, a mono or di-$C_{1-6}$ alkylamino group, a $C_{1-6}$ alkoxy-carbonylamino group, a carbamoyl group, a $C_{1-6}$ alkylcarbamoyl group, a $C_{6-14}$ aryl group, a $C_{1-3}$ alkylenedioxy group, a $C_{6-14}$ aryloxy group optionally substituted by a halogen atom and the like, and the like) 5- to 8-membered non-aromatic heterocyclic group containing, besides carbon atom, 1 to 3 hetero atoms selected from nitrogen atom, sulfur atom and oxygen atom (including a 5- to 8-membered cyclic amino group optionally containing, besides nitrogen atom, 1 to 3 hetero atoms such as sulfur atom, oxygen atom and the like, for example, pyrrolidinyl, tetrahydrofuryl, tetrahydrothienyl, piperidyl, tetrahydropyranyl, morpholinyl, thiomorpholinyl, piperazinyl and the like), (xviii) an optionally substituted (e.g., optionally substituted by a substituent selected from a halogen atom, a cyano group, a hydroxy group, a nitro group, a carboxyl group, a $C_{1-6}$ alkoxy group, a 5- to 8-membered non-aromatic heterocyclic group containing, besides carbon atom, 1 to 3 hetero atoms selected from the group consisting of nitrogen atom, oxygen atom and sulfur atom, optionally halogenated $C_{3-6}$ alkyl group such as methyl, ethyl, trifluoromethyl and the like, a formyl group, a $C_{1-6}$ alkyl-carbonyl group, a $C_{1-6}$ alkoxy-carbonyl group, an amino group, a mono or di-$C_{1-6}$ alkylamino group, a $C_{1-6}$ alkoxy-carbonylamino group, a carbamoyl group, a $C_{1-6}$ alkylcarbamoyl group, a $C_{6-14}$ aryl group, a $C_{1-3}$ alkylenedioxy group, a $C_{6-14}$ aryloxy group optionally substituted by a halogen atom and the like, and the like) 5- to 8-membered aromatic heterocyclic group containing, besides carbon atom, 1 to 3 hetero atoms selected from nitrogen atom, sulfur atom and oxygen atom (e.g., furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like), (xix) an optionally substituted (e.g., optionally substituted by a substituent selected from (1) optionally halogenated $C_{1-6}$ alkyl, (2) optionally halogenated $C_{3-8}$ cycloalkyl and (3) optionally substituted $C_{6-14}$ aryl group (e.g., optionally substituted by the optionally substituted $C_{6-14}$ aryl group of the aforementioned (viii)) ureido group, (xx) an oxo group and the like are used.

As preferable substituent that the "optionally substituted, nitrogen-containing heterocycle" represented by ring A (ring A') may have, for example, (i) a halogen atom,
(ii) a cyano group,
(iii) a hydroxy group,
(iv) a nitro group,
(v) an optionally substituted amino group (a mono- or di-$C_{1-6}$ alkylamino group, a $C_{7-16}$ aralkylamino group optionally substituted by a $C_{1-6}$ alkoxy group, a $C_{1-6}$ alkyl-carbonylamino group optionally substituted by a $C_{6-14}$ aryloxy group and $C_{1-6}$ alkylsulfonylamino group etc.),
(vi) an optionally substituted alkyl group (e.g., a $C_{1-6}$ alkyl group optionally substituted by a substituent selected from a halogen atom, a $C_{1-6}$ alkoxy group and a 5- to 8-membered non-aromatic heterocyclic group containing, besides carbon atom, 1 to 3 hetero atoms selected from the group consisting of nitrogen atom, oxygen atom and sulfur atom, and the like),
(vii) an optionally substituted $C_{6-14}$ aryl group (e.g., a $C_{6-14}$ aryl group optionally substituted by a substituent selected from a halogen atom, a $C_{1-6}$ alkoxy group and a 5- to 8-membered non-aromatic heterocyclic group containing, besides carbon atom, 1 to 3 hetero atoms selected from the group consisting of nitrogen atom, oxygen atom and sulfur atom and the like),
(viii) an optionally substituted $C_{1-6}$ alkoxy group (e.g., a $C_{1-6}$ alkoxy group optionally substituted by a substituent selected from a halogen atom, a hydroxy group, a $C_{3-7}$ cycloalkyl group, a $C_{7-16}$ aralkyloxy group, a 5- to 8-membered aromatic heterocyclic group containing, besides carbon atom, 1 to 3 hetero atoms selected from the group consisting of nitrogen atom, oxygen atom and sulfur atom, a 5- to 8-membered non-aromatic heterocyclic group containing, besides carbon atom, 1 to 3 hetero atoms selected from nitrogen atom and oxygen atom, which may have a carboxy group, and $C_{6-14}$ arylcarbonyl group and the like),
(ix) an optionally substituted aralkyloxy group (e.g., a $C_{7-16}$ aralkyloxy group optionally substituted by a substituent selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, aminosulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like),
(x) a thiol group,
(xi) an optionally halogenated $C_{1-6}$ alkylthio group,
(xii) a $C_{7-16}$ aralkylthio group,
(xiii) a 5- to 8-membered aromatic heterocycle containing, besides carbon atom, 1 to 3 hetero atoms selected from the group consisting of nitrogen atom, oxygen atom and sulfur atom-thio group,
(xiv) a mono- or di-$C_{1-6}$ alkylcarbamoyl-thio group
(xv) a $C_{1-6}$ alkylsulfonyl group,
(xvi) a carbamoyl group,
(xvii) a mono- or di-$C_{1-6}$ alkylamino-thiocarbonyloxy group,
(xviii) a 5- to 8-membered non-aromatic heterocyclic group containing, besides carbon atom, 1 to 3 hetero atoms selected from nitrogen atom, sulfur atom and oxygen atom,
(xix) a 5- to 8-membered aromatic heterocyclic group containing, besides carbon atom, 1 to 3 hetero atoms selected from nitrogen atom, sulfur atom and oxygen atom, and the like can be mentioned.

More preferable substituents that ring A (ring A') optionally have include, for example, a halogen atom, an optionally substituted $C_{1-6}$ alkyl group (e.g., a $C_{1-6}$ alkyl group optionally substituted by substituent(s) selected from a halogen atom, a $C_{1-6}$ alkoxy group and a 5- to 8-membered non-aromatic heterocyclic group containing, besides carbon atom, 1 to 3 hetero atoms selected from the group consisting of nitrogen atom, oxygen atom and sulfur atom), an optionally halogenated $C_{1-6}$ alkoxy group, a mono- or di-$C_{1-6}$ alkylamino group, an optionally halogenated $C_{1-6}$ alkylthio group, a nitro group, a cyano group and the like.

Of these, 1 to 3 substituents selected from a halogen atom, an optionally halogenated $C_{1-6}$ alkyl group and an optionally halogenated $C_{1-6}$ alkoxy group and the like are particularly preferable.

The substituent of ring A (ring A') may be present at any substitutable position on the ring, and when two or more substituents are present, the substituents may be the same or different and, the number thereof may be about 0-4. The number of the substituents is preferably about 0-3.

When ring A has a nitrogen atom, it may form a quaternary ammonium salt and, for example, a salt may be formed with an anion such as a halogen ion (e.g., Cl⁻, Br⁻, I⁻ and the like), a sulfuric acid ion, a hydroxy ion and the like.

(2) "Ring B (Ring B')"

Ring B is an optionally substituted monocyclic homocycle or an optionally substituted monocyclic heterocycle, and ring B' is an optionally substituted homocycle or an optionally substituted heterocycle.

As the "monocyclic homocycle (monocyclic hydrocarbon comprising carbon atoms)" represented by ring B, for example, a 3- to 10-membered, preferably 5- to 9-membered, monocyclic hydrocarbon, more preferably a 5- or 6-membered monocyclic hydrocarbon and the like can be mentioned and, specifically, for example, benzene, $C_{3-10}$ cycloalkane (e.g., cyclopropane, cyclobutane, cyclopentane, cyclohexane, cycloheptane, cyclooctane and the like), $C_{4-10}$ cycloalkene (e.g., cyclobutene, cyclopentene, cyclohexene, cycloheptene, cycloheptadiene, cyclooctene and the like) and the like are used. Of these, as ring B, for example, a 6-membered monocyclic homocycle, such as benzene, cyclohexane and the like, are preferable, and a benzene ring is particularly preferable.

As the "homocycle (cyclic hydrocarbon comprising carbon atoms)", represented by ring B', for example, a 3- to 14-membered cyclic hydrocarbon and the like can be mentioned, and specifically, for example, a $C_{6-14}$ aryl ring, $C_{3-10}$ cycloalkane (e.g., cyclopropane, cyclobutane, cyclopentane, cyclohexane, cycloheptane, cyclooctane and the like), $C_{4-10}$ cycloalkene (e.g., cyclobutene, cyclopentene, cyclohexene, cycloheptene, cycloheptadiene, cyclooctene and the like) and the like are used.

Specifically, besides the aforementioned monocyclic homocycles, indene, naphthalene, anthracene, fluorene, phenanthrene and derivatives thereof (e.g., (partial) hydrides thereof and the like) and the like are used.

As the "monocyclic heterocycle" represented by ring B, for example, a 3 to 9-membered monocyclic heterocycle containing, besides carbon atom, 1 to 3 hetero atoms selected from nitrogen atom, sulfur atom, oxygen atom and the like, preferably a 5- to 9-membered monocyclic heterocycle, more preferably a 5- or 6-membered monocyclic heterocycle, particularly preferably a 5- or 6-membered monocyclic aromatic heterocycle, can be mentioned. Specifically, for example, pyridine, pyrazine, pyrimidine, pyridazine, pyrrole, imidazole, pyrazole, triazole, pyrrolidine, imidazoline, imidazolidine, piperidine, piperazine, triazine, tetrahydropyridine, dihydropyridine, tetrahydropyrazine, tetrahydropyrimidine, tetrahydropyridazine, pyrroline (dihydropyrrole), pyrazoline (dihydropyrazole), hexahydropyrimidine, hexahydropyridazine, thiazole, isothiazole, oxazole, isoxazole, oxazoline, oxazolidine, morpholine, thiazoline (dihydrothiazole), isothiazolidine (dihydroisothiazole), isooxazoline (dihydroisoxazole), thiazolidine (tetrahydrothiazole), isothiazolidine (tetrahydroisothiazole), isooxazolidine (tetrahydroisoxazole), furan, thiophene, pyran, dioxane, dihydropyran, dihydrothiophene, dihydrofuran, tetrahydrothiophene, tetrahydrofuran, tetrahydropyran and the like can be mentioned.

As preferable monocyclic heterocycle, for example, (i) a 6-membered monocyclic nitrogen-containing heterocycle containing, besides carbon atom, 1 or 2 nitrogen atoms (e.g., pyridine, pyrazine ring and the like) or (ii) a 5-membered monocyclic sulfur-containing heterocycle containing, besides carbon atom, one sulfur atom (e.g., thiophene ring and the like) and the like can be mentioned, with particular preference given to thiophene ring.

As the "heterocycle" represented by ring B', for example, a 3- to 12-membered heterocycle containing, besides carbon atom, 1 to 3 hetero atoms selected from nitrogen atom, sulfur atom, oxygen atom and the like are used, and specifically, aromatic fused heterocycle and the like are used besides the aforementioned monocyclic heterocycle.

As the aromatic fused heterocyclic group, for example, a 8- to 12-membered aromatic fused heterocycle such as benzofuran, benzothiophene, indole, benzimidazole, benzoxazole, coumarin, quinoline, isoquinoline, quinoxaline, quinazoline, phthalazine, naphthyridine, acridine, thianthrene, phenoxazine, phenothiazine, purine, xanthine, xanthene, pteridine and the like (preferably, a heterocycle wherein the aforementioned 5- or 6-membered monocyclic aromatic heterocycle is condensed with a benzene ring or a heterocycle wherein the same or different two heterocycles of the aforementioned 5- or 6-membered monocyclic aromatic heterocycle are condensed) and the like can be mentioned.

As the substituents that "monocyclic homocycle" and "monocyclic heterocycle" represented by ring B, and the "homocycle" and "heterocycle" represented by ring B' optionally have, those similar to the substituents that the aforementioned ring A (ring A') optionally have can be mentioned.

As preferable substituents that "homocycle or heterocycle" represented by ring B (ring B') may have, for example,
(i) a halogen atom,
(ii) a cyano group,
(iii) a hydroxy group,
(iv) a nitro group,
(v) an optionally substituted amino group (e.g., (a) a mono- or di-$C_{1-6}$ alkylamino group, (b) a $C_{7-16}$ aralkylamino group optionally substituted by a $C_{1-6}$ alkoxy group, (c) a $C_{1-6}$ alkyl-carbonylamino group optionally substituted by a $C_{6-14}$ aryloxy group, (d) a $C_{1-6}$ alkylsulfonylamino group and (e) a $C_{7-16}$ aralkyl-carbonylamino group etc.),
(vi) an optionally substituted alkyl group (e.g., a $C_{1-6}$ alkyl group optionally substituted by (a) a halogen atom, (b) a $C_{1-6}$ alkoxy group, (c) a substituent selected from a 5- to 8-membered non-aromatic heterocyclic group containing, besides carbon atom, 1 to 3 hetero atoms selected from the group consisting of nitrogen atom, oxygen atom and sulfur atom, (d) $C_{7-16}$ aralkyloxy optionally substituted by a carboxyl group, $C_{1-6}$ alkoxy-carbonyl, $C_{1-6}$ alkyl-aminocarbonyl, a cyano group, halogen or carboxyl-$C_{1-6}$ alkyl, (e) $C_{6-14}$ aryl-aminocarbonyl optionally substituted by a carboxyl group or $C_{1-6}$ alkoxy-carbonyl, (f) $C_{6-14}$ aryl-carbonylamino optionally substituted by a carboxyl group or $C_{1-6}$ alkoxy-carbonyl, (g) $C_{6-14}$ aryloxy optionally substituted by a carboxyl group, (h) $C_{6-14}$ aryl-carbonyloxy optionally substituted by hydroxy-$C_{1-6}$ alkyl, (i) N—$C_{1-6}$ alkyl-N—$C_{7-16}$ aralkylamino, (j) N—$C_{1-6}$ alkyl-carbonyl-N—$C_{7-16}$ aralkyl-amino, (k) $C_{7-16}$ aralkylthio, (l) an azide group, (m) a cyano group, (n) $C_{1-6}$ alkoxy-carbonyl, (o) a hydroxy group and the like),
(vii) an optionally substituted $C_{6-14}$ aryl group (e.g., a $C_{6-14}$ aryl group optionally substituted by a halogen atom, a $C_{1-6}$ alkoxy group, substituent(s) selected from 5- to 8-membered non-aromatic heterocyclic group containing, besides carbon atom, 1 to 3 hetero atoms selected from the group consisting of nitrogen atom, oxygen atom and sulfur atom, a carboxyl group and the like),
(viii) an optionally substituted $C_{1-6}$ alkoxy group (e.g., a $C_{1-6}$ alkoxy group optionally substituted by substituent(s) selected from (a) a halogen atom, (b) a hydroxy group, (c) a $C_{3-7}$ cycloalkyl group, (d) a $C_{7-16}$ aralkyloxy group, (e) a 5- to 8-membered aromatic heterocyclic group containing, besides carbon atom, 1 to 3 hetero atoms selected from the group consisting of nitrogen atom, oxygen atom and sulfur atom, (f) a 5- to 8-membered non-aromatic heterocyclic group containing, besides carbon atom, 1 to 3 hetero atoms selected from nitrogen atom and oxygen atom, which may have a carboxy group or a carbonyl group, and (g) a $C_{6-14}$ arylcarbonyl group and the like), (ix) an optionally substituted aralkyloxy group (e.g., a $C_{7-16}$ aralkyloxy group optionally substituted by a substituent selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like)

(x) an optionally substituted aryloxy group (e.g., a $C_{6-14}$ aryloxy group optionally substituted by substituent(s) selected from (a) a halogen atom, (b) a cyano group, (c) a carboxyl group, (d) a $C_{1-6}$ alkyl group optionally having a carboxyl group, (e) a $C_{1-6}$ alkoxy group optionally having a carboxyl group, (f) an amino group, (g) a $C_{1-6}$ alkoxycarbonyl group, (h) a carbamoyl group, (i) a 5- to 8-membered aromatic heterocyclic group containing, besides carbon atom, 1 to 3 hetero atoms selected from the group consisting of nitrogen atom, oxygen atom and sulfur atom, which may have hydroxy or $C_{1-6}$ alkoxy, (j) an amino-sulfonylamino group optionally having $C_{1-6}$ alkoxycarbonyl group and (k) a 5- to 8-membered non-aromatic heterocyclic group containing, besides carbon atom, 1 to 3 hetero atoms selected from the group consisting of nitrogen atom, oxygen atom and sulfur atom and the like), (xi) a thiol group, (xii) an optionally halogenated $C_{1-6}$ alkylthio group, (xiii) a $C_{7-16}$ aralkylthio group, (xiv) a 5- to 8-membered aromatic heterocycle containing, besides carbon atom, 1 to 3 hetero atoms selected from the group consisting of nitrogen atom, oxygen atom and sulfur atom-thio group, (xv) a mono- or di-$C_{1-6}$ alkylcarbamoyl-thio group (xvi) a $C_{1-6}$ alkylsulfonyl group, (xvii) a carbamoyl group, (xviii) a mono- or di-$C_{1-6}$ alkylamino-thiocarbonyloxy group, (xix) a 5- to 8-membered non-aromatic heterocyclic group containing, besides carbon atom, 1 to 3 hetero atoms selected from nitrogen atom, sulfur atom and oxygen atom, (xx) a 5- to 8-membered aromatic heterocyclic group containing, besides carbon atom, 1 to 3 hetero atoms selected from nitrogen atom, sulfur atom and oxygen atom, and the like, (xxi) a $C_{7-16}$ aralkyl-carbamoyl group optionally substituted by a carboxyl group or a $C_{1-6}$ alkoxycarbonyl group, (xxii) an oxo group and the like can be mentioned.

More preferable substituents that ring B optionally have include, for example, a halogen atom, an optionally substituted $C_{1-6}$ alkyl group (e.g., a $C_{1-6}$ alkyl group optionally substituted by a halogen atom, a $C_{1-6}$ alkoxy group, substituent(s) selected from a 5- to 8-membered non-aromatic heterocyclic group containing, besides carbon atom, 1 to 3 hetero atoms selected from the group consisting of nitrogen atom, oxygen atom and sulfur atom, a $C_{7-16}$ aralkyloxy optionally substituted by a carboxyl group, a $C_{6-14}$ aryl-aminocarbonyl optionally substituted by a carboxyl group, $C_{6-14}$ aryl-carbonylamino optionally substituted by a carboxyl group, a $C_{6-14}$ aryloxy optionally substituted by a carboxyl group and the like), an optionally halogenated $C_{1-6}$ alkoxy group, a mono- or di-$C_{1-6}$ alkylamino group, an optionally halogenated $C_{1-6}$ alkylthio group, a nitro group, a cyano group, an optionally substituted aralkyloxy group (e.g., a $C_{7-16}$ aralkyloxy group optionally substituted by substituent(s) selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, an amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like), an optionally substituted aryloxy group (e.g., a $C_{6-14}$ aryloxy group optionally substituted by substituent(s) selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, an amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like ), a $C_{6-14}$ aryl group optionally substituted by a carboxyl group, a carbamoyl group optionally substituted by a $C_{7-16}$ aralkyl optionally substituted by a carboxyl group and an amino group optionally substituted by $C_{7-16}$ aralkyl-carbonyl and the like.

Of these, 1 to 3 substituents selected from a halogen atom, an optionally halogenated $C_{1-6}$ alkyl group, a $C_{1-6}$ alkyl group substituted by a $C_{7-16}$ aralkyloxy optionally substituted by a carboxyl group, a $C_{1-6}$ alkyl group substituted by a $C_{6-14}$ aryl-aminocarbonyl optionally substituted by a carboxyl group, a $C_{1-6}$ alkyl group substituted by a $C_{6-14}$ aryl-carbonylamino optionally substituted by a carboxyl group, a $C_{1-6}$ alkyl group substituted by a $C_{6-14}$ aryloxy optionally substituted by a carboxyl group, an optionally halogenated $C_{1-6}$ alkoxy group, an optionally substituted aralkyloxy group (e.g., a $C_{7-16}$ aralkyloxy group optionally substituted by substituent(s) selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, an amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like), an optionally substituted aryloxy group (e.g., a $C_{6-14}$ aryloxy group optionally substituted by substituent(s) selected from a halogen atom, a cyano group, a carboxyl group, a $C_{1-6}$ alkyl group optionally having a carboxyl group, a $C_{1-6}$ alkoxy group optionally having a carboxyl group, an amino group, a $C_{1-6}$ alkoxycarbonyl group, a carbamoyl group, a 5- to 8-membered aromatic heterocyclic group containing, besides carbon atom, 1 to 3 hetero atoms selected from the group consisting of nitrogen atom, oxygen atom and sulfur atom, an amino-sulfonylamino group optionally having a $C_{1-6}$ alkoxycarbonyl group and a 5- to 8-membered non-aromatic heterocyclic group containing, besides carbon atom, 1 to 3 hetero atoms selected from the group consisting of nitrogen atom, oxygen atom and sulfur atom and the like), a $C_{6-14}$ aryl group optionally substituted by a carboxyl group, a carbamoyl group optionally substituted by a $C_{7-16}$ aralkyl optionally substituted by a carboxyl group and an amino group optionally substituted by a $C_{7-16}$ aralkyl-carbonyl and the like are preferable.

Particularly, 1 to 3 substituents selected from (1) a $C_{1-6}$ alkyl group, (2) a $C_{1-6}$ alkyl group substituted by a $C_{7-16}$ aralkyloxy optionally substituted by a carboxyl group, (3) a $C_{1-6}$ alkyl group substituted by a $C_{6-14}$ aryl-aminocarbonyl optionally substituted by a carboxyl group, (4) a $C_{1-6}$ alkyl group substituted by a $C_{6-14}$ aryl-carbonylamino optionally substituted by a carboxyl group, (5) a $C_{1-6}$ alkyl group substituted by a $C_{6-14}$ aryloxy optionally substituted by a carboxyl group, (6) a $C_{6-14}$ aryloxy group optionally substituted by a carboxyl group, (7) a $C_{7-16}$ aralkyloxy group optionally substituted by a carboxyl group, (8) a $C_{6-14}$ aryl group optionally substituted by a carboxyl group, (9) a carbamoyl group optionally substituted by a $C_{7-16}$ aralkyl optionally substituted by a carboxyl group, (10) an amino group optionally substituted by $C_{7-16}$ aralkyl-carbonyl and (11) a halogen atom and the like are preferable.

The substituent of ring B may be present at any substitutable position on the ring, and when two or more substituents are present, the substituents may be the same or different and, the number thereof may be about 0-4. The number of the substituents is preferably about 0-3.

When ring B has a nitrogen atom, it may form a quaternary ammonium salt and, for example, a salt may be formed with an anion such as a halogen ion (e.g., $Cl^-$, $Br^-$, $I^-$ and the like), a sulfuric acid ion, a hydroxy ion and the like.

(3) $R^1$, $R^2$ $R^1$ and $R^2$ are each a hydrogen atom or an optionally substituted hydrocarbon group.

As the "hydrocarbon group" of the "optionally substituted hydrocarbon group" represented by $R^1$ or $R^2$, for example, an alkyl group, an alkenyl group, an alkynyl group, a cycloalkyl group, an aryl group and the like can be mentioned. It is preferably an alkyl group, a cycloalkyl group or an aryl group, and particularly preferably an alkyl group.

As the "alkyl group", a linear or branched one having 1 to 6 carbon atoms is used, and preferably, for example, a linear or branched alkyl group having 1 to 4 carbon atoms such as methyl, ethyl, propyl, isopropyl, butyl, isobutyl, sec-butyl, tert-butyl and the like is used.

As the "alkenyl group", for example, an alkenyl group having 2 to 6 carbon atoms, such as ethenyl, propenyl, isopropenyl, butenyl, isobutenyl, sec-butenyl and the like, is used, and preferably, for example, an alkenyl group having 2 to 4 carbon atoms, such as ethenyl, propenyl, isopropenyl and the like, is used.

As the "alkynyl group", for example, an alkynyl group having 2 to 6 carbon atoms, such as ethynyl, propynyl, butynyl, isobutynyl and the like, is used, and preferably, for example, an alkynyl group having 2 to 4 carbon atoms, such as ethynyl, propynyl and the like is used.

As the "cycloalkyl group", for example, a $C_{3-8}$ cycloalkyl group, such as cyclopropyl, cyclobutyl, cyclopentyl, cyclohexyl, cycloheptyl, cyclooctyl and the like, is used, and preferably, for example, a $C_{3-6}$ cycloalkyl group such as cyclopropyl, cyclobutyl, cyclopentyl, cyclohexyl and the like, is used.

As the "aryl group", for example, an aryl group having 6 to 14 carbon atoms, such as phenyl, naphthyl, anthryl, phenanthryl and the like, is used, and preferably, for example, an aryl group having 6 to 10 carbon atoms, such as phenyl, naphthyl and the like, is used.

As the substituents that the "hydrocarbon group" represented by $R^1$ or $R^2$ optionally have, specifically,
  (i) a halogen atom,
  (ii) a cyano group,
  (iii) a hydroxy group,
  (iv) the above-mentioned optionally substituted amino group (same as the "optionally substituted amino group" that the "optionally substituted, nitrogen-containing heterocycle" represented by the aforementioned ring A optionally has),
  (v) the above-mentioned optionally substituted alkyl group (same as the "optionally substituted alkyl group" that the "optionally substituted, nitrogen-containing heterocycle" optionally has),
  (vi) the above-mentioned optionally substituted aralkyloxy group (same as the "optionally substituted aralkyloxy group" that the "optionally substituted, nitrogen-containing heterocycle" optionally has)
  (vii) the above-mentioned optionally substituted $C_{6-14}$ aryl group (same as the "optionally substituted $C_{6-14}$ aryl group" that the "optionally substituted, nitrogen-containing heterocycle" represented by the aforementioned ring A optionally has),
  (viii) the above-mentioned optionally substituted $C_{1-6}$ alkoxy group (same as the "optionally substituted $C_{1-6}$ alkoxy group" that the "optionally substituted, nitrogen-containing heterocycle" represented by the aforementioned ring A optionally has),
  (ix) a thiol group,
  (x) a $C_{1-6}$ alkylthio group,
  (xi) a $C_{7-16}$ aralkylthio group,
  (xii) a 5- to 8-membered aromatic heterocycle containing, besides carbon atom, 1 to 3 hetero atoms selected from the group consisting of nitrogen atom, oxygen atom and sulfur atom-thio group,
  (xiii) a $C_{1-6}$ alkylsulfonyl group,
  (xiv) a carbamoyl group,
  (xv) a mono- or di-$C_{1-6}$ alkylamino-thiocarbonyloxy group,
  (xvi) the above-mentioned mono- or di-$C_{1-6}$ alkylcarbamoyl-thio group,
  (xvii) a nitro group,
  (xviii) a carboxyl group,
  (xix) a $C_{1-6}$ alkoxy-carbonyl group and
  (xx) a $C_{1-6}$ alkyl-carbonyl group and the like can be mentioned.

As $R^1$ and $R^2$, each is preferably a hydrogen atom or an optionally substituted lower alkyl group.

As the "optionally substituted lower alkyl group", for example, a $C_{1-6}$ alkyl group optionally substituted by the aforementioned substituent of the "optionally substituted alkyl group" (e.g., methyl, ethyl, propyl, isopropyl, butyl, isobutyl, sec-butyl, tert-butyl) and the like are used.

As $R^1$ and $R^2$, a hydrogen atom is particularly preferable.

As the partial structure represented by the formula

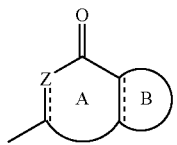

[II]

to which the aforementioned ring A and ring B are related, or as the partial structure represented by the formula

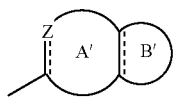

[II']

to which the aforementioned ring A' and ring B' are related, one wherein the aforementioned preferable embodiments of the aforementioned ring A, ring B and Z are combined, or one wherein the aforementioned preferable embodiments of the aforementioned ring A', ring B' and Z are combined, is used. Particularly,

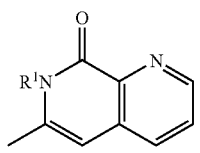 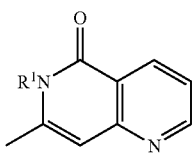

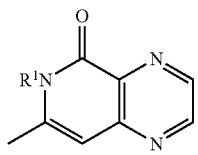 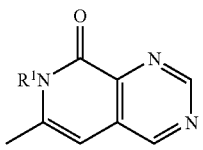

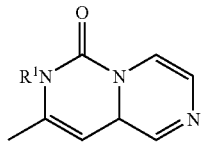 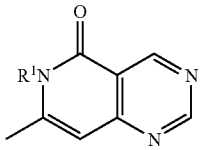

 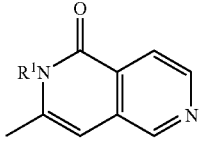

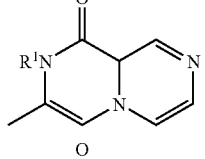 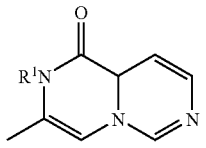

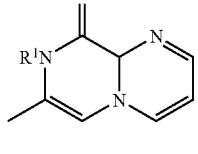 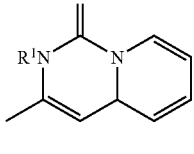

-continued

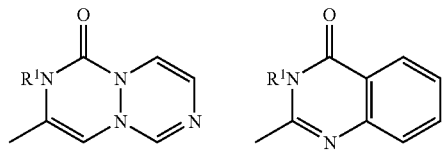

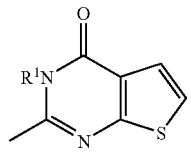 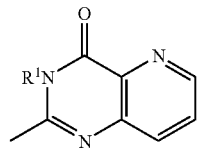

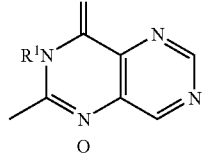 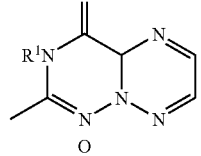

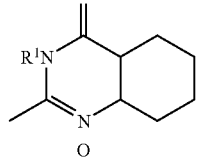 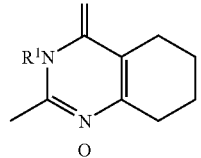

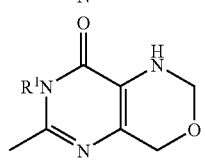 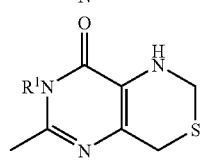

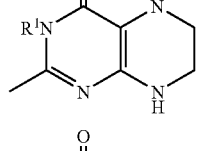 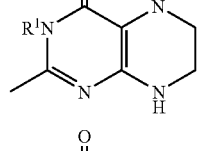

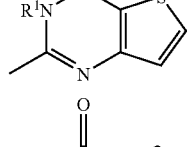 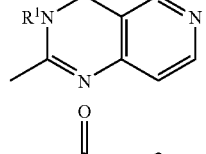

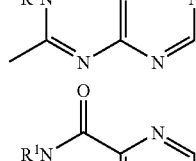 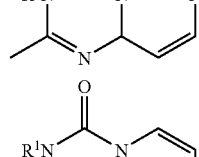

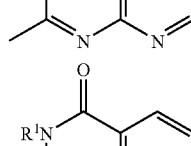 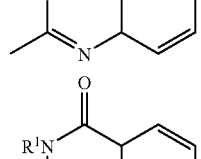

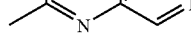 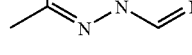

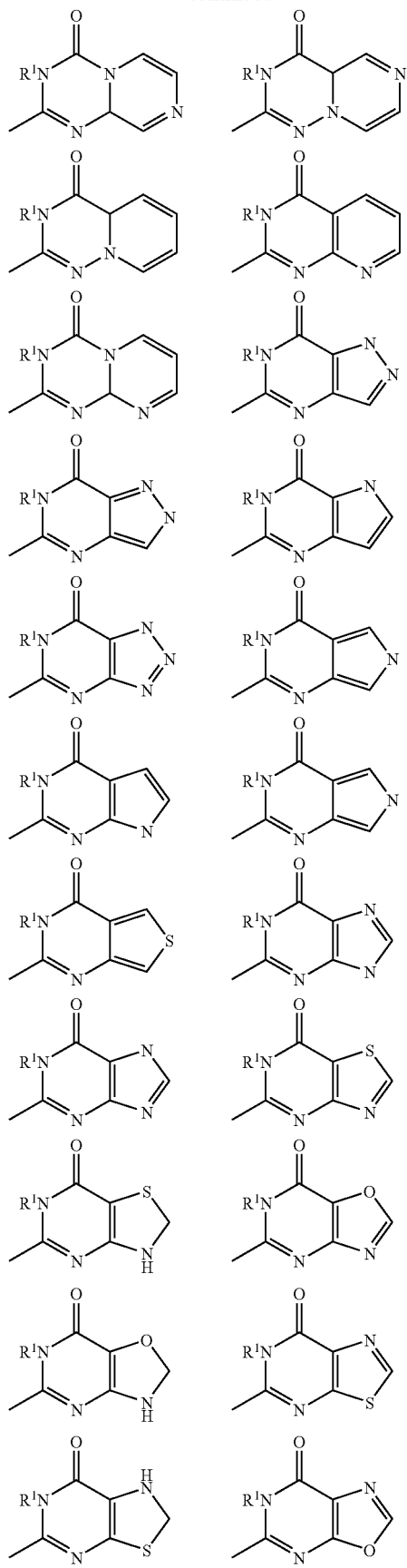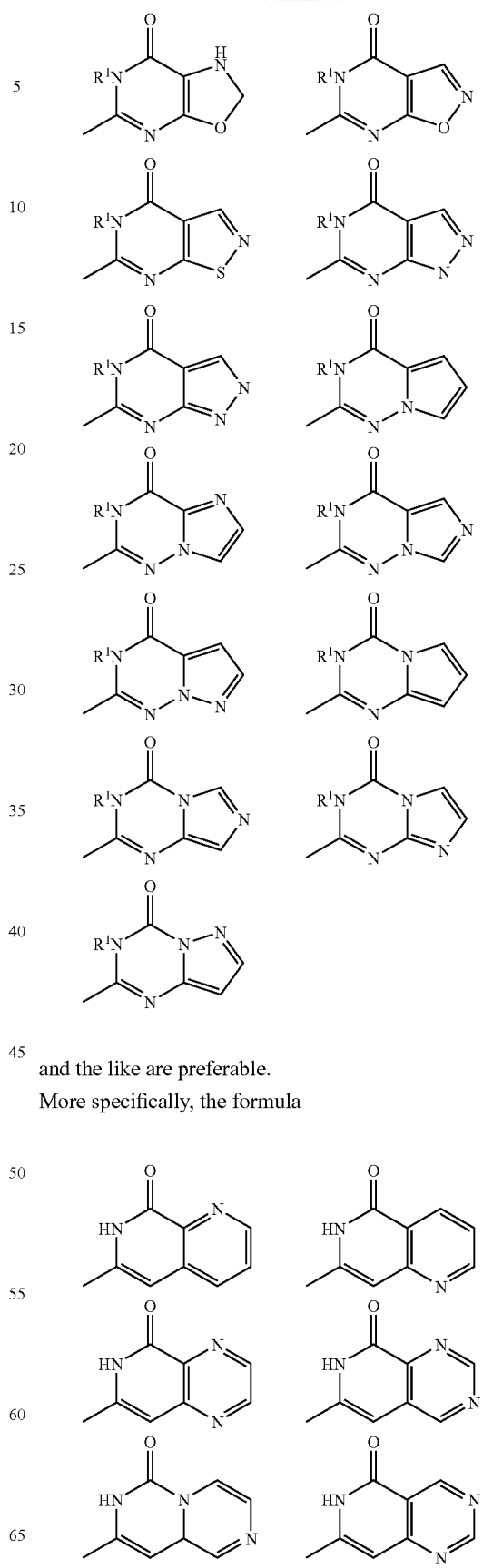
and the like are preferable.
More specifically, the formula
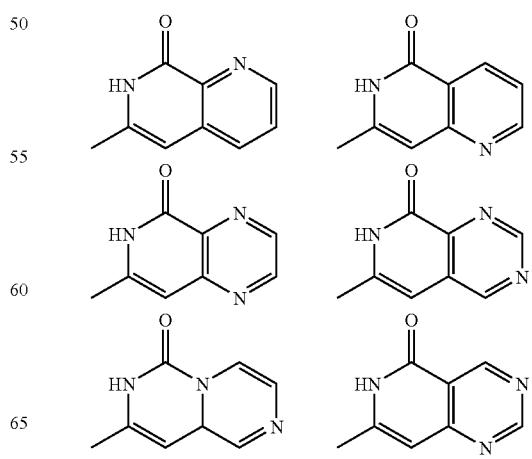

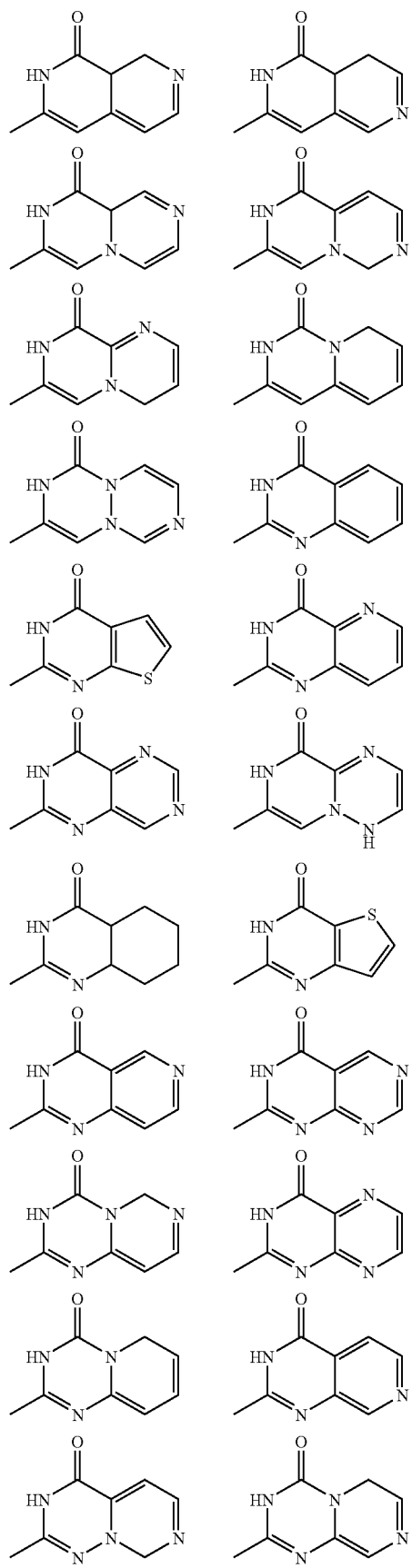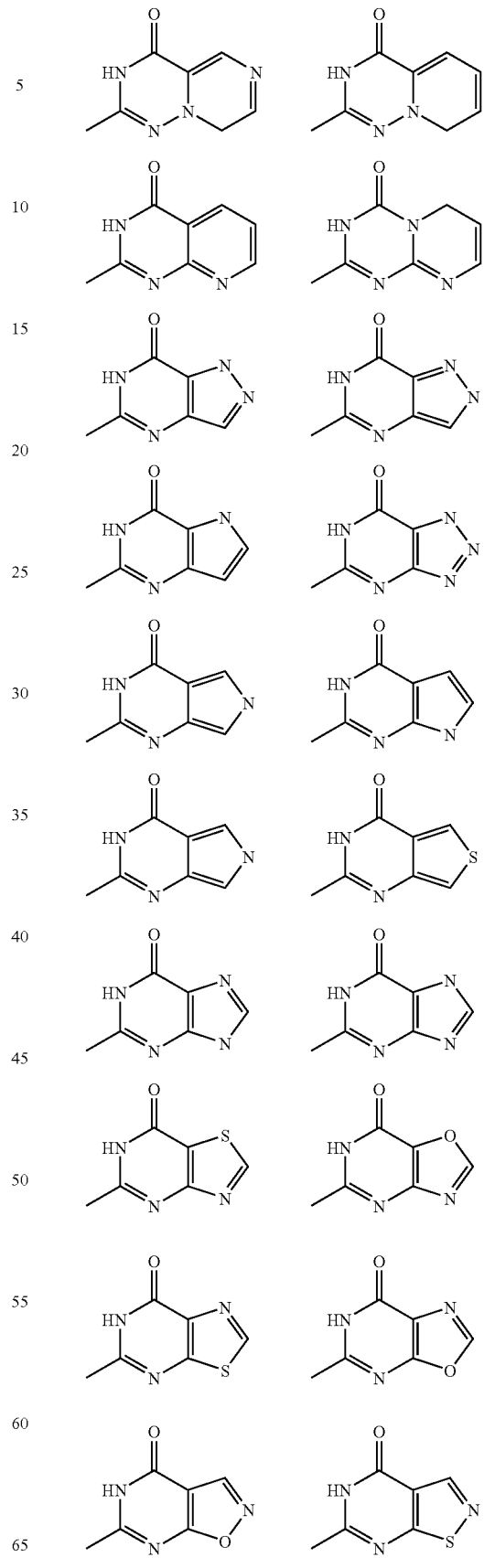

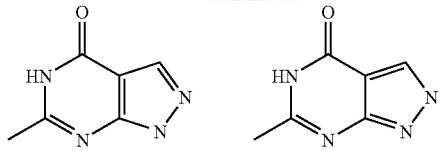

and the like are preferable. Above all,

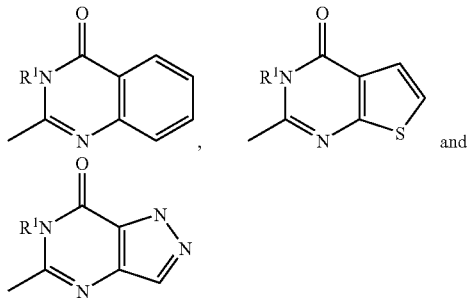

wherein R¹ is a hydrogen atom or an optionally substituted hydrocarbon group, are preferable, and

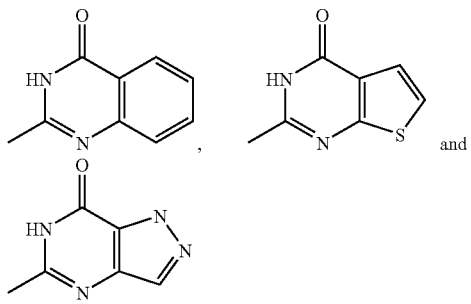

are particularly preferable.

In addition,

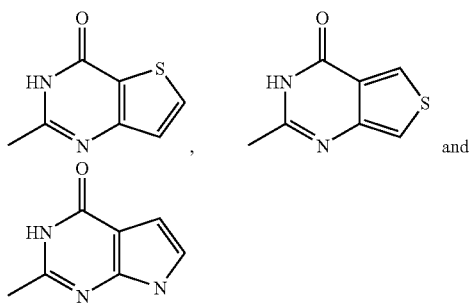

are also preferable embodiments.

As the particularly preferable embodiments,

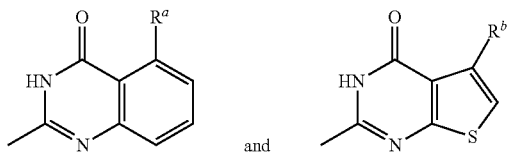

wherein $R^a$ and $R^b$ are each a (1) a $C_{1-6}$ alkyl group, (2) a $C_{1-6}$ alkyl group substituted by a $C_{7-16}$ aralkyloxy optionally substituted by a carboxy group, (3) a $C_{1-6}$ alkyl group substituted by a $C_{6-14}$ aryl-aminocarbonyl optionally substituted by a carboxy group, (4) a $C_{1-6}$ alkyl group substituted by a $C_{6-14}$ aryl-carbpnylamino optionally substituted by a carboxyl group, (5) a $C_{1-6}$ alkyl group substituted by a $C_{6-14}$ aryloxy optionally substituted by a carboxy group, (6) a $C_{6-14}$ aryloxy group optionally substituted by a carboxyl group, (7) a $C_{7-16}$ aralkyloxy group optionally substituted by a carboxyl group, (8) a $C_{6-14}$ aryl group optionally substituted by a carboxyl group, (9) a carbamoyl group optionally substituted by a $C_{7-16}$ aralkyl optionally substituted by a carboxyl group or (10) an amino group optionally substituted by a $C_{7-16}$ aralkyl-carbonyl, can be mentioned.

(4) "X" and "Y"

X is an optionally substituted spacer having 1 to 6 atoms, Y is a bond or an optionally substituted spacer having 1 to 6 atoms.

When the partial structure represented by

[II]

in the formula [I] is

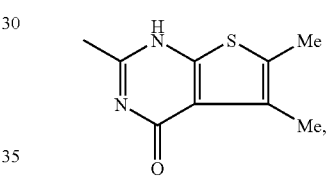

X is an optionally substituted spacer having 1, 3 or 4 carbon atoms.

As the element included in X or Y, a hetero atom selected from nitrogen atom, sulfur atom, oxygen atom and the like, and the like can be mentioned, besides carbon atom. As the kind of the bond, a double bond and a triple bond can be mentioned, besides a single bond.

As the "spacer having 1 to 6 atoms" of the "optionally substituted spacer having 1 to 6 atoms" represented by X or Y, specifically, —(CR$_{X1}$R$_{X2}$)$_w$— represented by aliphatic hydrocarbon group (wherein R$_{X1}$ and R$_{X2}$ are the same or different and each is a hydrogen atom or the same or different substituents, and w is an integer of 1 to 6 for "X" or "Y"), any binding form containing, besides carbon atom, hetero atom selected from nitrogen atom, sulfur atom and oxygen atom, such as —NR$_{X1}$—, —S—, —O—, —NR$_{X1}$CO—, —CONR$_{X1}$—, —CR$_{X1}$R$_{X2}$S—, -SCR$_{X1}$R$_{X2}$—, —OCR$_{X1}$R$_{X2}$—, —CR$_{X1}$R$_{X2}$O—, —NR$_{X1}$NR$_{X2}$—, —CR$_{X1}$R$_{X2}$CR$_{X3}$R$_{X4}$—, —NR$_{X1}$SO$_2$—, —SO$_2$NR$_{X1}$—, —CR$_{X1}$CO—, —COCR$_{X1}$—, —NR$_{X1}$CR$_{X2}$CR$_{X3}$NR$_{X4}$—, —CR$_{X1}$—CO—NR$_{X2}$—NR$_{X3}$—,
—NR$_{X1}$CR$_{X2}$CR$_{X3}$NR$_{X4}$—, —NR$_{X1}$NR$_{X2}$CSNR$_{X3}$—, —NR$_{X1}$NR$_{X2}$CONR$_{X3}$—, —R$_{X1}$C=CR$_{X2}$—, —N=N—, —CR$_{X1}$=N—, —N=CR$_{X1}$—, —NR$_{X1}$—N=CR$_{X2}$—, —NR$_{X1}$NR$_{X2}$—CO—CR$_{X3}$=CR$_{X4}$—,
—N=NCOCR$_{X1}$R$_{X2}$—, —N=NCSCR$_{X1}$R$_{X2}$—, —N=NCOCR$_{X1}$R$_{X2}$—, —N=NCONR$_{X1}$—, —N=NCSNR$_{X1}$— and the like, or any combination thereof (wherein R$_{X3}$ and R$_{X4}$ are as defined for the above-mentioned R$_{X1}$ and R$_{X2}$).

As the "substituent" represented by $R_{x1}$-$R_{x4}$, those similar to the "substituent" of the "optionally substituted hydrocarbon group" represented by the aforementioned $R^1$ and the like, as well as an oxo group, a thioxo group and the like can be mentioned.

As the "substituent" of the "optionally substituted spacer having 1 to 6 atoms" represented by X or Y, for example, those similar to the "substituent" of the "optionally substituted hydrocarbon group" represented by the aforementioned $R^1$ and the like, as well as an oxo group, a thioxo group and the like can be mentioned. When a substituent is present, the substituent is preferably 1 or 2 substituents selected from (1) a halogen atom, (2) a $C_{1-6}$ alkyl group or $C_{1-6}$ alkoxy group optionally substituted by 1 or 2 substituents selected from i) a halogen atom, ii) a $C_{1-6}$ alkoxy group, iii) a nitro group, iv) a cyano group, v) a hydroxy group, vi) an amino group, vii) a mono- or di-$C_{1-6}$ alkylamino group, viii) a carboxyl group, ix) a $C_{1-6}$ alkoxy-carbonyl group and x) a $C_{1-6}$ alkyl-carbonyl group, (3) a nitro group, (4) a cyano group, (5) a hydroxy group, (6) an amino group, (7) a mono- or di-$C_{1-6}$ alkylamino group, (8) a carboxyl group, (9) a $C_{1-6}$ alkoxy-carbonyl group and (10) a $C_{1-6}$ alkyl-carbonyl group and the like, or an oxo group or a thioxo group.

Of those mentioned above, as X or Y, for example, the aforementioned optiohally substituted spacer represented by the formula —$(CH_2)_n$—$X^1$—$(CH_2)_m$— [$X^1$ is O, $NR^3$ ($R^3$ is a hydrogen atom or an optionally substituted lower alkyl group), $SO_2$ or $CH_2$, n and m are each an integer of 0 to 3, n+m<6] or an optionally substituted $C_{1-6}$ alkylene group is preferable. Of these, an optionally substituted $C_{1-6}$ alkylene group (particularly a methylene group) is preferable, and an unsubstituted $C_{1-6}$ alkylene group (particularly a methylene group) is particularly preferable.

(5) "Ring C (Ring C')"

Ring C is (1) an optionally substituted homocycle or (2) an optionally substituted heterocycle other than a ring represented by the formula

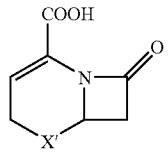

(X' is S, O, SO or $CH_2$), and ring C' is an optionally substituted homocycle or heterocycle.

As the "homocycle" represented by ring C or ring C', those similar to the ones exemplified for the aforementioned "homocycle" represented by ring B' are used. Of these, 6-membered homocycles such as a benzene ring, a cyclohexene ring and the like are preferable, and a benzene ring and the like are particularly preferable.

As the "heterocycle" represented by ring C, for example, a 3- to 12-membered heterocycle containing, besides carbon atom, 1 to 3 hetero atoms selected from nitrogen atom, sulfur atom, oxygen atom and the like (specifically, monocyclic heterocycle, aromatic fused heterocycle exemplified for ring B'), preferably a 3- to 9-membered, preferably 5- to 9-membered, more preferably 5- or 6-membered, heterocycle containing, besides carbon atom, 1 to 3 nitrogen atoms, which is other than a ring represented by the formula

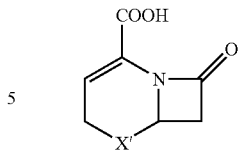

(X' is S, O, SO or $CH_2$) is used. Specifically, pyridine, pyrazine, pyrimidine, pyridazine, pyrrole, imidazole, pyrazole, triazole, pyrrolidine, imidazoline, imidazolidine, piperidine, piperazine, triazine, tetrahydropyridine, dihydropyridine, tetrahydropyrazine, tetrahydropyrimidine, tetrahydropyridazine, dihydropyrrole, dihydroimidazole, dihydropyrazole, hexahydropyrimidine, hexahydropyridazine, thiazole, isothiazole, oxazole, isoxazole, oxazoline, oxazolidine, thiazine, oxazine, morpholine, dihydrothiazole, dihydroisothiazole, dihydrooxazole, dihydroisoxazole, tetrahydrothiazole, tetrahydroisothiazole, tetrahydrooxazole, tetrahydroisoxazole, furan, thiophene, pyran, dioxane, dihydropyran, dihydrothiophene, dihydrofuran, tetrahydrothiophene, tetrahydrofuran, tetrahydropyran, benzofuran, benzothiophene, indole, benzimidazole, benzoxazole, coumarin, quinoline, isoquinoline, quinoxaline, quinazoline, phthalazine, naphthyridine, acridine, thianthrene, phenoxazine, phenothiazine, purine, xanthine, xanthene, pteridine and the like can be mentioned.

As the "heterocycle" represented by ring C', those similar to the "heterocycle" represented by the aforementioned ring B are used.

Of those mentioned above, as ring C or ring C', for example, (i) a 6-membered nitrogen-containing heterocycle containing, besides carbon atom, 1 or 2 nitrogen atoms (e.g., pyridine, pyrazine ring and the like) or (ii) a 5-membered aromatic sulfur-containing heterocycle containing, besides carbon atom, one sulfur atom (e.g., thiophene ring and the like) and the like can be mentioned, with particular preference given to a pyridine ring.

As the substituent that ring C (ring C') may have, those similar to the substituents that the aforementioned ring A (ring A') optionally have are used. Of these, (i) a halogen atom,
(ii) a cyano group,
(iii) a formyl group,
(vi) an optionally substituted amino group (e.g., an amino group optionally substituted by substituent(s) selected from $C_{1-6}$ alkyl optionally substituted by $C_{1-6}$ alkoxy, $C_{1-6}$ alkyl-carbonyl (e.g., acetyl, propionyl, butyryl and the like), $C_{1-6}$ alkylsulfonyl, $C_{1-6}$ alkoxy-carbonyl (e.g., ethoxycarbonyl and the like), $C_{1-6}$ alkoxy-carbonyl-carbonyl, $C_{1-6}$ alkoxy-carbonyl-$C_{1-6}$ alkyl-carbonyl and a 5- to 8-membered non-aromatic heterocycle having, besides carbon atom, 1 to 3 hetero atoms selected from nitrogen atom and oxygen atom-carbonyl; an amino group mono- or di-substituted by an alkyl group (e.g., a mono- or di-$C_{1-6}$ alkylamino group such as methylamino, ethylamino, propylamino, dimethylamino, diethylamino group and the like (particularly, mono- or di-$C_{1-4}$ alkylamino group); a formylamino group, a pyrimidinylmethylamino group and the like), a cyclic amino group (e.g., a 5- to 8-membered cyclic amino group optionally containing, besides nitrogen atom, 1 to 3 hetero atoms from oxygen atom, sulfur atom and the like (e.g., pyrrolidino, piperidino, morpholino group and the like) and the like), an aryl-carbonylamino group (e.g., a $C_{6-14}$ aryl-carbonylamino group such as benzoylamino group and the like, and the like), an alkylsulfonylamino group (e.g., a $C_{1-6}$ alkylsulfonylamino group such as methylsulfonylamino, ethylsulfonylamino, propylsulfonylamino group and the like, and the like), (v) an optionally substituted alkyl group (e.g., an alkyl group or cycloalkyl group optionally substituted by a halogen atom, an amino group, an alkylamino group, a carboxyl group, an alkoxycarbonyl group, a hydroxy group, an aryl group, an alkoxy group, an aralkyloxy group, an alkylcarbonylamino group, an alkoxycarbonylamino group, an alkylcarbonyloxy group, a heterocyclic group, an alkylsulfonylamino group, a ureido group, an alkylureido group and a heterocycle-carbonylamino group and the like, and the like), more specifically, (a) a linear or branched alkyl group having 1 to 6 carbon atoms such as methyl, ethyl, propyl, isopropyl, butyl, isobutyl, sec-butyl, tert-butyl and the like or a cycloalkyl group (e.g., a $C_{3-8}$ cycloalkyl group such as cyclopropyl, cyclobutyl, cyclopentyl, cyclohexyl and the like, and the like), (b) a halogenated $C_{1-6}$ alkyl group or $C_{3-8}$ cycloalkyl group (e.g., chloromethyl, difluoromethyl, trichloromethyl, trifluoromethyl, 2-bromoethyl, 2,2,2-trifluoroethyl, 3,3,3-trifluoropropyl and the like), (c) a $C_{1-6}$-alkyl group or a $C_{3-8}$ cycloalkyl group, each substituted by an amino group (e.g., aminomethyl, 2-aminoethyl group and the like), (d) a $C_{1-6}$ alkyl group or a $C_{3-8}$ cycloalkyl group, each substituted by a mono- or di-$C_{1-6}$ alkylamino group (e.g., methylaminomethyl, dimethylaminomethyl, 2-methylaminoethyl, 2-dimethylaminoethyl group and the like), (e) a $C_{1-6}$ alkyl group or a $C_{3-8}$ cycloalkyl group, each substituted by a carboxyl group (e.g., carboxymethyl, carboxyethyl group and the like), (f) a $C_{1-6}$ alkyl group or a $C_{3-8}$ cycloalkyl group, each substituted by a $C_{1-6}$ alkoxy-carbonyl group (e.g., methoxycarbonylethyl, ethoxycarbonylethyl, tert-butoxycarbonylmethyl group and the like), (g) a $C_{1-6}$ alkyl group or a $C_{3-8}$ cycloalkyl group, each substituted by a hydroxy group (e.g., hydroxymethyl, hydroxyethyl group and the like), (h) a $C_{1-6}$ alkyl group or a $C_{3-8}$ cycloalkyl group, each substituted by a $C_{6-14}$ aryl group (e.g., benzyl and the like), (i) a $C_{1-6}$ alkyl group or a $C_{3-8}$ cycloalkyl group, each substituted by a $C_{1-6}$ alkoxy group, (j) a $C_{1-6}$ alkyl group or a $C_{3-8}$ cycloalkyl group, each substituted by a $C_{7-16}$ aralkyloxy group (e.g., benzyloxymethyl and the like), (k) a $C_{1-6}$ alkyl group or a $C_{3-8}$ cycloalkyl group, each substituted by a $C_{1-6}$ alkyl-carbonylamino group (e.g., acetylaminomethyl, acetylaminoethyl and the like), (l) a $C_{1-6}$ alkyl group or a $C_{3-8}$ cycloalkyl group, each substituted by a $C_{1-6}$ alkoxy-carbonylamino group (e.g., ethoxycarbonylaminoethyl, tert-butoxycarbonylaminoethyl group and the like), (m) a $C_{1-6}$ alkyl group or a $C_{3-8}$ cycloalkyl group, each substituted by a $C_{1-6}$ alkyl-carbonyloxy group (e.g., acetyloxymethyl group and the like), (n) a $C_{1-6}$ alkyl group or a $C_{3-8}$ cycloalkyl group, each substituted by a heterocyclic group (e.g., a 5- or 6-membered aromatic heterocyclic group containing 1 or 2 hetero atoms selected from oxygen atom, sulfur atom and nitrogen atom, such as furyl, thienyl, pyrrolyl and the like) (e.g., 2-furylmethyl group and the like), (o) a $C_{1-6}$ alkyl group or $C_{3-8}$ cycloalkyl group, each substituted by a $C_{1-6}$ alkylsulfonylamino group, (p) a $C_{1-6}$ alkyl group or $C_{3-8}$ cycloalkyl group, each substituted by a ureido group, (q) a $C_{1-6}$ alkyl group or $C_{3-8}$ cycloalkyl group, each substituted by a $C_{1-6}$ alkyl-ureido group, (r) a $C_{1-6}$ alkyl group or a $C_{3-8}$ cycloalkyl group, each substituted by a heterocyclic group (e.g., a 3- to 12-membered, preferably 5- or 6-membered, aromatic heterocyclic group containing, besides carbon atom, 1 to 3 hetero atoms selected from the group consisting of nitrogen atom, oxygen atom and sulfur atom, such as furyl, thienyl, pyrrolyl and the like, a 5- to 8-membered non-aromatic heterocyclic group containing, besides carbon atom, 1 to 3 hetero atoms selected from the group consisting of nitrogen atom, oxygen atom and sulfur atom)-carbonylamino group and the like, (vi) an optionally substituted aryl group (e.g., a $C_{6-14}$ aryl group optionally substituted by substituent(s) selected from a halogen atom, an amino group optionally having $C_{1-6}$ alkoxy-carbonyl, a $C_{1-6}$ alkoxy group, a carboxyl group, an optionally halogenated $C_{1-6}$ alkyl group such as methyl, ethyl, trifluoromethyl and the like and a $C_{1-6}$ alkyl-ureido group), (vii) a $C_{7-16}$ aralkyl group optionally substituted by $C_{1-6}$ alkoxy, (viii) an optionally substituted alkoxy group (e.g., a $C_{1-6}$ alkoxy group optionally substituted by substituent(s) selected from a halogen atom, $C_{1-6}$ alkoxy, $C_{1-6}$ alkoxy-carbonyl, carboxyl, a 5- to 8-membered aromatic heterocyclic group containing, besides carbon atom, 1 to 3 hetero atoms selected from the group consisting of nitrogen atom, oxygen atom and sulfur atom, which is optionally substituted by $C_{1-6}$ alkyl, a 5- to 8-membered non-aromatic heterocyclic group containing, besides carbon atom, 1 to 3 hetero atoms selected from the group consisting of nitrogen atom, oxygen atom and sulfur atom and a carbamoyl group optionally having $C_{1-6}$ alkyl and the like), (ix) an aryloxy group (e.g., a $C_{6-14}$ aryloxy group optionally substituted by substituent(s) selected from a halogen atom and $C_{1-6}$ alkoxy and the like), an aralkyloxy group (e.g., a $C_{7-16}$ aralkyloxy group optionally substituted by substituent(s) selected from a halogen atom, $C_{1-6}$ alkoxy, $C_{1-3}$ alkylenedioxy and $C_{6-14}$ aryl and the like), a 5- to 8-membered non-aromatic heterocyclic-oxy group containing, besides carbon atom, 1 to 3 hetero atoms selected from the group consisting of nitrogen atom, oxygen atom and sulfur atom, a formyloxy group, an aminocarbonyloxy group, a mono- or di-alkylaminocarbonyloxy group (e.g., a mono- or di-$C_{1-6}$ alkylaminocarbonyloxy group such as methylaminocarbonyloxy, ethylaminocarbonyloxy, dimethylaminocarbonyloxy, a diethylamino-carbonyloxy group and the like, and the like), an alkylcarbonyloxy group (e.g., a $C_{1-6}$ alkyl-carbonyloxy group such as acetyloxy, propionyloxy, butyryloxy and the like, and the like), each of which is optionally substituted, (x) a 5- to 8-membered aromatic heterocyclic group containing, besides carbon atom, 1 to 3 hetero atoms selected from the group consisting of nitrogen atom, oxygen atom and sulfur atom, which is optionally substituted by $C_{6-14}$ aryloxy optionally substituted by a halogen atom (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like), (xi) an optionally substituted 5- to 8-membered non-aromatic heterocyclic group containing, besides carbon atom, 1 to 3 hetero atoms selected from the group consisting of nitrogen atom, oxygen atom and sulfur atom (which is optionally substituted by substituent(s) selected from, for example, a halogen atom, a cyano group, a hydroxy group, a nitro group, a carboxyl group, a $C_{1-6}$ alkoxy group, a 5- to 8-membered non-aromatic heterocyclic group containing, besides carbon atom, 1 to 3 hetero atoms selected from the group consisting of nitrogen atom, oxygen atom and sulfur atom, an optionally halogenated $C_{1-6}$ alkyl group such as methyl, ethyl, trifluoromethyl and the like, a formyl group, a $C_{1-6}$ alkyl-carbonyl group, a $C_{1-6}$ alkoxy-carbonyl group, an amino group, a mono- or di-$C_{1-6}$ alkylamino group, a $C_{1-6}$ alkoxy-carbonylamino group, a carbamoyl group, a $C_{1-6}$ alkylcarbamoyl group, a $C_{6-14}$ aryl group, a $C_{1-3}$ alkylenedioxy group, a $C_{6-14}$ aryloxy group optionally substituted by a halogen atom and the like, and the like) (e.g., pyrrolidinyl, tetrahydrofuryl, tetrahydrothienyl, piperidyl, tetrahydropyranyl, morpholinyl, thiomorpholinyl, piperazinyl and the like), (xii) an optionally substituted thiol group (e.g., an optionally halogenated alkylthio group (e.g., a $C_{1-6}$ alkylthio group optionally substituted by a halogen atom such as fluorine, chlorine and the like, such as methylthio, difluoromethylthio, trifluoromethylthio, ethylthio, propylthio, isopropylthio, butylthio and the like (particularly a $C_{1-4}$ alkylthio group) and the like)), (xiii) a carboxyl group, (xiv) an optionally substituted carbonyl group (e.g., an alkoxy-carbonyl group (e.g., a $C_{1-6}$ alkoxy-carbonyl group such as methoxycarbonyl, ethoxycarbonyl, propoxycarbonyl, butoxycarbonyl, an isobutoxycarbonyl group and the like, and the like), an aralkyloxy-carbonyl group (e.g., a $C_{7-16}$ aralkyloxy-carbonyl group such as a benzyloxycarbonyl group and the like, and the like), an aryloxy-carbonyl group (e.g., a $C_{6-14}$ aryloxy-carbonyl group such as a phenoxycarbonyl group and the like, and the like), an alkylcarbonyl group (e.g., a $C_{1-6}$ alkylcarbonyl group such as methylcarbonyl, ethylcarbonyl, butylcarbonyl and the like, and the like), a cycloalkyl-carbonyl group (e.g., a $C_{3-8}$ cycloalkyl-carbonyl group such as cyclopentylcarbonyl, a cyclohexylcarbonyl group and the like, and the like), an aryl-carbonyl group (e.g., a $C_{6-14}$ aryl-carbonyl group such as a benzoyl group and the like, and the like), (xv) an optionally substituted carbamoyl group (e.g., a thiocarbamoyl group, a mono- or di-alkyl-carbamoyl group (e.g., a mono- or di-$C_{1-6}$ alkyl-carbamoyl group such as methylcarbamoyl, ethylcarbamoyl, propylcarbamoyl, butylcarbamoyl, diethylcarbamoyl, a dibutylcarbamoyl group and the like, and the like)), (xvi) an optionally substituted sulfonyl group (e.g., an alkylsulfonyl group (e.g., a $C_{1-6}$ alkylsulfonyl group such as methylsulfonyl, a ethylsulfonyl group, a propylsulfonyl group and the like, and the like), a cycloalkyl-sulfonyl group (e.g., a $C_{3-8}$ cycloalkylsulfonyl group such as cyclopentylsulfonyl, a cyclohexylsulfonyl group and the like, and the like), an arylsulfonyl group (e.g., a $C_{6-14}$ arylsulfonyl group such as phenylsulfonyl, a naphthylsulfonyl group and the like, and the like), an aralkyl-sulfonyl group (e.g., a $C_{7-15}$ aralkylsulfonyl group such as a benzylsulfonyl group and the like, and the like)), (xvii) a $C_{1-6}$ alkyl-ureido group (e.g., methylureido), (xviii) a nitro group and the like are preferable, moreover, (i) a halogen atom, (ii) a cyano group, (iii) an optionally substituted amino group (e.g., an amino group optionally substituted by substituent(s) selected from $C_{1-6}$ alkyl optionally having $C_{1-6}$ alkoxy, $C_{1-6}$ alkyl-carbonyl, $C_{1-6}$ alkylsulfonyl, $C_{1-6}$ alkoxy-carbonyl, $C_{1-6}$ alkoxy-carbonyl-carbonyl, $C_{1-6}$ alkoxy-carbonyl-$C_{1-6}$ alkyl-carbonyl and a 5- to 8-membered non-aromatic heterocycle having, besides carbon atom, 1 to 3 hetero atoms selected from nitrogen atom and oxygen atom-carbonyl; mono- or di-$C_{1-6}$ alkylamino group), (iv) an optionally substituted alkyl group (e.g., a $C_{1-6}$ alkyl group optionally substituted by substituent(s) selected from a halogen atom, amino, $C_{1-6}$ alkyl-carbonylamino, $C_{1-6}$ alkylsulfonylamino, a 5- to 8-membered non-aromatic heterocycle having, besides carbon atom, 1 to 3 hetero atoms selected from nitrogen atom and oxygen atom-carbonylamino, $C_{1-6}$ alkoxy-carbonyl-carbonylamino, a 5- to 8-membered non-aromatic heterocyclic group containing, besides carbon atom, 1 to 3 hetero atoms selected from nitrogen atom and oxygen atom and $C_{1-6}$ alkyl-ureido), (v) an optionally substituted aryl group (e.g., a $C_{6-14}$ aryl group optionally substituted by substituent(s) selected from a halogen atom, amino optionally having $C_{1-6}$ alkoxy-carbonyl, $C_{1-6}$ alkoxy, carboxyl and $C_{1-6}$ alkyl-ureido), (vi) a $C_{7-16}$ aralkyl group optionally substituted by $C_{1-6}$ alkoxy, (vii) an optionally substituted alkoxy group (e.g., a $C_{1-6}$ alkoxy group optionally substituted by substituent(s) selected from a halogen atom, $C_{1-6}$ alkoxy, $C_{1-6}$ alkoxy-carbonyl, carboxyl, a 5- to 8-membered aromatic heterocyclic group containing, besides carbon atom, 1 to 3 hetero atoms selected from the group consisting of nitrogen atom, oxygen atom and sulfur atom, which is optionally substituted by $C_{1-6}$ alkyl, a 5- to 8-membered non-aromatic heterocyclic group containing, besides carbon atom, 1 to 3 hetero atoms selected from the group consisting of nitrogen atom, oxygen atom and sulfur atom and a carbamoyl group optionally having $C_{1-6}$ alkyl and the like), (viii) an optionally substituted aryloxy group (e.g., a $C_{6-14}$ aryloxy group optionally substituted by substituent(s) selected from a halogen atom and $C_{1-6}$ alkoxy and the like), (ix) an optionally substituted aralkyloxy group (e.g., a $C_{7-16}$ aralkyloxy group optionally substituted by substituent(s) selected from a halogen atom, $C_{1-6}$ alkoxy, $C_{1-3}$ alkylenedioxy and $C_{6-14}$ aryl and the like), (x) a 5- to 8-membered non-aromatic heterocyclic-oxy group containing, besides carbon atom, 1 to 3 hetero atoms selected from the group consisting of nitrogen atom, oxygen atom and sulfur atom, (xi) a 5- to 8-membered aromatic heterocyclic group containing, besides carbon atom, 1 to 3 hetero atoms selected from the group consisting of nitrogen atom, oxygen atom and sulfur atom, which is optionally substituted by $C_{6-14}$ aryloxy optionally substituted by a halogen atom, (xii) a 5- to 8-membered non-aromatic heterocyclic group containing, besides carbon atom, 1 to 3 hetero atoms selected from the group consisting of nitrogen atom, oxygen atom and sulfur atom, (xiii) a $C_{1-6}$ alkoxy-carbonyl group,
(xiv) an optionally halogenated alkylthio group,
(xv) a nitro group and the like are preferable.

As the substituent that ring C (ring C') may have, for example, a halogen atom, an optionally substituted alkyl group (e.g., a $C_{1-6}$ alkyl group optionally substituted by substituent(s) elected from a halogen atom, amino, $C_{1-6}$ alkyl-carbonylamino, $C_{1-6}$ alkylsulfonylamino, a 5- to 8-membered non-aromatic heterocycle having, besides carbon atom, 1 to 3 hetero atoms selected from nitrogen atom and oxygen atom-carbonylamino, $C_{1-6}$ alkoxy-carbonyl-carbonylamino, a 5- to 8-membered non-aromatic heterocyclic group containing, besides carbon atom, 1 to 3 hetero atoms selected from nitrogen atom and oxygen atom and $C_{1-6}$ alkyl-ureido), an optionally halogenated $C_{1-6}$ alkoxy group, a mono- or di-$C_{1-6}$ alkylamino group, an optionally halogenated $C_{1-6}$ alkylthio group, a nitro group, a cyano group and the like are preferable.

Of these, particularly, 1 to 3 substituents selected from a halogen atom, an optionally halogenated $C_{1-6}$ alkyl group and an optionally halogenated $C_{1-6}$ alkoxy group, and the like are more preferable.

The substituent of ring C or ring C' may be present at any substitutable position on the ring, and when two or more substituents are present, the substituents may be the same or different and, the number thereof may be about 0-4. The number of the substituents is preferably about 0-3.

When ring C or ring C' has a nitrogen atom, it may form a quaternary ammonium salt and, for example, a salt may be formed with an anion such as a halogen ion (e.g., Cl⁻, Br⁻, I⁻ and the like), a sulfuric acid ion, a hydroxy ion and the like.

As a compound represented by the formula [I] or [I'], a compound wherein preferable embodiments of each symbol mentioned above are optionally combined is preferably used. Of these, (1-1) a compound represented by the formula

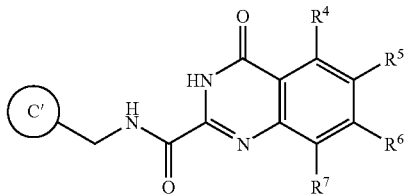

wherein $R^4$, $R^5$, $R^6$ and $R^7$ are each
(i) a hydrogenatom,
(ii) a halogen atom,
(iii) a cyano group,
(iv) a hydroxy group,
(v) an amino group optionally substituted by substituent(s) selected from (a) a $C_{7-16}$ aralkyl group optionally substituted by a $C_{1-6}$ alkoxy group, (b) a $C_{1-6}$ alkyl-carbonyl group optionally substituted by a $C_{6-14}$ aryloxy group and (c) a $C_{1-6}$ alkylsulfonyl group,
(vi) a $C_{1-6}$ alkyl group optionally substituted by substituent(s) selected from (a) a halogen atom, (b) a $C_{1-6}$ alkoxy group, (c) a 5- to 8-membered non-aromatic heterocyclic group containing, besides carbon atom, 1 to 4 hetero atoms selected from nitrogen atom, oxygen atom and sulfur atom and (d) a $C_{7-16}$ aralkyloxy optionally substituted by a carboxyl group,
(vii) a $C_{6-14}$ aryl group, (viii) $C_{1-6}$ alkoxy group optionally substituted by substituent(s) selected from (a) a halogen atom, (b) a hydroxy group, (c) $C_{3-7}$ cycloalkyl group, (d) a $C_{7-16}$ aralkyloxy group, (e) a 5- to 8-membered aromatic heterocyclic group having, besides carbon atom, 1 to 4 hetero atoms selected from nitrogen atom, oxygen atom and sulfur atom, (f) a 5- to 8-membered non-aromatic heterocyclic group containing, besides carbon atom, 1 to 3 hetero atoms selected from nitrogen atom and oxygen atom, which optionally have a carboxy group, and (g) $C_{6-14}$ arylcarbonyl group,
(ix) a $C_{7-16}$ aralkyloxy group optionally substituted by substituent(s) selected from (a) a halogen atom, (b) a cyano group, (c) a carboxyl group, (d) a $C_{1-6}$ alkyl group optionally having a carboxyl group, (e) a $C_{1-6}$ alkoxy group optionally having a carboxyl group, (f) an amino group, (g) a $C_{1-6}$ alkoxycarbonyl group, (h) a carbamoyl group, (i) a 5- to 8-membered aromatic heterocyclic group containing, besides carbon atom, 1 to 3 hetero atoms selected from the group consisting of nitrogen atom, oxygen atom and sulfur atom, (j) an amino-sulfonylamino group optionally having a $C_{1-6}$ alkoxycarbonyl group and (k) a 5- to 8-membered non-aromatic heterocyclic group containing, besides carbon atom, 1 to 3 hetero atoms selected from nitrogen atom, oxygen atom and sulfur atom,
(x) a 5- to 8-membered non-aromatic heterocyclic group containing, besides carbon atom, 1 to 3 heteroatoms selected from nitrogen atom and oxygen atom,
(xi) a thiol group,
(xii) a $C_{1-6}$ alkylthio group,
(xiii) a $C_{7-16}$ aralkylthio group
(xiv) a 5- to 8-membered aromatic heterocycle containing, besides carbon atom, 1 to 3 hetero atoms selected from the group consisting of nitrogen atom, oxygen atom and sulfur atom-thio group,
(xv) a $C_{1-6}$ alkylsulfonyl group,
(xvi) a carbamoyl group,
(xvii) a mono- or di-$C_{1-6}$ alkylamino-thiocarbonyloxy group,
(xviii) a mono- or di-$C_{1-6}$ alkylcarbamoyl-thio group,
(xix) a nitro group or
(xx) a 5- to 8-membered aromatic heterocyclic group containing, besides carbon atom, 1 to 3 hetero atoms selected from nitrogen atom and oxygen atom,
ring C' is a $C_{6-14}$ aryl ring or a 5- to 8-membered heterocyclic group containing 1 to 3 hetero atoms selected from nitrogen atom and oxygen atom, which is optionally substituted by substituent(s) selected from
(i) a halogen atom,
(ii) a cyano group,
(iii) an amino group optionally substituted by substituent(s) selected from (a) $C_{1-6}$ alkyl optionally having $C_{1-6}$ alkoxy, (b) $C_{1-6}$ alkyl-carbonyl, (c) $C_{1-6}$ alkylsulfonyl, (d) $C_{1-6}$ alkoxy-carbonyl, (e) $C_{1-6}$ alkoxy-carbonyl-carbonyl, (f) $C_{1-6}$ alkoxy-carbonyl-$C_{1-6}$ alkyl-carbonyl and (g) a 5- to 8-membered non-aromatic heterocycle having, besides carbon atom, 1 to 3 hetero atoms selected from nitrogen atom and oxygen atom-carbonyl,
(iv) a $C_{1-6}$ alkyl group optionally substituted by substituent(s) selected from (a) a halogen atom, (b) $C_{1-6}$ alkyl-carbonylamino, (c) $C_{1-6}$ alkylsulfonylamino, (d) a 5- to 8-membered non-aromatic heterocycle having, besides carbon atom, 1 to 3 hetero atoms selected from nitrogen atom and oxygen atom-carbonylamino, (e) $C_{1-6}$ alkoxy-carbonyl-carbonylamino, (f) a 5- to 8-membered aromatic heterocycle having, besides carbon atom, 1 to 3 hetero atoms selected from nitrogen atom and oxygen atom-carbonylamino and (g) a 5- to 8-membered non-aromatic heterocyclic group containing, besides carbon atom, 1 to 3 hetero atoms selected from nitrogen atom and oxygen atom, (v) a $C_{6-14}$ aryl group optionally substituted by substituent(s) selected from (a) a halogen atom, (b) amino optionally having $C_{1-6}$ alkoxy-carbonyl, (c) $C_{1-6}$ alkoxy and (d) carboxyl, (vi) a $C_{7-16}$ aralkyl group optionally substituted by $C_{1-6}$ alkoxy, (vii) a $C_{1-6}$ alkoxy group optionally substituted by substituent(s) selected from (a) a halogen atom, (b) $C_{1-6}$ alkoxy, (c) $C_{1-6}$ alkoxy-carbonyl, (d) carboxyl, (e) a 5- to 8-membered aromatic heterocyclic group containing, besides carbon atom, 1 to 3 hetero atoms selected from the group consisting of nitrogen atom, oxygen atom and sulfur atom, which is optionally substituted by $C_{1-6}$ alkyl, (f) a 5- to 8-membered non-aromatic heterocyclic group containing, besides carbon atom, 1 to 3 hetero atoms selected from nitrogen atom and oxygen atom and (g) carbamoyl optionally having $C_{1-6}$ alkyl, (viii) a $C_{6-14}$ aryloxy group optionally substituted by substituent(s) selected from (a) a halogen atom and (b) $C_{1-6}$ alkoxy, (ix) a $C_{6-14}$ aryloxy group optionally substituted by substituent(s) selected from (a) a halogen atom, (b) amino optionally having $C_{1-6}$ alkoxy-carbonyl, (c) $C_{1-6}$ alkoxy and (d) carboxyl, (x) a $C_{7-16}$ aralkyloxy group optionally substituted by substituent(s) selected from (a) a halogen atom, (b) $C_{1-6}$ alkoxy, (c) $C_{1-3}$ alkylenedioxy and (d) $C_{6-14}$ aryl, (xi) a 5- to 8-membered non-aromatic heterocyclic-oxy group containing, besides carbon atom, 1 to 3 hetero atoms selected from nitrogen atom and oxygen atom, (xii) a 5- to 8-membered aromatic heterocyclic group containing, besides carbon atom, 1 to 3 hetero atoms selected from the group consisting of nitrogen atom, oxygen atom and sulfur atom optionally substituted by $C_{6-14}$ aryloxy optionally having a halogen atom, (xiii) a 5- to 8-membered non-aromatic heterocyclic group containing, besides carbon atom, 1 to 3 hetero atoms selected from nitrogen atom and oxygen atom, (xiv) a $C_{1-6}$ alkoxy-carbonyl group and (xv) a $C_{1-6}$ alkylureido group provided that when $R^3$, $R^4$, $R^5$ and $R^6$ are hydrogen atoms, ring C' is an aromatic ring or a heterocycle containing 1 to 3 hetero atoms selected from nitrogen atom and oxygen atom, which has the aforementioned substituent(s), or (1-2) a compound represented by the formula

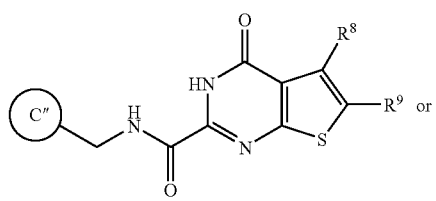

or

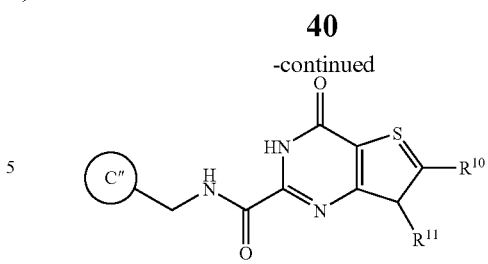

wherein $R^8$, $R^9$, $R^{10}$ and $R^{11}$ are each
(i) a hydrogen atom,
(ii) a $C_{1-6}$ alkyl group optionally substituted by $C_{7-16}$ aralkyloxy optionally having carboxyl, $C_{6-14}$ aryl-aminocarbonyl optionally having a carboxyl group or $C_{6-14}$ aryl-carbonylamino optionally having carboxyl,
(iii) a $C_{6-14}$ aryl group optionally having carboxyl,
(iv) a carbamoyl group optionally substituted by $C_{7-16}$ aralkyl optionally having carboxyl or
(v) an amino group optionally substituted by $C_{7-16}$ aralkylcarbonyl, and C" ring is
(i) a $C_{6-14}$ aryl ring optionally substituted by substituent(s) selected from (a) a halogen atom, (b) $C_{1-6}$ alkoxy optionally having a 5- to 8-membered non-aromatic heterocycle containing, besides carbon atom, 1 to 3 hetero atoms selected from nitrogen atom and oxygen atom or a halogen atom, (c) $C_{1-6}$ alkyl optionally having a halogen atom or $C_{1-6}$ alkylthio, or
(ii) a 5- to 8-membered aromatic heterocyclic group containing, besides carbon atom, 1 to 3 hetero atoms selected from nitrogen atom and oxygen atom, which is optionally substituted by a $C_{1-6}$ alkoxy group optionally having a 5- to 8-membered non-aromatic heterocycle containing, besides carbon atom, 1 to 3 hetero atoms selected from the group consisting of nitrogen atom, oxygen atom and sulfur atom, and furthermore,
(2) compounds of Examples 1-415 and the like are preferably used.

(6) Tautomerism

Moreover, the compound represented by the formula [I] and a salt thereof produce tautomers, but any tautomer is encompassed in the present invention, and a compound represented by the formula [I] and a salt thereof may be any of solvates, hydrates, non-solvates and non-hydrates.

(7) From the compounds having various structures produced by the above-mentioned combinations, N-{(1S,2R)-1-(3,5-difluorobenzyl)-3-[(3-ethylbenzyl) amino]-2-hydroxypropyl}-5,6-dimethyl-4-oxo-1,4-dihydrothieno [2,3-d]pyrimidine-2-carboxamide and 6-chloro-N-((1S,2R,4S)-4-[(dimethylamino)carbonyl]-2-{[(5-methyl-4,5,6,7-tetrahydrothiazolo[5,4-c]pyridin-2-yl)carbonyl] amino}cyclohexyl)-4-oxo-1,4-dihydroquinazoline-2-carboxamide are excluded.

The present invention moreover provides production methods of a compound represented by the formula [I] or a salt thereof.

A compound represented by the formula [I] or a salt thereof and a starting compound thereof can be produced by a method known per se, for example, a method shown in the following scheme and the like. In the following, "room temperature" generally means 0 to 30° C. and each symbol in the chemical structural formulas described in the scheme means as defined above unless otherwise specified. The compounds in the formulas include embodiments forming a salt, and as such salt, for example, those similar to the salt of compound [I] and the like can be mentioned.

The compounds obtained in respective steps can be used in the form of a reaction mixture or as a crude product for the next reaction. They can also be isolated from the reaction mixture by conventional methods, and can be easily purified by separation means such as recrystallization, distillation, chromatography and the like.

The reaction scheme is shown in the following. When a compound in the formula is commercially available, the commercially available product may be used as it is.

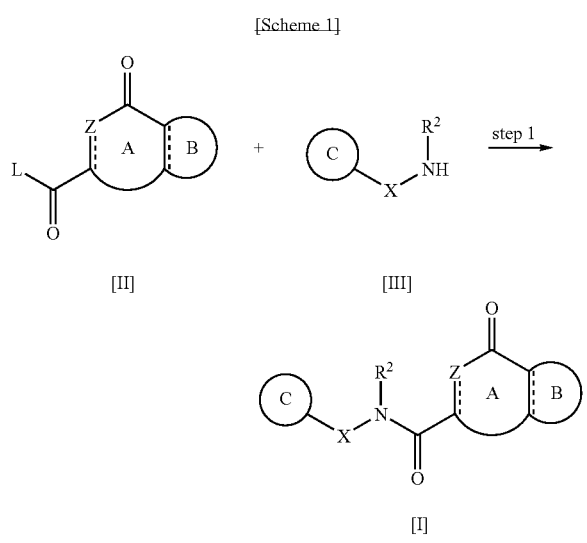

wherein L is a leaving group, and other symbols are as defined above.

(Step 1)

Compound [II] is amidated with compound [III] to give compound [I].

Here, as the leaving group represented by L in the compound represented by the formula [II], for example, an alkoxy group ($C_{1-16}$ alkoxy group such as methoxy, ethoxy and the like), an optionally substituted aralkyloxy group (a $C_{7-16}$ aralkyloxy group optionally substituted by a nitro group, such as benzyl group, p-nitrobenzyloxy group and the like), a hydroxy group, a halogen atom (e.g., chlorine, bromine, iodine and the like), a substituted sulfonyloxy group (e.g., a $C_{1-6}$ alkyl sulfonyloxy group or a $C_{6-14}$ aryl sulfonyloxy group optionally substituted by $C_{1-6}$ alkyl, such as methanesulfonyloxy, p-toluenesulfonyloxy and the like), an acyloxy group (a $C_{1-6}$ alkanoyloxy group or a $C_{6-14}$ arylcarbonyloxy group such as acetoxy, benzoyloxy and the like), an oxy group substituted by a hetero ring or an aryl group (succinimide, benzotriazole, quinoline, 4-nitrophenyl and the like), and the like can be mentioned. In this reaction, a compound represented by the formula [III] or a salt thereof is used in an amount of 1-10 mol, preferably 1-5 mol, per 1 mol of a compound represented by the formula [II] or a salt thereof.

In this reaction, as a reaction solvent, for example, alcohols such as methanol, ethanol and the like, ethers such as dioxane, tetrahydrofuran and the like, aromatic hydrocarbons such as benzene, toluene, xylene and the like, esters such as ethyl acetate and the like, halogenated hydrocarbons such as chloroform, dichloromethane and the like, nitriles such as acetonitrile and the like, amides such as N,N-dimethylformamide, N,N-dimethylacetamide and the like, sulfoxides such as dimethyl sulfoxide and the like, and the like are used alone or as a mixed solvent of two or more kinds thereof.

In this reaction, moreover, the reaction can be advantageously carried out by adding a base. As such base, for example, an inorganic base (alkali metal hydroxides such as sodium hydroxide, potassium hydroxide and the like, alkali metal hydrogen carbonates such as sodium hydrogen carbonate, potassium hydrogen carbonate and the like, alkali metal carbonates such as sodium carbonate, potassium carbonate, cesium carbonate and the like, alkali metal hydrides such as sodium hydride, potassium hydride and the like, alkali metal amides such as sodium amide and the like, alkoxides such as sodium methoxide, sodium ethoxide and the like and the like), an organic base (aliphatic amines such as trimethylamine, triethylamine, diisopropylethylamine and the like, aromatic amines such as pyridine and the like, and the like) and the like can be used. While the amount of the base to be used varies depending on the kind of the compound and solvent to be used, and other reaction conditions, it is generally 0.1-10 mol, preferably 0.2-5 mol, per 1 mol of a compound represented by the formula [II] or a salt thereof. The reaction is generally carried out in the temperature range of from −50° C. to 200° C., preferably −20° C. to 150° C., and, while the reaction time varies depending on the kind of the compound, reaction temperature and the like, it is about 1-96 hrs., preferably 1-48 hrs.

A compound represented by the formula [II] or a salt thereof can be easily produced by a method known per se or a method analogous thereto. For example, ethyl 4-oxo-3,4-dihydro-quinazoline-2-carboxylate is a known compound described in J. Org. Chem. Vol. 27, pp. 4672-4674 (1962).

When ring A is a pyrimidine ring, the compound can be obtained according to the method described in the following scheme.

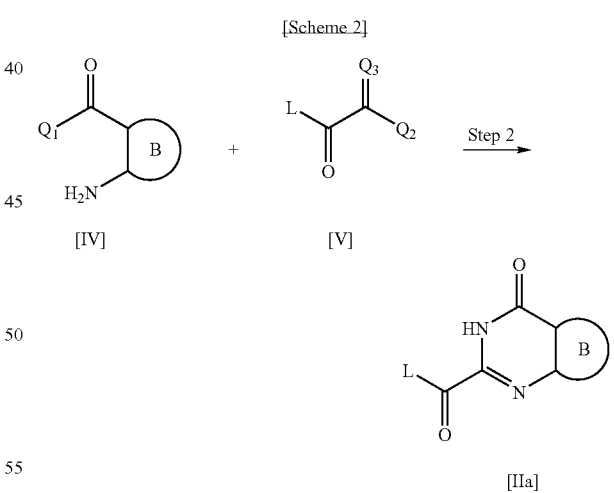

wherein $Q_1$ and $Q_2$ are each an alkoxy group, a hydroxy group or an amino group, $Q_3$ is an oxygen atom or a nitrogen atom, and other symbols are as defined above.

As the alkoxy group represented by $Q_1$ or $Q_2$, a $C_{1-6}$ alkoxy group such as methoxy, ethoxy and the like and the like is used.

(Step 2)

When $Q_1$ is $NH_2$, the objective compound can be produced from compound [IV] and compound [V] according to a method known per se. Here, a compound represented by the formula [V] or a salt thereof can be used in an amount of 1-10 mol, preferably 1-5 mol, per 1 mol of a compound represented by the formula [IV] or a salt thereof, and as the solvent, those similar to the ones exemplified for the above-mentioned Step 1 can be used.

[Scheme 3]

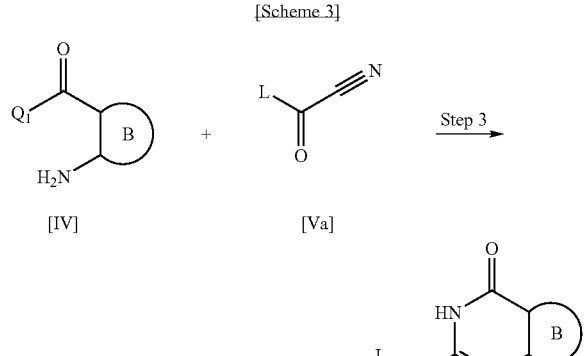

wherein each symbol is as defined above.
(Step 3)

A compound wherein $Q_1$ is alkoxy can be produced from compound [IV] and compound [Va] according to a method known per se. Here, a compound represented by the formula [Va] or a salt thereof can be used in an amount of 1-10 mol, preferably 1-5 mol, per 1 mol of a compound represented by the formula [IV] or a salt thereof. As the solvent, those similar to the ones exemplified for the above-mentioned Step 1 can be used.

In this reaction, moreover, the reaction can be advantageously carried out by adding an acid. As such acid, for example, inorganic acids (hydrochloric acid, bromic acid, sulfuric acid and the like), organic acids (aliphatic carboxylic acids such as acetic acid, trifluoroacetic acid and the like, and the like) and the like can be mentioned. While the amount of the acid to be used varies depending on the kind of the compound and solvent to be used, and other reaction conditions, it is generally 0.1-50 mol, preferably 0.5-10 mol, per 1 mol of a compound represented by the formula [IV] or a salt thereof. The reaction is generally carried out in the temperature range of from −50° C. to 200° C., preferably −20° C. to 150° C. and, while the reaction time varies depending on the kind of the compound, reaction temperature and the like, it is about 1-96 hrs., preferably 1-48 hrs.

[Scheme 4]

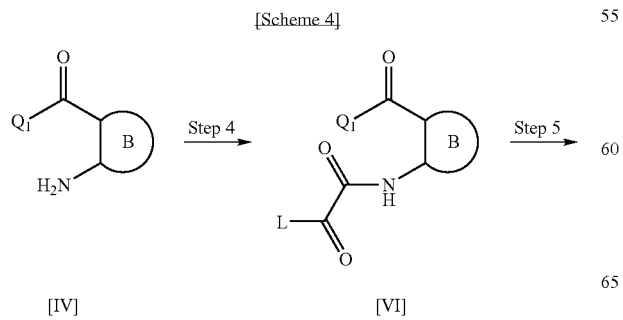

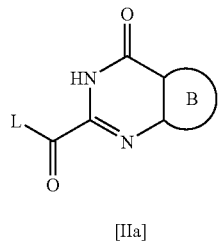

wherein each symbol is as defined above.
(Step 4 and Step 5)

The objective compound can be produced by acylating the amino group of compound [IV], and cyclizing the obtained compound [VI] in the presence of an acid or base. As the solvent for the acylation reaction from compound [IV] to compound [VI], those similar to the ones exemplified for the above-mentioned steps can be used.

In this reaction, moreover, the reaction can be advantageously carried out by adding a base. As such base, those similar to the ones exemplified for the above-mentioned Step 1 can be used. While the amount of the base to be used varies depending on the kind of the compound and solvent to be used, and other reaction conditions, it is generally 0.1-10 mol, preferably 0.2-5 mol, per 1 mol of a compound represented by the formula [IV] or a salt thereof. The reaction is generally carried out in the temperature range of from −50° C. to 200° C., preferably −20° C. to 150° C. and, while the reaction time varies depending on the kind of the compound, reaction temperature and the like, it is about 1-96 hrs., preferably 1-48 hrs.

As the solvent for the cyclization reaction from compound [VI] to compound [IIa], those similar to the ones exemplified for the above-mentioned Step 1 can be used.

In this reaction, moreover, the reaction can be advantageously carried out by adding an acid. As such acid, those similar to the ones exemplified for the above-mentioned Step 3 can be used. While the amount of the acid to be used varies depending on the kind of the compound and solvent to be used, and other reaction conditions, it is generally 0.1-50 mol, preferably 0.5-10 mol, per 1 mol of a compound represented by the formula [VI] or a salt thereof. The reaction is generally carried out in the temperature range of from −50° C. to 200° C., preferably −20° C. to 150° C. While the reaction time varies depending on the kind of the compound, reaction temperature and the like, it is about 1-96 hrs., preferably 1-48 hrs.

[Scheme 5]

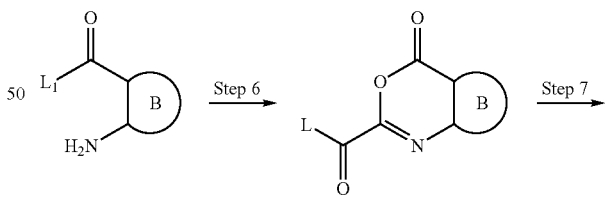

wherein each symbol is as defined above.

(Step 6 and Step 7)

When $L_1$ is OH, compound [IV] is cyclized to give oxazine ring compound [VII], and compound [VII] is treated with ammonia or ammonium salt to give compound [IIa]. As the solvent for the oxazine cyclization reaction from compound [IV] to compound [VII], those similar to the ones exemplified for the above-mentioned Step 1 can be used.

In this reaction, moreover, the reaction can be advantageously carried out by adding a base. As such base, those similar to the ones exemplified for the above-mentioned Step 1 can be used. While the amount of the base to be used varies depending on the kind of the compound and solvent to be used, and other reaction conditions, it is generally 0.1-10 mol, preferably 0.2-5 mol, per 1 mol of a compound represented by the formula [IV] or a salt thereof. The reaction can be generally carried out in the temperature range of from −50° C. to 200° C., preferably −20° C. to 150° C. While the reaction time varies depending on the kind of the compound, reaction temperature and the like, it is about 1-96 hrs., preferably 1-48 hrs.

As the solvent for the reaction to give condensed pyrimidine compound [IIa] from compound [VII], those similar to the ones exemplified for the above-mentioned Step 1 can be used.

In this reaction, moreover, the reaction can be advantageously carried out by adding a base. As such base, those similar to the ones exemplified for the above-mentioned Step 1 can be used.

In the production of compound [I], when ring B has a leaving group $L^2$, the compound can be also produced by nucleophilic substitution reaction.

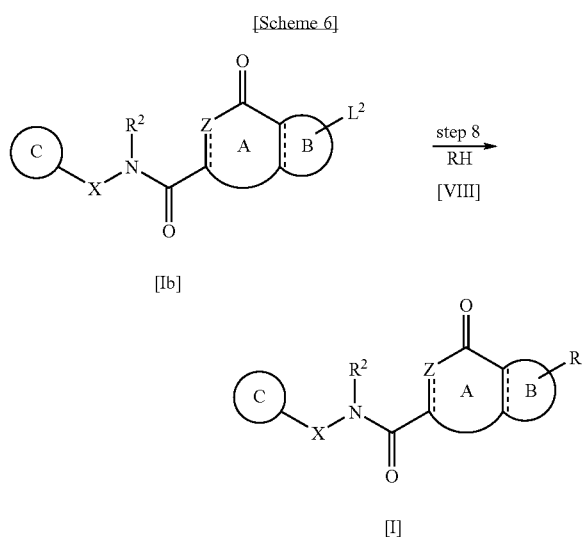

wherein $L^2$ is a leaving group, R is a substituent that ring B optionally has, and other symbols are as defined above.

(Step 8)

As the leaving group $L^2$, a halogen atom (fluorine, chlorine, bromine or iodine and the like), an alkoxy group ($C_{1-6}$ alkoxy group such as methoxy, ethoxy and the like), an acyl group ($C_{1-6}$ alkanoyl group or $C_{6-14}$ arylcarbonyl group such as acetyl, benzoyl and the like) and the like can be mentioned. As the nucleophilic agent, amine, alkoxide and carbon nucleophilic agent can be mentioned.

In this reaction, a compound represented by the formula [VIII] or a salt thereof can be used in an amount of 1-10 mol, preferably 1-5 mol, per 1 mol of a compound represented by the formula [Ib] or a salt thereof. As a reaction solvent, those similar to the ones exemplified for the above-mentioned steps can be used.

In this reaction, moreover, the reaction can be advantageously carried out by adding a base. As such base, those similar to the ones exemplified for the above-mentioned Step 1 can be used. While the amount of the base to be used varies depending on the kind of the compound and solvent to be used, and other reaction conditions, it is generally 0.1-10 mol, preferably 0.2-5 mol, per 1 mol of a compound represented by the formula [VIII] or a salt thereof. The reaction is generally carried out in the temperature range of from −50° C. to 200° C., preferably −20° C. to 150° C. While the reaction time varies depending on the kind of the compound, reaction temperature and the like, it is about 1-96 hrs., preferably 1-48 hrs.

When ring A is pyridine, the compound can be obtained according to the method described in the following scheme.

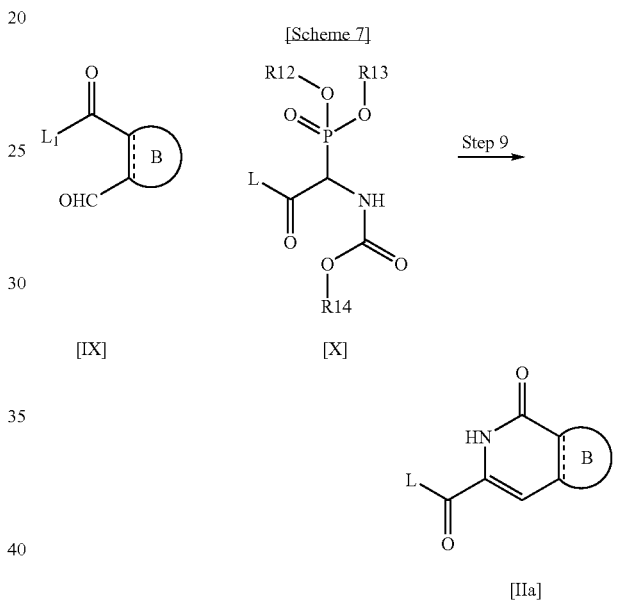

wherein $R^{12}$, $R^{13}$, $R^{14}$ are the same or different and each is $C_{1-3}$ alkyl, and other symbols are as defined above.

(Step 9)

A fused pyridine ring compound [IIa] can be produced from compound [IX] and compound [X].

In this reaction, a compound represented by the formula [X] or a salt thereof can be used in an amount of 1-10 mol, preferably 1-5 mol, per 1 mol of a compound represented by the formula [IX] or a salt thereof. As a reaction solvent, those similar to the ones exemplified for the above-mentioned Step 1 can be used.

In this reaction, moreover, the reaction can be advantageously carried out by adding a base. As such base, those similar to the ones exemplified for the above-mentioned Step 1 can be used. While the amount of the base to be used varies depending on the kind of the compound and solvent to be used, and other reaction conditions, it is generally 0.1-10 mol, preferably 0.2-5 mol, per 1 mol of a compound represented by the formula [IX] or a salt thereof. The reaction is generally carried out in the temperature range of from −50° C. to 200° C., preferably −20° C. to 150° C. While the reaction time varies depending on the kind of the compound, reaction temperature and the like, it is about 1-96 hrs., preferably 1-48 hrs.

In each of the reactions mentioned above, when the starting compounds have an amino group, a carboxyl group or a hydroxy group as a substituent, such groups may be protected with the protecting groups which are generally used in peptide chemistry and the like. In such case, if necessary, such protecting groups can be removed to obtain the objective compounds after the reactions. Such protecting groups can be introduced or removed by methods known per se, such as the method described in *Protective Groups in Organic Synthesis*, 3$^{rd}$ Ed. (1999), edited by Theodara W. Greene, Peter G. M. Wuts, published by Wiley-Interscience, or an analogous method thereto.

The above-mentioned reactions may be further combined with one or more of known hydrolysis reaction, deprotection reaction, acylation reaction, alkylation reaction, oxidization reaction, cyclization reaction, carbon chain elongation reaction and substituent exchange reaction on demand, whereby compound [I] can be also produced.

The compound [I] can be isolated and purified by a known means, such as phase transfer, concentration, solvent extraction, fractionation, liquid conversion, crystallization, recrystallization, chromatography and the like.

When compound (I) is obtained as a free compound, it can be converted to an objective salt by a method known per se or a method analogous thereto, and when it is conversely obtained as a salt, it can be converted to a free form or different objective salt by a method known per se or a method analogous thereto.

As the salt of compound [I], for example, metal salt, ammonium salt, salts with organic base, salts with inorganic acid, salts with organic acid, salts with basic or acidic amino acid and the like can be mentioned. As preferable examples of metal salt, for example, alkali metal salts such as sodium salt, potassium salt and the like, alkaline earth metal salts such as calcium salt, magnesium salt, barium salt and the like; aluminum salt and the like can be mentioned. As preferable examples of salts with organic base, for example, salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like can be mentioned. As preferable examples of salts with inorganic acid, for example, salts with hydrochloric acid, hydrobromic acid, nitric acid, sulfuric acid, phosphoric acid and the like can be mentioned. As preferable examples of salts with basic amino acid, for example, salts with arginine, lysin, ornithine and the like can be mentioned. As preferable examples of salts with acidic amino acid, for example, salts with aspartic acid, glutamic acid and the like can be mentioned. Of these, pharmaceutically acceptable salts are preferable. When, for example, the compound has an acidic functional group therein, inorganic salts such as alkali metal salts (e.g., sodium salt, potassium salt etc.), alkaline earth metal salts (e.g., calcium salt, magnesium salt, barium salt etc.) and the like, ammonium salt and the like, and when the compound has a basic functional group therein, for example, salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like can be mentioned.

The compound [I] of the present invention may be used as a prodrug, and such prodrug means a compound which is converted to compound (I) as a result of a reaction with an enzyme, gastric acid etc. under physiological conditions in vivo. Thus, the compound is converted into compound (I) by enzymatical oxidation, reduction, hydrolysis etc., or by hydrolysis due to gastric acid etc.

As a prodrug of compound (I), a compound obtained by subjecting an amino group of compound (I) to an acylation, alkylation or phosphorylation (e.g., a compound obtained by subjecting an amino group of compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group in compound (I) to an acylation, alkylation, phosphorylation and boration (e.g., a compound obtained by subjecting a hydroxy group of compound (I) to an acetylation, palmitoylation, propanoylation, pivaloylation, succinylation, fumarylation, alanylation, dimethylaminomethylcarbonylation, etc.); a compound obtained by subjecting a carboxyl group of compound (I) to an esterification or amidation (e.g., a compound obtained by subjecting a carboxyl group of compound (I) to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification and methylamidation, etc.) and the like.

These compounds can be produced from compound (I) by a method known per se.

In addition, the prodrug of compound (I) may be a compound, which is converted to compound (I) under the physiological conditions, as described in *Pharmaceutical Research and Development*, Vol. 7 (Drug Design), pp. 163-198 (1990), published by Hirokawa Publishing Co.

The compound [I] or a salt thereof or a prodrug thereof of present invention (hereinafter to be abbreviated as compound [I]) has a superior MMP inhibitory activity, particularly an MMP-13 inhibitory activity.

Moreover, the compound [I] of the present invention shows low toxicity and is safe.

Accordingly, the compound [I] of the present invention having superior MMP inhibitory action, particularly MMP-13 inhibitory action, is useful as a safe drug for the prophylaxis or treatment of all MMP associated diseases, such as joint disease (e.g., osteoarthritis, rheumatoid arthritis (articular rheumatism) and the like), osteoporosis, cancer (e.g., tumor and the like such as primary, metastatic or recurrent tumors such as breast cancer, prostate cancer, pancreatic cancer, stomach cancer, lung cancer, colorectal cancer (colon cancer, rectal cancer, anal cancer), cancer of esophangus, duodenal cancer, head and neck cancer (lingual cancer, pharyngeal cancer, laryngeal cancer), cerebral tumor, schwannoma, non-small-cell lung cancer, lung small cell carcinoma, liver cancer, kidney cancer, biliary tract cancer, uterine cancer (endometrial cancer, cervical cancer), ovarian cancer, bladder cancer, skin cancer, angioma, malignant lymphoma, malignant melanoma, thyroid cancer, osteoncus, angiofibroma, retina sarcoma, penile cancer, pediatric solid tumor, Kaposi's sarcoma, Kaposi's sarcoma caused by AIDS, tumor of the maxillary sinus, fibrous histiocytoma, leiomyosarcoma, rhabdomyosarcoma, liposarcoma, hysteromyoma, osteoblastoma, osteosarcoma, chondrosarcoma, cancerous mesothelioma, leukemia and the like, and the like), periodontal disease, cornea ulcer, chronic ulcer, pathologic bone resorption (Paget's disease and the like), nephritis, angiogenesis, aneurysm, arteriosclerosis, emphysema, chronic obstructive pulmonary disease (COPD), liver cirrhosis, autoimmune disease (Crohn's disease, Sjogren's disease and the like), infiltration or metastasis of cancer and the like, in mammals (e.g., mice, rats, hamsters, rabbits, cats, dogs, bovines, sheep, monkeys, humans, etc.), or as a contraceptive, particularly as a drug for the prophylaxis or treatment of osteoarthritis or rheumatoid arthritis.

The pharmaceutical preparations comprising compound [I] of the present invention may be in any solid preparations of powders, granules, tablets, capsules and the like, and in any liquid forms of syrups, emulsions, injections and the like.

The pharmaceutical preparations of the present invention can be produced by any conventional methods, for example, blending, kneading, granulation, tabletting, coating, sterilization, emulsification, etc., in accordance with the forms of the preparations to be produced. For the production of such pharmaceutical preparations, for example, each of the items in General Principles for pharmaceutical preparations in the Japanese Pharmacopoeia, can be made reference to. In addition, the pharmaceutical preparations of the present invention may be formulated into a sustained release preparation containing active ingredients and biodegradable polymer compounds. The sustained release preparation can be produced according to the method described in JP-A-9-263545.

In the pharmaceutical preparations of the present invention, the content of compound [I] varies depending on the form of the preparation, but is generally in about 0.01 to 100% by weight, preferably about 0.1 to 50% by weight, more preferably 0.5 to 20% by weight, of the total weight of the preparation.

When compound [I] of the present invention is used as the above-mentioned pharmaceutical preparations, it may be used alone, or in admixture with a suitable, pharmacologically acceptable carrier, such as excipients (e.g., starch, lactose, sucrose, calcium carbonate, calcium phosphate, etc.), binders (e.g., starch, gum arabic, carboxymethyl cellulose, hydroxypropyl cellulose, crystalline cellulose, alginic acid, gelatin, polyvinyl pyrrolidone, etc.), lubricants (e.g., stearic acid, magnesium stearate, calcium stearate, talc, etc.), disintegrants (e.g., calcium carboxymethylcellulose, talc, etc.,) diluents (e.g., water for injection, physiological saline, etc.) and, if desired, with the additives (e.g., stabilizer, preservative, colorant, fragrance, dissolution aid, emulsifier, buffer, isotonic agent, etc.) and the like by conventional methods. The compound can be formulated into solid preparations such as powder, fine granule, granule, tablet, capsule, etc., or into the liquid preparations such as injection, etc., and can be administered orally or parenterally. Further, compound [I] can be administered in the form of a formulation for local administration or directly on the diseased part having an articular disease. In the latter case, injection is preferred. The compound [I] can be also administrated as a parenteral formulation for local administration (e.g., a formulation for injection for intramuscular, subcutaneous, intraorgan and on-site (in the vicinity of a joint) routes, a solid form such as implant, granule, powder, a liquid form such as suspension, an ointment, etc.).

For example, a practical formulation for injection can be obtained by mixing compound [I] with a dispersant (e.g., surfactant such as Tween 80, HCO-60, etc., carboxymethyl cellulose, sodium alginate, polysaccharide such as hyaluronic acid, polysorbate, etc.), a preservative (e.g., methylparaben, propylparaben, etc.), an isotonic agent (e.g., sodium chloride, mannitol, sorbitol, glucose, etc.), a buffer (e.g., calcium carbonate, etc.), a pH adjusting agent (e.g., sodium phosphate, potassium phosphate, etc.) and the like, into an aqueous suspension. Further, thus obtained formulation is made into a practically usable formulation for injection by dispersing it with an oil of plant origin such as sesame oil or corn oil, or with a mixture thereof with phospholipids such as lecithin, or with medium chain triglyceride (e.g., Miglyol 812, etc.) as in a suspension in oil.

In particular, when such formulation is administered directly into the joint cavity of a patient suffering from an articular disease for local administration, the formulation can be produced by dispersing compound [I] in a hyaluronic acid preparation for injection (for example, product by Kaken Pharmaceutical Co., Ltd.; Arts) as dispersing medium. The hyaluronic acid used in the dispersing medium may be a non-toxic salt thereof, and examples include an alkali metal salt such as sodium, potassium and the like, or an alkali earth metal salt such as magnesium, calcium and the like, a sodium salt being particularly preferred. The molecular weight of hyaluronic acid or a non-toxic salt thereof is about 200,000 to about 5,000,000 (measured by the viscosity method), preferably about 500,000 to about 3,000,000, and more preferably about 700,000 to 2,500,000.

The final concentration of hyaluronic acid or sodium hyaluronate in this dispersion is suitably less than 1% (W/V) for viscosity from the aspects of easiness of various handling and administration and the like, preferably from about 0.02 to less than 1%, and even more preferably from about 0.1 to 1% (W/V).

The dispersing medium may contain a pH adjusting agent, local anesthetic, antibiotics, a solubilizing agent, an isotonic agent, anti-adsorption agent, glycosaminoglycan, polysaccharides and the like by a method known per se. Preferred examples include mannitol, sorbitol, table salt, glycine, ammonium acetate, or an aqueous protein that can be administered into body fluid without exhibiting any substantial pharmacological activity. The glycosaminoglycan include hyaluronic acid, chondroitin, chondroitin sulfate A, chondroitin sulfate C, dermatan sulfate, heparin, heparan sulfate, keratan sulfate and the like. The polysaccharide include an acidic polysaccharide such as arginic acid.

The above-mentioned aqueous protein may be anything that is soluble in water, a physiological saline or a buffer, and examples include human serum albumin, human serum globulin, collagen, gelatin and the like. The pH adjusting agent include, for example, glycine, ammonium acetate, citric acid, hydrochloric acid, sodium hydroxide and the like. The local anesthetic include, for example, chlorobutanol, xylocaine hydrochloride and the like. The antibiotic include, for example, gentamicin and the like. The solubilizing agent include, for example, glycerin, polyethylene glycol 400 and the like. The isotonic agent include, for example, mannitol, sorbitol, sodium chloride and the like. The anti-adsorption agent include, for example, polyoxyethylenesorbitan monooleate and the like.

Furthermore, when the dispersing medium contains an aqueous protein, the content of the aqueous protein in the preparation for a single dose is preferably 0.05 to 50 mg, more preferably 0.5 to 20 mg, and even more preferably 0.75 to 10 mg. Such preparation may contain phosphoric acid or a salt thereof (e.g., sodium phosphate, potassium phosphate, etc.).

When a preparation for injection contains phosphoric acid or a salt thereof, the concentration of sodium phosphate or potassium phosphate in the preparation for injection is about 0.1 mM to 500 mM, and preferably about 1 mM to 100 mM.

Sterilization of a preparation may be carried out by operating the entire production process under aseptic conditions, sterilizing with γ-rays, adding a preservative, and the like, without being particularly limited.

The prophylactic and therapeutic agent of the invention can be used in combination with other agents. For example, when compound [I] is used as a therapeutic agent for articular diseases, it can be used in combination with (i) a cyclooxygenase inhibitor (Cox-I or Cox-II inhibitor), (ii) a disease-modified anti-rheumatoid drug and immune suppressant, (iii) a biological formulation, (iv) an analgesic and anti-inflammatory agent, (v) a therapeutic agent for bone diseases, (vi) p38MAP kinase inhibitor and/or an inhibitor of TNF-α production inhibitor, or (vii) c-JUN N-terminal kinase (JNK) inhibitor. Further, when compound [I] is used as an anticancer agent, it can be used in combination with (viii) other anticancer agents.

(i) A cyclooxygenase inhibitor (Cox-I or Cox-II inhibitor) include, for example, a salicylic acid derivative such as Celecoxib, Rofecoxib, aspirin and the like, Diclofenac, Indomethacin, Loxoprofen and the like.

(ii) A disease-modified anti-rheumatoid drug and immune suppressant include, for example, methotrexate, Leflunomid, Prograf, sulfasalazine, D-penicilamine, oral metallic agent, T-cell differentiation controlling agent and the like.

(iii) A biological formulation include, for example, a monoclonal antibody (e.g., anti-TNF-α antibody, anti-IL-12 antibody, anti-IL-6 antibody, anti-ICAM-I antibody, ani-CD4 antibody, etc.), soluble receptor (e.g., soluble TNF-α receptor, etc.), proteinaceous ligand (IL-1 receptor antagonist, etc.) and the like.

(iv) An analgesic and anti-inflammatory agent include, for example, centrally active analgesic (e.g., morphine, codeine, pentazocine, etc.), steroids (e.g., prednisolone, hydrocortisone, methylprednisolone, dexamethasone, betamethasone, etc.), anti-inflammatory enzymes (e.g., bromelain, lysozyme, proctase, etc.) and the like.

(v) A therapeutic agent for bone diseases (e.g., fracture, refracture, osteoporosis, osteomalacia, Paget's disease, spastic myelitis, chronic rheumatoid arthritis, destruction of articular tissues in modified gonarthritis and its analogous diseases, etc.) include, for example, a calcium preparation (e.g., calcium carbonate, etc.), a calcitonin preparation, a vitamin D preparation (e.g., alpha-calcidol, etc.), sex hormones (e.g., estrogen, estradiol, etc.), prostaglandin $A_1$, bisphosphonic acids, ipriflavones, fluorine compounds (e.g., sodium fluoride, etc.), vitamin $K_2$, bone morphogenic proteins (BMP), fibroblast growth factor (FGF), platelet-derived growth factor (PDGF), transforming growth factor (TGF-β), insulin-like growth factor-1 and -2 (IGF-1 and -2), parathyroid hormone (PTH) and the like.

(vi) A p38MAP kinase inhibitor and/or TNF-α production inhibitor include compounds described in the publications of, for example, WO98/57966, WO98/56377, WO98/25619, WO98/07425, WO98/06715, U.S. Pat. No. 5,739,143, WO97/35855, WO97/33883, WO97/32583, WO97/25048, WO97/25046, WO96/10143, WO96/21654, WO95/07922, WO00/09525, WO99/17776, WO99/01131, WO98/28292, WO97/25047, WO97/25045, U.S. Pat. No. 5,658,903, WO96/21452, WO99/18942, U.S. Pat. Nos. 5,756,499, 5,864,036, 6,046,208, 5,716,955, 5,811,549, 5,670,527, 5,969,184, WO00/31072, WO00/31063, WO00/20402, WO00/18738, WO00/17175, WO00/12497, WO00/12074, WO00/07991, WO00/07980, WO00/02561, U.S. Pat. No. 6,096,711, WO99/64400, WO99/61440, WO99/59959, WO99/58523, WO99/58502, WO99/57101, WO99/32111, WO99/32110, WO99/26657, WO99/20624, WO99/18942, WO99/15164, WO99/00357, WO98/52940, WO98/52937, WO98/52558, WO98/06715, WO97/22256, WO96/21452, WO00/43366, WO00/42003, WO00/42002, WO00/41698, WO00/41505, WO00/40243, WO00/34303, WO00/25791, WO00/17204, WO00/10563, U.S. Pat. No. 6,080,546, WO99/61426, WO99/32463, WO99/32121, WO99/17776, WO98/28292, WO98/27098, WO98/25619, WO98/20868, WO97/35855, WO97/32583, WO97/25048, WO97/25047, WO97/25046, WO97/25045, U.S. Pat. No. 5,658,903, WO96/40143, WO96/21654, WO00/55153, WO00/55120, WO00/26209, U.S. Pat. Nos. 6,046,208, 5,756,499, 5,864,036, JP-A-2000-86657, WO99/59960, WO99/21859, WO99/03837, WO99/01449, WO99/01136, WO99/01130, U.S. Pat. No. 5,905,089, WO98/57966, WO98/52941, WO98/47899, WO98/07425, WO97/33883, WO00/42213, WO99/58128, WO00/04025, WO00/40235, WO00/31106, WO97/46228, WO00/59904, WO00/42003, WO00/42002, WO00/41698, WO00/10563, WO00/64894, WO99/61426, WO99/32463, U.S. Pat. No. 6,002,008, WO98/43960, WO98/27098, WO97/35856, WO97/35855, WO96/22985 and JP-A-61-145167.

(vii) A JNK inhibitor include compounds described in the publications of, for example, WO00/35906, WO00/35909, WO00/35921, WO00/64872, WO00/75118 and WO02/62792.

(viii) An anticancer agent include, for example, 6—O—(N-chloroacetylcarbamoyl) fumagillol, bleomycin, methotrexate, actinomycin D, mitomycin C, daunorubicin, adriamycin, neocartinostatin, cytosine arabinoside, fluorouracil, tetrahydrofuryl-5-fluorouracil, picibanil, lentinan, levamisole, bestatin, azimexone, glytilitin, doxorubicin hydrochloride, acrarubicin hydrochloride, bleomycin hydrochloride, hepromycin sulfate, vincristine sulfate, vinblastine sulfate, irinotecan hydrochloride, cyclophosphamide, melphalan, busulphan, thiotepa, procarbazine hydrochloride, cisplatin, azathioprine, mercaptopurine, tegafur, carmofur, cytarabine, methyl testosterone, propionic acid testosterone, testosterone enanthate, mepitiostan, fosfestrol, chlormadinone acetate, leuprorelin acetate, buserelin acetate and the like.

When used in combination, the administration interval for compound [I] and the combination drug is not particularly limited. Compound [I] or a pharmaceutical composition thereof, and the drug for combination or a pharmaceutical composition thereof, may be administered to a subject of administration either simultaneously or with a time interval. The dose of the drug for combination may be determined to be in accordance with the clinically used dose, and can be suitably selected according to the subject of administration, administration route, type of disease, organization and the like.

The form of administration for combination is not particularly limited, and compound [I] and the drug for combination may be combined at the time of administration. Such form of administration include, for example, (1) administration of a single preparation which can be obtained by simultaneously formulating compound [I] or a pharmaceutical composition thereof with the drug for combination or a pharmaceutical composition thereof; (2) simultaneous administration by an identical route of administration, of two preparations which can be obtained by separately formulating compound [I] or a pharmaceutical composition thereof and the drug for combination or a pharmaceutical composition thereof; (3) administration with a time interval by an identical route of administration, of two preparations which can be obtained by separately formulating compound [I] or a pharmaceutical composition thereof with the drug for combination or a pharmaceutical composition thereof; (4) simultaneous administration by different routes of administration, of two preparations which can be obtained by separately formulating compound [I] or a pharmaceutical composition thereof with the drug for combination or a pharmaceutical composition thereof; (5) administration with a time interval by different routes of administration, of two preparations which can be obtained by separately formulating compound [I] or a pharmaceutical composition thereof with the drug for combination or a pharmaceutical composition thereof (for example, administration in the order of compound [I] or a pharmaceutical thereof and then the drug for combination or a pharmaceutical thereof, or administration in the reverse order), and the like.

The mixing ratio for compound [I] with the drug for combination in the combination of the present invention can be appropriately selected according to the subject of administration, the administration route, type of disease and the like.

For example, the content of compound [I] present in the combination of the present invention may vary depending on the type of preparation, but it is typically about 0.01 to 100% by weight, preferably about 0.1 to about 50% by weight, and more preferably about 0.5 to about 20% by weight, with respect to the whole preparation.

The content of the drug for combination present in the combination of the present invention may vary depending on the type of preparation, but it is typically about 0.01 to 100% by weight, preferably about 0.1 to about 50% by weight, and more preferably about 0.5 to about 20% by weight, with respect to the whole preparation.

The content of an additive such as carrier present in the lo combination of the present invention may vary depending on the type of preparation, but it is typically about 1 to 99.99% by weight, and preferably about 10 to 90% by weight, with respect to the whole preparation.

When compound [I] and the drug for combination are each separately formulated, the same contents may be used.

The dose may vary depending on the type of compound [I] or a pharmaceutically acceptable salt thereof, the administration route, symptoms, age of the patient, but in the case of administering orally to an adult patient having osteoarthritis, for example, the daily dose of compound [I] per kg body weight is about 0.005 to 50 mg, preferably about 0.05 to 10 mg, and more preferably about 0.2 to 4 mg, which can be administered in portions in 1 to 3 times.

When the pharmaceutical composition of the present invention is a sustained-release formulation, the dose may vary depending on the type and content of compound [I], type of formulation, the duration of drug release, the animal subject of administration (e.g., mammals such as human, rat, mouse, cat, dog, rabbit, cattle, pig, etc.) and purpose of administration, but in the case of parenteral administration, the release amount from the preparation is preferably from about 0.1 mg to about 100 mg of compound [I] per week.

For a drug for combination, the dose can be set to any level within the scope that side-effects do not occur. The daily dose for a drug for combination may vary depending on the extent of symptoms, the age, sex, body weight, and sensitivity of the subject of administration, the time and interval of administration, the properties, formulation, type of the pharmaceutical preparation, type of the active ingredient, and the like and may not be particularly limited. However, the dose of the drug, for example, in oral administration to a mammal is typically about 0.001 to 2000 mg, preferably about 0.01 to 500 mg, and more preferably about 0.1 to 100 mg per kg of body weight, which is typically administered in portions in 1 to 4 times.

When an agent for combination of the invention is administered, compound [I] and a drug for combination may be administered simultaneously; a drug for combination may be first administered, followed by compound [I]; or compound [I] may be administered first, followed by a drug for combination. When the administration is carried out with a time interval, the time interval may vary depending on the effective component to be administered, formulation, route of administration and the like. For example, when a drug for combination is first administered, compound [I] can be administered within 1 minute to 3 days from the point of administration of the drug for combination, preferably within 10 minutes to 1 day, and more preferably within 15 minutes to 1 hour. When compound [I] is administered first, a drug for combination can be administered within 1 minute to 1 day from the point of administration of compound [I], preferably within 10 minutes to 6 hours, and more preferably within 15 minutes to 1 hour. The pharmaceutical composition of the present invention is low in toxicity and thus can be used safely. In particular, the compounds of the Examples shown below exhibit excellent absorbability when administered orally, and thus can be used advantageously as an oral preparation.

Since compound [I], a salt thereof and a prodrug thereof of the present invention have a superior MMP inhibitory action, particularly an MMP-13 inhibitory action, they are useful as safe drugs for the prophylaxis or treatment of all MMP asocciated diseases, such as joint disease (e.g., osteoarthritis, rheumatoid arthritis and the like), osteoporosis, cancer, periodontal disease, cornea ulcer, chronic ulcer, pathologic bone resorption (Paget's disease and the like), nephritis, angiogenesis, aneurysm, arteriosclerosis, emphysema, chronic obstructive pulmonary disease (COPD), liver cirrhosis, autoimmune disease (Crohn's disease, Sjogren's disease and the like), infiltration or metastasis of cancer and the like, or as contraceptives.

EXAMPLES

The present invention is explained in detail in the following by referring to Examples and Reference Examples. The present invention is not limited in any way by the examples and may be changed without departing from the scope of the present invention.

An elution in column chromatography in each Example was performed under the observation by a TLC (Thin Layer Chromatography), unless otherwise specified. TLC was performed using a 60F$_{254}$ manufactured by Merck as a TLC plate. Detection was made by an UV detector or by means of a color development with a phosphomolybdic acid or a ninhydrin reagent. Silica gel 60 (70 to 230 mesh size) manufactured by Merck was employed as silica gel for column chromatography. A 60F$_{254}$ plate manufactured by Merck was employed as preparative TLC plate. A room temperature referred herein typically means a temperature from about 10° C. to 35° C.

NMR (Nuclear Magnetic Resonance) spectra were measured using a VARIAN model Gemini-200 spectrometer ($^1$H-NMR: 200 MHz or 300 MHz) or a BRUKER model DPX300 ($^1$H-NMR: 300 MHz). An internal standard was tetramethylsilane and all δ values are represented in ppm. Abbreviations employed here are described below. DMF: N,N-dimethylformamide, THF: tetrahydrofuran, EtOH: ethanol, DMA: N,N-dimethylacetamide, CDCl$_3$: deuterated chloroform, DMSO-d$_6$: deuterated dimethyl sulfoxide, Hz: hertz, J: coupling constant, m: multiplet, q: quartet, t: triplet, d: doublet, s: singlet, br: broad, dd: double doublet, dq: double quartet.

Example 1

N-{[3-(methyloxy)phenyl]methyl}-4-oxo-3,4-dihydroquinazoline-2-carboxamide

To a solution of ethyl 4-oxo-3,4-dihydroquinazoline-2-carboxylate (1.42 g, 6.53 mmol) obtained by a method described in Journal of Organic Chemistry (1978), 43(23), 4485-7 etc. in THF (25 mL) were added 3-methoxybenzylamine (1.19 g, 8.71 mmol) and triethylamine (1.1 mL, 7.89 mmol), and the mixture was stirred overnight at room temperature. The reaction mixture was extracted with 10% aqueous potassium carbonate and ethyl acetate. The organic layer was washed with water and saturated brine, dried and concentrated. The obtained crude crystals were recrystallized from ethanol-diethyl ether to give the title compound (1.09 g, 54%).
melting point: 186-189° C.

The following Example 2 to Example 53 except Example 15 were synthesized in the same manner as in Example 1.

Example 2

N-({6-[(4-fluorophenyl)oxy]pyridin-3-yl}methyl)-4-oxo-3,4-dihydroquinazoline-2-carboxamide The compound was synthesized using 1-{6-[(4-fluorophenyl)oxy]pyridin-3-yl}methanamine (synthesized by a method described in WO 2003091242 A1 etc.) instead of 3-methoxybenzylamine.
melting point: 208-209° C.

Example 3

4-oxo-N-{[4-(phenyloxy)phenyl]methyl}-3,4-dihydroquinazoline-2-carboxamide

The compound was synthesized using 4-phenoxybenzylamine instead of 3-methoxybenzylamine.
melting point: 178-179° C.

Example 4

4-oxo-N-{[3-(phenyloxy)phenyl]methyl}-3,4-dihydroquinazoline-2-carboxamide

The compound was synthesized using 3-phenoxybenzylamine instead of 3-methoxybenzylamine.
melting point: 189-190° C.

Example 5

N-(biphenyl-4-ylmethyl)-4-oxo-3,4-dihydroquinazoline-2-carboxamide

The compound was synthesized using 4-phenylbenzylamine instead of 3-methoxybenzylamine.
melting point: 210-211° C.

Example 6

N-(biphenyl-3-ylmethyl)-4-oxo-3,4-dihydroquinazoline-2-carboxamide

The compound was synthesized using 3-phenylbenzylamine instead of 3-methoxybenzylamine.
melting point: 175-176° C.

Example 7

N-[(4-fluorophenyl)methyl]-4-oxo-3,4-dihydroquinazoline-2-carboxamide

The compound was synthesized using 4-fluorobenzylamine instead of 3-methoxybenzylamine.
melting point: 211-214° C.

Example 8

N-(biphenyl-2-ylmethyl)-4-oxo-3,4-dihydroquinazoline-2-carboxamide

The compound was synthesized using 2-phenylbenzylamine instead of 3-methoxybenzylamine.
melting point: 182-183° C.

Example 9

4-oxo-N-({3-[(trifluoromethyl)oxy]phenyl}methyl)-3,4-dihydroquinazoline-2-carboxamide The compound was synthesized using 3-(trifluoromethoxy)benzylamine instead of 3-methoxybenzylamine.
melting point: 198-200° C.

Example 10

4-oxo-N-{[3-(trifluoromethyl)phenyl]methyl}-3,4-dihydroquinazoline-2-carboxamide The compound was synthesized using 3-(trifluoromethyl)benzylamine instead of 3-methoxybenzylamine.
melting point: 224-225° C.

Example 11

N-[(3-methylphenyl)methyl]-4-oxo-3,4-dihydroquinazoline-2-carboxamide

The compound was synthesized using 3-methylbenzylamine instead of 3-methoxybenzylamine.
melting point: 184-185° C.

Example 12

N-{[2-(methyloxy)phenyl]methyl}-4-oxo-3,4-dihydroquinazoline-2-carboxamide

The compound was synthesized using 2-methoxybenzylamine instead of 3-methoxybenzylamine.
melting point: 234-235° C.

Example 13

N-{[2-(methyloxy)pyridin-4-yl]methyl}-4-oxo-3,4-dihydroquinazoline-2-carboxamide The compound was synthesized using [(2-methoxypyridin-4-yl)methyl]amine (synthesized by a method described in Journal of Medicinal Chemistry (1993), 36(15), 2362-2372) instead of 3-methoxybenzylamine.
melting point: 186-189° C.

Example 14

4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 169-172° C.

Example 15

N-{[3-(aminomethyl)phenyl]methyl}-4-oxo-3,4-dihydroquinazoline-2-carboxamide hydrochloride 1,1-Dimethylethyl {[3-({[(4-oxo-3,4-dihydroquinazolin-2-yl)carbonyl]amino}methyl)phenyl]methyl}carbamate (1.50g, 3.67 mmol) obtained in Example 53 was stirred in 4N hydrogen chloride/ethyl acetate for 5 hrs. The reaction mixture was concentrated under reduced pressure, and the obtained crude crystals were recrystallized from ethyl acetate to give the title compound as a white powder (1.25 g, 99%).
melting point: 287-290° C.

Example 16

N-[(2-{[3-methyl-3-(methyloxy)butyl]oxy}pyridin-4-yl)methyl]-4-oxo-3,4-dihydroquinazoline-2-carboxamide The compound was synthesized using [(2-{[3-methyl-3-(methyloxy)butyl]oxy}pyridin-4-yl)methyl]amine obtained in Reference Example 47 instead of 3-methoxybenzylamine.
melting point: 166-167° C.

Example 17

N-({2-[(furan-3-ylmethyl)oxy]pyridin-4-yl}methyl)-4-oxo-3,4-dihydroquinazoline-2-carboxamide The compound was synthesized using ({2-[(furan-3-ylmethyl)oxy]pyridin-4-yl}methyl)amine obtained in Reference Example 35 instead of 3-methoxybenzylamine.
melting point: 167-168° C.

Example 18

N-[(2-{[3-(methyloxy)propyl]oxy}pyridin-4-yl)methyl]-4-oxo-3,4-dihydroquinazoline-2-carboxamide The compound was synthesized using [(2-{[3-(methyloxy)propyl]oxy}pyridin-4-yl)methyl]amine obtained in Reference Example 45 instead of 3-methoxybenzylamine.
melting point: 154-155° C.

Example 19

N-[(2-{[3-(methyloxy)propyl]amino}pyridin-4-yl)methyl]-4-oxo-3,4-dihydroquinazoline-2-carboxamide The compound was synthesized using 4-(aminomethyl)-N-[3-(methyloxy)propyl]pyridine-2-amine obtained in Reference Example 79 instead of 3-methoxybenzylamine.
melting point: 189-191° C.

Example 20

4-oxo-N-{[2-(tetrahydrofuran-3-yloxy)pyridin-4-yl]methyl}-3,4-dihydroquinazoline-2-carboxamide The compound was synthesized using {[2-(tetrahydrofuran-3-yloxy)pyridin-4-yl]methyl}amine obtained in Reference Example 75 instead of 3-methoxybenzylamine.
melting point: 215-216° C.

Example 21

N-[(2-{[(3-methyloxetan-3-yl)methyl]oxy}pyridin-4-yl)methyl]-4-oxo-3,4-dihydroquinazoline-2-carboxamide The compound was synthesized using [(2-{[(3-methyloxetan-3-yl)methyl]oxy}pyridin-4-yl)methyl]amine obtained in Reference Example 33 instead of 3-methoxybenzylamine.
melting point: 196-197° C.

Example 22

N-[(2-{[3-(ethyloxy)propyl]amino}pyridin-4-yl)methyl]-4-oxo-3,4-dihydroquinazoline-2-carboxamide The compound was synthesized using 4-(aminomethyl)-N-[3-(ethyloxy)propyl]pyridine-2-amine obtained in Reference Example 81 instead of 3-methoxybenzylamine.
melting point: 149-150° C.

Example 23

N-{[2-({3-[(1-methylethyl)oxy]propyl}amino)pyridin-4-yl]methyl}-4-oxo-3,4-dihydroquinazoline-2-carboxamide The compound was synthesized using 4-(aminomethyl)-N-{3-[(1-methylethyl)oxy]propyl}pyridine-2-amine obtained in Reference Example 83 instead of 3-methoxybenzylamine.
melting point: 162-163° C.

Example 24

4-oxo-N-{[2-(tetrahydro-2H-pyran-4-yloxy)pyridin-4-yl]methyl}-3,4-dihydroquinazoline-2-carboxamide The compound was synthesized using {[2-(tetrahydro-2H-pyran-4-yloxy)pyridin-4-yl]methyl}amine obtained in Reference Example 77 instead of 3-methoxybenzylamine.
melting point: 255-257° C.

Example 25

N-({2-[(furan-2-ylmethyl)oxy]pyridin-4-yl}methyl)-4-oxo-3,4-dihydroquinazoline-2-carboxamide The compound was synthesized using ({2-[(furan-2-ylmethyl)oxy]pyridin-4-yl}methyl)amine obtained in Reference Example 37 instead of 3-methoxybenzylamine.
melting point: 162-163° C.

Example 26

4-oxo-N-({2-[(phenylmethyl)oxy]pyridin-4-yl}methyl)-3,4-dihydroquinazoline-2-carboxamide The compound was synthesized using ({2-[(phenylmethyl)oxy]pyridin-4-yl}methyl)amine obtained in Reference Example 49 instead of 3-methoxybenzylamine.
melting point: 179-180° C.

Example 27

N-({2-[(4-fluorophenyl)oxy]pyridin-4-yl}methyl)-4-oxo-3,4-dihydroquinazoline-2-carboxamide The compound was synthesized using ({2-[(4-fluorophenyl)oxy]pyridin-4-yl}methyl)amine obtained in Reference Example 71 instead of 3-methoxybenzylamine.
melting point: 204-205° C.

Example 28

N-[(2-{[3,4-bis(methyloxy)phenyl]oxy}pyridin-4-yl)methyl]-4-oxo-3,4-dihydroquinazoline-2-carboxamide The compound was synthesized using [(2-{[3,4-bis(methyloxy)phenyl]oxy}pyridin-4-yl)methyl]amine obtained in Reference Example 73 instead of 3-methoxybenzylamine.
melting point: 190-191° C.

Example 29

4-oxo-N-({3-[(tetrahydrofuran-3-ylmethyl)oxy]phenyl}methyl)-3,4-dihydroquinazoline-2-carboxamide The compound was synthesized using 1-{3-[(tetrahydrofuran-3-ylmethyl)oxy]phenyl}methanamine obtained in Reference Example 85 instead of 3-methoxybenzylamine.
melting point: 161° C.

Example 30

N-[(3-morpholin-4-ylphenyl)methyl]-4-oxo-3,4-dihydroquinazoline-2-carboxamide

The compound was synthesized using 1-(3-morpholin-4-ylphenyl)methanamine obtained in Reference Example 94 instead of 3-methoxybenzylamine.
melting point: 253-254° C.

Example 31

N-[(3-cyanophenyl)methyl]-4-oxo-3,4-dihydroquinazoline-2-carboxamide

The compound was synthesized using 3-(aminomethyl)benzonitrile (synthesized by a method described in FR 1582452 etc.) instead of 3-methoxybenzylamine.
melting point: 232° C.

Example 32

4-oxo-N-({2-[(tetrahydro-2H-pyran-4-ylmethyl)oxy]pyridin-4-yl}methyl)-3,4-dihydroquinazoline-2-carboxamide The compound was synthesized using ({2-[(tetrahydro-2H-pyran-4-ylmethyl)oxy]pyridin-4-yl}methyl)amine obtained in Reference Example 31 instead of 3-methoxybenzylamine.
melting point: 196-197° C.

Example 33

4-oxo-N-({2-[(3-thienylmethyl)oxy]pyridin-4-yl}methyl)-3,4-dihydroquinazoline-2-carboxamide The compound was synthesized using ({2-[(3-thienylmethyl)oxy]pyridin-4-yl}methyl)amine obtained in Reference Example 39 instead of 3-methoxybenzylamine.
melting point: 176-178° C.

Example 34

N-{[2-({[4-(methyloxy)phenyl]methyl}oxy)pyridin-4-yl]methyl}-4-oxo-3,4-dihydroquinazoline-2-carboxamide The compound was synthesized using {[2-({[4-(methyloxy)phenyl]methyl}oxy)pyridin-4-yl]methyl}amine obtained in Reference Example 57 instead of 3-methoxybenzylamine.
melting point: 192-195° C.

Example 35

4-oxo-N-{[3-(3-oxo-3,4-dihydro-2H-1,4-benzooxazin-6-yl)phenyl]methyl}-3,4-dihydroquinazoline-2-carboxamide The compound was synthesized using 6-[3-(aminomethyl)phenyl]-2H-1,4-benzooxazin-3(4H)-one obtained in Reference Example 93 instead of 3-methoxybenzylamine.
melting point: 299-300° C.

Example 36

N-{[2-({[3-(methyloxy)phenyl]methyl}oxy)pyridin-4-yl]methyl}-4-oxo-3,4-dihydroquinazoline-2-carboxamide The compound was synthesized using {[2-({[3-(methyloxy)phenyl]methyl}oxy)pyridin-4-yl]methyl}amine obtained in Reference Example 55 instead of 3-methoxybenzylamine.
melting point: 148-149° C.

Example 37

N-({2-[(1,3-benzodioxol-5-ylmethyl)oxy]pyridin-4-yl}methyl)-4-oxo-3,4-dihydroquinazoline-2-carboxamide The compound was synthesized using ({2-[(1,3-benzodioxol-5-ylmethyl)oxy]pyridin-4-yl}methyl)amine obtained in Reference Example 59 instead of 3-methoxybenzylamine.
melting point: 176-177° C.

Example 38

N-[(2-{[(3-fluorophenyl)methyl]oxy}pyridin-4-yl)methyl]-4-oxo-3,4-dihydroquinazoline-2-carboxamide The compound was synthesized using [(2-{[(3-fluorophenyl)methyl]oxy}pyridin-4-yl)methyl]amine obtained in Reference Example 51 instead of 3-methoxybenzylamine.
melting point: 179-180° C.

Example 39

N-[(2-{[(4-fluorophenyl)methyl]oxy}pyridin-4-yl)methyl]-4-oxo-3,4-dihydroquinazoline-2-carboxamide The compound was synthesized using [(2-{[(4-fluorophenyl)methyl]oxy}pyridin-4-yl)methyl]amine obtained in Reference Example 53 instead of 3-methoxybenzylamine.
melting point: 212-213° C.

Example 40

4-oxo-N-({2-[(pyridine-2-ylmethyl)oxy]pyridin-4-yl}methyl)-3,4-dihydroquinazoline-2-carboxamide The compound was synthesized using ({2-[(pyridine-2-ylmethyl)oxy]pyridin-4-yl}methyl)amine obtained in Reference Example 67 instead of 3-methoxybenzylamine.
melting point: 166-171° C.

Example 41

4-oxo-N-({2-[(pyridine-3-ylmethyl)oxy]pyridin-4-yl}methyl)-3,4-dihydroquinazoline-2-carboxamide The compound was synthesized using ({2-[(pyridine-3-ylmethyl)oxy]pyridin-4-yl}methyl)amine obtained in Reference Example 65 instead of 3-methoxybenzylamine.
melting point: 186-188° C.

Example 42

4-oxo-N-({2-[(pyridin-4-ylmethyl)oxy]pyridin-4-yl}methyl)-3,4-dihydroquinazoline-2-carboxamide The compound was synthesized using ({2-[(pyridin-4-ylmethyl)oxy]pyridin-4-yl}methyl)amine obtained in Reference Example 63 instead of 3-methoxybenzylamine.
melting point: 230-231° C.

Example 43

N-[(2-{[(5-methylisoxazol-3-yl)methyl]oxy}pyridin-4-yl)methyl]-4-oxo-3,4-dihydroquinazoline-2-carboxamide The compound was synthesized using [(2-{[(5-methylisoxazol-3-yl)methyl]oxy}pyridin-4-yl)methyl]amine obtained in Reference Example 41 instead of 3-methoxybenzylamine.
melting point: 176-179° C.

Example 44

N-[(2-{[(3,5-dimethylisoxazol-4-yl)methyl]oxy}pyridin-4-yl)methyl]-4-oxo-3,4-dihydroquinazoline-2-carboxamide The compound was synthesized using [(2-{[(3,5-dimethylisoxazol-4-yl)methyl]oxy}pyridin-4-yl)methyl]amine obtained in Reference Example 43 instead of 3-methoxybenzylamine.
melting point: 198-202° C.

Example 45

N-({2-[(biphenyl-4-ylmethyl)oxy]pyridin-4-yl}methyl)-4-oxo-3,4-dihydroquinazoline-2-carboxamide The compound was synthesized using ({2-[(biphenyl-4-ylmethyl)oxy]pyridin-4-yl}methyl)amine obtained in Reference Example 61 instead of 3-methoxybenzylamine.
melting point: 209-211° C.

Example 46

N-{[2-(ethyloxy)pyridin-4-yl]methyl}-4-oxo-3,4-dihydroquinazoline-2-carboxamide

The compound was synthesized using {[2-(ethyloxy)pyridin-4-yl]methyl}amine obtained in Reference Example 69 instead of 3-methoxybenzylamine.
melting point: 153-157° C.

Example 47

N-{[4-fluoro-3-(methyloxy)phenyl]methyl}-4-oxo-3,4-dihydroquinazoline-2-carboxamide The compound was synthesized using 4-fluoro-3-methoxybenzylamine (synthesized by a method described in WO03/029224 A1) instead of 3-methoxybenzylamine.
melting point: 190-194° C.

Example 48

N-(4-morpholin-4-ylbutyl)-4-oxo-3,4-dihydroquinazoline-2-carboxamide

The compound was synthesized using 4-(4-aminobutyl)morpholine (synthesized by a method described in Journal of Medicinal Chemistry (1997), 40(24), 3915-3925) instead of 3-methoxybenzylamine.
melting point: 114-117° C.

Example 49

N-(3-morpholin-4-ylpropyl)-4-oxo-3,4-dihydroquinazoline-2-carboxamide

The compound was synthesized using N-(3-aminopropyl)morpholine instead of 3-methoxybenzylamine.
melting point: 163-164° C.

Example 50

N-{2-[3-(methyloxy)phenyl]ethyl}-4-oxo-3,4-dihydroquinazoline-2-carboxamide

The compound was synthesized using 2-(3-methoxyphenyl)ethylamine instead of 3-methoxybenzylamine.
melting point: 143-148° C.

Example 51

N-{[3-(ethyloxy)phenyl]methyl}-4-oxo-3,4-dihydroquinazoline-2-carboxamide

The compound was synthesized using 1-[3-(ethyloxy)phenyl]methanamine hydrochloride obtained in Reference Example 87 instead of 3-methoxybenzylamine.
melting point: 181° C.

Example 52 methyl 5-{[3-({[(4-oxo-3,4-dihydroquinazolin-2-yl)carbonyl]amino}methyl)phenyl]oxy}pentanoate The compound was synthesized using methyl 5-{[3-(aminomethyl)phenyl]oxy}pentanoate hydrochloride obtained in Reference Example 91 instead of 3-methoxybenzylamine.
melting point: 133-134° C.

Example 53

1,1-dimethylethyl {[3-({[(4-oxo-3,4-dihydroquinazolin-2-yl)carbonyl]amino}methyl)phenyl]methyl}carbamate The compound was synthesized using t-butyl N-[3-(aminomethyl)benzyl]carbamate instead of 3-methoxybenzylamine.
melting point: 180-183° C.

The following Examples 54 to 66 were synthesized in the same manner as in Example 1 from ethyl 6-fluoro-4-oxo-3,4-dihydroquinazoline-2-carboxylate obtained in Reference Example 7.

Example 54

6-fluoro-N-{[3-(methyloxy)phenyl]methyl}-4-oxo-3,4-dihydroquinazoline-2-carboxamide melting point: 177-179° C.

Example 55

6-fluoro-N-{[2-(methyloxy)phenyl]methyl}-4-oxo-3,4-dihydroquinazoline-2-carboxamide The compound was synthesized using 2-methoxybenzylamine instead of 3-methoxybenzylamine.
melting point: 192-194° C.

Example 56

6-fluoro-N-{[4-(methyloxy)phenyl]methyl}-4-oxo-3,4-dihydroquinazoline-2-carboxamide The compound was synthesized using 4-methoxybenzylamine instead of 3-methoxybenzylamine.
melting point: 187-189° C.

Example 57

6-fluoro-N-({2-[(furan-3-ylmethyl)oxy]pyridin-4-yl}methyl)-4-oxo-3,4-dihydroquinazoline-2-carboxamide The compound was synthesized using ({2-[(furan-3-ylmethyl)oxy]pyridin-4-yl}methyl)amine obtained in Reference Example 35 instead of 3-methoxybenzylamine.
melting point: 179-184° C.

Example 58

6-fluoro-N-[(2-{[3-(methyloxy)propyl]oxy}pyridin-4-yl)methyl]-4-oxo-3,4-dihydroquinazoline-2-carboxamide The compound was synthesized using [(2-{[3-(methyloxy)propyl]oxy}pyridin-4-yl)methyl]amine obtained in Reference Example 45 instead of 3-methoxybenzylamine.
melting point: 134-135° C.

Example 59

6-fluoro-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 181-183° C.

Example 60

6-fluoro-4-oxo-N-{[2-(tetrahydrofuran-3-yloxy)pyridin-4-yl]methyl}-3,4-dihydroquinazoline-2-carboxamide The compound was synthesized using {[2-(tetrahydrofuran-3-yloxy)pyridin-4-yl]methyl}amine obtained in Reference Example 75 instead of 3-methoxybenzylamine.
melting point: 173-175° C.

Example 61

6-fluoro-N-({2-[(4-fluorophenyl)oxy]pyridin-4-yl}methyl)-4-oxo-3,4-dihydroquinazoline-2-carboxamide The compound was synthesized using ({2-[(4-fluorophenyl)oxy]pyridin-4-yl}methyl)amine obtained in Reference Example 71 instead of 3-methoxybenzylamine.
melting point: 216-217° C.

Example 62

6-fluoro-4-oxo-N-({3-[(tetrahydrofuran-3-ylmethyl)oxy]phenyl}methyl)-3,4-dihydroquinazoline-2-carboxamide The compound was synthesized using 1-{3-[(tetrahydrofuran-3-ylmethyl)oxy]phenyl}methanamine obtained in Reference Example 85 instead of 3-methoxybenzylamine.
melting point: 169-170° C.

Example 63

6-fluoro-4-oxo-N-({2-[(tetrahydro-2H-pyran-4-ylmethyl)oxy]pyridin-4-yl}methyl)-3,4-dihydroquinazoline-2-carboxamide The compound was synthesized using ({2-[(tetrahydro-2H-pyran-4-ylmethyl)oxy]pyridin-4-yl}methyl)amine obtained in Reference Example 31 instead of 3-methoxybenzylamine.
melting point: 180-184° C.

Example 64

6-fluoro-N-{[2-(methyloxy)pyridin-4-yl]methyl}-4-oxo-3,4-dihydroquinazoline-2-carboxamide The compound was synthesized using [(2-methoxypyridin-4-yl)methyl]amine (synthesized by a method described in Journal of Medicinal Chemistry (1993), 36(15), 2362-2372) instead of 3-methoxybenzylamine.

melting point: 171-173° C.

Example 65

N-{[2-(ethyloxy)pyridin-4-yl]methyl}-6-fluoro-4-oxo-3,4-dihydroquinazoline-2-carboxamide The compound was synthesized using {[2-(ethyloxy)pyridin-4-yl]methyl}amine obtained in Reference Example 69 instead of 3-methoxybenzylamine.

melting point: 199-201° C.

Example 66

N-{[3-(ethyloxy)phenyl]methyl}-6-fluoro-4-oxo-3,4-dihydroquinazoline-2-carboxamide The compound was synthesized using 1-[3-(ethyloxy)phenyl]methanamine hydrochloride obtained in Reference Example 87 instead of 3-methoxybenzylamine.

melting point: 175-176° C.

The following Examples 67 to 82 were synthesized in the same manner as in Example 1 from ethyl 6-(methyloxy)-4-oxo-3,4-dihydroquinazoline-2-carboxylate obtained in Reference Example 8.

Example 67

6-(methyloxy)-N-{[3-(methyloxy)phenyl]methyl}-4-oxo-3,4-dihydroquinazoline-2-carboxamide melting point: 174-176° C.

Example 68

6-(methyloxy)-N-{[2-(methyloxy)phenyl]methyl}-4-oxo-3,4-dihydroquinazoline-2-carboxamide The compound was synthesized using 2-methoxybenzylamine instead of 3-methoxybenzylamine.

melting point: 223-226° C.

Example 69

6-(methyloxy)-N-{[4-(methyloxy)phenyl]methyl}-4-oxo-3,4-dihydroquinazoline-2-carboxamide The compound was synthesized using 4-methoxybenzylamine instead of 3-methoxybenzylamine.

melting point: 221-223° C.

Example 70

N-({2-[(furan-3-ylmethyl)oxy]pyridin-4-yl}methyl)-6-(methyloxy)-4-oxo-3,4-dihydroquinazoline-2-carboxamide The compound was synthesized using ({2-[(furan-3-ylmethyl)oxy]pyridin-4-yl}methyl)amine obtained in Reference Example 35 instead of 3-methoxybenzylamine.

melting point: 226-228° C.

Example 71

6-(methyloxy)-N-[(2-{[3-(methyloxy)propyl]oxy}pyridin-4-yl)methyl]-4-oxo-3,4-dihydroquinazoline-2-carboxamide The compound was synthesized using [(2-{[3-(methyloxy)propyl]oxy}pyridin-4-yl)methyl]amine obtained in Reference Example 45 instead of 3-methoxybenzylamine.

melting point: 161-163° C.

Example 72

6-(methyloxy)-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.

melting point: 200-202° C.

Example 73

6-(methyloxy)-4-oxo-N-{[2-(tetrahydrofuran-3-yloxy)pyridin-4-yl]methyl}-3,4-dihydroquinazoline-2-carboxamide The compound was synthesized using {[2-(tetrahydrofuran-3-yloxy)pyridin-4-yl]methyl}amine obtained in Reference Example 75 instead of 3-methoxybenzylamine.

melting point: 214-215° C.

Example 74

N-({2-[(4-fluorophenyl)oxy]pyridin-4-yl}methyl)-6-(methyloxy)-4-oxo-3,4-dihydroquinazoline-2-carboxamide The compound was synthesized using ({2-[(4-fluorophenyl)oxy]pyridin-4-yl}methyl)amine obtained in Reference Example 71 instead of 3-methoxybenzylamine.

melting point: 206-207° C.

Example 75

6-(methyloxy)-4-oxo-N-({3-[(tetrahydrofuran-3-ylmethyl)oxy]phenyl}methyl)-3,4-dihydroquinazoline-2-carboxamide The compound was synthesized using 1-{3-[(tetrahydrofuran-3-ylmethyl)oxy]phenyl}methanamine obtained in Reference Example 85 instead of 3-methoxybenzylamine.

melting point: 181° C.

Example 76

6-(methyloxy)-4-oxo-N-({2-[(tetrahydro-2H-pyran-4-ylmethyl)oxy]pyridin-4-yl}methyl)-3,4-dihydroquinazoline-2-carboxamide The compound was synthesized using ({2-[(tetrahydro-2H-pyran-4-ylmethyl)oxy]pyridin-4-yl}methyl)amine obtained in Reference Example 31 instead of 3-methoxybenzylamine.
melting point: 218-220° C.

Example 77

6-(methyloxy)-4-oxo-N-({2-[(3-thienylmethyl)oxy]pyridin-4-yl}methyl)-3,4-dihydroquinazoline-2-carboxamide The compound was synthesized using ({2-[(3-thienylmethyl)oxy]pyridin-4-yl}methyl)amine obtained in Reference Example 39 instead of 3-methoxybenzylamine.
melting point: 201-202° C.

Example 78

N-{[2-(ethyloxy)pyridin-4-yl]methyl}-6-(methyloxy)-4-oxo-3,4-dihydroquinazoline-2-carboxamide The compound was synthesized using {[2-(ethyloxy)pyridin-4-yl]methyl}amine obtained in Reference Example 69 instead of 3-methoxybenzylamine.
melting point: 211-213° C.

Example 79

N-{[3-(ethyloxy)phenyl]methyl}-6-(methyloxy)-4-oxo-3,4-dihydroquinazoline-2-carboxamide The compound was synthesized using 1-[3-(ethyloxy)phenyl]methanamine hydrochloride obtained in Reference Example 87 instead of 3-methoxybenzylamine.
melting point: 184-185° C.

Example 80 methyl 3-[({[6-(methyloxy)-4-oxo-3,4-dihydroquinazolin-2-yl]carbonyl}amino)methyl]benzoate The compound was synthesized using methyl 3-(aminomethyl)benzoate hydrochloride (synthesized by a method described in Pharmazie (1967), 22(9), 465-70 etc.) instead of 3-methoxybenzylamine.
melting point: 224-226° C.

Example 81 methyl 4-[({[6-(methyloxy)-4-oxo-3,4-dihydroquinazolin-2-yl]carbonyl}amino)methyl]benzoate The compound was synthesized using methyl 4-(aminomethyl)benzoate hydrochloride instead of 3-methoxybenzylamine.
melting point: 232-234° C.

Example 82 methyl 5-({3-[({[6-(methyloxy)-4-oxo-3,4-dihydroquinazolin-2-yl]carbonyl}amino)methyl]phenyl}oxy)pentanoate The compound was synthesized using methyl 5-{[3-(aminomethyl)phenyl]oxy}pentanoate hydrochloride obtained in Reference Example 91 instead of 3-methoxybenzylamine.
melting point: 141-142° C.

The following Example 83 to Example 85 were synthesized in the same manner as in Example 1, from ethyl 6-chloro-4-oxo-3,4-dihydroquinazoline-2-carboxylate obtained in Reference Example 98.

Example 83

6-chloro-N-{[3-(methyloxy)phenyl]methyl}-4-oxo-3,4-dihydroquinazoline-2-carboxamide melting point: 203-206° C.

Example 84

6-chloro-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 190-194° C.

Example 85

6-chloro-N-{[4-fluoro-3-(methyloxy)phenyl]methyl}-4-oxo-3,4-dihydroquinazoline-2-carboxamide The compound was synthesized using 4-fluoro-3-methoxybenzylamine (synthesized by a method described in WO03/029224 A1) instead of 3-methoxybenzylamine.
melting point: 206-208° C.

Example 86

N-{[3-(methyloxy)phenyl]methyl}-6-nitro-4-oxo-3,4-dihydroquinazoline-2-carboxamide The compound was synthesized in the same manner as in Example 1 using ethyl 6-nitro-4-oxo-3,4-dihydroquinazoline-2-carboxylate obtained in Reference Example 95.
melting point: 174-180° C.

The following Example 87 to Example 89 were synthesized in the same manner as in Example 1 from ethyl 6-methyl-4-oxo-3,4-dihydroquinazoline-2-carboxylate obtained in Reference Example 9.

Example 87

6-methyl-N-{[3-(methyloxy)phenyl]methyl}-4-oxo-3,4-dihydroquinazoline-2-carboxamide melting point: 175-177° C.

Example 88

6-methyl-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 190-192° C.

Example 89

N-({2-[(furan-3-ylmethyl)oxy]pyridin-4-yl}methyl)-6-methyl-4-oxo-3,4-dihydroquinazoline-2-carboxamide The compound was synthesized using ({2-[(furan-3-ylmethyl)oxy]pyridin-4-yl}methyl)amine obtained in Reference Example 35 instead of 3-methoxybenzylamine.
melting point: 171-173° C.

The following Example 90 and Example 91 were synthesized in the same manner as in Example 1 from ethyl 4-oxo-6-trifluoromethyl-3,4-dihydroquinazoline-2-carboxylate obtained in Reference Example 10.

Example 90

4-oxo-N-({2-[(tetrahydrofuran-3-ylmethyl)oxy]pyridin-4-yl}methyl)-6-(trifluoromethyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 184-186° C.

Example 91

N-{[3-(methyloxy)phenyl]methyl}-4-oxo-6-(trifluoromethyl)-3,4-dihydroquinazoline-2-carboxamide melting point: 186-187° C.

The following Example 92 and Example 93 were synthesized in the same manner as in Example 1 from ethyl 4-oxo-6-[(trifluoromethyl)oxy]-3,4-dihydroquinazoline-2-carboxylate obtained in Reference Example 11.

Example 92

4-oxo-N-({2-[(tetrahydrofuran-3-ylmethyl)oxy]pyridin-4-yl}methyl)-6-[(trifluoromethyl)oxy]-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 195-197° C.

Example 93

N-{[3-(methyloxy)phenyl]methyl}-4-oxo-6-[(trifluoromethyl)oxy]-3,4-dihydroquinazoline-2-carboxamide melting point: 156-159° C.

The following Example 94 and Example 95 were synthesized in the same manner as in Example 1 from ethyl 5-(methyloxy)-4-oxo-3,4-dihydroquinazoline-2-carboxylate obtained in Reference Example 12.

Example 94

5-(methyloxy)-N-{[3-(methyloxy)phenyl]methyl}-4-oxo-3,4-dihydroquinazoline-2-carboxamide melting point: 188-190° C.

Example 95

5-(methyloxy)-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 189-192° C.

The following Example 96 and Example 97 were synthesized in the same manner as in Example 1 from ethyl 7-(methyloxy)-4-oxo-3,4-dihydroquinazoline-2-carboxylate obtained in Reference Example 13.

Example 96

7-(methyloxy)-N-{[3-(methyloxy)phenyl]methyl}-4-oxo-3,4-dihydroquinazoline-2-carboxamide melting point: 228-230° C.

Example 97

7-(methyloxy)-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 208-210° C.

The following Example 98 and Example 99 were synthesized in the same manner as in Example 1 from ethyl 8-(methyloxy)-4-oxo-3,4-dihydroquinazoline-2-carboxylate obtained in Reference Example 14.

Example 98

8-(methyloxy)-N-{[3-(methyloxy)phenyl]methyl}-4-oxo-3,4-dihydroquinazoline-2-carboxamide melting point: 238-239° C.

Example 99

8-(methyloxy)-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 194-196° C.

The following Example 100 and Example 101 were synthesized in the same manner as in Example 1 from ethyl 6-amino-4-oxo-3,4-dihydroquinazoline-2-carboxylate obtained in Reference Example 96.

Example 100

6-amino-N-{[3-(methyloxy)phenyl]methyl}-4-oxo-3,4-dihydroquinazoline-2-carboxamide melting point: 223-225° C.

Example 101

6-amino-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 250-252° C.

The following Example 102 and Example 103 were synthesized in the same manner as in Example 1 from ethyl 4-oxo-6-[(phenylmethyl)oxy]-3,4-dihydroquinazoline-2-carboxylate obtained in Reference Example 15.

Example 102

N-{[3-(methyloxy)phenyl]methyl}-4-oxo-6-[(phenylmethyl)oxy]-3,4-dihydroquinazoline-2-carboxamide melting point: 179-182° C.

Example 103

4-oxo-6-[(phenylmethyl)oxy]-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 204-206° C.

The following Example 104 and Example 105 were synthesized in the same manner as in Example 1 from ethyl 6-iodo-4-oxo-3,4-dihydroquinazoline-2-carboxylate obtained in Reference Example 16.

Example 104

6-iodo-N-{[3-(methyloxy)phenyl]methyl}-4-oxo-3,4-dihydroquinazoline-2-carboxamide melting point: 219-220° C.

Example 105

6-iodo-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 204-207° C.

Example 106 and Example 107 were synthesized in the same manner as in Example 1 from ethyl 4-oxo-5-[(2-phenylethyl)oxy]-3,4-dihydroquinazoline-2-carboxylate obtained in Reference Example 19.

Example 106

N-{[3-(methyloxy)phenyl]methyl}-4-oxo-5-[(2-phenylethyl)oxy]-3,4-dihydroquinazoline-2-carboxamide melting point: 150-151° C.

Example 107

4-oxo-5-[(2-phenylethyl)oxy]-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 172-174° C.

Example 108 and Example 109 were synthesized in the same manner as in Example 1 from ethyl 5-methyl-4-oxo-3,4-dihydroquinazoline-2-carboxylate obtained in Reference Example 17.

Example 108

5-methyl-N-{[3-(methyloxy)phenyl]methyl}-4-oxo-3,4-dihydroquinazoline-2-carboxamide melting point: 150-152° C.

Example 109

5-methyl-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 164-165° C.

Example 110 to Example 112 were synthesized in the same manner as in Example 1 from ethyl 5-fluoro-4-oxo-3,4-dihydroquinazoline-2-carboxylate obtained in Reference Example 18.

Example 110

5-fluoro-N-{[3-(methyloxy)phenyl]methyl}-4-oxo-3,4-dihydroquinazoline-2-carboxamide melting point: 159-161° C.

Example 111

5-fluoro-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 187-189° C.

Example 112

5-fluoro-N-{[2-(methyloxy)pyridin-4-yl]methyl}-4-oxo-3,4-dihydroquinazoline-2-carboxamide The compound was synthesized using [(2-methoxypyridin-4-yl)methyl]amine (synthesized by a method described in Journal of Medicinal Chemistry (1993), 36(15), 2362-2372) instead of 3-methoxybenzylamine.
melting point: 189-191° C.

Example 113 to Example 115 were synthesized in the same manner as in Example 1 from ethyl 5,6-difluoro-4-oxo-3,4-dihydroquinazoline-2-carboxylate obtained in Reference Example 22.

Example 113

5,6-difluoro-N-{[3-(methyloxy)phenyl]methyl}-4-oxo-3,4-dihydroquinazoline-2-carboxamide melting point: 189-191° C.

Example 114

5,6-difluoro-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 198-199° C.

Example 115

5,6-difluoro-N-{[2-(methyloxy)pyridin-4-yl]methyl}-4-oxo-3,4-dihydroquinazoline-2-carboxamide The compound was synthesized using [(2-methoxypyridin-4-yl)methyl]amine (synthesized by a method described in Journal of Medicinal Chemistry (1993), 36(15), 2362-2372) instead of 3-methoxybenzylamine.
melting point: 214-216° C.

Example 116 and Example 117 were synthesized in the same manner as in Example 1 from ethyl 6-(morpholin-4-ylmethyl)-4-oxo-3,4-dihydroquinazoline-2-carboxylate obtained in Reference Example 20.

Example 116

N-{[3-(methyloxy)phenyl]methyl}-6-(morpholin-4-ylmethyl)-4-oxo-3,4-dihydroquinazoline-2-carboxamide melting point: 126-129° C.

Example 117

6-(morpholin-4-ylmethyl)-4-oxo-N-({2-[(tetrahydrofuran-3-ylmethyl)oxy]pyridin-4-yl}methyl)-3,4-dihydroquinazoline-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 186-189° C.

Example 118

6-[(methyloxy)methyl]-4-oxo-N-({2-[(tetrahydrofuran-3-ylmethyl)oxy]pyridin-4-yl}methyl)-3,4-dihydroquinazoline-2-carboxamide The title compound was obtained in the same manner as in Example 1 as a white powder from methyl 6-[(methyloxy)methyl]-4-oxo-3,4-dihydroquinazoline-2-carboxylate obtained in Reference Example 21, using ({2-[(tetrahydrofuran-3-ylmethyl)oxy]pyridin-4-yl}methyl)amine obtained in Reference Example 29 instead of 3-methoxybenzylamine.
melting point: 132-134° C.

Example 119 and Example 120 were synthesized in the same manner as in Example 1 from ethyl 6-cyano-4-oxo-3,4-dihydroquinazoline-2-carboxylate obtained in Reference Example 23.

Example 119

6-cyano-4-oxo-N-({2-[(tetrahydro-2H-pyran-4-ylmethyl)oxy]pyridin-4-yl}methyl)-3,4-dihydroquinazoline-2-carboxamide The compound was synthesized using ({2-[(tetrahydro-2H-pyran-4-ylmethyl)oxy]pyridin-4-yl}methyl)amine obtained in Reference Example 31 instead of 3-methoxybenzylamine.
melting point: 218-222° C.

Example 120

6-cyano-N-{[4-fluoro-3-(methyloxy)phenyl]methyl}-4-oxo-3,4-dihydroquinazoline-2-carboxamide The compound was synthesized using 4-fluoro-3-methoxybenzylamine (synthesized by a method described in WO03/029224 A1) instead of 3-methoxybenzylamine.
melting point: 242-244° C.

Example 121

2-{[6,7-bis(methyloxy)-3,4-dihydroisoquinolin-2(1H)-yl]carbonyl}quinazolin-4(3H)-one To a suspension of 4-oxo-3,4-dihydroquinazoline-2-carboxylic acid (150 mg, 0.788 mmol) obtained by a method described in Journal of Medicinal Chemistry (1979), 22(1), 44-8 etc. in THF (4 mL) were added oxalyl chloride (103 μL, 1.18 mmol) and DMF (one drop) and the mixture was stirred at room temperature for 12 hrs. The solvent was evaporated under reduced pressure. The obtained residue was suspended in THF (4 mL) again, 6,7-bis(methyloxy)-1,2,3,4-tetrahydroisoquinoline hydrochloride (136 mg, 0.946 mmol) and triethylamine (241 μL, 1.73 mmol) were added, and the mixture was stirred at room temperature for 12 hrs. The solvent was evaporated under reduced pressure. The residue was extracted with ethyl acetate, washed 3 times with 1N hydrochloric acid and saturated brine and dried over anhydrous sodium sulfate. The solvent was evaporated under reduced pressure. The obtained residue was purified by preparative TLC to give the title compound (8.2 mg, 2.8%) as a colorless solid.
melting point: 104-105° C.

Example 122

2-[(4-phenylpiperidin-1-yl)carbonyl]quinazolin-4(3H)-one

The title compound was obtained in the same manner as in Example 121 using 4-phenylpiperidine instead of 6,7-bis(methyloxy)-1,2,3,4-tetrahydroisoquinoline hydrochloride.
melting point: 151-152° C.

Example 123

2-[(4-phenylpiperazin-1-yl)carbonyl]quinazolin-4(3H)-one

The title compound was obtained in the same manner as in Example 121 using 1-phenylpiperazine instead of 6,7-bis(methyloxy)-1,2,3,4-tetrahydroisoquinoline hydrochloride.
melting point: 217-218° C.

Example 124

2-{[4-(phenyloxy)piperidin-1-yl]carbonyl}quinazolin-4(3H)-one

The title compound was obtained in the same manner as in Example 121 using 4-phenoxy-piperidine instead of 6,7-bis(methyloxy)-1,2,3,4-tetrahydroisoquinoline hydrochloride.
melting point: 154-155° C.

Example 125

N-({3-[(methylsulfonyl)amino]phenyl}methyl)-4-oxo-3,4-dihydroquinazoline-2-carboxamide To a solution of N-[(3-aminophenyl)methyl]-4-oxo-3,4-dihydroquinazoline-2-carboxamide (100 mg, 0.340 mmol) obtained in Example 227 in THF (2 mL) were added methanesulfonyl chloride (31.6 µL) and triethylamine (56.8 µL, 0.408 mmol), and the mixture was stirred at room temperature for 12 hrs. The solvent was evaporated under reduced pressure. The obtained residue was extracted with ethyl acetate, washed with water and saturated brine, and dried over anhydrous sodium sulfate. Then the solvent was evaporated under reduced pressure and the obtained crude crystals were recrystallized from ethyl acetate to give the title compound (112 mg, 88%) as a white powder.
melting point: 240-248° C.

Example 126

N-[(3-{[(methylamino)carbonyl]amino}phenyl)methyl]-4-oxo-3,4-dihydroquinazoline-2-carboxamide The title compound was obtained in the same manner as in Example 125 from N-[(3-aminophenyl)methyl]-4-oxo-3,4-dihydroquinazoline-2-carboxamide obtained in Example 227 and methylisocyanate.
melting point: 331-332° C.

Example 127

N-{[3-(acetylamino)phenyl]methyl}-4-oxo-3,4-dihydroquinazoline-2-carboxamide

The title compound was obtained in the same manner as in Example 125 from N-[(3-aminophenyl)methyl]-4-oxo-3,4-dihydroquinazoline-2-carboxamide obtained in Example 227 and acetyl chloride.
melting point: 260-265° C.

Example 128

Methyl oxo{[3-({[(4-oxo-3,4-dihydroquinazolin-2-yl)carbonyl]amino}methyl)phenyl]amino}acetate The title compound was obtained in the same manner as in Example 125 from N-[(3-aminophenyl)methyl]-4-oxo-3,4-dihydroquinazoline-2-carboxamide obtained in Example 227 and methyl chloro(oxo)acetate.
melting point: 228-229° C.

Example 129

Methyl 3-oxo-3-{[3-({[(4-oxo-3,4-dihydroquinazolin-2-yl)carbonyl]amino}methyl)phenyl]amino}propanoate The title compound was obtained in the same manner as in Example 125 from N-[(3-aminophenyl)methyl]-4-oxo-3,4-dihydroquinazoline-2-carboxamide obtained in Example 227 and methyl 3-chloro-3-oxopropanoate.
melting point: 211-212° C.

Example 130

Methyl [3-({[(4-oxo-3,4-dihydroquinazolin-2-yl)carbonyl]amino}methyl)phenyl]carbamate The title compound was obtained in the same manner as in Example 125 from N-[(3-aminophenyl)methyl]-4-oxo-3,4-dihydroquinazoline-2-carboxamide obtained in Example 227 and methyl chloroformate.
melting point: 262-263° C.

Example 131

N-[(3-{[(methylsulfonyl)amino]methyl}phenyl)methyl]-4-oxo-3,4-dihydroquinazoline-2-carboxamide The title compound was obtained in the same manner as in Example 125 from N-{[3-(aminomethyl)phenyl]methyl}-4-oxo-3,4-dihydroquinazoline-2-carboxamide hydrochloride obtained in Example 15 and methanesulfonyl chloride.
melting point: 194° C.

Example 132

N-{[3-({[(methylamino)carbonyl]amino}methyl)phenyl]methyl}-4-oxo-3,4-dihydroquinazoline-2-carboxamide The title compound was obtained in the same manner as in Example 125 from N-{[3-(aminomethyl)phenyl]methyl}-4-oxo-3,4-dihydroquinazoline-2-carboxamide hydrochloride obtained in Example 15 and methylisocyanate.
melting point: 228-229° C.

Example 133

N-({3-[(acetylamino)methyl]phenyl}methyl)-4-oxo-3,4-dihydroquinazoline-2-carboxamide The title compound was obtained in the same manner as in Example 125 from N-{[3-(aminomethyl)phenyl]methyl}-4-oxo-3,4-dihydroquinazoline-2-carboxamide hydrochloride obtained in Example 15 and acetyl chloride.
melting point: 242-257° C.

Example 134

Methyl oxo({[3-({[(4-oxo-3,4-dihydroquinazolin-2-yl)carbonyl]amino}methyl)phenyl]methyl}amino)acetate The title compound was obtained in the same manner as in Example 125 from N-{[3-(aminomethyl)phenyl]methyl}-4- oxo-3,4-dihydroquinazoline-2-carboxamide hydrochloride obtained in Example 15 and methyl chloro(oxo)acetate.
melting point: 193-194° C.

Example 135

4-oxo-N-({3-[(tetrahydrofuran-3-ylcarbonyl)amino] phenyl}methyl)-3,4-dihydroquinazoline-2-carboxamide The title compound was obtained in the same manner as in Example 125 from N-[(3-aminophenyl)methyl]-4-oxo-3,4-dihydroquinazoline-2-carboxamide obtained in Example 227 and tetrahydrofuran-3-carbonyl chloride (synthesized by a method described in Chemische Berichte (1988), 121(3), 485-92 etc.).
melting point: 225° C.

Example 136

N-({3-[(furan-3-ylcarbonyl)amino]phenyl}methyl)-4-oxo-3,4-dihydroquinazoline-2-carboxamide The title compound was obtained in the same manner as in Example 125 from N-[(3-aminophenyl)methyl]-4-oxo-3,4-dihydroquinazoline-2-carboxamide obtained in Example 227 and furan-3-carbonyl chloride (synthesized by the method described in U.S. Pat. No. 3,551,571).
melting point: 249° C.

Example 137

4-oxo-N-[(3-{[(tetrahydrofuran-3-ylcarbonyl)amino] methyl}phenyl)methyl]-3,4-dihydroquinazoline-2-carboxamide The title compound was obtained in the same manner as in Example 125 from N-{[3-(aminomethyl)phenyl]methyl}-4-oxo-3,4-dihydroquinazoline-2-carboxamide hydrochloride obtained in Example 15 and tetrahydrofuran-3-carbonyl chloride (synthesized by a method described in Chemische Berichte (1988), 121(3), 485-92 etc.).
melting point: 189-190° C.

Example 138

N-[(3-{[(furan-3-ylcarbonyl)amino]methyl}phenyl) methyl]-4-oxo-3,4-dihydroquinazoline-2-carboxamide The title compound was obtained in the same manner as in Example 125 from N-{[3-(aminomethyl)phenyl]methyl}-4-oxo-3,4-dihydroquinazoline-2-carboxamide hydrochloride obtained in Example 15 and furan-3-carbonyl chloride (synthesized by a method described in U.S. Pat. No. 3,551,571).
melting point: 227-228° C.

Example 139

N-{[3-(methyloxy)phenyl]methyl}-4-oxo-6-(propanoylamino)-3,4-dihydroquinazoline-2-carboxamide To a solution of 6-amino-N-{[3-(methyloxy)phenyl]methyl}-4-oxo-3,4-dihydroquinazoline-2-carboxamide (120 mg, 370 mmol) obtained in Example 100 and triethylamine (60 μL) in THF (15 mL) was added propionyl chloride (0.04 mL) at 0° C., and the mixture was stirred at room temperature for 1 hr. 10% aqueous citric acid solution was added to the reaction mixture and the mixture was extracted with ethyl acetate. The organic layer was washed with water, saturated aqueous sodium hydrogen carbonate and saturated brine, dried and concentrated. The obtained residue was recrystallized from ethyl acetate-diethyl ether to give the title compound (83 mg, 59%).
melting point: 222-223° C.
The following Example 140 to Example 143 were synthesized in the same manner as in Example 139.

Example 140

6-(acetylamino)-N-{[3-(methyloxy)phenyl]methyl}-4-oxo-3,4-dihydroquinazoline-2-carboxamide The compound was synthesized using acetyl chloride instead of propionyl chloride.
melting point: 209-210° C.

Example 141

N-{[3-(methyloxy)phenyl]methyl}-6-[(methylsulfonyl)amino]-4-oxo-3,4-dihydroquinazoline-2-carboxamide The compound was synthesized using methylsulfonyl chloride instead of propionyl chloride.
melting point: 245-248° C.

Example 142

6-[(methylsulfonyl)amino]-4-oxo-N-({2-[(tetrahydrofuran-3-ylmethyl)oxy]pyridin-4-yl}methyl)-3,4-dihydroquinazoline-2-carboxamide The compound was synthesized using 6-amino-4-oxo-N-({2-[(tetrahydrofuran-3-ylmethyl)oxy]pyridin-4-yl}methyl)-3,4-dihydroquinazoline-2-carboxamide obtained in Example 101 instead of 6-amino-N-{[3-(methyloxy)phenyl]methyl}-4-oxo-3,4-dihydroquinazoline-2-carboxamide and methylsulfonyl chloride instead of propionyl chloride.
melting point: 198-201° C.

Example 143

N-{[3-(methyloxy)phenyl]methyl}-4-oxo-6-{[(phenyloxy)acetyl]amino}-3,4-dihydroquinazoline-2-carboxamide The compound was synthesized using phenoxyacetyl chloride instead of propionyl chloride.
melting point: 207-209° C.

Example 144

6-hydroxy-N-{[3-(methyloxy)phenyl]methyl}-4-oxo-3,4-dihydroquinazoline-2-carboxamide To a suspension of N-{[3-(methyloxy)phenyl]methyl}-4-oxo-6-[(phenylmethyl)oxy]-3,4-dihydroquinazoline-2-carboxamide (2.00 g, 4.81 mmol) obtained in Example 102 in THF (50 mL)—methanol (20 mL) was added 10% palladium carbon (500 mg) under hydrogen atmosphere (1 atm), and the mixture was stirred at room temperature for 3 hrs. Insoluble material was filtered off, and the reaction mixture was concentrated to give the title compound as a pale-yellow powder (1.60 g, 100%). A part of the crude crystals (150 mg) was recrystallized from ethanol to give the title compound as a white powder (129 mg).
melting point: 268-271° C.

Example 145

6-(ethyloxy)-N-{[3-(methyloxy)phenyl]methyl}-4-oxo-3,4-dihydroquinazoline-2-carboxamide To a solution of 6-hydroxy-N-{[3-(methyloxy)phenyl]methyl}-4-oxo-3,4-dihydroquinazoline-2-carboxamide (120 mg, 368 µmol) obtained in Example 144 in THF (3 mL)-DMF (1 mL) were added cesium carbonate (120 mg, 368 µmol) and ethyl iodide (29 µL, 368 µmol) and the mixture was stirred at room temperature for 1 hr. Cesium carbonate (120 mg, 368 µmol) and ethyl iodide (58 µL, 736 µmol) were added again, and the mixture was stirred at room temperature for 3 hrs. The reaction mixture was partitioned between ethyl acetate and water, and the organic layer was washed with saturated brine. After drying over anhydrous sodium sulfate, the layer was concentrated, and the obtained concentrated residue was purified by preparative HPLC. The obtained crude crystals were recrystallized from ethanol to give the title compound as a white powder (27 mg, 21%).
melting point: 163-165 ° C.

Example 146

6-cyano-N-{[3-(methyloxy)phenyl]methyl}-4-oxo-3,4-dihydroquinazoline-2-carboxamide To a suspension of 6-iodo-N-{[3-(methyloxy)phenyl]methyl}-4-oxo-3,4-dihydroquinazoline-2-carboxamide (1.00 g, 2.30 mmol) obtained in Example 104 and zinc cyanide (148 mg, 1.26 mmol) in DMF (10 mL) was added tetrakis(triphenylphosphine)palladium(0) (132 mg, 115 µmol) and the mixture was stirred under nitrogen atmosphere at 80° C. for 3 hrs. After allowing to cool to room temperature, the reaction mixture was concentrated under reduced pressure. The obtained concentrated residue was suspended in ethyl acetate, and insoluble material was collected by filtration to give the title compound as a white powder (537 mg, 70%). A part of the crude crystals (200 mg) were recrystallized from ethanol to give the title compound as a white powder (193 mg).
melting point: 206-208° C.

Example 147

6-cyano-4-oxo-N-({2-[(tetrahydrofuran-3-ylmethyl)oxy]pyridin-4-yl}methyl)-3,4-dihydroquinazoline-2-carboxamide To a suspension of 6-iodo-4-oxo-N-({2-[(tetrahydrofuran-3-ylmethyl)oxy]pyridin-4-yl}methyl)-3,4-dihydroquinazoline-2-carboxamide (500 mg, 988 mol) obtained in Example 105 and zinc cyanide (63.8 mg, 543 µmol) in DMF (5 mL) was added tetrakis(triphenylphosphine)palladium(0) (57.1 mg, 49.4 µmol), and the mixture was stirred under nitrogen atmosphere at 80° C. for 3 hrs. After allowing to cool to room temperature, the reaction mixture was concentrated under reduced pressure. The obtained concentrated residue was dissolved in ethyl acetate-THF, and the solution was washed with water and saturated brine. The solution was dried over anhydrous sodium sulfate, concentrated and the obtained crude crystals were recrystallized from ethanol to give the title compound as a pale-yellow powder (141 mg, 35%).
melting point: 230-233° C.

Example 148

4-oxo-$N^2$-({2-[(tetrahydrofuran-3-ylmethyl)oxy]pyridin-4-yl}methyl)-3,4-dihydroquinazoline-2,6-dicarboxamide 6-Cyano-4-oxo-N-({2-[(tetrahydrofuran-3-ylmethyl)oxy]pyridin-4-yl}methyl)-3,4-dihydroquinazoline-2-carboxamide (240 mg, 593 µmol) obtained in Example 147 was dissolved in conc. sulfuric acid (2 mL), and the mixture was stirred at room temperature for 1 hr, and stirred with heating at 50° C. for 2 hrs. The reaction mixture was poured onto ice, and basified with sodium hydrogen carbonate. After extraction with a mixed solvent of ethyl acetate-THF, the mixture was washed with saturated brine. After drying over anhydrous sodium sulfate, the mixture was concentrated. The obtained crude crystals were recrystallized from ethanol to give the title compound as a pale-yellow powder (154 mg, 61%).
melting point: 237-239° C.

Example 149

N-{[3-(methyloxy)phenyl]methyl}-6-[({[3-(methyloxy)phenyl]methyl}amino)methyl]-4-oxo-3,4-dihydroquinazoline-2-carboxamide A solution of ethyl 6-(bromomethyl)-4-oxo-3,4-dihydroquinazoline-2-carboxylate (300 mg, 964 mol) obtained in Reference Example 20, Step 1 and 3-methoxybenzylamine (529 mg, 3.86 mmol) in DMF (6 mL) was stirred with heating at 90° C. for 4 hrs. The reaction mixture was concentrated under reduced pressure and ethyl acetate and 1N hydrochloric acid were added. The precipitated insoluble material was collected by filtration, and washed with ethyl acetate. The obtained solid was suspended in saturated aqueous sodium hydrogen carbonate, and extracted with ethyl acetate. The organic layer was washed with saturated brine and, after drying over anhydrous sodium sulfate, the mixture was concentrated. The obtained crude crystals were recrystallized from ethanol to give the title compound as a pale-yellow powder (125 mg, 28%).
melting point: 134-136° C.

Example 150

N-{[3-(methyloxy)phenyl]methyl}-4-oxo-6-phenyl-3,4-dihydroquinazoline-2-carboxamide To a suspension of 6-iodo-N-{[3-(methyloxy)phenyl]methyl}-4-oxo-3,4-dihydroquinazoline-2-carboxamide (300 mg, 689 µmol) obtained in Example 104, phenylboronic acid (126 mg, 1.03 mmol) and 2M aqueous sodium carbonate solution (515 µL, 1.03 mmol) in toluene (3 mL)—ethanol (1 mL) was added tetrakis(triphenylphosphine)palladium(0) (16 mg, 14 µmol), and the mixture was heated under reflux under a nitrogen atmosphere for 6 hrs. Phenylboronic acid (41 mg, 340 µmol), 2M aqueous sodium carbonate solution (515 µL, 1.03 mmol) and tetrakis(triphenylphosphine)palladium (16 mg, 14 µmol) were added again, and the mixture was heated under reflux under a nitrogen atmosphere for 12 hrs. After allowing to cool to room temperature, the reaction mixture was concentrated under reduced pressure. The obtained concentrated residue was partitioned between ethyl acetate and water. The organic layer was washed with saturated brine and, after drying over anhydrous sodium sulfate, the organic layer was concentrated. The obtained crude crystals were recrystallized from ethanol to give the title compound as a white powder (170 mg, 64%). melting point: 202-204° C.

Example 151

N-{[3-(methyloxy)phenyl]methyl}-4-oxo-6-(1,3-thiazol-2-ylthio)-3,4-dihydroquinazoline-2-carboxamide A solution of tris(dibenzylidenacetone)dipalladium(0) (13 20 mg, 14 ρmol) and 9,9-dimethyl-4,5-bis(diphenylphosphino)xanthene (16 mg, 28 μmol) in toluene (6 mL) was stirred under a nitrogen atmosphere at room temperature for 5 min. To this mixture were added 6-iodo-N-{[3-(methyloxy)phenyl]methyl}-4-oxo-3,4-dihydroquinazoline-2-carboxamide (300 mg, 689 μmol) obtained in Example 104, 2-mercaptothiazole (81 mg, 689 μmol) and potassium tert-butyrate (240 mg, 2.14 mmol), and the mixture was stirred with heating at 100° C. for 4 hrs. After allowing to cool to room temperature, the reaction mixture was concentrated under reduced pressure. The obtained concentrated residue was partitioned between ethyl acetate and water. The organic layer was washed with saturated brine and, after drying over anhydrous sodium sulfate, the organic layer was concentrated. The obtained concentrated residue was purified by silica gel column chromatography (50-83% ethyl acetate/hexane), and recrystallized from ethanol to give the title compound as a yellow powder (63.5 mg, 21%).

melting point: 170-172° C.

Example 152

O-{2-[({[3-(methyloxy)phenyl]methyl}amino)carbonyl]-4-oxo-3,4-dihydroquinazolin-6-yl}dimethylthiocarbamate To a solution of 6-hydroxy-N-{[3-(methyloxy)phenyl]methyl}-4-oxo-3,4-dihydroquinazoline-2-carboxamide (500 mg, 1.54 mmol) obtained in Example 144 and N,N-dimethylthiocarbamoyl chloride (380 mg, 3.08 mmol) in DMF (5 mL) was added 1,4-diazabicyclo[2.2.2]octane (345 mg, 3.08 mmol), and the mixture was stirred at room temperature for 2 hrs. Reaction mixture was poured into water (30 mL) under ice-cooling. The precipitated insoluble material was collected by filtration and the solid was washed with water, ethanol and diethyl ether to give the title compound as a white powder (608 mg, 96%).

melting point: 207-209° C.

Example 153

S-{2-[({[3-(methyloxy)phenyl]methyl}amino)carbonyl]-4-oxo-3,4-dihydroquinazolin-6-yl}dimethylthiocarbamate A mixture of O-{2-[({[3-(methyloxy)phenyl]methyl}amino)carbonyl]-4-oxo-3,4-dihydroquinazolin-6-yl}dimethylthiocarbamate (540 mg, 1.31 mmol) obtained in Example 152 and N,N-diethylaniline (5 mL) was stirred with heating at 210° C. for 7 hrs. After allowing to cool to room temperature, the reaction mixture was poured into 3N hydrochloric acid (30 mL). The precipitated insoluble material was collected by filtration and the solid was washed with water, ethanol and diethyl ether to give the title compound as a pale-gray powder (440 mg, 82%).

melting point: 171-173 ° C.

Example 154

6-mercapto-N-{[3-(methyloxy)phenyl]methyl}-4-oxo-3,4-dihydroquinazoline-2-carboxamide To a suspension of S-{2-[({[3-(methyloxy)phenyl]methyl}amino)carbonyl]-4-oxo-3,4-dihydroquinazolin-6-yl}dimethylthiocarbamate (380 mg, 921 μmol) obtained in Example 153 in methanol (10 mL) was added potassium hydroxide (259 mg, 4.61 mmol) and the mixture was heated under reflux for 2 hrs. After allowing to cool to room temperature, the reaction mixture was concentrated under reduced pressure, and the concentrated residue was dissolved in water. The mixture was acidified (pH 2-3) with 1N hydrochloric acid, and extracted with a mixed solvent of ethyl acetate-THF. The organic layer was washed with saturated brine and, after drying over anhydrous sodium sulfate, the organic layer was concentrated. The obtained concentrated residue was crystallized from ethanol to give the title compound as a pale-yellow powder (300 mg, 95%).

melting point: 170-172° C.

Example 155

N-{[3-(methyloxy)phenyl]methyl}-6-(methylthio)-4-oxo-3,4-dihydroquinazoline-2-carboxamide To a solution of 6-mercapto-N-{[3-(methyloxy)phenyl]methyl}-4-oxo-3,4-dihydroquinazoline-2-carboxamide (270 mg, 791 μmol) obtained in Example 154 and methyl iodide (49 μL, 791 μmol) in THF (5 mL) was added triethylamine (110 μL, 791 μmol), and the mixture was stirred with heating at room temperature for 1 hr. The reaction mixture was partitioned between ethyl acetate and water. The organic layer was washed with saturated brine and, after drying over anhydrous sodium sulfate, the organic layer was concentrated. The obtained concentrated residue was crystallized from ethanol to give the title compound as a pale-yellow powder (240 mg, 85%).

melting point: 168-170° C.

Example 156

N-{[3-(methyloxy)phenyl]methyl}-6-(methylsulfonyl)-4-oxo-3,4-dihydroquinazoline-2-carboxamide To a solution of N-{[3-(methyloxy)phenyl]methyl}-6-(methylthio)-4-oxo-3,4-dihydroquinazoline-2-carboxamide (60 mg, 170 μmol) obtained in Example 155 in chloroform (2 mL) was added m-chloroperbenzoic acid (84 mg, 340 μmol) under ice-cooling, and the mixture was stirred with heating at room temperature for 2 hrs. The reaction mixture was partitioned between ethyl acetate and water. The organic layer was washed with saturated brine and, after drying over anhydrous sodium sulfate, the organic layer was concentrated. The obtained concentrated residue was crystallized from ethanol to give the title compound as a pale-yellow powder (62 mg, 95%).

melting point: 186-188° C.

Example 157

N-{[3-(methyloxy)phenyl]methyl}-4-oxo-6-[(2-oxo-2-phenylethyl)oxy]-3,4-dihydroquinazoline-2-carboxamide To a suspension of 6-hydroxy-N-{[3-(methyloxy)phenyl]methyl}-4-oxo-3,4-dihydroquinazoline-2-carboxamide (300 mg, 922 μmol) obtained in Example 144 and phenacyl bromide (201 mg, 1.01 mmol) in acetone (2 mL) was added potassium carbonate (191 mg, 1.38 mmol), and mixture was stirred with heating at 60° C. for 2 hrs. Phenacyl bromide (50 mg, 250 μmol) was added again, and the mixture was stirred with heating at 60° C. for 2 hrs. The reaction mixture was partitioned between ethyl acetate and water. The organic layer was washed with saturated brine, dried over anhydrous sodium sulfate and concentrated. The obtained concentrated residue was purified by preparative HPLC to give the title compound as a white powder (144 mg, 35%).
melting point: 168-169° C.

Example 158

N-{[3-(methyloxy)phenyl]methyl}-4-oxo-6-(1H-tetrazol-5-yl)-3,4-dihydroquinazoline-2-carboxamide To a solution of 6-cyano-N-{[3-(methyloxy)phenyl]methyl}-4-oxo-3,4-dihydroquinazoline-2-carboxamide (100 mg, 299 μmol) obtained in Example 146 in DMF (3 mL) were added sodium azide (97.0 mg, 1.50 mmol) and ammonium chloride (80.0 mg, 1.50 mmol), and the mixture was stirred with heating at 80° C. for 24 hrs. After allowing to cool to room temperature, water was added to the reaction mixture. The precipitated insoluble material was collected by filtration. The solid was washed with water and ethyl acetate, suspended in ethanol and heated under reflux. After allowing to cool to room temperature, insoluble material was collected by filtration to give the title compound as a white powder (105 mg, 93%).
melting point: 258-260° C.

Example 159

N-{[3-(methyloxy)phenyl]methyl}-4-oxo-5-[(phenylmethyl)oxy]-3,4-dihydroquinazoline-2-carboxamide To a solution of benzyl alcohol (99 mg, 920 μmol) in DMA (6 mL) was added sodium hydride (60% in oil dispersion, 122 mg, 3.06 mmol), and the mixture was stirred at room temperature for 30 min. To the reaction mixture was added 5-fluoro-N-{[3-(methyloxy)phenyl]methyl}-4-oxo-3,4-dihydroquinazoline-2-carboxamide (200 mg, 611 μmol) obtained in Example 110, and the mixture was stirred with heating at 80° C. for 1 hr. The reaction mixture was cooled to room temperature, and adjusted to pH 3-4 with 1N hydrochloric acid. The mixture was extracted with a mixed solvent of ethyl acetate-THF. The organic layer was washed with water and saturated brine and, after drying over anhydrous sodium sulfate, the organic layer was concentrated under reduced pressure. The obtained concentrated residue was crystallized from ethanol to give the title compound as a pale-yellow powder (207 mg, 81%).
melting point: 188-190° C.
The following Example 160 to Example 174 were synthesized in the same manner as in Example 159.

Example 160

N-{[3-(methyloxy)phenyl]methyl}-4-oxo-5-[(3-phenylpropyl)oxy]-3,4-dihydroquinazoline-2-carboxamide The compound was synthesized using 3-phenylpropanol instead of benzyl alcohol.
melting point: 165-167° C.

Example 161

N-{[3-(methyloxy)phenyl]methyl}-4-oxo-5-[(2-phenylethyl)thio]-3,4-dihydroquinazoline-2-carboxamide The compound was synthesized using 2-phenethylethanethiol instead of benzyl alcohol.
melting point: 178-180° C.

Example 162

4-[({2-[({[3-(methyloxy)phenyl]methyl}amino)carbonyl]-4-oxo-3,4-dihydroquinazolin-5-yl}oxy)methyl]benzoic acid The compound was synthesized using 4-(hydroxymethyl)benzoic acid instead of benzyl alcohol.
melting point: 268-270° C.

Example 163

5-{[(4-fluorophenyl)methyl]oxy}-N-{[3-(methyloxy)phenyl]methyl}-4-oxo-3,4-dihydroquinazoline-2-carboxamide The compound was synthesized using 4-fluorobenzyl alcohol instead of benzyl alcohol.
melting point: 216-218° C.

Example 164

N-{[3-(methyloxy)phenyl]methyl}-5-({[4-(methyloxy)phenyl]methyl}oxy)-4-oxo-3,4-dihydroquinazoline-2-carboxamide The compound was synthesized using 4-methoxybenzyl alcohol instead of benzyl alcohol.
melting point: 197-199° C.

Example 165

N-{[3-(methyloxy)phenyl]methyl}-4-oxo-5-[(pyridine-3-ylmethyl)oxy]-3,4-dihydroquinazoline-2-carboxamide The compound was synthesized using 3-pyridinemethanol instead of benzyl alcohol.
melting point: 191-193° C.

Example 166

3-[({2-[({[3-(methyloxy)phenyl]methyl}amino)carbonyl]-4-oxo-3,4-dihydroquinazolin-5-yl}oxy)methyl]benzoic acid The compound was synthesized using 3-(hydroxymethyl)benzoic acid instead of benzyl alcohol.
melting point: 246-248° C.

Example 167

2-[({2-[({[3-(methyloxy)phenyl]methyl}amino)carbonyl]-4-oxo-3,4-dihydroquinazolin-5-yl}oxy)methyl]benzoic acid The compound was synthesized using 2-(hydroxymethyl)benzoic acid instead of benzyl alcohol.
melting point: 193-195° C.

Example 168

N-{[3-(methyloxy)phenyl]methyl}-5-[(2-methyl-2-phenylpropyl)oxy]-4-oxo-3,4-dihydroquinazoline-2-carboxamide The compound was synthesized using 2-methyl-2-phenylpropan-1-ol instead of benzyl alcohol.
melting point: 145-147° C.

Example 169

5-[(2-cyclohexylethyl)oxy]-N-{[3-(methyloxy)phenyl]methyl}-4-oxo-3,4-dihydroquinazoline-2-carboxamide The compound was synthesized using 2-cyclohexylethanol instead of benzyl alcohol.
melting point: 130-132° C.

Example 170

N-{[3-(methyloxy)phenyl]methyl}-4-oxo-5-[(2-piperidin-1-ylethyl)oxy]-3,4-dihydroquinazoline-2-carboxamide The compound was synthesized using N-(2-hydroxyethyl)piperidine instead of benzyl alcohol.
melting point: 225-227° C.

Example 171

N-{[3-(methyloxy)phenyl]methyl}-5-[(2-morpholin-4-ylethyl)oxy]-4-oxo-3,4-dihydroquinazoline-2-carboxamide The compound was synthesized using N-(2-hydroxyethyl)morpholine instead of benzyl alcohol.
melting point: 130-132° C.

Example 172

N-{[3-(methyloxy)phenyl]methyl}-4-oxo-5-({2-[(phenylmethyl)oxy]ethyl}oxy)-3,4-dihydroquinazoline-2-carboxamide The compound was synthesized using 2-(benzyloxy)ethanol instead of benzyl alcohol.
melting point: 136-138° C.

Example 173

({4-[({2-[({[3-(methyloxy)phenyl]methyl}amino)carbonyl]-4-oxo-3,4-dihydroquinazolin-5-yl}oxy)methyl]phenyl}oxy)acetic acid The compound was synthesized using 4-(hydroxymethyl)phenoxyacetic acid instead of benzyl alcohol.
melting point: 133-135° C.

Example 174

{4-[({2-[({[3-(methyloxy)phenyl]methyl}amino)carbonyl]-4-oxo-3,4-dihydroquinazolin-5-yl}oxy)methyl]phenyl}acetic acid The compound was synthesized using 4-(hydroxymethyl)phenylacetic acid instead of benzyl alcohol.
melting point: 215-217° C.

Example 175

4-oxo-5-[(phenylmethyl)oxy]-N-({2-[(tetrahydrofuran-3-ylmethyl)oxy]pyridin-4-yl}methyl)-3,4-dihydroquinazoline-2-carboxamide The compound was synthesized in the same manner as in Example 159 from 5-fluoro-4-oxo-N-({2-[(tetrahydrofuran-3-ylmethyl)oxy]pyridin-4-yl}methyl)-3,4-dihydroquinazoline-2-carboxamide obtained in Example 111.
melting point: 190-192° C.

The following Example 176 to Example 181 were synthesized in the same manner as in Example 159 from 5,6-difluoro-N-{[3-(methyloxy)phenyl]methyl}-4-oxo-3,4-dihydroquinazoline-2-carboxamide obtained in Example 113.

Example 176

6-fluoro-5-{[(4-fluorophenyl)methyl]oxy}-N-{[3-(methyloxy)phenyl]methyl}-4-oxo-3,4-dihydroquinazoline-2-carboxamide The compound was synthesized using 4-fluorobenzyl alcohol instead of benzyl alcohol.
melting point: 195-197° C.

Example 177

4-[({6-fluoro-2-[({[3-(methyloxy)phenyl]methyl}amino)carbonyl]-4-oxo-3,4-dihydroquinazolin-5-yl}oxy)methyl]benzoic acid The compound was synthesized using 4-(hydroxymethyl)benzoic acid instead of benzyl alcohol.
melting point: 248-250° C.

Example 178

6-fluoro-N-{[3-(methyloxy)phenyl]methyl}-4-oxo-5-[(2-phenylethyl)oxy]-3,4-dihydroquinazoline-2-carboxamide The compound was synthesized using 2-phenylethanol instead of benzyl alcohol.
melting point: 134-135° C.

Example 179

4-[2-({6-fluoro-2-[({[3-(methyloxy)phenyl]methyl}amino)carbonyl]-4-oxo-3,4-dihydroquinazolin-5-yl}oxy)ethyl]benzoic acid A solution of 5,6-difluoro-N-{[3-(methyloxy)phenyl]methyl}-4-oxo-3,4-dihydroquinazoline-2-carboxamide (500 mg, 1.45 mmol) obtained in Example 113 and 4-(2-hydroxyethyl)benzoic acid (241 mg, 1.45 mmol) in DMA (5 mL) was added dropwise to a suspension of 60% sodium hydride (165 mg, 4.34 mmol) in DMA (2.5 mL) at room temperature and the mixture was stirred at room temperature for 30 min. and then at 80° C. for 1.5 hrs with heating. The reaction mixture was ice-cooled, and water (5 mL), ethyl acetate (10 mL), 1N hydrochloric acid (6 mL) and hexane (10 mL) were successively added dropwise. The precipitated solid was collected by filtration, and washed with water and methanol. The obtained solid was suspended in methanol, and the mixture was stirred with heating at 70° C. for 30 min. The mixture was allowed to cool to room temperature, and the precipitated solid was collected by filtration, and washed with methanol to give the title compound as a pale-yellow powder (501 mg, 70%).

melting point: 227-229° C.

$^1$H NMR (300 MHz, DMSO-d$_6$) δ: 3.18 (2H, t, J=6.9 Hz), 3.73 (3H, s), 4.32 (2H, t, J=6.9 Hz), 4.44 (2H, d, J=6.0 Hz), 6.81-6.84 (1H, m), 6.89-6.92 (2H, m), 7.46 (2H, d, J=8.4 Hz), 7.24 (1H, t, J=8.1 Hz), 7.53 (1H, dd, J=6.3, 4.8 Hz), 7.79 (1H, t, J=9.6 Hz), 7.87 (2H, d, J=8.1 Hz), 9.50 (1H, t, J=6.3 Hz), 12.20 (1H, bs), 12.87 (1H, bs).

Example 180

6-fluoro-5-{[2-(4-fluorophenyl)ethyl]oxy}-N-{[3-(methyloxy)phenyl]methyl}-4-oxo-3,4-dihydroquinazoline-2-carboxamide The compound was synthesized using 2-(4-fluorophenyl)ethanol instead of benzyl alcohol.

melting point: 146-148° C.

Example 181

5-{[2-(4-aminophenyl)ethyl]oxy}-6-fluoro-N-{[3-(methyloxy)phenyl]methyl}-4-oxo-3,4-dihydroquinazoline-2-carboxamide The compound was synthesized using 2-(4-aminophenyl)ethanol instead of benzyl alcohol.

melting point: 129-131° C.

The following Example 182 and Example 183 were synthesized in the same manner as in Example 159 from 5,6-difluoro-4-oxo-N-({2-[(tetrahydrofuran-3-ylmethyl)oxy]pyridin-4-yl}methyl)-3,4-dihydroquinazoline-2-carboxamide obtained in Example 114.

Example 182

6-fluoro-5-{[(4-fluorophenyl)methyl]oxy}-4-oxo-N-({2-[(tetrahydrofuran-3-ylmethyl)oxy]pyridin-4-yl}methyl)-3,4-dihydroquinazoline-2-carboxamide The compound was synthesized using 4-fluorobenzyl alcohol instead of benzyl alcohol.

melting point: 183-185° C.

Example 183

4-{[(6-fluoro-4-oxo-2-{[({2-[(tetrahydrofuran-3-ylmethyl)oxy]pyridin-4-yl}methyl)amino]carbonyl}-3,4-dihydroquinazolin-5-yl)oxy]methyl}benzoic acid The compound was synthesized using 4-(hydroxymethyl)benzoic acid instead of benzyl alcohol.

melting point: 263-265° C.

Example 184

4-[({6-fluoro-2-[({[2-(methyloxy)pyridin-4-yl]methyl}amino)carbonyl]-4-oxo-3,4-dihydroquinazolin-5-yl}oxy)methyl]benzoic acid The compound was synthesized in the same manner as in Example 159 from 4-(hydroxymethyl)benzoic acid and 5,6-difluoro-N-{[2-(methyloxy)pyridin-4-yl]methyl}-4-oxo-3,4-dihydroquinazoline-2-carboxamide obtained in Example 115.

melting point: 231-233° C.

Example 185

N-{[3-(methyloxy)phenyl]methyl}-4-oxo-5-[(2-phenylethyl)amino]-3,4-dihydroquinazoline-2-carboxamide A solution of 5-fluoro-N-{[3-(methyloxy)phenyl]methyl}-4-oxo-3,4-dihydroquinazoline-2-carboxamide (100 mg, 309 µmol) obtained in Example 110 and 2-phenylethylamine (187 mg, 1.55 mmol) in N,N-dimethylacetamide (2 mL) was stirred with heating at 80° C. for 2 days. 2-Phenylethylamine (93 mg, 770 µmol) was added, and the mixture was stirred with heating at 80° C. for one day. The reaction mixture was concentrated under reduced pressure and ethyl acetate was added. The mixture was washed with 0.1N hydrochloric acid and saturated brine. After drying over anhydrous sodium sulfate, the mixture was concentrated under reduced pressure. The obtained concentrated residue was crystallized from ethanol to give the title compound as a yellow powder (68 mg, 51%).

melting point: 164-166° C.

Example 186

6-fluoro-N-{[3-(methyloxy)phenyl]methyl}-5-({[3-(methyloxy)phenyl]methyl}amino)-4-oxo-3,4-dihydroquinazoline-2-carboxamide The compound was synthesized in the same manner as in Example 185 from 5,6-difluoro-N-{[3-(methyloxy)phenyl]methyl}-4-oxo-3,4-dihydroquinazoline-2-carboxamide obtained in Example 113 and 3-methoxybenzylamine.

melting point: 141-143° C.

Example 187

5-{[(4-cyanophenyl)methyl]oxy}-N-{[3-(methyloxy)phenyl]methyl}-4-oxo-3,4-dihydroquinazoline-2-carboxamide To a solution of 5-fluoro-N-{[3-(methyloxy)phenyl]methyl}-4-oxo-3,4-dihydroquinazoline-2-carboxamide (1.40 g, 4.28 mmol) obtained in Example 110 in N,N-dimethylacetamide (20 mL) was added sodium hydride (60% in oil dispersion, 856 mg, 21.4 mmol), and the mixture was stirred at room temperature for 30 min. To the reaction mixture was added 4-iodobenzyl alcohol (1.50 g, 6.42 mmol), and the mixture was stirred with heating at 80° C. for 1 hr. The reaction mixture was cooled to room temperature, adjusted to pH 3-4 with 1N hydrochloric acid, and diluted with a mixed solvent of ethyl acetate-THF. The organic layer was washed with water and saturated brine and, after drying over anhydrous sodium sulfate, the organic layer was concentrated under reduced pressure to give a pale-yellow powder (1.70 g). To a suspension (10 mL) of the above-mentioned pale-yellow powder (1.14 g) and zinc cyanide (72 mg, 610 µmol) in DMF was added tetrakis(triphenylphosphine)palladium(0) (64 mg, 55 µmol) and the mixture was stirred under a nitrogen atmosphere at 80° C. for 6 hrs. After allowing to cool to room temperature, the reaction mixture was concentrated under reduced pressure. The obtained concentrated residue was dissolved in ethyl acetate-THF, and the mixture was washed with water and saturated brine. After drying over anhydrous sodium sulfate, the mixture was concentrated. The obtained concentrated residue was purified by silica gel column chromatography (25-50% ethyl acetate/hexane). The obtained crude crystals were recrystallized from ethanol to give the title compound as a white powder (46 mg, 0.4%).
melting point: 218-220° C.

Example 188

Ethyl 4-[({2-[({[3-(methyloxy)phenyl]methyl}amino)carbonyl]-4-oxo-3,4-dihydroquinazolin-5-yl}oxy)methyl]benzoate To a suspension of 4-[({2-[({[3-(methyloxy)phenyl]methyl}amino)carbonyl]-4-oxo-3,4dihydroquinazolin-5-yl}oxy)methyl]benzoic acid (100 mg, 218 μmol) obtained in Example 162 and EtOH (100 μL) in THF (4 mL) were added 1-ethyl-3-(3-dimethylaminopropyl)carbodiimide hydrochloride (63 mg, 326 μmol) and 4-dimethylaminopyridine (2.5 mg, 21 μmol), and the mixture was stirred at 40° C. for 15 hrs. The reaction mixture was diluted with ethyl acetate, and washed with 0.1N hydrochloric acid, water and saturated brine. The mixture was dried over anhydrous sodium sulfate and concentrated under reduced pressure. The obtained concentrated residue was crystallized from ethanol to give the title compound as a white powder (95 mg, 89%).
melting point: 205-207° C.

Example 189

5-({[4-(aminocarbonyl)phenyl]methyl}oxy)-N-{[3-(methyloxy)phenyl]methyl}-4-oxo-3,4-dihydroquinazoline-2-carboxamide To a suspension of 4-[({2-[({[3-(methyloxy)phenyl]methyl}amino)carbonyl]-4-oxo-3,4-dihydroquinazolin-5-yl}oxy)methyl]benzoic acid (100 mg, 218 μmol) obtained in Example 162 in THF (4 mL) were added 1-ethyl-3-(3-dimethylaminopropyl)carbodiimide hydrochloride (63 mg, 326 μmol) and 1-hydroxy-1H-benzotriazole ammonium salt (50 mg, 326 μmol), and the mixture was stirred at 40° C. for 15 hrs. 1-Ethyl-3-(3-dimethylaminopropyl)carbodiimide hydrochloride (63 mg, 326 μmol), 1-hydroxy-1H-benzotriazole ammonium salt (50 mg, 326 μmol) and DMF (2 mL) were added again, and the mixture was stirred at 40° C. for 3 hrs. The reaction mixture was diluted with a mixed solvent of ethyl acetate-THF, and washed with water, 0.1N hydrochloric acid, saturated aqueous sodium hydrogen carbonate and saturated brine. After drying over anhydrous sodium sulfate, the mixture was concentrated under reduced pressure. The obtained concentrated residue was crystallized from ethanol to give the title compound as a white powder (80 mg, 80%).
melting point: 267-269° C.

Example 190

5-hydroxy-N-{[3-(methyloxy)phenyl]methyl}-4-oxo-3,4-dihydroquinazoline-2-carboxamide To a solution of 2-(4-chlorophenyl)ethanol (87 mg, 556 μmol) in DMA (5 mL) was added sodium hydride (60% in oil, 92 mg, 2.32 mmol), and the mixture was stirred at room temperature for 30 min. 5-Fluoro-N-{[3-(methyloxy)phenyl]methyl}-4-oxo-3,4-dihydroquinazoline-2-carboxamide (150 mg, 463 μmol) obtained in Example 110 was added, and the mixture was stirred with heating at 80° C. for 1 hr. The reaction mixture was cooled to room temperature, adjusted to pH 3-4 with 1N hydrochloric acid, and diluted with ethyl acetate. The organic layer was washed with water and saturated brine and, after drying over anhydrous sodium sulfate, the organic layer was concentrated under reduced pressure. The obtained concentrated residue was crystallized from ethanol to give the title compound as a pale-yellow powder (110 mg, 73%).
melting point: 187-189° C.

Example 191

6-fluoro-5-hydroxy-N-{[3-(methyloxy)phenyl]methyl}-4-oxo-3,4-dihydroquinazoline-2-carboxamide To a solution of 5,6-difluoro-N-{[3-(methyloxy)phenyl]methyl}-4-oxo-3,4-dihydroquinazoline-2-carboxamide (100 mg, 290 μmol) obtained in Example 113 in N,N-dimethylacetamide (2 mL) was added sodium hydride (60% in oil dispersion, 46 mg, 1.16 mmol), and the mixture was stirred at room-temperature for 15 min. 2-Phenylethanol (53 mg, 430 μmol) was added, and the mixture was stirred with heating at room temperature for 3 hrs. The reaction mixture was adjusted to pH 3-4 with 1N hydrochloric acid, and diluted with ethyl acetate. The organic layer was washed with water and saturated brine and, after drying over anhydrous sodium sulfate, the organic layer was concentrated under reduced pressure. The concentrated residue was purified by preparative HPLC. The obtained crude crystals were crystallized from ethanol to give the title compound as a pale-yellow powder (25 mg, 25%).
melting point: 201-203° C.

Example 192

N-{[3-(methyloxy)phenyl]methyl}-4-oxo-5-({[4-(1H-tetrazol-5-yl)phenyl]methyl}oxy)-3,4-dihydroquinazoline-2-carboxamide To a solution of 5-{[(4-cyanophenyl)methyl]oxy}-N-{[3-(methyloxy)phenyl]methyl}-4-oxo-3,4-dihydroquinazoline-2-carboxamide (130 mg, 295 μmol) obtained in Example 187 in DMF (5 mL) were added sodium azide (96 mg, 1.48 mmol) and ammonium chloride (79 mg, 1.48 mmol), and the mixture was stirred with heating at 100° C. for 15 hrs. Sodium azide (96 mg, 1.48 mmol) and ammonium chloride (79 mg, 1.48 mmol) were added again, and the mixture was stirred with heating at 100° C. for 15 hrs. After allowing to cool to room temperature, 1N hydrochloric acid and water were added to the reaction mixture, and the mixture was extracted with a mixed solvent of ethyl acetate-THF. The organic layer was washed with saturated brine and, after drying over anhydrous sodium sulfate, the organic layer was concentrated under reduced pressure. The obtained concentrated residue was crystallized from ethanol to give the title compound as a pale-yellow powder (100 mg, 70%).
melting point: 227-229° C.

Example 193

5-[(2-hydroxyethyl)oxy]-N-{[3-(methyloxy)phenyl]methyl}-4-oxo-3,4-dihydroquinazoline-2-carboxamide To a solution of N-{[3-(methyloxy)phenyl]methyl}-4-oxo-5-({2-[(phenylmethyl)oxy]ethyl}oxy)-3,4-dihydroquinazoline-2-carboxamide (670 mg, 1.46 mmol) obtained in Example 172 in THF (14 mL)-methanol (6 mL) was added 10% palladium carbon (300 mg), and the mixture was stirred under a hydrogen atmosphere (1 atm) at room temperature for 18 hrs. Insoluble material was filtered off, and the reaction mixture was concentrated and dissolved in methanol (20 mL). 10% Palladium carbon (300 mg) was added again, under a hydrogen atmosphere (3 atm), and the mixture was stirred at room temperature for 4 hrs. Insoluble material was filtered off, the reaction mixture was concentrated, and the concentrated residue was crystallized from ethanol to give the title compound as a white powder (327 mg, 61%).

melting point: 173-174° C.

Example 194

5-[(2-hydroxyethyl)oxy]-N-{[3-(methyloxy)phenyl] methyl}-4-oxo-1,2,3,4-tetrahydroquinazoline-2-carboxamide In the same manner as in Example 193, the title compound was obtained as a pale-yellow amorphous form (62 mg, 11%).

$^1$H-NMR (300MHz, DMSO-$d_6$) δ: 3.57-3.66 (2H, m), 3.67 (3H, s), 3.90-3.97 (1H, m), 4.08-4.14 (1H, m), 4.24 (2H, d, J=5.7 Hz), 4.86-4.89 (1H, m), 5.19-5.24 (1H, m), 6.35 (1H, d, J=8.1 Hz), 6.43 (1H, d, J=8.1 Hz), 6.64-6.77 (3H, m), 7.12-7.18 (3H, m), 8.04 (1H, d, J=5.4 Hz), 8.45 (1H, t, J=5.4 Hz).

Example 195

1-[2-({2-[({[3-(methyloxy)phenyl]methyl}amino) carbonyl]-4-oxo-3,4-dihydroquinazolin-5-yl}oxy) ethyl]piperidine-4-carboxylic acid To a suspension of 5-[(2-hydroxyethyl)oxy]-N-{[3-(methyloxy)phenyl]methyl}-4-oxo-3,4-dihydroquinazoline-2-carboxamide (240 mg, 650 μmol) obtained in Example 193 in THF (6 mL) were added triethylamine (181 μL, 1.30 mmol) and p-toluenesulfonyl chloride (186 mg, 975 μmol), and the mixture was stirred at room temperature for 15 hrs. Triethylamine (362 μL, 2.60 mmol), p-toluenesulfonyl chloride (372 mg, 1.95 mmol) and DMF (2 mL) were added again, and the mixture was stirred at room temperature for 15 hrs. The reaction mixture was diluted with ethyl acetate, the organic layer was washed with water and saturated brine and, after drying over anhydrous sodium sulfate, the organic layer was concentrated under reduced pressure. The concentrated residue was purified by silica gel column chromatography (50-83% ethyl acetate/hexane) to give 2-[(1-(dimethylamino)-2-{[3-(methyloxy)phenyl]methyl}-3,9-dioxo-1,2,3,9-tetrahydroimidazo[5,1-b]quinazolin-8-yl)oxy]ethyl 4-methylbenzenesulfonate as a white powder (164 mg, 44%). To a suspension (10 mL) of the above-mentioned compound (125 mg, 216 μmol) and ethyl isonipecotate (40 mg, 259 μmol) in acetonitrile was added N-ethyldiisopropylamine (75 μL, 430 μmol), and the mixture was stirred with heating at 50° C. for 12 hrs. After allowing to cool to room temperature, the reaction mixture was diluted with ethyl acetate, and washed with water and saturated brine. After drying over anhydrous sodium sulfate, the mixture was concentrated. The obtained concentrated residue was dissolved in acetic acid (4 mL). 6N hydrochloric acid (0.8 mL) was added, and the reaction mixture was stirred with heating at 80° C. for 12 hrs. The reaction mixture was concentrated under reduced pressure, water was added, and the mixture was adjusted to pH 5 with 1N aqueous sodium hydroxide solution. The precipitated insoluble material was collected by filtration, and the solid was washed with water to give the title compound as a white powder (77 mg, 74% for 2 steps).

melting point: 127-130° C.

Example 196

1,1-dimethylethyl [({4-[2-({6-fluoro-2-[({[3-(methyloxy)phenyl]methyl}amino)carbonyl]-4-oxo-3,4-dihydroquinazolin-5-yl}oxy)ethyl]phenyl}amino) sulfonyl]carbamate A suspension (6 mL) of 5-{[2-(4-aminophenyl)ethyl] oxy}-6-fluoro-N-{[3-(methyloxy)phenyl]methyl}-4-oxo-3, 4-dihydroquinazoline-2-carboxamide (100 mg, 216 μmol) obtained in Example 181 and {[(1,1-dimethylethyl)oxy]carbonyl}{[4-(dimethyliminio)pyridin-1(4H)-yl] sulfonyl}azanide (synthesized by a method described in *Org. Lett.*, 2001, 3(14), 2241 etc.) (78 mg, 259 μmol) in THF was stirred with heating at 50° C. for 15 hrs. The reaction mixture was diluted with ethyl acetate. The organic layer was washed with 0.1N hydrochloric acid, water and saturated brine and, after drying over anhydrous sodium sulfate, the organic layer was concentrated under reduced pressure to give the title compound as a pale-yellow amorphous form (140 mg, 100%).

$^1$H-NMR (300 MHz, DMSO-$d_6$) δ: 1.33-1.36 (9H, m), 3.05 (2H, t, J=7.5 Hz), 3.73 (3H, s), 4.21-4.26 (2H, m), 4.44 (2H, d, J=6.3 Hz), 4.90 (2H, bs), 6.81-6.83 (1H, m), 6.89-6.92 (2H, m), 7.09 (2H, d, J=8.4 Hz), 7.21-7.29 (3H, m), 7.53 (1H, dd, J=9.3, 4.8 Hz), 7.79 (1H, t, J=9.6 Hz), 9.49-9.53 (1H, m), 10.15 (1H, bs), 11.15 (1H, bs), 12.15 (1H, bs).

Example 197

5-[(2-{4-[(aminosulfonyl)amino]phenyl}ethyl)oxy]-6-fluoro-N-{[3-(methyloxy)phenyl]methyl}-4-oxo-3, 4-dihydroquinazoline-2-carboxamide To a solution of 1,1-dimethylethyl [({4-[2-({6-fluoro-2-[({[3-(methyloxy)phenyl]methyl}amino)carbonyl]-4-oxo-3,4-dihydroquinazolin-5-yl}oxy)ethyl]phenyl}amino)sulfonyl]carbamate (138 mg, 216 μmol) obtained in Example 196 in ethyl acetate (2 mL)-THF (1 mL) was added 4N hydrogen chloride-ethyl acetate (2 mL), and the mixture was stirred at room temperature for 15 hrs. The reaction mixture was concentrated under reduced pressure and crystallized from ethanol to give the title compound as a white powder (58 mg, 50%).

melting point: 204-206° C.

Example 198

6-fluoro-N-{[3-(methyloxy)phenyl]methyl}-4-oxo-5-({2-[4-(5-oxo-1,5-dihydro-4H-1,2,4-triazol-4-yl) phenyl]ethyl}oxy)-3,4-dihydroquinazoline-2-carboxamide To a suspension of 5-{[2-(4-aminophenyl)ethyl]oxy}-6-fluoro-N-{[3-(methyloxy)phenyl]methyl}-4-oxo-3,4-dihydroquinazoline-2-carboxamide (100 mg, 216 μmol) obtained in Example 181, methyl carbazate (21 mg, 240 μmol) and trimethyl orthoformate (25 mg, 240 μmol) in methanol (3 mL) was added p-toluenesulfonic acid monohydrate (1.6 mg, 8.6 μmol), and the mixture was stirred with heating at 50° C. for 4 hrs. Methyl carbazate (7 mg, 80 μmol) and trimethyl orthoformate (8 mg, 80 μmol) were added again, and the mixture was stirred with heating at 50° C. for 2 hrs. The reaction mixture was cooled to room temperature, a solution of sodium methylate (44 mg, 810 μmol) in methanol (1 mL) was added, and the mixture was stirred with heating at 50° C. for 5 hrs. The reaction mixture was cooled to room temperature, and adjusted to pH 3-4 with 1N hydrochloric acid. The mixture was extracted with a mixed solvent of ethyl acetate-THF. The organic layer was washed with water and saturated brine and, after drying over anhydrous sodium sulfate, the organic layer was concentrated under reduced pressure. The obtained concentrated residue was crystallized from ethanol to give the title compound as a pale-yellow powder (99 mg, 86%).
melting point: 196-198° C.

Example 199

5-({2-[4-(2,5-dioxoimidazolidin-1-yl)phenyl]ethyl}oxy)-6-fluoro-N-{[3-(methyloxy)phenyl]methyl}-4-oxo-3,4-dihydroquinazoline-2-carboxamide To a solution of ethyl isocyanatoacetate (46 mg, 350 μmol) in THF (3 mL) was added 5-{[2-(4-aminophenyl)ethyl]oxy}-6-fluoro-N-{[3-(methyloxy)phenyl]methyl}-4-oxo-3,4-dihydroquinazoline-2-carboxamide (150 mg, 324 μmol) obtained in Example 181, and the mixture was stirred at room temperature for 3 hrs. Ethyl isocyanatoacetate (15 mg, 110 μmol) was added again, and the mixture was stirred at room temperature for 1 hr. The reaction mixture was concentrated under reduced pressure, ethanol (4 mL), THF (3 mL) and 6N hydrochloric acid (4 mL) were added and the mixture was heated under reflux for 8 hrs. The reaction mixture was cooled to room temperature, the precipitated solid was collected by filtration, and the solid was washed with ethanol to give the title compound as a pale-yellow powder (155 mg, 88%).
melting point: 181-183° C.

Example 200

{[3-({[(4-oxo-3,4-dihydroquinazolin-2-yl)carbonyl]amino}methyl)phenyl]oxy}acetic acid The title compound was obtained in the same manner as in Example 203 from methyl {[3-({[(4-oxo-3,4-dihydroquinazolin-2-yl)carbonyl]amino}methyl)phenyl]oxy}acetate obtained in Example 228.
melting point: 223-224° C.

Example 201

5-{[3-({[(4-oxo-3,4-dihydroquinazolin-2-yl)carbonyl]amino}methyl)phenyl]oxy}pentanoic acid The title compound was obtained in the same manner as in Example 203 from methyl 5-{[3-({[(4-oxo-3,4-dihydroquinazolin-2-yl)carbonyl]amino}methyl)phenyl]oxy}pentanoate obtained in Example 52.
melting point: 182-183° C.

Example 202

N-[(3-{[2-(methylamino)-2-oxoethyl]oxy}phenyl)methyl]-4-oxo-3,4-dihydroquinazoline-2-carboxamide The title compound was obtained in the same manner as in Example 121 from {[3-({[(4-oxo-3,4-dihydroquinazolin-2-yl)carbonyl]amino}methyl)phenyl]oxy}acetic acid obtained in Example 200 and 40% aqueous methylamine solution.
melting point: 201° C.

Example 203

4-[({[6-(methyloxy)-4-oxo-3,4-dihydroquinazolin-2-yl]carbonyl}amino)methyl]benzoic acid A mixture of methyl 4-[({[6-(methyloxy)-4-oxo-3,4-dihydroquinazolin-2-yl]carbonyl}amino)methyl]benzoate (250 mg, 0.681 mmol) obtained in Example 81, 4N aqueous sodium hydroxide solution (1 mL), THF (5 mL), MeOH (5 mL) and water (5 mL) was stirred at 80° C. for 30 min. The solvent was evaporated under reduced pressure, and the mixture was extracted with a mixture of ethyl acetate-THF. The mixture was washed with 1N hydrochloric acid-saturated brine and saturated brine. After drying over anhydrous sodium sulfate, the solvent was evaporated under reduced pressure. The obtained crude crystals were recrystallized from ethyl acetate to give the title compound (232 mg, 97%) as a white powder.
melting point: 287-288° C.

Example 204

3-[({[6-(methyloxy)-4-oxo-3,4-dihydroquinazolin-2-yl]carbonyl}amino)methyl]benzoic acid The title compound was obtained in the same manner as in Example 203 from methyl 3-[({[6-(methyloxy)-4-oxo-3,4-dihydroquinazolin-2-yl]carbonyl}amino)methyl]benzoate obtained in Example 80.
melting point: 290° C.

Example 205

5-({3-[({[6-(methyloxy)-4-oxo-3,4-dihydroquinazolin-2-yl]carbonyl}amino)methyl]phenyl}oxy)pentanoic acid The title compound was obtained in the same manner as in Example 203 from methyl 5-({3-[({[6-(methyloxy)-4-oxo-3,4-dihydroquinazolin-2-yl]carbonyl}amino)methyl]phenyl}oxy)pentanoate obtained in Example 82.
melting point: 218° C.

Example 206

(−)-6-fluoro-4-oxo-N-({2-[(tetrahydrofuran-3-ylmethyl)oxy]pyridin-4-yl}methyl)-3,4-dihydroquinazoline-2-carboxamide 6-Fluoro-4-oxo-N-({2-[(tetrahydrofuran-3-ylmethyl)oxy]pyridin-4-yl}methyl)-3,4-dihydroquinazoline-2-carboxamide (250 mg) obtained in Example 59 was purified by preparative HPLC, the eluate showing a shorter retention time was concentrated, added hexane and dried to give the title compound as a white powder (110 mg).
HPLC Preparative Conditions
Column: CHIRALPAK AS 50 mmID×500 mmL (CC001)
Mobile phase: n-hexane/ethanol=1/1
Flow rate: 70 mL/min
Temperature: 26° C.
Detection: UV 220 nm
1 shot 40 mg
$[\alpha]_D^{20}$=−12.9° (c=0.498, CHCl$_3$)

Example 207

(+)-6-fluoro-4-oxo-N-({2-[(tetrahydrofuran-3-ylmethyl)oxy]pyridin-4-yl}methyl)-3,4-dihydroquinazoline-2-carboxamide The title compound was obtained in the same manner as in Example 206 as a white powder (109 mg) from the eluate showing a longer retention time and using 6-fluoro-4-oxo-N-({2-[(tetrahydrofuran-3-ylmethyl)oxy]pyridin-4-yl}methyl)-3,4-dihydroquinazoline-2-carboxamide (250 mg) obtained in Example 59.

$[\alpha]_D^{20}$=+11.1° (c=0.481, CHCl$_3$)

Example 208

1-methyl-N-{[3-(methyloxy)phenyl]methyl}-4-oxo-1,4-dihydroquinazoline-2-carboxamide The compound was synthesized in the same manner as in Example 1 from ethyl 1-methyl-4-oxo-1,4-dihydroquinazoline-2-carboxylate obtained by a method described in Chemical & Pharmaceutical Bulletin (1983), 31(7), 2234-43 etc.
melting point: 209-212° C.

The following Example 209 and Example 210 were synthesized in the same manner as in Example 1 from ethyl 4-oxo-3,4-dihydrothieno[2,3-d]pyrimidine-2-carboxylate obtained in Reference Example 26.

Example 209

N-{[3-(methyloxy)phenyl]methyl}-4-oxo-3,4-dihydrothieno[2,3-d]pyrimidine-2-carboxamide melting point: 179-182° C.

Example 210

4-oxo-N-({2-[(tetrahydrofuran-3-ylmethyl)oxy]pyridin-4-yl}methyl)-3,4-dihydrothieno[2,3-d]pyrimidine-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 163-166° C.

Example 211

N-{[4-bromo-3-(methyloxy)phenyl]methyl}-4-oxo-3,4-dihydrothieno[2,3-d]pyrimidine-2-carboxamide To a solution of N-{[3-(methyloxy)phenyl]methyl}-4-oxo-3,4-dihydrothieno[2,3-d]pyrimidine-2-carboxamide (281 mg, 892 μmol) obtained in Example 209 in chloroform (6 mL) was added N-bromosuccinimide (159 mg, 892 μmol), and the mixture was stirred at room temperature for 2 hrs. N-Bromosuccinimide (159 mg, 892 μmol) was added again, and the mixture was stirred at room temperature for 2 hrs. The reaction mixture was concentrated under reduced pressure and partitioned between ethyl acetate and water. The organic layer was washed with saturated brine. After drying over anhydrous sodium sulfate, the organic layer was concentrated. The obtained concentrated residue was purified by preparative HPLC and the obtained crude crystals were crystallized from ethanol to give the title compound as a yellow powder (49 mg, 14%).
melting point: 196-198° C.

Example 212

5-methyl-N-{[3-(methyloxy)phenyl]methyl}-4-oxo-3,4-dihydrothieno[2,3-d]pyrimidine-2-carboxamide The compound was synthesized in the same manner as in Example 1 from ethyl 5-methyl-4-oxo-3,4-dihydrothieno[2,3-d]pyrimidine-2-carboxylate obtained by a method described in U.S. Pat. No. 4,054,656.
melting point: 148-151° C.

Example 213

5-methyl-4-oxo-N-({2-[(tetrahydrofuran-3-ylmethyl)oxy]pyridin-4-yl}methyl)-3,4-dihydrothieno[2,3-d]pyrimidine-2-carboxamide The compound was synthesized in the same manner as in Example 1 from ethyl 5-methyl-4-oxo-3,4-dihydrothieno[2,3-d]pyrimidine-2-carboxylate obtained by the method described in U.S. Pat. No. 4,054,656, using ({2-[(tetrahydrofuran-3-ylmethyl)oxy]pyridin-4-yl}methyl)amine obtained in Reference Example 29 instead of 3-methoxybenzylamine.
melting point: 171° C.

Example 214

6-methyl-4-oxo-N-({2-[(tetrahydrofuran-3-ylmethyl)oxy]pyridin-4-yl}methyl)-3,4-dihydrothieno[2,3-d]pyrimidine-2-carboxamide The compound was synthesized in the same manner as in Example 1 from ethyl 6-methyl-4-oxo-3,4-dihydrothieno[2,3-d]pyrimidine-2-carboxylate obtained by a method described in BE 859818 19780417 etc., using ({2-[(tetrahydrofuran-3-ylmethyl)oxy]pyridin-4-yl}methyl)amine obtained in Reference Example 29 instead of 3-methoxybenzylamine.
melting point: 202-203° C.

Example 215

5,6-dimethyl-4-oxo-N-({2-[(tetrahydrofuran-3-ylmethyl)oxy]pyridin-4-yl}methyl)-3,4-dihydrothieno[2,3-d]pyrimidine-2-carboxamide The compound was synthesized in the same manner as in Example 1 from ethyl 5,6-dimethyl-4-oxo-3,4-dihydrothieno[2,3-d]pyrimidine-2-carboxylate obtained by a method described in U.S. Pat. No. 4,054,656 19771018 etc., using ({2-[(tetrahydrofuran-3-ylmethyl)oxy]pyridin-4-yl}methyl)amine obtained in Reference Example 29 instead of 3-methoxybenzylamine.
melting point: 183° C.

Example 216

N-{[3-(methyloxy)phenyl]methyl}-4-oxo-5-{[(phenylmethyl)oxy]methyl}-3,4-dihydrothieno[2,3-d]pyrimidine-2-carboxamide Step 1

A mixture of ethyl 5-methyl-4-oxo-3,4-dihydrothieno[2,3-d]pyrimidine-2-carboxylate obtained by the method described in U.S. Pat. No. 4,054,656 (1.00 g, 4.20 mmol), N-bromosuccinimide (784 mg, 4.41 mmol), 2,2'-azo-bis-isobutyronitrile (68.9 mg, 0.420 mmol) and carbon tetrachloride (30 mL) was refluxed under heating for 3 hrs. The solvent was evaporated under reduced pressure. The obtained residue was extracted with ethyl acetate, and the mixture was washed with water (3 times) and saturated brine and, after drying over anhydrous sodium sulfate, the solvent was evaporated. The obtained crude crystals were recrystallized from ethyl acetate to give ethyl 5-(bromomethyl)-4-oxo-3,4-dihydrothieno[2,3-d]pyrimidine-2-carboxylate (662 mg, 50%) as a pale-yellow powder.

melting point: 176° C.

Step 2

To a solution of benzyl alcohol (157 μL) in THF (10 mL) was gradually added 60% sodium hydride (116 mg, 3.03 mmol), and the mixture was stirred at room temperature for 10 min. Ethyl 5-(bromomethyl)-4-oxo-3,4-dihydrothieno[2,3-d]pyrimidine-2-carboxylate (400 mg, 1.26 mmol) obtained in Step 1 was added at once, and the mixture was stirred at room temperature for 1 hr. The solvent was evaporated under reduced pressure and the residue was extracted with ethyl acetate. The mixture was washed with 1N hydrochloric acid and 1N hydrochloric acid-saturated brine and, after drying over anhydrous sodium sulfate, the solvent was evaporated. The residue was suspended in diethyl ether, filtrated, dried and suspended in THF (5 mL). Oxalyl chloride (550 μL, 6.31 mmol) and DMF (one drop) were added, and the mixture was stirred at room temperature for 2.5 hrs. The solvent was evaporated under reduced pressure. The obtained residue was dissolved in EtOH-THF (1:1) solution, and the mixture was stirred at room temperature for 12 hrs. The solvent was evaporated under reduced pressure and the residue was extracted with ethyl acetate, washed with water and saturated brine, and dried over anhydrous sodium sulfate. The solvent was evaporated under reduced pressure. The obtained residue was purified by silica gel column chromatography (20-40% ethyl acetate/hexane) to give ethyl 4-oxo-5-{[(phenylmethyl)oxy]methyl}-3,4-dihydrothieno[2,3-d]pyrimidine-2-carboxylate (68.7 mg, 16%) as a colorless powder.

melting point: 155-156° C.

Step 3

The title compound was obtained in the same manner as in Example 1 from ethyl 4-oxo-5-{[(phenylmethyl)oxy]methyl}-3,4-dihydrothieno[2,3-d]pyrimidine-2-carboxylate obtained in Step 2.

melting point: 145° C.

Example 217

4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid To a solution of methyl 4-(hydroxymethyl)benzoate (2.88 g, 17.3 mmol) in THF (35 mL) was gradually added 60% sodium hydride (664 mg, 17.3 mmol) at 0° C., and the mixture was stirred at the same temperature for 30 min. Ethyl 5-(Bromomethyl)-4-oxo-3,4-dihydrothieno[2,3-d]pyrimidine-2-carboxylate (1.69 g, 5.33 mmol) obtained in Example 216, Step 1 was added at once, and the mixture was stirred at room temperature for 12 hrs. The solvent was evaporated under reduced pressure and the residue was extracted with ethyl acetate, the mixture was washed with 1N hydrochloric acid and saturated brine and, after drying over anhydrous sodium sulfate, the solvent was evaporated. The residue was suspended in diethyl ether, filtrated, dried and 690 mg (1.84 mmol) was suspended in THF (7 mL). Oxalyl chloride (804 μL, 9.22 mmol) and DMF (one drop) were added, and the mixture was stirred at room temperature for 5 hrs. The solvent was evaporated under reduced pressure. The obtained residue was dissolved in an EtOH-THF (1:1, 5 mL) solution, and the mixture was stirred at room temperature for 12 hrs. The solvent was evaporated under reduced pressure and the residue was extracted with ethyl acetate, washed with saturated aqueous sodium hydrogen carbonate solution (twice), 1N hydrochloric acid and saturated brine, and dried over anhydrous sodium sulfate. The solvent was evaporated under reduced pressure. The obtained residue was suspended in diethyl ether, filtrated, dried and stirred in EtOH (12 mL) with 1-[3-(methyloxy)phenyl]methanamine (707 μL, 5.53 mmol) at 80° C. for 12 hrs. The solvent was evaporated under reduced pressure, the residue was extracted with ethyl acetate, washed with 0.1N hydrochloric acid (twice), water and saturated brine. After drying over anhydrous sodium sulfate, the solvent was evaporated. The residue was suspended in diethyl ether, filtrated, dried and dissolved in THF-MeOH-water (1:1:1, 45 mL). A solution (1150 μL, 4.61 mmol) of 4N aqueous sodium hydroxide was added, and the mixture was stirred at 80° C. for 1 hr. The solvent was evaporated under reduced pressure and acidified with 1N hydrochloric acid. The mixture was extracted with a mixture of ethyl acetate-THF and washed with saturated brine. After drying over anhydrous sodium sulfate, the solvent was evaporated. The obtained crude crystals were recrystallized from ethyl acetate to give the title compound (348 mg, 39%) as a white powder.

melting point: 229-230° C.

$^1$H-NMR (300MHz, DMSO-$d_6$) δ: ppm 3.73 (3 H, s), 4.41 (2 H, d, J=6.0 Hz), 4.74 (2 H, s), 4.89 (2 H, s), 6.82 (1 H, dd, J=8.5, 1.9 Hz), 6.86-6.97 (2 H, m), 7.24 (1 H, t, J=8.1 Hz), 7.51 (2 H, d, J=8.1 Hz), 7.63 (1 H, s), 7.93 (2 H, d, J=8.3 Hz), 9.66 (1 H, t, J=6.4 Hz), 12.51 (1 H, s), 12.87 (1 H, s).

Example 218

Ethyl 4-({[(4-oxo-2-{[({2-[(tetrahydrofuran-3-ylmethyl)oxy]pyridin-4-yl}methyl)amino]carbonyl}-3,4-dihydrothieno[2,3-d]pyrimidin-5-yl)methyl]oxy}methyl)benzoate A mixture of 4-({[(4-oxo-2-{[({2-[(tetrahydrofuran-3-ylmethyl)oxy]pyridin-4-yl}methyl)amino]carbonyl}-3,4-dihydrothieno[2,3-d]pyrimidin-5-yl)methyl]oxy}methyl)benzoic acid (100 mg, 0.182 mmol) obtained in Example 220, 1-ethyl-3-(3-dimethylaminopropyl)-carbodiimide hydrochloride (46.9 mg, 0.273 mmol), N,N-dimethylpyridine-4-amine (2.2 mg, 0.018 mmol), EtOH (100 μL, 1.72 mmol) and THF (4 mL) was stirred at room temperature for 12 hrs. The solvent was evaporated under reduced pressure, and the mixture was extracted with a mixture of ethyl acetate-THF, and washed with 0.1N hydrochloric acid (twice) and saturated brine and, after drying over anhydrous sodium sulfate, the solvent was evaporated under reduced pressure. The obtained crude crystals were recrystallized from ethyl acetate to give the title compound (78 mg, 74%) as a white powder.

melting point: 225° C.

Example 219

4-oxo-5-{[(phenylmethyl)oxy]methyl}-N-({2-[(tetrahydrofuran-3-ylmethyl)oxy]pyridin-4-yl}methyl)-3,4-dihydrothieno[2,3-d]pyrimidine-2-carboxamide The title compound was synthesized in the same manner as in Example 1 from ethyl 4-oxo-5-{[(phenylmethyl)oxy]methyl}-3,4-dihydrothieno[2,3-d]pyrimidine-2-carboxylate obtained in Example 216, Step 2, using ({2-[(tetrahydrofuran-3-ylmethyl)oxy]pyridin-4-yl}methyl)amine obtained in Reference Example 29 instead of 3-methoxybenzylamine.

melting point: 141-142° C.

Example 220

4-({[(4-oxo-2-{[({2-[(tetrahydrofuran-3-ylmethyl)oxy]pyridin-4-yl}methyl)amino]carbonyl}-3,4-dihydrothieno[2,3-d]pyrimidin-5-yl)methyl]oxy}methyl)benzoic acid The compound was synthesized in the same manner as in Example 217, using ({2-[(tetrahydrofuran-3-ylmethyl)oxy]pyridin-4-yl}methyl)amine obtained in Reference Example 29, instead of 1-[3-(methyloxy)phenyl]methanamine.
melting point: 209° C.

Example 221 and Example 222 were synthesized in the same manner as in Example 1 from ethyl 4-oxo-3,4-dihydrothieno[3,2-d]pyrimidine-2-carboxylate obtained in Reference Example 27.

Example 221

N-{[3-(methyloxy)phenyl]methyl}-4-oxo-3,4-dihydrothieno[3,2-d]pyrimidine-2-carboxamide melting point: 201-202° C.

Example 222

4-oxo-N-({2-[(tetrahydrofuran-3-ylmethyl)oxy]pyridin-4-yl}methyl)-3,4-dihydrothieno[3,2-d]pyrimidine-2-carboxamide The compound was synthesized using ({2-[(tetrahydrofuran-3-ylmethyl)oxy]pyridin-4-yl}methyl)amine obtained in Reference Example 29 instead of 3-methoxybenzylamine.
melting point: 181-183° C.

Example 223

N-{[3-(methyloxy)phenyl]methyl}-4-oxo-3,4-dihydropyrido[2,3-d]pyrimidine-2-carboxamide The compound was synthesized in the same manner as in Example 1 from ethyl 4-oxo-3,4-dihydropyrido[2,3-d]pyrimidine-2-carboxylate obtained in Reference Example 24.
melting point: 181-183° C.

Example 224

N-{[3-(methyloxy)phenyl]methyl}-4-oxo-3,4-dihydropyrido[3,4-d]pyrimidine-2-carboxamide The compound was synthesized in the same manner as in Example 1 from ethyl 4-oxo-3,4-dihydropyrido[3,4-d]pyrimidine-2-carboxylate obtained in Reference Example 25.
melting point: 231-233° C.

Example 225

N-{[3-(methyloxy)phenyl]methyl}-1-oxo-1,2-dihydroisoquinoline-3-carboxamide

A solution of 1-oxo-1,2-dihydroisoquinoline-3-carboxylic acid (105 mg) obtained in Reference Example 99, 3-methoxybenzylamine (98 mg), 1-hydroxy-1-H-benzotriazole monohydrate (95 mg) and 1-ethyl-3-(3-dimethylaminopropyl)carbodiimide hydrochloride (130 mg) in DMF (5 mL) was stirred at room temperature for 1 day. 10% Aqueous citric acid solution was added to the reaction mixture and the mixture was extracted with ethyl acetate. The organic layer was washed with water, aqueous sodium hydrogen carbonate and saturated brine, dried and concentrated. The obtained crude crystals were washed with ethyl acetate to give the title compound (39 mg).
melting point: 206-210° C.

Example 226

1-oxo-N-({2-[(tetrahydrofuran-3-ylmethyl)oxy]pyridin-4-yl}methyl)-1,2-dihydroisoquinoline-3-carboxamide The compound was synthesized in the same manner as in Example 225, using ({2-[(tetrahydrofuran-3-ylmethyl)oxy]pyridin-4-yl}methyl)amine obtained in Reference Example 29 instead of 3-methoxybenzylamine.
melting point: 208-210° C.

Example 227

N-[(3-aminophenyl)methyl]-4-oxo-3,4-dihydroquinazoline-2-carboxamide

The title compound was obtained in the same manner as in Example 1 using 3-aminobenzylamine instead of 3-methoxybenzylamine.
melting point: 229-238° C.

Example 228

Methyl {[3-({[(4-oxo-3,4-dihydroquinazolin-2-yl)carbonyl]amino}methyl)phenyl]oxy}acetate The title compound was obtained in the same manner as in Example 1 using methyl {[3-(aminomethyl)phenyl]oxy}acetate hydrochloride obtained in Reference Example 89 instead of 3-methoxybenzylamine.
melting point: 154° C.

The structural formulas of compounds synthesized in Examples 1-228 are described in the following.

TABLE 1

| Example No. | Ar | R1 | R2 | R3 | R4 |
|---|---|---|---|---|---|
| 1 | 3-methoxyphenyl | H | H | H | H |
| 2 | 4-fluorophenyl-O-(5-methylpyridin-2-yl) | H | H | H | H |

TABLE 1-continued

| Example No. | Ar | R1 | R2 | R3 | R4 |
|---|---|---|---|---|---|
| 3 | 4-phenoxyphenylmethyl | H | H | H | H |
| 4 | 3-phenoxyphenylmethyl | H | H | H | H |
| 5 | 4-biphenylmethyl | H | H | H | H |
| 6 | 3-biphenylmethyl | H | H | H | H |
| 7 | 4-fluorophenylmethyl | H | H | H | H |
| 8 | 2-biphenylmethyl | H | H | H | H |
| 9 | 3-(trifluoromethoxy)phenylmethyl | H | H | H | H |
| 10 | 3-(trifluoromethyl)phenylmethyl | H | H | H | H |

TABLE 2

| Example No. | Ar | R1 | R2 | R3 | R4 |
|---|---|---|---|---|---|
| 11 | 3-methylphenyl | H | H | H | H |
| 12 | 2-methoxyphenyl | H | H | H | H |
| 13 | 2-methoxy-4-methylpyridin-yl | H | H | H | H |
| 14 | (tetrahydrofuran-3-yl)methoxy-4-methylpyridinyl | H | H | H | H |
| 15 | 3-aminomethylphenyl | H | H | H | H |
| 16 | (2-methoxy-2-methylpropoxy)-4-methylpyridinyl | H | H | H | H |
| 17 | (furan-3-yl)methoxy-4-methylpyridinyl | H | H | H | H |
| 18 | 2-(3-methoxypropoxy)-4-methylpyridinyl | H | H | H | H |
| 19 | 2-(3-methoxypropylamino)-4-methylpyridinyl | H | H | H | H |
| 20 | 2-(tetrahydrofuran-3-yloxy)-4-methylpyridinyl | H | H | H | H |
| 21 | 2-((3-methyloxetan-3-yl)methoxy)-4-methylpyridinyl | H | H | H | H |

TABLE 3

| Example No. | Ar | R1 | R2 | R3 | R4 |
|---|---|---|---|---|---|
| 22 | Me-O-CH2CH2CH2-NH-(4-methylpyridin-2-yl) | H | H | H | H |
| 23 | (Me)2CH-O-CH2CH2-NH-(4-methylpyridin-2-yl) | H | H | H | H |
| 24 | (tetrahydropyran-4-yl)-O-(4-methylpyridin-2-yl) | H | H | H | H |
| 25 | (furan-2-yl)-CH2-O-(4-methylpyridin-2-yl) | H | H | H | H |
| 26 | phenyl-CH2-O-(4-methylpyridin-2-yl) | H | H | H | H |
| 27 | (4-fluorophenyl)-O-(4-methylpyridin-2-yl) | H | H | H | H |
| 28 | (3,4-dimethoxyphenyl)-O-(4-methylpyridin-2-yl) | H | H | H | H |
| 29 | (tetrahydrofuran-3-yl)-CH2-O-(3-methylphenyl) | H | H | H | H |
| 30 | 4-(3-methylphenyl)morpholine | H | H | H | H |
| 31 | 3-methylbenzonitrile | H | H | H | H |

TABLE 3-continued

| Example No. | Ar | R1 | R2 | R3 | R4 |
|---|---|---|---|---|---|
| 32 | (tetrahydropyran-4-yl)-CH2-O-(4-methylpyridin-2-yl) | H | H | H | H |

TABLE 4

| Example No. | Ar | R1 | R2 | R3 | R4 |
|---|---|---|---|---|---|
| 33 | (thiophen-3-yl)-CH2-O-(4-methylpyridin-2-yl) | H | H | H | H |
| 34 | (4-methoxyphenyl)-CH2-O-(4-methylpyridin-2-yl) | H | H | H | H |
| 35 | 6-(3-methylphenyl)-3,4-dihydro-2H-benzo[b][1,4]oxazin-3-imine | H | H | H | H |
| 36 | (3-methoxyphenyl)-CH2-O-(4-methylpyridin-2-yl) | H | H | H | H |
| 37 | (benzo[d][1,3]dioxol-5-yl)-CH2-O-(4-methylpyridin-2-yl) | H | H | H | H |
| 38 | (3-fluorophenyl)-CH2-O-(4-methylpyridin-2-yl) | H | H | H | H |

TABLE 4-continued

| Example No. | Ar | R1 | R2 | R3 | R4 |
|---|---|---|---|---|---|
| 39 | 4-fluorobenzyloxy-4-methylpyridine | H | H | H | H |
| 40 | (pyridin-2-yl)methoxy-4-methylpyridine | H | H | H | H |
| 41 | (pyridin-3-yl)methoxy-4-methylpyridine | H | H | H | H |
| 42 | (pyridin-4-yl)methoxy-4-methylpyridine | H | H | H | H |

TABLE 5

| Example No. | Ar | R1 | R2 | R3 | R4 |
|---|---|---|---|---|---|
| 43 | (5-methylisoxazol-3-yl)methoxy-4-methylpyridine | H | H | H | H |
| 44 | (3,5-dimethylisoxazol-4-yl)methoxy-4-methylpyridine | H | H | H | H |
| 45 | (biphenyl-4-yl)methoxy-4-methylpyridine | H | H | H | H |
| 46 | 2-ethoxy-4-methylpyridine | H | H | H | H |
| 47 | 2-fluoro-5-methyl-methoxybenzene | H | H | H | H |
| 48 | 4-pentylmorpholine | H | H | H | H |
| 49 | 4-butylmorpholine | H | H | H | H |

TABLE 5-continued

| Example No. | Ar | R1 | R2 | R3 | R4 |
|---|---|---|---|---|---|
| 50 | 3-ethyl-methoxybenzene (Me-O, Et) | H | H | H | H |
| 51 | 3-methyl-ethoxybenzene (MeCH2O, Me) | H | H | H | H |
| 52 | methyl 5-(3-methylphenoxy)pentanoate | H | H | H | H |
| 53 | tert-butyl (3-methylbenzyl)carbamate | H | H | H | H |

TABLE 6

| Example No. | Ar | R1 | R2 | R3 | R4 |
|---|---|---|---|---|---|
| 54 | 3-methyl-methoxybenzene | H | F | H | H |
| 55 | 2-methyl-methoxybenzene | H | F | H | H |
| 56 | 4-methyl-methoxybenzene | H | F | H | H |
| 57 | 2-(furan-3-ylmethoxy)-4-methylpyridine | H | F | H | H |
| 58 | 2-(3-methoxypropoxy)-4-methylpyridine | H | F | H | H |
| 59 | 4-methyl-2-((tetrahydrofuran-3-yl)methoxy)pyridine | H | F | H | H |
| 60 | 4-methyl-2-((tetrahydrofuran-3-yl)oxy)pyridine | H | F | H | H |
| 61 | 2-(4-fluorophenoxy)-4-methylpyridine | H | F | H | H |
| 62 | 3-((tetrahydrofuran-3-yl)methoxy)toluene | H | F | H | H |
| 63 | 4-methyl-2-((tetrahydro-2H-pyran-4-yl)methoxy)pyridine | H | F | H | H |
| 64 | 2-methoxy-4-methylpyridine | H | F | H | H |

TABLE 7
| Example No. | Ar | R1 | R2 | R3 | R4 |
|---|---|---|---|---|---|
| 65 | 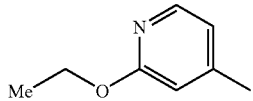 | H | F | H | H |
| 66 | 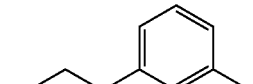 | H | F | H | H |
| 67 | 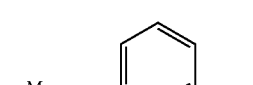 | H | OMe | H | H |
| 68 | 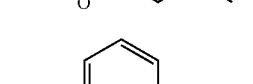 | H | OMe | H | H |
| 69 | 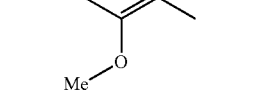 | H | OMe | H | H |
| 70 | 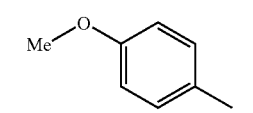 | H | OMe | H | H |
| 71 | 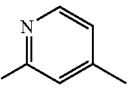 | H | OMe | H | H |
| 72 | 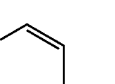 | H | OMe | H | H |
| 73 | 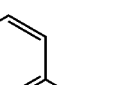 | H | OMe | H | H |
| 74 | 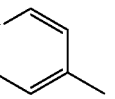 | H | OMe | H | H |
| 75 | 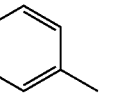 | H | OMe | H | H |
TABLE 8
| Example No. | Ar | R1 | R2 | R3 | R4 |
|---|---|---|---|---|---|
| 76 | 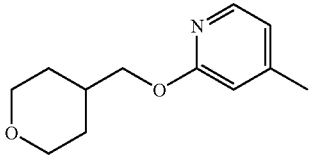 | H | OMe | H | H |
| 77 | 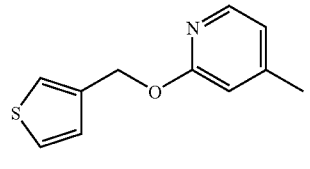 | H | OMe | H | H |
| 78 | 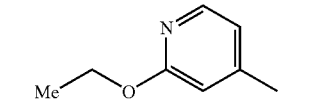 | H | OMe | H | H |
| 79 | 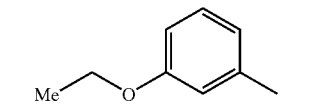 | H | OMe | H | H |

TABLE 8-continued
| Example No. | Ar | R1 | R2 | R3 | R4 |
|---|---|---|---|---|---|
| 80 | 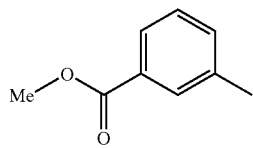 | H | OMe | H | H |
| 81 | 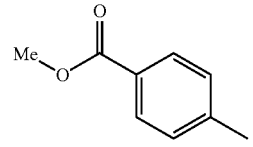 | H | OMe | H | H |
| 82 | 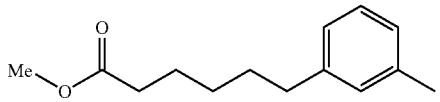 | H | OMe | H | H |
| 83 | 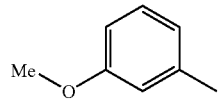 | H | Cl | H | H |
| 84 | 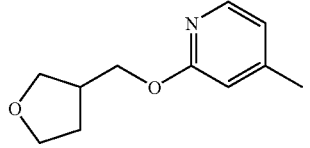 | H | Cl | H | H |
| 85 | 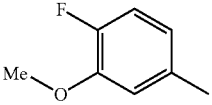 | H | Cl | H | H |
TABLE 9
| Example No. | Ar | R1 | R2 | R3 | R4 |
|---|---|---|---|---|---|
| 86 | 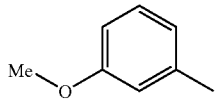 | H | NO$_2$ | H | H |
| 87 | 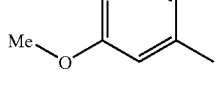 | H | Me | H | H |
| 88 | 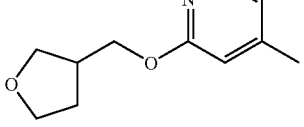 | H | Me | H | H |
| 89 | 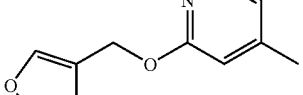 | H | Me | H | H |
| 90 | 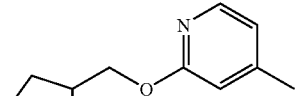 | H | CF$_3$ | H | H |
| 91 | 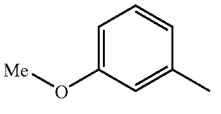 | H | CF$_3$ | H | H |

TABLE 9-continued
| Example No. | Ar | R1 | R2 | R3 | R4 |
|---|---|---|---|---|---|
| 92 | 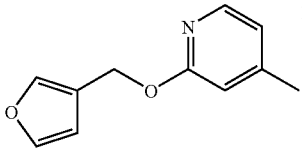 | H | OCF$_3$ | H | H |
| 93 | 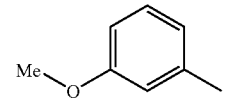 | H | OCF$_3$ | H | H |
| 94 | 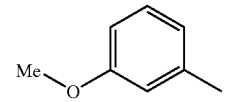 | OMe | H | H | H |
TABLE 9-continued
| Example No. | Ar | R1 | R2 | R3 | R4 |
|---|---|---|---|---|---|
| 95 | 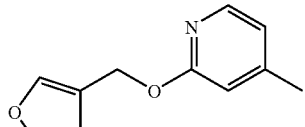 | OMe | H | H | H |
| 96 | 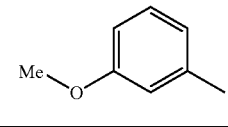 | H | H | OMe | H |
TABLE 10
| Example No. | Ar | R1 | R2 | R3 | R4 |
|---|---|---|---|---|---|
| 97 | 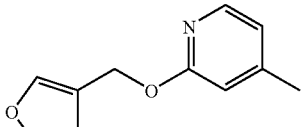 | H | H | OMe | H |
| 98 | 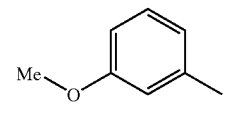 | H | H | H | OMe |
| 99 | 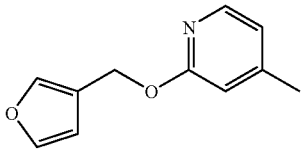 | H | H | H | OMe |
| 100 | 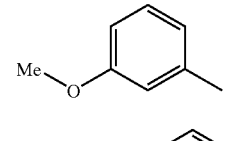 | H | NH$_2$ | H | H |
| 101 | 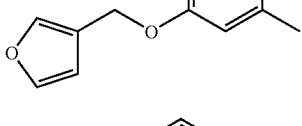 | H | NH$_2$ | H | H |
| 102 | 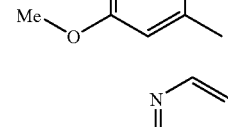 | H | OCH$_2$Ph | H | H |
| 103 | 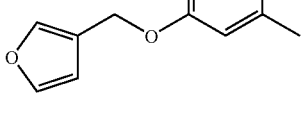 | H | OCH$_2$Ph | H | H |

TABLE 10-continued
| Example No. | Ar | R1 | R2 | R3 | R4 |
|---|---|---|---|---|---|
| 104 | 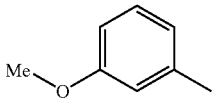 | H | I | H | H |
| 105 | 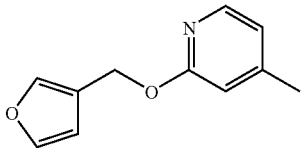 | H | I | H | H |
| 106 | 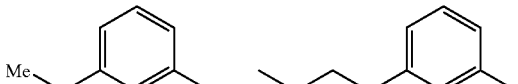 | 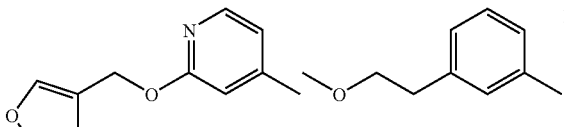 | H | H | H |
| 107 | 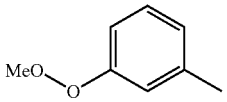 | | H | H | H |
TABLE 11
| Example No. | Ar | R1 | R2 | R3 | R4 |
|---|---|---|---|---|---|
| 108 | 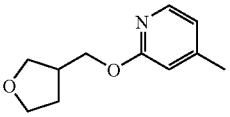 | Me | H | H | H |
| 109 | 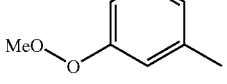 | Me | H | H | H |
| 110 | 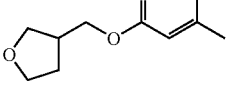 | F | H | H | H |
| 111 | 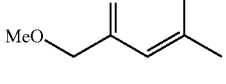 | F | H | H | H |
| 112 | 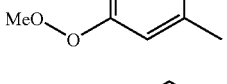 | F | H | H | H |
| 113 | 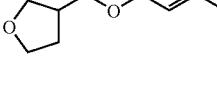 | F | F | H | H |
| 114 | | F | F | H | H |
| 115 | 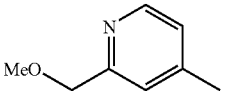 | F | F | H | H |
| 116 |  | H |  | H | H |
| 117 | 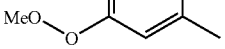 | H |  | H | H |
| 118 | 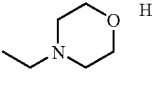 | H | CH$_2$OMe | H | H |
TABLE 12
| Example No. | Ar | R1 | R2 | R3 | R4 |
|---|---|---|---|---|---|
| 119 |  | H | CN | H | H |

TABLE 12-continued

| Example No. | Ar | R1 | R2 | R3 | R4 |
|---|---|---|---|---|---|
| 120 | 2-F, 5-Me, 4-MeO-phenyl | H | CN | H | H |
| 125 | 3-(MeSO2NH)-phenyl with methyl | H | H | H | H |
| 126 | 3-(MeNHC(O)NH)-phenyl with methyl | H | H | H | H |
| 127 | 3-(AcNH)-phenyl with methyl | H | H | H | H |
| 128 | 3-(MeOC(O)C(O)NH)-phenyl with methyl | H | H | H | H |
| 129 | 3-(MeOC(O)CH2C(O)NH)-phenyl with methyl | H | H | H | H |

TABLE 13

| Example No. | Ar | R1 | R2 | R3 | R4 |
|---|---|---|---|---|---|
| 130 | 3-(MeOC(O)NH)-phenyl with methyl | H | H | H | H |
| 131 | 3-(MeSO2NHCH2)-phenyl with methyl | H | H | H | H |
| 132 | 3-(MeNHC(O)NHCH2)-phenyl with methyl | H | H | H | H |
| 133 | 3-(AcNHCH2)-phenyl with methyl | H | H | H | H |
| 134 | 3-(MeOC(O)C(O)NHCH2)-phenyl with methyl | H | H | H | H |
| 135 | 3-(tetrahydrofuran-3-yl-C(O)NH)-phenyl with methyl | H | H | H | H |
| 136 | 3-(furan-3-yl-C(O)NH)-phenyl with methyl | H | H | H | H |
| 137 | 3-(tetrahydrofuran-3-yl-C(O)NHCH2)-phenyl with methyl | H | H | H | H |
| 138 | 3-(furan-3-yl-C(O)NHCH2)-phenyl with methyl | H | H | H | H |
| 139 | 3-MeO-phenyl with methyl | H | NHCOEt | H | H |
| 140 | 2-(tetrahydrofuran-3-ylmethoxy)-4-methylpyridin-yl | H | NHCOMe | H | H |

TABLE 14

| Example No. | Ar | R1 | R2 | R3 | R4 |
|---|---|---|---|---|---|
| 141 | 3-MeO-phenyl with methyl | H | NHMs | H | H |
| 142 | 2-(tetrahydrofuran-3-ylmethoxy)-4-methylpyridin-yl | H | NHMs | H | H |
| 143 | 3-MeO-phenyl with methyl | H | NHCOCH2OPh | H | H |

TABLE 15
| Example No. | Ar | R1 | R2 | R3 | R4 |
|---|---|---|---|---|---|
| 144 | 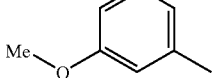 | H | OH | H | H |
| 145 | 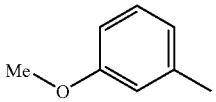 | H | OEt | H | H |
| 146 | 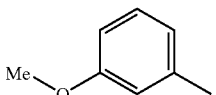 | H | CN | H | H |
| 147 | 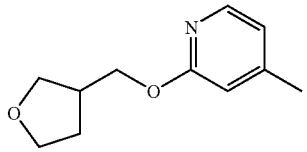 | H | CN | H | H |
| 148 | 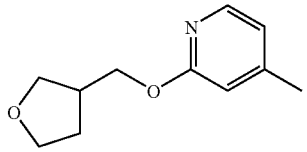 | H | CONH$_2$ | H | H |
| 149 | 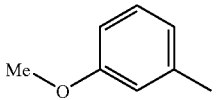 | H | 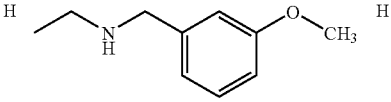 | H | H |
| 150 | 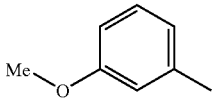 | H | Ph | H | H |
| 151 | 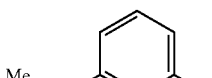 | H | 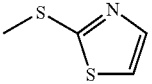 | H | H |
| 152 | 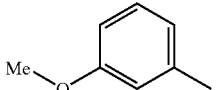 | H | OCSNMe$_2$ | H | H |
TABLE 16
| Example No. | Ar | R1 | R2 | R3 | R4 |
|---|---|---|---|---|---|
| 153 | 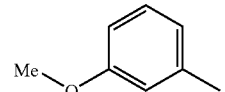 | H | SCONMe$_2$ | H | H |
| 154 | 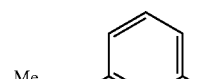 | H | SH | H | H |

TABLE 16-continued

| Example No. | Ar | R1 | R2 | R3 | R4 |
|---|---|---|---|---|---|
| 155 | 3-MeO-C6H4- | H | SMe | H | H |
| 156 | 3-MeO-C6H4- | H | SO2Me | H | H |
| 157 | 3-MeO-C6H4- | H | OCH2COPh | H | H |
| 158 | 3-MeO-C6H4- | H | 5-methyl-1H-tetrazol-yl | H | H |
| 159 | 3-MeO-C6H4- | OCH2Ph | H | H | H |
| 160 | 3-MeO-C6H4- | OCH2CH2CH2Ph | H | H | H |
| 161 | 3-MeO-C6H4- | SCH2CH2Ph | H | H | H |
| 162 | 3-MeO-C6H4- | 4-(OCH2)-C6H4-COOH | H | H | H |

TABLE 17

| Example No. | Ar | R1 | R2 | R3 | R4 |
|---|---|---|---|---|---|
| 163 | 3-MeO-C6H4- | 4-F-C6H4-CH2O- | H | H | H |
| 164 | 3-MeO-C6H4- | 4-MeO-C6H4-CH2O- | H | H | H |
| 165 | 3-MeO-C6H4- | (pyridin-3-yl)-CH2O- | H | H | H |

TABLE 18
| Example No. | Ar | R1 | R2 | R3 | R4 |
|---|---|---|---|---|---|
| 166 | 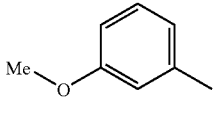 | 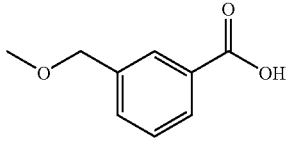 | H | H | H |
| 167 | 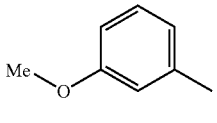 | 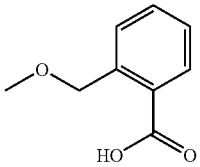 | H | H | H |
| 168 | 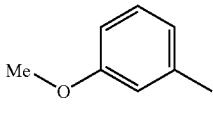 | 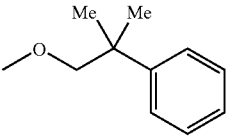 | H | H | H |
| 169 | 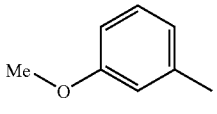 | 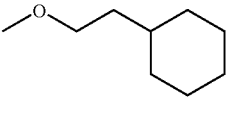 | H | H | H |
| 170 | 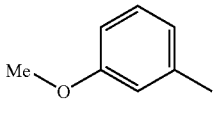 | 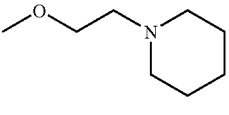 | H | H | H |
| 171 | 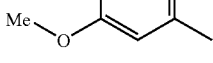 |  | H | H | H |
| 172 | 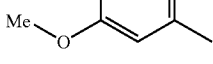 |  | H | H | H |
| 173 | 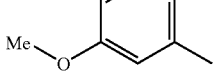 | 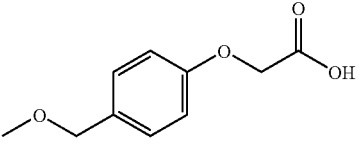 | H | H | H |
| 174 | 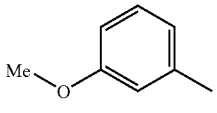 | 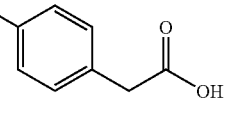 | H | H | H |
TABLE 19
| Example No. | Ar | R1 | R2 | R3 | R4 |
|---|---|---|---|---|---|
| 175 | 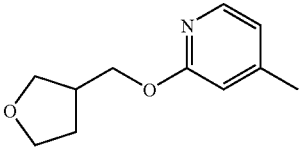 | 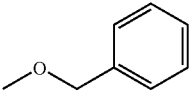 | H | H | H |

TABLE 19-continued
| Example No. | Ar | R1 | R2 | R3 | R4 |
|---|---|---|---|---|---|
| 176 | 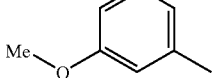 | 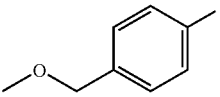 | F | H | H |
| 177 | 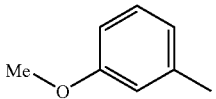 | 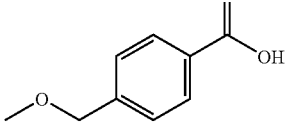 | F | H | H |
| 178 | 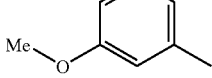 | 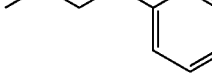 | F | H | H |
| 179 | 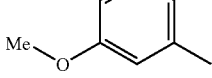 | 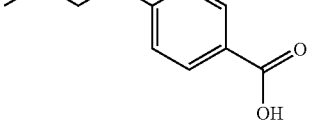 | F | H | H |
| 180 | 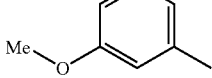 | 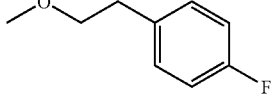 | F | H | H |
| 181 | 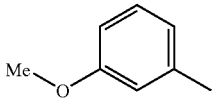 | 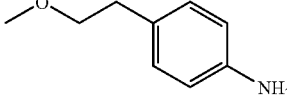 | H | H | H |
| 182 | 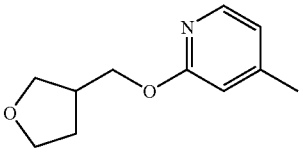 | 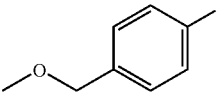 | F | H | H |
| 183 | 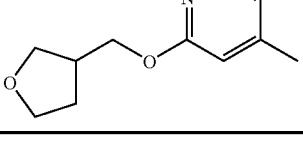 | 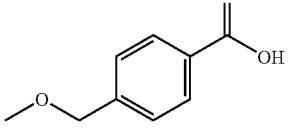 | F | H | H |
TABLE 20
| Example No. | Ar | R1 | R2 | R3 | R4 |
|---|---|---|---|---|---|
| 184 | 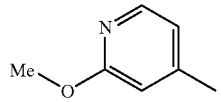 | 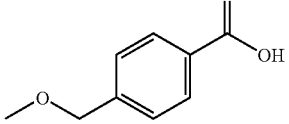 | F | H | H |
| 185 | 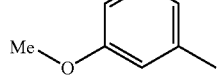 | NHCH$_2$CH$_2$Ph | H | H | H |

TABLE 20-continued
| Example No. | Ar | R1 | R2 | R3 | R4 |
|---|---|---|---|---|---|
| 186 | 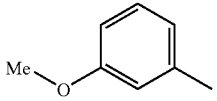 | 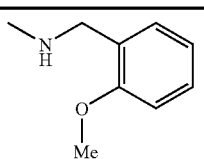 | F | H | H |
TABLE 21
| Example No. | Ar | R1 | R2 | R3 | R4 |
|---|---|---|---|---|---|
| 187 | 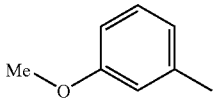 | 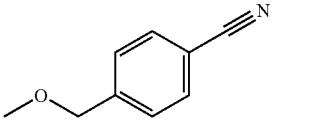 | H | H | H |
| 188 | 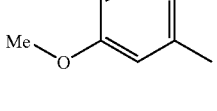 | 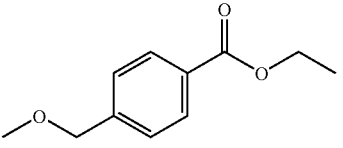 | H | H | H |
| 189 | 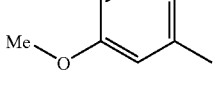 | 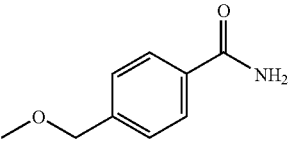 | H | H | H |
| 190 | 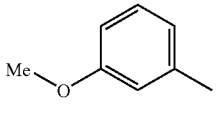 | OH | H | H | H |
| 191 | 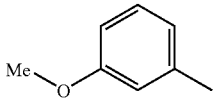 | OH | F | H | H |
| 192 | 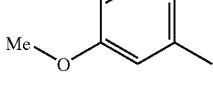 | 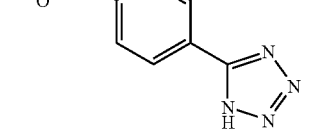 | H | H | H |
| 193 | 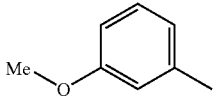 | 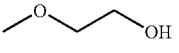 | H | H | H |
| 195 | 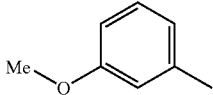 | 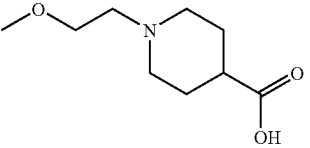 | H | H | H |

TABLE 21-continued

| Example No. | Ar | R1 | R2 | R3 | R4 |
|---|---|---|---|---|---|
| 196 | 3-MeO-phenyl-O-CH2CH2- | 4-(NHS(O)2NHC(O)O-tBu)phenyl | F | H | H |

TABLE 22

| Example No. | Ar | R1 | R2 | R3 | R4 |
|---|---|---|---|---|---|
| 197 | 3-MeO-phenyl-O-CH2CH2- | 4-(NHS(O)2NH2)phenyl | F | H | H |
| 198 | 3-MeO-phenyl-O-CH2CH2- | 4-(5-oxo-4,5-dihydro-1H-1,2,4-triazol-4-yl)phenyl | F | H | H |
| 199 | 3-MeO-phenyl-O-CH2CH2- | 4-(2,5-dioxoimidazolidin-1-yl)phenyl | F | H | H |
| 200 | 3-methylphenoxy-CH2-COOH | H | H | H | H |
| 201 | 3-methylphenoxy-(CH2)3-COOH | H | H | H | H |
| 202 | 3-methylphenoxy-CH2-C(O)NHMe | H | H | H | H |
| 203 | 4-methylbenzoic acid (OH) | H | OMe | H | H |
| 204 | 3-methylbenzoic acid | H | OMe | H | H |

TABLE 22-continued

| Example No. | Ar | R1 | R2 | R3 | R4 |
|---|---|---|---|---|---|
| 205 | HOOC-(CH2)3-O-(3-methylphenyl) | H | OMe | H | H |
| 206 | (tetrahydrofuran-3-yl)methyl-O-(4-methylpyridin-2-yl), (−)-form | H | F | H | H |
| 207 | (tetrahydrofuran-3-yl)methyl-O-(4-methylpyridin-2-yl), (+)-form | H | F | H | H |

TABLE 23

| Example No. | Compound structure |
|---|---|
| 121 | 6,7-dimethoxy-1,2,3,4-tetrahydroisoquinolin-2-yl carbonyl-quinazolin-4(3H)-one |
| 122 | 4-phenylpiperidin-1-yl carbonyl-quinazolin-4(3H)-one |
| 123 | 4-phenylpiperazin-1-yl carbonyl-quinazolin-4(3H)-one |
| 124 | 4-phenoxypiperidin-1-yl carbonyl-quinazolin-4(3H)-one |
| 194 | N-(3-methoxybenzyl)-5-(2-hydroxyethoxy)-4-oxo-1,2,3,4-tetrahydroquinazoline-2-carboxamide |
| 208 | N-(3-methoxybenzyl)-1-methyl-4-oxo-1,4-dihydroquinazoline-2-carboxamide |

TABLE 24
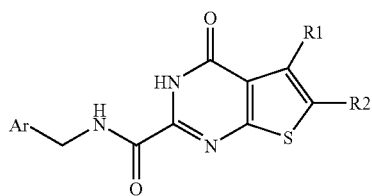
| Example No. | Ar | R1 | R2 |
|---|---|---|---|
| 209 | 3-MeO-phenyl | H | H |
| 210 | 4-methyl-2-(tetrahydrofuran-3-ylmethoxy)pyridin-yl | H | H |
| 211 | 2-Br-5-MeO-phenyl | H | H |
| 212 | 3-MeO-phenyl | Me | H |
| 213 | 4-methyl-2-(tetrahydrofuran-3-ylmethoxy)pyridin-yl | Me | H |
| 214 | 4-methyl-2-(tetrahydrofuran-3-ylmethoxy)pyridin-yl | H | Me |
| 215 | 4-methyl-2-(tetrahydrofuran-3-ylmethoxy)pyridin-yl | Me | Me |
| 216 | 3-MeO-phenyl | $CH_2OCH_2Ph$ | H |
| 217 | 3-MeO-phenyl | 4-(ethoxymethyl)benzoic acid | H |

TABLE 24-continued

| Example No. | Ar | R1 | R2 |
|---|---|---|---|
| 218 | (tetrahydrofuran-3-ylmethoxy)-4-methylpyridin-2-yl | 4-(ethoxymethyl)benzoic acid ethyl ester | H |

TABLE 25

| Example No. | Ar | R1 | R2 |
|---|---|---|---|
| 219 | (tetrahydrofuran-3-ylmethoxy)-4-methylpyridin-2-yl | CH$_2$OCH$_2$Ph | H |
| 220 | (tetrahydrofuran-3-ylmethoxy)-4-methylpyridin-2-yl | 4-(ethoxymethyl)benzoic acid | H |

TABLE 26

| Example No. | Ar | R1 | R2 |
|---|---|---|---|
| 221 | 3-methoxyphenyl | H | H |
| 222 | (tetrahydrofuran-3-ylmethoxy)-4-methylpyridin-2-yl | H | H |

TABLE 27

| Example No. | Compound structure |
|---|---|
| 223 | 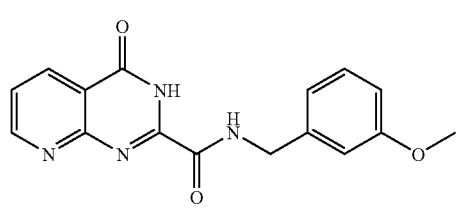 [SMILES: COc1cccc(CNC(=O)c2nc3ncccc3c(=O)[nH]2)c1] |
| 224 | 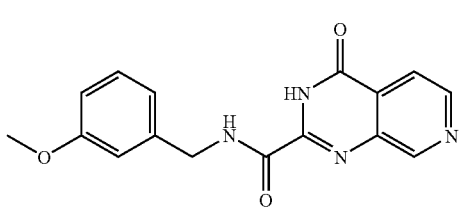 [SMILES: COc1cccc(CNC(=O)c2nc3cnccc3c(=O)[nH]2)c1] |

TABLE 27-continued

| Example No. | Compound structure |
|---|---|
| 225 | 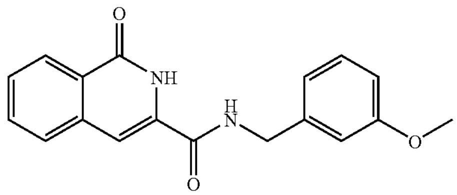 [SMILES: COc1cccc(CNC(=O)c2cc3ccccc3c(=O)[nH]2)c1] |
| 226 | 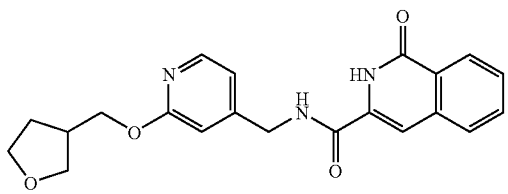 [SMILES: O=C(NCc1ccnc(OCC2CCOC2)c1)c1cc2ccccc2c(=O)[nH]1] |
| 227 | 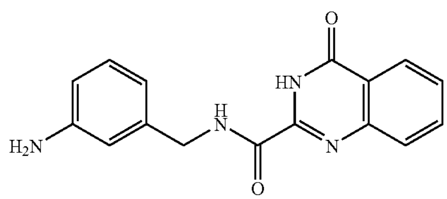 [SMILES: Nc1cccc(CNC(=O)c2nc3ccccc3c(=O)[nH]2)c1] |
| 228 | 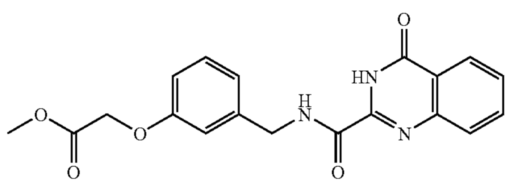 [SMILES: COC(=O)COc1cccc(CNC(=O)c2nc3ccccc3c(=O)[nH]2)c1] |

Example 229

6-cyano-N-{[2-(methyloxy)pyridin-4-yl]methyl}-4-oxo-3,4-dihydroquinazoline-2-carboxamide

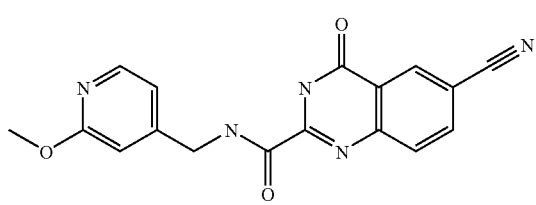 [SMILES: COc1cc(CNC(=O)c2nc3ccc(C#N)cc3c(=O)[nH]2)ccn1]

The title compound was obtained by a method similar to that of Example 1 using [(2-methoxypyridin-4-yl)methyl]amine (synthesized by a method described in Journal of Medicinal Chemistry (1993), 36(15), 2362-2372) instead of 3-methoxybenzylamine.

melting point: 246-247° C.

Example 230

6-cyano-N-{[2-(ethyloxy)pyridin-4-yl]methyl}-4-oxo-3,4-dihydroquinazoline-2-carboxamide

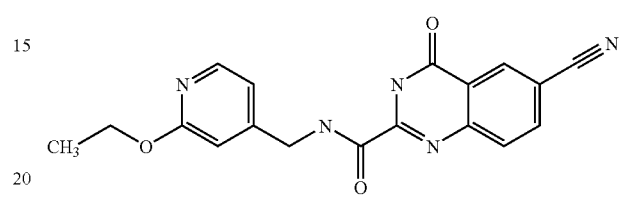

The title compound was obtained by a method similar to that of Example 1 using {[2-(ethyloxy)pyridin-4-yl]methyl}amine obtained in Reference Example 69 instead of 3-methoxybenzylamine.

melting point: 230-231° C.

Example 231

6-cyano-4-oxo-N-({2-[(3-thienylmethyl)oxy]pyridin-4-yl}methyl)-3,4-dihydroquinazoline-2-carboxamide

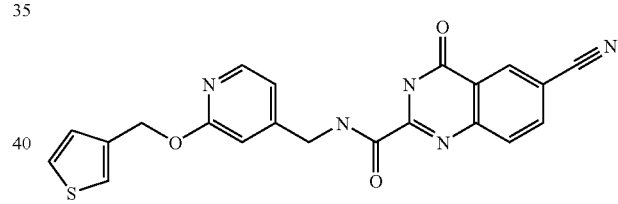

The title compound was obtained by a method similar to that of Example 1 using ({2-[(3-thienylmethyl)oxy]pyridin-4-yl}methyl)amine obtained in Reference Example 39 instead of 3-methoxybenzylamine.

melting point: 244-246° C.

Example 232

6-cyano-4-oxo-N-{[2-({3-[(phenylmethyl)oxy]propyl}oxy)pyridin-4-yl]methyl}-3,4-dihydroquinazoline-2-carboxamide

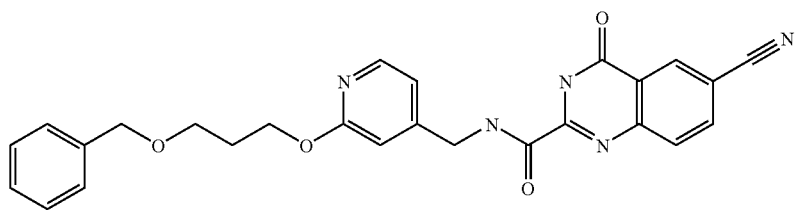 [SMILES: N#Cc1ccc2nc(C(=O)NCc3ccnc(OCCCOCc4ccccc4)c3)[nH]c(=O)c2c1]

The title compound was obtained by a method similar to that of Example 1 using {[2-({3-[(phenylmethyl)oxy]propyl}oxy)pyridin-4-yl]methyl}amine obtained in Reference Example 106 instead of 3-methoxybenzylamine.
melting point: 145-146° C.

Example 233

4-oxo-N-{[2-({2-[(phenylmethyl)oxy]ethyl}oxy)pyridin-4-yl]methyl}-3,4-dihydroquinazoline-2-carboxamide

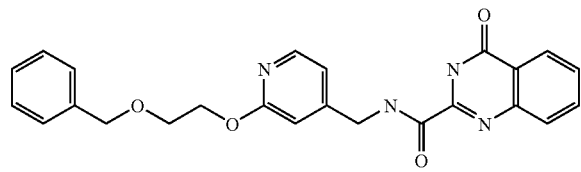 [SMILES: O=C(NCc1ccnc(OCCOCc2ccccc2)c1)c1nc2ccccc2c(=O)[nH]1]

{[2-({2-[(Phenylmethyl)oxy]ethyl}oxy)pyridin-4-yl]methyl}amine was obtained as a yellow oil by a method similar to that of Reference Example 31 from 2-({2-[(phenylmethyl)oxy]ethyl}oxy)pyridine-4-carbonitrile synthesized in Reference Example 107. The title compound was obtained by a method similar to that of Example 1 using {[2-({2-[(phenylmethyl)oxy]ethyl}oxy)pyridin-4-yl]methyl}amine instead of 3-methoxybenzylamine.
melting point: 171-172° C.

Example 234

6-cyano-N-{[5-(methyloxy)pyridin-3-yl]methyl}-4-oxo-3,4-dihydroquinazoline-2-carboxamide

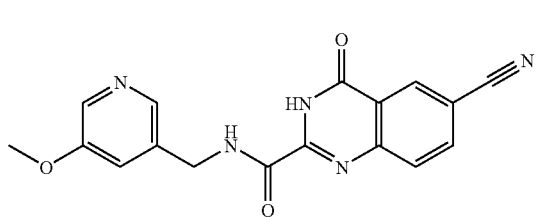 [SMILES: COc1cncc(CNC(=O)c2nc3ccc(C#N)cc3c(=O)[nH]2)c1]

{[5-(Methyloxy)pyridin-3-yl]methyl}amine was obtained as a green oil by a method similar to that of Reference Example 29 from 5-(methyloxy)pyridine-3-carbonitrile synthesized in Reference Example 104. The title compound was obtained by a method similar to that of Example 1 using {[5-(methyloxy)pyridin-3-yl]methyl}amine instead of 3-methoxybenzylamine.
melting point: 267-268° C.

Example 235

6-cyano-N-{[3-(ethyloxy)phenyl]methyl}-4-oxo-3,4-dihydroquinazoline-2-carboxamide

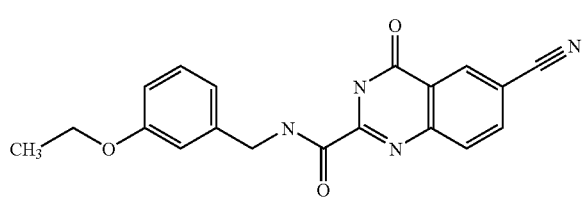 [SMILES: CCOc1cccc(CNC(=O)c2nc3ccc(C#N)cc3c(=O)[nH]2)c1]

The title compound was obtained by a method similar to that of Example 1 using 1-[3-(ethyloxy)phenyl]methanamine hydrochloride obtained in Reference Example 87 instead of 3-methoxybenzylamine.
melting point: 216-218° C.

Example 236

6-cyano-N-({3-[(difluoromethyl)oxy]phenyl}methyl)-4-oxo-3,4-dihydroquinazoline-2-carboxamide

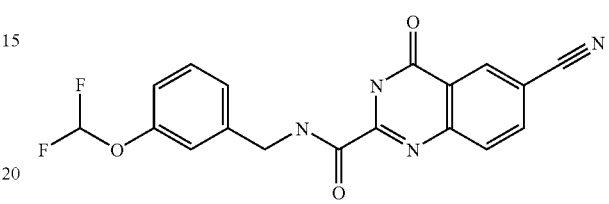

The title compound was obtained by a method similar to that of Example 1 using ({3-[(difluoromethyl)oxy]phenyl}methyl)amine instead of 3-methoxybenzylamine.
melting point: 261-263° C.

Example 237

N-({3-[(difluoromethyl)oxy]phenyl}methyl)-4-oxo-3,4-dihydroquinazoline-2-carboxamide

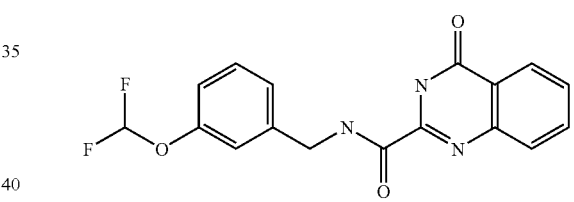

The title compound was obtained by a method similar to that of Example 1 using ({3-[(difluoromethyl)oxy]phenyl}methyl)amine instead of 3-methoxybenzylamine.
melting point: 202-203° C.

Example 238

Ethyl 4-{[3-({[(4-oxo-3,4-dihydroquinazolin-2-yl)carbonyl]amino}methyl)phenyl]oxy}butanoate

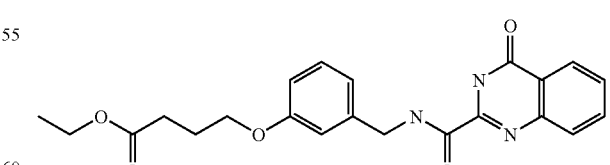

The title compound was obtained by a method similar to that of Example 1 using ethyl 4-{[3-(aminomethyl)phenyl]oxy}butanoate hydrochloride obtained in Reference Example 109 instead of 3-methoxybenzylamine.
melting point: 132-134° C.

Example 239

4-{[3-({[(4-oxo-3,4-dihydroquinazolin-2-yl)carbonyl]amino}methyl)phenyl]oxy}butanoic acid

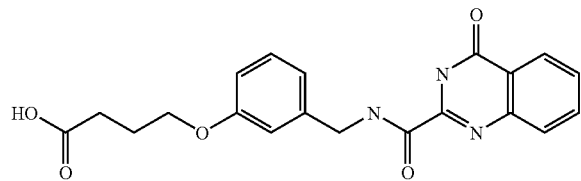 [SMILES: O=C(O)CCCOc1cccc(CNC(=O)c2nc3ccccc3c(=O)[nH]2)c1]

A mixture of ethyl 4-{[3-({[(4-oxo-3,4-dihydroquinazolin-2-yl)carbonyl]amino}methyl)phenyl]oxy}butanoate (525 mg, 1.28 mmol) obtained in Example 238, 4N aqueous sodium hydroxide solution (1.6 mL), THF (10 mL), MeOH (10 mL) and water (10 mL) was stirred at 100° C. for 2 hrs. The mixture was allowed to cool to room temperature and the solvent was evaporated under reduced pressure. Water and 1N hydrochloric acid (6.41 mL) were added to the concentrated residue and the resulting precipitate was collected by filtration, washed with water and dried. The obtained crude crystals were recrystallized from ethanol to give the title compound (339 mg, 69%) as a white powder.

melting point: 259-260° C.

Example 240

N-(3-methoxybenzyl)-7-oxo-2-(3-phenylpropyl)-6,7-dihydro-2H-pyrazolo[4,3-d]pyrimidine-5-carboxamide

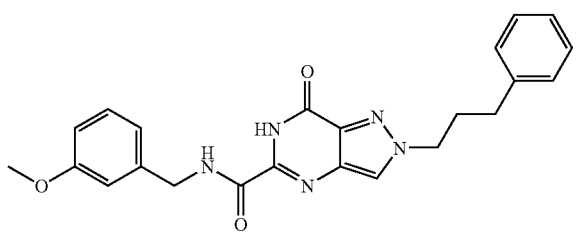 [SMILES: COc1cccc(CNC(=O)c2nc3cn(CCCc4ccccc4)nc3c(=O)[nH]2)c1]

A solution of ethyl 7-oxo-2-(3-phenylpropyl)-6,7-dihydro-2H-pyrazolo[4,3-d]pyrimidine-5-carboxylate (102 mg, 0.313 mmol) obtained in Reference Example 113 and 3-methoxybenzylamine (90 mg, 0.656 mmol) in ethanol (5 ml) was refluxed under heating overnight. After allowing to cool, the solvent was evaporated under reduced pressure, 10% aqueous citric acid solution was added, and the mixture was extracted with ethyl acetate. The organic layer was washed with water and saturated brine, dried and concentrated. The obtained crude crystals were recrystallized from ethanol-diisopropyl ether to give the title compound (103 mg).

$^1$H-NMR (300 MHz, CDCl$_3$) δ: 2.30-2.42 (2H, m), 2.64 (2H, t, J=7.4 Hz) 3.81 (3H, s), 4.35 (2H, t, J=7.0 Hz), 4.61 (2H, d, J=6.0 Hz), 6.83-6.96 (3H, m), 7.13-7.22 (2H, m), 7.22-7.33 (4H, m), 7.84 (1H, s), 7.90 (1H, s), 10.02 (1H, s).

melting point: 122-124° C.

Example 241

N-(4-fluoro-3-methoxybenzyl)-7-oxo-2-(3-phenylpropyl)-6,7-dihydro-2H-pyrazolo[4,3-d]pyrimidine-5-carboxamide

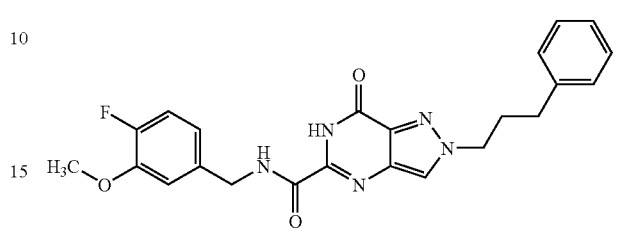

A solution of ethyl 7-oxo-2-(3-phenylpropyl)-6,7-dihydro-2H-pyrazolo[4,3-d]pyrimidine-5-carboxylate (101 mg, 0.309 mmol) obtained in Reference Example 113, 4-fluoro-3-methoxybenzylamine hydrochloride (synthesized by the method described in WO03/029224 A1; 156 mg, 0.814 mmol) and triethylamine (0.13 ml, 0.933 mmol) in ethanol (5 ml) was refluxed under heating overnight. After allowing to cool, the solvent was evaporated under reduced pressure, 10% aqueous citric acid solution was added, and the mixture was extracted with ethyl acetate. The organic layer was washed with water and saturated brine, dried and concentrated. The obtained crude crystals were recrystallized from ethanol-diisopropyl ether to give the title compound (103 mg).

$^1$H-NMR (300 MHz, CDCl$_3$) δ: 2.30-2.41 (2H, m), 2.64 (2H, t, J=7.4 Hz), 3.89 (3H, s), 4.35 (2H, t, J=7.0 Hz), 4.58 (2H, d, J=6.3 Hz), 6.84-6.92 (1H, m), 6.95 (1H, d, J=8.0 Hz), 7.06 (1H, dd, J=10.9, 8.4 Hz), 7.16 (2H, d, J=7.4 Hz), 7.21-7.33 (3H, m), 7.83-7.94 (2H, m), 10.01 (1H, s).

melting point: 137-140° C.

Example 242

4-oxo-N-(piperidin-3-ylmethyl)-3,4-dihydroquinazoline-2-carboxamide

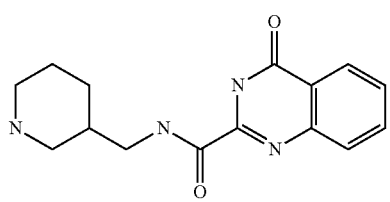 [SMILES: O=C(NCC1CCCNC1)c1nc2ccccc2c(=O)[nH]1]

A solution of ethyl 4-oxo-3,4-dihydroquinazoline-2-carboxylate (2.19 g, 10.0 mmol) and 1-piperidin-3-ylmethanamine (1.74 g, 15.2 mmol) in DMF (10 ml) was stirred at 100° C. for 3 hrs. After allowing to cool, ethyl acetate was added to the reaction mixture, and the precipitate was collected by filtration. The collected solid was washed with Et$_2$O to give the title compound (2.612 g).

melting point: 216-220° C. (dec.)

Example 243

N-(3-methoxybenzyl)-7-oxo-1-(3-phenylpropyl)-6,7-dihydro-1H-pyrazolo[4,3-d]pyrimidine-5-carboxamide

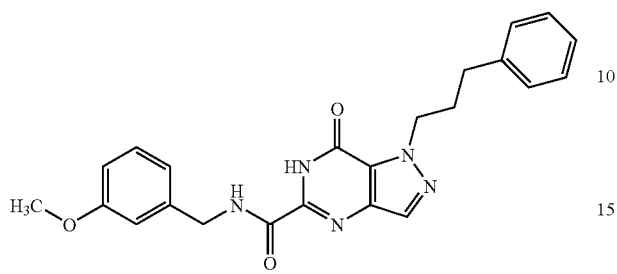

A solution of ethyl 7-oxo-1-(3-phenylpropyl)-6,7-dihydro-1H-pyrazolo[4,3-d]pyrimidine-5-carboxylate (165 mg, 0.506 mmol) obtained in Reference Example 115 and 3-methoxybenzylamine (137 mg, 1.00 mmol) in ethanol (5 ml) was refluxed under heating for 7 hrs. After allowing to cool, the precipitated crude crystals were collected by filtration and washed with diisopropyl ether to give the title compound (177 mg).

$^1$H-NMR (300 MHz, DMSO-$d_6$) δ: 2.12-2.19 (2H, m), 2.53-2.59 (2H, m), 3.73 (3H, s), 4.41 (2H, d, J=6.4 Hz), 4.61 (2H, t, J=6.9 Hz), 6.80-6.84 (1H, m), 6.88-6.91 (2H, m), 7.15-7.21 (3H, m), 7.22-7.26 (3H, m), 8.12 (1H, s), 9.57 (1H, t, J=6.3 Hz), 12.26 (1H, s).

Anal. Calcd for $C_{23}H_{23}N_5O_3$: C, 66.17; H, 5.55; N, 16.78. Found: C, 66.02; H, 5.53; N, 16.86.

melting point: 138-140° C.

Example 244

N-(4-fluoro-3-methoxybenzyl)-7-oxo-1-(3-phenylpropyl)-6,7-dihydro-1H-pyrazolo[4,3-d]pyrimidine-5-carboxamide

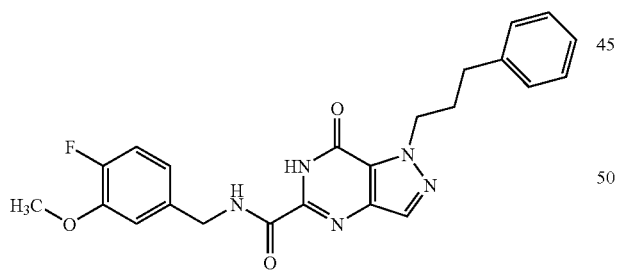

A solution of ethyl 7-oxo-1-(3-phenylpropyl)-6,7-dihydro-1H-pyrazolo[4,3-d]pyrimidine-5-carboxylate (203 mg, 0.622 mmol) obtained in Reference Example 115, 4-fluoro-3-methoxybenzylamine hydrochloride (synthesized by the method described in WO03/029224 A1; 237 mg, 1.24 mmol) and triethylamine (0.17 ml, 1.22 mmol) in ethanol (10 ml) was refluxed under heating for 24 hrs. After allowing to cool, water was added. The precipitated crude crystals were collected by filtration, and washed with water, ethanol and diisopropyl ether to give the title compound (199 mg).

$^1$H-NMR (300 MHz, DMSO-$d_6$) δ: 2.07-2.20 (2H, m), 2.52-2.58 (2H, m), 3.81 (3H, s), 4.40 (2H, d, J=6.2 Hz), 4.59 (2H, t, J=6.8 Hz), 6.86 (1H, s), 7.12-7.19 (5H, m), 7.21-7.27 (2H, m), 8.11 (1H, s), 9.57 (1H, t, J=6.4 Hz), 12.24 (1H, s).

Anal. Calcd for $C_{23}H_{22}N_5O_3F$: C, 63.44; H, 5.09; N, 16.08. Found: C, 63.12; H, 5.07; N, 16.13.

melting point: 155-157° C.

Example 245 ethyl 4-[(2-{[(3-methoxybenzyl)amino]carbonyl}-4-oxo-3,4-dihydrothieno[2,3-d]pyrimidin-5-yl)methoxy]benzoate

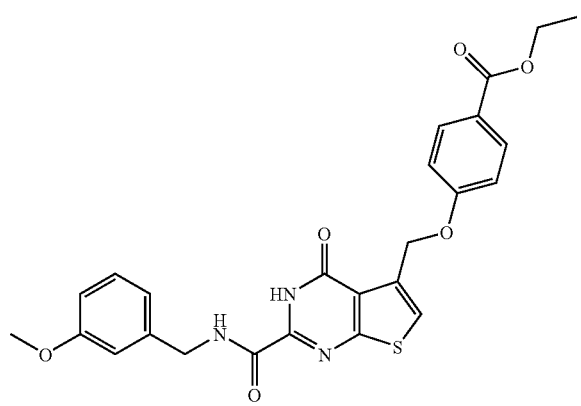 [SMILES: CCOC(=O)c1ccc(OCc2csc3nc(C(=O)NCc4cccc(OC)c4)[nH]c(=O)c23)cc1]

A solution of ethyl 5-{[4-(ethoxycarbonyl)phenoxy]methyl}-4-oxo-3,4-dihydrothieno[2,3-d]pyrimidine-2-carboxylate (0.203 g, 0.504 mmol) obtained in Reference Example 116 and 3-methoxybenzylamine (0.151 g, 1.10 mmol) in ethanol (5 ml) was refluxed under heating for 6 hrs. After allowing to cool, the precipitated crude crystals were collected by filtration, and washed with ethyl acetate and diethyl ether to give the title compound (169 mg).

$^1$H-NMR (300 MHz, DMSO-$d_6$) δ: 1.31 (3H, t, J=7.1 Hz), 3.74 (3H, s), 4.28 (2H, q, J=7.0 Hz), 4.43 (2H, d, J=6.4 Hz), 5.48 (2H, s), 6.80-6.87 (1H, m), 6.88-6.94 (2H, m), 7.13 (2H, d, J=9.0 Hz), 7.24 (1H, t, J=8.1 Hz), 7.74 (1H, s), 7.93 (2H, d, J=8.9 Hz), 9.68 (1H, t, J=6.3 Hz), 12.56 (1H, s).

melting point: 230-232° C.

Example 246

4-[(2-{[(3-methoxybenzyl)amino]carbonyl}-4-oxo-3,4-dihydrothieno[2,3-d]pyrimidin-5-yl)methoxy]benzoic acid

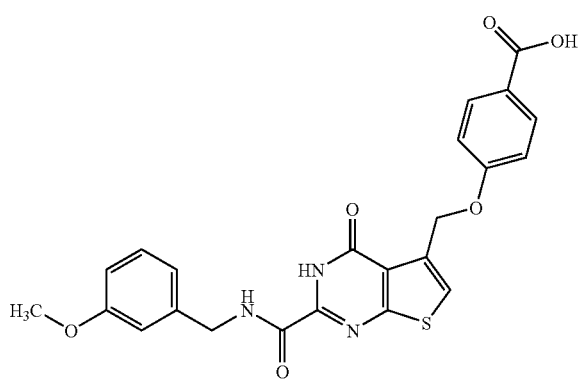 [SMILES: COc1cccc(CNC(=O)c2nc3scc(COc4ccc(C(=O)O)cc4)c3c(=O)[nH]2)c1]

To a solution of ethyl 4-[({2-[({[3-(methyloxy)phenyl]methyl}amino)carbonyl]-4-oxo-3,4-dihydrothieno[2,3-d]pyrimidin-5-yl}methyl)oxy]benzoate (152 mg, 0.308 mmol) obtained in Reference Example 245 in THF (8 ml) and methanol (4 ml) was added 4N aqueous sodium hydroxide solution and the mixture was refluxed under heating for 6 hrs. After allowing to cool, 10% aqueous citric acid solution was added, and the solvent was evaporated under reduced pressure. The obtained crude crystals were washed with water, ethanol and diethyl ether to give the title compound (143 mg).

melting point: 297-299° C.

Example 247 ethyl 4-[(2-{[(4-fluoro-3-methoxybenzyl)amino]carbonyl}-4-oxo-3,4-dihydrothieno[2,3-d]pyrimidin-5-yl)methoxy]benzoate

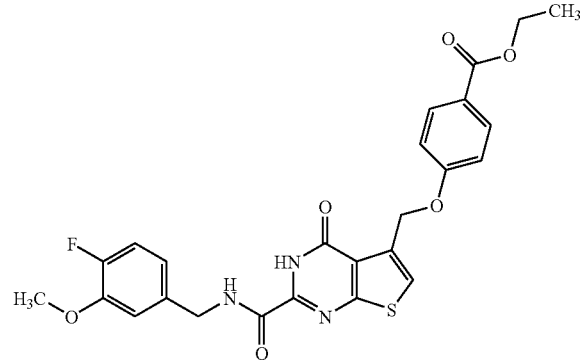 [SMILES: CCOC(=O)c1ccc(OCc2csc3nc(C(=O)NCc4ccc(F)c(OC)c4)[nH]c(=O)c23)cc1]

A solution of ethyl 5-{[4-(ethoxycarbonyl)phenoxy]methyl}-4-oxo-3,4-dihydrothieno[2,3-d]pyrimidine-2-carboxylate (0.301 g, 0.75 mmol) obtained in Reference Example 116, 4-fluoro-3-methoxybenzylamine hydrochloride (0.289 g, 1.5 mmol) and triethylamine (0.32 ml, 2.3 mmol) in ethanol (15 ml) was refluxed under heating for 6 hrs. After allowing to cool, the solvent was evaporated under reduced pressure. The obtained crude crystals were collected by filtration, and washed with water, ethanol and diethyl ether to give the title compound (232 mg).

$^1$H-NMR (300 MHz, DMSO-$d_6$) δ: 1.31 (3H, t, J=7.2 Hz), 3.83 (3H, s), 4.28 (2H, q, J=7.1 Hz), 4.42 (2H, d, J=6.4 Hz), 5.48 (2H, s), 6.85-6.93 (1H, m), 7.09-7.21 (4H, m), 7.74 (1H, m), 7.93 (2H, d, J=8.9 Hz), 9.68 (1H, t, J=6.3 Hz), 12.58 (1H, s).

melting point: 247-250° C.

Example 248

4-[(2-{[(4-fluoro-3-methoxybenzyl)amino]carbonyl}-4-oxo-3,4-dihydrothieno[2,3-d]pyrimidin-5-yl)methoxy]benzoic acid

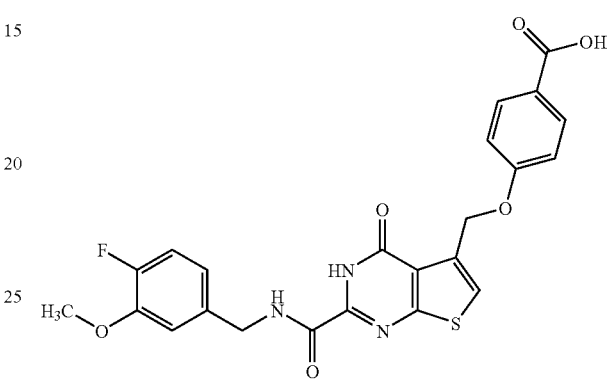

To a solution of ethyl 4-[({2-[({[4-fluoro-3-(methyloxy)phenyl]methyl}amino)carbonyl]-4-oxo-3,4-dihydrothieno[2,3-d]pyrimidin-5-yl}methyl)oxy]benzoate (160 mg, 0.313 mmol) obtained in Example 247 in THF (30 ml) and methanol (10 ml) was added 2N aqueous sodium hydroxide solution (0.5 ml) and the mixture was refluxed under heating for 7 hrs. After allowing to cool, 1N hydrochloric acid was added, and the mixture was extracted with ethyl acetate. The organic layer was washed with saturated brine, dried and concentrated. The obtained crude crystals were recrystallized from THF-diisopropyl ether to give the title compound (64 mg).

melting point: 276-281° C.

Example 249 methyl 4-[2-(5-{[(3-methoxybenzyl)amino]carbonyl}-7-oxo-6,7-dihydro-1H-pyrazolo[4,3-d]pyrimidin-1-yl)ethoxy]benzoate

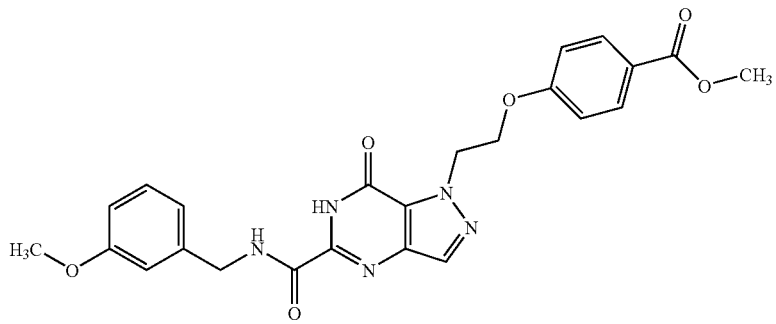

A solution of ethyl 1-[2-({4-[(methyloxy)carbonyl]phenyl}oxy)ethyl]-7-oxo-6,7-dihydro-1H-pyrazolo[4,3-d]pyrimidine-5-carboxylate (0.081 g, 0.21 mmol) obtained in Reference Example 118 and 3-methoxybenzylamine (0.073 g, 0.53 mmol) in ethanol (10 ml) was refluxed under heating for 24 hrs. After allowing to cool, 10% aqueous citric acid solution was added, and the mixture was extracted with ethyl acetate. The organic layer was washed with water and saturated brine, dried and concentrated. The obtained crude crystals were recrystallized from ethyl acetate-hexane to give the title compound (107 mg).

$^1$H-NMR (300 MHz, CDCl$_3$) δ: 3.81 (3H, s), 3.86 (3H, s), 4.51 (2H, t, J=5.5 Hz), 4.61 (2H, d, J=6.2 Hz), 5.08 (2H, t, J=5.5 Hz), 6.86 (4H, d, J=10.6 Hz), 6.93 (1H, d, J=7.9 Hz), 7.27-7.32 (1H, m), 7.94 (4H, d, J=10.7 Hz), 10.20 (1H, s).
melting point: 174-177° C.

Example 250

4-[2-(5-{[(3-methoxybenzyl)amino]carbonyl}-7-oxo-6,7-dihydro-1H-pyrazolo[4,3-d]pyrimidin-1-yl)ethoxy]benzoic acid

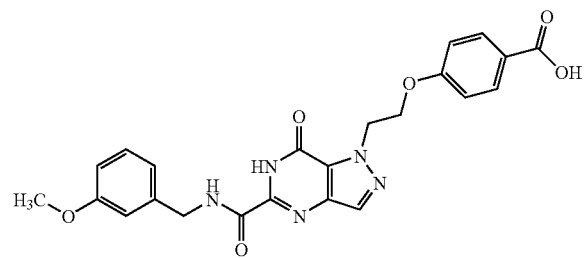 [SMILES: COc1cccc(CNC(=O)c2nc3cnn(CCOc4ccc(C(=O)O)cc4)c3c(=O)[nH]2)c1]

To a solution of methyl 4-[(2-{5-[({[3-(methyloxy)phenyl]methyl}amino)carbonyl]-7-oxo-6,7-dihydro-1H-pyrazolo[4,3-d]pyrimidin-1-yl}ethyl)oxy]benzoate (89 mg, 0.186 mmol) obtained in Example 249 in THF (6 ml) and methanol (3 ml) was added 2N aqueous sodium hydroxide solution (0.5 ml), and the mixture was refluxed under heating overnight. After allowing to cool, 10% aqueous citric acid solution was added, and the mixture was extracted with ethyl acetate. The organic layer was washed with saturated brine, dried and concentrated. The obtained crude crystals were recrystallized from THF-diisopropyl ether to give the title compound (86 mg).

$^1$H-NMR (300 MHz, DMSO-d$_6$) δ: 3.73 (3H, s), 4.41 (2H, d, J =6.4 Hz), 4.53 (2H, t, J=5.2 Hz), 4.99 (2H, t, J=5.2 Hz), 6.79-6.86 (1H, m), 6.87-6.97 (4H, m), 7.23 (1H, t, J=8.1 Hz), 7.83 (2H, d, J=8.9 Hz), 8.16 (1H, s), 9.57 (1H, t, J=6.3 Hz), 12.34 (1H, s), 12.62 (1H, s).
Anal. Calcd for C$_{23}$H$_{21}$N$_5$O$_6$·0.5H$_2$O: C, 58.47; H, 4.69; N, 14.82. Found: C, 58.79; H, 4.49; N, 14.62.
melting point: 230-231° C.

Example 251 ethyl (2-{[(3-methoxybenzyl)amino]carbonyl}-4-oxo-3,4-dihydrothieno[2,3-d]pyrimidin-5-yl)acetate

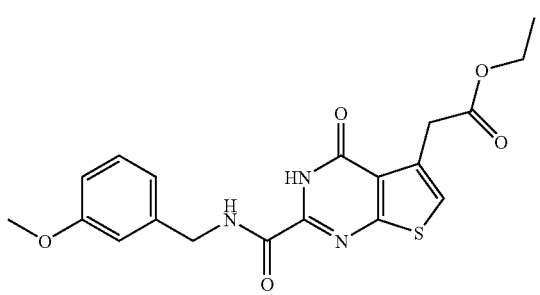 [SMILES: CCOC(=O)Cc1csc2nc(C(=O)NCc3cccc(OC)c3)[nH]c(=O)c12]

A solution of ethyl 5-(2-ethoxy-2-oxoethyl)-4-oxo-3,4-dihydrothieno[2,3-d]pyrimidine-2-carboxylate (0.805 g, 2.59 mmol) obtained in Reference Example 119 and 3-methoxybenzylamine (0.717 g, 5.19 mmol) in ethanol (30 ml) was refluxed under heating for 6 hrs. After allowing to cool, diethyl ether was added, and the precipitated crude crystals were collected by filtration and washed with diethyl ether to give the title compound (0.849 g).

$^1$H-NMR (300 MHz, DMSO-d$_6$) δ: 1.18 (3H, t, J=7.2 Hz), 3.73 (3H, s), 3.97 (2H, s), 4.07 (2H, q, J=7.1 Hz), 4.42 (2H, d, J=6.4 Hz), 6.79-6.85 (1H, m), 6.88-6.92 (2H, m), 7.24 (1H, t, J=8.1 Hz), 7.51 (1H, s), 9.64 (1H, t, J=6.4 Hz), 12.38 (1H, s).
Anal. Calcd for C$_{19}$H$_{19}$N$_3$O$_5$S: C, 56.85; H, 4.77; N, 10.47. Found: C, 56.84; H, 4.71; N, 10.44.
melting point: 169-171° C.

Example 252 methyl 4-[2-(5-{[(4-fluoro-3-methoxybenzyl)amino]carbonyl}-7-oxo-6,7-dihydro-1H-pyrazolo[4,3-d]pyrimidin-1-yl)ethoxy]benzoate

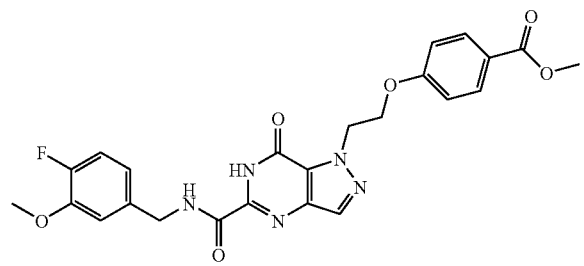

A solution of ethyl 1-[2-({4-[(methyloxy)carbonyl]phenyl}oxy)ethyl]-7-oxo-6,7-dihydro-1H-pyrazolo[4,3-d]pyrimidine-5-carboxylate (0.205 g, 0.531 mmol) obtained in Reference Example 118, 4-fluoro-3-methoxybenzylamine hydrochloride (synthesized by the method described in WO03/029224 A1; 0.208 g, 1.09 mmol) and triethylamine (0.16 ml, 1.17 mmol) in ethanol (15 ml) was refluxed under heating for 14 hrs. After allowing to cool, the solvent was evaporated under reduced pressure. The obtained crude crystals were collected by filtration, and washed with water and diethyl ether to give the title compound (217 mg).

$^1$H-NMR (300 MHz, DMSO-d$_6$) δ: 3.79 (3H, s), 3.82 (3H, s), 4.41 (2H, d, J=6.4 Hz), 4.54 (2H, t, J=5.1 Hz), 4.99 (2H, t, J=5.1 Hz), 6.84-6.92 (1H, m, J=8.2, 4.5, 1.9 Hz), 6.96 (2H, d, J=8.9 Hz), 7.09-7.22 (2H, m), 7.85 (2H, d, J=8.7 Hz), 8.15 (1H, s), 9.58 (1H, t, J=6.4 Hz), 12.38 (1H, s).
Anal. Calcd for C$_{24}$H$_{22}$N$_5$O$_6$F·0.25H$_2$O: C, 57.66; H, 4.54; N, 14.01. Found: C, 57.62; H, 4.51; N, 14.16.

Example 253

4-[2-(5-{[(4-fluoro-3-methoxybenzyl)amino]carbonyl}-7-oxo-6,7-dihydro-1H-pyrazolo[4,3-d]pyrimidin-1-yl)ethoxy]benzoic acid

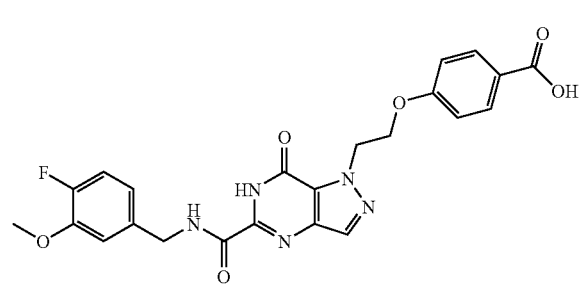 [SMILES: COc1cc(CNC(=O)c2nc3cnn(CCOc4ccc(C(=O)O)cc4)c3c(=O)[nH]2)ccc1F]

To a solution of methyl 4-[2-(5-{[(4-fluoro-3-methoxybenzyl)amino]carbonyl}-7-oxo-6,7-dihydro-1H-pyrazolo[4, 3-d]pyrimidin-1-yl)ethoxy]benzoate (183 mg, 0.369 mmol) obtained in Example 252 in THF (12 ml) and methanol (6 ml) was added 2N aqueous sodium hydroxide solution (1.0 ml), and the mixture was refluxed under heating overnight. After allowing to cool, 10% aqueous citric acid solution was added, and the mixture was extracted with ethyl acetate. The organic layer was washed with saturated brine, dried and concentrated. The obtained crude crystals were recrystallized from THF-methanol to give the title compound (129 mg).

$^1$H-NMR (300 MHz, DMSO-d$_6$) δ: 3.82 (3H, s), 4.41 (2H, d, J =6.2 Hz), 4.53 (2H, t, J=5.1 Hz), 4.99 (2H, t, J=5.1 Hz), 6.84-6.91 (1H, m, 1H), 6.94 (2H, d, J=8.9 Hz), 7.09-7.20 (2H, m), 7.83 (2H, d, J=8.9 Hz), 8.16 (1H, s), 9.59 (1H, t, J=6.2 Hz), 12.27-12.70 (2H, m).

melting point: 228-230° C.

Example 254

5-(2-hydroxyethyl)-N-(3-methoxybenzyl)-4-oxo-3,4-dihydrothieno[2,3-d]pyrimidine-2-carboxamide

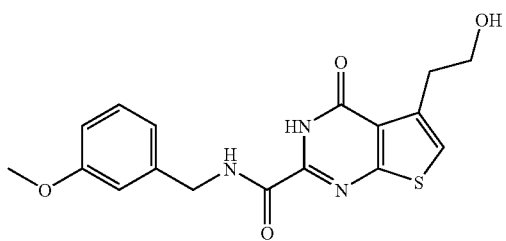 [SMILES: COc1cccc(CNC(=O)c2nc3scc(CCO)c3c(=O)[nH]2)c1]

To a solution of ethyl {2-[({[3-(methyloxy)phenyl]methyl}amino)carbonyl]-4-oxo-3,4-dihydrothieno[2,3-d]pyrimidin-5-yl}acetate (0.597 g, 1.5 mmol) obtained in Example 251 in THF (15 ml) was added lithium aluminum hydride (0.055 g, 1.4 mmol) at 0° C. The reaction mixture was stirred at 0° C. for 1 hr and water was added carefully. The insoluble material was filtered off, and the filtrate was concentrated under reduced pressure. The obtained solid was washed with a mixed solution of ethyl acetate/hexane (1/1) to give the title compound (0.289 g) as an amorphous solid.

$^1$H-NMR (300 MHz, DMSO-d$_6$) δ: 3.08 (2H, t, J=6.5 Hz), 3.65 (2H, s), 3.73 (3H, s), 4.41 (2H, d, J=6.2 Hz), 5.19 (1H, s), 6.78-6.86 (1H, m), 6.86-6.95 (2H, m), 7.12 (1H, s), 7.23 (1H, t, J=8.1 Hz), 9.35 (1H, s).

Example 255

3-methoxybenzyl 5-{2-[(methylsulfonyl)oxy]ethyl}-4-oxo-3,4-dihydrothieno[2,3-d]pyrimidine-2-carboxylate

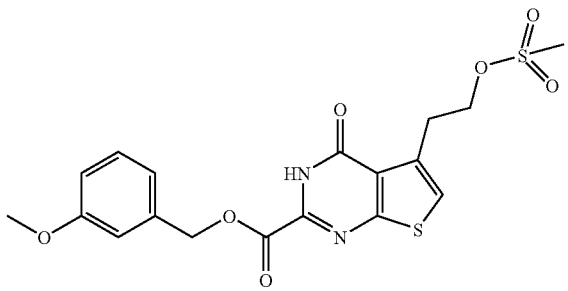

To a solution of 5-(2-hydroxyethyl)-N-{[3-(methyloxy)phenyl]methyl}-4-oxo-3,4-dihydrothieno[2,3-d]pyrimidine-2-carboxamide (319 mg, 0.89 mmol) obtained in Example 254 and triethylamine (0.37 ml, 2.7 mmol) in N,N-dimethylacetamide (8 ml) was added methanesulfonyl chloride (0.21 ml, 2.7 mmol) at 0° C. The reaction mixture was stirred at room temperature for 1 hr, water was added, and the mixture was extracted with ethyl acetate. The organic layer was washed with water and saturated brine, dried, concentrated under reduced pressure. The residue was purified by silica gel chromatography to give the title compound (0.218 g).

$^1$H-NMR (300 MHz, CDCl$_3$) δ: 2.97 (3H, s), 3.45 (2H, t, J=6.2 Hz), 3.82 (3H, s), 4.56 (2H, t, J=6.4 Hz), 4.62 (2H, d, J=6.0 Hz), 6.85-6.96 (3H, m), 7.21 (1H, s), 7.30 (1H, td, J=7.4, 1.6 Hz), 7.93 (1H, t, J=5.8 Hz), 10.23 (1H, s).

Example 256 ethyl {4-[(2-{[(3-methoxybenzyl)amino]carbonyl}-4-oxo-3,4-dihydrothieno[2,3-d]pyrimidin-5-yl)methoxy]phenyl}acetate

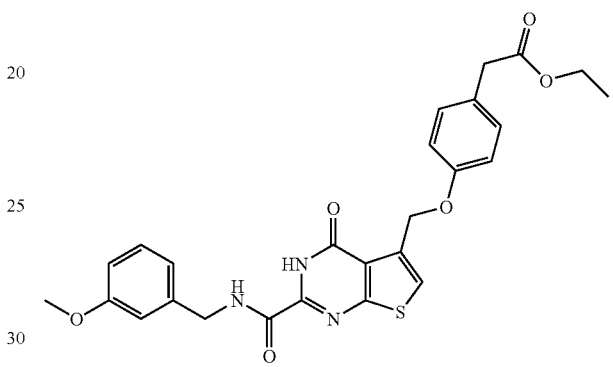

To a suspension of 60% oily sodium hydride (0.28 g, 7.0 mmol) in THF (10 ml) was added dropwise a solution of ethyl 5-(bromomethyl)-4-oxo-3,4-dihydrothieno[2,3-d]pyrimidine-2-carboxylate (1.507 g, 4.8 mmol) obtained in Example 216 step 1 and ethyl p-hydroxyphenylacetate (0.94 g, 5.2 mmol) in THF (30 ml) at 0° C. The reaction mixture was stirred overnight at room temperature, added to 10% aqueous citric acid solution, and the mixture was extracted with THF/ethyl acetate. The organic layer was washed with saturated aqueous sodium hydrogen carbonate and saturated brine, dried and concentrated under reduced pressure. The obtained solid was washed with a mixed solution of ethyl acetate-hexane (1/1) to give ethyl 5-[({4-[2-(ethyloxy)-2-oxoethyl]phenyl}oxy)methyl]-4-oxo-3,4-dihydrothieno[2,3-d]pyrimidine-2-carboxylate (479 mg).

A mixed solution of ethyl 5-[({4-[2-(ethyloxy)-2-oxoethyl]phenyl}oxy)methyl]-4-oxo-3,4-dihydrothieno[2,3-d]pyrimidine-2-carboxylate (479 mg) and 3-methoxybenzylamine (0.34 g, 2.48 mmol) in THF (10 ml)-ethanol (10 ml) was refluxed under heating for 3 hrs. The solvent was evaporated under reduced pressure, and the residue was dissolved in a mixed solution of ethyl acetate and THF. The mixture was washed with 10% aqueous citric acid solution and saturated brine, dried and concentrated under reduced pressure. The obtained crude crystals were dissolved in THF, activated carbon was added, the activated carbon was filtered off and the filtrate was concentrated. The obtained crude crystals were recrystallized from THF-diisopropyl ether to give the title compound (0.407 g).

$^1$H-NMR (300 MHz, DMSO-d$_6$) δ: 1.18 (3H, t, J=7.2 Hz), 3.58 (2H, s), 3.74 (3H, s), 4.06 (2H, q, J=7.2 Hz), 4.43 (2H, d, J=6.2 Hz), 5.38 (2H, s), 6.77-6.85 (1H, m), 6.89-6.99 (4H, m), 7.17-7.27 (3H, m), 7.69 (1H, s), 9.67 (1H, t, J=6.4 Hz), 12.52 (1H, s).

Anal. Calcd for C$_{26}$H$_{25}$N$_3$O$_6$S.H$_2$O: C, 59.42; H, 5.18; N, 8.00. Found: C, 59.40; H, 4.75; N, 8.40.

melting point: 175-178° C.

Example 257

{4-[(2-{[(3-methoxybenzyl)amino]carbonyl}-4-oxo-3,4-dihydrothieno[2,3-d]pyrimidin-5-yl)methoxy]phenyl}acetic acid

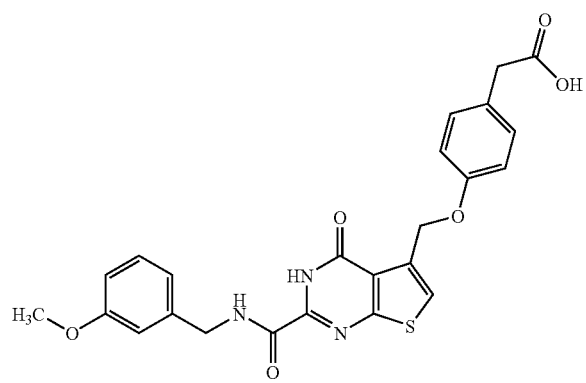 [SMILES: COc1cccc(CNC(=O)c2nc3scc(COc4ccc(CC(=O)O)cc4)c3c(=O)[nH]2)c1]

To a mixed solution of ethyl {4-[({2-[({[3-(methyloxy)phenyl]methyl}amino)carbonyl]-4-oxo-3,4-dihydrothieno[2,3-d]pyrimidin-5-yl}methyl)oxy]phenyl}acetate (0.35 g, 0.69 mmol) obtained in Example 256 in THF (5 ml)-methanol (5 ml) was added 2N aqueous sodium hydroxide solution (1.8 ml) and the mixture was refluxed under heating for 8 hrs. After allowing to cool, 1N hydrochloric acid was added, and the mixture was extracted with a mixed solution of THF-ethyl acetate. The organic layer was washed with saturated brine, dried and concentrated under reduced pressure. The obtained crude crystals were recrystallized from THF-diisopropyl ether to give the title compound (0.191 g).

$^1$H-NMR (300 MHz, DMSO-$d_6$) δ: 3.49 (2H, s), 3.74 (3H, s), 4.43 (2H, d, J=6.40 Hz), 5.39 (2H, s), 6.82 (1H, ddd, J=8.19, 2.35, 0.94 Hz), 6.89-6.98 (4H, m), 7.16-7.27 (3H, m), 7.68 (1H, s), 9.67 (1H, t, J=6.4 Hz), 12.23 (1H, s), 12.52 (1H, s).

Anal. Calcd for $C_{24}H_{21}N_3O_6 \cdot S$: C, 60.12; H, 4.41; N, 8.76. Found: C, 59.71; H, 4.56; N, 8.54.

melting point: 228-230° C.

Example 258

4-[2-(2-{[(3-methoxybenzyl)amino]carbonyl}-4-oxo-3,4-dihydrothieno[2,3-d]pyrimidin-5-yl)ethoxy]benzoic acid

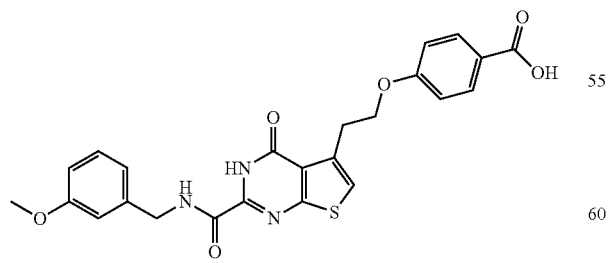

To a solution of ethyl 4-{[2-(6-(dimethylamino)-7-{[3-(methyloxy)phenyl]methyl}-4,8-dioxo-4,6,7,8-tetrahydroimidazo[1,5-a]thieno[2,3-d]pyrimidin-3-yl)ethyl]oxy}benzoate (0.100 g, 0.18 mmol) obtained in Reference Example 121 in acetic acid (3 ml) was added 6N hydrochloric acid (1 ml), and the mixture was stirred with heating at 80° C. for 24 hrs. After allowing to cool, the precipitated solid was collected by filtration, washed with water, ethanol and diethyl ether, suspended in ethanol, and the mixture was stirred with heating at 80° C. for 1 hr. After allowing to cool, the precipitated solid was collected by filtration, and washed with ethanol and diethyl ether to give the title compound (57 mg).

$^1$H-NMR (300 MHz, DMSO-$d_6$) δ: 3.40 (2H, t, J=6.8 Hz), 3.73 (3H, s, 3 H), 4.33 (2H, t, J=6.9 Hz), 4.42 (2H, d, J=6.4 Hz), 6.79-6.84 (1H, m, 1 H), 6.87-6.93 (2H, m), 7.05 (2H, d, J=9.0 Hz), 7.24 (1H, t, J=8.1 Hz), 7.53 (1H, s), 7.87 (2H, d, J=8.9 Hz), 9.63 (1H, t, J=6.4 Hz), 12.52 (2H, s).

melting point: 237-241° C.

Example 259

5,6-difluoro-N-{[4-fluoro-3-(methyloxy)phenyl]methyl}-4-oxo-3,4-dihydroquinazoline-2-carboxamide

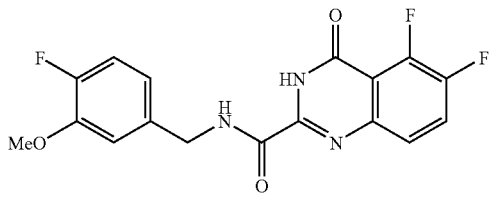 [SMILES: COc1cc(CNC(=O)c2nc3ccc(F)c(F)c3c(=O)[nH]2)ccc1F]

A suspension of ethyl 5,6-difluoro-4-oxo-3,4-dihydroquinazoline-2-carboxylate (1.00 g, 3.93 mmol) obtained in Reference Example 22, 1-[4-fluoro-3-(methyloxy)phenyl]methanamine hydrochloride (1.13 g, 5.90 mmol) synthesized by the method described in WO03/029224 A1 and N,N-diisopropylethylamine (1.03 mL, 5.90 mmol) in ethanol (15 mL) was stirred with heating at 80° C. for 6 hrs. The reaction mixture was allowed to cool to room temperature, and the precipitated solid was collected by filtration. The solid was washed with ethanol to give the title compound as a pale-yellow powder (960 mg, 67%).

melting point: 197-199° C.

$^1$H-NMR (300 MHz, DMSO-$d_6$) δ: 3.82 (3H, s), 4.44 (2H, d, J=6.3 Hz), 6.86-6.91 (1H, m), 7.12-7.18 (2H, m), 7.59-7.64 (1H, m), 7.92-8.01 (1H, m), 9.57 (1H, t, J=6.3 Hz), 12.45 (1H, bs).

Example 260

5,6-difluoro-N-{[2-({[4-(methyloxy)phenyl]methyl}oxy)pyridin-4-yl]methyl}-4-oxo-3,4-dihydroquinazoline-2-carboxamide

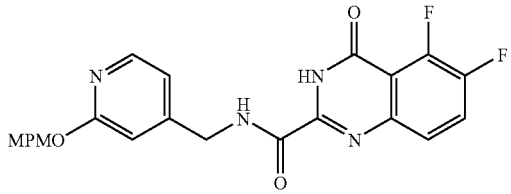

A suspension of ethyl 5,6-difluoro-4-oxo-3,4-dihydroquinazoline-2-carboxylate (500 mg, 1.97 mmol) obtained in Reference Example 22 and {[2-({[4-(methyloxy)phenyl]methyl}oxy)pyridin-4-yl]methyl}amine (577 mg, 2.36 mmol) obtained in Reference Example 57 in ethanol (10 mL)-DMA (4 mL) was stirred with heating at 80° C. for 4 hrs. The reaction mixture was allowed to cool to room temperature, and concentrated under reduced pressure. The concentrated residue was partitioned between ethyl acetate and water. The organic layer was washed with water and saturated brine, and dried over anhydrous sodium sulfate. The solvent was evaporated under reduced pressure and the concentrated residue was crystallized from ethanol to give the title compound as a pale-yellow powder (669 mg, 75%).

melting point: 166-168° C.

$^1$H-NMR (300 MHz, DMSO-$d_6$) δ: 3.74 (3H, s), 4.45 (2H, d, J=5.7 Hz), 5.24 (2H, s), 6.73 (1H, s), 6.89-6.95 (3H, m), 7.36 (2H, d, J=9.0 Hz), 7.60-7.64 (1H, m), 7.92-8.01 (1H, m), 8.11 (1H, d, J=5.4 Hz), 9.63 (1H, t, J=6.0 Hz), 12.46 (1H, bs).

Example 261

5,6-difluoro-4-oxo-N-(pyridin-4-ylmethyl)-3,4-dihydroquinazoline-2-carboxamide

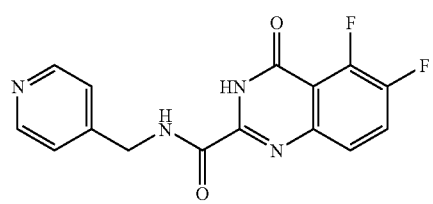 [SMILES: O=C(NCc1ccncc1)c1nc2ccc(F)c(F)c2c(=O)[nH]1]

A suspension of ethyl 5,6-difluoro-4-oxo-3,4-dihydroquinazoline-2-carboxylate (1.00 g, 3.93 mmol) obtained in Reference Example 22 and 1-pyridin-4-ylmethanamine (638 mg, 5.90 mmol) in ethanol (20 mL) was stirred with heating at 80° C. for 15 hrs. The reaction mixture was allowed to cool to room temperature, and the precipitated solid was collected by filtration. The solid was washed with ethanol to give the title compound as a white powder (1.11 g, 89%).

melting point: 229-232° C.

$^1$H-NMR (300 MHz, DMSO-$d_6$) δ: 4.49 (2H, d, J=6.3 Hz), 7.32 (2H, d, J=6.0 Hz), 7.64-7.59 (1H, m), 8.01-7.91 (1H, m), 8.50 (2H, d, J=6.0 Hz), 9.66 (1H, t, J=6.3 Hz), 12.44 (1H, bs).

The following Example 262 to Example 265 were synthesized from 5,6-difluoro-N-{[3-(methyloxy)phenyl]methyl}-4-oxo-3,4-dihydroquinazoline-2-carboxamide obtained in Example 113, by a method similar to that of Example 159.

Example 262

{4-[({6-fluoro-2-[({[3-(methyloxy)phenyl]methyl}amino)carbonyl]-4-oxo-3,4-dihydroquinazolin-5-yl}oxy)methyl]phenyl}acetic acid

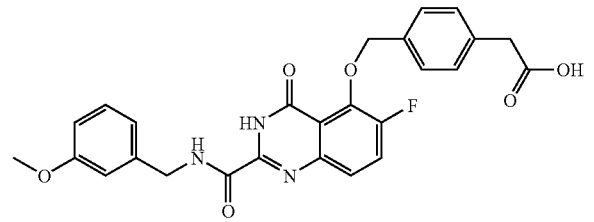 [SMILES: COc1cccc(CNC(=O)c2nc3ccc(F)c(OCc4ccc(CC(=O)O)cc4)c3c(=O)[nH]2)c1]

The compound was synthesized using[4-(hydroxymethyl)phenyl]acetic acid instead of benzyl alcohol.
melting point: 218-220° C.

Example 263

5-[(biphenyl-4-ylmethyl)oxy]-6-fluoro-N-{[3-(methyloxy)phenyl]methyl}-4-oxo-3,4-dihydroquinazoline-2-carboxamide

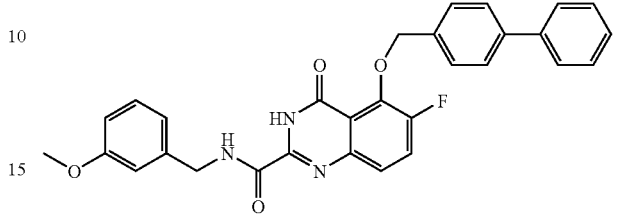

The compound was synthesized using biphenyl-4-ylmethanol instead of benzyl alcohol.
melting point: 187-189° C.

Example 264

5-[(1-benzothien-2-ylmethyl)oxy]-6-fluoro-N-{[3-(methyloxy)phenyl]methyl}-4-oxo-3,4-dihydroquinazoline-2-carboxamide

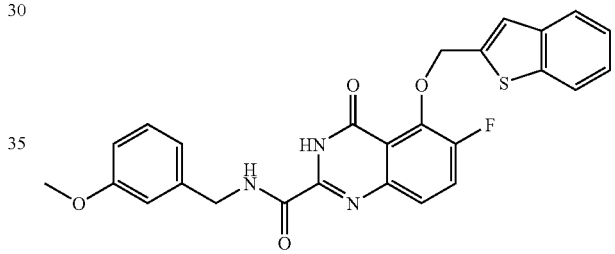

The compound was synthesized using 1-benzothien-2-ylmethanol instead of benzyl alcohol.
melting point: 191-193° C.

Example 265

6-fluoro-N-{[3-(methyloxy)phenyl]methyl}-4-oxo-5-{[-(2-oxopyrrolidin-1-yl)ethyl]oxy}-3,4-dihydroquinazoline-2-carboxamide

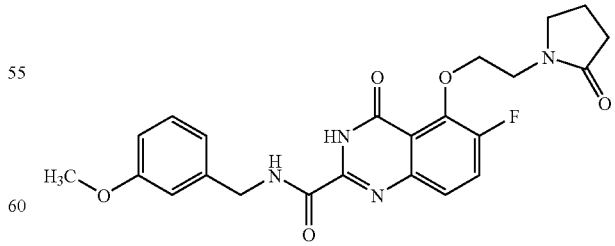

The compound was synthesized using1-(2-hydroxyethyl)pyrrolidin-2-one instead of benzyl alcohol.
melting point: 189-191° C.

The following Example 266 to Example 269 were synthesized from 5,6-difluoro-N-{[4-fluoro-3-(methyloxy)phenyl]

methyl}-4-oxo-3,4-dihydroquinazoline-2-carboxamide obtained in Example 259, by a method similar to that of Example 159.

Example 266

4-[({6-fluoro-2-[({[4-fluoro-3-(methyloxy)phenyl]methyl}amino)carbonyl]-4-oxo-3,4-dihydroquinazolin-5-yl}oxy)methyl]benzoic acid

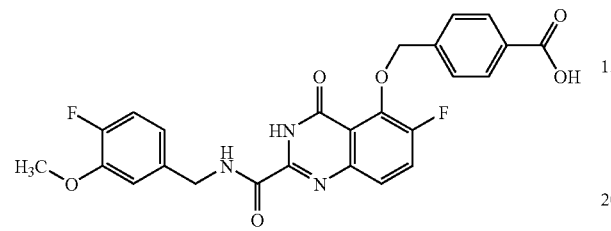

The compound was synthesized using 4-(hydroxymethyl)benzoic acid instead of benzyl alcohol.
melting point: 268-270° C.

Example 267

4-[2-({6-fluoro-2-[({[4-fluoro-3-(methyloxy)phenyl]methyl}amino)carbonyl]-4-oxo-3,4-dihydroquinazolin-5-yl}oxy)ethyl]benzoic acid

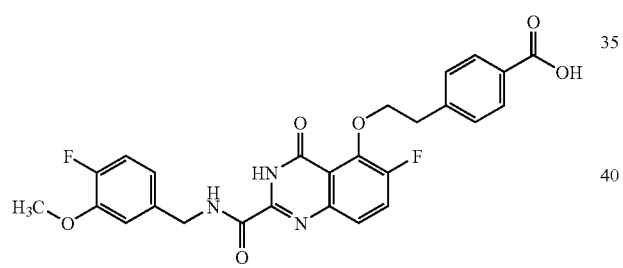

The compound was synthesized using 4-(2-hydroxyethyl)benzoic acid instead of benzyl alcohol.
melting point: 242-244° C.

Example 268

5-[({4-[3-(ethyloxy)-5-methylisoxazol-4-yl]phenyl}methyl)oxy]-6-fluoro-N-{[4-fluoro-3-(methyloxy)phenyl]methyl}-4-oxo-3,4-dihydroquinazoline-2-carboxamide

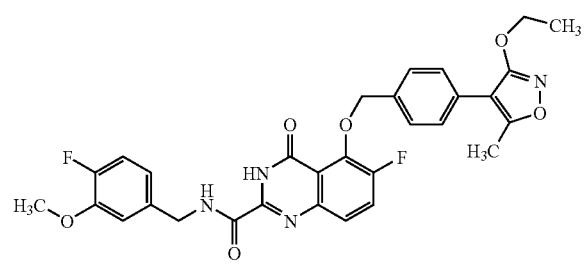 [SMILES: CCOc1noc(C)c1-c1ccc(COc2c(F)ccc3nc(C(=O)NCc4ccc(F)c(OC)c4)[nH]c(=O)c23)cc1]

The compound was synthesized using {4-[3-(ethyloxy)-5-methylisoxazol-4-yl]phenyl}methanol obtained in Reference Example 122 instead of benzyl alcohol.
melting point: 177-179° C.

Example 269

5-[(2-{4-[3-(ethyloxy)-5-methylisoxazol-4-yl]phenyl}ethyl)oxy]-6-fluoro-N-{[4-fluoro-3-(methyloxy)phenyl]methyl}-4-oxo-3,4-dihydroquinazoline-2-carboxamide

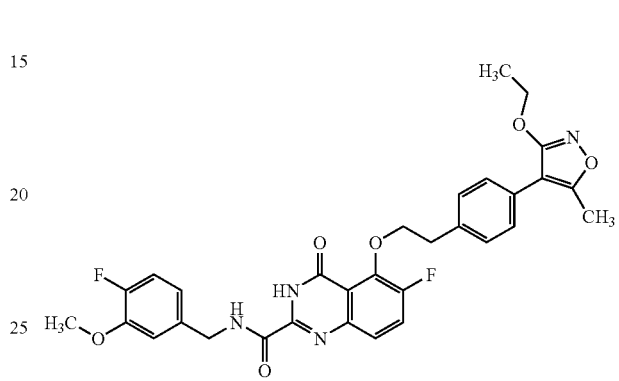

The compound was synthesized using 2-{4-[3-(ethyloxy)-5-methylisoxazol-4-yl]phenyl}ethanol obtained in Reference Example 123 instead of benzyl alcohol.
melting point: 170-172° C.

Example 270

6-fluoro-N-{[4-fluoro-3-(methyloxy)phenyl]methyl}-5-({2-[4-(3-hydroxy-5-methylisoxazol-4-yl)phenyl]ethyl}oxy)-4-oxo-3,4-dihydroquinazoline-2-carboxamide

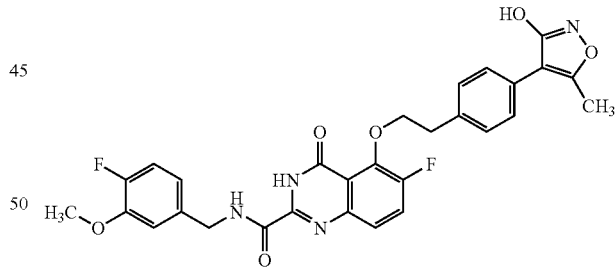

A mixture of 5-[(2-{4-[3-(ethyloxy)-5-methylisoxazol-4-yl]phenyl}ethyl)oxy]-6-fluoro-N-{[4-fluoro-3-(methyloxy)phenyl]methyl}-4-oxo-3,4-dihydroquinazoline-2-carboxamide (95 mg, 160 μmol) obtained in Example 269 and a 25% solution of hydrogen bromide in acetic acid (3 mL) was stirred with heating at 80° C. for 1 hr. The mixture was allowed to cool to room temperature, and concentrated under reduced pressure. The concentrated residue was suspended in ethanol (2 ml) and the mixture was heated under reflux for 15 min. The mixture was again allowed to cool to room temperature, and the precipitated solid was collected by filtration and washed with ethanol to give the title compound as a white powder (67 mg, 74%).
melting point: 240-242° C.

Example 271

6-fluoro-5-{[(4-fluorophenyl)methyl]oxy}-N-{[2-(methyloxy)pyridin-4-yl]methyl}-4-oxo-3,4-dihydroquinazoline-2-carboxamide

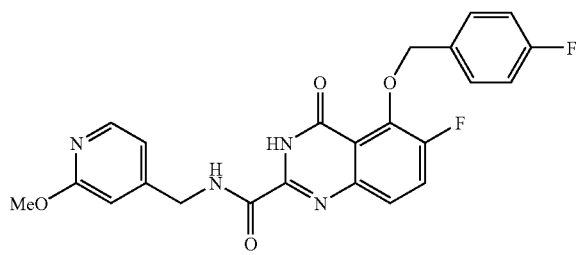 [SMILES: COc1cc(CNC(=O)c2nc3ccc(F)c(OCc4ccc(F)cc4)c3c(=O)[nH]2)ccn1]

The compound was synthesized from 5,6-difluoro-N-{[2-(methyloxy)pyridin-4-yl]methyl}-4-oxo-3,4-dihydroquinazoline-2-carboxamide obtained in Example 115 and (4-fluorophenyl)methanol by a method similar to that of Example 159.

melting point: 190-192° C.

Example 272

6-fluoro-5-{[(4-fluorophenyl)methyl]oxy}-4-oxo-N-(pyridin-4-ylmethyl)-3,4-dihydroquinazoline-2-carboxamide

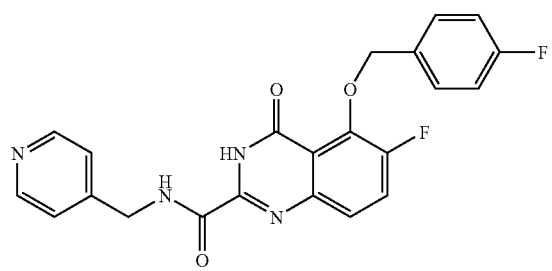 [SMILES: O=C(NCc1ccncc1)c1nc2ccc(F)c(OCc3ccc(F)cc3)c2c(=O)[nH]1]

The compound was synthesized from 5,6-difluoro-4-oxo-N-(pyridin-4-ylmethyl)-3,4-dihydroquinazoline-2-carboxamide obtained in Example 261 and (4-fluorophenyl)methanol by a method similar to that of Example 159.

melting point: 218-220° C.

Example 273

6-fluoro-5-{[(4-fluorophenyl)methyl]oxy}-N-{[2-({[4-(methyloxy)phenyl]methyl}oxy)pyridin-4-yl]methyl}-4-oxo-3,4-dihydroquinazoline-2-carboxamide

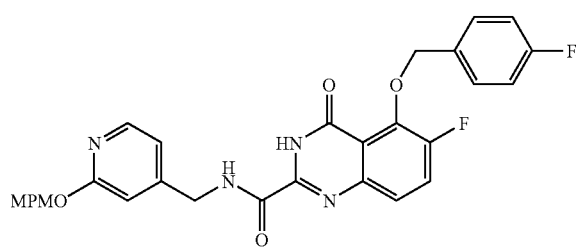

The compound was synthesized from 5,6-difluoro-N-{[2-({[4-(methyloxy)phenyl]methyl}oxy)pyridin-4-yl]methyl}-4-oxo-3,4-dihydroquinazoline-2-carboxamide obtained in Example 260 and (4-fluorophenyl)methanol by a method similar to that of Example 159.

melting point: 165-167° C.

Example 274

6-fluoro-5-{[(4-fluorophenyl)methyl]oxy}-4-oxo-N-[(2-oxo-1,2-dihydropyridin-4-yl)methyl]-3,4-dihydroquinazoline-2-carboxamide

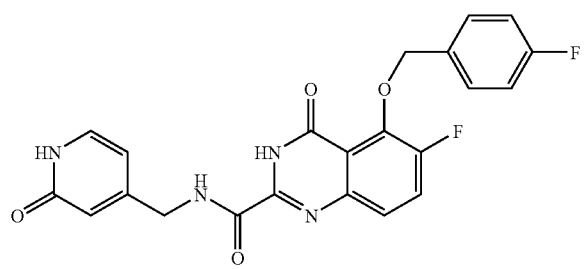 [SMILES: O=C(NCc1cc[nH]c(=O)c1)c1nc2ccc(F)c(OCc3ccc(F)cc3)c2c(=O)[nH]1]

6-Fluoro-5-{[(4-fluorophenyl)methyl]oxy}-N-{[2-({[4-(methyloxy)phenyl]methyl}oxy)pyridin-4-yl]methyl}-4-oxo-3,4-dihydroquinazoline-2-carboxamide(105 mg, 188 μmol) obtained in Example 273 was dissolved in 0.5% trifluoroacetic acid-containing dichloromethane (6 mL) and the mixture was stirred at room temperature for 3 hrs. The reaction mixture was concentrated under reduced pressure and crystallized from ethyl acetate. The precipitated crystals were collected by filtration, and washed with ethyl acetate to give the title compound as a pale-yellow powder (73 mg, 89%).

melting point: 248-250° C.

Example 275

5,6-difluoro-4-oxo-N-[(2-oxo-1,2-dihydropyridin-4-yl)methyl]-3,4-dihydroquinazoline-2-carboxamide

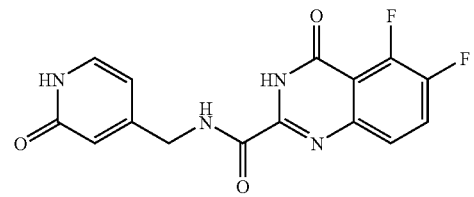 [SMILES: O=C(NCc1cc[nH]c(=O)c1)c1nc2ccc(F)c(F)c2c(=O)[nH]1]

The compound was synthesized from 5,6-difluoro-N-{[2-({[4-(methyloxy)phenyl]methyl}oxy)pyridin-4-yl]methyl}-4-oxo-3,4-dihydroquinazoline-2-carboxamide obtained in Example 260 by a method similar to that of Example 274.

melting point: 285-287° C.

Example 276

N-{[3-(methyloxy)phenyl]methyl}-4-oxo-5-{[(phenylmethyl)oxy]methyl}-3,4-dihydroquinazoline-2-carboxamide

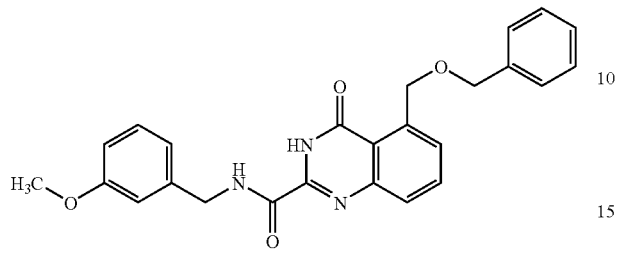

The compound was synthesized using ethyl 4-oxo-5-{[(phenylmethyl)oxy]methyl}-3,4-dihydroquinazoline-2-carboxylate obtained in Reference Example 124 and 3-methoxybenzylamine by a method similar to that of Example 1.

melting point: 160-161° C.

Example 277

N-{[3-(methyloxy)phenyl]methyl}-5-{[methyl(phenylmethyl)amino]methyl}-4-oxo-3,4-dihydroquinazoline-2-carboxamide

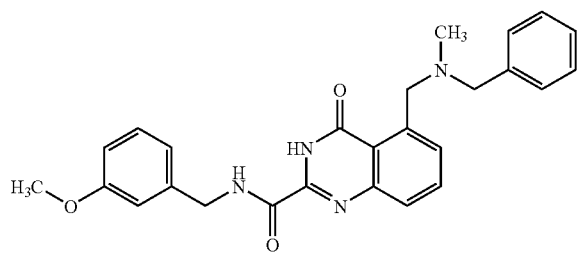 [SMILES: COc1cccc(CNC(=O)c2nc3cccc(CN(C)Cc4ccccc4)c3c(=O)[nH]2)c1]

The compound was synthesized using ethyl5-{[methyl(phenylmethyl)amino]methyl}-4-oxo-3,4-dihydroquinazoline-2-carboxylate obtained in Reference Example 126 and 3-methoxybenzylamine by a method similar to that of Example 1.

melting point: 127-128° C.

Example 278

5-{[acetyl(phenylmethyl)amino]methyl}-N-{[3-(methyloxy)phenyl]methyl}-4-oxo-3,4-dihydroquinazoline-2-carboxamide To a suspension of ethyl5-(bromomethyl)-4-oxo-3,4-dihydroquinazoline-2-carboxylate (300 mg, 0.964 mmol) obtained in Reference Example 125 in THF (6 mL)-DMF (2 mL) were added pyridine (0.078 mL, 0.964 mmol) and 1-phenylmethanamine (0.116 mL, 1.06 mmol) at 0° C., and the mixture was stirred at 0° C. for 30 min. and then at room temperature for 30 hrs. The reaction mixture was cooled again to 0° C., and pyridine (0.156 mL, 1.93 mmol) and acetyl chloride (0.150 mL, 2.12 mmol) were added, and the mixture was stirred at room temperature for 15 hrs. The reaction mixture was partitioned between ethyl acetate and water and the organic layer was washed with saturated brine, and dried over anhydrous sodium sulfate. The solvent was evaporated under reduced pressure, and diethyl ether-ethanol was added to the concentrated residue. The precipitated solid was collected by filtration to give ethyl 5-{[acetyl(phenylmethyl)amino]methyl}-4-oxo-3,4-dihydroquinazoline-2-carboxylate as a white powder (190 mg). The title compound was synthesized using the aforementioned ethyl 5-{[acetyl(phenylmethyl)amino]methyl}-4-oxo-3,4-dihydroquinazoline-2-carboxylate and 3-methoxybenzylamine, by a method similar to that of Example 1.

melting point: 210-212° C.

Example 279 ethyl 4-{[({2-[({[3-(methyloxy)phenyl]methyl}amino)carbonyl]-4-oxo-3,4-dihydroquinazolin-5-yl}methyl)oxy]methyl}benzoate

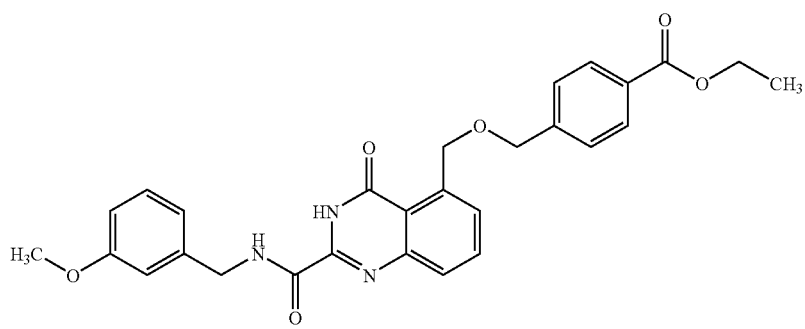 [SMILES: CCOC(=O)c1ccc(COCc2cccc3nc(C(=O)NCc4cccc(OC)c4)[nH]c(=O)c23)cc1]

A suspension of ethyl 5-{[({4-[(ethyloxy)carbonyl]phenyl}methyl)oxy]methyl}-4-oxo-3,4-dihydroquinazoline-2-carboxylate (200 mg, 487 µmol) obtained in Reference Example 151 and 3-methoxybenzylamine (100 mg, 731 µmol) in ethanol (6 mL) was stirred with heating at 80° C. for 15 hrs. The mixture was allowed to cool to room temperature, and the precipitated solid was collected by filtration and washed with ethanol and diethyl ether to give the title compound as a white powder (222 mg, 91%).

melting point: 183-185° C.

$^1$H-NMR (300 MHz, DMSO-$d_6$) δ: 1.33 (3H, t, J=6.9 Hz), 3.74 (3H, s), 4.32 (2H, q, J=6.9 Hz), 4.45 (2H, d, J=6.6 Hz), 4.81 (2H, s), 5.23 (2H, s), 6.82-6.85 (1H, m), 6.91-6.93 (2H, m), 7.25 (1H, t, J=8.1 Hz), 7.57 (2H, d, J=7.8 Hz), 7.70 (1H, d, J=7.8 Hz), 7.81-7.91 (2H, m), 7.98 (2H, d, J=7.8 Hz), 9.53 (1H, t, J=6.6 Hz), 12.17 (1H, bs).

Example 280

4-{[({2-[({[3-(methyloxy)phenyl]methyl}amino)carbonyl]-4-oxo-3,4-dihydroquinazolin-5-yl}methyl)oxy]methyl}benzoic acid

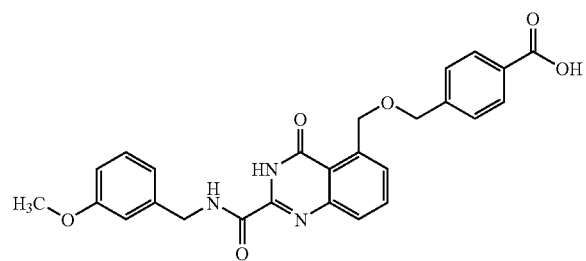 [SMILES: COc1cccc(CNC(=O)c2nc3cccc(COCc4ccc(C(=O)O)cc4)c3c(=O)[nH]2)c1]

To a suspension of ethyl 4-{[({2-[({[3-(methyloxy)phenyl]methyl}amino)carbonyl]-4-oxo-3,4-dihydroquinazolin-5-yl}methyl)oxy]methyl}benzoate (160 mg, 319 µmol) obtained in Example 279 in THF (3 mL)-methanol (3 mL)-water (3 mL) was added 4N aqueous sodium hydroxide solution (0.200 mL, 798 µmol), and the mixture was stirred with heating at 80° C. for 2 hrs. The mixture was allowed to cool to room temperature, acidified with 1N hydrochloric acid (ca. 2 mL), and THF and methanol were evaporated under reduced pressure. The solid in the concentrated residue was collected by filtration, and the obtained solid was washed with water. The obtained solid was again suspended in ethanol, and the mixture was stirred with heating at 80° C. for 30 min. The mixture was allowed to cool to room temperature, and the precipitated solid was collected by filtration, and washed with ethanol to give the title compound as a white powder (130 mg, 86%).

melting point: 230-232° C.

$^1$H-NMR (300 MHz, DMSO-$d_6$) δ: 3.73 (3H, s), 4.45 (2H, d, J=6.3 Hz), 4.79 (2H, s), 5.22 (2H, s), 6.84-6.80 (1H, m), 6.89-6.92 (2H, m), 7.24 (1H, t, J=8.1 Hz), 7.54 (2H, d, J=8.1 Hz), 7.69 (1H, d, J=7.8 Hz), 7.80-7.90 (2H, m), 7.95 (2H, d, J=7.8 Hz), 9.51 (1H, t, J=6.3 Hz), 12.16 (1H, bs), 12.90 (1H, bs).

Example 281

4-[2-({2-[({[3-(methyloxy)phenyl]methyl}amino)carbonyl]-4-oxo-3,4-dihydroquinazolin-5-yl}oxy)ethyl]benzoic acid

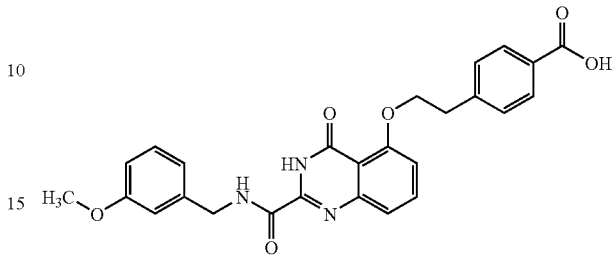

A solution of 5-fluoro-N-{[3-(methyloxy)phenyl]methyl}-4-oxo-3,4-dihydroquinazoline-2-carboxamide (1.00 g, 3.06 mmol) obtained in Example 110 and 4-(2-hydroxyethyl)benzoic acid (0.508 g, 3.06 mmol) in DMA (20 mL) was added dropwise to a suspension of 60% sodium hydride (0.466 g, 12.2 mmol) in DMA (10 mL) at room temperature. The reaction mixture was stirred at room temperature for 30 min. and the mixture was stirred with heating at 90° C. for 2 hrs. The mixture was allowed to cool to room temperature, water (60 mL) was added, and the aqueous layer was washed with ethyl acetate (60 mL×3). The aqueous layer was acidified with 1N hydrochloric acid (ca. 18 mL), and the object product was extracted with ethyl acetate (60 mL×2). The organic layers were combined, washed with 0.1N hydrochloric acid (60 mL×2) and saturated brine, and dried over anhydrous sodium sulfate. The solvent was evaporated under reduced pressure, and the concentrated residue was crystallized from methanol to give the title compound as a white powder (170 mg, 12%).

melting point: 228-230° C.

Example 282

Sodium 4-[({6-fluoro-2-[({[3-(methyloxy)phenyl]methyl}amino)carbonyl]-4-oxo-3,4-dihydroquinazolin-5-yl}oxy)methyl]benzoate

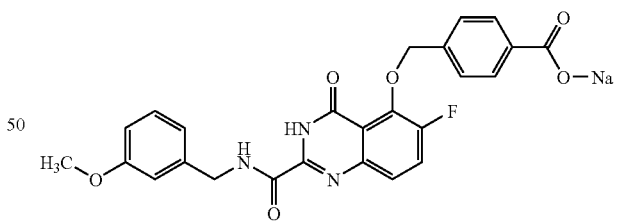

4-[({6-Fluoro-2-[({[3-(methyloxy)phenyl]methyl}amino)carbonyl]-4-oxo-3,4-dihydroquinazolin-5-yl}oxy)methyl]benzoic acid (200 mg, 419 µmol) obtained in Example 177 was dissolved in a mixed solvent of THF (32 mL) and ethanol (8 mL) with heating at 70° C., and an aqueous solution (2 mL) of sodium hydrogen carbonate (35.0 mg, 419 µmol) was added dropwise to this solution at 70° C. The reaction mixture was heated at 70° C. for 15 min. and stirred at room temperature 2 hrs. THF and ethanol were evaporated under reduced pressure, the concentrated residue was suspended in ethanol and the mixture was stirred with heating at 80° C. for 30 min. The mixture was allowed to cool to room temperature, and the precipitated solid was collected by filtration and washed with ethanol to give the title compound as a white powder (195 mg, 93%).

melting point: 289-292° C.

$^1$H-NMR (300 MHz, DMSO-d$_6$) δ: 3.74 (3H, s), 4.45 (2H, d, J=6.3 Hz), 5.14 (2H, s), 6.83 (1H, dd, J=8.1, 2.4 Hz), 6.90-6.93 (2H, m), 7.25 (1H, t, J=8.1 Hz), 7.47-7.52 (3H, m),7.68 (1H, t, J=9.6 Hz), 7.88 (2H, d, J=8.1 Hz), 9.41 (1H, t, J=6.3 Hz).

Example 283

Potassium 4-[({6-fluoro-2-[({[3-(methyloxy)phenyl]methyl}amino)carbonyl]-4-oxo-3,4-dihydroquinazolin-5-yl}oxy)methyl]benzoate

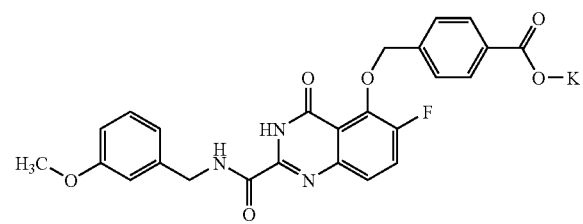

4-[({6-Fluoro-2-[({[3-(methyloxy)phenyl]methyl}amino)carbonyl]-4-oxo-3,4-dihydroquinazolin-5-yl}oxy)methyl]benzoic acid obtained in Example 177 (100 mg, 209 μmol) was dissolved in a mixed solvent of THF (16 mL) and ethanol (4 mL) with heating at 70° C., and an aqueous solution (2 mL) of potassium hydrogen carbonate (21.0 mg, 209 μmol) was added dropwise to this solution at 70° C. The reaction mixture was heated at 70° C. for 15 min. and the mixture was stirred at room temperature for 2 hrs. THF and ethanol were evaporated under reduced pressure, and the concentrated residue was suspended in ethanol. The mixture was stirred with heating at 80° C. for 30 min. The mixture was allowed to cool to room temperature, and the precipitated solid was collected by filtration and washed with ethanol to give the title compound as a white powder (90 mg, 84%).

melting point: 237-240° C.

$^1$H-NMR (300 MHz, DMSO-d$_6$) δ: 3.74 (3H, s), 4.44 (2H, d, J=6.3 Hz), 5.13 (2H, s), 6.82 (1H, dd, J=8.1, 2.4 Hz), 6.90-6.93 (2H, m), 7.25 (1H, t, J=8.1 Hz), 7.44-7.50 (3H, m), 7.66 (1H, t, J=9.9 Hz), 7.86 (2H, d, J=7.8 Hz), 9.36 (1H, t, J=6.3 Hz).

Example 284

Disodium 4-[({6-fluoro-2-[({[3-(methyloxy)phenyl]methyl}amino)carbonyl]-4-oxo-4H-quinazolin-3-id-5-yl}oxy)methyl]benzoate

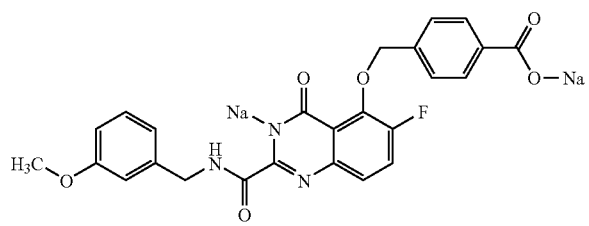

4-[({6-Fluoro-2-[({[3-(methyloxy)phenyl]methyl}amino)carbonyl]-4-oxo-3,4-dihydroquinazolin-5-yl}oxy)methyl]benzoic acid (100 mg, 209 μmol) obtained in Example 177 was dissolved in a mixed solvent of THF (16 mL) and ethanol (4 mL) with heating at 70° C. An aqueous solution (2 mL) of sodium hydrogen carbonate (35.0 mg, 419 μmol) was added dropwise to this solution at 70° C. and the reaction mixture was heated at 70° C. for 15 min. and then stirred at room temperature for 2 hrs. The precipitated solid was collected by filtration and washed with ethanol to give the title compound as a white powder (77 mg, 71%).

melting point: 330° C.

$^1$H-NMR (300 MHz, DMSO-d$_6$) δ: 3.74 (3H, s), 4.44 (2H, d, J=6.0 Hz), 5.10 (2H, s), 6.80-6.83 (1H, m), 6.89-6.92 (2H, m), 7.24 (1H, t, J=8.1 Hz), 7.39-7.45 (4H, m), 7.83 (2H, d, J=7.8 Hz), 9.17 (1H, t, J=6.3 Hz).

Example 285

Dipotassium 4-[({6-fluoro-2-[({[3-(methyloxy)phenyl]methyl}amino)carbonyl]-4-oxo-4H-quinazolin-3-id-5-yl}oxy)methyl]benzoate

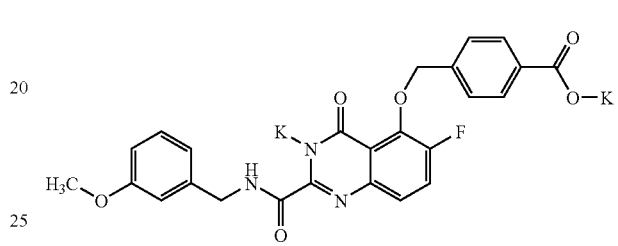

4-[({6-Fluoro-2-[({[3-(methyloxy)phenyl]methyl}amino)carbonyl]-4-oxo-3,4-dihydroquinazolin-5-yl}oxy)methyl]benzoic acid (100 mg, 209 μmol) obtained in Example 177 was dissolved in a mixed solvent of THF (16 mL) and ethanol (4 mL) with heating at 70° C., and aqueous solution (2 mL) of potassium hydrogen carbonate (41.9 mg, 418 μmol) was added dropwise to this solution at 70° C. The reaction mixture was heated at 70° C. for 15 min. and then stirred at room temperature for 2 hrs. The precipitated solid was collected by filtration, and washed with ethanol to give the title compound as a white powder (104 mg, 90%).

melting point: 290° C.

$^1$H-NMR (300 MHz, DMSO-d$_6$) δ: 3.74 (3H, s), 4.42 (2H, d, J=6.3 Hz), 5.09 (2H, s), 6.80-6.83 (1H, m), 6.89-6.92 (2H, m), 7.21-7.31 (2H, m), 7.36-7.42 (3H, m), 7.79 (2H, d, J=7.8 Hz), 9.02 (1H, t, J=6.3 Hz).

Example 286

Sodium 4-[2-({6-fluoro-2-[({[3-(methyloxy)phenyl]methyl}amino)carbonyl]-4-oxo-3,4-dihydroquinazolin-5-yl}oxy)ethyl]benzoate

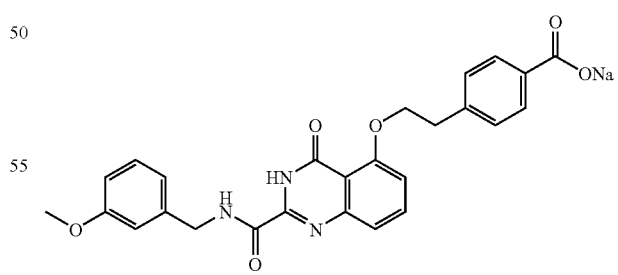

4-[2-({6-Fluoro-2-[({[3-(methyloxy)phenyl]methyl}amino)carbonyl]-4-oxo-3,4-dihydroquinazolin-5-yl)oxy}ethyl]benzoic acid (300 mg, 610 μmol) obtained in Example 179 was dissolved in a mixed solvent of THF (10 mL) and methanol (2.5 mL) with heating at 80° C., and aqueous solution (2.5 mL) of sodium hydrogen carbonate (51.2 mg, 610 μmol) was added dropwise to this solution at 80° C. The reaction mixture was heated at 80° C. for 10 min.

and THF and methanol were evaporated under reduced pressure. The concentrated residue was suspended in methanol (10 mL) and the mixture was stirred with heating at 80° C. for 20 min. The mixture was allowed to cool to room temperature, and the precipitated solid was collected by filtration and washed with methanol to give the title compound as a pale-yellow powder (250 mg, 80%).

7.40-7.44 (2H, m), 7.78 (2H, d, J=8.1 Hz), 9.22 (1H, t, J=6.3 Hz).

Example 288 calcium bis(4-{[({2-[({[3-(methyloxy)phenyl]methyl}amino)carbonyl]-4-oxo-3,4-dihydrothieno[2,3-d]pyrimidin-5-yl}methyl)oxy]methyl}benzoate)

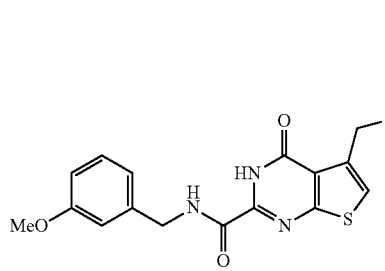
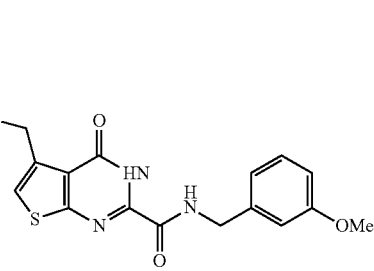

melting point: 319-321° C.

¹H-NMR (300MHz, DMSO-d₆) δ: 3.11 (2H, t, J=6.6 Hz), 3.73 (3H, s), 4.27 (2H, t, J=6.9 Hz), 4.43 (2H, d, J=6.0 Hz), 6.79-6.91 (3H, m), 7.20-7.29 (3H, m), 7.45-7.50 (1H, m), 7.65 (1H, t, J=9.6 Hz), 7.80 (2H, d, J=7.5 Hz), 9.39 (1H, t, J=6.0 Hz).

Example 287

Disodium 4-[2-({6-fluoro-2-[({[3(methyloxy)phenyl]methyl}amino)carbonyl]-4-oxo-4H-quinazolin-3-id-5-yl}oxy)ethyl]benzoate

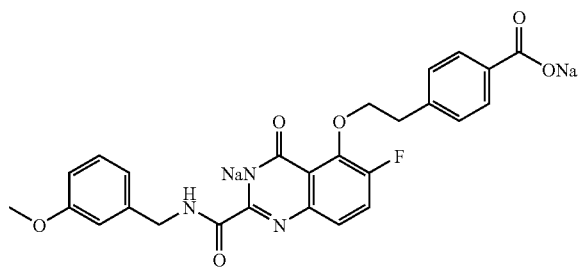

4-[2-({6-Fluoro-2-[({[3-(methyloxy)phenyl]methyl}amino)carbonyl]-4-oxo-3,4-dihydroquinazolin-5-yl}oxy)ethyl]benzoic acid (300 mg, 610 µmol) obtained in Example 179 was dissolved in a mixed solvent of THF (9 mL) and methanol (3 mL) with heating at 80° C., and aqueous solution (3 mL) of sodium hydrogen carbonate (103 mg, 0.122 mmol) was added dropwise to this solution at 80° C. The reaction mixture was heated at 80° C. for 10 min. and THF and methanol were evaporated under reduced pressure. The concentrated residue was suspended in ethanol (10 mL) and the mixture was stirred with heating at 80° C. for 20 min. The mixture was allowed to cool to room temperature, and the precipitated solid was collected by filtration and washed with ethanol to give the title compound as a white powder (285 mg, 87%).

melting point: 331-333° C.

¹H-NMR (300 MHz, DMSO-d₆) δ: 3.05 (2H, t, J=7.5 Hz), 3.72 (3H, s), 4.22 (2H, t, J=7.5 Hz), 4.44 (2H, d, J=6.0 Hz), 6.80 (1H, d, J=7.5 Hz), 6.86-6.92 (2H, m), 7.15-7.25 (3H, m),

To a solution of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (200 mg, 417 µmol) obtained in Example 217 and 1N aqueous sodium hydroxide solution (4.17 mL, 417 µmol) in methanol (16 mL)-water (4 mL) was added dropwise an aqueous solution (4 mL) of calcium chloride (23.1 mg, 209 µmol) at 80° C. The reaction mixture was heated at 80° C. for 30 min., and allowed to cool to room temperature. The precipitated crystals were collected by filtration and washed with water and suspended again in methanol. The mixture was stirred with heating at 80° C. for 20 min. The mixture was allowed to cool to room temperature, and the precipitated solid was collected by filtration and washed with methanol to give the title compound as a white powder (190 mg, 91%).

melting point: 350° C.

¹H-NMR (300MHz, DMSO-d₆) δ: 3.72 (3H, s), 4.40 (2H, d, J=6.0 Hz), 4.71 (2H, s), 4.88 (2H, s), 6.79-6.90 (3H, m), 7.22 (1H, t, J=8.1 Hz), 7.44-7.50 (3H, m), 7.91 (2H, d, J=8.1 Hz), 9.51 (1H, m).

Example 289 ethyl 4-[({[2-({[(3-methylphenyl)methyl]amino}carbonyl)-4-oxo-3,4-dihydrothieno[2,3-d]pyrimidin-5-yl]methyl}oxy)methyl]benzoate

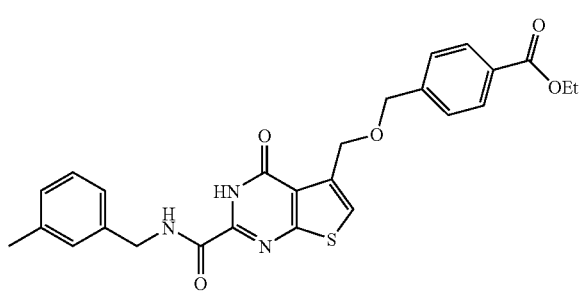 [SMILES: CCOC(=O)c1ccc(COCc2csc3nc(C(=O)NCc4cccc(C)c4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3-methylphenyl)methanamine (0.175 g, 1.44 mmol) in ethanol (8 mL) was stirred with heating at 80° C. for 15 hrs. The mixture was allowed to cool to room temperature, and the precipitated solid was collected by filtration and washed with ethanol to give the title compound as a white powder (398 mg, 84%). melting point: 198-200° C.

Example 290 ethyl 4-[({2-({[(3-ethylphenyl)methyl]
amino}carbonyl)-4-oxo-3,4-dihydrothieno[2,3-d]
pyrimidin-5-yl]methyl}oxy)methyl]benzoate

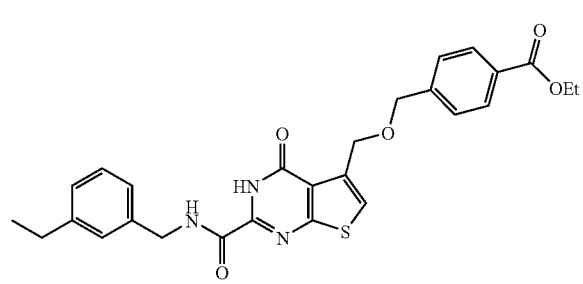

A suspension of ethyl 5-{[({4-[(ethyloxy)carbonyl]
phenyl}methyl)oxy]methyl}-4-oxo-3,4-dihydrothieno[2,3-d]pyrimidine-2-carboxylate (0.300 g, 0.720 mmol) obtained in Reference Example 158 and 1-(3-ethylphenyl)methanamine (0.195 g, 1.44 mmol) obtained in Reference Example 127 in DMA (6 mL) was stirred with heating at 80° C. for 15 hrs. The solvent was evaporated under reduced pressure, and the concentrated residue was suspended in ethanol. The precipitated solid was collected by filtration and washed with ethanol to give the title compound as a white powder (276 mg, 76%).

melting point: 196-198° C.

Example 291 ethyl 4-[({2-({[(3-chlorophenyl)methyl]
amino}carbonyl)-4-oxo-3,4-dihydrothieno[2,3-d]
pyrimidin-5-yl]methyl}oxy)methyl]benzoate

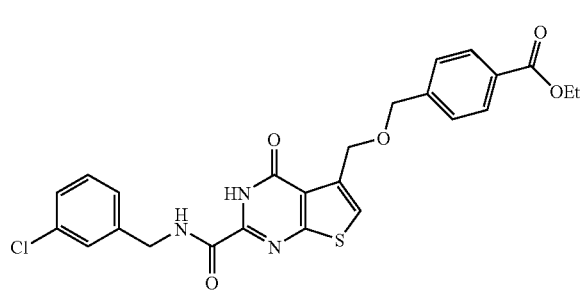 [SMILES: CCOC(=O)c1ccc(COCc2csc3nc(C(=O)NCc4cccc(Cl)c4)[nH]c(=O)c23)cc1]

A suspension of ethyl 5-{[({4-[(ethyloxy)carbonyl]
phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3-chlorophenyl)methanamine (0.204 g, 1.44 mmol) in ethanol (8 mL) was stirred with heating at 80° C. for 15 hrs. The mixture was allowed to cool to room temperature and the precipitated solid was collected by filtration and washed with ethanol to give the title compound as a white powder (426 mg, 87%).

melting point: 236-238° C.

Example 292 ethyl 4-{[({2-[({[3-(methylthio)phenyl]
methyl}amino)carbonyl]-4-oxo-3,4-dihydrothieno[2,3-d]pyrimidin-5-yl}methyl)oxy]methyl}benzoate

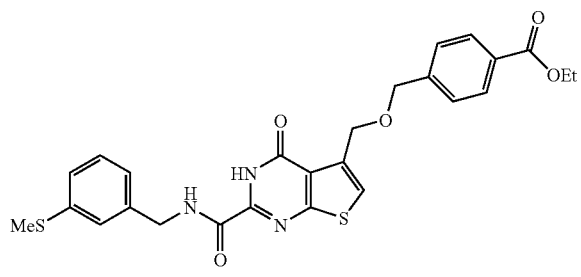 [SMILES: CCOC(=O)c1ccc(COCc2csc3nc(C(=O)NCc4cccc(SC)c4)[nH]c(=O)c23)cc1]

A suspension of ethyl 5-{[({4-[(ethyloxy)carbonyl]
phenyl}methyl)oxy]methyl}-4-oxo-3,4-dihydrothieno[2,3-d]pyrimidine-2-carboxylate (0.300 g, 0.720 mmol) obtained in Reference Example 158, 1-[3-(methylthio)phenyl]methanamine hydrochloride (0.232 g, 1.22 mmol) obtained in Reference Example 129 and triethylamine (0.175 g, 1.73 mmol) in ethanol (15 mL) was stirred with heating at 80° C. for 15 hrs. The mixture was allowed to cool to room temperature and the precipitated solid was collected by filtration and washed with ethanol to give the title compound as a white powder (311 mg, 82%).

melting point: 207-209° C.

Example 293 ethyl 4-{[({4-oxo-2-[({[3-(trifluoromethyl)phenyl]
methyl}amino)carbonyl]-3,4-dihydrothieno[2,3-d]
pyrimidin-5-yl}methyl)oxy]methyl}benzoate

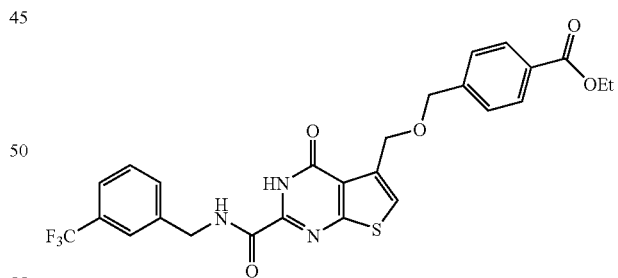

A suspension of ethyl5-{[({4-[(ethyloxy)carbonyl]
phenyl}methyl)oxy]methyl}-4-oxo-3,4-dihydrothieno[2,3-d]pyrimidine-2-carboxylate (0.400 g, 0.961 mmol) obtained in Reference Example 158 and 1-[3-(trifluoromethyl)phenyl]methanamine (0.252 g, 1.44 mmol) in ethanol (8 mL) was stirred with heating at 80° C. for 15 hrs. The mixture was allowed to cool to room temperature and the precipitated solid was collected by filtration and washed with ethanol to give the title compound as a white powder (433 mg, 83%).

melting point: 235-237° C.

Example 294 ethyl 4-({[(4-oxo-2-{[({3-[(trifluoromethyl)oxy]phenyl}methyl)amino]carbonyl}-3,4-dihydrothieno[2,3-d]pyrimidin-5-yl)methyl]oxy}methyl)benzoate

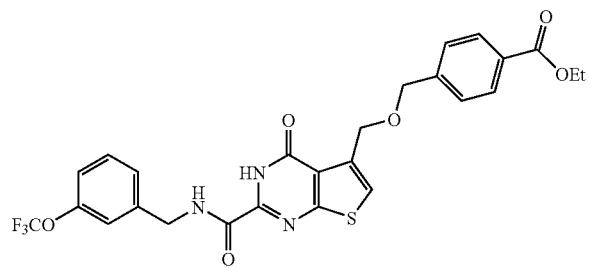 [SMILES: CCOC(=O)c1ccc(COCc2csc3nc(C(=O)NCc4cccc(OC(F)(F)F)c4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-{3-[(trifluoromethyl)oxy]phenyl}methanamine (0.276 g, 1.44 mmol) in ethanol (8 mL) was stirred with heating at 80° C. for 15 hrs. The mixture was allowed to cool to room temperature and the precipitated solid was collected by filtration and washed with ethanol to give the title compound as a white powder (440 mg, 82%).

melting point: 232-234° C.

Example 295 ethyl 4-({[(4-oxo-2-{[(pyridin-4-ylmethyl)amino]carbonyl}-3,4-dihydrothieno[2,3-d]pyrimidin-5-yl)methyl]oxy}methyl)benzoate

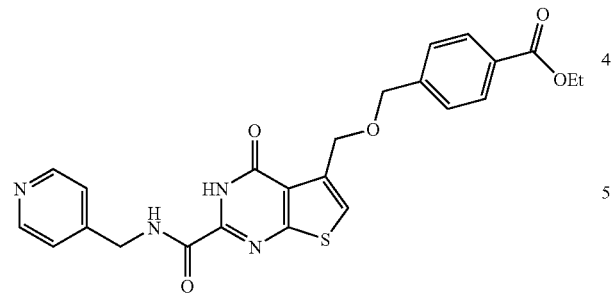

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.300 g, 0.720 mmol) obtained in Reference Example 158 and 1-pyridin-4-ylmethanamine (0.156 g, 1.44 mmol) in DMA (6 mL) was stirred with heating at 80° C. for 15 hrs. The solvent was evaporated under reduced pressure, and the concentrated residue was suspended in ethanol. The precipitated solid was collected by filtration and washed with ethanol to give the title compound as a white powder (252 mg, 73%).

melting point: 256-258° C.

Example 296 ethyl 4-[({[2-({[(3-fluorophenyl)methyl]amino}carbonyl)-4-oxo-3,4-dihydrothieno[2,3-d]pyrimidin-5-yl]methyl}oxy)methyl]benzoate

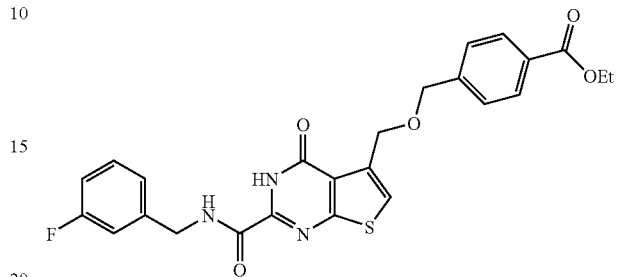

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3-fluorophenyl)methanamine (0.204 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (421 mg, 88%).

melting point: 240-241° C.

Example 297 ethyl 4-[({[2-({[(4-fluorophenyl)methyl]amino}carbonyl)-4-oxo-3,4-dihydrothieno[2,3-d]pyrimidin-5-yl]methyl}oxy)methyl]benzoate

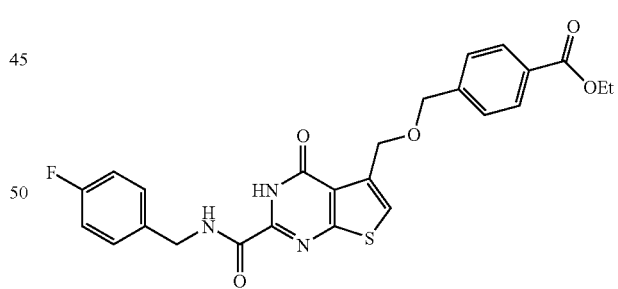

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(4-fluorophenyl)methanamine (0.204 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (422 mg, 89%).

melting point: 252-254° C.

Example 298 ethyl 4-{[({2-[({[4-(methyloxy)phenyl]methyl}amino)carbonyl]-4-oxo-3,4-dihydrothieno[2,3-d]pyrimidin-5-yl}methyl)oxy]methyl}benzoate

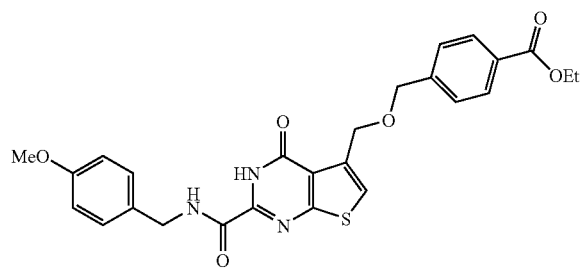 [SMILES: CCOC(=O)c1ccc(COCc2csc3nc(C(=O)NCc4ccc(OC)cc4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-[4-(methyloxy)phenyl]methanamine (0.224 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (429 mg, 88%).

melting point: 206-208° C.

Example 299 ethyl 4-({[(4-oxo-2-{[(2-phenylethyl)amino]carbonyl}-3,4-dihydrothieno[2,3-d]pyrimidin-5-yl)methyl]oxy}methyl)benzoate

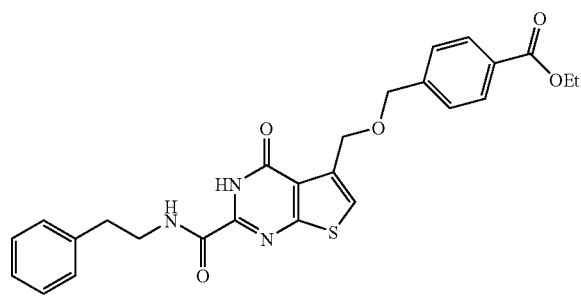 [SMILES: CCOC(=O)c1ccc(COCc2csc3nc(C(=O)NCCc4ccccc4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 2-phenylethaneamine (0.198 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (423 mg, 90%).

melting point: 194-196° C.

Example 300 ethyl 4-[({[2-({[(3,4-difluorophenyl)methyl]amino}carbonyl)-4-oxo-3,4-dihydrothieno[2,3-d]pyrimidin-5-yl]methyl}oxy)methyl]benzoate

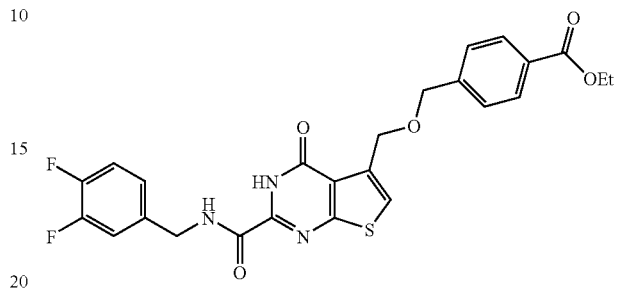

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3,4-difluorophenyl)methanamine (0.234 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (463 mg, 94%).

melting point: 254-256° C.

Example 301 ethyl 4-[({[2-({[(3-chloro-4-fluorophenyl)methyl]amino}carbonyl)-4-oxo-3,4-dihydrothieno[2,3-d]pyrimidin-5-yl]methyl}oxy)methyl]benzoate

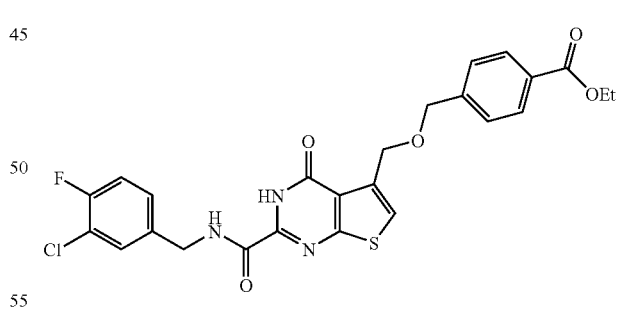

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3-chloro-4-fluorophenyl)methanamine (0.261 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a white powder (478 mg, 94%).

melting point: 249-251° C.

Example 302 ethyl 4-[({[2-({[(3-bromo-4-fluorophenyl)methyl]
amino}carbonyl)-4-oxo-3,4-dihydrothieno[2,3-d]
pyrimidin-5-yl]methyl}oxy)methyl]benzoate

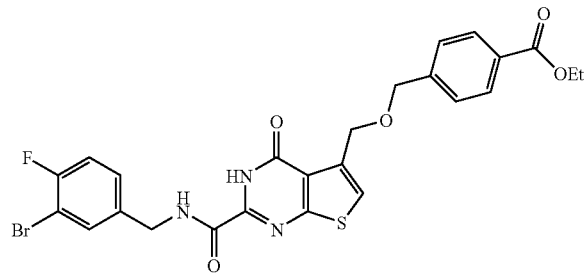 [SMILES: CCOC(=O)c1ccc(COCc2csc3nc(C(=O)NCc4ccc(F)c(Cl)c4)[nH]c(=O)c23)cc1]

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.400 g, 0.961 mmol) obtained
in Reference Example 158, 1-(3-bromo-4-fluorophenyl)
methanamine hydrochloride (0.393 g, 1.63 mmol) and tri-
ethylamine (0.233 g, 2.31 mmol) in ethanol (12 mL) was
stirred with heating at 80° C. for 15 hrs. The mixture was
allowed to cool to room temperature and the precipitated solid
was collected by filtration and washed with ethanol to give the
title compound as a white powder (500 mg, 91%).

melting point: 241-243° C.

Example 303 ethyl 4-[({[2-({[(4-fluoro-3-methylphenyl)methyl]
amino}carbonyl)-4-oxo-3,4-dihydrothieno[2,3-d]
pyrimidin-5-yl]methyl}oxy)methyl]benzoate

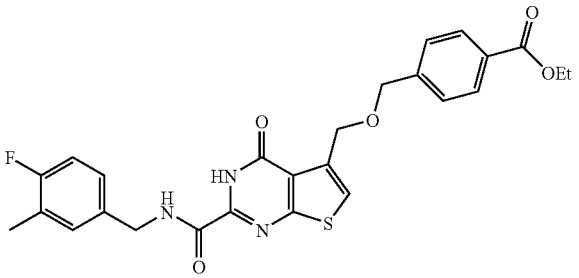 [SMILES: CCOC(=O)c1ccc(COCc2csc3nc(C(=O)NCc4ccc(F)c(C)c4)[nH]c(=O)c23)cc1]

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.400 g, 0.961 mmol) obtained
in Reference Example 158 and 1-(4-fluoro-3-methylphenyl)
methanamine (0.227 g, 1.63 mmol) in ethanol (15 mL) was
stirred with heating at 80° C. for 15 hrs. The mixture was
allowed to cool to room temperature and the precipitated solid
was collected by filtration and washed with ethanol to give the
title compound as a white powder (463 mg, 94%).

melting point: 232-234° C.

Example 304 ethyl 4-({[(2-{[({3-[(methyloxy)methyl]
phenyl}methyl)amino]carbonyl}-4-oxo-3,4-dihy-
drothieno[2,3-d]pyrimidin-5-yl)methyl]oxy}methyl)
benzoate

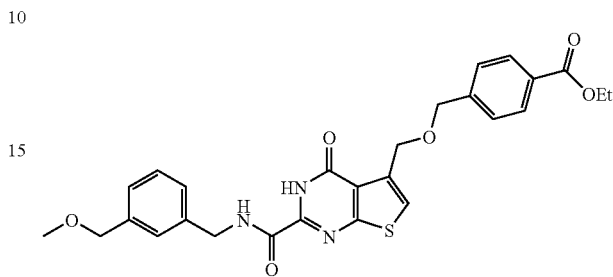

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.400 g, 0.961 mmol) obtained
in Reference Example 158 and 1-{3-[(methyloxy)methyl]
phenyl}methanamine (0.247 g, 1.63 mmol) obtained in Ref-
erence Example 131 in ethanol (15 mL) was stirred with
heating at 80° C. for 15 hrs. The mixture was allowed to cool
to room temperature and the precipitated solid was collected
by filtration and washed with ethanol to give the title com-
pound as a white powder (450 mg, 90%).

melting point: 189-191° C.

Example 305 ethyl 4-{[({2-[({[3-(methylsulfonyl)phenyl]
methyl}amino)carbonyl]-4-oxo-3,4-dihydrothieno[2,
3-d]pyrimidin-5-yl}methyl)oxy]methyl}benzoate

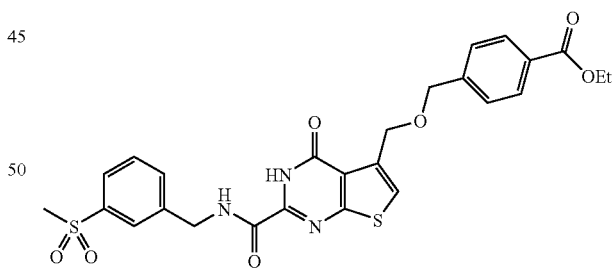

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.280 g, 0.672 mmol) obtained
in Reference Example 158 and 1-[3-(methylsulfonyl)phenyl]
methanamine (0.212 g, 1.14 mmol) obtained in Reference
Example 134 in ethanol (12 mL) was stirred with heating at
80° C. for 15 hrs. The mixture was allowed to cool to room
temperature and the precipitated solid was collected by filtra-
tion and washed with ethanol to give the title compound as a
white powder (463 mg, 94%).

melting point: 245-247° C.

Example 306 ethyl 4-{[({2-[({[3-(methylsulfinyl)phenyl]methyl}amino)carbonyl]-4-oxo-3,4-dihydrothieno[2,3-d]pyrimidin-5-yl}methyl)oxy]methyl}benzoate

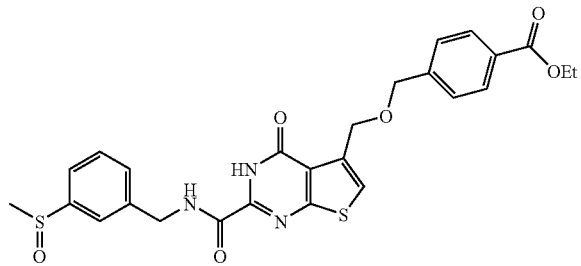 [SMILES: CCOC(=O)c1ccc(COCc2csc3nc(C(=O)NCc4cccc(S(C)=O)c4)[nH]c(=O)c23)cc1]

To a solution of ethyl 4-{[({2-[({[3-(methylthio)phenyl]methyl}amino)carbonyl]-4-oxo-3,4-dihydrothieno[2,3-d]pyrimidin-5-yl}methyl)oxy]methyl}benzoate (0.300 g, 0.573 mmol) obtained in Example 292 in chloroform (30 mL) was added 3-chloroperbenzoic acid (0.132 g, 0.573 mmol) at room temperature, and the mixture was stirred at room temperature for 4 hrs. The reaction mixture was concentrated under reduced pressure and the concentrated residue was suspended in ethanol (15 mL), and the mixture was stirred with heating at 80° C. 15 hr. The mixture was allowed to cool to room temperature and the precipitated solid was collected by filtration and washed with methanol to give the title compound as a white powder (295 mg, 95%).

melting point: 184-186° C.

Example 307 ethyl 4-({[(4-oxo-2-{[(pyridin-3-ylmethyl)amino]carbonyl}-3,4-dihydrothieno[2,3-d]pyrimidin-5-yl)methyl]oxy}methyl)benzoate

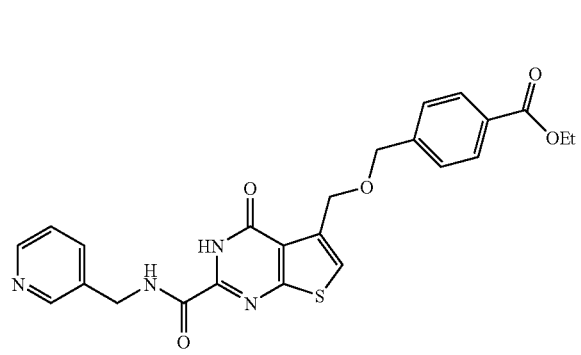

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-pyridin-3-ylmethanamine (0.177 g, 1.63 mmol) in ethanol (12 mL) was stirred with heating at 80° C. for 15 hrs. The mixture was allowed to cool to room temperature and the precipitated solid was collected by filtration and washed with ethanol to give the title compound as a lo white powder (429 mg, 93%).

melting point: 229-231° C.

Example 308 ethyl 4-({[(2-{[({3-[(methylthio)methyl]phenyl}methyl)amino]carbonyl}-4-oxo-3,4-dihydrothieno[2,3-d]pyrimidin-5-yl)methyl]oxy}methyl)benzoate

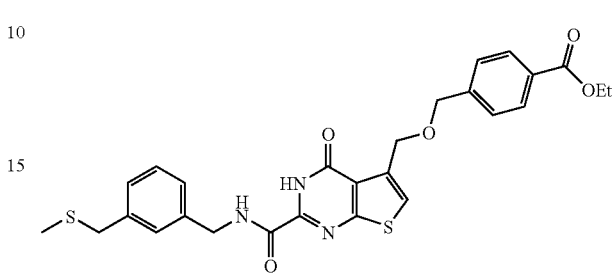

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (1.00 g, 2.40 mmol) obtained in Reference Example 158 and 1-{3-[(methylthio)methyl]phenyl}methanamine (0.683 g, 4.08 mmol) obtained in Reference Example 136 in ethanol (40 mL) was stirred with heating at 80° C. for 15 hrs. The mixture was allowed to cool to room temperature and the precipitated solid was collected by filtration and washed with ethanol to give the title compound as a white powder (1.19 g, 92%).

melting point: 185-186° C.

Example 309 ethyl 4-({[(2-{[({3-[(methylsulfinyl)methyl]phenyl}methyl)amino]carbonyl}-4-oxo-3,4-dihydrothieno[2,3-d]pyrimidin-5-yl)methyl]oxy}methyl)benzoate

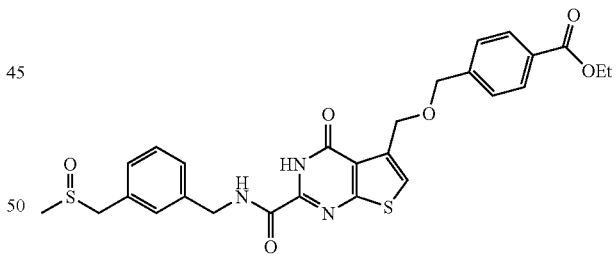

To a solution of ethyl 4-({[(2-{[({3-[(methylthio)methyl]phenyl}methyl)amino]carbonyl}-4-oxo-3,4-dihydrothieno[2,3-d]pyrimidin-5-yl)methyl]oxy}methyl)benzoate (0.400 g, 0.744 mmol) obtained in Example 308 in chloroform (20 mL) was added 3-chloroperbenzoic acid (0.186 g, 0.744 mmol) at 0° C., and the mixture was stirred at room temperature 2 hr. The reaction mixture was concentrated under reduced pressure and the concentrated residue was suspended in ethanol (15 mL). The mixture was stirred with heating at 80° C. for 15 hrs. The mixture was allowed to cool to room temperature and the precipitated solid was collected by filtration and washed with methanol to give the title compound as a white powder (380 mg, 92%).

melting point: 195-196° C.

Example 310 ethyl 4-({[(2-{[({3-[(methylsulfonyl)methyl]
phenyl}methyl)amino]carbonyl}-4-oxo-3,4-dihy-
drothieno[2,3-d]pyrimidin-5-yl)methyl]oxy}methyl)
benzoate

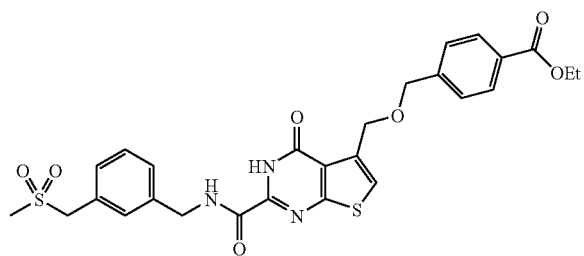 [SMILES: CCOC(=O)c1ccc(COCc2csc3nc(C(=O)NCc4cccc(CS(C)(=O)=O)c4)[nH]c(=O)c23)cc1]

To a solution of ethyl 4-({[(2-{[({3-[(methylthio)methyl]
phenyl}methyl)amino]carbonyl}-4-oxo-3,4-dihydrothieno
[2,3-d]pyrimidin-5-yl)methyl]oxy}methyl)benzoate (0.280
g, 0.744 mmol) obtained in Example 308 in chloroform (15
mL) was added 3-chloroperbenzoic acid (0.260 g, 1.04
mmol) at room temperature, and the mixture was stirred at
room temperature for 4 hrs. The reaction mixture was con-
centrated under reduced pressure and the concentrated resi-
due was suspended in ethanol (15 mL). The mixture was
stirred with heating at 80° C. for 15 hrs. The mixture was
allowed to cool to room temperature and the precipitated solid
was collected by filtration and washed with methanol to give
the title compound as a white powder (279 mg, 94%).

melting point: 227-229° C.

Example 311 ethyl 4-({[(2-{[({3-[methyl(trifluoroacetyl)amino]
phenyl}methyl)amino]carbonyl}-4-oxo-3,4-dihy-
drothieno[2,3-d]pyrimidin-5-yl)methyl]oxy}methyl)
benzoate

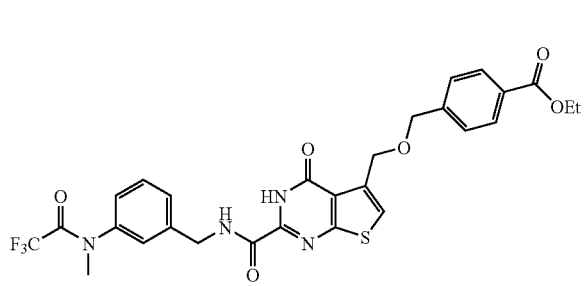 [SMILES: CCOC(=O)c1ccc(COCc2csc3nc(C(=O)NCc4cccc(N(C)C(=O)C(F)(F)F)c4)[nH]c(=O)c23)cc1]

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.200 g, 0.480 mmol) obtained
in Reference Example 158, N-[3-(aminomethyl)phenyl]-2,2,
2-trifluoro-N-methylacetamide hydrochloride (0.219 g,
0.816 mmol) obtained in Reference Example 141 and triethy-
lamine (0.121 g, 1.20 mmol) in ethanol (16 mL) was stirred
with heating at 80° C. for 24 hrs. The mixture was allowed to
cool to room emperature and the precipitated solid was col-
lected by filtration and washed with ethanol to give the title
compound as a white powder (216 mg, 75%).

melting point: 208-209° C.

Example 312 ethyl 4-[({[4-oxo-2-({[(3-propylphenyl)methyl]
amino}carbonyl)-3,4-dihydrothieno[2,3-d]pyrimidin-
5-yl]methyl}oxy)methyl]benzoate

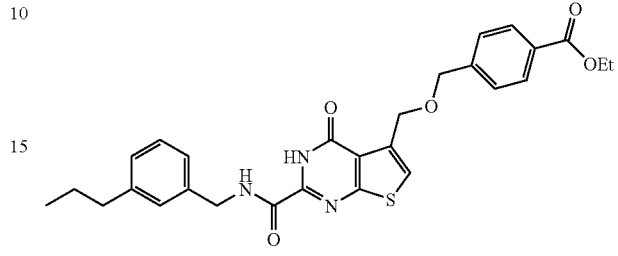

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.200 g, 0.480 mmol) obtained
in Reference Example 158 and 1-(3-propylphenyl)metha-
namine (0.122 g, 0.816 mmol) obtained in Reference
Example 137 in ethanol (12 mL) was stirred with heating at
80° C. for 15 hrs. The mixture was allowed to cool to room
temperature and the precipitated solid was collected by filtra-
tion and washed with ethanol to give the title compound as a
white powder (215 mg, 86%).

melting point: 181-182° C.

Example 313 ethyl 4-[({[2-({[(3-ethyl-4-fluorophenyl)methyl]
amino}carbonyl)-4-oxo-3,4-dihydrothieno[2,3-d]
pyrimidin-5-yl]methyl}oxy)methyl]benzoate

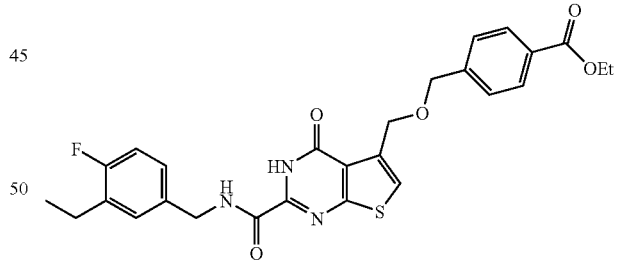

A suspension of ethyl 5-{[({4-[(ethyloxy)carbonyl]
phenyl}methyl)oxy]methyl}-4-oxo-3,4-dihydrothieno[2,3-
d]pyrimidine-2-carboxylate (0.350 g, 0.840 mmol) obtained
in Reference Example 158 and 1-(3-ethyl-4-fluorophenyl)
methanamine (0.219 g, 1.43 mmol) obtained in Reference
Example 138 in ethanol (15 mL) was stirred with heating at
80° C. for 48 hrs. The mixture was allowed to cool to room
temperature and the precipitated solid was collected by filtra-
tion and washed with ethanol to give the title compound as a
white powder (370 mg, 84%).

melting point: 204-206° C.

Example 314 ethyl 4-[({[2-({[(3-bromophenyl)methyl]amino}carbonyl)-4-oxo-3,4-dihydrothieno[2,3-d]pyrimidin-5-yl]methyl}oxy)methyl]benzoate

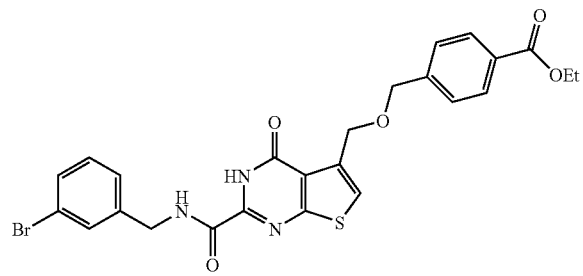

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158, 1-(3-bromophenyl)methanamine hydrochloride (0.363 g, 1.63 mmol) and triethylamine (0.243 g, 2.40 mmol) in ethanol (16 mL) was stirred with heating at 80° C. for 24 hrs. The mixture was allowed to cool to room temperature and the precipitated solid was collected by filtration and washed with ethanol to give the title compound as a white powder (490 mg, 92%).

melting point: 226-227° C.

Example 315 ethyl 4-{[({2-[({[4-fluoro-3(trifluoromethyl)phenyl]methyl}amino)carbonyl]-4-oxo-3,4-dihydrothieno[2,3-d]pyrimidin-5-yl}methyl)oxy]methyl}benzoate

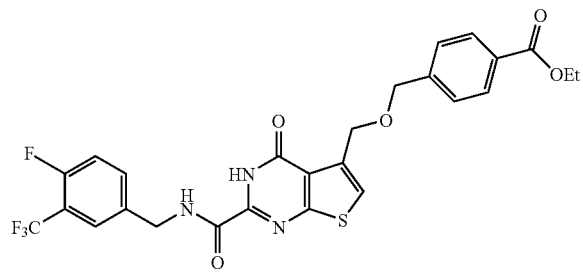 [SMILES: CCOC(=O)c1ccc(COCc2csc3nc(C(=O)NCc4ccc(Cl)c(C(F)(F)F)c4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.350 g, 0.840 mmol) obtained in Reference Example 158 and 1-[4-fluoro-3-(trifluoromethyl)phenyl]methanamine (0.315 g, 1.63 mmol) in ethanol (16 mL) was stirred with heating at 80° C. for 15 hrs. The mixture was allowed to cool to room temperature and the precipitated solid was collected by filtration and washed with ethanol to give the title compound as a white powder (397 mg, 73%).

melting point: 227-229° C.

Example 316 ethyl 4-[({[2-({[(3,4-dichlorophenyl)methyl]amino}carbonyl)-4-oxo-3,4-dihydrothieno[2,3-d]pyrimidin-5-yl]methyl}oxy)methyl]benzoate

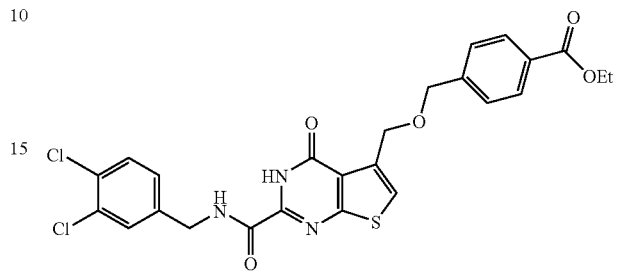

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-(3,4-dichlorophenyl)methanamine (0.287 g, 1.63 mmol) in ethanol (16 mL) was stirred with heating at 80° C. for 15 hrs. The mixture was allowed to cool to room temperature and the precipitated solid was collected by filtration and washed with ethanol to give the title compound as a white powder (475 mg, 91%).

melting point: 253-254° C.

Example 317 ethyl 4-{[({2-[({[4-chloro-3-(trifluoromethyl)phenyl]methyl}amino)carbonyl]-4-oxo-3,4-dihydrothieno[2,3-d]pyrimidin-5-yl}methyl)oxy]methyl}benzoate

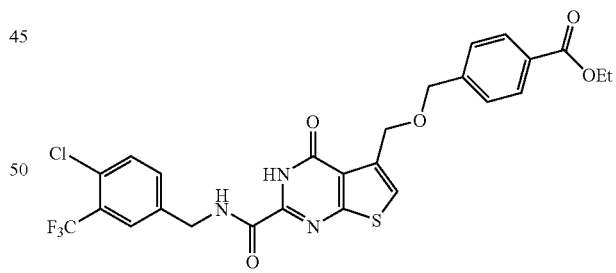

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158 and 1-[4-chloro-3-(trifluoromethyl)phenyl]methanamine (0.342 g, 1.63 mmol) in ethanol (16 mL) was stirred with heating at 80° C. for 24 hrs. The mixture was allowed to cool to room temperature and the precipitated solid was collected by filtration and washed with ethanol to give the title compound as a white powder (500 mg, 90%).

melting point: 238-239° C.

Example 318 ethyl 4-{[({2-[({[2-(methyloxy)pyridin-4-yl]methyl}amino)carbonyl]-4-oxo-3,4-dihydrothieno[2,3-d]pyrimidin-5-yl}methyl)oxy]methyl}benzoate

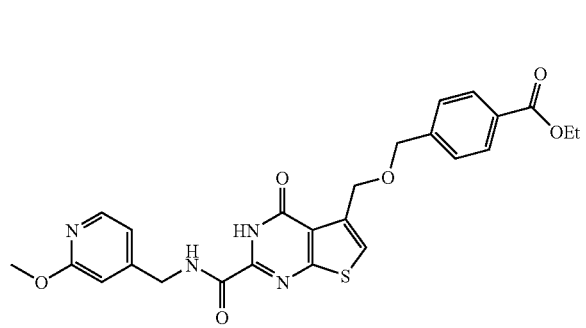 [SMILES: CCOC(=O)c1ccc(COCc2csc3nc(C(=O)NCc4ccnc(OC)c4)[nH]c(=O)c23)cc1]

A suspension of ethyl 5-{[({4-[(ethyloxy)carbonyl]phenyl}methyl)oxy]methyl}-4-oxo-3,4-dihydrothieno[2,3-d]pyrimidine-2-carboxylate (0.400 g, 0.961 mmol) obtained in Reference Example 158, 1-[2-(methyloxy)pyridin-4-yl]methanamine (synthesized by a method described in Journal of Medicinal Chemistry (1993), 36(15), 2362-2372.) (0.226 g, 1.63 mmol) and triethylamine (0.243 g, 2.40 mmol) in ethanol (16 mL) was stirred with heating at 80° C. for 48 hrs. The mixture was allowed to cool to room temperature and the precipitated solid was collected by filtration and washed with ethanol to give the title compound as a white powder (348 mg, 71%).

melting point: 215-216° C.

Example 319

5-methyl-N-{[3-(methyloxy)phenyl]methyl}-4-oxo-3,4-dihydrothieno[3,4-d]pyrimidine-2-carboxamide

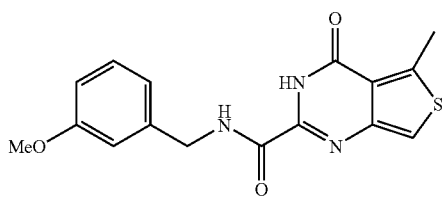 [SMILES: COc1cccc(CNC(=O)c2nc3csc(C)c3c(=O)[nH]2)c1]

A suspension of ethyl 5-methyl-4-oxo-3,4-dihydrothieno[3,4-d]pyrimidine-2-carboxylate (0.150 g, 0.630 mmol) obtained in Reference Example 142 and 3-methoxybenzylamine (0.130 g, 0.945 mmol) in ethanol (3 mL) was stirred with heating at 80° C. for 15 hrs. The mixture was allowed to cool to room temperature and the precipitated solid was collected by filtration and washed with ethanol. The obtained solid was purified by silica gel column chromatography (50% ethyl acetate/hexane). The obtained crude crystals were crystallized from diethyl ether to give the title compound as a pale-yellow powder (158 mg, 76%).

melting point: 168-170° C.

Example 320

5,6-dimethyl-N-{[3-(methyloxy)phenyl]methyl}-4-oxo-3,4-dihydrofuro[2,3-d]pyrimidine-2-carboxamide

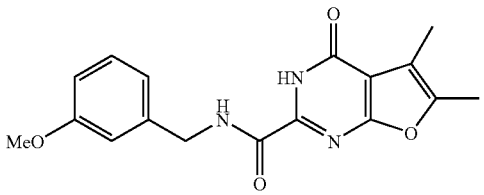 [SMILES: COc1cccc(CNC(=O)c2nc3oc(C)c(C)c3c(=O)[nH]2)c1]

A suspension of ethyl 5,6-dimethyl-4-oxo-3,4-dihydrofuro[2,3-d]pyrimidine-2-carboxylate (0.100 g, 0.423 mmol) obtained in Reference Example 148 and 3-methoxybenzylamine (0.0870 g, 0.635 mmol) in ethanol (4 mL) was stirred with heating at 80° C. for 12 hrs. The mixture was allowed to cool to room temperature and the precipitated solid was collected by filtration and washed with ethanol to give the title compound as a white powder (122 mg, 88%).

melting point: 178-180° C.

Example 321

6-methyl-N-{[3-(methyloxy)phenyl]methyl}-4-oxo-4,7-dihydro-3H-pyrrolo[2,3-d]pyrimidine-2-carboxamide

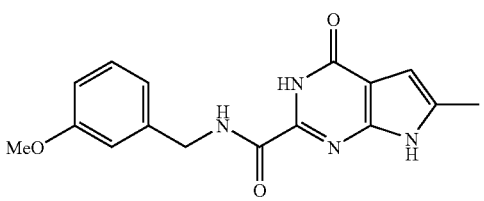 [SMILES: COc1cccc(CNC(=O)c2nc3[nH]c(C)cc3c(=O)[nH]2)c1]

A solution of ethyl 6-methyl-4-oxo-4,7-dihydro-3H-pyrrolo[2,3-d]pyrimidine-2-carboxylate (0.100 g, 0.452 mmol) obtained in Reference Example 143, 3-methoxybenzylamine (0.0930 g, 0.678 mmol) and N,N-diisopropylethylamine (0.0876 g, 0.678 mmol) in DMA (2 mL) was stirred with heating at 80° C. for 15 hrs. The reaction mixture was concentrated under reduced pressure and the concentrated residue was crystallized from ethanol to give the title compound as a white powder (121 mg, 86%).

melting point: 255-256° C.

Example 322

3-methyl-N-{[3-(methyloxy)phenyl]methyl}-4-oxo-4,5-dihydroisoxazolo[5,4-d]pyrimidine-6-carboxamide

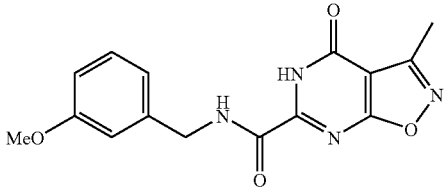 [SMILES: COc1cccc(CNC(=O)c2nc3onc(C)c3c(=O)[nH]2)c1]

The title compound was synthesized by a method similar to that Example 1 from ethyl 3-methyl-4-oxo-4,5-dihydroisoxazolo[5,4-d]pyrimidine-6-carboxylate (synthesized by a method described in Heterocycles (1996), 42(2), 691.) and 3-methoxybenzylamine.

melting point: 236-237° C.

Example 323

6,7-dimethyl-N-{[3-(methyloxy)phenyl]methyl}-4-oxo-4,7-dihydro-3H-pyrrolo[2,3-d]pyrimidine-2-carboxamide

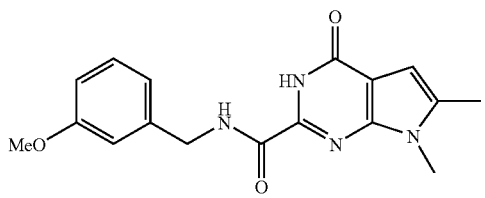 [SMILES: COc1cccc(CNC(=O)c2nc3c(cc(C)n3C)c(=O)[nH]2)c1]

The title compound was synthesized by a method similar to that Example 1 from ethyl 6,7-dimethyl-4-oxo-4,7-dihydro-3H-pyrrolo[2,3-d]pyrimidine-2-carboxylate obtained in Reference Example 144 and 3-methoxybenzylamine.

melting point: 205-207° C.

Example 324

1,3-dimethyl-N-{[3-(methyloxy)phenyl]methyl}-4-oxo-4,5-dihydro-1H-pyrazolo[3,4-d]pyrimidine-6-carboxamide

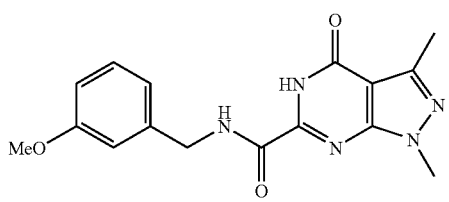 [SMILES: COc1cccc(CNC(=O)c2nc3c(c(C)nn3C)c(=O)[nH]2)c1]

The title compound was synthesized by a method similar to that Example 1 from ethyl 1,3-dimethyl-4-oxo-4,5-dihydro-1H-pyrazolo[3,4-d]pyrimidine-6-carboxylate obtained in Reference Example 149 and 3-methoxybenzylamine.

melting point: 186-188° C.

Example 325

Methyl 2-[({[3-(methyloxy)phenyl]methyl}amino)carbonyl]-4-oxo-3,4-dihydrothieno[3,4-d]pyrimidine-5-carboxylate

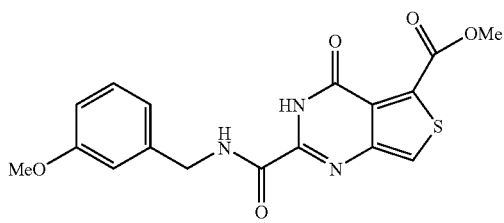 [SMILES: COC(=O)c1scc2nc(C(=O)NCc3cccc(OC)c3)[nH]c(=O)c12]

The title compound was synthesized by a method similar to that Example 1 from 5-methyl 2-ethyl 4-oxo-3,4-dihydrothieno[3,4-d]pyrimidine-2,5-dicarboxylate obtained in Reference Example 150 and 3-methoxybenzylamine.

melting point: 173-174° C.

Example 326

6-methyl-N-{[3-(methyloxy)phenyl]methyl}-7-(methylsulfonyl)-4-oxo-4,7-dihydro-3H-pyrrolo[2,3-d]pyrimidine-2-carboxamide

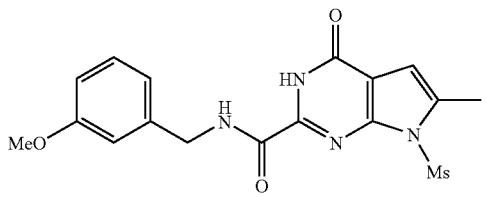 [SMILES: COc1cccc(CNC(=O)c2nc3c(cc(C)n3S(C)(=O)=O)c(=O)[nH]2)c1]

Step 1

To a solution of 6-methyl-N-{[3-(methyloxy)phenyl]methyl}-4-oxo-4,7-dihydro-3H-pyrrolo[2,3-d]pyrimidine-2-carboxamide (0.100 g, 0.320 mmol) obtained in Example 321 in DMA (2 mL) were added triethylamine (0.648 g, 6.40 mmol) and methanesulfonyl chloride (0.496 g, 6.40 mmol), and the mixture was stirred at room temperature for 27 hrs. The reaction mixture was partitioned between ethyl acetate and water. The organic layer was washed with water and saturated brine, and dried over anhydrous sodium sulfate. The solvent was evaporated under reduced pressure, and the concentrated residue was crystallized from ethanol to give 6-methyl-2-[({[3-(methyloxy)phenyl]methyl}amino)carbonyl]-7-(methylsulfonyl)-7H-pyrrolo[2,3-d]pyrimidin-4-yl methanesulfonate as a pale-yellow powder (100 mg, 73%).

Step 2

To a solution of 6-methyl-2-[({[3-(methyloxy)phenyl]methyl}amino)carbonyl]-7-(methylsulfonyl)-7H-pyrrolo[2,3-d]pyrimidin-4-yl methanesulfonate (0.099 g, 0.211 mmol) in THF (2 mL)-methanol (2 mL) was added 1N aqueous sodium hydroxide solution (0.247 mL, 0.247 mmol), and the mixture was stirred at room temperature for 2 hrs. 1N Hydrochloric acid (0.247 mL, 0.247 mmol) was added to the reaction mixture, and the reaction mixture was partitioned between ethyl acetate and water. The organic layer was washed with water and saturated brine, and dried over anhydrous sodium sulfate. The solvent was evaporated under reduced pressure, and the concentrated residue was crystallized from ethanol to give the title compound as a pale-yellow powder (28 mg, 33%).

melting point: 211-213° C.

Example 327

4-[({[2-({[(3-methylphenyl)methyl]amino}carbonyl)-4-oxo-3,4-dihydrothieno[2,3-d]pyrimidin-5-yl]methyl}oxy)methyl]benzoic acid

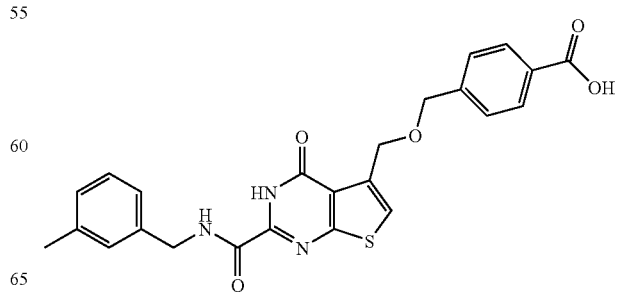

To a suspension of ethyl 4-[({[2-({[(3-methylphenyl)methyl]amino}carbonyl)-4-oxo-3,4-dihydrothieno[2,3-d]pyrimidin-5-yl]methyl}oxy)methyl]benzoate (0.288 g, 0.586 mmol) obtained in Example 289 in THF (3 mL)-methanol (3 mL)-water (3 mL) was added 4N aqueous sodium hydroxide solution (0.366 mL, 1.47 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (252 mg, 93%).

melting point: 237-239° C.

Example 328

4-[({[2-({[(3-ethylphenyl)methyl]amino}carbonyl)-4-oxo-3,4-dihydrothieno[2,3-d]pyrimidin-5-yl]methyl}oxy)methyl]benzoic acid

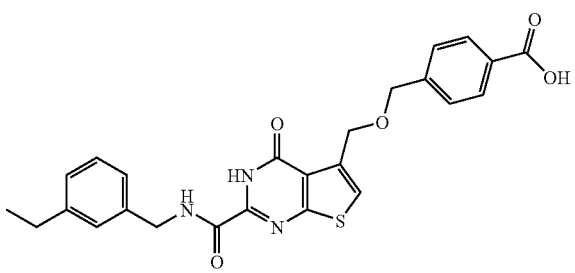 [SMILES: CCc1cccc(CNC(=O)c2nc3scc(COCc4ccc(C(=O)O)cc4)c3c(=O)[nH]2)c1]

To a suspension of ethyl 4-[({[2-({[(3-ethylphenyl)methyl]amino}carbonyl)-4-oxo-3,4-dihydrothieno[2,3-d]pyrimidin-5-yl]methyl}oxy)methyl]benzoate (0.200 g, 0.396 mmol) obtained in Example 290 in THF (2 mL) -methanol(2 mL)-water (2 mL) was added 4N aqueous sodium hydroxide solution (0.248 mL, 0.990 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (177 mg, 94%).

melting point: 240-242° C.

Example 329

4-[({[2-({[(3-chlorophenyl)methyl]amino}carbonyl)-4-oxo-3,4-dihydrothieno[2,3-d]pyrimidin-5-yl]methyl}oxy)methyl]benzoic acid

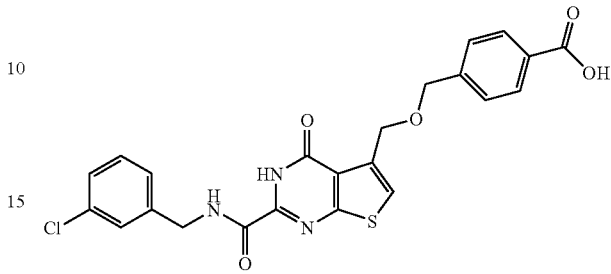

To a suspension of ethyl 4-[({[2-({[(3-chlorophenyl)methyl]amino}carbonyl)-4-oxo-3,4-dihydrothieno[2,3-d]pyrimidin-5-yl]methyl}oxy)methyl]benzoate (0.316 g, 0.617 mmol) obtained in Example 291 in THF (3 mL)-methanol(3 mL)-water (3 mL) was added 4N aqueous sodium hydroxide solution (0.386 mL, 1.54 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (280 mg, 94%).

melting point: 236-238° C.

Example 330

4-{[({2-[({[3-(methylthio)phenyl]methyl}amino)carbonyl]-4-oxo-3,4-dihydrothieno[2,3-d]pyrimidin-5-yl}methyl)oxy]methyl}benzoic acid

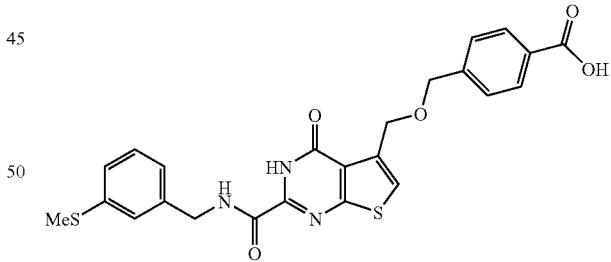

To a suspension of ethyl 4-{[({2-[({[3-(methylthio)phenyl]methyl}amino)carbonyl]-4-oxo-3,4-dihydrothieno[2,3-d]pyrimidin-5-yl}methyl)oxy]methyl}benzoate (0.200 g, 0.382 mmol) obtained in Example 292 in THF (2 mL)-methanol(2 mL)-water (2 mL) was added 4N aqueous sodium hydroxide solution (0.239 mL, 0.955 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (175 mg, 92%).

melting point: 252-254° C.

Example 331

4-{[({4-oxo-2-[({[3-(trifluoromethyl)phenyl]methyl}amino)carbonyl]-3,4-dihydrothieno[2,3-d]pyrimidin-5-yl}methyl)oxy]methyl}benzoic acid

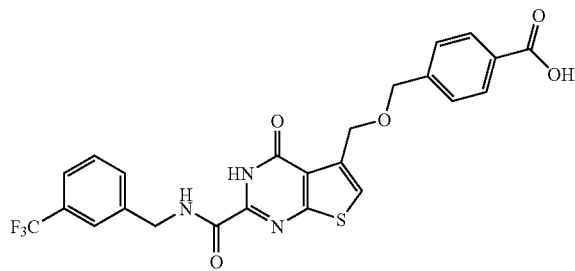 [SMILES: O=C(O)c1ccc(COCc2csc3nc(C(=O)NCc4cccc(C(F)(F)F)c4)[nH]c(=O)c23)cc1]

To a suspension of ethyl 4-{[({4-oxo-2-[({[3-(trifluoromethyl)phenyl]methyl}amino)carbonyl]-3,4-dihydrothieno[2,3-d]pyrimidin-5-yl}methyl)oxy]methyl}benzoate (0.323 g, 0.592 mmol) obtained in Example 293 in THF (3 ml)-methanol (3 mL)-water (3 mL) was added 4N aqueous sodium hydroxide solution (0.370 mL, 1.48 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (285 mg, 93%).

melting point: 261-263° C.

Example 332

4-({[(4-oxo-2-{[({3-[(trifluoromethyl)oxy]phenyl}methyl)amino]carbonyl}-3,4-dihydrothieno[2,3-d]pyrimidin-5-yl)methyl]oxy}methyl)benzoic acid

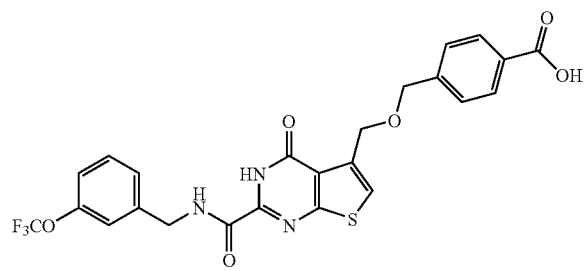 [SMILES: O=C(O)c1ccc(COCc2csc3nc(C(=O)NCc4cccc(OC(F)(F)F)c4)[nH]c(=O)c23)cc1]

To a suspension of ethyl 4-({[(4-oxo-2-{[({3-[(trifluoromethyl)oxy]phenyl}methyl)amino]carbonyl}-3,4-dihydrothieno[2,3-d]pyrimidin-5-yl)methyl]oxy}methyl)benzoate (0.330 g, 0.588 mmol) obtained by Example 294 in THF (3 mL)-methanol (3 mL)-water (3 mL) was added 4N aqueous sodium hydroxide solution (0.368 mL, 1.47 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (286 mg, 91%).

melting point: 248-250° C.

Example 333

4-({[(4-oxo-2-{[(pyridin-4-ylmethyl)amino]carbonyl}-3,4-dihydrothieno[2,3-d]pyrimidin-5-yl)methyl]oxy}methyl)benzoic acid hydrochloride

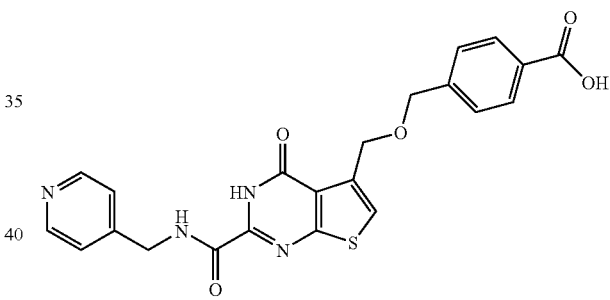

To a suspension of ethyl 4-({[(4-oxo-2-{[(pyridine-4-ylmethyl)amino]carbonyl}-3,4-dihydrothieno[2,3-d]pyrimidin-5-yl)methyl]oxy}methyl)benzoate (0.200 g, 0.418 mmol) obtained in Example 295 in THF (2 mL)-methanol (2 mL)-water (2 mL) was added 4N aqueous sodium hydroxide solution (0.261 mL, 1.05 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (170 mg, 90%).

melting point: 288-291° C.

Example 334

4-[({2-({[(3-fluorophenyl)methyl]amino}carbonyl)-4-oxo-3,4-dihydrothieno[2,3-d]pyrimidin-5-yl]methyl}oxy)methyl]benzoic acid

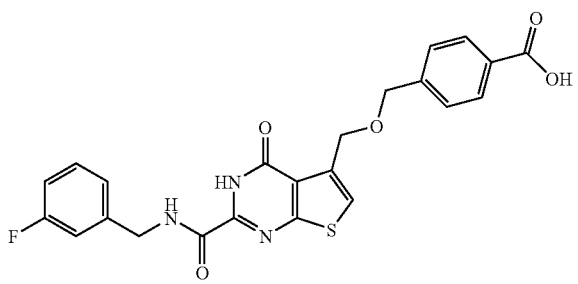 [SMILES: O=C(O)c1ccc(COCc2csc3nc(C(=O)NCc4cccc(F)c4)[nH]c(=O)c23)cc1]

To a suspension of ethyl 4-[({2-({[(3-fluorophenyl)methyl]amino}carbonyl)-4-oxo-3,4-dihydrothieno[2,3-d]pyrimidin-5-yl]methyl}oxy)methyl]benzoate (0.340 g, 0.686 mmol) obtained in Example 296 in THF (3 mL)-methanol (3 mL)-water (3 mL) was added 4N aqueous sodium hydroxide solution (0.429 mL, 1.72 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (293 mg, 90%).

melting point: 256-280° C.

Example 335

4-[({2-({[(4-fluorophenyl)methyl]amino}carbonyl)-4-oxo-3,4-dihydrothieno[2,3-d]pyrimidin-5-yl]methyl}oxy)methyl]benzoic acid

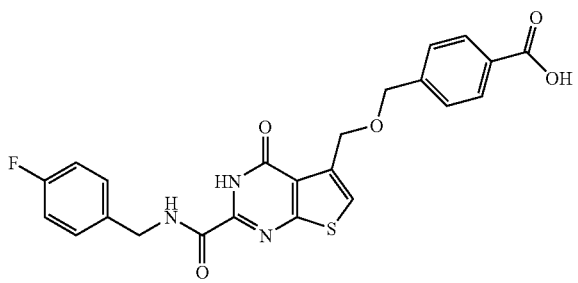 [SMILES: O=C(O)c1ccc(COCc2csc3nc(C(=O)NCc4ccc(F)cc4)[nH]c(=O)c23)cc1]

To a suspension of ethyl 4-[({2-({[(4-fluorophenyl)methyl]amino}carbonyl)-4-oxo-3,4-dihydrothieno[2,3-d]pyrimidin-5-yl]methyl}oxy)methyl]benzoate (0.340 g, 0.686 mmol) obtained in Example 297 in THF (3 mL)-methanol (3 mL)-water (3 mL) was added 4N aqueous sodium hydroxide solution (0.429 mL, 1.72 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (298 mg, 93%).

melting point: 267-269° C.

Example 336

4-{[({2-[({[4-(methyloxy)phenyl]methyl}amino)carbonyl]-4-oxo-3,4-dihydrothieno[2,3-d]pyrimidin-5-yl}methyl)oxy]methyl}benzoic acid

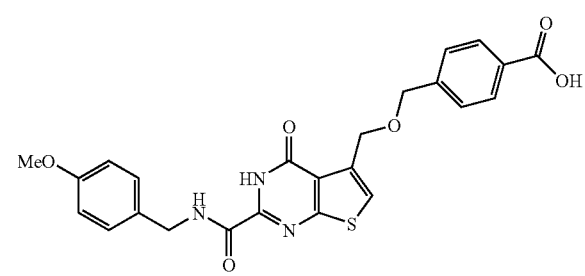 [SMILES: COc1ccc(CNC(=O)c2nc3scc(COCc4ccc(C(=O)O)cc4)c3c(=O)[nH]2)cc1]

To a suspension of ethyl 4-{[({2-[({[4-(methyloxy)phenyl]methyl}amino)carbonyl]-4-oxo-3,4-dihydrothieno[2,3-d]pyrimidin-5yl}methyl)oxy]methyl}benzoate (0.340 g, 0.670 mmol) obtained in Example 298 in THF (3 mL)-methanol (3 mL)-water (3 mL) was added 4N aqueous sodium hydroxide solution (0.419 mL, 1.68 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (285 mg, 89%).

melting point: 271-273° C.

Example 337

4-({[(4-oxo-2-{[(2-phenylethyl)amino]carbonyl}-3,4-dihydrothieno[2,3-d]pyrimidin-5-yl)methyl]oxy}methyl)benzoic acid

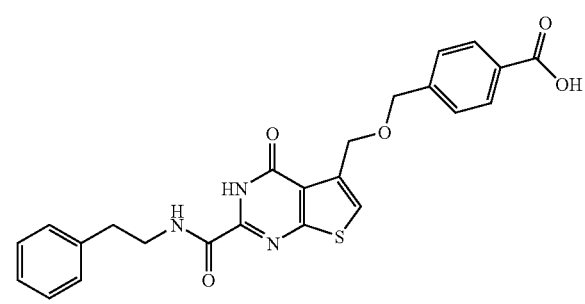 [SMILES: O=C(O)c1ccc(COCc2csc3nc(C(=O)NCCc4ccccc4)[nH]c(=O)c23)cc1]

To a suspension of ethyl 4-({[(4-oxo-2-{[(2-phenylethyl)amino]carbonyl}-3,4-dihydrothieno[2,3-d]pyrimidin-5-yl)

methyl]oxy}methyl)benzoate (0.340 g, 0.692 mmol) obtained in Example 299 in THF (3 mL)-methanol (3 mL)-water (3 mL) was added 4N aqueous sodium hydroxide solution (0.433 mL, 1.73 mmol), and the mixture was stirred with heating at 80° C. for 2 hrs. The mixture was allowed to cool to room temperature, and acidified with 1N hydrochloric acid (about 3 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (306 mg, 95%).

melting point: 227-229° C.

Example 338

4-[({[2-({[(3,4-difluorophenyl)methyl]amino}carbonyl)-4-oxo-3,4-dihydrothieno[2,3-d]pyrimidin-5-yl]methyl}oxy)methyl]benzoic acid

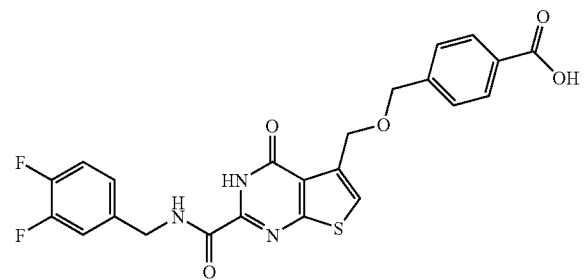 [SMILES: O=C(O)c1ccc(COCc2csc3nc(C(=O)NCc4ccc(F)c(F)c4)[nH]c(=O)c23)cc1]

To a suspension of ethyl 4-[({[2-({[(3,4-difluorophenyl)methyl]amino}carbonyl)-4-oxo-3,4-dihydrothieno[2,3-d]pyrimidin-5-yl]methyl}oxy)methyl]benzoate (0.380 g, 0.740 mmol) obtained in Example 300 in THF (2 mL)- methanol (2 mL)-water (2 mL) was added 4N aqueous sodium hydroxide solution (0.463 mL, 1.85 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (331 mg, 92%).

melting point: 249-251° C.

Example 339

4-[({[2-({[(3-chloro-4-fluorophenyl)methyl]amino}carbonyl)-4-oxo-3,4-dihydrothieno[2,3-d]pyrimidin-5-yl]methyl}oxy)methyl]benzoic acid

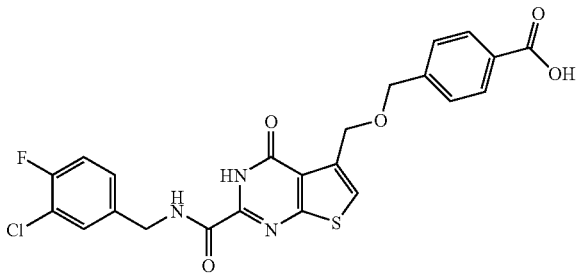 [SMILES: O=C(O)c1ccc(COCc2csc3nc(C(=O)NCc4ccc(F)c(Cl)c4)[nH]c(=O)c23)cc1]

To a suspension of ethyl 4-[({[2-({[(3-chloro-4-fluorophenyl)methyl]amino}carbonyl)-4-oxo-3,4-dihydrothieno[2,3-d]pyrimidin-5-yl]methyl}oxy)methyl]benzoate (0.390 g, 0.736 mmol) obtained in Example 301 in THF (2 mL)-methanol (2 mL)-water (2 mL) was added 4N aqueous sodium hydroxide solution (0.460 mL, 1.84 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in ethanol again, and the mixture was stirred with heating at 80° C. for 20 min. The mixture was allowed to cool to room temperature, and the precipitated solid was collected by filtration, and washed with ethanol to give the title compound as a white powder (330 mg, 89%).

melting point: 228-230° C.
$^1$H-NMR (300 MHz, DMSO-d$_6$) δ: 4.42 (2H, d, J=6.6 Hz), 4.74 (2H, s), 4.88 (2H, s), 7.34-7.40 (2H, m), 7.48-7.56 (3H, m), 7.63 (1H, s), 7.93 (2H, d, J=8.1 Hz), 9.71 (1H, t, J=6.3 Hz), 12.44 (1H, bs), 12.92 (1H, bs)

Example 340

4-[({[2-({[(3-bromo-4-fluorophenyl)methyl]amino}carbonyl)-4-oxo-3,4-dihydrothieno[2,3-d]pyrimidin-5-yl]methyl}oxy)methyl]benzoic acid

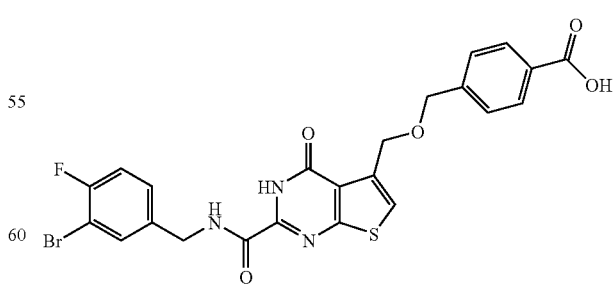

To a suspension of ethyl 4-[({[2-({[(3-bromo-4-fluorophenyl)methyl]amino}carbonyl)-4-oxo-3,4-dihydrothieno[2,3-d]pyrimidin-5-yl]methyl}oxy)methyl]benzoate (0.430 g, 0.749 mmol) obtained in Example 302 in THF (3 mL)-methanol (3 mL)-water (3 mL) was added 4N aqueous sodium hydroxide solution (0.468 mL, 1.87 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (380 mg, 93%).

melting point: 231-233° C.

Example 341

4-[({[2-({[(4-fluoro-3-methylphenyl)methyl] amino}carbonyl)-4-oxo-3,4-dihydrothieno[2,3-d] pyrimidin-5-yl]methyl}oxy)methyl]benzoic acid

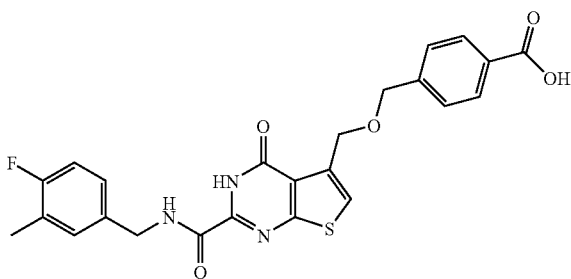

To a suspension of ethyl 4-[({[2-({[(4-fluoro-3-methylphenyl)methyl]amino}carbonyl)-4-oxo-3,4-dihydrothieno [2,3-d]pyrimidin-5-yl]methyl}oxy)methyl]benzoate (0.410 g, 0.805 mmol) obtained in Example 303 in THF (3 mL)-methanol (3 mL)-water (3 mL) was added 4N aqueous sodium hydroxide solution (0.503 mL, 2.01 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (340 mg, 88%).

melting point: 246-248° C.

$^1$H-NMR (300 MHz, DMSO-$d_6$) δ: 2.20 (3H, s), 4.38 (2H, d, J=6.3 Hz), 4.74 (2H, s), 4.88 (2H, s), 7.06 (1H, t, J=9.0 Hz), 7.14-7.24 (2H, m), 7.50 (2H, d, J=8.1 Hz), 7.62 (1H, s), 7.93 (2H, d, J=8.1 Hz), 9.65 (1H, t, J=6.3 Hz), 12.42 (1H, bs), 12.90 (1H, bs).

Example 342

4-({[(2-{[({3-[(methyloxy)methyl]phenyl}methyl) amino]carbonyl}-4-oxo-3,4-dihydrothieno[2,3-d] pyrimidin-5-yl)methyl]oxy}methyl)benzoic acid

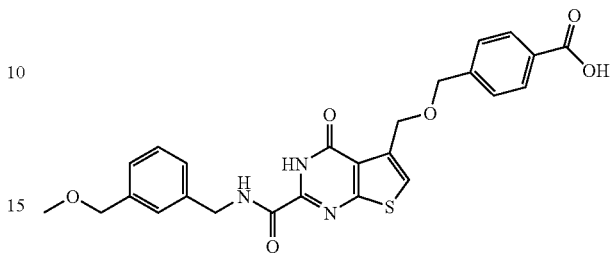

To a suspension of ethyl 4-({[(2-{[({3-[(methyloxy)methyl]phenyl}methyl)amino]carbonyl}-4-oxo-3,4-dihydrothieno[2,3-d]pyrimidin-5-yl)methyl]oxy}methyl)benzoate (0.380 g, 0.729 mmol) obtained in Example 304 in THF (3 mL)-methanol (3 mL)-water (3 mL) was added 4N aqueous sodium hydroxide solution (0.456 mL, 1.82 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (342 mg, 95%).

melting point: 242-244° C.

Example 343

4-{[({2-[({[3-(methylsulfonyl)phenyl] methyl}amino)carbonyl]-4-oxo-3,4-dihydrothieno[2, 3-d]pyrimidin-5-yl}methyl)oxy]methyl}benzoic acid

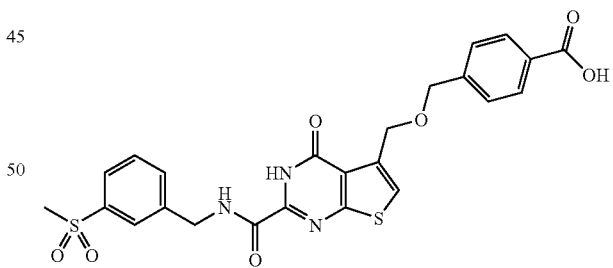

To a suspension of ethyl 4-{[({2-[({[3-(methylsulfonyl) phenyl]methyl}amino)carbonyl]-4-oxo-3,4-dihydrothieno [2,3-d]pyrimidin-5-yl}methyl)oxy]methyl}benzoate (0.27.8 g, 0.500 mmol) obtained in Example 305 in THF (3 mL)-methanol (3 mL)-water (3 mL) was added 4N aqueous sodium hydroxide solution (0.313 mL, 1.25 mmol), and the mixture was stirred with heating at 80° C. for 2 hrs. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (240 mg, 91%). melting point: 265-267° C.

Example 344

4-{[({2-[({[3-(methylsulfinyl)phenyl]methyl}amino)carbonyl]-4-oxo-3,4-dihydrothieno[2,3-d]pyrimidin-5-yl}methyl)oxy]methyl}benzoic acid

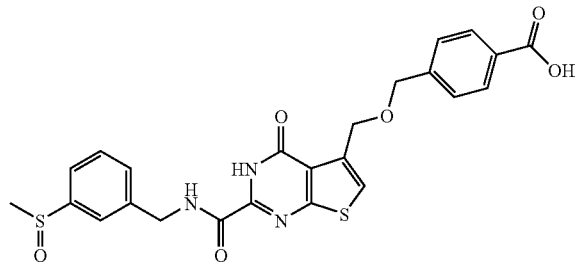 [SMILES: CS(=O)c1cccc(CNC(=O)c2nc3scc(COCc4ccc(C(=O)O)cc4)c3c(=O)[nH]2)c1]

To a suspension of ethyl 4-{[({2-[({[3-(methylsulfinyl)phenyl]methyl}amino)carbonyl]-4-oxo-3,4-dihydrothieno[2,3-d]pyrimidin-5-yl}methyl)oxy]methyl}benzoate (0.250 g, 0.463 mmol) obtained in Example 306 in THF (4 mL)-methanol (4 mL)-water (4 mL) was added 4N aqueous sodium hydroxide solution (0.290 mL, 1.16 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (228 mg, 96%).

melting point: 227-228° C.

Example 345

4-({[(4-oxo-2-{[(pyridin-3-ylmethyl)amino]carbonyl}-3,4-dihydrothieno[2,3-d]pyrimidin-5-yl)methyl]oxy}methyl)benzoic acid

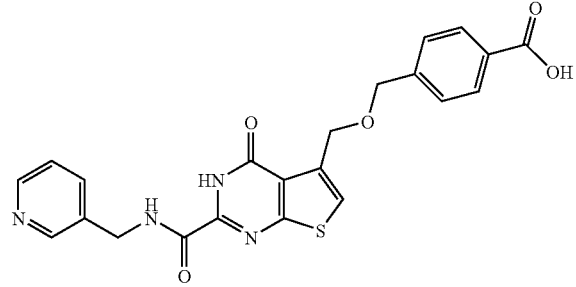 [SMILES: O=C(O)c1ccc(COCc2csc3nc(C(=O)NCc4cccnc4)[nH]c(=O)c23)cc1]

To a suspension of ethyl 4-({[(4-oxo-2-{[(pyridin-3-ylmethyl)amino]carbonyl}-3,4-dihydrothieno[2,3-d]pyrimidin-5-yl)methyl]oxy}methyl)benzoate (0.349 g, 0.729 mmol) obtained in Example 307 in THF (3 mL)-methanol (3 mL)-water (3 mL) was added 4N aqueous sodium hydroxide solution (0.456 mL, 1.82 mmol), and the mixture was stirred with heating at 80° C. for 1 hr. The mixture was allowed to cool to room temperature, and weakly acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (286 mg, 87%).

melting point: 309-311° C.

Example 346

4-({[(2-{[({3-[(methylthio)methyl]phenyl}methyl)amino]carbonyl}-4-oxo-3,4-dihydrothieno[2,3-d]pyrimidin-5-yl)methyl]oxy}methyl)benzoic acid

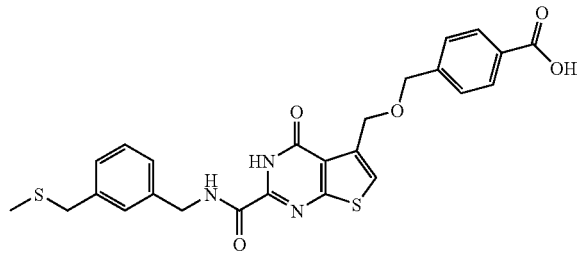

To suspension of ethyl 4-({[(2-{[({3-[(methylthio)methyl]phenyl}methyl)amino]carbonyl}-4-oxo-3,4-dihydrothieno[2,3-d]pyrimidin-5-yl)methyl]oxy}methyl)benzoate (0.300 g, 0.558 mmol) obtained in Example 308 in THF (4 mL)-methanol (4 mL)-water (4 mL) was added 4N aqueous sodium hydroxide solution (0.349 mL, 1.39 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (271 mg, 95%).

melting point: 222-223° C.

Example 347

4-({[(2-{[({3-[(methylsulfinyl)methyl]phenyl}methyl)amino]carbonyl}-4-oxo-3,4-dihydrothieno[2,3-d]pyrimidin-5-yl)methyl]oxy}methyl)benzoic acid

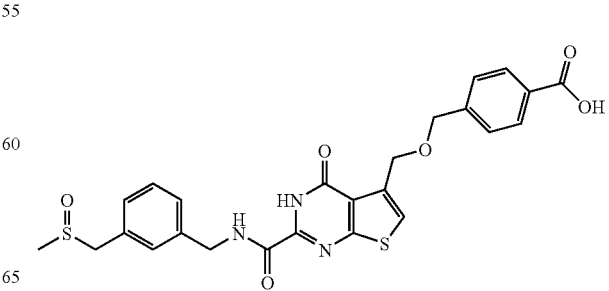

To suspension of ethyl 4-({[(2-{[({3-[(methylsulfinyl)methyl]phenyl}methyl)amino]carbonyl}-4-oxo-3,4-dihydrothieno[2,3-d]pyrimidin-5-yl)methyl]oxy}methyl)benzoate (0.330 g, 0.596 mmol) obtained in Example 309 in THF (4 mL)-methanol (4 mL)-water (4 mL) was added 4N aqueous sodium hydroxide solution (0.373 mL, 1.49 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (283 mg, 90%).

melting point: 198-200° C.

Example 348

4-({[(2-{[({3-[(methylsulfonyl)methyl]phenyl}methyl)amino]carbonyl}-4-oxo-3,4-dihydrothieno[2,3-d]pyrimidin-5-yl)methyl]oxy}methyl)benzoic acid

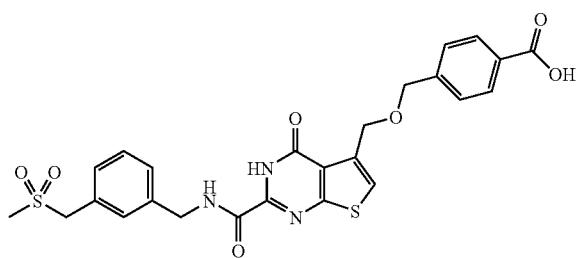 [SMILES: CS(=O)(=O)Cc1cccc(CNC(=O)c2nc3scc(COCc4ccc(C(=O)O)cc4)c3c(=O)[nH]2)c1]

To a suspension of ethyl 4-({[(2-{[({3-[(methylsulfonyl)methyl]phenyl}methyl)amino]carbonyl}-4-oxo-3,4-dihydrothieno[2,3-d]pyrimidin-5-yl)methyl]oxy}methyl)benzoate (0.230 g, 0.404 mmol) obtained in Example 310 in THF (4 mL)-methanol (4 mL)-water (4 mL) was added 4N aqueous sodium hydroxide solution (0.252 mL, 1.01 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (205 mg, 94%).

melting point: 246-248° C.

Example 349

4-{[({2-[({[3-(methylamino)phenyl]methyl}amino)carbonyl]-4-oxo-3,4-dihydrothieno[2,3-d]pyrimidin-5-yl}methyl)oxy]methyl}benzoic acid

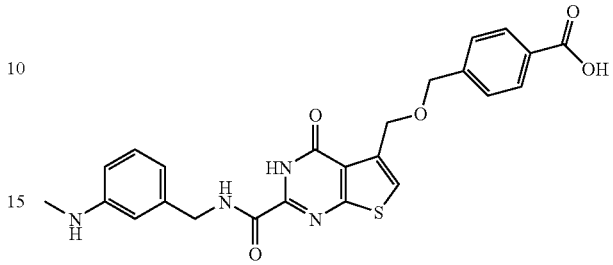

To a suspension of ethyl 4-({[(2-{[({3-[methyl(trifluoroacetyl)amino]phenyl}methyl)amino]carbonyl}-4-oxo-3,4-dihydrothieno[2,3-d]pyrimidin-5-yl)methyl]oxy}methyl)benzoate (0.170 g, 0.282 mmol) obtained in Example 311 in THF (4 mL)-methanol (4 mL)-water (4 mL) was added 4N aqueous sodium hydroxide solution (0.247 mL, 0.987 mmol), and the mixture was stirred with heating at 80° C. for 1 hr. The mixture was allowed to cool to room temperature, and weakly acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (125 mg, 93%).

melting point: 223-224° C.

Example 350

4-[({[4-oxo-2-({[(3-propylphenyl)methyl]amino}carbonyl)-3,4-dihydrothieno[2,3-d]pyrimidin-5-yl]methyl}oxy)methyl]benzoic acid

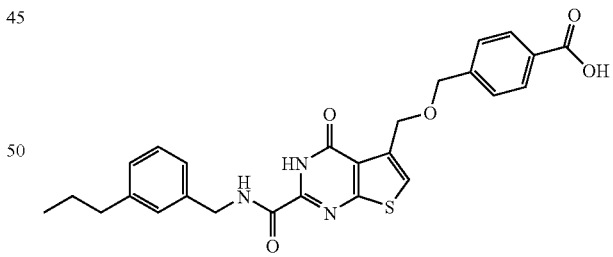

To a suspension of ethyl 4-[({[4-oxo-2-({[(3-propylphenyl)methyl]amino}carbonyl)-3,4-dihydrothieno[2,3-d]pyrimidin-5-yl]methyl}oxy)methyl]benzoate (0.170 g, 0.327 mmol) obtained in Example 312 in THF (4 mL)-methanol (4 mL)-water (4 mL) was added 4N aqueous sodium hydroxide solution (0.204 mL, 0.818 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (142 mg, 88%).

melting point: 235-237° C.

Example 351

4-[({[2-({[(3-ethyl-4-fluorophenyl)methyl]amino}carbonyl)-4-oxo-3,4-dihydrothieno[2,3-d]pyrimidin-5-yl]methyl}oxy)methyl]benzoic acid

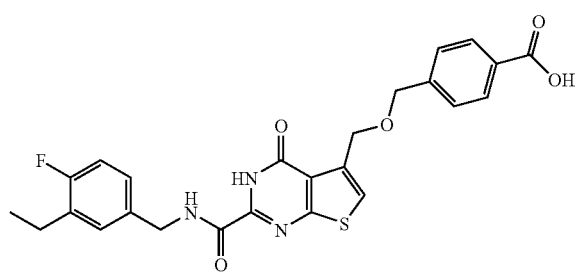 [SMILES: CCc1cc(CNC(=O)c2nc3scc(COCc4ccc(C(=O)O)cc4)c3c(=O)[nH]2)ccc1F]

To a suspension of ethyl 4-[({[2-({[(3-ethyl-4-fluorophenyl)methyl]amino}carbonyl)-4-oxo-3,4-dihydrothieno[2,3-d]pyrimidin-5-yl]methyl}oxy)methyl]benzoate (0.295 g, 0.563 mmol) obtained in Example 313 in THF (4 mL)-methanol (4 mL)-water (4 mL) was added 4N aqueous sodium hydroxide solution (0.352 mL, 1.41 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid as suspended in methanol again, and the mixture was stirred with heating at 80° C. for 20 min. The mixture was allowed to cool to room temperature, and the precipitated solid was collected by filtration, and washed with methanol to give the title compound as a white powder (260 mg, 93%).

melting point: 229-231° C.

Example 352

4-[({[2-({[(3-bromophenyl)methyl]amino}carbonyl)-4-oxo-3,4-dihydrothieno[2,3-d]pyrimidin-5-yl]methyl}oxy)methyl]benzoic acid

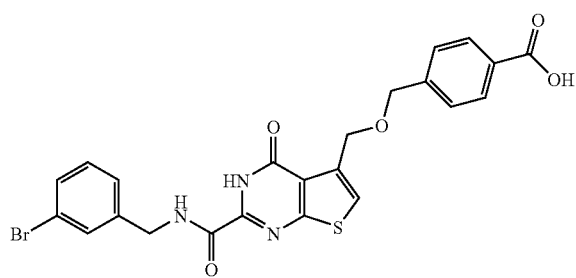

To a suspension of ethyl 4-[({[2-({[(3-bromophenyl)methyl]amino}carbonyl)-4-oxo-3,4-dihydrothieno[2,3-d]pyrimidin-5-yl]methyl}oxy)methyl]benzoate (0.400 g, 0.719 mmol) obtained in Example 314 in THF (4 mL)-methanol (4 mL)-water (4 mL) was added 4N aqueous sodium hydroxide solution (0.449 mL, 1.80 mmol), and the mixture was stirred with heating at 80° C. for 1 hr. The mixture was allowed to cool to room temperature, and acidified with 1N hydrochloric acid (about 2.5 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (350 mg, 92%).

melting point: 231-233° C.

Example 353

4-{[({2-[({[4-fluoro-3-(trifluoromethyl)phenyl]methyl}amino)carbonyl]-4-oxo-3,4-dihydrothieno[2,3-d]pyrimidin-5-yl}methyl)oxy]methyl}benzoic acid

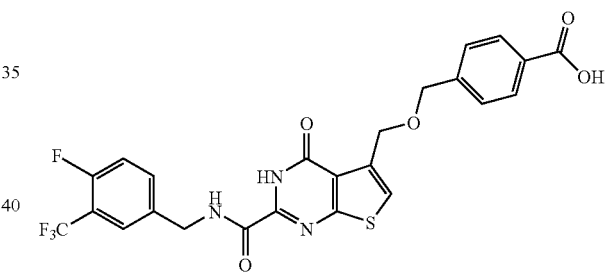

To a suspension of ethyl 4-{[({2-[({[4-fluoro-3-(trifluoromethyl)phenyl]methyl}amino)carbonyl]-4-oxo-3,4-dihydrothieno[2,3-d]pyrimidin-5-yl}methyl)oxy]methyl}benzoate (0.310 g, 0.550 mmol) obtained in Example 315 in THF (4 mL)-methanol (4 mL)-water (4 mL) was added 4N aqueous sodium hydroxide solution (0.344 mL, 1.38 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (270 mg, 92%).

melting point: 258-259° C.

Example 354

4-[({[2-({[(3,4-dichlorophenyl)methyl]amino}carbonyl)-4-oxo-3,4-dihydrothieno[2,3-d]pyrimidin-5-yl]methyl}oxy)methyl]benzoic acid

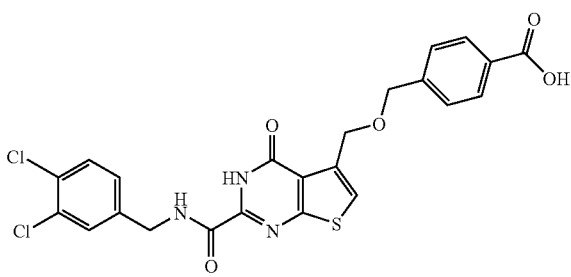

To a suspension of ethyl 4-[({[2-({[(3,4-dichlorophenyl)methyl]amino}carbonyl)-4-oxo-3,4-dihydrothieno[2,3-d]pyrimidin-5-yl]methyl}oxy)methyl]benzoate (0.390 g, 0.714 mmol) obtained in Example 316 in THF (4 mL)-methanol (4 mL)-water (4 mL) was added 4N aqueous sodium hydroxide solution (0.446 mL, 1.78 mmol), and the mixture was stirred with heating at 80° C. for 1 hr. The mixture was allowed to cool to room temperature, and acidified with 1N hydrochloric acid (about 2 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (320 mg, 87%).

melting point: 252-253° C.

Example 355

4-{[({2-[({[4-chloro-3-(trifluoromethyl)phenyl]methyl}amino)carbonyl]-4-oxo-3,4-dihydrothieno[2,3-d]pyrimidin-5-yl}methyl)oxy]methyl}benzoic acid

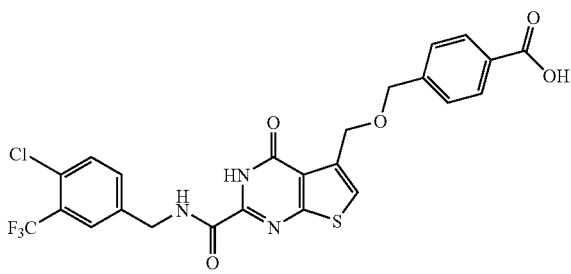 [SMILES: O=C(O)c1ccc(COCc2csc3nc(C(=O)NCc4ccc(F)c(C(F)(F)F)c4)[nH]c(=O)c23)cc1]

To a suspension of ethyl 4-{[({2-[({[4-chloro-3-(trifluoromethyl)phenyl]methyl}amino)carbonyl]-4-oxo-3,4-dihydrothieno[2,3-d]pyrimidin-5-yl}methyl)oxy]methyl}benzoate (0.400 g, 0.690 mmol) obtained in Example 317 in THF (4 mL)-methanol (4 mL)-water (4 mL) was added 4N aqueous sodium hydroxide solution (0.431 mL, 1.72 mmol), and the mixture was stirred with heating at 80° C. for 1 hr. The mixture was allowed to cool to room temperature, and acidified with 1N hydrochloric acid (about 2.5 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (350 mg, 92%).

melting point: 269-270° C.

Example 356

4-{[({2-[({[2-(methyloxy)pyridin-4-yl]methyl}amino)carbonyl]-4-oxo-3,4-dihydrothieno[2,3-d]pyrimidin-5-yl}methyl)oxy]methyl}benzoic acid

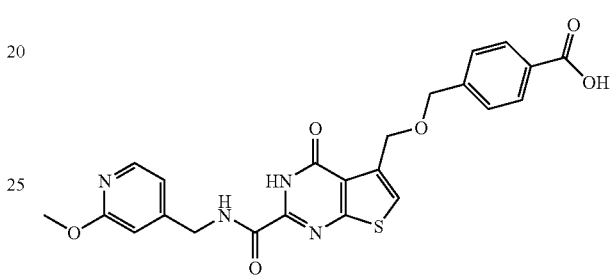

To a suspension of ethyl 4-{[({2-[({[2-(methyloxy)pyridin-4-yl]methyl}amino)carbonyl]-4-oxo-3,4-dihydrothieno[2,3-d]pyrimidin-5-yl}methyl)oxy]methyl}benzoate (0.210 g, 0.413 mmol) obtained in Example 318 in THF (4 mL)-methanol (4 mL)-water (4 mL) was added 4N aqueous sodium hydroxide solution (0.258 mL, 1.03 mmol), and the mixture was stirred with heating at 80° C. for 1 hr. The mixture was allowed to cool to room temperature, and weakly acidified with 1N hydrochloric acid (about 1 mL). THF and methanol were evaporated under reduced pressure, and the solid in the concentrated residue was collected by filtration. The obtained solid was washed with water. The obtained solid was suspended in methanol again, and the mixture was stirred with heating at 80° C. for 20 min. The mixture was allowed to cool to room temperature, and the precipitated solid was collected by filtration, and washed with methanol to give the title compound as a white powder (175 mg, 88%).

melting point: 240-242° C.

Example 357

5,6-difluoro-N-[(4-fluoro-3-methylphenyl)methyl]-4-oxo-3,4-dihydroquinazoline-2-carboxamide

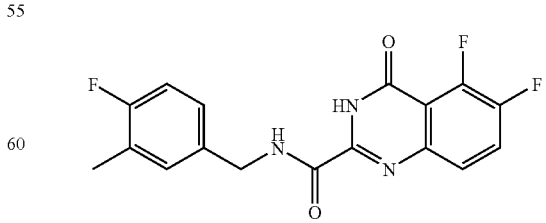

A suspension of ethyl 5,6-difluoro-4-oxo-3,4-dihydroquinazoline-2-carboxylate (1.50 g, 5.90 mmol) obtained in Reference Example 22 and 1-(4-fluoro-3-methylphenyl)

methanamine (1.23 g, 8.85 mmol) in ethanol (30 mL) was stirred with heating at 90° C. for 3 hrs. The mixture was allowed to cool to room temperature, and the precipitated solid was filtered off. The filtrate was concentrated and the concentrated residue was purified by preparative HPLC. The obtained crude crystals were washed with ethanol to give the title compound as a white powder (170 mg, 8%).

melting point: 185-186° C.

$^1$H-NMR (300MHz, DMSO-d$_6$) δ: 2.21 (3H, d, J=1.9 Hz), 4.41 (2H, d, J=6.4 Hz), 7.04-7.13 (1H, m), 7.15-7.29 (2H, m), 7.56-7.67 (1H, m), 7.88-8.04 (1H, m), 9.54 (1H, t, J=6.3 Hz), 12.45 (1H, s).

Example 358

6-chloro-5-fluoro-N-{[3-(methyloxy)phenyl]methyl}-4-oxo-3,4-dihydroquinazoline-2-carboxamide

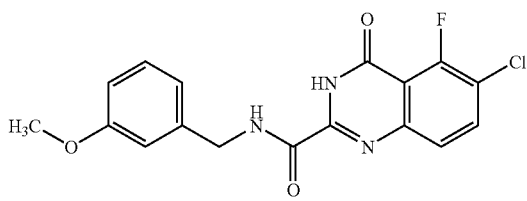 [SMILES: COc1cccc(CNC(=O)c2nc3ccc(Cl)c(F)c3c(=O)[nH]2)c1]

A suspension of ethyl 6-chloro-5-fluoro-4-oxo-3,4-dihydroquinazoline-2-carboxylate (1.50 g, 5.54 mmol) obtained in Reference Example 154 and 3-methoxybenzylamine (1.14 g, 8.31 mmol) in ethanol (30 mL) was stirred with heating at 90° C. for 3 hrs. The reaction mixture was allowed to cool to room temperature, and the precipitated solid was filtered off. The filtrate was concentrated and the concentrated residue was purified by preparative HPLC. The obtained crude crystals were washed with ethanol to give the title compound as a white powder (175 mg, 9%).

melting point: 207-209° C.

$^1$H-NMR (300MHz, DMSO-d$_6$) δ: 3.74 (3H, s), 4.44 (2H, d, J=6.4 Hz), 6.79-6.86 (1H, m), 6.88-6.94 (2H, m), 7.25 (1H, t, J=8.1 Hz), 7.59 (1H, dd, J=8.9, 1.3 Hz), 8.01 (1H, dd, J=8.9, 7.5 Hz), 9.55 (1H, t, J=6.3 Hz), 12.52 (1H, s).

Example 359

4-(2-{[6-fluoro-2-({[(4-fluoro-3-methylphenyl)methyl]amino}carbonyl)-4-oxo-3,4-dihydroquinazolin-5-yl]oxy}ethyl)benzoic acid

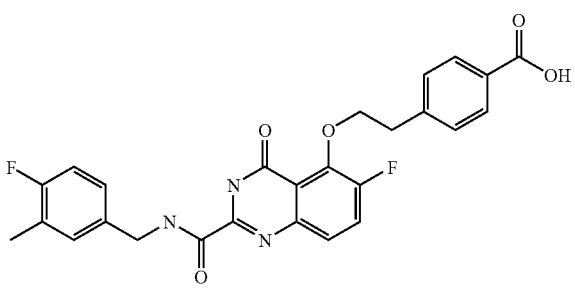 [SMILES: Cc1cc(CNC(=O)c2nc3ccc(F)c(OCCc4ccc(C(=O)O)cc4)c3c(=O)[nH]2)ccc1F]

A solution of 5,6-difluoro-N-[(4-fluoro-3-methylphenyl)methyl]-4-oxo-3,4-dihydroquinazoline-2-carboxamide (500 mg, 1.44 mmol) obtained in Example 357 and 4-(2-hydroxyethyl)benzoic acid (263 mg, 1.58 mmol) in DMA (10 mL) was added dropwise to a suspension of 60% sodium hydride (202 mg, 5.04 mmol) in DMA (6 mL) at room temperature, and the mixture was stirred at room temperature for 30 min. and then at 70° C. for 2 hrs with heating. The reaction mixture was ice-cooled and water (4 mL), ethyl acetate (8 mL), 1N hydrochloric acid (7 mL) and hexane (8 mL) were successively added dropwise. The precipitated solid was collected by filtration, and washed with ethanol and water. The obtained solid was dissolved in 0.2N aqueous sodium hydroxide solution (40 mL) and washed with ethyl acetate (50 mL×2). The aqueous layer was acidified with 2N hydrochloric acid. The precipitated solid was collected by filtration and washed with water. The obtained solid was suspended in methanol and the mixture was stirred with heating at 70° C. for 20 min. The mixture was allowed to cool to room temperature, and the precipitated solid was collected by filtration and washed with methanol to give the title compound as a white powder (182 mg, 26%).

melting point: 267-268° C.

$^1$H-NMR (300 MHz, DMSO-d$_6$) δ: 2.21 (3H, d, J=1.9 Hz), 3.17 (2H, t, J=6.9 Hz), 4.31 (2H, t, J=6.8 Hz), 4.41 (2H, d, J=6.4 Hz), 7.04-7.13 (1H, m), 7.15-7.28 (2H, m, J=21.0, 5.6 Hz), 7.45 (2H, d, J=8.3 Hz), 7.52 (1H, dd, J=8.9, 4.6 Hz), 7.78 (1H, dd, J=10.4, 9.0 Hz), 7.86 (2H, d, J=8.1 Hz), 9.51 (1H, t, J=6.3 Hz), 11.86-12.94 (2H, m).

Example 360

4-[2-({6-chloro-2-[({[3-(methyloxy)phenyl]methyl}amino)carbonyl]-4-oxo-3,4-dihydroquinazolin-5-yl}oxy)ethyl]benzoic acid

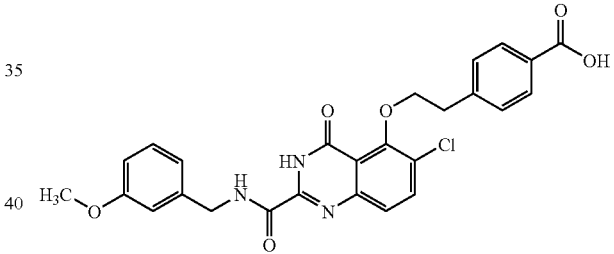

The compound was synthesized by a method similar to that of Example 159 from 6-chloro-5-fluoro-N-{[3-(methyloxy)phenyl]methyl}-4-oxo-3,4-dihydroquinazoline-2-carboxamide obtained in Example 358 and 4-(2-hydroxyethyl)benzoic acid.

A solution of 6-chloro-5-fluoro-N-{[3-(methyloxy)phenyl]methyl}-4-oxo-3,4-dihydroquinazoline-2-carboxamide (500 mg, 1.38 mmol) obtained in Example 358 and 4-(2-hydroxyethyl)benzoic acid (253 mg, 1.52 mmol) in DMA (10 mL) was added dropwise to a suspension of 60% sodium hydride (193 mg, 4.84 mmol) in DMA (6 mL) at room temperature, and the mixture was stirred at room lo temperature for 30 min. and then at 70° C. for 1.5 hr with heating. The reaction mixture was ice-cooled, and water (4 mL), ethyl acetate (8 mL), 1N hydrochloric acid (7 mL) and hexane (8 mL) were successively added dropwise.

The precipitated solid was collected by filtration, and washed with ethanol and water. The obtained solid was dissolved in 0.2N aqueous sodium hydroxide solution (40 mL) and washed with ethyl acetate (50 mL×2). The aqueous layer was acidified with 2N hydrochloric acid, and the precipitated solid was collected by filtration and washed with water. The obtained solid was suspended in methanol, and the mixture was stirred with heating at 70° C. for 20 min. The mixture was allowed to cool to room temperature, and the precipitated solid was collected by filtration and washed with methanol to give the title compound as a white powder (222 mg, 32%).

melting point: 226-227° C.

$^1$H-NMR (300 MHz, DMSO-$d_6$) δ: 3.24 (2H, t, J=6.8 Hz), 3.74 (3H, s), 4.27 (2H, t, J=6.9 Hz), 4.44 (2H, d, J=6.4 Hz), 6.80-6.86 (1H, m), 6.88-6.94 (2H, m), 7.25 (1H, t, J=8.1 Hz), 7.47 (2H, d, J=8.3 Hz), 7.52 (1H, d, J=8.7 Hz), 7.88 (2H, d, J=8.3 Hz), 7.92 (1H, d, J=8.9 Hz), 9.53 (1H, t, J=6.4 Hz), 12.51 (2H, s).

Example 361

6-fluoro-N-[(4-fluoro-3-methylphenyl)methyl]-5-{[(4-fluoro-3-methylphenyl)methyl]amino}-4-oxo-3,4-dihydroquinazoline-2-carboxamide

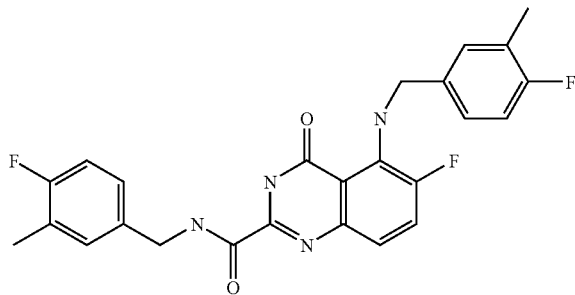 [SMILES: Cc1cc(CNC(=O)c2nc3ccc(F)c(NCc4ccc(F)c(C)c4)c3c(=O)[nH]2)ccc1F]

A suspension of ethyl 5,6-difluoro-4-oxo-3,4-dihydroquinazoline-2-carboxylate (1.50 g, 5.90 mmol) obtained in Reference Example 22 and 1-(4-fluoro-3-methylphenyl)methanamine (1.23 g, 8.85 mmol) in ethanol (30 mL) was stirred with heating at 90° C. for 3 hrs. The reaction mixture was allowed to cool to room temperature, the precipitated solid was filtered off and the filtrate was concentrated. The concentrated residue was purified by preparative HPLC and the obtained crude crystals were washed with ethanol to give the title compound as a yellow powder (33 mg, 1%).

melting point: 182-183° C.

$^1$H-NMR (300 MHz, DMSO-$d_6$) δ: 2.17-2.24 (6H, m, J=2.1, 2.1 Hz), 4.39 (2H, d, J=6.4 Hz), 4.53-4.61 (2H, m), 6.89 (1H, dd, J=8.8, 4.1 Hz), 7.03-7.12 (2H, m), 7.13-7.30 (4H, m), 7.47 (1H, dd, J=14.3, 8.7 Hz), 9.14 (1H, s), 9.43 (1H, t, J=5.8 Hz), 12.19 (1H, s).

Example 362

6-chloro-N-{[3-(methyloxy)phenyl]methyl}-5-({[3-(methyloxy)phenyl]methyl}amino)-4-oxo-3,4-dihydroquinazoline-2-carboxamide

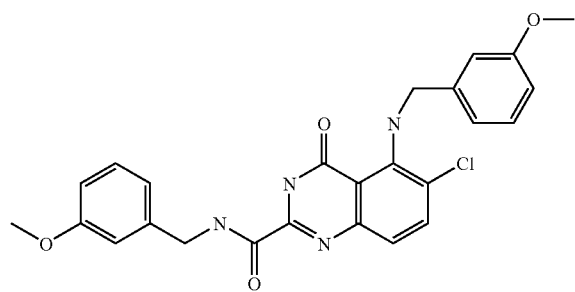

The compound was synthesized by a method similar to that of Example 361 from ethyl 6-chloro-5-fluoro-4-oxo-3,4-dihydroquinazoline-2-carboxylate obtained in Reference Example 154 and 3-methoxybenzylamine.

melting point: 126-128° C.

Example 363

5-({[(4-cyanophenyl)methyl]oxy}methyl)-N-{[3-(methyloxy)phenyl]methyl}-4-oxo-3,4-dihydrothieno[2,3-d]pyrimidine-2-carboxamide

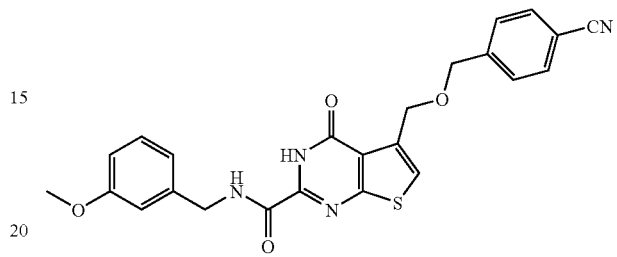

A mixture of ethyl 5-({[(4-cyanophenyl)methyl]oxy}methyl)-4-oxo-3,4-dihydrothieno[2,3-d]pyrimidine-2-carboxylate (150 mg, 0.406 mmol) obtained in Reference Example 155, 1-[3-(methyloxy)phenyl]methanamine (0.156 mL, 1.22 mmol) and ethanol (3 mL) was stirred at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (147 mg, 79%).

melting point: 205° C.

$^1$H NMR (300 MHz, DMSO-$d_6$) δ 3.73 (3 H, s), 4.42 (2H, d, J=6.4 Hz), 4.76 (2 H, s), 4.89 (2 H, d, J=1.1 Hz), 6.79-6.93 (3 H, m), 7.24 (1 H, t, J=8.1 Hz), 7.55-7.66 (3 H, m), 7.77-7.90 (2 H, m), 9.65 (1 H, t, J=6.4 Hz), 12.44 (1 H, s).

Example 364

5-({[(4-fluorophenyl)methyl]oxy}methyl)-N-{[3-(methyloxy)phenyl]methyl}-4-oxo-3,4-dihydrothieno[2,3-d]pyrimidine-2-carboxamide

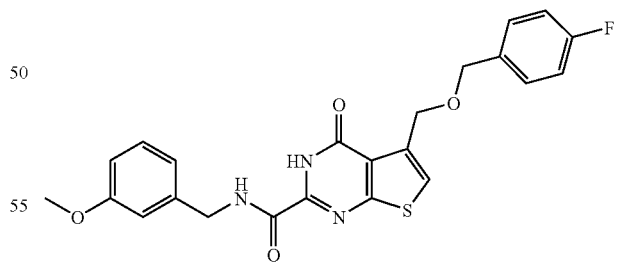

A mixture of ethyl 5-({[(4-fluorophenyl)methyl]oxy}methyl)-4-oxo-3,4-dihydrothieno[2,3-d]pyrimidine-2-carboxylate (80 mg, 0.221 mmol) obtained in Reference Example 156, 1-[3-(methyloxy)phenyl]methanamine (0.0848 mL, 0.662 mmol) and ethanol (2 mL) was stirred at 80° C. for 12 hrs. The reaction mixture was concentrated under reduced pressure and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (81 mg, 81%).

melting point: 166° C.

$^1$H NMR (300 MHz, DMSO-d$_6$) δ 3.73 (3 H, s), 4.41 (2 H, d, J=6.0 Hz), 4.64 (2 H, s), 4.85 (2 H, d, J=0.8 Hz), 6.74-6.94 (3 H, m), 7.11-7.30 (3 H, m), 7.38-7.49 (2 H, m), 7.59 (1 H, s), 9.64 (1 H, s), 12.42 (1 H, s).

Example 365 ethyl 4-{[({2-[({[3-(ethyloxy)phenyl]methyl}amino) carbonyl]-4-oxo-3,4-dihydrothieno[2,3-d]pyrimidin-5-yl}methyl)oxy]methyl}benzoate

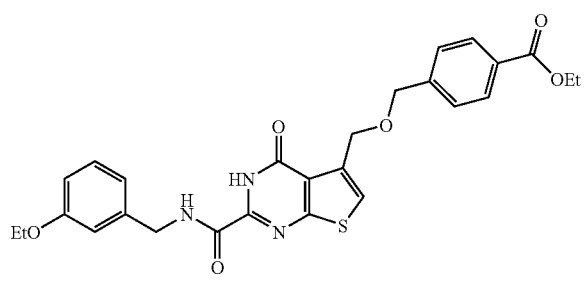 [SMILES: CCOC(=O)c1ccc(COCc2csc3nc(C(=O)NCc4cccc(OCC)c4)[nH]c(=O)c23)cc1]

To a mixture of ethyl 5-{[({4-[(ethyloxy)carbonyl] phenyl}methyl)oxy]methyl}-4-oxo-3,4-dihydrothieno[2,3-d]pyrimidine-2-carboxylate (350 mg, 0.840 mmol) obtained in Reference Example 158 and ethanol (15 mL) were added 1-[3-(ethyloxy)phenyl]methanamine hydrochloride (315 mg, 1.68 mmol) obtained in Reference Example 87 and N,N-diisopropylethylamine (0.585 mL, 3.36 mmol), and the mixture was stirred at 85° C. for 12 hrs. The reaction mixture was concentrated under reduced pressure. Ethyl acetate and THF were added to the obtained residue, and the organic layer was washed with 1N hydrochloric acid, water and saturated brine, dried over anhydrous sodium sulfate and concentrated under reduced pressure. The concentrated residue was crystallized from ethyl acetate to give the title compound as a white powder (383 mg, 87%).

melting point: 194° C.

$^1$H NMR (300 MHz, DMSO-d$_6$) δ 1.27-1.39 (6 H, m), 3.99 (2 H, q, J=7.0 Hz), 4.31 (2 H, q, J=7.0 Hz), 4.41 (2 H, d, J=6.4 Hz), 4.75 (2 H, s), 4.89 (2 H, d, J=0.9 Hz), 6.75-6.93 (3 H, m), 7.22 (1 H, t, J=8.0 Hz), 7.54 (2H, d, J=8.5 Hz), 7.63 (1 H, s), 7.89-8.02 (2 H, m), 9.63 (1 H, t, J=6.4 Hz), 12.18 (1 H, s).

Example 366

4-{[({2-[({[3-(ethyloxy)phenyl]methyl}amino)carbonyl]-4-oxo-3,4dihydrothieno[2,3-d]pyrimidin-5-yl}methyl)oxy]methyl}benzoic acid

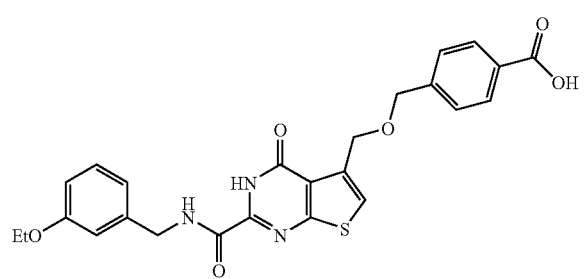 [SMILES: CCOc1cccc(CNC(=O)c2nc3scc(COCc4ccc(C(=O)O)cc4)c3c(=O)[nH]2)c1]

A mixture of ethyl 4-{[({2-[({[3-(ethyloxy)phenyl] methyl}amino)carbonyl]-4-oxo-3,4-dihydrothieno[2,3-d] pyrimidin-5-yl}methyl)oxy]methyl}benzoate (220 mg, 0.422 mol) obtained in Example 365 and 4N aqueous sodium hydroxide solution (0.527 mL) was stirred in a mixed solvent of water (3 mL), methanol (3 mL) and THF (3 mL) at 80° C. for 2 hrs. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (192 mg, 92%).

melting point: 240° C.

$^1$H NMR (300 MHz, DMSO-d$_6$) δ 1.31 (3 H, t, J=7.0 Hz), 3.99 (2 H, q, J=7.0 Hz), 4.41 (2 H, d, J=6.2 Hz), 4.74 (2 H, s), 4.89 (2 H, d, J=0.9 Hz), 6.74-6.93 (3 H, m), 7.22 (1 H, t, J=8.1 Hz), 7.51 (2 H, d, J=8.5 Hz), 7.63 (1 H, s), 7.94 (2 H, d, J=8.3 Hz), 9.64 (1 H, t, J=6.4 Hz), 12.44 (1 H, s), 12.90 (1 H, s).

Example 367 ethyl 4-({[(4-oxo-2-{[(phenylmethyl)amino]carbonyl}-3,4-dihydrothieno[2,3-d]pyrimidin-5-yl)methyl] oxy}methyl)benzoate

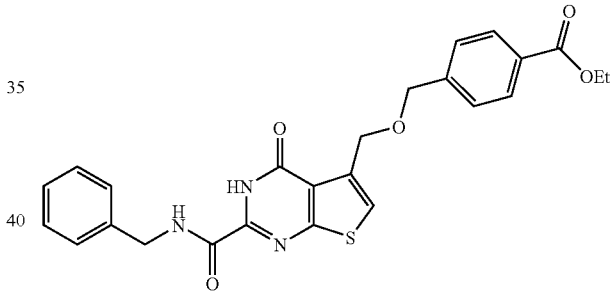

To a mixture of ethyl 5-{[({4-[(ethyloxy)carbonyl] phenyl}methyl)oxy]methyl}-4-oxo-3,4-dihydrothieno[2,3-d]pyrimidine-2-carboxylate (350 mg, 0.840 mmol) obtained in Reference Example 158 and ethanol (15 mL) was added benzylamine (0.184 mL, 1.68 mmol), and the mixture was stirred at 85° C. for 12 hrs. The reaction mixture was concentrated under reduced pressure, and ethyl acetate and THF were added to the obtained residue. The organic layer was washed with 1N hydrochloric acid, water and saturated brine, dried over anhydrous sodium sulfate and concentrated under reduced pressure. The concentrated residue was crystallized from ethyl acetate to give the title compound as a white powder (368 mg, 92%).

melting point: 229° C.

$^1$H NMR (300 MHz, DMSO-d$_6$) δ 1.32 (3 H, t, J=7.1 Hz), 4.31 (2 H, q, J=7.0 Hz), 4.45 (2 H, d, J=6.4 Hz), 4.75 (2 H, s), 4.89 (2 H, d, J=0.9 Hz), 7.19-7.37 (5 H, m), 7.53 (2 H, d, J=8.1 Hz), 7.63 (1 H, s), 7.95 (2 H, d, J=8.3 Hz), 9.67 (1 H, t, J=6.3 Hz), 12.43 (1 H, s).

Example 368

4-({[(4-oxo-2-{[(phenylmethyl)amino]carbonyl}-3,4-dihydrothieno[2,3-d]pyrimidin-5-yl)methyl]oxy}methyl)benzoic acid

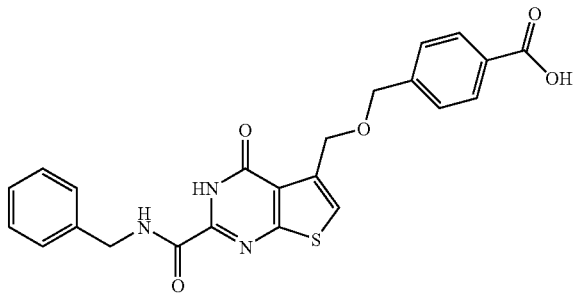 [SMILES: O=C(O)c1ccc(COCc2csc3nc(C(=O)NCc4ccccc4)[nH]c(=O)c23)cc1]

A mixture of ethyl 4-({[(4-oxo-2-{[(phenylmethyl)amino]carbonyl}-3,4-dihydrothieno[2,3-d]pyrimidin-5-yl)methyl]oxy}methyl)benzoate (220 mg, 0.461 mmol) obtained in Example 367 and 4N aqueous sodium hydroxide solution (0.576 mL, 2.30 mmol) was stirred in a mixed solvent of water (3 mL), methanol (3 mL) and THF (3 mL) at 80° C. for 2 hrs. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (187 mg, 90%).

melting point: 268-269° C.

$^1$H NMR (300 MHz, DMSO-$d_6$) δ 4.45 (2 H, d, J=6.4 Hz), 4.74 (2 H, s), 4.89 (2 H, s), 7.19-7.38 (5 H, m), 7.51 (2 H, d, J=8.3 Hz), 7.63 (1 H, s), 7.93 (2 H, d, J=8.1 Hz), 9.68 (1 H, t, J=6.4 Hz), 12.44 (1 H, s), 12.88 (1 H, s).

Example 369 ethyl 4-{[({2-[({[4-fluoro-3-(methyloxy)phenyl]methyl}amino)carbonyl]-4-oxo-3,4-dihydrothieno[2,3-d]pyrimidin-5-yl}methyl)oxy]methyl}benzoate

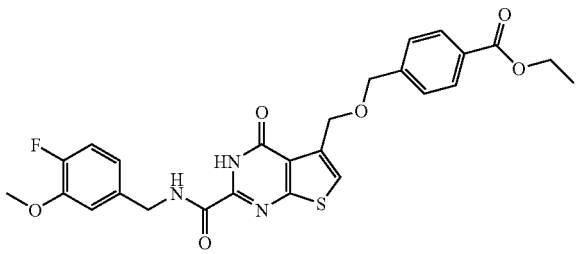 [SMILES: CCOC(=O)c1ccc(COCc2csc3nc(C(=O)NCc4ccc(F)c(OC)c4)[nH]c(=O)c23)cc1]

To a mixture of ethyl 5-{[({4-[(ethyloxy)carbonyl]phenyl}methyl)oxy]methyl}-4-oxo-3,4-dihydrothieno[2,3-d]pyrimidine-2-carboxylate (350 mg, 0.840 mmol) obtained in Reference Example 158 and DMA (10 mL) were added 1-[4-fluoro-3-(methyloxy)phenyl]methanamine hydrochloride (242 mg, 1.26 mmol) (synthesized by a method described in WO03/029224 A1) and N,N-diisopropylethylamine (0.293 mL, 1.68 mmol) and the mixture was stirred at 90° C. for 12 hrs. The reaction mixture was concentrated under reduced pressure, and ethyl acetate and THF were added to the obtained residue. The organic layer was washed with 1N hydrochloric acid, water and saturated brine, dried over anhydrous sodium sulfate and concentrated under reduced pressure. The concentrated residue was crystallized from ethyl acetate to give the title compound as an opalescent powder (283 mg, 64%).

melting point: 215-216° C.

$^1$H NMR (300 MHz, DMSO-$d_6$) δ 1.32 (3 H, t, J=7.2 Hz), 3.82 (3 H, s), 4.31 (2 H, q, J=7.1 Hz), 4.41 (2 H, d, J=6.4 Hz), 4.75 (2 H, s), 4.89 (2 H, d, J=1.1 Hz), 6.78-6.95 (1 H, m), 7.06-7.22 (2 H, m), 7.53 (2 H, d, J=8.5 Hz), 7.63 (1H, s), 7.88-8.01 (2 H, m), 9.66 (1 H, t, J=6.3 Hz), 12.43 (1 H, s).

Example 370

4-{[({2-[({[4-fluoro-3-(methyloxy)phenyl]methyl}amino)carbonyl]-4-oxo-3,4-dihydrothieno[2,3-d]pyrimidin-5-yl}methyl)oxy]methyl}benzoic acid

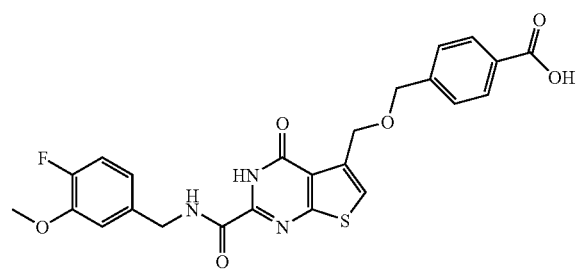 [SMILES: COc1cc(CNC(=O)c2nc3scc(COCc4ccc(C(=O)O)cc4)c3c(=O)[nH]2)ccc1F]

A mixture of ethyl 4-{[({2-[({[4-fluoro-3-(methyloxy)phenyl]methyl}amino)carbonyl]-4-oxo-3,4-dihydrothieno[2,3-d]pyrimidin-5-yl}methyl)oxy]methyl}benzoate (210 mg, 0.400 mmol) obtained in Example 369 and 4N aqueous sodium hydroxide solution (0.500 mL) was stirred in a mixed solvent of water (3 mL), methanol (3 mL) and THF (3 mL) at 80° C. for 2 hrs. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (194 mg, 98%).

melting point: 225-226° C.

$^1$H NMR (300 MHz, DMSO-$d_6$) δ 3.82 (3 H, s), 4.41 (2 H, d, J=6.2 Hz), 4.74 (2 H, s), 4.89 (2 H, d, J=0.9 Hz), 6.83-6.95 (1 H, m), 7.08-7.21 (2 H, m), 7.51 (2 H, d, J=8.5 Hz), 7.63 (1 H, s), 7.93 (2 H, d, J=8.3 Hz), 9.66 (1 H, t, J=6.3 Hz), 12.45 (1 H, s), 12.91 (1 H, s).

Example 371

Disodium 4-{[({2-[({[4-fluoro-3-(methyloxy)phenyl]methyl}amino)carbonyl]-4-oxo-4H-thieno[2,3-d]pyrimidin-3-id-5-yl}methyl)oxy]methyl}benzoate

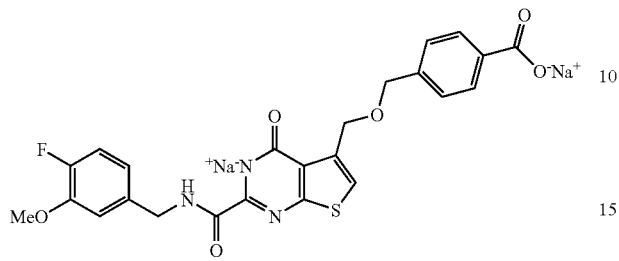

To a mixed solution of 4-{[({2-[({[4-fluoro-3-(methyloxy)phenyl]methyl}amino)carbonyl]-4-oxo-3,4-dihydrothieno[2,3-d]pyrimidin-5-yl}methyl)oxy]methyl}benzoic acid (500 mg, 1.01 mmol) obtained in Example 370 in THF (80 mL) and methanol (40 mL) was added an aqueous solution (10 mL) of sodium hydrogen carbonate (169 mg, 2.01 mmol) at 90° C. The mixture was stirred at 90° C. for 30 min. and the reaction mixture was concentrated under reduced pressure. Ethanol was added to the obtained residue. The ethanol suspension was stirred at 90° C. for 1 hr and allowed to cool to room temperature. The precipitated solid was collected by filtration, washed with ethanol and dried to give the title compound as a white powder (406 mg, 75%).

melting point: >300° C.

$^1$H NMR (300 MHz, DMSO-d$_6$) δ 3.81 (3 H, s), 4.38 (2 H, d, J=6.4 Hz), 4.63 (2 H, s), 4.88 (2 H, s), 6.81-6.91 (1 H, m), 6.98 (1 H, s), 7.07-7.18 (2 H, m), 7.28 (2 H, d, J=7.9 Hz), 7.83 (2 H, d, J=8.1 Hz), 9.04 (1 H, t, J=6.4 Hz).

Example 372

[2-({[(3-chlorophenyl)methyl]amino}carbonyl)-4-oxo-3,4-dihydrothieno[2,3-d]pyrimidin-5-yl]methyl 4-(hydroxymethyl)benzoate

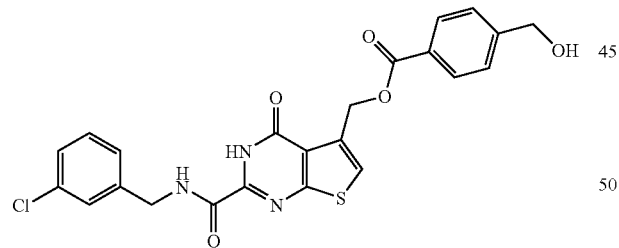

A mixture of ethyl 5-[({[4-(hydroxymethyl)phenyl]carbonyl}oxy)methyl]-4-oxo-3,4-dihydrothieno[2,3-d]pyrimidine-2-carboxylate (200 mg, 0.515 mmol) obtained in Reference Example 159 and 1-(3-chlorophenyl)methanamine (219 mg, 1.55 mmol) was stirred in ethanol (5 mL) at 85° C. for 2 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (74 mg, 30%).

melting point: 247-248° C.

$^1$H NMR (300 MHz, DMSO-d$_6$) δ 4.46 (2 H, d, J=6.2 Hz), 4.58 (2 H, d, J=5.5 Hz), 5.38 (1 H, t, J=5.7 Hz), 5.61 (2 H, s), 7.25-7.52 (6 H, m), 7.80 (1 H, s), 7.98 (2 H, d, J=8.3 Hz), 9.74 (1 H, t, J=5.9 Hz), 12.55 (1 H, s).

Example 373

(4-oxo-2-{[({3-[(trifluoromethyl)oxy]phenyl}methyl)amino]carbonyl}-3,4-dihydrothieno[2,3-d]pyrimidin-5-yl)methyl 4-(hydroxymethyl)benzoate

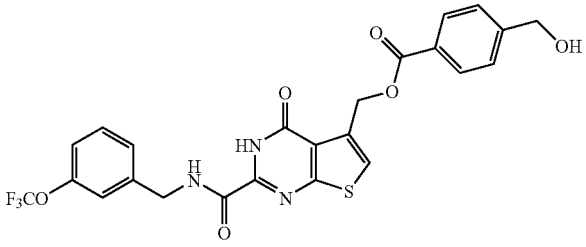 [SMILES: O=C(OCc1csc2nc(C(=O)NCc3cccc(OC(F)(F)F)c3)[nH]c(=O)c12)c1ccc(CO)cc1]

A mixture of ethyl 5-[({[4-(hydroxymethyl)phenyl]carbonyl}oxy)methyl]-4-oxo-3,4-dihydrothieno[2,3-d]pyrimidine-2-carboxylate (200 mg, 0.515 mmol) obtained in Reference Example 159 and 1-{3-[(trifluoromethyl)oxy]phenyl}methanamine (295 mg, 1.55 mmol) was stirred in ethanol (5 mL) at 85° C. for 4 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (140 mg, 51%).

melting point: 162-163° C.

$^1$H NMR (300 MHz, DMSO-d$_6$) δ 4.50 (2 H, d, J=6.6 Hz), 4.58 (2 H, d, J=5.7 Hz), 5.38 (1 H, t, J=5.7 Hz), 5.61 (2 H, s), 7.17-7.54 (6 H, m), 7.80 (1 H, s), 7.98 (2 H, d, J=8.3 Hz), 9.77 (1 H, t, J=6.4 Hz), 12.57 (1 H, s).

Example 374

{2-[({[3-(ethyloxy)phenyl]methyl}amino)carbonyl]-4-oxo-3,4-dihydrothieno[2,3-d]pyrimidin-5-yl}methyl 4-(hydroxymethyl)benzoate

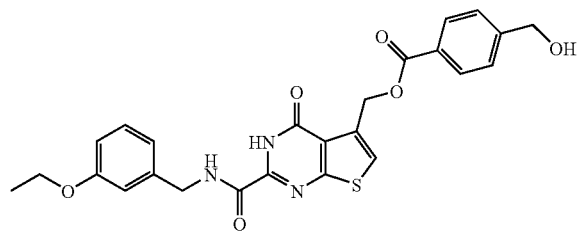 [SMILES: CCOc1cccc(CNC(=O)c2nc3scc(COC(=O)c4ccc(CO)cc4)c3c(=O)[nH]2)c1]

A mixture of ethyl 5-[({[4-(hydroxymethyl)phenyl]carbonyl}oxy)methyl]-4-oxo-3,4-dihydrothieno[2,3-d]pyrimidine-2-carboxylate (200 mg, 0.515 mmol) obtained in Reference Example 159, 1-[3-(ethyloxy)phenyl]methanamine hydrochloride (290 mg, 1.55 mmol) and N,N-diisopropylethylamine (0.357 mL, 2.06 mmol) was stirred in ethanol (5 mL) at 85° C. for 8 hrs. The reaction mixture was concentrated under reduced pressure. Ethyl acetate (500 mL) was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (177 mg, 70%).

melting point: 188° C.

$^1$H NMR (300 MHz, DMSO-d$_6$) δ 1.31 (3 H, t, J=7.0 Hz), 4.00 (2 H, q, J=7.0 Hz), 4.42 (2 H, d, J=6.4 Hz), 4.58 (2 H, d, J=5.7 Hz), 5.38 (1 H, t, J=5.7 Hz), 5.61 (2 H, s), 6.73-6.94 (3 H, m), 7.22 (1 H, t, J=8.0 Hz), 7.47 (2 H, d, J=8.1 Hz), 7.79 (1 H, s), 7.98 (2 H, d, J=8.1 Hz), 9.66 (1 H, t, J=6.4 Hz), 12.54 (1 H, s).

Example 375

{2-[({[4-(methyloxy)phenyl]methyl}amino)carbonyl]-4-oxo-3,4-dihydrothieno[2,3-d]pyrimidin-5-yl}methyl 4-(hydroxymethyl)benzoate

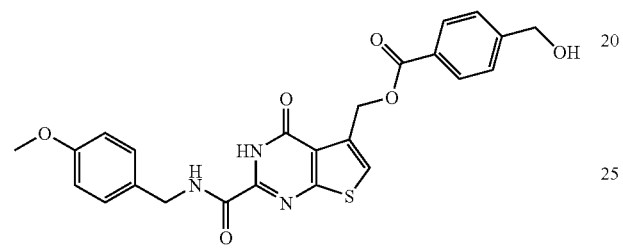

A mixture of ethyl 5-[({[4-(hydroxymethyl)phenyl]carbonyl}oxy)methyl]-4-oxo-3,4-dihydrothieno[2,3-d]pyrimidine-2-carboxylate (200 mg, 0.515 mmol) obtained in Reference Example 159 and 1-[4-(methyloxy)phenyl]methanamine (212 mg, 1.55 mmol) was stirred in ethanol (5 mL) at 85° C. for 4 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (133 mg, 54%).

melting point: 208° C.

$^1$H NMR (300 MHz, DMSO-d$_6$) δ 3.73 (3 H, s), 4.38 (2 H, d, J=6.4 Hz), 4.59 (2 H, d, J=5.3 Hz), 5.38 (1 H, t, J=5.8 Hz), 5.61 (2 H, s), 6.89 (2 H, d, J=8.3 Hz), 7.27 (2 H, d, J=8.3 Hz), 7.47 (2 H, d, J=7.5 Hz), 7.79 (1 H, s), 7.98 (2 H, d, J=8.1 Hz), 9.62 (1 H, t, J=5.8 Hz), 12.52 (1 H, s).

Example 376

{2-[({[3-(methyloxy)phenyl]methyl}amino)carbonyl]-4-oxo-3,4-dihydrothieno[2,3-d]pyrimidin-5-yl}methyl 4-(hydroxymethyl)benzoate

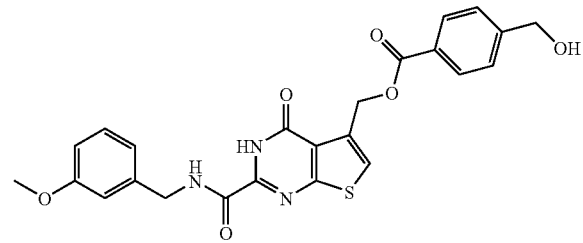 [SMILES: COc1cccc(CNC(=O)c2nc3scc(COC(=O)c4ccc(CO)cc4)c3c(=O)[nH]2)c1]

A mixture of ethyl 5-[({[4-(hydroxymethyl)phenyl]carbonyl}oxy)methyl]-4-oxo-3,4-dihydrothieno[2,3-d]pyrimidine-2-carboxylate (100 mg, 0.257 mmol) obtained in Reference Example 159, 1-[3-(methyloxy)phenyl]methanamine (0.0494 mL, 0.386 mmol) and N,N-diisopropylethylamine (0.224 mL, 1.29 mmol) was stirred in ethanol (5 mL) at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (87.4 mg, 71%).

melting point: 185-186° C.

$^1$H NMR (300 MHz, DMSO-d$_6$) δ 3.74 (3 H, s), 4.43 (2 H, d, J=6.2 Hz), 4.59 (2 H, d, J=5.1 Hz), 5.38 (1 H, t, J=5.6 Hz), 5.61 (2 H, s), 6.76-6.94 (3 H, m), 7.24 (1 H, t, J=8.1 Hz), 7.47 (2 H, d, J=8.1 Hz), 7.79 (1 H, s), 7.98 (2 H, d, J=8.3 Hz), 9.67 (1 H, t, J=6.3 Hz), 12.54 (1 H, s).

Example 377 ethyl 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoate

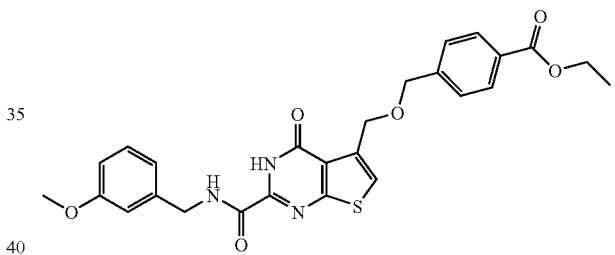

To a mixture of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (110 mg, 0.229 mmol) obtained in Example 217, 1-ethyl-3-(3-dimethylaminopropyl)carbodiimide hydrochloride (65.9 mg, 0.344 mol), 4-dimethylaminopyridine (2.70 mg, 0.0220 mol) and THF (5 mL) was added ethanol (0.134 mL, 2.29 mmol), and the mixture was stirred at room temperature for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (85.5 mg, 74%).

melting point: 173° C.

$^1$H NMR (300 MHz, DMSO-d$_6$) δ 1.32 (3 H, t, J=7.1 Hz), 3.73 (3 H, s), 4.31 (2 H, q, J=7.2 Hz), 4.42 (2 H, d, J=6.2 Hz), 4.75 (2 H, s), 4.89 (2 H, d, J=0.9 Hz), 6.79-6.85 (1 H, m), 6.87-6.93 (2 H, m), 7.24 (1 H, t, J=8.1 Hz), 7.54 (2 H, d, J=8.5 Hz), 7.63 (1 H, s), 7.88-8.03 (2 H, m), 9.65 (1 H, t, J=6.5 Hz), 12.42 (1 H, s).

Example 378

5-{[({4-[(methylamino)carbonyl]phenyl}methyl)oxy]methyl}-N-{[3-(methyloxy)phenyl]methyl}-4-oxo-3,4-dihydrothieno[2,3-d]pyrimidine-2-carboxamide

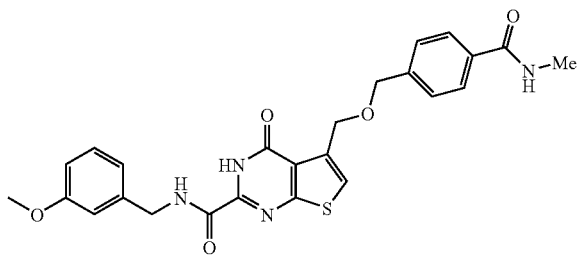 [SMILES: CNC(=O)c1ccc(COCc2csc3nc(C(=O)NCc4cccc(OC)c4)[nH]c(=O)c23)cc1]

To a mixture of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (110 mg, 0.229 mmol) obtained in Example 217, 1-ethyl-3-(3-dimethylaminopropyl)carbodiimide hydrochloride (65.9 mg, 0.344 mol), 4-dimethylaminopyridine (283 mg, 2.31 mol) and THF (5 mL) was added methylamine hydrochloride (155 mg, 2.29 mmol) The mixture was stirred at room temperature for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (75.9 mg, 67%).

melting point: 190-191° C.

$^1$H NMR (300 MHz, DMSO-$d_6$) δ 2.78 (3 H, d, J=4.5 Hz), 3.73 (3 H, s), 4.42 (2 H, d, J=6.4 Hz), 4.71 (2 H, s), 4.87 (2 H, d, J=0.8 Hz), 6.82 (1 H, dd, J=8.9, 1.8 Hz), 6.86 -6.97 (2 H, m), 7.24 (1 H, t, J=8.1 Hz), 7.46 (2 H, d, J=8.1 Hz), 7.62 (1 H, s), 7.82 (2 H, d, J=8.1 Hz), 8.42 (1 H, d, J=4.5 Hz), 9.65 (1 H, t, J=6.4 Hz), 12.42 (1 H, s).

Example 379

5-[({[4-(aminocarbonyl)phenyl]methyl}oxy)methyl]-N-{[3-(methyloxy)phenyl]methyl}-4-oxo-3,4-dihydrothieno[2,3-d]pyrimidine-2-carboxamide

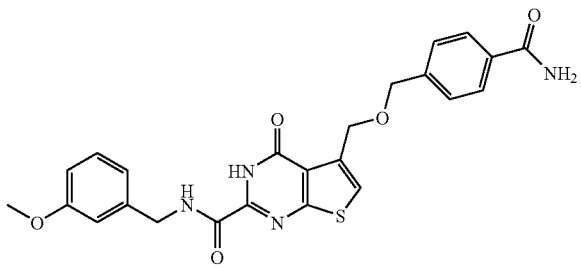 [SMILES: COc1cccc(CNC(=O)c2nc3scc(COCc4ccc(C(N)=O)cc4)c3c(=O)[nH]2)c1]

To a mixture of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (200 mg, 0.417 mmol) obtained in Example 217 and THF (2 mL) were added oxalyl chloride (0.0500 mL, 0.573 mmol) and DMF (1 drop) and the mixture was stirred at room temperature for 1 hr. The reaction mixture was concentrated under reduced pressure. To a suspension of the concentrated residue in THF (3 mL) was added 28% aqueous ammonia (2 mL), and the mixture was stirred at room temperature for 10 min. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate-THF to give the title compound as a white powder (173 mg, 87%).

melting point: 224° C.

$^1$H NMR (300 MHz, DMSO-$d_6$) δ 3.73 (3 H, s), 4.42 (2 H, d, J=6.2 Hz), 4.71 (2 H, s), 4.87 (2 H, d, J=1.1 Hz), 6.76-6.95 (3 H, m), 7.18-7.28 (1 H, m), 7.34 (1 H, s), 7.47 (2 H, t, J=7.6 Hz), 7.62 (1 H, s), 7.86 (2 H, d, J=8.3 Hz), 7.95 (1 H, s), 9.64 (1 H, t, J=6.4 Hz), 12.43 (1 H, s).

Example 380

5-[({[4-(hydroxymethyl)phenyl]methyl}oxy)methyl]-N-{[3-(methyloxy)phenyl]methyl}-4-oxo-3,4-dihydrothieno[2,3-d]pyrimidine-2-carboxamide

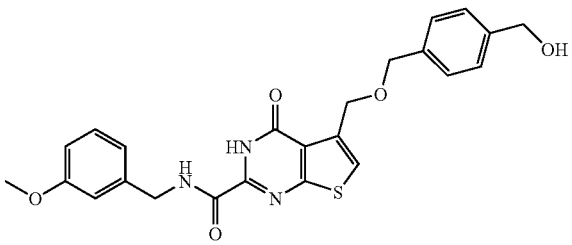 [SMILES: COc1cccc(CNC(=O)c2nc3scc(COCc4ccc(CO)cc4)c3c(=O)[nH]2)c1]

To a mixture of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (1200 mg, 2.50 mmol) obtained in Example 217 and THF (12 mL) were added oxalyl chloride (0.419 mL, 4.80 mmol) and DMF (1 drop), and the mixture was stirred at room temperature for 1.5 hrs. The reaction mixture was concentrated under reduced pressure. A Mixture of the concentrated residue and sodium borohydride (189 mg, 5.01 mmol) was stirred in DMA (15 mL) at room temperature for 5 min. The reaction mixture was stirred until generation of gas ceased and concentrated under reduced pressure. Ethyl acetate was added to the obtained residue. The organic layer was washed with water, 1N hydrochloric acid, water and saturated brine, dried over anhydrous sodium sulfate and concentrated under reduced pressure. The concentrated residue was crystallized from ethyl acetate to give the title compound as a white powder (753 mg, 65%).

melting point: 156-157° C.

$^1$H NMR (300 MHz, DMSO-$d_6$) δ 3.73 (3 H, s), 4.42 (2 H, d, J=6.4 Hz), 4.49 (2 H, d, J=5.7 Hz), 4.64 (2 H, s), 4.83 (2 H, d, J=1.1 Hz), 5.16 (1 H, t, J=5.7 Hz), 6.75-6.95 (3 H, m), 7.19-7.28 (1 H, m), 7.28-7.39 (4 H, m), 7.58 (1 H, s), 9.64 (1 H, t, J=6.5 Hz), 12.39 (1 H, s).

Example 381

5-{[({4-[(methyloxy)methyl]phenyl}methyl)oxy]
methyl}-N-{[3-(methyloxy)phenyl]methyl}-4-oxo-3,
4-dihydrothieno[2,3-d]pyrimidine-2-carboxamide

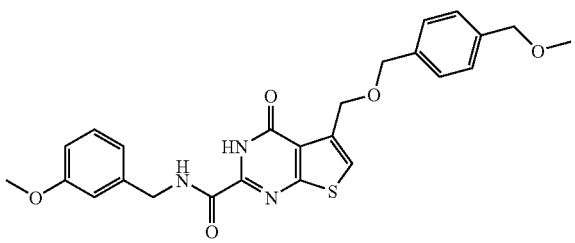

To a mixture of 5-[({[4-(hydroxymethyl)phenyl]
methyl}oxy)methyl]-N-{[3-(methyloxy)phenyl]methyl}-4-
oxo-3,4-dihydrothieno[2,3-d]pyrimidine-2-carboxamide
(100 mg, 0.215 mmol) obtained in Example 380 and THF (2
mL) were added methanesulfonyl chloride (0.0266 mL, 0.344
mmol) and triethylamine (0.0929 mL, 0.667 mmol), and the
mixture was stirred at room temperature for 18 1 hr. The
reaction mixture was concentrated under reduced pressure,
and ethyl acetate was added to the obtained residue. The
organic layer was washed with water and saturated brine,
dried over anhydrous sodium sulfate and concentrated under
reduced pressure. To a mixture of the concentrated residue
and sodium methylate (58.1 mg, 1.08 mmol) were added
methanol (2 mL) and THF (2 mL) and the mixture was stirred
at 80° C. for 1 hr. The reaction mixture was concentrated
under reduced pressure, and ethyl acetate was added to the
obtained residue. The organic layer was washed with 1N
hydrochloric acid and saturated brine, dried over anhydrous
sodium sulfate and concentrated under reduced pressure. The
concentrated residue was crystallized from ethyl acetate to
give the title compound as a white powder (68.5 mg, 66%).

melting point: 156-157° C.

$^1$H NMR (300 MHz, DMSO-$d_6$) δ 3.28 (3 H, s), 3.73 (3 H, s) 4.34-4.48 (4 H, m), 4.65 (2 H, s), 4.85 (2 H, d, J=0.9 Hz), 6.77-6.95 (3 H, m), 7.18-7.40 (5 H, m), 7.59 (1 H, s), 9.64 (1 H, t, J=6.0 Hz), 12.42 (1H, s).

Example 382

(4-{[({2-[({[3-(methyloxy)phenyl]methyl}amino)
carbonyl]-4-oxo-3,4-dihydrothieno[2,3-d]pyrimidin-
5-yl}methyl)oxy]methyl}phenyl)methyl acetate

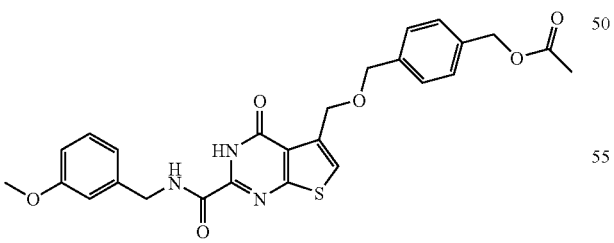

To a mixture of 5-[({[4-(hydroxymethyl)phenyl]
methyl}oxy)methyl]-N-{[3-(methyloxy)phenyl]methyl}-4-
oxo-3,4-dihydrothieno[2,3-d]pyrimidine-2-carboxamide
(100 mg, 0.215 mmol) obtained in Example 380 and THF (2
mL) were added acetyl chloride (0.0245 mL, 0.344 mmol)
and pyridine (0.174 mL, 2.15 mmol) and the mixture was
stirred at room temperature for 2 hrs. The reaction mixture
was concentrated under reduced pressure, and ethyl acetate
was added to the obtained residue. The organic layer was
washed with 1N hydrochloric acid and saturated brine, dried
over anhydrous sodium sulfate and concentrated under
reduced pressure. The concentrated residue was crystallized
from ethyl acetate to give the title compound as a white
powder (91 mg, 83%).

melting point: 170° C.

$^1$H NMR (300 MHz, DMSO-$d_6$) δ 2.06 (3 H, s), 3.73 (3 H, s), 4.42 (2 H, d, J=6.2 Hz), 4.66 (2 H, s), 4.85 (2 H, d, J=1.3 Hz), 5.07 (2 H, s), 6.76-6.95 (3 H, m), 7.24 (1 H, t, J=8.1 Hz), 7.31-7.44 (4 H, m), 7.59 (1 H, t, J=1.2 Hz), 9.64 (1 H, t, J=6.4 Hz), 12.42 (1 H, s).

Example 383

Sodium 4-{[({2-[({[3-(methyloxy)phenyl]
methyl}amino)carbonyl]-4-oxo-3,4-dihydrothieno[2,
3-d]pyrimidin-5-yl}methyl)oxy]methyl}benzoate

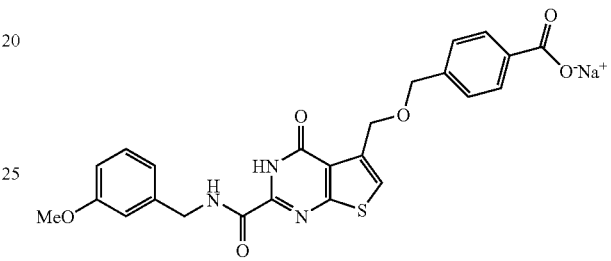

To a mixed solution of 4-{[({2-[({[3-(methyloxy)phenyl]
methyl}amino)carbonyl]-4-oxo-3,4-dihydrothieno[2,3-d]
pyrimidin-5-yl}methyl)oxy]methyl}benzoic acid (150 mg,
0.313 mmol) obtained in Example 217 in THF (24 mL) and
ethanol (6 mL) was added an aqueous solution (3 mL) of
sodium hydrogen carbonate (26.3 mg, 0.313 mmol) at 90° C.
and the mixture was stirred for 30 min. The reaction mixture
was concentrated under reduced pressure, and ethanol (18
mL) was added to the obtained residue and the ethanol suspension
was stirred at 90° C. for 30 min. After allowing to
cool to room temperature, the precipitated solid was collected
by filtration, washed with ethanol and dried to give the title
compound as a white powder (114 mg, 73%).

melting point: 276-278° C.

$^1$H NMR (300 MHz, DMSO-$d_6$) δ 3.73 (3 H, s), 4.40 (2 H, d, J=6.2 Hz), 4.69 (2 H, s), 4.89 (2 H, s), 6.73-6.94 (3 H, m), 7.15-7.30 (2 H, m), 7.40 (2 H, d, J=8.3 Hz), 7.88 (2 H, d, J=8.1 Hz), 9.27 (1 H, s).

Example 384

Disodium 4-{[({2-[({[3-(methyloxy)phenyl]
methyl}amino)carbonyl]-4-oxo-4H-thieno[2,3-d]
pyrimidin-3-id-5-yl}methyl)oxy]methyl}benzoate

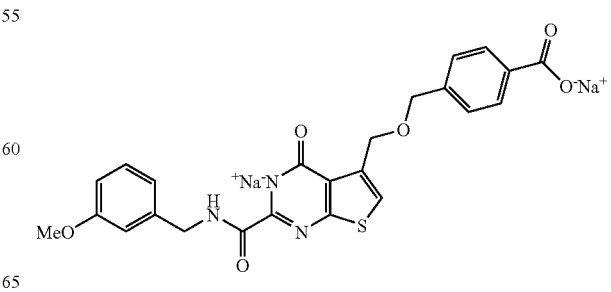

To a mixed solution of 4-{[({2-[({[3-(methyloxy)phenyl]
methyl}amino)carbonyl]-4-oxo-3,4-dihydrothieno[2,3-d]

pyrimidin-5-yl}methyl)oxy]methyl}benzoic acid (150 mg, 0.313 mmol) obtained in Example 217 in THF (24 mL) and ethanol (6 mL) was added an aqueous solution (3 mL) of sodium hydrogen carbonate (52.6 mg, 0.626 mmol) and the mixture was stirred for 30 min. The reaction mixture was concentrated under reduced pressure, ethanol (18 mL) was added to the obtained residue, and the ethanol suspension was stirred at 90° C. for 30 min. The mixture was allowed to cool to room temperature, and the precipitated solid was collected by filtration, washed with ethanol and dried to give the title compound as a white powder (149 mg, 91%).

melting point: >300° C.

$^1$H NMR (300 MHz, DMSO-$d_6$) δ 3.73 (3 H, s), 4.40 (2 H, d, J=6.4 Hz), 4.63 (2 H, s), 4.88 (2 H, d, J=1.3 Hz), 6.74-6.94 (3 H, m), 6.98 (1 H, t, J=1.3 Hz), 7.14-7.33 (3 H, m), 7.84 (2 H, d, J=8.1 Hz), 9.03 (1 H, t, J=6.4 Hz).

Example 385

Potassium 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoate

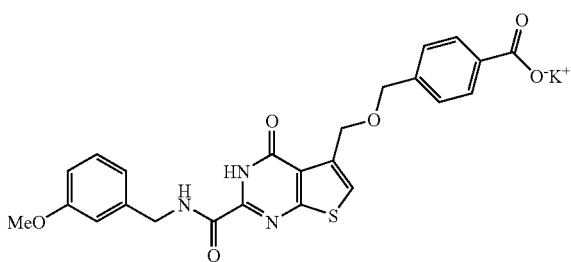

To a mixed solution of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (150 mg, 0.313 mmol) obtained in Example 217 in THF (24 mL) and ethanol (6 mL) was added an aqueous solution (3 mL) of potassium hydrogen carbonate (31.3 mg, 0.313 mmol) at 90° C. and the mixture was stirred for 30 min. The reaction mixture was concentrated under reduced pressure, ethanol (18 mL) was added to the obtained residue, and the ethanol suspension was stirred at 90° C. for 30 min. The mixture was allowed to cool to room temperature, and the precipitated solid was collected by filtration, washed with ethanol and dried to give the title compound as a white powder (140 mg, 87%).

melting point: 281-282° C.

$^1$H NMR (300 MHz, DMSO-$d_6$) δ 3.73 (3 H, s), 4.40 (2 H, d, J=6.4 Hz), 4.69 (2 H, s), 4.89 (2 H, d, J=1.1 Hz), 6.73-6.95 (3 H, m), 7.19-7.27 (2 H, m), 7.40 (2 H, d, J=8.1 Hz), 7.88 (2 H, d, J=8.1 Hz), 9.24 (1 H, t, J=6.1 Hz).

Example 386

Dipotassium 4-{[({2-[({[3-(methyloxy)phenyl]methyl}amino)carbonyl]-4-oxo-4H-thieno[2,3-d]pyrimidin-3-id-5-yl}methyl)oxy]methyl}benzoate

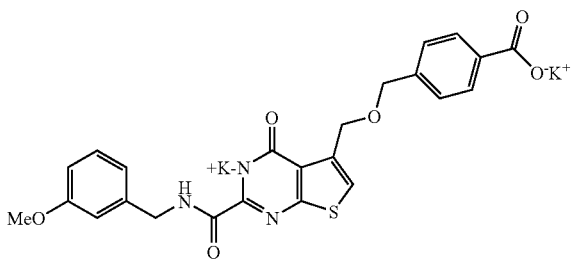

To a mixed solution of 4-{[({2-[({[3-(methyloxy)phenyl]methyl}amino)carbonyl]-4-oxo-3,4-dihydrothieno[2,3-d]pyrimidin-5-yl}methyl)oxy]methyl}benzoic acid (150 mg, 0.313 mmol) obtained in Example 217 in THF (24 mL) and ethanol (6 mL) was added an aqueous solution (3 mL) of potassium hydrogen carbonate (62.6 mg, 0.626 mmol) at 90° C. and the mixture was stirred for 30 min. The reaction mixture was concentrated under reduced pressure, ethanol (18 mL) was added to the obtained residue, and the ethanol suspension was stirred at 90° C. for 30 min. The mixture was allowed to cool to room temperature, and the precipitated solid was collected by filtration, washed with ethanol and dried to give the title compound as a white powder (161 mg, 93%).

melting point: >300° C.

$^1$H NMR (300 MHz, DMSO-$d_6$) δ 3.73 (3 H, s), 4.39 (2 H, d, J=6.4 Hz), 4.61 (2 H, s), 4.88 (2 H, d, J=1.3 Hz), 6.74-6.92 (3 H, m), 6.94 (1 H, t, J=1.3 Hz), 7.17-7.29 (3 H, m), 7.80 (2 H, d, J=8.1 Hz), 8.94 (1 H, t, J=6.4 Hz).

Example 387

N-{[3-(methyloxy)phenyl]methyl}-5-{[methyl(phenylmethyl)amino]methyl}-4-oxo-3,4-dihydrothieno[2,3-d]pyrimidine-2-carboxamide

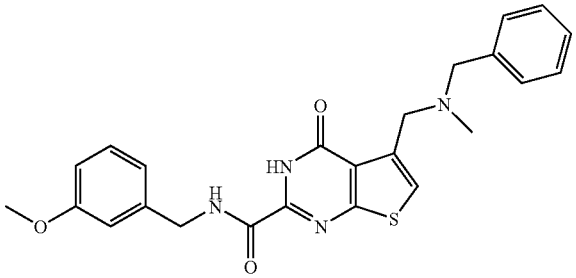 [SMILES: COc1cccc(CNC(=O)c2nc3scc(CN(C)Cc4ccccc4)c3c(=O)[nH]2)c1]

A mixture of ethyl 5-{[methyl(phenylmethyl)amino]methyl}-4-oxo-3,4-dihydrothieno[2,3-d]pyrimidine-2-carboxylate (150 mg, 0.420 mmol) obtained in Reference Example 160 and 1-[3-(methyloxy)phenyl]methanamine (0.0967 mL, 0.756 mmol) was stirred in ethanol (3 mL) at 90° C. for 1 hr. The reaction mixture was concentrated under reduced pressure, and ethyl acetate was added to the obtained residue. The organic layer was washed with phosphate buffer (pH=6.86) and saturated brine, dried over anhydrous sodium sulfate and concentrated under reduced pressure. The concentrated residue was crystallized from ethyl acetate to give the title compound as a white powder (110 mg, 58%).

melting point: 127° C.

$^1$H NMR (300 MHz, DMSO-d$_6$) δ 2.18 (3 H, s), 3.60 (2 H, s), 3.73 (3 H, s), 3.94 (2 H, s), 4.42 (2 H, d, J=6.4 Hz), 6.78-6.86 (1 H, m), 6.87-6.93 (2 H, m), 7.17-7.44 (6 H, m), 7.59 (1 H, s), 9.63 (1 H, s), 12.34 (1 H, s).

Example 388

N-{[3-(methyloxy)phenyl]methyl}-4-oxo-5-{[(phenylmethyl)thio]methyl}-3,4-dihydrothieno[2,3-d]pyrimidine-2-carboxamide

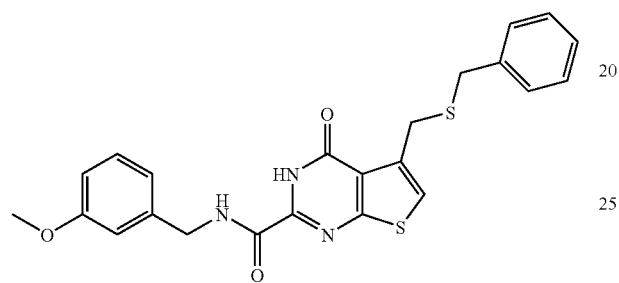

A mixture of ethyl 4-oxo-5-{[(phenylmethyl)thio]methyl}-3,4-dihydrothieno[2,3-d]pyrimidine-2-carboxylate (150 mg, 0.416 mmol) obtained in Reference Example 161 and 1-[3-(methyloxy)phenyl]methanamine (0.133 mL, 1.04 mmol) was stirred in ethanol (3 mL) at 90° C. for 1 hr. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from an ethyl acetate-hexane mixed solvent to give the title compound as a white powder (126 mg, 67%).

melting point: 126° C.

$^1$H NMR (300 MHz, DMSO-d$_6$) δ 3.73 (2 H, s), 3.74 (3 H, s) 3.99 (2 H, s), 4.42 (2 H, d, J=6.4 Hz), 6.79-6.93 (3 H, m), 7.19-7.32 (6 H, m), 7.51 (1 H, s), 9.64 (1 H, t, J=6.1 Hz), 12.42 (1 H, s).

Example 389

6-methyl-N-{[3-(methyloxy)phenyl]methyl}-4-oxo-3,4-dihydrothieno[2,3-d]pyrimidine-2-carboxamide

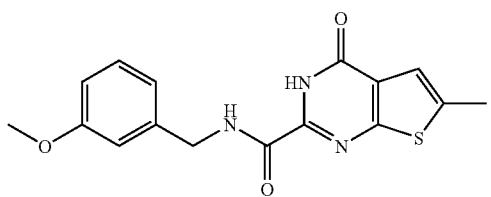

A mixture of ethyl 6-methyl-4-oxo-3,4-dihydrothieno[2,3-d]pyrimidine-2-carboxylate (synthesized according to a method of BE 859818 19780417 and the like) (180 mg, 0.756 mmol), 1-[3-(methyloxy)phenyl]methanamine (0.145 mL, 1.13 mmol) and ethanol (3 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (210 mg, 84%).

melting point: 187° C.

$^1$H NMR (300 MHz, DMSO-d$_6$) δ 2.55 (3 H, d, J=1.1 Hz), 3.73 (3 H, s), 4.41 (2 H, d, J=6.4 Hz), 6.78-6.94 (3 H, m), 7.13-7.30 (2 H, m), 9.63 (1 H, t, J=6.3 Hz), 12.39 (1 H, s).

Example 390

5,6-dimethyl-N-{[3-(methyloxy)phenyl]methyl}-4-oxo-3,4-dihydrothieno[2,3-d]pyrimidine-2-carboxamide

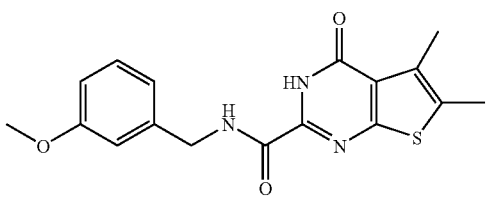

A mixture of ethyl 5,6-dimethyl-4-oxo-3,4-dihydrothieno[2,3-d]pyrimidine-2-carboxylate (synthesized according to a method of U.S. Pat. No. 4,054,656 19771018 and the like) (200 mg, 0.793 mmol), 1-[3-(methyloxy)phenyl]methanamine (0.203 mL, 1.59 mmol) and ethanol (3 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (228 mg, 84%).

melting point: 194° C.

$^1$H NMR (300 MHz, DMSO-d$_6$) δ 2.40 (3 H, s), 2.42 (3 H, s), 3.73 (3 H, s), 4.40 (2 H, d, J=6.4 Hz), 6.78-6.93 (3 H, m), 7.18-7.29 (1 H, m), 9.60 (1 H, t, J=6.3 Hz), 12.17 (1 H, s).

Example 391

5-(cyanomethyl)-N-{[3-(methyloxy)phenyl]methyl}-4-oxo-3,4-dihydrothieno[2,3-d]pyrimidine-2-carboxamide

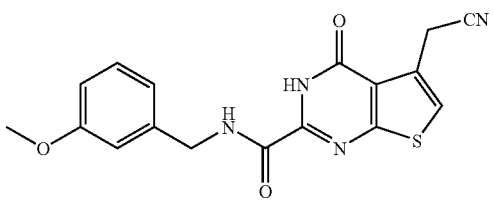 [SMILES: COc1cccc(CNC(=O)c2nc3scc(CC#N)c3c(=O)[nH]2)c1]

A mixture of ethyl 5-(cyanomethyl)-4-oxo-3,4-dihydrothieno[2,3-d]pyrimidine-2-carboxylate (270 mg, 1.03 mmol) obtained in Reference Example 162, 1-[3-(methyloxy)phenyl]methanamine (0.197 mL, 1.54 mmol) and ethanol (5 mL) was stirred at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a brown powder (275 mg, 76%).

melting point: 217° C.

$^1$H NMR (300 MHz, DMSO-d$_6$) δ 3.73 (3 H, s), 4.27 (2 H, d, J=0.9 Hz), 4.42 (2 H, d, J=6.4 Hz), 6.78-6.94 (3 H, m), 7.24 (1 H, t, J=8.1 Hz), 7.69 (1 H, t, J=0.9 Hz), 9.66 (1 H, t, J=6.4 Hz), 12.60 (1 H, s).

Example 392

{2-[({[3-(methyloxy)phenyl]methyl}amino)carbonyl]-4-oxo-3,4-dihydrothieno[2,3-d]pyrimidin-5-yl}acetic acid

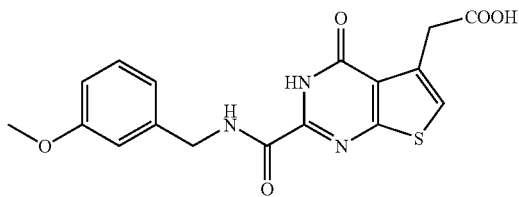 [SMILES: COc1cccc(CNC(=O)c2nc3scc(CC(=O)O)c3c(=O)[nH]2)c1]

A mixture of 5-(cyanomethyl)-N-{[3-(methyloxy)phenyl]methyl}-4-oxo-3,4-dihydrothieno[2,3-d]pyrimidine-2-carboxamide (200 mg, 0.564 mmol) obtained in Example 391, 2N aqueous sodium hydroxide solution (4 mL, 8 mmol) and ethanol (2 mL) was stirred at 100° C. for 1 hr. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a brown powder (131 mg, 62%).

melting point: 228-229° C.

$^1$H NMR (300 MHz, DMSO-d$_6$) δ 3.73 (3 H, s), 3.91 (2 H, s), 4.42 (2 H, d, J=6.2 Hz), 6.77-6.93 (3 H, m), 7.24 (1 H, t, J=8.1 Hz), 7.49 (1 H, s), 9.64 (1 H, t, J=6.3 Hz), 12.25 (1 H, s), 12.38 (1 H, s).

Example 393

N-{[3-(methyloxy)phenyl]methyl}-4-oxo-5-[2-oxo-2-(phenylamino)ethyl]-3,4-dihydrothieno[2,3-d]pyrimidine-2-carboxamide

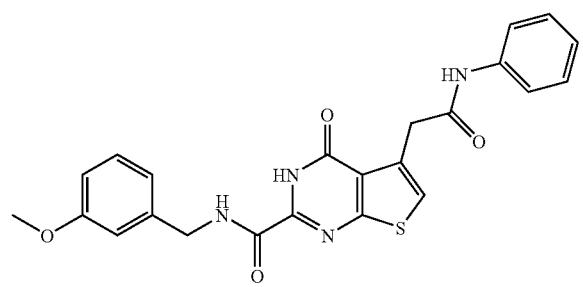 [SMILES: COc1cccc(CNC(=O)c2nc3scc(CC(=O)Nc4ccccc4)c3c(=O)[nH]2)c1]

To a mixture of {2-[({[3-(methyloxy)phenyl]methyl}amino)carbonyl]-4-oxo-3,4-dihydrothieno[2,3-d]pyrimidin-5-yl}acetic acid (200 mg, 0.536 mmol) obtained in Example 392 and THF (3 mL) was added oxalyl chloride (0.140 mL, 1.61 mmol). The mixture was stirred at room temperature for 15 hrs. and the reaction mixture was concentrated under reduced pressure. THF (3.0 mL), aniline (0.146 mL, 1.61 mmol) and pyridine (0.217 mL, 2.68 mmol) were added to the obtained residue and the mixture was stirred at room temperature for 1 hr. The reaction mixture was concentrated under reduced pressure, and ethyl acetate was added to the obtained residue. The organic layer was washed with saturated aqueous sodium hydrogen carbonate, 1N hydrochloric acid, and saturated brine, dried over anhydrous sodium sulfate and concentrated under reduced pressure. The obtained residue was crystallized from ethyl acetate to give the title compound as a white powder (154 mg, 64%).

melting point: 194-195° C.

$^1$H NMR (300 MHz, DMSO-d$_6$) δ 3.73 (3 H, s), 3.94-4.12 (2 H, m), 4.42 (2 H, d, J=6.4 Hz), 6.78-6.94 (3 H, m), 7.02 (1 H, t, J=7.3 Hz), 7.19-7.34 (3 H, m), 7.49-7.63 (3 H, m), 9.64 (1 H, t, J=6.4 Hz), 10.14 (1 H, s), 12.42 (1 H, s).

Example 394 ethyl 4-[({2-[({[3-(methyloxy)phenyl]methyl}amino)carbonyl]-4-oxo-3,4-dihydrothieno[2,3-d]pyrimidin-5-yl}acetyl)amino]benzoate

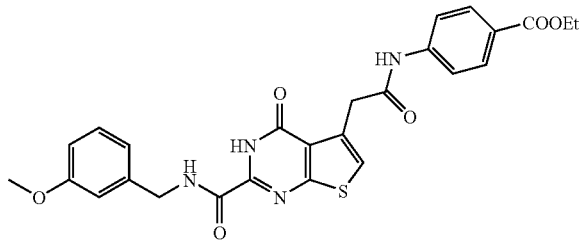 [SMILES: CCOC(=O)c1ccc(NC(=O)Cc2csc3nc(C(=O)NCc4cccc(OC)c4)[nH]c(=O)c23)cc1]

To a mixture of {2-[({[3-(methyloxy)phenyl]methyl}amino)carbonyl]-4-oxo-3,4-dihydrothieno[2,3-d]pyrimidin-5-yl}acetic acid (350 mg, 0.937 mmol) obtained in Example 392 and THF (3 mL) was added oxalyl chloride (0.245 mL, 2.81 mmol) and the mixture was stirred at room temperature for 15 hrs. The reaction mixture was concentrated under reduced pressure, THF (3 mL), ethyl 4-aminobenzoate (464 mg, 2.81 mmol) and pyridine (0.379 mL, 4.69 mmol) were added to the obtained residue and the mixture was stirred at room temperature for 1 hr. The reaction mixture was concentrated under reduced pressure, and ethyl acetate was added to the obtained residue. The organic layer was washed with aqueous sodium hydrogen carbonate, 1N hydrochloric acid and saturated brine, dried over anhydrous sodium sulfate and concentrated under reduced pressure. The concentrated residue was crystallized from ethyl acetate to give the title compound as a pale-yellow powder (370 mg, 76%).

melting point: 222-223° C.

$^1$H NMR (300 MHz, DMSO-d$_6$) δ 1.30 (3 H, t, J=7.2 Hz), 3.73 (3 H, s), 4.07 (2 H, s), 4.28, (2 H, q, J=7.1 Hz), 4.42 (2 H, d, J=6.2 Hz), 6.77-6.95 (3 H, m), 7.24 (1 H, t, J=8.1 Hz), 7.52

(1 H, s), 7.71 (2 H, d, J=8.9 Hz), 7.90 (2 H, d, J=8.7 Hz), 9.64 (1 H, s), 10.52 (1 H, s), 12.42 (1 H, s).

Example 395

4-[({2-[({[3-(methyloxy)phenyl]methyl}amino)carbonyl]-4-oxo-3,4-dihydrothieno[2,3-d]pyrimidin-5-yl}acetyl)amino]benzoic acid

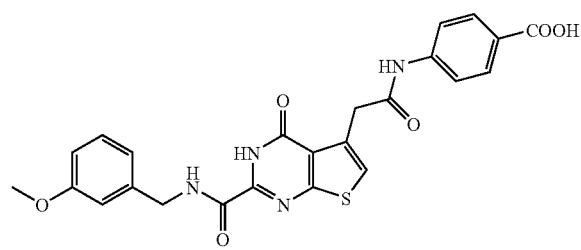 [SMILES: COc1cccc(CNC(=O)c2nc3scc(CC(=O)Nc4ccc(C(=O)O)cc4)c3c(=O)[nH]2)c1]

A mixture of ethyl 4-[({2-[({[3-(methyloxy)phenyl]methyl}amino)carbonyl]-4-oxo-3,4-dihydrothieno[2,3-d]pyrimidin-5-yl}acetyl)amino]benzoate (188 mg, 86%) obtained in Example 394, 12N aqueous sodium hydroxide solution (0.0920 mL, 1.11 mmol), THF (1 mL), methanol (1 mL) and water (1 mL) was stirred at 80° C. for 1 hr. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a pale-yellow powder (188 mg, 86%).

melting point: 279° C.

$^1$H NMR (300 MHz, DMSO-$d_6$) δ 3.73 (3 H, s), 4.07 (2 H, s) 4.42 (2 H, d, J=6.4 Hz), 6.73-6.96 (3 H, m), 7.24 (1 H, t, J=8.1 Hz), 7.52 (1 H, s), 7.69 (2 H, d, J=8.9 Hz), 7.87 (2 H, d, J=8.9 Hz), 9.61 (1 H, s), 10.54 (1 H, s), 12.51 (2 H, s).

Example 396

5,6-dibromo-N-{[3-(methyloxy)phenyl]methyl}-4-oxo-3,4-dihydrothieno[2,3-d]pyrimidine-2-carboxamide

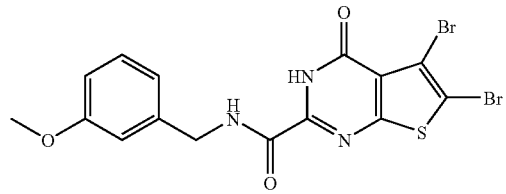 [SMILES: COc1cccc(CNC(=O)c2nc3sc(Br)c(Br)c3c(=O)[nH]2)c1]

A mixture of ethyl5,6-dibromo-4-oxo-3,4-dihydrothieno[2,3-d]pyrimidine-2-carboxylate (200 mg, 0.524 mmol) obtained in Reference Example 163, 1-[3-(methyloxy)phenyl]methanamine (0.101 mL, 0.785 mmol) and ethanol (5 mL) was stirred at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a pale-yellow powder (188 mg, 76%).

melting point: 189° C.

$^1$H NMR (300 MHz, DMSO-$d_6$) δ 3.73 (3 H, s), 4.40 (2 H, d, J=6.4 Hz), 6.80-6.92 (3 H, m), 7.23 (1 H, t, J=8.1 Hz), 9.72 (1 H, t, J=6.3 Hz), 12.75 (1 H, s).

Example 397

N-{[3-(methyloxy)phenyl]methyl}-4-oxo-5-[(phenylacetyl)amino]-3,4-dihydrothieno[2,3-d]pyrimidine-2-carboxamide

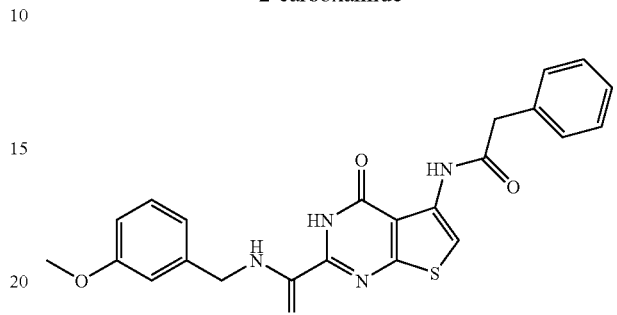

A mixture of ethyl 4-oxo-5-[(phenylacetyl)amino]-3,4-dihydrothieno[2,3-d]pyrimidine-2-carboxylate (100 mg, 0.280 mmol) obtained in Reference Example 167, 1-[3-(methyloxy)phenyl]methanamine (0.0895 mL, 0.700 mmol) and ethanol (3 mL) was stirred at 90° C. for. 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a pale-brown powder (117 mg, 93%).

melting point: 201° C.

$^1$H NMR (300 MHz, DMSO-$d_6$) δ 3.73 (3 H, s), 3.80 (2 H, s), 4.41 (2 H, d, J=6.2 Hz), 6.77-6.94 (3 H, m), 7.18-7.42 (6 H, m), 7.86 (1 H, s), 9.67 (1 H, t, J=6.4 Hz), 9.93 (1 H, s), 12.78 (1 H, s).

Example 398

6-bromo-N-{[3-(methyloxy)phenyl]methyl}-4-oxo-3,4-dihydrothieno[2,3-d]pyrimidine-2-carboxamide

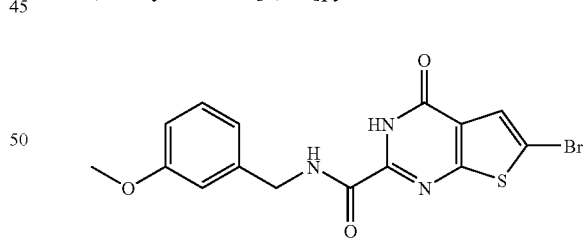

A mixture of ethyl 6-bromo-4-oxo-3,4-dihydrothieno[2,3-d]pyrimidine-2-carboxylate (120 mg, 0.396 mmol) obtained in Reference Example 164, 1-[3-(methyloxy)phenyl]methanamine (0.152 mL, 1.19 mmol) and ethanol (3 mL) was stirred at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a pale-brown powder (142 mg, 91%).

melting point: 179° C.

$^1$H NMR (300 MHz, DMSO-$d_6$) δ 3.73 (3 H, s), 4.40 (2 H, d, J=6.2 Hz), 6.72-6.98 (3 H, m), 7.23 (1 H, t, J=8.1 Hz), 7.66 (1 H. s), 9.71 (1 H, t, J=6.3 Hz), 12.66 (1 H, s).

Example 399

5-(3-bromophenyl)-N-{[3-(methyloxy)phenyl]methyl}-4-oxo-3,4-dihydrothieno[2,3-d]pyrimidine-2-carboxamide

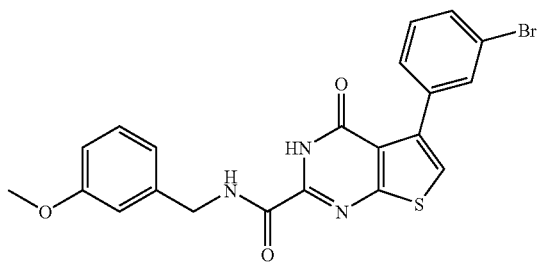 [SMILES: COc1cccc(CNC(=O)c2nc3scc(-c4cccc(Br)c4)c3c(=O)[nH]2)c1]

A mixture of ethyl 5-(3-bromophenyl)-4-oxo-3,4-dihydrothieno[2,3-d]pyrimidine-2-carboxylate (800 mg, 2.11 mmol) obtained in Reference Example 168, 1-[3-(methyloxy)phenyl]methanamine (0.472 mL, 3.70 mmol) and ethanol (10 ml) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from diethyl ether to give the title compound as a white powder (900 mg, 90.7%).

melting point: 127° C.

$^1$H NMR (300 MHz, DMSO-$d_6$) δ 3.74 (3 H, s), 4.44 (2 H, d, J=6.4 Hz), 6.81 (1 H, d, J=2.3 Hz), 6.89-6.94 (2 H, m), 7.25 (1 H, t, J=8.1 Hz), 7.37 (1 H, t, J=7.-8 Hz), 7.56 (2 H, ddd, J=7.9, 3.2, 1.8 Hz), 7.75 (1 H, t, J=1.7 Hz), 7.79 (1 H, s), 9.68 (1 H, t, J=6.6 Hz), 12.46 (1 H, s).

Example 400

3'-{2-[({[3-(methyloxy)phenyl]methyl}amino)carbonyl]-4-oxo-3,4-dihydrothieno[2,3-d]pyrimidin-5-yl}biphenyl-4-carboxylic acid

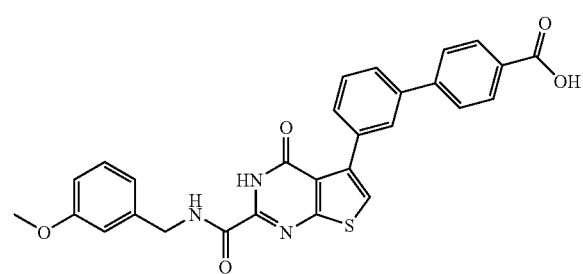 [SMILES: COc1cccc(CNC(=O)c2nc3scc(-c4cccc(-c5ccc(C(=O)O)cc5)c4)c3c(=O)[nH]2)c1]

A mixture of 5-(3-bromophenyl)-N-{[3-(methyloxy)phenyl]methyl}-4-oxo-3,4-dihydrothieno[2,3-d]pyrimidine-2-carboxamide (200 mg, 0.425 mmol) obtained in Example 399, 4-ethoxycarbonylphenylboronic acid (198 mg, 1.02 mmol), tetrakis(triphenylphosphine)palladium (0) (20.0 mg, 0.017 mmol), 2N sodium carbonate (0.532 mL, 1.06 mmol) and toluene (10 mL) was stirred under microwave irradiation at 145° C. for 10 min. Ethyl acetate was added to the reaction mixture, and the organic layer was washed with saturated aqueous sodium hydrogen carbonate, water, 1N hydrochloric acid and saturated brine, dried over anhydrous sodium sulfate and concentrated under reduced pressure. 12N Aqueous sodium hydroxide solution (0.0883 mL, 1.06 mmol), THF (3 mL), methanol (3 mL) and water (3 mL) were added to the concentrated residue and the mixture was stirred at 80° C. for 1.5 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (163 mg, 75%).

melting point: 259-260° C.

$^1$H NMR (300 MHz, DMSO-$d_6$) δ 3.74 (3 H, s), 4.44 (2 H, d, J=6.4 Hz), 6.79-6.96 (3 H, m), 7.25 (1 H, t, J=8.1 Hz), 7.48-7.65 (2 H, m), 7.69-7.78 (1 H, m), 7.80-7.89 (3 H, m), 7.93 (1 H, d), 8.03 (2 H, d, J=8.3 Hz), 9.69 (1 H, s), 12.51 (1 H, s), 12.82 (1 H, s).

Example 401

N-{[3-(methyloxy)phenyl]methyl}-4-oxo-5-phenyl-3,4-dihydrothieno[2,3-d]pyrimidine-2-carboxamide

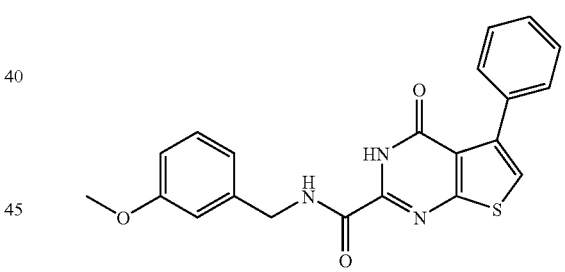

A mixture of 5-(3-bromophenyl)-N-{[3-(methyloxy)phenyl]methyl}-4-oxo-3,4-dihydrothieno[2,3-d]pyrimidine-2-carboxamide (200 mg, 0.425 mmol) obtained by Example 399, 10% palladium carbon (50% wet) (300 mg), THF (3 mL) and ethanol (3 mL) was stirred at room temperature under a hydrogen atmosphere (1 atm) for 12 hrs. The insoluble material was filtered off, and the filtrate was concentrated under reduced pressure. The obtained residue was crystallized from ethyl acetate to give the title compound as a white powder (136 mg, 82%).

melting point: 177-178° C.

$^1$H NMR (300 MHz, DMSO-$d_6$) δ 3.74 (3 H, s), 4.44 (2 H, d, J=6.4 Hz), 6.78-6.95 (3 H, m), 7.19-7.30 (1 H, m), 7.32-7.46 (3 H, m), 7.49-7.58 (2 H, m), 7.68 (1 H, s), 9.68 (1 H, t, J=6.3 Hz), 12.35 (1 H, s).

Example 402 ethyl 5-methyl-2-[({[3-(methyloxy)phenyl]
methyl}amino)carbonyl]-4-oxo-3,4-dihydrothieno[2,
3-d]pyrimidine-6-carboxylate

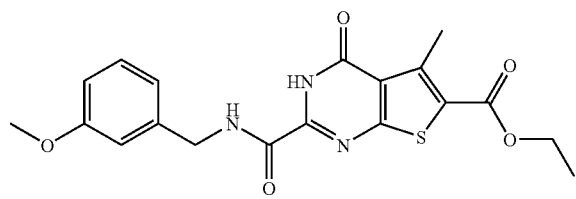 [SMILES: CCOC(=O)c1sc2nc(C(=O)NCc3cccc(OC)c3)[nH]c(=O)c2c1C]

A mixture of diethyl 5-methyl-4-oxo-3,4-dihydrothieno[2,3-d]pyrimidine-2,6-dicarboxylate (800 mg, 2.58 mmol) obtained in Reference Example 169, 1-[3-(methyloxy)phenyl]methanamine (0.990 mL, 7.73 mmol), ethanol (40 mL) and THF (40 mL) was stirred at 90° C. for 18 hrs. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (1010 mg, 98%).

melting point: 223-224° C.

$^1$H NMR (300 MHz, DMSO-$d_6$) δ 1.31 (3 H, t, J=7.1 Hz), 2.85 (3 H, s), 3.73 (3 H, s), 4.33 (2 H, q, J=7.0 Hz), 4.41 (2 H, d, J=6.4 Hz), 6.78-6.94 (3 H, m), 7.24 (1 H, t, J=8.1 Hz), 9.67 (1 H, t, J=6.0 Hz).

Example 403

5-methyl-2-[({[3-(methyloxy)phenyl]methyl}amino)carbonyl]-4-oxo-3,4-dihydrothieno[2,3-d]pyrimidine-6-carboxylic acid

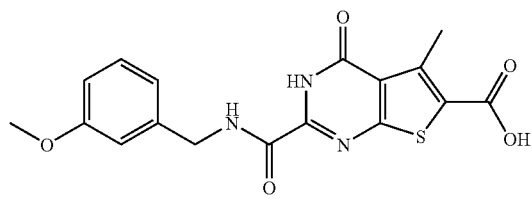 [SMILES: COc1cccc(CNC(=O)c2nc3sc(C(=O)O)c(C)c3c(=O)[nH]2)c1]

A mixture of ethyl 5-methyl-2-[({[3-(methyloxy)phenyl]methyl}amino)carbonyl]-4-oxo-3,4-dihydrothieno[2,3-d]pyrimidine-6-carboxylate obtained in Example 402 (800 mg, 1.99 mmol), 12N aqueous sodium hydroxide solution (0.415 mL, 4.98 mmol), THF (7 mL), methanol (7 mL) and water (7 mL) was stirred at 80° C. for 1 hr. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (718 mg, 96%).

melting point: >300° C.

$^1$H NMR (300 MHz, DMSO-$d_6$) δ 2.83 (3 H, s), 3.73 (3 H, s), 4.41 (2 H, d, J=6.4 Hz), 6.75-6.96 (3 H, m), 7.24 (1 H, t, J=8.1 Hz), 9.72 (1 H, t, J=6.4 Hz), 12.53 (1 H, s), 13.45 (1 H, s).

Example 404

5-methyl-$N^2$-{[3-(methyloxy)phenyl]methyl}-4-oxo-3,4-dihydrothieno[2,3-d]pyrimidine-2,6-dicarboxamide

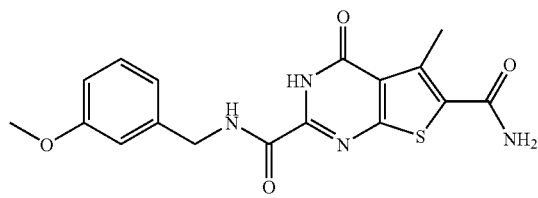 [SMILES: COc1cccc(CNC(=O)c2nc3sc(C(N)=O)c(C)c3c(=O)[nH]2)c1]

To a mixture of 5-methyl-2-[({[3-(methyloxy)phenyl]methyl}amino)carbonyl]-4-oxo-3,4-dihydrothieno[2,3-d]pyrimidine-6-carboxylic acid (150 mg, 0.402 mmol) obtained in Example 403 and THF (3 mL) were added oxalyl chloride (0.105 ml, 1.21 mmol) and DMF (1 drop), and the mixture was stirred at room temperature for 2 hrs. The reaction mixture was concentrated under reduced pressure, THF (3 mL) and 28% aqueous ammonia (2.20 mmol, 36.2 mmol) were added to the obtained residue, and the mixture was stirred for 12 hrs. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (121 mg, 81%).

melting point: 258° C.

$^1$H NMR (300 MHz, DMSO-$d_6$) δ 2.73 (3 H, s), 3.73 (3 H, s), 4.41 (2 H, d, J=6.4 Hz), 6.77-6.94 (3 H, m), 7.24 (1 H, t, J=8.1 Hz), 7.70 (2 H, s), 9.62 (1 H, s), 12.45 (1 H, s).

Example 405

N-{[3-(methyloxy)phenyl]methyl}-4-oxo-5-{[(phenylcarbonyl)amino]methyl}-3,4-dihydrothieno[2,3-d]pyrimidine-2-carboxamide

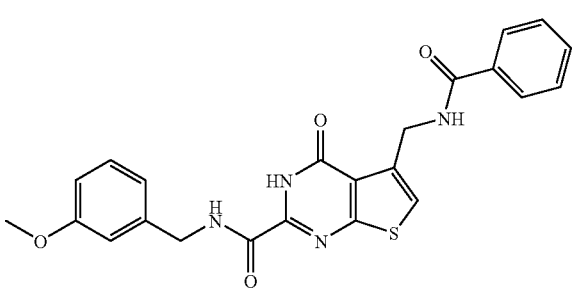 [SMILES: COc1cccc(CNC(=O)c2nc3scc(CNC(=O)c4ccccc4)c3c(=O)[nH]2)c1]

A mixture of ethyl 4-oxo-5-{[(phenylcarbonyl)amino]methyl}-3,4-dihydrothieno[2,3-d]pyrimidine-2-carboxylate (100 mg, 0.280 mmol) obtained in Reference Example 172, 1-[3-(methyloxy)phenyl]methanamine (0.107 mL, 0.840 mmol) and ethanol (3 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (103 mg, 82%).

melting point: 195-196° C.

¹H NMR (300 MHz, DMSO-d₆) δ 3.73 (3 H, s), 4.42 (2 H, d, J=6.2 Hz), 4.80 (2 H, d, J=5.1 Hz), 6.74-6.98 (3 H, m), 7.24 (1 H, t, J=8.1 Hz), 7.38-7.62 (4 H, m), 7.82-7.98 (2 H, m), 9.02 (1 H, s), 9.64 (1 H, t, J=6.3 Hz), 12.52 (1 H, s).

Example 406 methyl 4-{[({2-[({[3-(methyloxy)phenyl]methyl}amino)carbonyl]-4-oxo-3,4-dihydrothieno[2,3-d]pyrimidin-5-yl}methyl)amino]carbonyl}benzoate

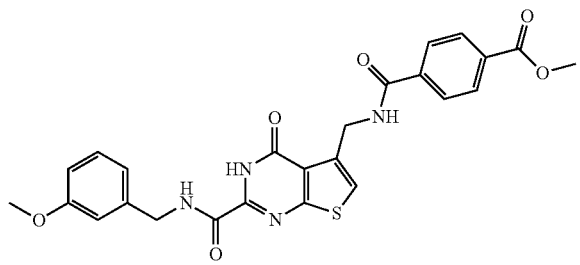

A mixture of ethyl 5-{[({4-[(methyloxy)carbonyl]phenyl}carbonyl)amino]methyl}-4-oxo-3,4-dihydrothieno[2,3-d]pyrimidine-2-carboxylate (350 mg, 0.843 mmol) obtained in Reference Example 173, 1-[3-(methyloxy)phenyl]methanamine (0.324 mL, 2.53 mmol) and ethanol (5 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (379 mg, 89%).

melting point: 237° C.
¹H NMR (300 MHz, DMSO-d₆) δ 3.73 (3 H, s), 3.89 (3 H, s) 4.42 (2 H, d, J=6.4 Hz), 4.80 (2 H, d, J=5.7 Hz), 6.80-6.93 (3 H, m), 7.24 (1 H, t, J=8.1 Hz), 7.41-7.46 (1 H, m), 8.00-8.08 (4 H, m), 9.26 (1 H, s), 9.59 (1 H, s), 12.52 (1 H, s).

Example 407

4-{[({2-[({[3-(methyloxy)phenyl]methyl}amino)carbonyl]-4-oxo-3,4-dihydrothieno[2,3-d]pyrimidin-5-yl}methyl)amino]carbonyl}benzoic acid

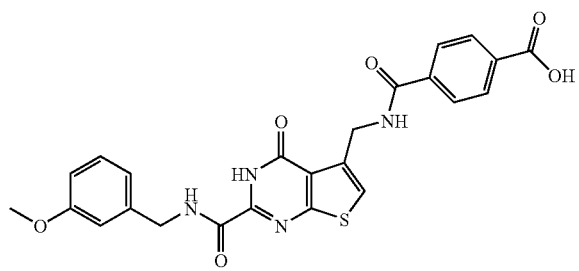 [SMILES: COc1cccc(CNC(=O)c2nc3scc(CNC(=O)c4ccc(C(=O)O)cc4)c3c(=O)[nH]2)c1]

A mixture of methyl 4-{[({2-[({[3-(methyloxy)phenyl]methyl}amino)carbonyl]-4-oxo-3,4-dihydrothieno[2,3-d]pyrimidin-5-yl}methyl)amino]carbonyl}benzoate (275 mg, 0.543 mmol) obtained in Example 406, 12N aqueous sodium hydroxide solution (0.113 mL, 1.36 mmol), THF (2 mL), methanol (2 mL) and water (2 mL) was stirred at 90° C. for 1 hr. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (263 mg, 98%).

melting point: 285-286° C.
¹H NMR. (300 MHz, DMSO-d₆) δ 3.74 (3 H, s), 4.42 (2 H, d, J=6.2 Hz), 4.81 (2 H, d, J=5.3 Hz), 6.80-6.93 (3 H, m), 7.21-7.27 (1 H, m), 7.46 (1 H, s), 7.98-8.06 (4 H, m), 9.15 (1 H, t, J=5.8 Hz), 9.66 (1 H, t, J=6.3 Hz), 12.53 (1 H, s), 13.07 (1 H, s).

Example 408

5-(azidomethyl)-N-{[3-(methyloxy)phenyl]methyl}-4-oxo-3,4-dihydrothieno[2,3-d]pyrimidine-2-carboxamide

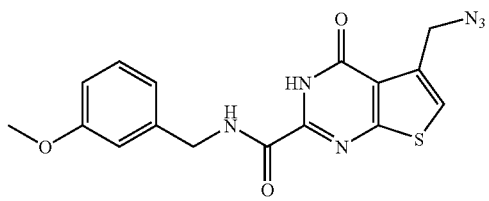 [SMILES: COc1cccc(CNC(=O)c2nc3scc(CN=[N+]=[N-])c3c(=O)[nH]2)c1]

A mixture of ethyl 5-(azidomethyl)-4-oxo-3,4-dihydrothieno[2,3-d]pyrimidine-2-carboxylate (120 mg, 0.430 mmol) obtained in Reference Example 170, 1-[3-(methyloxy)phenyl]methanamine (0.0825 mL, 0.645 mmol) and ethanol (5 mL) was stirred at 80° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (147 mg, 92%).

melting point: 191° C.
¹H NMR (300 MHz, DMSO-d₆) δ 3.73 (3 H, s), 4.42 (2 H, d, J=6.2 Hz), 4.76 (2 H, s), 6.74-6.95 (3 H, m), 7.24 (1 H, t, J=8.1 Hz), 7.74 (1 H, s), 9.65 (1 H, t, J=6.5 Hz), 12.56 (1 H, s).

Example 409

N²-{[3-(methyloxy)phenyl]methyl}-4-oxo-N⁵-(phenylmethyl)-3,4-dihydrothieno[2,3-d]pyrimidine-2,5-dicarboxamide

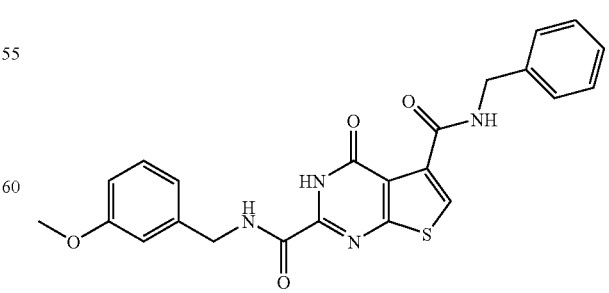

A mixture of ethyl 4-oxo-5-{[(phenylmethyl)amino]carbonyl}-3,4-dihydrothieno[2,3-d]pyrimidine-2-carboxylate (200 mg, 0.560 mmol) obtained in Reference Example 177, 1-[3-(methyloxy)phenyl]methanamine (0.215 mL, 1.68 mmol) and ethanol (5 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (214 mg, 85%).

melting point: 217° C.

$^1$H NMR (300 MHz, DMSO-d$_6$) δ 3.73 (3 H, s), 4.43 (2 H, d, J=6.2 Hz), 4.56 (2 H, d, J=5.5 Hz), 6.80-6.85 (1 H, m), 6.89-6.93 (2 H, m), 7.21-7.29 (2 H, m), 7.30-7.38 (4 H, m); 8.52 (1 H, s), 9.74 (1 H, s), 11.29 (1 H, s), 13.16 (1 H, s).

Example 410 ethyl 4-{[({2-[({[3-(methyloxy)phenyl]methyl}amino)carbonyl]-4-oxo-3,4-dihydrothieno[2,3-d]pyrimidin-5-yl}carbonyl)amino]methyl}benzoate

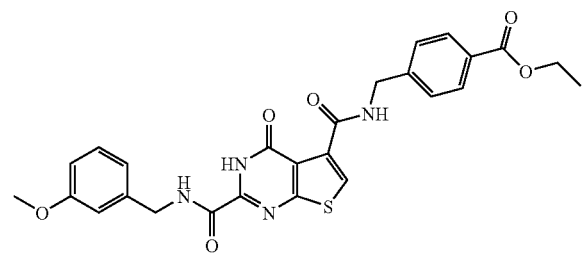 [SMILES: CCOC(=O)c1ccc(CNC(=O)c2csc3nc(C(=O)NCc4cccc(OC)c4)[nH]c(=O)c23)cc1]

A mixture of ethyl 5-{[({4-[(ethyloxy)carbonyl]phenyl}methyl)amino]carbonyl}-4-oxo-3,4-dihydrothieno[2,3-d]pyrimidine-2-carboxylate (300 mg, 0.699 mmol) obtained in Reference Example 178, 1-[3-(methyloxy)phenyl]methanamine (0.268 mL, 2.10 mmol) and ethanol (10 mL) was stirred at 90° C. for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (331 mg, 91%).

melting point: 229-230° C.

$^1$H NMR (300 MHz, DMSO-d$_6$) δ 1.31 (3 H, t, J=7.1 Hz), 3.73 (3 H, s), 4.31 (2 H, q, J=7.1 Hz), 4.44 (2 H, d, J=6.2 Hz), 4.64 (2 H, d, J=5.3 Hz), 6.78-6.96 (3 H, m), 7.24 (1 H, t, J=8.1 Hz), 7.49 (2 H, d, J=8.3 Hz), 7.88-7.97 (2 H, m), 8.51 (1 H, s), 9.73 (1 H, t, J=6.0 Hz), 11.39 (1 H, s), 13.20 (1 H, s).

Example 411

4-{[({2-[({[3-(methyloxy)phenyl]methyl}amino)carbonyl]-4-oxo-3,4-dihydrothieno[2,3-d]pyrimidin-5-yl}carbonyl)amino]methyl}benzoic acid

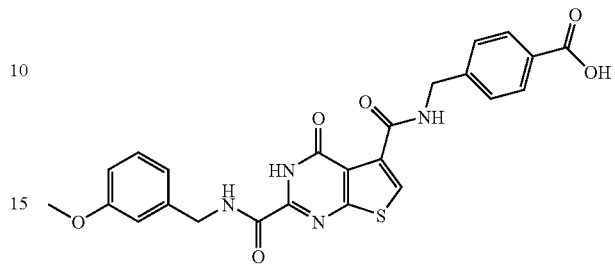

A mixture of ethyl 4-{[({2-[({[3-(methyloxy)phenyl]methyl}amino)carbonyl]-4-oxo-3,4-dihydrothieno[2,3-d]pyrimidin-5-yl}carbonyl)amino]methyl}benzoate (330 mg, 0.634 mmol) obtained in Example 410, 12N aqueous sodium hydroxide solution (0.132 mL, 1.59 mmol), THF (2 mL), methanol (2 mL) and water (2 mL) was stirred at 90° C. for 1 hr. The reaction mixture was concentrated under reduced pressure, and ethyl acetate and THF were added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (294 mg, 94%).

melting point: 254-255° C.

$^1$H NMR (300 MHz, DMSO-d$_6$) δ 3.73 (3 H, s), 4.44 (2 H, d, J=6.4 Hz), 4.64 (2 H, d, J=5.5 Hz), 6.74-6.97 (3 H, m), 7.24 (1 H, t, J=8.1 Hz), 7.47 (2 H, d, J=8.3 Hz), 7.91 (2 H, d, J=8.3 Hz), 8.52 (1 H, s), 9.76 (1 H, t, J=6.4 Hz), 11.32 (1 H, t, J=5.6 Hz), 13.19 (1 H, s).

Example 412

2-[({[3-(methyloxy)phenyl]methyl}amino)carbonyl]-4-oxo-3,4-dihydrothieno[2,3-d]pyrimidine-5-carboxylic acid

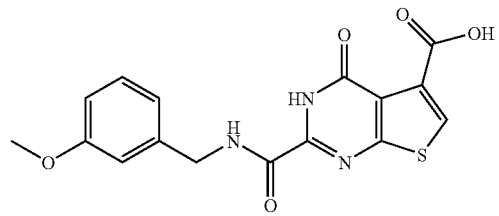 [SMILES: COc1cccc(CNC(=O)c2nc3scc(C(=O)O)c3c(=O)[nH]2)c1]

A mixture of 2-[(ethyloxy)carbonyl]-4-oxo-3,4-dihydrothieno[2,3-d]pyrimidine-5-carboxylic acid (5.00 g, 18.6 mmol) obtained in Reference Example 176, 1-[3-(methyloxy)phenyl]methanamine (7.16 mL, 56.0 mmol), N,N-diisopropylethylamine (29.0 mL, 168 mmol) and ethanol (50 mL) was stirred at 90° C. for 20 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a brown powder (4.5 g, 67%).

melting point: 236-237° C.

¹H NMR, (300 MHz, DMSO-d₆) δ 3.74 (3 H, s), 4.45 (2 H, d, J=6.4 Hz), 6.76-6.96 (3 H, m), 7.25 (1 H, t, J=8.1 Hz), 8.65 (1 H, s), 9.82 (1 H, t, J=6.3 Hz), 13.85 (1 H, s), 15.44 (1 H, s).

Example 413

5-amino-N-{[3-(methyloxy)phenyl]methyl}-4-oxo-3,4-dihydrothieno[2,3-d]pyrimidine-2-carboxamide

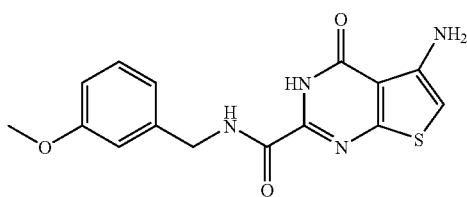 [SMILES: COc1cccc(CNC(=O)c2nc3scc(N)c3c(=O)[nH]2)c1]

To a mixture of 2-[({[3-(methyloxy)phenyl]methyl}amino)carbonyl]-4-oxo-3,4-dihydrothieno[2,3-d]pyrimidine-5-carboxylic acid (4.45 g, 12.4 mmol) obtained in Example 412 and toluene (45 mL) were added triethylamine (10.0 mL, 74.3 mmol) and diphenyl azidophosphate (6.90 mL, 32.2 mmol) and the mixture was stirred at 100° C. for 2 min. t-Butanol (12.0 mL, 124 mmol) was added and the mixture was stirred at 100° C. for 12 hrs. The reaction mixture was concentrated under reduced pressure, and ethyl acetate was added to the obtained residue. The organic layer was washed with saturated aqueous sodium hydrogen carbonate and saturated brine, dried over anhydrous sodium sulfate and concentrated under reduced pressure. A mixture of the concentrated residue and a 4N solution (45.0 mL) of hydrogen chloride in ethyl acetate was stirred for 12 hrs. and concentrated under reduced pressure. 12N Aqueous sodium hydroxide solution (4.10 mL, 49.5 mmol), THF (15 mL), methanol (15 mL) and water (15 mL) were added to the obtained residue and the reaction mixture was stirred at 80° C. for. 2 hrs. The reaction mixture was neutralized with 1N hydrochloric acid, and concentrated under reduced pressure. Ethyl acetate was added to the obtained residue, and the organic layer was washed with saturated aqueous sodium hydrogen carbonate and saturated brine, dried over anhydrous sodium sulfate and concentrated under reduced pressure to give the title compound as a brown foam (1.18 g, 26%).

¹H NMR (300 MHz, DMSO-d₆) δ 3.66-3.78 (3 H, m), 4.40 (2 H, d, J=6.4 Hz), 6.72-7.33 (5 H, m), 9.57 (1 H, t, J=6.3 Hz), 11.59 (1 H, s).

Example 414 ethyl 4-[2-({2-[({[3-(methyloxy)phenyl]methyl}amino)carbonyl]-4-oxo-3,4-dihydrothieno[2,3-d]pyrimidin-5-yl}amino)-2-oxoethyl]benzoate

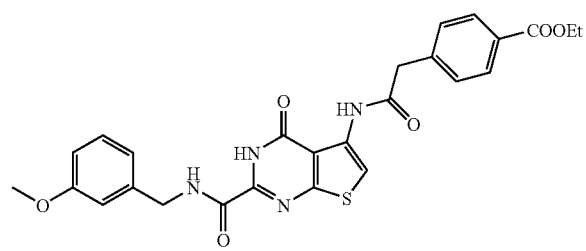 [SMILES: CCOC(=O)c1ccc(CC(=O)Nc2csc3nc(C(=O)NCc4cccc(OC)c4)[nH]c(=O)c23)cc1]

To a mixture of {4-[(ethyloxy)carbonyl]phenyl}acetic acid (215 mg, 1.033 mmol, obtained by the method described in *J. Med. Chem.* (2001), 44(5), 814-821 and the like) and THF (3 mL) were added oxalyl chloride (0.183 mL, 2.10 mmol) and DMF (1 drop), and the mixture was stirred at room temperature for 2 hrs. The reaction mixture was concentrated under reduced pressure, THF (3 mL), 5-amino-N-{[3-(methyloxy)phenyl]methyl}-4-oxo-3,4-dihydrothieno[2,3-d]pyrimidine-2-carboxamide (276 mg, 0.837 mmol) obtained in Example 413 and pyridine (0.418 mL, 5.17 mmol) were added to the obtained residue, and the mixture was stirred at room temperature for 2 hrs. The reaction mixture was concentrated under reduced pressure and ethyl acetate was added to the obtained residue. The organic layer was washed with 1N hydrochloric acid and saturated brine, dried over anhydrous sodium sulfate and concentrated under reduced pressure. 1N Aqueous sodium hydroxide solution (2 mL), ethanol (1 mL) and THF (1 mL) were added to the concentrated residue and the reaction mixture was stirred at room temperature for 12 hrs. The reaction mixture was concentrated under reduced pressure, and ethyl acetate was added to the obtained residue. The organic layer was washed with water and saturated brine, dried over anhydrous sodium sulfate and concentrated under reduced pressure. The concentrated residue was crystallized from ethyl acetate to give the title compound as a brown powder (29.6 mg, 5.5%).

melting point: 218-219° C.

¹H NMR (300 MHz, DMSO-d₆) δ 1.32 (3 H, t, J=7.1 Hz), 3.73 (3 H, s), 3.93 (2 H, s), 4.31 (2 H, q, J=7.0 Hz), 4.41 (2 H, d, J=6.2 Hz), 6.77-6.95 (3 H, m), 7.23 (1 H, t, J=8.1 Hz), 7.52 (2 H, d, J=8.3 Hz), 7.86 (1 H, s), 7.95 (2 H, d, J=8.3 Hz), 9.67 (1 H, t, J=6.1 Hz), 9.95 (1 H, s), 12.79 (1 H, s).

Example 415

4-[2-({2-[({[3-(methyloxy)phenyl]methyl}amino)carbonyl]-4-oxo-3,4-dihydrothieno[2,3-d]pyrimidin-5-yl}amino)-2-oxoethyl]benzoic acid

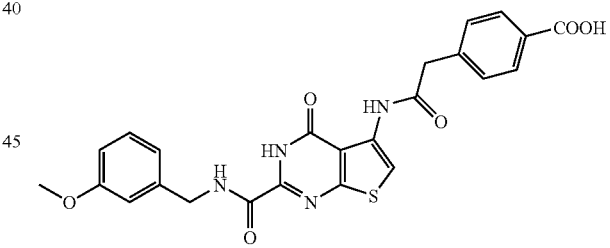

To a mixture of {4-[(ethyloxy)carbonyl]phenyl}acetic acid (215 mg, 1.033 mmol) obtained by the method described in J. Med. Chem., (2001), 44 (5), 814-821 and the like and THF (3 mL) were added oxalyl chloride (0.183 mL, 2.10 mmol) and DMF (1 drop), and the mixture was stirred at room temperature for 2 hrs. The reaction mixture was concentrated under reduced pressure, THF (3 mL), 5-amino-N-{[3-(methyloxy)phenyl]methyl}-4-oxo-3,4-dihydrothieno[2,3-d]pyrimidine-2-carboxamide (276 mg, 0.837 mmol) obtained in Example 413 and pyridine (0.418 mL, 5.17 mmol) were added to the obtained residue and the mixture was stirred at room temperature for 2 hrs. The reaction mixture was concentrated under reduced pressure and ethyl acetate was added to the obtained residue. The organic layer was washed with 1N hydrochloric acid and saturated brine, dried over anhydrous sodium sulfate and concentrated under reduced pressure. 1N Aqueous sodium hydroxide solution (2 mL), ethanol (1 mL) and THF (1 mL) were added to the concentrated residue and the reaction mixture was stirred at room temperature for 12 hrs. The reaction mixture was concentrated under reduced pressure and ethyl acetate was added to the obtained residue. The organic layer was washed with water and saturated brine and the obtained aqueous layer was acidified with 1N hydrochloric acid. The mixture was extracted with ethyl acetate, and the organic layer was washed with 1N hydrochloric acid and saturated brine, dried over anhydrous sodium sulfate and concentrated under reduced pressure. The concentrated residue was crystallized from ethyl acetate to give the title compound as a brown powder (83.9 mg, 17%).
melting point: 218-219° C.
$^1$H NMR (300 MHz, DMSO-$d_6$) δ 3.73 (3 H, s), 3.92 (2 H, s), 4.40 (2 H, d, J=6.4 Hz), 6.73-6.96 (3 H, m), 7.23 (1 H, t, J=8.1 Hz), 7.49 (2 H, d, J=8.3 Hz), 7.87 (1 H, s), 7.93 (2 H, d, J=8.3 Hz), 9.67 (1 H, t, J=6.5 Hz), 9.94 (1 H, s), 12.79 (1 H, s), 12.91 (1 H, s).

REFERENCE EXAMPLE

The following Reference Example 1 to Reference Example 4 were synthesized in the same manner as in Example 1.

Reference Example 1

4-oxo-N-(pyridine-2-ylmethyl)-3,4-dihydroquinazoline-2-carboxamide

The compound was synthesized using 2-(aminomethyl) pyridine instead of 3-methoxybenzylamine.
melting point: 187-188° C.

Reference Example 2

4-oxo-N-(pyridine-3-ylmethyl)-3,4-dihydroquinazoline-2-carboxamide

The compound was synthesized using 3-(aminomethyl) pyridine instead of 3-methoxybenzylamine.
melting point: 228-229° C.

Reference Example 3

4-oxo-N-(pyridin-4-ylmethyl)-3,4-dihydroquinazoline-2-carboxamide

The compound was synthesized using 4-(aminomethyl) pyridine instead of 3-methoxybenzylamine.
melting point: 266-267° C.

Reference Example 4

4-oxo-N-(phenylmethyl)-3,4-dihydroquinazoline-2-carboxamide

The compound was synthesized using benzylamine instead of 3-methoxybenzylamine.
melting point: 193-195° C.

Reference Example 5

N-methyl-4-oxo-N-(phenylmethyl)-3,4-dihydroquinazoline-2-carboxamide

The title compound was obtained in the same manner as in, Example 121 using N-methylbenzylamine instead of 6,7-bis(methyloxy)-1,2,3,4-tetrahydroisoquinoline hydrochloride.
melting point: 153-154° C.

Reference Example 6

3-methyl-N-{[3-(methyloxy)phenyl]methyl}-4-oxo-3,4-dihydroquinazoline-2-carboxamide The compound was synthesized using in the same manner as in Example 1 using ethyl 3-methyl-4-oxo-3,4-dihydroquinazoline-2-carboxylate obtained in Reference Example 97 instead of ethyl 4-oxo-3,4-dihydroquinazoline-2-carboxylate.
melting point: 87-88° C.

Reference Example 7 ethyl 6-fluoro-4-oxo-3,4-dihydroquinazoline-2-carboxylate

Step 1
To a solution of 2-amino-5-fluorobenzamide (2.00 g, 13.0 mmol) and triethylamine (1.45 g, 14.3 mmol) in THF (40 mL) was added dropwise ethyl chloroglyoxylate (1.95 g, 14.3 mmol) under ice-cooling, and the mixture was stirred at room temperature for 2 hrs. The reaction mixture was diluted with ethyl acetate, the mixture was washed with water and saturated brine, dried over sodium sulfate and concentrated under reduced pressure. The obtained concentrated residue was washed with ethanol to give ethyl ((2-(aminocarbonyl)-4-fluorophenyl)amino)(oxo)acetate as a white powder (2.88 g, 87%).
Step 2
To a suspension of ethyl ((2-(aminocarbonyl)-4-fluorophenyl)amino)(oxo)acetate (1.50 g, 5.90 mmol) in EtOH (30 mL) was added dropwise sodium ethylate (20% ethanol solution, 2.40 g, 7.08 mmol) under ice-cooling, and the mixture was stirred for 2 hrs. The reaction mixture was adjusted to pH 3-4 by adding 1N hydrochloric acid, and the precipitated insoluble material was collected by filtration. The filtered cake was washed with water and ethanol to give the title compound as a white powder (1.05 g, 75%).
$^1$H-NMR (200MHz, DMSO-$d_6$) δ: 1.36 (3H, t, J=7.2 Hz), 4.39 (2H, q, J=7.2 Hz), 7.77-7.97 (3H, m).

Reference Example 8 ethyl 6-(methyloxy)-4-oxo-3,4-dihydroquinazoline-2-carboxylate

Step 1
To a solution of 5-methoxy-2-nitrobenzoic acid (18.0 g, 91.3 mmol) and DMF (0.1 mL) in THF (150 mL) was dropwise added oxalyl chloride (12.7 g, 100 mmol) under ice-cooling, and the mixture was stirred at 0° C. for 1 hr. The mixture was stirred at room temperature for 3 hrs. and this solution was added dropwise to aqueous ammonia (7% aqueous solution, 200 mL) under ice-cooling. The reaction solution was concentrated under reduced pressure and THF was evaporated. The precipitated insoluble material was collected by filtration and the filtered cake was washed with water to give 5-methoxy-2-nitrobenzamide as a pale-yellow powder (10.0 g, 56%).
Step 2
To a solution (250 mL) of 5-methoxy-2-nitrobenzamide (9.70 g, 49.4 mmol) in MeOH was added 10% Pd—C (2.00 g), and the mixture was stirred under a hydrogen atmosphere (1 atm) at room temperature for 6 hrs. Insoluble material was filtered off and the filtrate was concentrated to give 2-amino-5-methoxybenzamide as a pale-yellow powder (8.20 g, 99%).

Step 3

To a solution of 2-amino-5-methoxybenzamide (1.50 g, 9.03 mmol) and triethylamine (1.00 g, 9.93 mmol) in THF (40 mL) was added dropwise ethyl chloroglyoxylate (1.36 g, 9.93 mmol) under ice-cooling, and the mixture was stirred at room temperature for 2 hrs. Water was added to the reaction mixture, and the precipitated insoluble material was collected by filtration. The filtered cake was washed with water and ethanol to give ethyl ((2-(aminocarbonyl)-4-methoxyphenyl)amino)(oxo)acetate as a pale-yellow powder (2.42 g, 100%).

Step 4

To a suspension of ethyl ((2-(aminocarbonyl)-4-methoxyphenyl)amino) (oxo)acetate (1.50 g, 5.63 mmol) in EtOH (30 mL) was added dropwise sodium ethylate (20% ethanol solution, 2.30 g, 6.76 mmol) under ice-cooling, and the mixture was stirred for 2 hrs. The reaction mixture was adjusted to pH 3-4 by adding 1N hydrochloric acid, and the precipitated insoluble material was collected by filtration. The filtered cake was washed with water and ethanol to give the title compound as a white powder (1.04 g, 74%).

$^1$H-NMR (200MHz, DMSO-$d_6$) δ: 1.35 (3H, t, J=7.2 Hz), 3.91 (3H, s), 4.38 (2H, q, J=7.2 Hz), 7.49 (1H, dd, J=3.0, 8.8 Hz), 7.57 (1H, d, J=3.0 Hz), 7.79 (1H, d, J=8.8 Hz).

Reference Example 9

Ethyl 6-methyl-4-oxo-3,4-dihydroquinazoline-2-carboxylate

Step 1

To a solution of 5-methyl-2-nitrobenzoic acid (17.0 g, 93.8 mmol) and DMF (0.1 mL) in THF (150 mL) was added dropwise oxalyl chloride (13.1 g, 103 mmol) under ice-cooling, and the mixture was stirred at room temperature for 3 hrs. This solution was added dropwise to aqueous ammonia (8% aqueous solution, 210 mL) under ice-cooling. The reaction solution was concentrated under reduced pressure and THF was evaporated. The precipitated insoluble material was collected by filtration and the filtered cake was washed with water to give 5-methyl-2-nitrobenzamide as a pale-yellow powder (15.3 g, 90%).

Step 2

To a solution of 5-methyl-2-nitrobenzamide (15.0 g, 83.3 mmol) in MeOH (300 mL) was added 10% Pd—C (2.50 g), and the mixture was stirred under a hydrogen atmosphere (1 atm) at room temperature for 12 hrs. Insoluble material was filtered off and the filtrate was concentrated to give 2-amino-5-methylbenzamide as a white powder (12.4 g, 99%).

Step 3

To a solution of 2-amino-5-methylbenzamide (5.80 g, 38.6 mmol) and triethylamine (4.69 g, 46.3 mmol) in THF (200 mL) was added dropwise ethyl chloroglyoxylate (5.80 g, 42.5 mmol) under ice-cooling, and the mixture was stirred at room temperature for 3 hrs. The reaction mixture was diluted with ethyl acetate, washed with water and saturated brine, dried over sodium sulfate and concentrated under reduced pressure. The obtained concentrated residue was washed with ethanol to give ethyl ((2-(aminocarbonyl)-4-methylphenyl)amino)(oxo)acetate as a white powder (9.83 g, 100%).

Step 4

To a suspension of ethyl ((2-(aminocarbonyl)-4-methylphenyl)amino) (oxo)acetate (4.90 g, 19.6 mmol) in EtOH (100 mL) was added dropwise sodium ethylate (20% ethanol solution, 7.33 g, 21.5 mmol) under ice-cooling, and the mixture was stirred at room temperature for 2 hrs. The reaction mixture was poured into 0.25N hydrochloric acid (200 mL) under ice-cooling, and the precipitated insoluble material was collected by filtration. The filtered cake was washed with water and ethanol to give the title compound as a pale orange powder (2.90 g, 64%).

$^1$H-NMR (200MHz, DMSO-$d_6$) δ: 1.36 (3H, t, J=7.2 Hz), 2.48 (3H, s), 4.39 (2H, q, J=7.2 Hz), 7.69-7.79 (2H, m), 7.98 (1H, s).

Reference Example 10 ethyl 4-oxo-6-(trifluoromethyl)-3,4-dihydroquinazoline-2-carboxylate

Step 1

To a solution of 2-nitro-5-(trifluoromethyl)aniline (5.00 g, 24.3 mmol) and concentrated hydrochloric acid (6.1 mL) in water (50 mL) was added dropwise under ice-cooling, an aqueous solution (15 mL) of sodium nitrite (1.84 g, 26.7 mmol), and the mixture was stirred at room temperature for 1 hr. Insoluble material was filtered off and to the obtained filtrate under ice-cooling, an aqueous solution (20 mL) of copper cyanide (2.91 g, 29.2 mmol) and sodium cyanide (600 mg, 12.2 mmol) was added dropwise. Toluene (9 mL) was added, and the mixture was stirred at room temperature for 15 hrs. The reaction mixture was diluted with chloroform. The mixture was washed with water and saturated brine, dried over sodium sulfate and concentrated under reduced pressure. The obtained concentrated residue was suspended in ethanol (100 mL), and hydrazine monohydrate (2.43 g, 48.6 mmol) was added. While heating the mixture to 45° C., Raney Ni (1.2 g) was added in several times, and the mixture was stirred at 60° C. for 1 hr. and heated under reflux for 2 hrs. After allowing to cool to room temperature, insoluble material was filtered off and the filtrate was concentrated under reduced pressure. The obtained concentrated residue was dissolved in ethyl acetate, and the mixture was washed with water and saturated brine, dried over sodium sulfate and concentrated under reduced pressure. The concentrated residue was purified by silica gel column chromatography (33-50% ethyl acetate/hexane) to give 2-amino-5-trifluoromethylbenzamide as a brown powder (792 mg, 16% for 2 steps).

Step 2

To a solution of 2-amino-5-trifluoromethylbenzamide (760 mg, 3.72 mmol) and triethylamine (452 mg, 4.46 mmol) in THF (20 mL) was added dropwise ethyl chloroglyoxylate (560 mg, 4.10 mmol) under ice-cooling, and the mixture was stirred at room temperature for 2 hrs. The reaction mixture was diluted with ethyl acetate, washed with water and saturated brine, dried over sodium sulfate and concentrated under reduced pressure. The obtained concentrated residue was washed with ethanol to give ethyl ((2-(aminocarbonyl)-4-trifluoromethylphenyl)amino) (oxo)acetate as a brown powder (1.13 g, 99%).

Step 3

To a suspension of ethyl ((2-(aminocarbonyl)-4-trifluoromethylphenyl)amino)(oxo)acetate (1.10 g, 3.62 mmol) in EtOH (15 mL) was added dropwise sodium ethylate (20% ethanol solution, 1.23 g, 3.62 mmol) under ice-cooling, and the mixture was stirred under ice-cooling for 30 min. and at room temperature for 30 min. 1N Hydrochloric acid (5 mL) and water (15 mL) were added to the reaction mixture and the precipitated insoluble material was collected by filtration. The filtered cake was washed with water and ethanol to give the title compound as a brown powder (545 mg, 53%).

$^1$H-NMR (200 MHz, DMSO-$d_6$) δ: 1.37 (3H, t, J=7.0 Hz), 4.41 (2H, q, J=7.0 Hz), 8.03 (1H, d, J=8.8 Hz), 8.20 (1H, dd, J=2.2, 8.8 Hz), 8.42-8.38 (1H, m).

Reference Example 11 ethyl 4-oxo-6-[(trifluoromethyl)oxy]-3,4-dihydro-quinazoline-2-carboxylate

Step 1

5-(Trifluoromethoxy)isatin (2.00 g, 8.65 mmol) was dissolved in 1N aqueous sodium hydroxide solution (150 mL) and aqueous hydrogen peroxide (30-35%, 2.45 mL) was added dropwise at room temperature to this solution. The reaction mixture was stirred at room temperature for 20 min., and adjusted to pH 3-4 by adding 1N hydrochloric acid. The precipitated insoluble material was collected by filtration, and washed with water to give 5-(trifluoromethoxy)anthranilic acid as a brown powder (1.88 g, 98%).

Step 2

To a solution of 5-(trifluoromethoxy)anthranilic acid (1.88 g, 8.50 mmol) in THF (40 mL) bis(trichloromethyl)carbonate (840 mg, 2.83 mmol) was added, and the mixture was stirred with heating at 60° C. for 15 hrs. The reaction mixture was concentrated under reduced pressure, 2N aqueous ammonia (50 mL) was added, and the mixture was stirred with heating at 50° C. for 2 hrs. The mixture was extracted with ethyl acetate, and the organic layer was washed with saturated brine, dried over sodium sulfate and concentrated under reduced pressure. The obtained concentrated residue was purified by silica gel column chromatography (67% ethyl acetate/hexane) to give 2-amino-5-(trifluoromethoxy)benzamide as a yellow powder (809 mg, 43%).

Step 3

To a solution of 2-amino-5-(trifluoromethoxy)benzamide (780 mg, 3.54 mmol) and triethylamine (430 mg, 4.25 nmol) in THF (20 mL) was added dropwise ethyl chloroglyoxylate (532 mg, 3.90 mmol) under ice-cooling, and the mixture was stirred at room temperature for 2 hrs. The reaction mixture was diluted with ethyl acetate, washed with water and saturated brine, dried over sodium sulfate and concentrated under reduced pressure. The obtained concentrated residue was washed with ethanol to give ethyl ((2-(aminocarbonyl)-4-(trifluoromethoxy)phenyl)amino) (oxo)acetate as a yellow powder (1.13 g, 99%).

Step 4

To a suspension of ethyl ((2-(aminocarbonyl)-4-(trifluoromethoxy)phenyl)amino)(oxo)acetate (1.10 g, 3.44 mmol) in EtOH (15 mL) was added dropwise sodium ethylate (20% ethanol solution, 1.17 g, 3.44 mmol) under ice-cooling, and the mixture was stirred under ice-cooling for 30 min. and at room temperature for 30 min. 1N Hydrochloric acid (5 mL) and water (15 mL) were added to the reaction mixture. The precipitated insoluble material was collected by filtration. The filtered cake was washed with water and ethanol to give the title compound as a pale-yellow powder (728 mg, 70%).

$^1$H-NMR (200MHz, DMSO-$d_6$) δ: 1.36 (3H, t, J=7.2 Hz), 4.40 (2H, q, J=7.2 Hz), 7.85-7.91 (1H, m), 7.96-8.02 (2H, m).

Reference Example 12 ethyl 5-(methyloxy)-4-oxo-3,4-dihydroquinazoline-2-carboxylate

Step 1

To a solution of 2,6-dinitrobenzonitrile (6.00 g, 31.1 mmol) in MeOH (120 mL) was added dropwise a solution (30 mL) of sodium methylate (1.68 g, 31.1 mmol) in MeOH at room temperature, and the mixture was heated under reflux for 3 hrs. After allowing to cool to room temperature, the reaction mixture was concentrated under reduced pressure. Ethyl acetate was added to the concentrated residue, and the mixture was washed with water and saturated brine. After drying over sodium sulfate, the mixture was concentrated under reduced pressure to give 2-methoxy-6-nitrobenzonitrile as a brown powder (5.50 g, 99%).

Step 2

To a suspension of 2-methoxy-6-nitrobenzonitrile (2.60 g, 14.6 mmol) in ethanol (60 mL) was added hydrazine monohydrate (1.53 g, 30.7 mmol). While heating the mixture to 45° C., Raney Ni (600 mg) was added in several portions, and the mixture was stirred at 60 ° C. for 2 hrs. Raney Ni (300 mg) was added again, and the mixture was heated under reflux for 2 hrs. After allowing to cool to room temperature, insoluble material was filtered off, and the filtrate was concentrated under reduced pressure. Ethyl acetate was added to the obtained concentrated residue, and the mixture was extracted with 1N hydrochloric acid. The aqueous layer was basified with 1N aqueous sodium hydroxide solution and the mixture was extracted with ethyl acetate. The organic layer was washed with water and saturated brine, dried over sodium sulfate and concentrated under reduced pressure to lo give 2-amino-6-methoxybenzamide as a brown powder (980 mg, 40%).

Step 3

To a solution of 2-amino-6-methoxybenzamide (960 mg, 5.78 mmol) and triethylamine (701 mg, 6.93 mmol) in THF (20 mL) was added dropwise ethyl chloroglyoxylate (868 mg, 6.36 mmol) under ice-cooling, and the mixture was stirred at room temperature for 2 hrs. The reaction mixture was diluted with ethyl acetate, the mixture was washed with water and saturated brine, dried over sodium sulfate and concentrated under reduced pressure. The obtained concentrated residue was washed with ethanol, ethyl ((2-(aminocarbonyl)-3-methoxyphenyl)amino)(oxo)acetate to give a yellow powder (1.56 g, 100%).

Step 4

To a suspension of ethyl ((2-(aminocarbonyl)-3-methoxyphenyl)amino)(oxo)acetate (1.50 g, 5.63 mmol) in toluene (60 mL) was added p-toluenesulfonic acid monohydrate (535 mg, 2.81 mmol), and the mixture was heated under reflux for 15 hrs. p-Toluenesulfonic acid monohydrate (535 mg, 2.81 mmol) was added again, and the mixture was heated under reflux for 24 hrs. The reaction mixture was diluted with ethyl acetate, washed with water and saturated brine, dried over sodium sulfate and concentrated under reduced pressure. The obtained concentrated residue was washed with ethanol to give the title compound as a pale-yellow powder (304 mg, 22%).

$^1$H-NMR (200 MHz, DMSO-$d_6$) δ: 1.34 (3H, t, J=7.2 Hz), 3.89 (3H, s), 4.36 (2H, q, J=7.2 Hz), 7.15 (1H, d, J=8.0 Hz), 7.32 (1H, d, J=7.6 Hz), 7.76 (1H, t, J=8.2 Hz).

Reference Example 13 ethyl 7-(methyloxy)-4-oxo-3,4-dihydroquinazoline-2-carboxylate

Step 1

To a solution of 2,4-dinitrobenzonitrile (5.00 g, 25.9 mmol) in MeOH (100 mL) was added dropwise a solution (20 mL) of sodium methylate (1.40 g, 25.9 mmol) in MeOH at 0° C., and the mixture was stirred at room temperature for 3 hrs. and heated under reflux for 2 hrs. After allowing to cool to room temperature, insoluble material was filtered off, and the filtrate was concentrated under reduced pressure. MeOH-water (1:1) was added to the concentrated residue to give a suspension and insoluble material was collected by filtration.

The solid was washed with MeOH-water (1:1) to give a mixture (2.70 g) of 4-methoxy-2-nitrobenzonitrile and 2-methoxy-4-nitrobenzonitrile as a pale-yellow powder. The obtained pale-yellow powder was suspended in ethanol (80 mL) and hydrazine monohydrate (1.59 g, 31.8 mmol) was added. While heating the mixture to 45° C., Raney Ni (600 mg) was added in several portions, and the mixture was stirred at 60 ° C. for 1 hr. Raney Ni (600 mg) was added again, and the mixture was heated under reflux for 2 hrs. After allowing to cool to room temperature, insoluble material was filtered off, and the filtrate was concentrated under reduced pressure. Ethyl acetate was added to the obtained concentrated residue, and extracted with 1N hydrochloric acid (×3). The aqueous layer was basified with 1N aqueous sodium hydroxide solution and the mixture was extracted with ethyl acetate. The organic layer was washed with water and saturated brine, dried over sodium sulfate and concentrated under reduced pressure. The obtained concentrated residue was purified by silica gel column chromatography (67-75% ethyl acetate/hexane) to give 2-amino-4-methoxybenzamide as a pale-yellow powder (1.45 g, 34% for 2 steps).

Step 2

To a solution of 2-amino-4-methoxybenzamide (1.40 g, 8.42 mmol) and triethylamine (1.02 g, 10.1 mmol) in THF (30 mL) was added dropwise ethyl chloroglyoxylate (1.27 g, 9.27 mmol) under ice-cooling, and the mixture was stirred at room temperature for 2 hrs. The reaction mixture was diluted with ethyl acetate, washed with water and saturated brine, dried over sodium sulfate and concentrated under reduced pressure. The obtained concentrated residue was washed with ethanol to give ethyl ((2-(aminocarbonyl)-5-methoxyphenyl)amino) (oxo)acetate as a yellow powder (2.30 g, 100%).

Step 3

To a suspension (100 mL) of ethyl ((2-(aminocarbonyl)-5-methoxyphenyl)amino)(oxo)acetate (2.15 g, 8.08 mmol) in toluene was added p-toluenesulfonic acid monohydrate (1.54 g, 8.08 mmol), and the mixture was heated under reflux for 15 hrs. The reaction mixture was diluted with ethyl acetate-THF, washed with water and saturated brine, dried over sodium sulfate and concentrated under reduced pressure. Water was added to the obtained concentrated residue to give a suspension, and insoluble material was collected by filtration to give the title compound as a brown powder (549 mg, 27%).

$^1$H-NMR (200 MHz, DMSO-d$_6$) δ: 1.36 (3H, t, J=7.2 Hz), 3.92 (3H, s), 4.38 (2H, q, J=7.2 Hz), 7.21 (1H, dd, J=2.6, 8.8 Hz), 7.30 (1H, d, J=2.6 Hz), 8.07 (1H, d, J=8.8 Hz).

Reference Example 14 ethyl 8-(methyloxy)-4-oxo-3,4-dihydroquinazoline-2-carboxylate

Step 1

To a solution of 3-methoxyanthranilic acid (4.90 g, 29.3 mmol) in THF (40 mL) was added bis(trichloromethyl) carbonate (2.90 g, 9.77 mmol), and the mixture was stirred with heating at 60° C. for 15 hrs. The reaction mixture was concentrated under reduced pressure, 1N aqueous ammonia (150 mL) was added, and the mixture was stirred with heating at 60° C. for 2 hrs. The mixture was extracted with ethyl acetate, and the organic layer was washed with saturated brine, dried over sodium sulfate and concentrated under reduced pressure to give 2-amino-3-methoxybenzamide as a pale-yellow powder (3.65 g, 75%).

Step 2

To a solution of 2-amino-3-methoxybenzamide (3.50 g, 21.1 mmol) and triethylamine (2.56 g, 25.3 mmol) in THF (100 mL) was added dropwise ethyl chloroglyoxylate (3.16 g, 23.2 mmol) under ice-cooling, and the mixture was stirred, at room temperature for 2 hrs. Water was added to the reaction mixture, and the precipitated insoluble material was collected by filtration. The solid was washed with water to give ethyl ((2-(aminocarbonyl)-6-methoxyphenyl)amino)(oxo)acetate as a white powder (4.54 g, 81%).

Step 3

To a suspension (20 mL) of ethyl ((2-(aminocarbonyl)-6-methoxyphenyl)amino)(oxo)acetate (1.00 g, 3.76 mmol) in EtOH was added dropwise sodium ethylate (20% ethanol solution, 1.41 g, 4.13 mmol) under ice-cooling, and the mixture was stirred at room temperature for 1 hr. 1N Hydrochloric acid (5 mL) and water (20 mL) were added to the reaction mixture and the precipitated insoluble material was collected by filtration. The filtered cake was washed with water and ethanol to give the title compound as a pale-yellow powder (357 mg, 38%).

$^1$H-NMR (200 MHz, DMSO-d$_6$) δ: 1.36 (3H, t, J=7.2 Hz), 3.94 (3H, s), 4.39 (2H, q, J=7.2, Hz), 7.44 (1H, dd, J=1.4, 7.8 Hz), 7.58 (1H, t, J=7.8 Hz), 7.72 (1H, dd, J=1.4, 7.8 Hz).

Reference Example 15 ethyl 4-oxo-6-[(phenylmethyl)oxy]-3,4-dihydroquinazoline-2-carboxylate

Step 1

To a solution of 5-hydroxy-2-nitrobenzoic acid (10.0 g, 54.6 mmol) in DMF (200 mL) were added benzylbromide (20.5 g, 120 mmol) and potassium carbonate (18.9 g, 137 mmol), and the mixture was stirred at room temperature for 15 hrs. The reaction mixture was concentrated under reduced pressure and water was added to the concentrated residue. The precipitated insoluble material was collected by filtration and the solid was washed with water to give benzyl 5-benzyloxy-2-nitrobenzoate as a yellow powder (19.4 g, 98%).

Step 2

To a solution of benzyl 5-benzyloxy-2-nitrobenzoate (19.0 g, 52.2 mmol) in MeOH (100 mL) was added an aqueous solution (50 mL) of potassium hydroxide (8.79 g, 157 mmol), and the mixture was heated under reflux for 1 hr. After allowing to cool to room temperature, the reaction mixture was acidified with 4N hydrochloric-acid and concentrated under reduced pressure to evaporate MeOH. The mixture was extracted with ethyl acetate, and 1N aqueous sodium hydroxide solution (80 mL) was added to the organic layer. The precipitated insoluble material was collected by filtration and washed with ethyl acetate. The solid was dissolved in methanol and 1N hydrochloric acid (60 mL) was added. The mixture was extracted with ethyl acetate, and the organic layer was washed with saturated brine dried over sodium sulfate and concentrated to give 5-benzyloxy-2-nitrobenzoic acid as a pale-yellow powder (12.0 g, 84%).

Step 3

To a solution of 5-benzyloxy-2-nitrobenzoic acid (11.9 g, 43.6 mmol) and DMF (0.12 mL) in THF (120 mL) was added dropwise oxalyl chloride (6.08 g, 47.9 mmol) under ice-cooling, and the mixture was stirred at room temperature for 3 hrs. This solution was added dropwise to aqueous ammonia (3% aqueous solution, 270 mL) under ice-cooling. The reaction mixture was stirred at room temperature for 1 hr and the precipitated insoluble material was collected by filtration. The filtered cake was washed with water and diethyl ether to give 5-benzyloxy-2-nitrobenzamide as a pale-yellow powder (11.0 g, 93%).

Step 4

To a suspension of 5-benzyloxy-2-nitrobenzamide (10.5 g, 38.8 mmol) in EtOH (100 mL)-water (100 mL) were added ammonium chloride (10.0 g) and iron (10.0 g), and the mixture was heated under reflux for 1.5 hrs. Insoluble material was filtered off, and the filtrate was concentrated. The concentrated residue was partitioned between ethyl acetate and 1N aqueous sodium hydroxide solution and the organic layer was washed with saturated brine, dried over sodium sulfate and concentrated to give 2-amino-5-(benzyloxy)benzamide as a yellow powder (9.42 g, 100%).

Step 5

To a solution of 2-amino-5-(benzyloxy)benzamide (9.20 g, 38.0 mmol) and triethylamine (4.61 g, 45.6 mmol) in THF (200 mL) was added dropwise ethyl chloroglyoxylate (5.71 g, 41.8 mmol) under ice-cooling, and the mixture was stirred at room temperature for 2 hrs. Water was added to the reaction mixture, and the precipitated insoluble material was collected by filtration. The filtered cake was washed with water and ethanol to give ethyl ((2-(aminocarbonyl)-4-(benzyloxy)phenyl)amino) (oxo)acetate as a yellow powder (13.0g, 100%).

Step 6

To a suspension (180 mL) of ethyl ((2-(aminocarbonyl)-4-(benzyloxy)phenyl)amino)(oxo)acetate (12.5 g, 36.5 mmol) in EtOH was added dropwise sodium ethylate (20% ethanol solution, 13.7 g, 40.2 mmol) under ice-cooling, and the mixture was stirred at room temperature for 1 hr. This reaction mixture was added dropwise 0.3N hydrochloric acid (350 mL) under ice-coolihg, and the precipitated insoluble material was collected by filtration. The filtered cake was washed with water and ethanol to give the title compound as a pale-yellow powder (10.3 g, 87%).

$^1$H-NMR (200 MHz, DMSO-$d_6$) δ: 1.35 (3H, t, J=7.0 Hz), 4.38 (2H, q, J=7.0 Hz), 5.28 (2H, s), 7.34-7.59 (6H, m), 7.66 (1H, d, J=3.0 Hz), 7.80 (1H, d, J=8.8 Hz).

Reference Example 16 ethyl 6-iodo-4-oxo-3,4-dihydroquinazoline-2-carboxylate

Step 1

To a solution of 5-iodoanthranilic acid (25.0 g, 95.0 mmol) in THF (400 mL) was added bis(trichloromethyl)carbonate (9.40 g, 31.7 mmol), and the mixture was stirred with heating at 60° C. for 15 hrs. The reaction mixture was concentrated under reduced pressure, 2N aqueous ammonia (235 mL) was added, and the mixture was stirred with heating at 60° C. for 2 hrs. The mixture was extracted with ethyl acetate, and the organic layer was washed with saturated brine, dried over sodium sulfate and concentrated under reduced pressure. The obtained concentrated residue was suspended in diisopropy ether, and insoluble material was collected by filtration to give 2-amino-5-iodobenzamide as a white powder (15.9 g, 64%).

Step 2

To a solution of 2-amino-5-iodobenzamide (15.8 g, 60.3 mmol) and triethylamine (7.32 g, 72.4 mmol) in THF (300 mL) was added dropwise ethyl chloroglyoxylate (9.05 g, 66.3 mmol) under ice-cooling, and the mixture was stirred at room temperature for 2 hrs. Water was added to the reaction mixture, and the precipitated insoluble material was collected by filtration. The solid was washed with water to give ethyl ((2-(aminocarbonyl)-4-iodophenyl)amino)(oxo)acetate as a white powder (20.9 g, 96%).

Step 3

To a suspension (300 mL) of ethyl ((2-(aminocarbonyl)-4-iodophenyl)amino)(oxo)acetate (20.9 g, 57.7 mmol) in EtOH was added dropwise sodium ethylate (20% ethanol solution, 21.6 g, 63.5 mmol) under ice-cooling, and the mixture was stirred at room temperature for 1 hr. The reaction mixture was poured into 0.3N hydrochloric acid (600 mL) under ice-cooling and the precipitated insoluble material was collected by filtration. The filtered cake was washed with water and ethanol to give the title compound as a pale-pink powder (17.0 g, 86%).

$^1$H-NMR (200 MHz, DMSO-$d_6$) δ: 1.35 (3H, t, J=7.0 Hz), 4.38 (2H, q, J=7.0 Hz), 7.61 (1H, d, J=8.5 Hz), 8.18 (1H, dd, J=2.0, 8.5 Hz), 8.44 (1H, d, J=2.0 Hz).

Reference Example 17

Ethyl 5-methyl-4-oxo-3,4-dihydroquinazoline-2-carboxylate

Step 1

To a solution of 6-methylanthranilic acid (10.2 g, 67.5 mmol) in THF (100 mL) was added bis(trichloromethyl)carbonate (6.67 g, 22.5 mmol), and the mixture was stirred with heating at 50° C. for 15 hrs. The reaction mixture was concentrated under reduced pressure, 6N aqueous ammonia (100 mL) was added, and the mixture was stirred with heating at 60° C. for 3 hrs. The mixture was extracted with ethyl acetate, and the organic layer was washed with saturated brine, dried over sodium sulfate and concentrated under reduced pressure. The obtained concentrated residue was suspended in diisopropy ether, and insoluble material was collected by filtration to give 2-amino-6-methylbenzamide as a pale-yellow powder (1.35 g, 13%).

Step 2

To a solution of 2-amino-6-methylbenzamide (1.28 g, 8.52 mmol) and triethylamine (1.03 g, 10.2 mmol) in THF (30 mL) was added dropwise ethyl chloroglyoxylate (1.28 g, 9.38 mmol) under ice-cooling, and the mixture was stirred at room temperature for 3 hrs. The mixture was extracted with ethyl acetate, and the organic layer was washed with saturated brine, dried over sodium sulfate and concentrated under reduced pressure. The obtained concentrated residue was suspended in diisopropy ether-EtOH, and insoluble material was collected by filtration to give ethyl ((2-(aminocarbonyl)-3-methylphenyl)amino) (oxo)acetate as a white powder (1.85 g, 87%).

Step 3

To a suspension (15 mL) of ethyl ((2-(aminocarbonyl)-3-methylphenyl)amino)(oxo)acetate (760 mg, 3.04 mmol) in EtOH was added dropwise sodium ethylate (20% ethanol solution, 1.14 g, 3.34 mmol) under ice-cooling, and the mixture was stirred at room temperature for 2 hrs. 1N Hydrochloric acid (5 mL) was added to the reaction mixture, and the mixture was extracted with ethyl acetate. The organic layer was washed with saturated brine, dried over sodium sulfate and concentrated under reduced pressure. The obtained concentrated residue was suspended in diisopropy ether-EtOH, and insoluble material was collected by filtration to give the title compound as a white powder (450 mg, 64%).

$^1$H-NMR (200MHz, DMSO-$d_6$) δ: 1.36 (3H, t, J=7.2 Hz), 2.79 (3H, s), 4.37 (2H, q, J=7.2 Hz), 7.37 (1H, d, J=7.5 Hz), 7.61 (1H, d, J=7.5 Hz), 7.70 (1H, t, J=7.5 Hz), 12.35 (1H, bs).

Reference Example 18

Ethyl 5-fluoro-4-oxo-3,4-dihydroquinazoline-2-carboxylate

Step 1

To a solution of 2-amino-6-fluorobenzamide (3.80 g, 24.7 mmol) and triethylamine (2.99 g, 29.6 mmol) in THF (50 mL) was added dropwise ethyl chloroglyoxylate (3.70 g, 27.1 mmol) under ice-cooling, and the mixture was stirred at room temperature for 3 hrs. The mixture was partitioned between ethyl acetate and water, and the organic layer was washed with saturated brine, dried over sodium sulfate and concentrated under reduced pressure. The obtained concentrated residue was suspended in EtOH, and insoluble material was collected by filtration to give ethyl ((2-(aminocarbonyl)-3-fluorophenyl)amino)(oxo)acetate as a white powder (4.95 g, 79%).

Step 2

To a suspension of ethyl ((2-(aminocarbonyl)-3-fluorophenyl)amino)(oxo)acetate (2.45 g, 9.64 mmol) in EtOH (50 mL) was added dropwise sodium ethylate (20% ethanol solution, 3.61 g, 10.6 mmol) under ice-cooling, and the mixture was stirred at room temperature for 1 hr. 1N Hydrochloric acid (20 mL) was added to the reaction mixture and insoluble material was collected by filtration. The solid was washed with water and diethyl ether to give the title compound as a pale-yellow powder (1.29 g, 57%).

$^1$H-NMR (200MHz, DMSO-$d_6$) δ: 1.35 (3H, t, J=7.2 Hz), 4.37 (2H, q, J=7.2 Hz), 7.34-7.41 (1H, m), 7.62 (1H, d, J=8.1 Hz), 7.81-7.89 (1H, m), 12.64 (1H, bs).

Reference Example 19

Ethyl 4-oxo-5-[(2-phenylethyl)oxy]-3,4-dihydro-quinazoline-2-carboxylate

Step 1

To a solution of 2-phenylethanol (2.00 g, 10.4 mmol) in DMF (20 mL)-THF (5 mL) was added sodium hydride (60% oil dispersion, 460 mg, 11.4 mmol) under ice-cooling, and the mixture was stirred at room temperature for 30 min. A solution of 2,6-dinitrobenzonitrile (2.00 g, 10.4 mmol) in THF (5 mL) was added to this reaction mixture, and the mixture was stirred with heating at 90° C. for 3 hrs. After allowing to cool to room temperature, the reaction mixture was concentrated under reduced pressure. Ethyl acetate was added to the concentrated residue and the mixture was washed with water and saturated brine, dried over sodium sulfate and concentrated under reduced pressure. The obtained concentrated residue was suspended in EtOH and insoluble material was collected by filtration. The solid was washed with EtOH to give 2-nitro-6-((2-phenylethyl)oxy)benzonitrile as a brown powder (894 mg, 32%).

Step 2

To a suspension (20 mL) of 2-nitro-6-((2-phenylethyl)oxy) benzonitrile (850 mg, 3.17 mmol) in ethanol was added hydrazine monohydrate (333 mg, 6.65 mmol). While heating the mixture to 45° C., haney Ni (300 mg) was added in several portions, and the mixture was stirred at 60° C. for 1 hr., and heated under reflux for 1 hr. After allowing, to cool to room temperature, insoluble material was filtered off and concentrated under reduced pressure. Ethyl acetate was added to the obtained concentrated residue, and the mixture was extracted with 1N hydrochloric acid (×3). The aqueous layer was basified with 4N aqueous sodium hydroxide solution and the mixture was extracted with ethyl acetate. The organic layer was washed with water and saturated brine, dried over sodium sulfate and concentrated under reduced pressure. The obtained concentrated residue was suspended in diisopropy ether, and insoluble material was collected by filtration to give 2-amino-6-((2-phenylethyl)oxy)benzamide as a brown powder (358 mg, 44%).

Step 3

To a solution of 2-amino-6-((2-phenylethyl)oxy)benzamide (330 mg, 1.29 mmol) and triethylamine (170 mg, 1.68 mmol) in THF (8 mL) was added dropwise ethyl chloroglyoxylate (212 mg, 1.55 mmol) under ice-cooling, and the mixture was stirred at room temperature for 2 hrs. The reaction mixture was diluted with ethyl acetate, the mixture was washed with water and saturated brine, dried over sodium sulfate and concentrated under reduced pressure. The obtained concentrated residue was suspended in diisopropy ether, and insoluble material was collected by filtration to give ethyl ((2-(aminocarbonyl)-3-((2-phenylethyl)oxy)phenyl) amino)(oxo)acetate as a white powder (459 mg, 100%).

Step 4

To a suspension (9 mL) of ethyl ((2-(aminocarbonyl)-3-((2-phenylethyl)oxy)phenyl)amino)(oxo)acetate (450 mg, 1.26 mmol) in EtOH was added dropwise sodium ethylate (20% ethanol solution, 516 mg, 1.52 mmol) under ice-cooling, and the mixture was stirred at room temperature for 2 hrs. Sodium ethylate (20% ethanol solution, 516 mg, 1.52 mmol) was added dropwise again, and the mixture was stirred at room temperature for 1 hr. 0.5N Hydrochloric acid (10 mL) was added to the reaction mixture and the mixture was extracted with ethyl acetate. The organic layer was washed with saturated brine, dried over sodium sulfate and concentrated under reduced pressure. The obtained concentrated residue was washed with ethanol to give the title compound as a pale-yellow powder (200 mg, 47%).

$^1$H-NMR (200 MHz, DMSO-$d_6$) δ: 1.35 (3H, t, J=7.2 Hz), 3.10 (2H, t, J=6.6 Hz), 4.23-4.32 (2H, m), 4.37 (2H, q, J=7.2 Hz), 6.94-8.04 (8H, m), 12.20 (1H, bs).

Reference Example 20

Ethyl 6-(morpholin-4-ylmethyl)-4-oxo-3,4-dihydro-quinazoline-2-carboxylate

Step 1

To a suspension (25 mL) of ethyl 6-methyl-4-oxo-3,4-dihydroquinazoline-2-carboxylate (500 mg, 2.15 mmol) obtained in Reference Example 9 and N-bromosuccinimide (402 mg, 2.26 mmol) in chloroform was added 2,2'-azobis (isobutyronitrile) (18 mg, 110 μmol), and the mixture was heated under reflux for 2 hrs. Ethyl acetate was added to the reaction mixture, and insoluble material was collected by filtration. The solid was washed with ethyl acetate to give ethyl 6-(bromomethyl)-4-oxo-3,4-dihydroquinazoline-2-carboxylate as a white powder (547 mg, 100%).

Step 2

A suspension (10 mL) of ethyl 6-(bromomethyl)-4-oxo-3,4-dihydroquinazoline-2-carboxylate (500 mg, 1.61 mmol), morpholine (168 μL, 1.93 mmol) and triethylamine (367 μL, 2.41 mmol) in THF was stirred with heating at 40° C. for 1 hr. The reaction mixture was diluted with ethyl acetate, and extracted with 1N hydrochloric acid. The aqueous layer was basified with saturated aqueous sodium hydrogen carbonate and the mixture was extracted with a mixed solvent of ethyl acetate-THF (×2). The organic layer was washed with saturated brine, dried over sodium sulfate and concentrated. The obtained solid was washed with diethyl ether to give the title compound as a pale-yellow powder (240 mg, 47%).

$^1$H-NMR (200 MHz, DMSO-$d_6$) δ: 1.36 (3H, t, J=7.2 Hz), 2.40-2.60 (4H, m), 3.60-3.80 (6H, m), 4.39 (2H, q, J=7.2 Hz), 8.13 (1H, bs).

Reference Example 21

Methyl 6-[(methyloxy)methyl]-4-oxo-3,4-dihydro-quinazoline-2-carboxylate

To a suspension (3 mL) of ethyl 6-(bromomethyl)-4-oxo-3,4-dihydroquinazoline-2-carboxylate (320 mg, 1.03 mmol) obtained in Reference Example 20, Step 1 in MeOH was added a solution (3 mL) of sodium methylate (111 mg, 2.06 mmol) in MeOH under ice-cooling, and the mixture was stirred for 1 hr. A solution (3 mL) of sodium methylate (166 mg, 3.07 mmol) in MeOH was added again, and the mixture was stirred at room temperature for 2 hrs. The mixture was acidified with 1N hydrochloric acid and extracted with ethyl acetate (×2). The organic layer was washed with saturated brine, dried over sodium sulfate and concentrated. The obtained solid was washed with diethyl ether to give the title compound as a white powder (160 mg, 63%).

$^1$H-NMR (200MHz, DMSO-$d_6$) δ: 3.35 (3H, s), 3.93 (3H, s), 4.59 (2H, s), 7.80-7.83 (2H, m), 8.11-8.12 (1H, m).

Reference Example 22

Ethyl 5,6-difluoro-4-oxo-3,4-dihydroquinazoline-2-carboxylate

Step 1

To a solution of tert-butyl (3,4-difluorophenyl)carbamate (5.00 g, 21.8 mmol) synthesized according to the method described in literature (*Tetrahedron*, 1992, 48, 7373) in THF (50 mL) was added dropwise n-butyllithium (1.6 M hexane solution, 30 mL, 48.0 mmol) at −78° C., and the mixture was stirred at −78° C. for 3 hrs. A solution (15 mL) of ethyl chlorocarbonate (2.60 g, 24.0 mmol) in THF was added to the reaction mixture, and the mixture was stirred at −78° C. for 1 hr. Saturated aqueous ammonium chloride solution (50 mL) was added, and the mixture was partitioned between ethyl acetate and water. The organic layer was washed with saturated brine, dried over sodium sulfate, and the mixture was concentrated under reduced pressure to give a yellow oil (7.14 g). The obtained oil was dissolved in ethyl acetate (10 mL), 4N hydrochloric acid-ethyl acetate solution (40 mL) was added, and the mixture was stirred at room temperature for 3 hrs. Diethyl ether (20 mL) was added to the reaction mixture, and insoluble material was collected by filtration. The solid was washed with ethanol and ether to give ethyl 5,6-difluoroanthranilate hydrochloride as a white powder (2.91 g, 70% for 2 steps).

Step 2

Ethyl 5,6-difluoroanthranilate hydrochloride (2.50 g, 10.5 mmol) was suspended in 1N hydrochloric acid-acetic acid solution (50 mL), ethyl cyanoformate (1.14 g, 11.6 mmol) was added, and the mixture was stirred with heating at 80° C. for 3 hrs. After allowing to cool to room temperature, the reaction mixture was concentrated under reduced pressure. Ethanol was added to the obtained concentrated residue to give a suspension, and insoluble material was collected by filtration to give the title compound as a white powder (2.18 g, 82%).

$^1$H-NMR (300 MHz, DMSO-$d_6$) δ: 1.35 (3H, t, J=7.2 Hz), 4.38 (2H, q, J=7.2 Hz), 7.70 (1H, ddd, J=2.1, 7.5, 9.0 Hz), 7.92-8.02 (1H, m), 12.78 (1H, bs).

Reference Example 23

Ethyl 6-cyano-4-oxo-3,4-dihydroquinazoline-2-carboxylate

A suspension (10 mL) of ethyl 6-iodo-4-oxo-3,4-dihydroquinazoline-2-carboxylate (2.00 g, 5.81 mmol) synthesized in Reference Example 16, zinc cyanide (375 mg, 3.19 mmol) and tetrakis(triphenylphosphine)palladium (336 mg, 0.29 mmol) in DMF was stirred under an argon atmosphere at 80° C. for 5 hrs. After cooling to room temperature, ethyl acetate was added to the reaction mixture. The precipitated solid was collected by filtration, washed with ethyl acetate, diisopropy ether and water and dried over phosphorus pentoxide under reduced pressure to give the title compound as a pale-yellow powder (965 mg, 68%).

$^1$H-NMR (200 MHz, DMSO-$d_6$) δ: 1.35 (3H, t, J=6.8 Hz), 4.39 (2H, q, J=6.8 Hz), 7.96 (1H, d, J=8.4 Hz), 8.23 (1H, dd, J=1.8, 8.4 Hz), 8.55 (1H, d, J=1.8 Hz).

Reference Example 24

Ethyl 4-oxo-3,4-dihydropyrido[2,3-d]pyrimidine-2-carboxylate

Step 1

To a suspension (30 mL) of 2-aminonicotinic acid (2.50 g, 18.1 mmol) in pyridine was added dropwise ethyl chloroglyoxylate (4.94 g, 36.2 mmol) under ice-cooling, and the mixture was stirred at room temperature for 2 hrs. The mixture was further stirred at 50° C. for 1 hr, and the reaction mixture was concentrated under reduced pressure. Water was added to the concentrated residue to give a suspension, and insoluble material was collected by filtration to give ethyl 4-oxo-3,4-dihydropyrido[2,3-d]-1,3-oxazine-2-carboxylate as a pale-yellow powder (2.21 g, 56%).

$^1$H-NMR (200 MHz, CDCl$_3$) δ: 1.47 (3H, t, J=7.2 Hz), 4.52 (2H, q, J=7.2 Hz), 7.64 (1H, dd, J=8.0, 4.8 Hz), 8.61 (1H, dd, J=8.0, 1.8 Hz), 9.11 (1H, dd, J=4.8, 1.8 Hz).

Step 2

A suspension (30 mL) of ethyl 4-oxo-3,4-dihydropyrido [2,3-d]-1,3-oxazine-2-carboxylate (2.20 g, 9.99 mmol), ammonium acetate (770 mg, 9.99 mmol) and acetic acid (240 mg, 4.00 mmol) in EtOH was heated under reflux for 1 hr. The reaction mixture was cooled to room temperature and insoluble material was collected by filtration. The solid was washed with EtOH to give the title compound as a pale-yellow powder (1.11 g, 51%).

$^1$H-NMR (200MHz, DMSO-$d_6$) δ: 1.38 (3H, t, J=7.0 Hz), 4.41 (2H, q, J=7.0 Hz), 7.65 (1H, dd, J=7.8, 4.4 Hz), 8.56 (1H, dd, J=7.8, 1.8 Hz), 9.04 (1H, dd, J=4.4, 1.8 Hz).

Reference Example 25

Ethyl 4-oxo-3,4-dihydropyrido[3,4-d]pyrimidine-2-carboxylate

Step 1

To 10% aqueous sodium hydroxide solution (100 mL) was added bromine (1.93 mL, 38.6 mmol) under ice-cooling, and 1H-pyrrolo[3,4-c]pyridine-1,3 (2H)-dione (5.20 g, 35.1 mmol) was subsequently added. 10% Aqueous sodium hydroxide solution (60 mL) was added to the reaction mixture, and the mixture was stirred with heating at 90° C. for 40 min. After allowing to cool to room temperature, 50% sulfuric acid was added to adjust the reaction mixture to pH 3. The precipitated insoluble material was collected by filtration, and the solid was washed with water to give 3-aminoisonicotinic acid as a pale-yellow powder (5.00 g, 100%).

$^1$H-NMR (200MHz, DMSO-$d_6$) δ: 7.46 (1H, d, J=5.1 Hz), 7.73 (1H, d, J=5.1 Hz), 8.21 (1H, s).

Step 2

To a suspension (60 mL) of 3-aminoisonicotinic acid (4.84 g, 35.1 mmol, 100%) in pyridine was added dropwise ethyl chloroglyoxylate (9.58 g, 70.2 mmol) under ice-cooling, and the mixture was stirred at room temperature for 15 hrs. The reaction mixture was concentrated under reduced pressure and water was added to the concentrated residue to give a suspension. The insoluble material was collected by filtration to give, 3-{[(ethyloxy)(oxo)acetyl]amino}pyridine-4-carboxylic acid as a pale-yellow powder (3.74 g, 45%).

$^1$H-NMR (200 MHz, DMSO-$d_6$) δ: 1.33 (3H, t, J=7.0 Hz), 4.33 (2H, q, J=7.0 Hz), 7.88 (1H, d, J=5.0 Hz), 8.53 (1H, d, J=5.0 Hz), 9.71 (1H, s), 12.10 (1H, s).

Step 3

To a solution of 3-{[(ethyloxy)(oxo)acetyl]amino}pyridine-4-carboxylic acid (100 mg, 420 μmol) and DMF (30 μL) in THF (3 mL) was added dropwise oxalyl chloride (40 μL, 460 μmol) under ice-cooling, and the mixture was stirred at room temperature for 2 hrs. The reaction mixture was cooled with ice, 2 M, ammonia-ethanol solution (693 μL, 1.39 mmol) was added, and the mixture was stirred at 0° C. for 1 hr. The mixture was partitioned between ethyl acetate and water, and the organic layer was washed with saturated brine and dried over sodium sulfate. The filtrate was concentrated under reduced pressure to give ethyl {[4-(aminocarbonyl)pyridin-3-yl]amino}(oxo)acetate as a white powder (76 mg, 76%).

$^1$H-NMR (200MHz, DMSO-$d_6$) δ: 1.32 (3H, t, J=7.0 Hz), 4.31 (2H, q, J=7.4 Hz), 7.78 (1H, d, J=5.2 Hz), 8.17 (1H, bs), 8.50 (1H, d, J=5.2 Hz), 8.60 (1H, bs), 9.68 (1H, s).

Step 4

To a suspension (4 mL) of ethyl {[4-(aminocarbonyl)pyridin-3-yl]amino}(oxo)acetate (76 mg, 320 μmol) in EtOH was added dropwise sodium ethylate (20% ethanol solution, 120 mg, 350 μmol) under ice-cooling, and the mixture was stirred at room temperature for 1 hr. 1N Hydrochloric acid (0.5 mL) was added to the reaction mixture and the mixture was extracted with ethyl acetate. The organic layer was washed with saturated brine, dried over sodium sulfate and concentrated under reduced pressure to give the title compound as a white amorphous form (22 mg, 31%). The obtained compound was used for the next reaction without purification.

Reference Example 26

Ethyl 4-oxo-3,4-dihydrothieno[2,3-d]pyrimidine-2-carboxylate

Step 1

A solution (100 mL) of 2,5dihydroxy-1,4-dithiane (11.8 g, 155 mmol), cyanoacetamide (17.0 g, 202 mmol) and triethylamine (20 mL) in EtOH was heated at 70° C. for 4 hrs. The reaction mixture was cooled to room temperature, and concentrated under reduced pressure to about a half amount of the solution. Water was added to the concentrated residue and the precipitated insoluble material was collected by filtration. The solid was washed with water to give 2-amino-3-thiophenecarboxylic amide as a brown powder (15.3 g, 69%).

$^1$H-NMR (200MHz, DMSO-$d_6$) δ: 6.22 (1H, d, J=6.0 Hz), 7.04 (1H, d, J=6.0 Hz), 7.21 (2H, bs).

Step 2

To a solution of 2-amino-3-thiophenecarboxylic amide (5.00 g, 35.2 mmol) and triethylamine (5.39 mL, 38.7 mmol) in THF (200 mL) was added dropwise ethyl chloroglyoxylate (4.81 g, 35.2 mmol) under ice-cooling, and the mixture was stirred at room temperature for 1 hr. The mixture was partitioned between ethyl acetate and water, and the organic layer was washed with saturated brine, dried over sodium sulfate and concentrated under reduced pressure. The obtained concentrated residue was suspended in EtOH, and insoluble material was collected by filtration to give ethyl (3-(aminocarbonyl)-2-thiopheneamino)(oxo)acetate as a pale-yellow powder (8.32 g, 97%).

$^1$H-NMR (200MHz, DMSO-$d_6$) δ: 1.32 (3H, t, J=7.0 Hz), 4.33 (2H, q, J=7.0 Hz), 7.15 (1H, d, J=6.0 Hz), 7.50 (1H, d, J=6.0 Hz), 7.67 (1H, bs), 8.03 (1H, bs).

Step 3

To a suspension (50 mL) of ethyl (3-(aminocarbonyl)-2-thiopheneamino)(oxo)acetate (2.00 g, 8.26 mmol) in xylene was added p-toluenesulfonic acid monohydrate (314 mg, 1.65 mmol), and the mixture was heated under reflux for 3 hrs. p-Toluenesulfonic acid monohydrate (200 mg, 1.05 mmol) was added again, and the mixture was heated under reflux for 8 hrs. The reaction mixture was diluted with ethyl acetate, washed with water and saturated brine, dried over sodium sulfate and concentrated under reduced pressure. The obtained concentrated residue was purified by silica gel column chromatography (67% ethyl acetate/hexane) to give the title compound as a pale-yellow powder (531 mg, 29%).

$^1$H-NMR (200MHz, DMSO-$d_6$) δ: 1.35 (3H, t, J=7.2 Hz), 4.38 (2H, q, J=7.2 Hz), 7.49 (1H, d, J=5.6 Hz), 7.81 (1H, d, J=5.6 Hz).

Reference Example 27

Ethyl 4-oxo-3,4-dihydrothieno[3,2-d]pyrimidine-2-carboxylate

Step 1

To a suspension (100 mL) of 3-amino-2-thiophenecarboxylic acid (3.84 g, 26.5 mmol) in pyridine was added dropwise ethyl chloroglyoxylate (7.69 g, 56.3 mmol) under ice-cooling, and the mixture was stirred at room temperature for 2 hrs. The reaction mixture was concentrated under reduced pressure. Water was added to the concentrated residue to give a suspension, and insoluble material was collected by filtration to give ethyl 4-oxo-3,4-dihydrothieno-[3,2-d]-1,3-oxazine-2-carboxylate as a brown powder (4.86 g, 81%).

$^1$H-NMR (200MHz, DMSO-$d_6$) δ: 1.35 (3H, t, J=7.2 Hz), 4.39 (2H, q, J=7.2 Hz), 7.64 (1H, d, J=5.6 Hz), 8.49 (1H, d, J=5.6 Hz).

Step 2

A suspension (30 mL) of ethyl 4-oxo-3,4-dihydrothieno[3,2-d]-1,3-oxazine-2-carboxylate (2.50 g, 11.1 mmol) and ammonium acetate (941 mg, 12.2 mmol) in EtOH was heated under reflux for 1 hr. The reaction mixture was cooled to room temperature, and concentrated under reduced pressure. The concentrated residue was diluted with ethyl acetate and the mixture was washed with water and saturated brine, dried over sodium sulfate and concentrated under reduced pressure. The obtained concentrated residue was purified by silica gel column chromatography (67-80% ethyl acetate/hexane) to give the title compound as a brown powder (478 mg, 19%).

$^1$H-NMR (200MHz, DMSO-$d_6$) δ: 1.35 (3H, t, J=7.2 Hz), 4.38 (2H, q, J=7.2 Hz), 7.56 (1H, d, J=5.6 Hz), 8.28 (1H, d, J=5.6 Hz).

Reference Example 28

2-[(tetrahydrofuran-3-ylmethyl)oxy]pyridine-4-carbonitrile

To a suspension (1.0 mL) of sodium hydride (100 mg, 2.50 mmol) in THF was added tetrahydrofuran-3-ylmethanol (138 μL, 1.43 mmol) at room temperature, and the mixture was stirred at 50° C. for 30 min. The reaction mixture was cooled to room temperature, and a solution (1.0 mL) of 2-chloropyridine-4-carbonitrile (200 mg, 1.44 mmol) in THF was gradually added at room temperature. The mixture was stirred at room temperature for 30 min. and at 50° C. for 12 hrs. The reaction mixture was cooled to room temperature, water was added and THF was evaporated under reduced pressure. The concentrated residue was extracted with ethyl acetate. The organic layer was washed with saturated brine and, after drying over anhydrous sodium sulfate, concentrated under reduced pressure. The obtained residue was purified by silica gel column chromatography (10%-20% ethyl acetate/hexane) to give the title compound as a colorless oil (202 mg, 68%).

$^1$H-NMR (300 MHz, CDCl$_3$) δ: 1.64-1.83 (1H, m), 2.05-2.20 (1H, m), 2.64-2.86 (1H, m), 3.68 (1H, dd, J=8.9, 5.3 Hz), 3.74-3.84 (1H, m), 3.85-3.96 (2H, m), 4.19-4.42 (2H, m), 6.99 (1H, s), 7.07 (1H, dd, J=5.3, 1.1 Hz), 8.28 (1H, d, J=5.1 Hz).

Reference Example 29

({2-[(tetrahydrofuran-3-ylmethyl)oxy]pyridin-4-yl}methyl)amine

A solution of 2-[(tetrahydrofuran-3-ylmethyl)oxy]pyridine-4-carbonitrile (200 mg, 0.98 mmol) synthesized in Reference Example 28 and Raney Ni (3.0 g) in 5N ammonia solution in methanol was stirred at room temperature under 4.8 atm for 9 hrs. The catalyst was filtered off, and the filtrate was concentrated. The obtained green oil was purified by silica gel column chromatography (0%-25% methanol/ethyl acetate) to give the title compound as a pale-yellow oil (89 mg, 44%).

$^1$H-NMR (300 MHz, CDCl$_3$) δ: 1.58 (2H, s), 1.69-1.82 (1H, m), 2.01-2.18 (1H, m), 2.65-2.85 (1H, m), 3.61-3.99 (6H, m), 4.15-4.37 (2H, m), 6.71 (1H, s), 6.83 (1H, dd, J=5.4, 0.9 Hz), 8.07 (1H, d, J=5.5 Hz).

Reference Example 30

2-[(tetrahydro-2H-pyran-4-ylmethyl)oxy]pyridine-4-carbonitrile

The title compound was obtained as a white powder (184.2 mg, 63%) in the same manner as in Reference Example 28 from 2-chloropyridine-4-carbonitrile and tetrahydro-2H-pyran-4-ol.

$^1$H-NMR (300 MHz, CDCl$_3$) δ: 1.45 (2H, m), 1.73 (2H, m, J=13.0, 1.9 Hz), 2.06 (1H, m), 3.44 (2H, dt, J=11.8, 2.0 Hz), 4.02 (2H, m), 4.19 (2H, d, J=6.6 Hz), 6.98 (1H, m), 7.06 (1H, dd, J=5.1, 0.8 Hz), 8.28 (1H, d, J=5.3 Hz).

Reference Example 31

({2-[(tetrahydro-2H-pyran-4-ylmethyl)oxy]pyridin-4-yl}methyl)amine

A solution (100 mL) of 2-[(tetrahydro-2H-pyran-4-ylmethyl)oxy]pyridine-4-carbonitrile (10.6 g, 0.049 mol) synthesized in Reference Example 30 in THF was gradually added to a suspension (100 mL) of aluminum lithium hydride (1.85 g, 0.049 mol) in THF at 0° C., and the mixture was stirred for 15 min. Water and 1N aqueous sodium hydroxide solution were added to the reaction mixture. Insoluble material was filtered off and the filtrate was dried over anhydrous sodium sulfate, and concentrated under reduced pressure. The obtained oil was purified by silica gel column chromatography (0%-25% methanol/ethyl acetate) to give the title compound as a pale-yellow oil (11.0 g, 94%).

$^1$H-NMR (300 MHz, CDCl$_3$) δ: 1.45 (2H, m), 1.75 (2H, m), 2.04 (1H, m), 3.44 (2H, dt, J=11.8, 2.1 Hz), 3.85 (2H, s), 4.01 (2H, dd, J=11.5, 2.5 Hz), 4.15 (2H, d, J=6.6 Hz), 6.71 (1H, s), 6.82 (1H, m), 8.07 (1H, d, J=5.3 Hz).

Reference Example 32

2-{[(3-methyloxetan-3-yl)methyl]oxy}pyridine-4-carbonitrile

The title compound was obtained as a colorless oil (3.47 g, 79%) in the same manner as in Reference Example 28 from 2-chloropyridine-4-carbonitrile and (3-methyloxetan-3-yl)methanol.

$^1$H-NMR (200 MHz, CDCl$_3$) δ: 1.43 (3H, s), 4.43 (2H, s), 4.46 (2H, d, J=5.8 Hz), 4.62 (2H, d, J=5.8 Hz), 7.05-7.06 (1H, m), 7.10 (1H, dd, J=1.6, 5.2 Hz), 8.30 (1H, dd, J=1.6, 5.2 Hz).

Reference Example 33

[(2-{[(3-methyloxetan-3-yl)methyl]oxy}pyridin-4-yl)methyl]amine

The title compound was obtained as a yellow oil (2.12 g, 60%) in the same manner as in Reference Example 31 from 2-{[(3-methyloxetan-3-yl)methyl]oxy}pyridine-4-carbonitrile synthesized in Reference Example 32.

$^1$H-NMR (300 MHz, CDCl$_3$) δ: 1.43 (3H, s), 1.69 (2H, s), 3.86 (2H, s), 4.37 (2H, s), 4.44 (2H, d, J=5.8 Hz), 4.66 (2H, d, J=5.8 Hz), 6.78 (1H, s), 6.85 (1H, dd, J=5.3, 1.5 Hz), 8.08 (1H, d, J=5.3 Hz).

Reference Example 34

2-[(furan-3-ylmethyl)oxy]pyridine-4-carbonitrile

The title compound was obtained as a white powder (3.93 g, 91%) in the same manner as in Reference Example 28 from 2-chloropyridine-4-carbonitrile and furan-3-ylmethanol $^1$H-NMR (300 MHz, CDCl$_3$) δ: 5.29 (2H, s), 6.49 (1H, d, J=1.3 Hz) 7.01 (1H, s), 7.08 (1H, dd, J=5.3, 1.3 Hz), 7.42 (1H, t, J=1.6 Hz), 7.54 (1H, s), 8.32 (1H, d, J=5.3 Hz).

Reference Example 35

({2-[(furan-3-ylmethyl)oxy]pyridin-4-yl}methyl)amine

The title compound was obtained as a yellow oil (1.84 g, 60%) in the same manner as in Reference Example 29 from 2-[(furan-3-ylmethyl)oxy]pyridine-4-carbonitrile synthesized in Reference Example 34.

$^1$H-NMR (300 MHz, CDCl$_3$) δ: 1.43 (2H, s), 3.84 (2H, s), 5.25 (2H, s), 6.50 (1H, d, J=1.3 Hz), 6.73 (1H, s), 6.84 (1H, d, J=5.3 Hz), 7.41 (1H, dd, J=1.6 Hz), 7.52 (1H, s), 8.11 (1H, d, J=5.3 Hz).

Reference Example 36

2-[(furan-2-ylmethyl)oxy]pyridine-4-carbonitrile

The title compound was obtained as a yellow oil (2.54 g, 59%) in the same manner as in Reference Example 28 from 2-chloropyridine-4-carbonitrile and furan-2-ylmethanol.

$^1$H-NMR (300 MHz, CDCl$_3$) δ: 5.37 (2H, s), 6.38 (1H, dd, J=3.2, 1.9 Hz), 6.47 (1H, d, J=3.0 Hz), 7.01 (1H, s), 7.09 (1H, dd, J=5.2, 1.2 Hz), 7.43-7.47 (1H, m), 8.32 (1H, d, J=5.3 Hz).

Reference Example 37

({2-[(furan-2-ylmethyl)oxy]pyridin-4-yl}methyl)amine

The title compound was obtained as a yellow oil (1.91 g, 75%) in the same manner as in Reference Example 31 from 2-[(furan-2-ylmethyl)oxy]pyridine-4-carbonitrile synthesized in Reference Example 36.
$^1$H-NMR (300 MHz, CDCl$_3$) δ: 1.54 (2H, s), 3.84 (2H, s), 5.33 (2H, s), 6.37 (1H, dd, J=3.1, 1.8 Hz), 6.44 (1H, d, J=3.2 Hz), 6.74 (1H, s), 6.85 (1H, dd, J=5.3, 0.9 Hz), 7.41-7.46 (1H, m), 8.11 (1H, d, J=5.3 Hz).

Reference Example 38

2-[(3-thienylmethyl)oxy]pyridine-4-carbonitrile

The title compound was obtained as a colorless oil (3.87 g, 83%) in the same manner as in Reference Example 28 from 2-chloropyridine-4-carbonitrile and 3-thienylmethanol.
$^1$H-NMR (300 MHz, CDCl$_3$) δ: 5.41 (2H, s), 7.02 (1H, s), 7.08 (1H, dd, J=5.2, 1.2 Hz), 7.16 (1H, dd, J=4.8, 1.2 Hz), 7.34 (2H, m), 8.32 (1H, d, J=5.1 Hz).

Reference Example 39

({2-[(3-thienylmethyl)oxy]pyridin-4-yl}methyl)amine

The title compound was obtained as a yellow oil (3.54 g, 90%) in the same manner as in Reference Example 31 from 2-[(3-thienylmethyl)oxy]pyridine-4-carbonitrile synthesized in Reference Example 38.
$^1$H-NMR (300 MHz, CDCl$_3$) δ: 3.85 (2H, s), 5.39 (2H, s), 6.76 (1H, s), 6.85 (1H, dd, J=5.3, 1.3 Hz), 7.17 (1H, dd, J=4.9, 1.3 Hz), 7.33 (2H, m), 8.11 (1H, d, J=5.5 Hz).

Reference Example 40

2-{[(5-methylisoxazol-3-yl)methyl]oxy}pyridine-4-carbonitrile

The title compound was obtained as a white powder (575 mg, 25%) in the same manner as in Reference Example 28 from 2-chloropyridine-4-carbonitrile and (5-methylisoxazol-3-yl)methanol.
$^1$H-NMR (300 MHz, CDCl$_3$) δ: 2.43 (3H, d, J=0.75 Hz), 5.45 (2H, s), 6.07 (1H, s), 7.06 (1H, d, J=1.13 Hz), 7.13 (1H, dd, J=5.27, 1.32 Hz), 8.28-8.37 (1H, m).

Reference Example 41

[(2-{[(5-methylisoxazol-3-yl)methyl]oxy}pyridin-4-yl)methyl]amine

The title compound was obtained as a yellow oil (398 mg, 72%) in the same manner as in Reference Example 31 from 2-{[(5-methylisoxazol-3-yl)methyl]oxy}pyridine-4-carbonitrile synthesized in Reference Example 40.
$^1$H-NMR (300 MHz, CDCl$_3$) δ: 2.32-2.51 (5H, m), 3.87 (2H, s), 5.42 (2H, s), 6.07 (1H, s), 6.77 (1H, d, J=0.75 Hz), 6.88 (1H, dd, J=5.27, 1.51 Hz), 8.11 (1H, d, J=5.27 Hz).

Reference Example 42

2-{[(3,5-dimethylisoxazol-4-yl)methyl]oxy}pyridine-4-carbonitrile

The title compound was obtained as a white powder (1.18 g, 48%) in the same manner as in Reference Example 28 from 2-chloropyridine-4-carbonitrile and (3,5-dimethylisoxazol-4-yl)methanol.
$^1$H-NMR (300 MHz, CDCl$_3$) δ: 2.32 (3H, s), 2.46 (3H, s), 5.18 (2H, s), 6.98 (1H, s), 7.10 (1H, dd, J=5.09, 1.32 Hz), 8.30 (1H, d, J=5.27 Hz).

Reference Example 43

[(2-{[(3,5-dimethylisoxazol-4-yl)methyl]oxy}pyridin-4-yl)methyl]amine

The title compound was obtained as a yellow oil (880 mg, 77%) in the same manner as in Reference Example 31 from 2-{[(3,5-dimethylisoxazol-4-yl)methyl]oxy}pyridine-4-carbonitrile synthesized in Reference Example 42.
$^1$H-NMR (300 MHz, CDCl$_3$) δ: 2.09 (2H, d, J=8.85 Hz), 2.32 (3H, s), 2.45 (3H, s), 3.85 (2H, s), 5.14 (2H, s), 6.69 (1H, s), 6.85 (1H, dd, J=5.27, 1.32 Hz), 8.09 (1H, d, J=5.27 Hz).

Reference Example 44

2-{[3-(methyloxy)propyl]oxy}pyridine-4-carbonitrile

The title compound was obtained as a yellow oil (2.46 g, 59%) in the same manner as in Reference Example 28 from 2-chloropyridine-4-carbonitrile and 3-(methyloxy)propan-1-ol.
$^1$H-NMR (300 MHz, CDCl$_3$) δ: 1.95-2.14 (2H, m), 3.35 (3H, s), 3.54 (2H, t, J=6.2 Hz), 4.42 (2H, t, J=6.5 Hz), 6.98 (1H, d, J=1.3 Hz), 7.05 (1H, dd, J=5.3, 1.3 Hz), 8.07 (1H, m), 10.07 (1H, m).

Reference Example 45

[(2-{[3-(methyloxy)propyl]oxy}pyridin-4-yl)methyl]amine

The title compound was obtained as a yellow oil (649 mg, 64%) in the same manner as in Reference Example 29 from 2-{[3-(methyloxy)propyl]oxy}pyridine-4-carbonitrile synthesized in Reference Example 44.
$^1$H-NMR (300 MHz, CDCl$_3$) δ: 1.61 (2H, s), 1.91-2.15 (2H, m), 1.94-2.15 (2H, m), 3.21-3.45 (3H, m), 3.55 (2H, d, J=6.2 Hz), 3.83 (2H, s), 6.60-6.88 (2H, m), 7.95-8.16 (1H, m, J=3.6 Hz).

Reference Example 46

2-{[3-methyl-3-(methyloxy)butyl]oxy}pyridine-4-carbonitrile

The title compound was obtained as a yellow oil (2.91 g, 61%) in the same manner as in Reference Example 28 from 2-chloropyridine-4-carbonitrile and 3-methyl-3-(methyloxy)butan-1-ol.

¹H-NMR (300 MHz, CDCl₃) δ: 1.24 (6H, s), 2.00 (2H, m), 3.23 (3H, s), 4.43 (2H, m), 6.96 (1H, m), 7.05 (1H, dd, J=5.2, 1.2 Hz), 8.29 (1H, d, J=5.3 Hz).

Reference Example 47

[(2-{[3-methyl-3-(methyloxy)butyl]oxy}pyridin-4-yl)methyl]amine

The title compound was obtained as a yellow oil (2.05 g, 80%) in the same manner as in Reference Example 29 from 2-{[3-methyl-3-(methyloxy)butyl]oxy}pyridine-4-carbonitrile synthesized in Reference Example 46.

¹H-NMR (300 MHz, CDCl₃) δ: 1.24 (6H, s), 1.67 (2H, s), 1.99 (2H, t, J=7.4 Hz), 3.23 (3H, s), 3.84 (2H, s), 4.38 (2H, t, J=7.4 Hz), 6.68 (1H, s), 6.80 (1H, d, J=5.3 Hz), 8.09 (1H, d, J=5.3 Hz).

Reference Example 48

2-[(phenylmethyl)oxy]pyridine-4-carbonitrile

The title compound was obtained as a yellow oil (2.98 g, 65%) in the same manner as in Reference Example 28 from 2-chloropyridine-4-carbonitrile and phenylmethanol.

¹H-NMR (300 MHz, CDCl₃) δ: 5.41 (2H, s), 7.04 (1H, s), 7.08 (1H, dd, J=5.2, 1.2 Hz), 7.29-7.51 (5H, m), 8.32 (1H, d, J=5.1 Hz).

Reference Example 49

({2-[(phenylmethyl)oxy]pyridin-4-yl}methyl)amine

The title compound was obtained as a yellow oil (2.40 g, 80%) in the same manner as in Reference Example 31 from 2-[(phenylmethyl)oxy]pyridine-4-carbonitrile synthesized in Reference Example 48.

¹H-NMR (300 MHz, CDCl₃) δ: 1.55 (2H, s), 3.85 (2H, s), 5.38 (2H, s), 6.78 (1H, s), 6.85 (1H, dd, J=5.3, 0.9 Hz), 7.29-7.51 (5H, m), 8.11 (1H, d, J=5.3 Hz).

Reference Example 50

2-{[(3-fluorophenyl)methyl]oxy}pyridine-4-carbonitrile

The title compound was obtained as a white powder (3.66 g, 74%) in the same manner as in Reference Example 28 from 2-chloropyridine-4-carbonitrile and (3-fluorophenyl)methanol.

¹H-NMR (300 MHz, CDCl₃) δ: 5.40 (2H, s), 6.96-7.23 (5H, m), 7.30-7.39 (1H, m), 8.31 (1H, dd, J=5.2, 0.9 Hz).

Reference Example 51

[(2-{[(3-fluorophenyl)methyl]oxy}pyridin-4-yl)methyl]amine

The title compound was obtained as a yellow oil (2.70 g, 83%) in the same manner as in Reference Example 29 from 2-{[(3-fluorophenyl)methyl]oxy}pyridine-4-carbonitrile synthesized in Reference Example 50.

¹H-NMR (300 MHz, CDCl₃) δ: 3.86 (2H, s) 5.38 (2H, s), 6.80 (1H, s), 6.86 (1H, dd, J=5.3, 0.9 Hz), 6.99 (1H, td, J=8.4, 2.7 Hz), 7.13-7.24 (2H, m), 7.28-7.38 (1H, m), 8.10 (1H, d, J=5.3 Hz).

Reference Example 52

2-{[(4-fluorophenyl)methyl]oxy}pyridine-4-carbonitrile

The title compound was obtained as a white powder (3.14 g, 64%) in the same manner as in Reference Example 28 from 2-chloropyridine-4-carbonitrile and (4-fluorophenyl)methanol.

¹H-NMR (300 MHz, CDCl₃) δ: 5.37 (2H, s), 7.00-7.12 (m, 4H), 7.36-7.48 (2H, m), 8.31 (1H, d, J=5.1 Hz).

Reference Example 53

[(2-{[(4-fluorophenyl)methyl]oxy}pyridin-4-yl)methyl]amine

The title compound was obtained as a yellow oil (2.54 g, 83%) in the same manner as in Reference Example 29 from 2-{[(4-fluorophenyl)methyl]oxy}pyridine-4-carbonitrile synthesized in Reference Example 52.

¹H-NMR (300 MHz, CDCl₃) δ: 1.47 (2H, s), 3.85 (2H, s), 5.34 (2H, s), 6.77 (1H, s), 6.85 (1H, dd, J=5.3, 1.1 Hz), 7.00-7.11 (2H, m), 7.39-7.47 (2H, m), 8.10 (1H, d, J=5.3 Hz).

Reference Example 54

2-({[3-(methyloxy)phenyl]methyl}oxy)pyridine-4-carbonitrile

The title compound was obtained as a colorless oil (2.71 g, 52%) in the same manner as in Reference Example 28 from 2-chloropyridine-4-carbonitrile and [3-(methyloxy)phenyl]methanol.

¹H-NMR (300 MHz, CDCl₃) δ: 3.82 (3H, s), 5.38 (2H, s), 6.88 (1H, dd, J=8.2, 2.5 Hz), 6.94-7.13 (4H, m), 7.22-7.37 (1H, m), 8.32 (1H, d, J=5.3 Hz).

Reference Example 55

{[2-({[3-(methyloxy)phenyl]methyl}oxy)pyridin-4-yl]methyl}amine

The title compound was obtained as a yellow oil (2.00 g, 76%) in the same manner as in Reference Example 31 from 2-({[3-(methyloxy)phenyl]methyl}oxy)pyridine-4-carbonitrile synthesized in Reference Example 54.

¹H-NMR (300 MHz, CDCl₃) δ: 1.46 (2H, s), 3.82 (3H, s), 3.85 (2H, s), 5.36 (2H, s), 6.79 (1H, s), 6.82-6.92 (2H, m), 6.98-7.09 (2H, m), 7.23-7.35 (1H, m), 8.11 (1H, d, J=5.3 Hz).

Reference Example 56

2-({[4-(methyloxy)phenyl]methyl}oxy)pyridine-4-carbonitrile

The title compound was obtained as a white powder (3.43 g, 66%) in the same manner as in Reference Example 28 from 2-chloropyridine-4-carbonitrile and [4-(methyloxy)phenyl]methanol.

$^1$H-NMR (300 MHz, CDCl$_3$) δ: 3.82 (3H, s), 5.33 (2H, s), 6.91 (2H, m), 7.01 (1H, s), 7.07 (1H, dd, J=5.2, 1.2 Hz), 7.38 (2H, m), 8.32 (1H, d, J=5.3 Hz).

Reference Example 57

{[2-({[4-(methyloxy)phenyl]methyl}oxy)pyridin-4-yl]methyl}amine

The title compound was obtained as a yellow oil (2.37 g, 68%) in the same manner as in Reference Example 31 from 2-({[4-(methyloxy)phenyl]methyl}oxy)pyridine-4-carbonitrile synthesized in Reference Example 56.
$^1$H-NMR (300 MHz, CDCl$_3$) δ: 3.81 (3H, s), 3.84 (2H, s), 5.31 (2H, s), 6.75 (1H, s), 6.84 (1H, dd, J=5.3, 1.3 Hz), 6.91 (2H, m), 8.11 (1H, d, J=5.3 Hz).

Reference Example 58

2-[(1,3-benzodioxol-5-ylmethyl)oxy]pyridine-4-carbonitrile

The title compound was obtained as a white powder (3.09 g, 56%) in the same manner as in Reference Example 28 from 2-chloropyridine-4-carbonitrile and 1,3-benzodioxol-5-ylmethanol.
$^1$H-NMR (300 MHz, CDCl$_3$) δ: 5.30 (2H, s), 5.97 (2H, s), 6.77-6.83 (1H, m), 6.88-6.96 (2H, m), 7.01 (1H, s), 7.08 (1H, dd, J=5.2, 1.2 Hz), 8.31 (1H, d, J=5.3 Hz).

Reference Example 59

({2-[(1,3-benzodioxol-5-ylmethyl)oxy]pyridin-4-yl}methyl)amine

The title compound was obtained as a yellow oil (2.23 g, 73%) in the same manner as in Reference Example 31 from 2-[(1,3-benzodioxol-5-ylmethyl)oxy]pyridine-4-carbonitrile synthesized in Reference Example 58.
$^1$H-NMR (300 MHz, CDCl$_3$) δ: 1.55 (2H, s), 3.85 (2H, d), 5.28 (2H, s), 5.96 (2H, s), 6.75 (1H, s), 6.78-6.82 (1H, m), 6.84 (1H, dd, J=5.3, 0.9 Hz), 6.89-6.99 (2H, m), 8.10 (1H, d, J=5.3 Hz).

Reference Example 60

2-[(biphenyl-4-ylmethyl)oxy]pyridine-4-carbonitrile

The title compound was obtained as a white powder (230 mg, 47%) in the same manner as in Reference Example 28 from 2-chloropyridine-4-carbonitrile and biphenyl-4-ylmethanol.
$^1$H-NMR (300 MHz, CDCl$_3$) δ: 5.45 (2H, s), 7.05-7.07 (1H, m), 7.09 (1H, dd, J=5.1, 1.3 Hz), 7.31-7.65 (m, 9H), 8.33 (1H, dd, J=5.3, 0.8 Hz).

Reference Example 61

({2-[(biphenyl-4-ylmethyl)oxy]pyridin-4-yl}methyl)amine

The title compound as a pale-yellow powder (6.87 g, 45%) in the same manner as in Reference Example 31 from 2-[(biphenyl-4-ylmethyl)oxy]pyridine-4-carbonitrile synthesized in Reference Example 60.

$^1$H-NMR (300 MHz, CDCl$_3$) δ: 1.52 (2H, s), 3.85 (2H, s), 5.42 (2H, s), 6.79 (1H, s), 6.85 (1H, dd, J=5.3, 0.8 Hz), 7.29-7.65 (9H, m), 8.12 (1H, d, J=5.3 Hz).

Reference Example 62

2-[(pyridin-4-ylmethyl)oxy]pyridine-4-carbonitrile

The title compound was obtained as a white powder (3.01 g, 66%) in the same manner as in Reference Example 28 from 2-chloropyridine-4-carbonitrile and pyridin-4-ylmethanol.
$^1$H-NMR (300 MHz, CDCl$_3$) δ: 5.44 (2H, s), 7.13 (2H, m), 7.33 (2H, d, J=5.6 Hz), 8.30 (1H, m), 8.62 (2H, m).

Reference Example 63

({2-[(pyridin-4-ylmethyl)oxy]pyridin-4-yl}methyl)amine

The title compound was obtained as a yellow oil (1.12 g, 69%) in the same manner as in Reference Example 29 from 2-[(pyridin-4-ylmethyl)oxy]pyridine-4-carbonitrile synthesized in Reference Example 62.
$^1$H-NMR (300 MHz, CDCl$_3$) δ: 1.61 (2H, s), 3.88 (2H, s), 5.42-5.46 (2H, m), 6.68-7.04 (2H, m), 7.29-7.38 (2H, m), 8.07 (1H, d, J=5.27 Hz), 8.52-8.63 (2H, m).

Reference Example 64

2-[(pyridine-3-ylmethyl)oxy]pyridine-4-carbonitrile

The title compound was obtained as a white powder (2.52 g, 55%) in the same manner as in Reference Example 28 from 2-chloropyridine-4-carbonitrile and pyridin-3-ylmethanol.
$^1$H-NMR (300 MHz, CDCl$_3$) δ: 5.44 (2H, s), 7.05 (1H, s), 7.11 (1H, dd, J=5.1, 1.3 Hz), 7.32 (1H, dd, J=7.6, 4.6 Hz), 7.73-7.82 (1H, m), 8.27-8.37 (1H, m), 8.59 (1H, dd, J=4.9, 1.7 Hz), 8.71 (1H, d, J=1.9 Hz).

Reference Example 65

({2-[(pyridine-3-ylmethyl)oxy]pyridin-4-yl}methyl)amine

The title compound was obtained as a yellow oil (1.92 g, 75%) in the same manner as in Reference Example 29 from 2-[(pyridine-3-ylmethyl)oxy]pyridine-4-carbonitrile synthesized in Reference Example 64.
$^1$H-NMR (300 MHz, CDCl$_3$) δ: 1.62 (2H, s), 3.86 (2H, s), 5.31-5.50 (2H, m), 6.78 (1H, s), 6.87 (1H, d, J=4.9 Hz), 7.20-7.34 (1H, m), 7.71-7.82 (1H, m), 8.10 (1H, d, J=5.3 Hz) 8.56 (1H, dd, J=4.8, 1.6 Hz), 8.71 (1H, d, J=1.5 Hz).

Reference Example 66

2-[(pyridin-2-ylmethyl)oxy]pyridine-4-carbonitrile

The title compound was obtained as a white powder (2.15 g, 47%) in the same manner as in Reference Example 28 from 2-chloropyridine-4-carbonitrile and pyridin-2-ylmethanol.

¹H NMR (300 MHz, CDCl₃) δ: 5.54 (2H, s), 7.06-7.15 (2H, m), 7.18-7.32 (1H, m), 7.43 (1H, d, J=7.9 Hz), 7.63-7.78 (1H, m), 8.30 (1H, d, J=5.3 Hz), 8.62 (1H, d, J=4.7 Hz).

Reference Example 67

({2-[(pyridin-2-ylmethyl)oxy]pyridin-4-yl}methyl)amine

The title compound was obtained as a yellow oil (803 mg, 37%) in the same manner as in Reference Example 31 from 2-[(pyridin-2-ylmethyl)oxy]pyridine-4-carbonitrile synthesized in Reference Example 66.

¹H-NMR (300 MHz, CDCl₃) δ: 3.87 (2H, s), 5.53 (2H, m), 6.85 (2H, m), 7.21 (1H, dd, J=7.0, 5.5 Hz), 7.45 (1H, d, J=7.9 Hz), 7.69 (1H, m), 8.09 (1H, m) 8.61 (1H, m)

Reference Example 68

2-(ethyloxy)pyridine-4-carbonitrile

The title compound was obtained as a white powder (9.8 g, 92%) in the same manner as in Reference Example 28 from 2-chloropyridine-4-carbonitrile and ethanol.

¹H-NMR (300 MHz, CDCl₃) δ: 1.40 (3H, t, J=7.2 Hz), 4.39 (2H, q, J=7.2 Hz), 6.96 (1H, dd, J=0.6, 1.2 Hz), 7.04 (1H, dd, J=1.2, 5.4 Hz), 8.29 (1H, d, J=5.4 Hz).

Reference Example 69

{[2-(ethyloxy)pyridin-4-yl]methyl}amine

The title compound was obtained as a yellow oil (6.18 g, 63%) in the same manner as in Reference Example 31 from 2-(ethyloxy)pyridine-4-carbonitrile synthesized in Reference Example 68.

¹H-NMR (300 MHz, CDCl₃) δ: 1.39 (3H, t, J=7.2 Hz), 3.75 (2H, s), 3.85 (2H, s), 4.35 (2H, q, J=7.2 Hz), 6.69 (1H, s), 6.81 (1H, dd, J=0.9, 5.4 Hz), 8.09 (1H, d, J=5.4 Hz).

Reference Example 70

2-[(4-fluorophenyl)oxy]pyridine-4-carbonitrile

To a suspension of sodium hydride (300 mg, 7.50 mmol) in DMF (5.0 mL) was added 4-fluorophenol (810 mg, 7.23 mmol) at room temperature, and the mixture was stirred for 10 min. A solution (5.0 mL) of 2-chloropyridine-4-carbonitrile (1.0 g, 7.22 mmol) in DMF was gradually added at room temperature, and the mixture was stirred overnight at room temperature. The reaction mixture was extracted with water and ethyl acetate. The organic layer was washed with saturated brine and, after drying over anhydrous sodium sulfate, concentrated under reduced pressure. The obtained residue was purified by silica gel column chromatography (2%-20% ethyl acetate/hexane) to give the title compound as a colorless oil (1.3 g, 81%).

¹H-NMR (300 MHz, CDCl₃) δ: 7.10 (2H, s), 7.12 (1H, d, J=0.9 Hz), 7.17 (1H, s), 7.20 (1H, dd, J=5.1, 1.3 Hz), 8.30 (1H, d, J=5.1 Hz)

Reference Example 71

({2-[(4-fluorophenyl)oxy]pyridin-4-yl}methyl)amine

The title compound was obtained as a yellow oil (1.53 g, 60%) in the same manner as in Reference Example 29 from 2-[(4-fluorophenyl)oxy]pyridine-4-carbonitrile synthesized in Reference Example 70.

¹H-NMR (300 MHz, CDCl₃) δ: 1.44 (2H, s), 3.90 (2H, s), 6.88 (1H, s), 6.94 (1H, d, J=5.3 Hz), 7.07 (m, 4H), 8.09 (1H, d, J=5.1 Hz).

Reference Example 72

2-{[3,4-bis(methyloxy)phenyl]oxy}pyridine-4-carbonitrile

The title compound was obtained as a white powder (2.14 g, 40%) in the same manner as in Reference Example 70 from 2-chloropyridine-4-carbonitrile and 3,4-bis(methyloxy)phenol.

¹H-NMR (300 MHz, CDCl₃) δ: 3.86 (3H, s), 3.90 (3H, s), 6.70 (2H, m), 6.90 (1H, d, J=9.4 Hz), 7.13 (1H, s), 7.19 (1H, dd, J=5.1, 1.1 Hz), 8.34 (1H, d, J=5.1 Hz).

Reference Example 73

[(2-{[3,4-bis(methyloxy)phenyl]oxy}pyridin-4-yl)methyl]amine

The title compound was obtained as a yellow oil (1.46 g, 67%) in the same manner as in Reference Example 31 from 2-{[3,4-bis(methyloxy)phenyl]oxy}pyridine-4-carbonitrile synthesized in Reference Example 72.

¹H-NMR (300 MHz, CDCl₃) δ: 3.85 (3H, s), 3.89 (3H, s), 3.89 (2H, s), 6.69 (2H, m), 6.87 (2H, m), 6.94 (1H, d, J=5.3 Hz), 8.13 (1H, d, J=5.3 Hz).

Reference Example 74

2-(tetrahydrofuran-3-yloxy)pyridine-4-carbonitrile

The title compound was obtained as a yellow oil (2.22 g, 54%) in the same manner as in Reference Example 28 from 2-chloropyridine-4-carbonitrile and tetrahydrofuran-3-ol.

¹H-NMR (300 MHz, CDCl₃) δ: 2.07-2.20 (1H, m), 2.20-2.36 (1H, m), 3.86-4.08 (m, 4H), 8.51-5.63 (1H, m), 6.97-7.02 (1H, m), 7.08 (1H, dd, J=5.3, 1.3 Hz), 8.28 (1H, dd, J=5.3, 0.9 Hz).

Reference Example 75

{[2-(tetrahydrofuran-3-yloxy)pyridin-4-yl]methyl}amine

The title compound was obtained as a yellow oil (1.84 g, 60%) in the same manner as in Reference Example 29 from 2-[(furan-3-ylmethyl)oxy]pyridine-4-carbonitrile synthesized in Reference Example 74.

¹H-NMR (300 MHz, CDCl₃) δ: 1.50 (2H, s), 2.07-2.32 (2H, m), 3.83-4.08 (6H, m), 5.53-5.61 (1H, m), 6.71 (1H, s), 6.83 (1H, d, J=5.3 Hz), 8.06 (2H, d, J=5.3 Hz).

Reference Example 76

2-(tetrahydro-2H-pyran-4-yloxy)pyridine-4-carbonitrile

The title compound was obtained as a white powder (3.20 g, 73%) in the same manner as in Reference Example 28 from 2-chloropyridine-4-carbonitrile and tetrahydro-2H-pyran-4-ol.

¹H-NMR (300 MHz, CDCl₃) δ: 1.8 (2H, m), 2.1 (2H, m), 3.6 (2H, ddd, J=11.9, 9.0, 3.0 Hz), 4.0 (2H, ddd, J=11.9, 4.7, 4.5 Hz), 5.3 (1H, tt, J=8.5, 4.2 Hz), 7.0 (1H, s), 7.1 (1H, dd, J=5.2, 1.2 Hz), 8.3 (1H, dd, J=5.1, 0.6 Hz).

Reference Example 77

{[2-(tetrahydro-2H-pyran-4-yloxy)pyridin-4-yl]methyl}amine

The title compound was obtained as a yellow oil (2.59 g, 79%) in the same manner as in Reference Example 31 from 2-(tetrahydro-2H-pyran-4-yloxy)pyridine-4-carbonitrile synthesized in Reference Example 76.
$^1$H-NMR (300 MHz, CDCl$_3$) δ: 1.47 (2H, s), 1.71 (2H, m), 1.99 (2H, m), 3.55 (2H, m), 3.77 (2H, s), 3.91 (2H, m), 5.18 (1H, m), 6.64 (1H, s), 6.74 (1H, d, J=5.1 Hz), 7.99 (1H, d, J=5.1 Hz).

Reference Example 78

2-{[3-(methyloxy)propyl]amino}pyridine-4-carbonitrile

A solution (20 mL) of [3-(methyloxy)propyl]amine (1.61 mL, 14.44 mmol) and 2-chloropyridine-4-carbonitrile (1.0 g, 7.22 mmol) in THF was refluxed overnight with stirring. The reaction mixture was cooled to room temperature and concentrated under reduced pressure. The obtained residue was purified by silica gel column chromatography (20%-50% ethyl acetate/hexane) to give the title compound as a yellow powder (429 mg, 43%).
$^1$H-NMR (300 MHz, CDCl$_3$) δ: 1.90 (2H, tt, J=6.2, 6.0 Hz), 3.36 (3H, s), 3.41 (2H, dt, J=6.4 Hz), 3.52 (2H, t, J=5.7 Hz), 5.24 (1H, m), 6.57 (1H, s), 6.71 (1H, dd, J=5.1, 1.1 Hz), 8.18 (1H, d, J=5.3 Hz).

Reference Example 79

4-(aminomethyl)-N-[3-(methyloxy)propyl]pyridine-2-amine

The title compound was obtained as a yellow oil (161 mg, 79%) in the same manner as in Reference Example 29 from 2-[(4-fluorophenyl)oxy]pyridine-4-carbonitrile synthesized in Reference Example 78.
$^1$H-NMR (300 MHz, CDCl$_3$) δ: 1.62 (2H, s), 1.89 (2H, tt, J=6.4, 6.2 Hz), 3.33-3.44 (m, 5H), 3.51 (2H, t, J=5.9 Hz), 3.78 (2H, s), 4.83 (1H, s), 6.37 (1H, s), 6.50 (1H, dd, J=5.2, 1.2 Hz), 8.01 (1H, d, J=5.3 Hz).

Reference Example 80

2-{[3-(ethyloxy)propyl]amino}pyridine-4-carbonitrile

The title compound was obtained as a yellow oil (1.82 g, 41%) in the same manner as in Reference Example 78 from 2-chloropyridine-4-carbonitrile and [3-(ethyloxy)propyl]amine.
$^1$H-NMR (300 MHz, CDCl$_3$) δ: 1.23 (3H, t, J=7.1 Hz), 1.82-1.97 (2H, m), 3.35-3.61 (6H, m), 5.31 (1H, s), 6.57 (1H, d, J=1.1 Hz), 6.70 (1H, dd, J=5.1, 1.3 Hz), 8.18 (1H, d, J=5.1 Hz).

Reference Example 81

4-(aminomethyl)-N-[3-(ethyloxy)propyl]pyridine-2-amine

The title compound was obtained as a yellow oil (1.14 g, 75%) in the same manner as in Reference Example 29 from 2-{[3-(ethyloxy)propyl]amino}pyridine-4-carbonitrile synthesized in Reference Example 80.
$^1$H-NMR (300 MHz, CDCl$_3$) δ: 1.22 (3H, t, J=7.0 Hz), 1.59 (2H, s), 1.89 (2H, tt, J=6.3 Hz), 3.33-3.60 (m, 6H), 3.77 (2H, s), 4.83 (1H, s), 6.35 (1H, s), 6.50 (1H, d, J=5.3 Hz), 8.01 (1H, d, J=5.3 Hz).

Reference Example 82

2-({3-[(1-methylethyl)oxy]propyl}amino)pyridine-4-carbonitrile

The title compound was obtained as a yellow oil (1.97 g, 41%) in the same manner as in Reference Example 78 from 2-chloropyridine-4-carbonitrile and {3-[(1-methylethyl)oxy]propyl}amine.
$^1$H-NMR (300 MHz, CDCl$_3$) δ: 1.18 (6H, d, J=6.0 Hz), 1.81-1.94 (2H, m), 3.41 (2H, q, J=6.3 Hz), 3.50-3.64 (3H, m), 5.39 (1H, s), 6.55 (1H, s), 6.69 (1H, dd, J=5.2, 1.2 Hz), 8.18 (1H, d, J=5.1 Hz).

Reference Example 83

4-(aminomethyl)-N-{3-[(1-methylethyl)oxy]propyl}pyridine-2-amine

The title compound was obtained as a yellow oil (1.23 g, 77%) in the same manner as in Reference Example 29 from 2-({3-[(1-methylethyl)oxy]propyl}amino)pyridine-4-carbonitrile synthesized in Reference Example 82.
$^1$H-NMR (300 MHz, CDCl$_3$) δ: 1.17 (6H, d, J=6.0 Hz), 1.60 (2H, s), 1.87 (2H, tt, J=6.4, 6.2 Hz), 3.39 (2H, q, J=6.4 Hz), 3.49-3.64 (3H, m), 3.77 (2H, s), 4.88 (1H, s), 6.35 (1H, s), 6.47-6.53 (1H, m), 8.01 (1H, d, J=5.3 Hz).

Reference Example 84

3-[(tetrahydrofuran-3-ylmethyl)oxy]benzonitrile

To a suspension of 60% sodium hydride (1.94 g, 48.6 mmol) in DMF (200 mL) was gradually added 3-hydroxybenzonitrile (2.75 g, 23.1 mmol). The mixture was stirred at room temperature for 45 min. Tetrahydrofuran-3-ylmethyl methanesulfonate (synthesized by a method described in JP 08259562 A2 19961008 etc.) (5.00 g, 27.7 mmol) was added, and the mixture was stirred at room temperature for 1 hr and at 90° C. for 12 hrs. After allowing to cool to room temperature, the reaction mixture was concentrated under reduced pressure. The obtained residue was extracted with ethyl acetate and washed with water (twice), 1N aqueous sodium hydroxide solution and saturated brine. The mixture was dried over anhydrous sodium sulfate, and concentrated under reduced pressure. The obtained residue was purified by silica gel column chromatography (14-17% ethyl acetate/hexane) to give the title compound as a colorless oil (3.54 g, 75%).
$^1$H-NMR (300 MHz, CDCl$_3$) δ: 1.74 (1H, m), 2.14 (1H, m), 2.77 (1H, m), 3.85 (6H, m), 7.09 (2H, m), 7.22 (1H, m), 7.36 (1H, m).

Reference Example 85

1-{3-[(tetrahydrofuran-3-ylmethyl)oxy]phenyl}methanamine

A mixture of 3-[(tetrahydrofuran-3-ylmethyl)oxy]benzonitrile (1.54 g, 7.58 mmol) obtained in Reference Example 84, Raney-nickel (1.54 g), 28% aqueous ammonia, EtOH (15 mL) and THF (15 mL) was stirred under a hydrogen atmosphere at room temperature for 12 hrs. The precipitate was removed by filtration and filtrate was concentrated under reduced pressure to give the title compound as a pale-green oil (1.57 g, quantitatively).

$^1$H-NMR (300 MHz, DMSO-$d_6$) δ: 1.52-2.23 (4H, m), 2.55-2.85 (1H, m), 3.38-4.17 (8H, m), 6.27-7.58 (4H, m).

Reference Example 86

3-(ethyloxy)benzonitrile

The title compound was obtained as a colorless oil (5.76 g, 93%) in the same manner as in Reference Example 84 from 3-hydroxybenzonitrile.

$^1$H-NMR (300 MHz, CDCl$_3$) δ: 1.43 (3H, t, J=7.1 Hz), 4.05 (2H, q, J=7.0 Hz), 7.11 (2H, m), 7.23 (1H, m), 7.36 (1H, m).

Reference Example 87

1-[3-(ethyloxy)phenyl]methanamine hydrochloride

The title compound was obtained as a white powder (6.00 g, 85%) in the same manner as in Reference Example 85 from 3-(ethyloxy)benzonitrile obtained in Reference Example 86.
melting point: 137° C.

Reference Example 88

Methyl [(3-cyanophenyl)oxy]acetate

The title compound was obtained as a white powder (1.42 g, 88%) in the same manner as in Reference Example 84 from 3-hydroxybenzonitrile and methyl bromoacetate.
melting point: 66° C.

Reference Example 89

Methyl {[3-(aminomethyl)phenyl]oxy}acetate hydrochloride

A mixture of methyl [(3-cyanophenyl)oxy]acetate (1.00 g, 5.23 mmol) obtained in Reference Example 88, 10% palladium on carbon (containing 50% water), formic acid (10 mL) and MeOH (10 mL) was stirred under a hydrogen atmosphere at room temperature for 12 hrs. The precipitate was filtered off, and the filtrate was concentrated under reduced pressure. A solution (1.50 mL, 6.00 mmol) of 4N hydrogen chloride in ethyl acetate was added to the obtained residue. The mixture was stirred and the solvent was concentrated under reduced pressure. The obtained crude crystals were recrystallized from ethyl acetate to give the title compound as a white powder (854 mg, 70%).
melting point: 121° C.

Reference Example 90

Methyl 5-[(3-cyanophenyl)oxy]pentanoate

The title compound was obtained in the same manner as in Reference Example 84 as a white powder (4.29 g, 86%) from 3-hydroxybenzonitrile and methyl 5-bromopentanoate.
melting point: 36-37° C.

Reference Example 91

Methyl 5-{[3-(aminomethyl)phenyl]oxy}pentanoate hydrochloride

The title compound was obtained in the same manner as in Reference Example 89 as a white powder (788 mg, 79%) from methyl 5-[(3-cyanophenyl)oxy]pentanoate obtained in Reference Example 90.
melting point: 88° C.

Reference Example 92

3-(3-oxo-3,4-dihydro-2H-1,4-benzooxazin-6-yl)benzonitrile

A mixture of 6-bromo-2H-1,4-benzooxazin-3(4H)-one (synthesized by a method described in *Indian Journal of Chemistry* (1969), 7(7), 658-61 etc.) (3.00 g, 13.2 mmol), (3-cyanophenyl)boronic acid (1.93 g, 13.2 mmol), [1,1'-bis(diphenylphosphino)ferrocene]dichloropalladium(II) (1.10 g, 1.32 mmol), triethylamine (9.20 mL, 65.8 mmol) and DME (300 mL) was heated under reflux under a nitrogen atmosphere at 90° C. for 10 days. The solvent was evaporated under reduced pressure, and the obtained residue was purified by -silica gel column chromatography (20-50% ethyl acetate/hexane). The obtained crude crystals were recrystallized from ethyl acetate to give the title compound as a colorless powder (1.58 g, 48%).
melting point: 242° C.

Reference Example 93

6-[3-(aminomethyl)phenyl]-2H-1,4-benzooxazin-3(4H)-one

The title compound was obtained in the same manner as in Reference Example 85 as a white powder (34.2 mg, 84%) from 3-(3-oxo-3,4-dihydro-2H-1,4-benzooxazin-6-yl)benzonitrile obtained in Reference Example 92.
melting point: 235-236° C.

Reference Example 94

1-(3-morpholin-4-ylphenyl)methanamine

The title compound was obtained as a pale-green oil (1.00 g, 98%) in the same manner as in Reference Example 85 from 3-morpholin-4-ylbenzonitrile (synthesized by a method described in WO 9808848 A1 19980305 etc.).

$^1$H-NMR (300 MHz, DMSO-$d_6$) δ: 3.09 (4H, m), 3.22 (4H, s), 3.73 (4H, m), 7.07 (4H, m).

Reference Example 95

Ethyl 6-nitro-4-oxo-3,4-dihydroquinazoline-2-carboxylate

Step 1
A mixture of 2-amino-5-nitrobenzonitrile (25.39 g) and sulfuric acid (70 ml) was stirred at 130° C. for 40 min. The reaction mixture was gradually added to ice water, and the precipitate was collected by filtration and washed with water, ethanol and diethyl ether to give 2-amino-5-nitrobenzamide (24.63 g).

Step 2

To a solution of 2-amino-5-nitrobenzamide (18.10 g) and triethylamine (15 ml) in THF (100 mL) was added dropwise a solution of ethyl chloroglyoxylate (14.36 g) in THF (20 ml) under ice-cooling, and the mixture was stirred at 0° C. for 1 hr. 1N Hydrochloric acid was added to the reaction mixture and the mixture was extracted with ethyl acetate. The organic layer was washed with water, saturated aqueous sodium hydrogen carbonate and saturated brine, dried and concentrated. The obtained crude crystals were washed with diisopropy ether to give ethyl {[2-(aminocarbonyl)-4-nitrophenyl]amino}(oxo)acetate (8.1 g).

$^1$H NMR (300 MHz, DMSO-d$_6$) δ: 1.4 (t, J=7.1 Hz, 2 H), 3.3 (s, 3 H), 4.4 (q, J=7.1 Hz, 2 H), 8.0 (d, J=8.8 Hz, 1 H), 8.6 (dd, J=8.8, 2.7 Hz, 1 H), 8.8 (d, J=2.2 Hz, 1 H).

Step 3

To a suspension of ethyl {[2-(aminocarbonyl)-4-nitrophenyl]amino}(oxo)acetate (2.81 g) in EtOH (30 mL) was added dropwise sodium ethylate (20% ethanol solution, 3.47 g) under ice-cooling, and the mixture was stirred at room temperature for 12 hrs. 10% Aqueous citric acid solution was added to the reaction mixture, and the precipitate was washed with water, ethanol and diethyl ether to give the title compound (1.886 g).

melting point: 227-228° C.

Reference Example 96

Ethyl 6-amino-4-oxo-3,4-dihydroquinazoline-2-carboxylate

Step 1

To a mixed solution of ethyl {[2-(aminocarbonyl)-4-nitrophenyl]amino}(oxo)acetate (2.292 g) obtained in Reference Example 95, Step 2 in THF (100 ml)-ethanol (50 ml) was added 10% palladium carbon (405 mg), and the mixture was subjected to catalytic reduction under a hydrogen atmosphere at room temperature for 8 hrs. The catalyst was filtered off and the filtrate was concentrated. The obtained crude crystals were washed with diisopropy ether to give ethyl {[4-amino-2-(aminocarbonyl)phenyl]amino}(oxo)acetate (1.96 g).

Step 2

To a mixed solution of ethyl {[4-amino-2-(aminocarbonyl)phenyl]amino}(oxo)acetate (1.96 g) obtained in Step 1 in THF (60 ml)-ethanol (30 ml) was added dropwise sodium ethylate (20% ethanol solution, 2.82 g), and the mixture was stirred at room temperature for 12 hrs. 10% Aqueous citric acid solution was added to the reaction mixture and the mixture was extracted with ethyl acetate. The organic layer was dried and concentrated, and the obtained crude crystals were washed with diisopropy ether to give the title compound (738 mg).

melting point: 233-235° C.

Reference Example 97

Ethyl 3-methyl-4-oxo-3,4-dihydroquinazoline-2-carboxylate

A mixture of ethyl 4-oxo-1,4-dihydroquinazoline-2-carboxylate (1.091 g), methyl iodide (0.47 ml), potassium carbonate (1.031 g) and DMF (30 ml) was stirred at room temperature for 3 hrs. Water was added to the reaction mixture and the mixture was extracted with ethyl acetate. The organic layer was washed with water and saturated brine, dried and concentrated. The obtained crude crystals were recrystallized from ethyl acetate/hexane to give the title compound (432 mg).

melting point: 48-50° C.

Reference Example 98

Ethyl 6-chloro-4-oxo-3,4-dihydroquinazoline-2-carboxylate

2-Amino-5-chlorobenzamide (2.387 g) and diethyl oxalate were stirred at 175° C. for 6 hrs. The mixture was allowed to cool and the obtained crude crystals were washed with hot EtOH to give the title compound (2.051 g).

melting point: 249-251° C.

Reference Example 99

1-oxo-1,2-dihydroisoquinoline-3-carboxylic acid

To a mixed solution of methyl 1-oxo-1,2-dihydroisoquinoline-3-carboxylate (914 mg, synthesized by a method described in *Tetrahedron Lett.*, 1999, 40, 7935) in THF (10 ml)-methanol (10 ml) was added 1N aqueous sodium hydroxide solution (10 ml), and the mixture was stirred at room temperature for 12 hrs. The reaction mixture was acidified with 1N hydrochloric acid and the mixture was extracted with ethyl acetate. The organic layer was washed with saturated brine, dried and concentrated. The obtained crude crystals were washed with diisopropy ether to give the title compound (803 mg).

$^1$H NMR (CDCl$_3$) δ: 7.40 (1H, s), 7.59-7.69 (1H, m), 7.79 (1H, dt, J=1.4 Hz, 7.5 Hz), 7.88 (1H, d, J=7.0 Hz), 8.25 (1H, d, J=7.6 Hz), 10.90 (1H, br s).

Reference Example 100

Ethyl 2-quinazolinecarboxylate

To a solution of ethyl 4-chloro-quinazoline-2-carboxylate (1.128 g) and triethylamine (0.80 ml) in ethanol (8 ml) was added 10% palladium carbon (125 mg), and the mixture was subjected to catalytic reduction at room temperature and atmospheric pressure for 3 days. The catalyst was filtered off and the filtrate was concentrated. 10% Aqueous citric acid solution was added to the residue and the mixture was extracted with ethyl acetate. The organic layer was washed with water, aqueous sodium hydrogen carbonate and brine, dried and concentrated. The obtained crude crystals were recrystallized from ethyl acetate/hexane to give the title compound (618 mg).

melting point: 71-74° C.

Reference Example 101

N-(3-methoxybenzyl)-2-quinazolinecarboxamide

A solution of ethyl 2-quinazolinecarboxylate (136 mg) obtained in Reference Example 100, m-methoxybenzylamine (190 mg) and diisopropylethylamine (0.24 ml) in toluene (1 ml) was refluxed with heating for 7 hrs. 10% Aqueous citric acid solution was added to the reaction mixture and the mixture was extracted with ethyl acetate. The organic layer was washed with water, aqueous sodium hydrogen carbonate and brine, dried and concentrated. The residue was purified by silica gel chromatography (ethyl acetate/hexane=1/2-ethyl acetate) to give the title compound (163 mg, 83%).

melting point: 91-93° C.

Reference Example 102

Methyl 4-methoxy-2-quinazolinecarboxylate

To a solution of ethyl 4-chloro-quinazoline-2-carboxylate (985 mg) in methanol (10 ml) was added 28% sodium methylate methanol solution (4.05 g). The reaction mixture was refluxed with heating for 4 hrs. After allowing to cool, 10% aqueous citric acid solution was added, and the mixture was extracted with ethyl acetate. The organic layer was washed with water, aqueous sodium hydrogen carbonate and saturated brine, dried and concentrated. The obtained crude crystals were washed with diisopropy ether to give the title compound (169 mg, 19%).
melting point: 129-130° C.

Reference Example 103

4-methoxy-N-(3-methoxybenzyl)-2-quinazolinecarboxamide

A solution of methyl 4-methoxy-2-quinazolinecarboxylate (60 mg) obtained in Reference Example 102, m-methoxybenzylamine (172-mg) and diisopropylethylamine (0.05 ml) in toluene (2 ml) was refluxed with heating for 16 hrs. 10% Aqueous citric acid solution was added to the reaction mixture and the mixture was extracted with ethyl acetate. The organic layer was washed with water, aqueous sodium hydrogen carbonate and brine, dried and concentrated. The residue was purified by silica gel chromatography (ethyl acetate/hexane=1/2-ethyl acetate) to give the title compound (60 mg, 67%).
melting point: 129-130° C.

Reference Example 104

5-(methyloxy)pyridine-3-carbonitrile

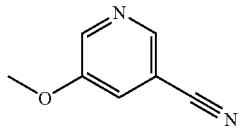

A suspension of 3,5-dibromopyridine (3.0 g, 12.6 mmol) and sodium methoxide (3.4 g, 62.9 mmol) in DMF (20 mL) was stirred at room temperature for 15 hrs and the solvent was evaporated under reduced pressure. The concentrated residue was extracted with ethyl acetate and water. The organic layer was washed with saturated brine, dried over anhydrous sodium sulfate and concentrated under reduced pressure. The obtained residue was purified by silica gel column chromatography (2%-20% ethyl acetate/hexane) to give 3-bromo-5-(methyloxy)pyridine as a white powder. (1.25 g, 53%). A suspension of the obtained 3-bromo-5-(methyloxy)pyridine (500 mg, 2.659 mmol), zinc cyanide (187 mg, 1.59 mmol) and tetrakistriphenylphosphine palladium (154 mg, 0.133 mmol) in DMF was reacted in a microwave reaction apparatus at 80° C. for 10 min. and then at 120° C. for 10 min. The mixture was allowed to cool to room temperature and the solvent was evaporated under reduced pressure. The concentrated residue was extracted with ethyl acetate. The organic layer was washed with saturated brine, dried over anhydrous sodium sulfate and concentrated under reduced pressure. The obtained residue was purified by silica gel column chromatography (2%-30% ethyl acetate/hexane) to give the title compound as a colorless oil (300 mg, 84%).

$^1$H-NMR (300 MHz, CDCl$_3$) δ: 3.91 (3H, s), 7.40 (1H, dd, J=2.8, 1.7 Hz), 8.49 (1H, d, J=1.5 Hz), 8.51 (1H, d, J=3.0 Hz).

Reference Example 105

2-({3-[(phenylmethyl)oxy]propyl}oxy)pyridine-4-carbonitrile

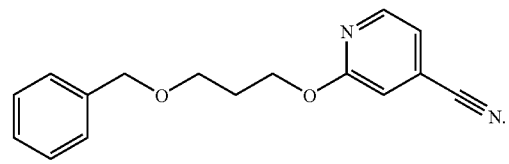 [SMILES: N#Cc1ccnc(OCCCOCc2ccccc2)c1]

The title compound was obtained as a white powder (6.27 g, 65%) from 2-chloropyridine-4-carbonitrile and 3-[(phenylmethyl)oxy]propan-1-ol by a method similar to that of Reference Example 28.
$^1$H-NMR (300 MHz, CDCl$_3$) δ: 2.04-2.14 (2H, m), 3.63 (2H, t, J=6.1 Hz), 4.45 (2H, t, J=6.3 Hz), 4.52 (2H, s), 6.94 (1H, s), 7.05 (1H, dd, J=5.1, 1.3 Hz), 7.27-7.34 (5H, m), 8.28 (1H, d, J=5.1 Hz).

Reference Example 106

{[2-({3-[(phenylmethyl)oxy]propyl}oxy)pyridin-4-yl]methyl}amine

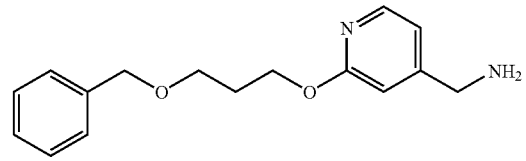 [SMILES: NCc1ccnc(OCCCOCc2ccccc2)c1]

The title compound was obtained as a yellow oil (1.89 g, 62%) from 2-({3-[(phenylmethyl)oxy]propyl}oxy)pyridine-4-carbonitrile synthesized in Reference Example 105 by a method similar to that of Reference Example 31.
$^1$H-NMR (300 MHz, CDCl$_3$) δ: 1.39 (2H, s), 2.04-2.14 (2H, m), 3.65 (2H, t, J=6.4 Hz), 3.84 (2H, s), 4.41 (2H, t, J=6.4 Hz), 4.52 (2H, s), 6.68 (1H, s), 6.81 (1H, dd, J=5.3, 1.3 Hz), 7.23-7.36 (5H, m), 8.08 (1H, d, J=5.3 Hz).

Reference Example 107

2-({2-[(phenylmethyl)oxy]ethyl}oxy)pyridine-4-carbonitrile

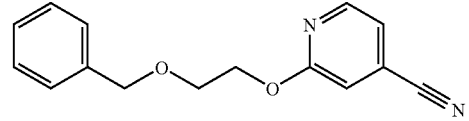 [SMILES: N#Cc1ccnc(OCCOCc2ccccc2)c1]

The title compound was obtained as a yellow oil (11.8 g, 64%) from 2-chloropyridine-4-carbonitrile and 2-[(phenylmethyl)oxy]ethanol by a method similar to that of Reference Example 28.
$^1$H-NMR (300 MHz, CDCl$_3$) δ: 3.79-3.86 (2H, m), 4.50-4.56 (2H, m), 4.61 (2H, s), 7.01-7.09 (2H, m), 7.27-7.40 (5H, m), 8.27 (1H, d, J=5.3 Hz).

Reference Example 108

Ethyl 4-[(3-cyanophenyl)oxy]butanoate

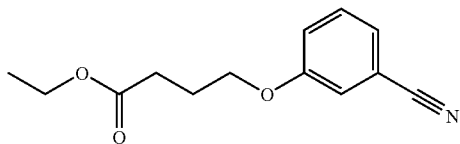 [SMILES: CCOC(=O)CCCOc1cccc(C#N)c1]

The title compound was obtained as a white powder (10.3 g, 99%) from 3-hydroxybenzonitrile and ethyl 4-hydroxybutanoate by a method similar to that of Reference Example 84.

$^1$H-NMR (300 MHz, CDCl$_3$) δ: 1.27 (3H, t, J=7.2 Hz), 2.13 (2H, tt, J=6.7 Hz), 2.52 (2H, t, J=7.2 Hz), 4.03 (2H, t, J=6.1 Hz), 4.16 (2H, q, J=7.2 Hz), 7.08-7.16 (2H, m), 7.21-7.26 (1H, m), 7.32-7.40 (1H, m).

Reference Example 109

Ethyl 4-{[3-(aminomethyl)phenyl]oxy}butanoate hydrochloride

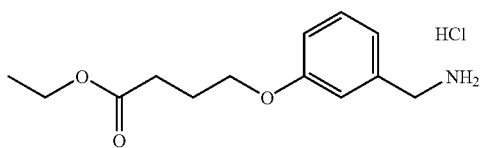 [SMILES: CCOC(=O)CCCOc1cccc(CN)c1 ; Cl]

The title compound was obtained as a white powder (7.79 g, 78%) from ethyl 4-[(3-cyanophenyl)oxy]butanoate obtained in Reference Example 108 by a method similar to that of Reference Example 89.

$^1$H-NMR (300 MHz, DMSO-d$_6$) δ: 1.18 (3H, t, J=7.2 Hz), 1.98 (2H, tt, J=6.8 Hz), 2.46 (2H, t, J=7.3 Hz), 3.95-4.03 (4H, m), 4.07 (2H, q, J=7.1 Hz), 6.92 (1H, dd, J=8.2, 2.2 Hz), 7.04 (1H, d, J=7.3 Hz), 7.12 (1H, s), 7.31 (1H, t, J=7.9 Hz), 8.26 (3H, s).

Reference Example 110

Methyl 4-nitro-1-(3-phenylpropyl)-1H-pyrazole-5-carboxylate

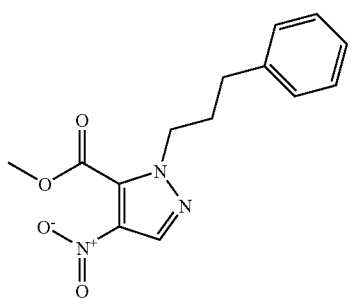 [SMILES: COC(=O)c1c([N+](=O)[O-])cnn1CCCc1ccccc1]

Reference Example 111

Methyl 4-nitro-1-(3-phenylpropyl)-1H-pyrazole-3-carboxylate

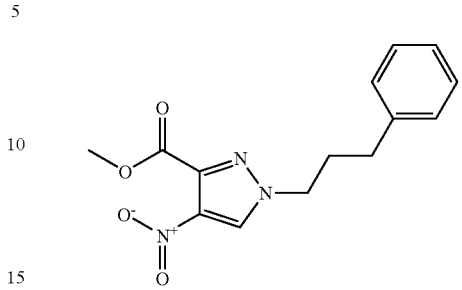

(Step 1)

Thionyl chloride (9.2 mL) was added dropwise to a solution of 4-nitro-1H-pyrazole-3-carboxylic acid (19.77 g, 125.9 mmol) in methanol (200 mL) at 0° C. The reaction mixture was stirred at room temperature overnight and the solvent was evaporated under reduced pressure. The residue was combined with water and extracted with ethyl acetate. The organic layer was washed with saturated aqueous sodium hydrogen carbonate solution and saturated brine, dried and concentrated. The obtained crude crystal was washed with diisopropyl ether to give methyl 4-nitro-1H-pyrazole-5-carboxylate (17.77 g, 82%).

$^1$H NMR (300 MHz, CDCl$_3$) δ: 4.06 (3H, s), 8.50 (1H, s).

(Step 2)

Methyl 4-nitro-1H-pyrazole-5-carboxylate (3.587 g, 21.0 mmol), (3-bromopropyl)benzene (4.178 g, 21.0 mmol) and potassium carbonate (2.940 g, 21.3 mmol) were added to acetone (100 ml). The reaction mixture was refluxed under heating for 3 hrs. After allowing to cool, water and ethyl acetate were added and the organic layer was separated. The organic layer was washed with saturated brine, dried and concentrated under reduced pressure. The residue was separated by silica gel column chromatography (ethyl acetate-hexane) to give methyl 4-nitro-1-(3-phenylpropyl)-1H-pyrazole-5-carboxylate (1.83 g) and methyl 4-nitro-1-(3-phenylpropyl)-1H-pyrazole-3-carboxylate (3.76 g).

Methyl 4-nitro-1-(3-phenylpropyl)-1H-pyrazole-5-carboxylate oil $^1$H-NMR (300 MHz, DMSO-d$_6$) δ: 2.16-2.28 (2H, m), 2.65 (2H, t, J=7.5 Hz), 3.96 (3H, s), 4.27 (2H, t, J=7.5 Hz), 7.14-7.34 (5H, m), 8.04 (1H, s).

methyl 4-nitro-1-(3-phenylpropyl)-1H-pyrazole-3-carboxylate melting point: 80-82° C.

Reference Example 112

Methyl 4-amino-1-(3-phenylpropyl)-1H-pyrazole-3-carboxylate

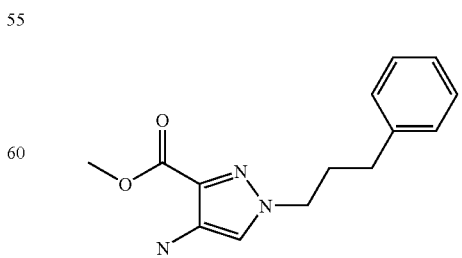

To a mixed solution of methyl 4-nitro-1-(3-phenylpropyl)-1H-pyrazole-3-carboxylate (638 mg, 2.21 mmol) obtained in Reference Example 111 in methanol (10 ml) and ethyl acetate (5 ml) was added 10% palladium carbon (0.20 g) to perform catalytic reduction under a hydrogen atmosphere (1 atm) overnight at room temperature. The catalyst was filtered off and the filtrate was concentrated under reduced pressure. The obtained crude crystals were washed with diisopropyl ether to give the title compound (564 mg).

$^1$H-NMR (300 MHz, CDCl$_3$) δ: 2.11-2.27 (2H, m), 2.62 (2H, t, J=7.7 Hz), 3.92 (3H,'s), 4.07 (2H, t, J=7.3 Hz), 6.95 (1H, s), 7.23-7.35 (5H, m).

Reference Example 113 ethyl 7-oxo-2-(3-phenylpropyl)-6,7-dihydro-2H-pyrazolo[4,3-d]pyrimidine-5-carboxylate

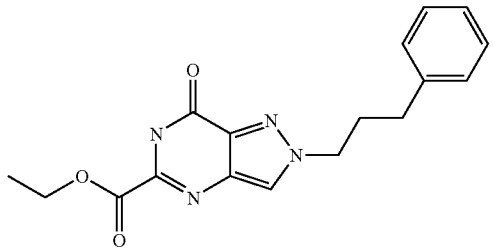 [SMILES: CCOC(=O)c1nc2cn(CCCc3ccccc3)nc2c(=O)[nH]1]

Methyl 4-amino-1-(3-phenylpropyl)-1H-pyrazole-3-carboxylate (421 mg, 1.62 mmol) obtained in Reference Example 112 and ethyl cyanoformate (177 mg, 1.79 mmol) were added to 1N hydrogen chloride-acetic acid (10 ml) and the mixture was stirred with heating at 90° C. for 4.5 hrs. After allowing to cool, water was added, and the precipitated crude crystals were collected by filtration and washed with water and diisopropyl ether to give the title compound (289 mg).

$^1$H-NMR (300 MHz, CDCl$_3$) δ: 1.46 (3H, t, J=7.2 Hz), 2.30-2.41 (2H, m, J=7.2, 7.2, 7.2, 7.2 Hz), 2.63 (2H, t, J=7.4 Hz), 4.35 (2H, t, J=7.0 Hz), 4.53 (2H, q, J=7.2 Hz), 7.15 (5H, s), 7.99 (1H, s), 9.77 (1H, s).

Anal. Calcd for C$_{17}$H$_{18}$N$_4$O$_3$: C, 62.57; H, 5.56; N, 17.17. Found: C, 62.36; H, 5.59; N, 17.17.

melting point: 195-197° C.

Reference Example 114

Methyl 4-amino-1-(3-phenylpropyl)-1H-pyrazole-5-carboxylate

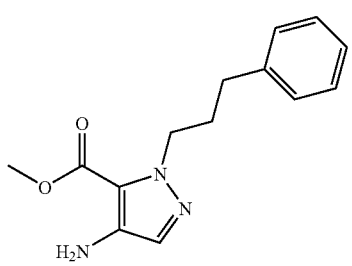 [SMILES: COC(=O)c1c(N)cnn1CCCc1ccccc1]

To a mixed solution of methyl 4-nitro-1-(3-phenylpropyl)-1H-pyrazole-5-carboxylate (1.117 g, 3.86 mmol) obtained in Reference Example 110 in methanol (20 ml)-ethyl acetate (10 ml) was added 10% palladium carbon (0.428 g) to perform catalytic reduction under a hydrogen atmosphere (1 atm) at room temperature for 8 hrs. The catalyst was filtered off, and the filtrate was concentrated under reduced pressure. The obtained crude crystals were washed with diisopropyl ether to give the title compound (1.280 g).

$^1$H-NMR (300 MHz, CDCl$_3$) δ: 2.05-2.15 (2H, m), 2.62 (2H, t), 3.86 (3H, s), 4.10 (2H, s), 4.44 (2H, t), 7.15-7.20 (2H, m), 7.23-7.30 (3H, m).

Reference Example 115 ethyl 7-oxo-1-(3-phenylpropyl)-6,7-dihydro-1H-pyrazolo[4,3-d]pyrimidine-5-carboxylate

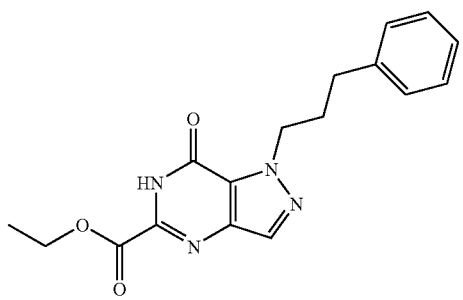 [SMILES: CCOC(=O)c1nc2cnn(CCCc3ccccc3)c2c(=O)[nH]1]

Methyl 4-amino-1-(3-phenylpropyl)-1H-pyrazole-5-carboxylate (1280 mg, 4.94 mmol) obtained in Reference Example 114 and ethyl cyanoformate (549 mg, 5.54 mmol) were added to 1N hydrogen chloride-acetic acid (30 ml), and the mixture was stirred with heating at 90° C. for 5 hrs. After allowing to cool, water was added, and the precipitated crude crystals were collected by filtration and washed with water, ethanol and diisopropyl ether to give the title compound (1.031 g).

$^1$H-NMR (300 MHz, DMSO-d$_6$) δ: 1.33 (3H, t, J=7.2 Hz), 2.09-2.19 (2H, m), 2.51-2.58 (2H, m), 4.34 (2H, q, J=7.1 Hz), 4.59 (2H, t, J=6.9 Hz), 7.12-7.19 (3H, m), 7.21-7.27 (2H, m), 8.18 (1H, s), 12.66 (1H, s).

Anal. Calcd for C$_{17}$H$_{18}$N$_4$O$_3$: C, 62.57; H, 5.56; N, 17.17. Found: C, 62.44; H, 5.57; N, 17.2.

melting point: 180-182° C.

Reference Example 116 ethyl 5-{[4-(ethoxycarbonyl)phenoxy]methyl}-4-oxo-3,4-dihydrothieno[2,3-d]pyrimidine-2-carboxylate

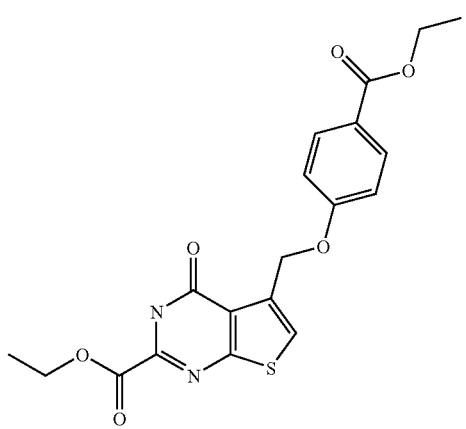 [SMILES: CCOC(=O)c1ccc(OCc2csc3nc(C(=O)OCC)[nH]c(=O)c23)cc1]

To a suspension of 60% oily sodium hydride (0.276 g, 11.5 mmol) in THF (10 ml) was added dropwise a solution of ethyl 5-(bromomethyl)-4-oxo-3,4-dihydrothieno[2,3-d]pyrimidine-2-carboxylate (1.500 g, 4.73 mmol) obtained in Example 216, step 1 and ethyl p-hydroxybenzoate (0.865 g, 5.21 mmol) in THF (30 ml) at 0° C. The reaction mixture was stirred overnight at room temperature and added to a 10% aqueous citric acid solution, and the mixture was extracted with THF/ethyl acetate. The organic layer was washed with saturated aqueous sodium hydrogen carbonate and saturated brine, dried and concentrated under reduced pressure. The obtained crude crystals were washed with a mixed solution of ethyl acetate-hexane (1/1) to give the title compound (820 mg).

melting point: 205-208° C.

Reference Example 117

Methyl 4-amino-1-[2-({4-[(methyloxy)carbonyl]phenyl}oxy)ethyl]-1H-pyrazole-5-carboxylate

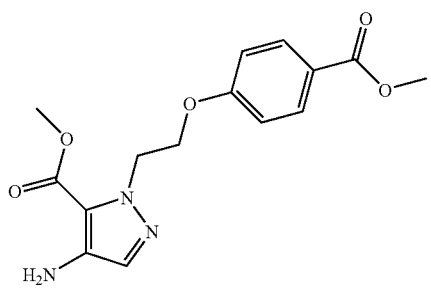 [SMILES: COC(=O)c1ccc(OCCn2ncc(N)c2C(=O)OC)cc1]

(Step 1)

Methyl 4-nitro-1H-pyrazole-5-carboxylate (5.37 g, 31.4 mmol) obtained in Reference Example 110, step 1, 4-[(2-bromoethyl)oxy]benzoate (8.15 g, 31.5 mmol) and otassium carbonate (4.37 g, 31.6 mmol) were added to acetone (150 ml). The reaction mixture was refluxed nder heating for 4 hrs. After allowing to cool, a mixed solution of water and ethyl acetate/THF was added to separate the organic layer. The organic layer was washed with saturated brine, dried and concentrated under reduced pressure. The obtained solid was washed with hexane to give a mixture (7.42 g) of methyl 1-[2-({4-[(methyloxy)carbonyl]phenyl}oxy)ethyl]-4-nitro-1H-pyrazole-5-carboxylate and methyl 1-[2-({4-[(methyloxy)carbonyl]phenyl}oxy)ethyl]-4-nitro-1H-pyrazole-3-carboxylate.

(Step 2)

To a mixed solution of the mixture (7.42 g) of methyl 1-[2-({4-[(methyloxy)carbonyl]phenyl}oxy)ethyl]-4-nitro-1H-pyrazole-5-carboxylate and methyl 1-[2-({4-[(methyloxy)carbonyl]phenyl}oxy)ethyl]-4-nitro-1H-pyrazole-3-carboxylate in THF (200 ml)-methanol (100 ml) was added 10% palladium carbon (1.17 g) to perform catalytic reduction under a hydrogen atmosphere overnight at room temperature. The catalyst was filtered off, and the filtrate was concentrated. The precipitated methyl 4-amino-1-[2-({4-[(methyloxy)carbonyl]phenyl}oxy)ethyl]-1H-pyrazole-3-carboxylate (3.62 g) was filtered off and the filtrate was concentrated. The residue was purified by silica gel column chromatography to give the title compound (2.18 g).

$^1$H-NMR (300 MHz, CDCl$_3$) δ: 3.88 (3H, s), 3.93 (3H, s), 4.33-4.40 (2H, m), 4.44-4.51 (2H, m), 6.85-6.91 (2H, m), 7.15 (1H, s), 7.95-8.01 (2H, m).

Reference Example 118 ethyl 1-[2-({4-[(methyloxy)carbonyl]phenyl}oxy)ethyl]-7-oxo-6,7-dihydro-1H-pyrazolo[4,3-d]pyrimidine-5-carboxylate

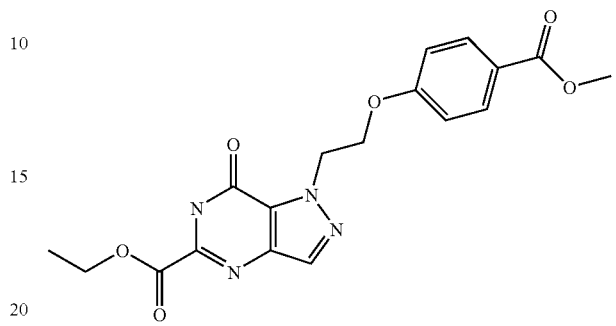

Methyl 4-amino-1-[2-({4-[(methyloxy)carbonyl]phenyl}oxy)ethyl]-1H-pyrazole-5-carboxylate (2.180 g, 6.83 mmol) obtained in Reference Example 117 and ethyl cyanoformate (811 mg, 8.18 mmol) were added to 1N hydrogen chloride-acetic acid (40 ml) and the mixture was stirred with heating at 90° C. for 4 hrs. After allowing to cool, diethyl ether was added, and the precipitated crude crystals were collected by filtration and washed with diethyl ether to give the title compound (1.793 g).

$^1$H-NMR (300 MHz, CDCl$_3$) δ: 1.48 (3H, t, J=7.1 Hz), 3.87 (3H, s), 4.49-4.59 (4H, m), 5.09 (2H, t, J=5.5 Hz), 6.85 (2H, d, J=9.0 Hz), 7.94 (2H, d, J=9.0 Hz), 8.13 (1H, s), 9.99 (1H, s).

melting point: 194-196° C.

Reference Example 119 ethyl 5-(2-ethoxy-2-oxoethyl)-4-oxo-3,4-dihydrothieno[2,3-d]pyrimidine-2-carboxylate

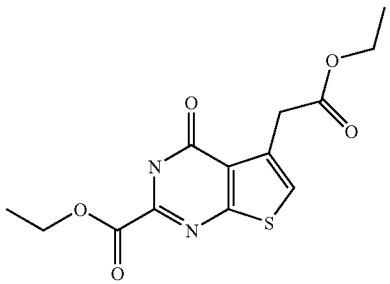 [SMILES: CCOC(=O)Cc1csc2nc(C(=O)OCC)[nH]c(=O)c12]

Ethyl 2-amino-4-[2-(ethyloxy)-2-oxoethyl]thiophene-3-carboxylate (synthesized by a method described in Monatshefet Chemie, 132, 279 (2001), 2.197 g, 8.538 mmol) and ethyl cyanoformate (1.017 g, 10.0 mmol) were added to 1N hydrogen chloride-acetic acid (50 ml), and the mixture was stirred with heating at 90° C. for 5 hrs. After allowing to cool, diethyl ether was added, the precipitated solid was collected by filtration, and dissolved in ethanol (100 ml). Thionyl chloride (0.3 ml, 4.1 mmol) was added dropwise to this solution at 0° C. and the mixture was stirred at room temperature for 1 hr. The solvent was evaporated under reduced pressure and the obtained crude crystals were washed with ethyl acetate to give the title compound (1.026 g).

$^1$H-NMR (300 MHz, DMSO-d$_6$) δ: 1.18 (3H, t, J=7.1 Hz), 1.34 (3H, t, J=7.1 Hz), 3.98 (2H, s), 4.08 (2H, q, J=7.0 Hz), 4.37 (2H, q, J=7.2 Hz), 7.58 (1H, s), 12.79 (1H, s).
Anal. Calcd for C$_{13}$H$_{14}$N$_2$O$_5$S.0.5H$_2$O: C, 48.90; H, 4.73; N, 8.77. Found: C, 49.2; H, 4.64; N, 9.25.
melting point: 182-184° C.

Reference Example 120

2-[6-(dimethylamino)-7-(3-methoxybenzyl)-4,8-dioxo-4,6,7,8-tetrahydroimidazo[1,5-a]thieno[2,3-d]pyrimidin-3-yl]ethyl methanesulfonate

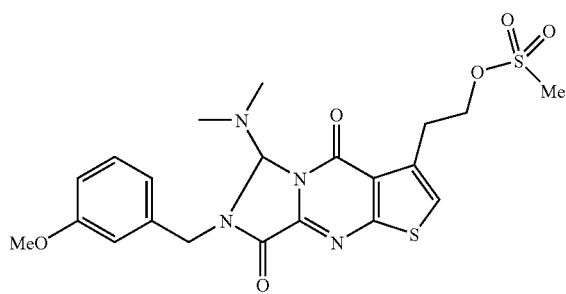 [SMILES: COc1cccc(CN2C(=O)c3nc4scc(CCOS(C)(=O)=O)c4c(=O)n3C2N(C)C)c1]

To a solution of oxalyl chloride (0.11 ml, 1.2 mmol) in THF (10 ml) was added DMF (0.1 ml, 1.3 mmol) at 0° C. The obtained suspension was stirred at room temperature for 30 min. and a solution of [3-(methyloxy)phenyl]methyl 5-{2-[(methylsulfonyl)oxy]ethyl}-4-oxo-3,4-dihydrothieno[2,3-d]pyrimidine-2-carboxylate (0.213 g, 0.49 mmol) obtained in Example 255 in THF (10 ml) was added at room temperature. The reaction mixture was stirred at room temperature for 4 hrs., and water was added. The mixture was extracted with ethyl acetate. The organic layer was washed with saturated brine, dried and concentrated under reduced pressure. The residue was purified by silica gel chromatography to give the title compound (0.164 g).
$^1$H-NMR (300 MHz, CDCl$_3$) δ: 2.47 (6H, s), 2.94 (3H, s), 3.34-3.59 (2H, m), 3.80 (3H, s), 4.04-4.18 (1H, m), 4.45-4.60 (2H, m), 5.26 (1H, d, J=14.1 Hz), 5.98 (1H, s), 6.84-6.94 (3H, m), 7.21-7.32 (2H, m).

Reference Example 121 ethyl 4-{2-[6-(dimethylamino)-7-(3-methoxybenzyl)-4,8-dioxo-4,6,7,8-tetrahydroimidazo[1,5-a]thieno[2,3-d]pyrimidin-3-yl]ethoxy}benzoate

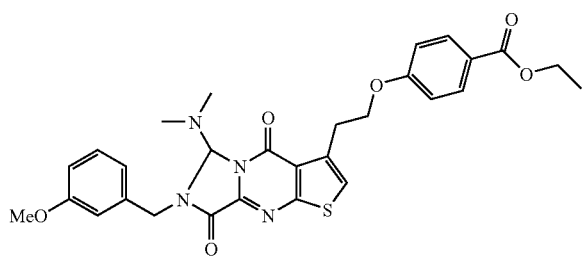 [SMILES: CCOC(=O)c1ccc(OCCc2csc3nc4n(c(=O)c23)C(N(C)C)N(Cc2cccc(OC)c2)C4=O)cc1]

2-(6-(Dimethylamino)-7-{[3-(methyloxy)phenyl]methyl}-4,8-dioxo-4,6,7,8-tetrahydroimidazo[1,5-a]thieno[2,3-d]pyrimidin-3-yl)ethyl methanesulfonate (0.155 g, 0.31 mmol) obtained in Reference Example 120, ethyl p-hydroxybenzoate (0.059 g, 0.35 mmol) and potassium carbonate (0.052 g, 0.38 mmol) were added to DMF (10 ml). The reaction mixture was stirred at 80° C. for 1 hr. and allowed to cool. Water was added to the reaction mixture, and the mixture was extracted with ethyl acetate. The organic layer was washed with saturated brine, dried and concentrated under reduced pressure. The obtained residue was purified by silica gel chromatography to give the title compound (0.103 g).
$^1$H-NMR (300 MHz, CDCl$_3$) δ: 1.37 (3H, t, J=7.1 Hz), 2.48 (6H, s), 3.41-3.59 (2H, m), 3.80 (3H, s), 4.14 (1H, d, J=14.1 Hz), 4.24-4.38 (4H, m), 5.26 (1H, d, J=14.1 Hz), 5.98 (1H, s), 6.85-6.94 (5H, m), 7.22 (1H, s), 7.25-7.31 (1H, m), 7.93-7.99 (2H, m).

Reference Example 122

{4-[3-(ethyloxy)-5-methylisoxazol-4-yl]phenyl}methanol

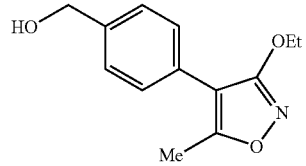 [SMILES: CCOc1noc(C)c1-c1ccc(CO)cc1]

To a solution of 3-(ethyloxy)-4-iodo-5-methylisoxazole (0.900 g, 3.56 mmol, synthesized by a method described in *Tetrahedron*, 2001, 57, 2195) in DMA (10 mL) was added bis(triphenylphosphine)dichloropalladium (II) (0.125 g, 0.178 mmol) and the mixture was stirred under a nitrogen atmosphere for 15 min. Water (10 mL), sodium hydrogen carbonate (0.897 g, 10.7 mmol) and [4-(hydroxymethyl)phenyl]boronic acid (0.810 g, 5.34 mmol) were added, and the mixture was stirred with heating at 80° C. for 15 hrs under an argon atmosphere. The mixture was allowed to cool to room temperature and partitioned between diethyl ether and water. The organic layer was washed with 1N aqueous sodium hydroxide solution, water and saturated brine, and dried over anhydrous sodium sulfate. The solvent was evaporated under reduced pressure, and the concentrated residue was purified by silica gel column chromatography (33% ethyl acetate/hexane) to give the title compound as a brown powder (798 mg, 96%).
$^1$H-NMR (200 MHz, CDCl$_3$) δ: 1.43 (3H, t, J=7.0 Hz), 1.71 (1H, t, J=7.0 Hz), 2.45 (3H, s), 4.37 (2H, q, J=7.0 Hz), 4.73 (2H, d, J=5.6 Hz), 7.43 (4H, bs).

Reference Example 123

2-{4-[3-(ethyloxy)-5-methylisoxazol-4-yl]phenyl}ethanol

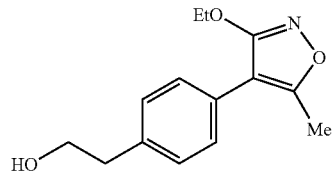 [SMILES: CCOc1noc(C)c1-c1ccc(CCO)cc1]

(Step 1)

To a solution of 2-(4-bromophenyl)ethanol (3.00 g, 14.9 mmol) in THF (60 mL) was added 1.6 M butyllithium/hexane solution (23.3 mL, 37.3 mmol) at −78° C. and the mixture was stirred at −78° C. for 1 hr and then at room temperature for 30 min. The reaction mixture was cooled again to −78° C. and triisopropylboric acid (7.02 g, 37.3 mmol) was added. The mixture was gradually heated to room temperature. Saturated aqueous ammonium chloride solution (150 mL) was added and the mixture was extracted with ethyl acetate. The organic layer was washed with saturated brine, and dried over anhydrous sodium sulfate. The solvent was evaporated under reduced pressure, and the concentrated residue was purified by silica gel column chromatography (67-100% ethyl acetate/hexane-9% methanol/ethyl acetate) to give [4-(2-hydroxyethyl)phenyl]boronic acid as a colorless amorphous form (925 mg, 37%).

(Step 2)

To a solution of 3-(ethyloxy)-4-iodo-5-methylisoxazole (0.864 g, 3.41 mmol, synthesized by the method described in Tetrahedron, 2001, 57, 2195) in DMA (15 mL) was added bis(triphenylphosphine)dichloropalladium (II) (0.120 g, 0.171 mmol), and the mixture was stirred under a nitrogen atmosphere for 15 min. Water (10 mL), sodium hydrogen carbonate (0.859 g, 10.2 mmol) and the above-mentioned [4-(2-hydroxyethyl)phenyl]boronic acid (0.850 g, 5.12 mmol) were added, and the mixture was stirred with heating at 80° C. for 15 hrs. under an argon atmosphere. The mixture was allowed to cool to room temperature, and partitioned between diethyl ether and water. The organic layer was washed with 1N aqueous sodium hydroxide solution, water and saturated brine, and dried over anhydrous sodium sulfate. The solvent was evaporated under reduced pressure, and the concentrated residue was purified by silica gel column chromatography (33% ethyl acetate/hexane) to give the title compound as a brown powder (770 mg, 91%).

$^1$H-NMR (200 MHz, CDCl$_3$) δ: 1.44 (3H, t, J=7.0 Hz), 1.40-1.47 (1H, m), 2.44 (3H, s), 2.90 (2H, t, J=6.4 Hz), 3.85-3.95 (2H, m), 4.37 (2H, q, J=7.0 Hz), 7.25-7.31 (2H, m), 7.36-7.41 (2H, m).

Reference Example 124 ethyl 4-oxo-5-{[(phenylmethyl)oxy]methyl}-3,4-dihydroquinazoline-2-carboxylate

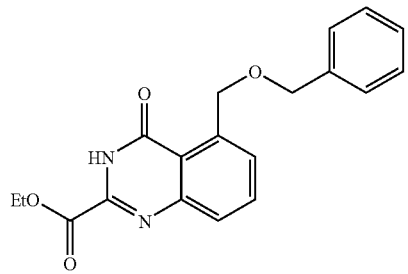 [SMILES: CCOC(=O)c1nc2cccc(COCc3ccccc3)c2c(=O)[nH]1]

(Step 1)

To a solution of ethyl 5-methyl-4-oxo-3,4-dihydroquinazoline-2-carboxylate (1.50 g, 6.46 mmol) obtained in Reference Example 17 in DMF (30 mL) was added 60% sodium hydride (284 mg, 7.10 mmol) at 0° C., and the mixture was stirred at room temperature for 30 min. The mixture was cooled to 0° C. again, {2-[(chloromethyl)oxy]ethyl}(trimethyl)silane (1.25 mL, 7.10 mmol) was added at 0° C., and the mixture was stirred at room temperature for 12 hrs. The reaction mixture was partitioned between ethyl acetate and water, and the organic layer was washed with water and saturated brine, and dried over anhydrous sodium sulfate. The solvent was evaporated under reduced pressure, and the concentrated residue was purified by silica gel column chromatography (17-50% ethyl acetate/hexane) to give ethyl 5-methyl-4-oxo-3-({[2-(trimethylsilyl)ethyl]oxy}methyl)-3,4-dihydroquinazoline-2-carboxylate as a pale-yellow oil (1.80 g, 77%).

(Step 2)

To a suspension of ethyl 5-methyl-4-oxo-3-({[2-(trimethylsilyl)ethyl]oxy}methyl)-3,4-dihydroquinazoline-2-carboxylate (1.70 g, 4.69 mmol) and N-bromosuccinimide (918 mg, 5.16 mmol) in chloroform (30 mL) was added 2,2'-azobis(isobutyronitrile) (38 mg, 234 μmol) and the mixture was heated under reflux for 3 hrs. The reaction mixture was partitioned between ethyl acetate and water, and the organic layer was washed with saturated brine and dried over anhydrous sodium sulfate. The solvent was evaporated under reduced pressure, and the concentrated residue was suspended in diethyl ether and the precipitated solid was collected by filtration. The obtained solid was purified by silica gel column chromatography (17% ethyl acetate/hexane) to give ethyl 5-(bromomethyl)-4-oxo-3-({[2-(trimethylsilyl)ethyl]oxy}methyl)-3,4-dihydroquinazoline-2-carboxylate as a pale-yellow oil (819 mg, 40%).

(Step 3)

To a solution of benzyl alcohol (108 mg, 0.996 mmol) in THF (2 mL) was added 60% sodium hydride (36.0 mg, 0.906 mmol), and the mixture was stirred at room temperature for 30 min. To this suspension was added a solution of ethyl 5-(bromomethyl)-4-oxo-3-({[2-(trimethylsilyl)ethyl]oxy}methyl)-3,4-dihydroquinazoline-2-carboxylate (200 mg, 0.453 mmol) in THF (3 mL), and the mixture was stirred at room temperature for 3 hrs. Saturated ammonium chloride was added, and the mixture was extracted with ethyl acetate. The organic layer was washed with water and saturated brine and dried over anhydrous sodium sulfate. The solvent was evaporated under reduced pressure to give ethyl 4-oxo-5-{[(phenylmethyl)oxy]methyl}-3-({[2-(trimethylsilyl)ethyl]oxy}methyl)-3,4-dihydroquinazoline-2-carboxylate as a yellow oil (220 mg). To a solution of the obtained yellow oil (200 mg) in dichloromethane (8 mL) was added trifluoroacetic acid (2 mL) at 0° C. and the mixture was stirred at 0° C. for 1 hr. and then at room temperature for 2 hrs. The solvent was evaporated under reduced pressure from the reaction mixture, and the concentrated residue was purified by silica gel column chromatography (33%-100% ethyl acetate/hexane) to give the title compound as a brown powder (42 mg, 27%).

$^1$H-NMR (200 MHz, CDCl$_3$) δ: 1.49 (3H, t, J=7.2 Hz), 4.57 (2H, q, J=7.2 Hz), 4.76 (2H, s), 5.32 (2H, s), 7.30-7.46 (5H, m), 7.78-7.86 (2H, m), 7.97-8.01 (1H, m), 9.92 (1H, bs).

Reference Example 125 ethyl 5-(bromomethyl)-4-oxo-3,4-dihydroquinazoline-2-carboxylate

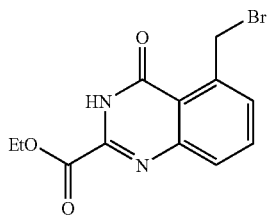 [SMILES: CCOC(=O)c1nc2cccc(CBr)c2c(=O)[nH]1]

To a suspension of ethyl 5-methyl-4-oxo-3,4-dihydroquinazoline-2-carboxylate (3.00 g, 12.9 mmol) obtained in Reference Example 17 and N-bromosuccinimide (2.53 g, 14.2 mmol) in chloroform (60 mL) was added 2,2'-azobis(isobutyronitrile) (106 mg, 645 μmol), and the mixture was heated under reflux for 1 hr. The reaction mixture was concentrated under reduced pressure, ethyl acetate was added to the concentrated residue, and the precipitated solid was collected by filtration and washed with ethyl acetate to give the title compound as a white powder (3.17 g, 79%).

$^1$H-NMR (300 MHz, CDCl$_3$) δ: 1.36 (3H, t, J=6.9 Hz), 4.39 (2H, q, J=6.9 Hz), 5.38 (2H, s), 7.67-7.69 (1H, m), 7.77-7.87 (2H, m), 12.66 (1H, bs).

Reference Example 126 ethyl 5-{[methyl(phenylmethyl)amino]methyl}-4-oxo-3,4-dihydroquinazoline-2-carboxylate

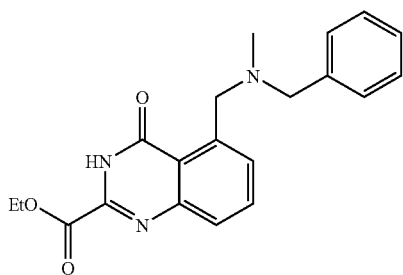

To a suspension of ethyl 5-(bromomethyl)-4-oxo-3,4-dihydroquinazoline-2-carboxylate (300 mg, 0.964 mmol) obtained in Reference Example 125 in THF (6 mL)-DMF (2 mL) were added pyridine (0.078 mL, 0.964 mmol) and N-methyl-1-phenylmethanamine (117 mg, 0.964 mmol) at 0° C. and the mixture was stirred at room temperature for 2 hrs. 1N Hydrochloric acid (2 mL) and water were added to the reaction mixture and the mixture was washed with ethyl acetate. 1N Aqueous sodium hydroxide solution (4 mL) was added to the aqueous layer and the object product was extracted with ethyl acetate. The organic layer was dried over anhydrous sodium sulfate and the solvent was evaporated under reduced pressure. Diethyl ether was added to the concentrated residue and the precipitated solid was collected by filtration to give the title compound as a white powder (200 mg, 59%).

$^1$H-NMR (300 MHz, CDCl$_3$) δ: 1.67 (3H, t, J=7.2 Hz), 2.50 (3H, s), 3.99 (2H, bs), 4.58 (2H, s), 4.69 (2H, q, J=6.9 Hz), 7.56-7.71 (5H, m), 8.02 (1H, d, J=9.0 Hz), 8.13-8.22 (2H, m), 12.69 (1H, bs).

Reference Example 127

1-(3-ethylphenyl)methanamine

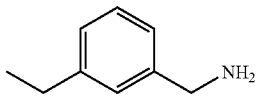

(Step 1)

A suspension of 1-bromo-3-ethylbenzene (2.00 g, 10.8 mmol), zinc cyanide (698 mg, 5.94 mmol) and tetrakis(triphenylphosphine)palladium (624 mg, 0.540 mmol) in DMF (20 mL) was stirred at 80° C. for 4 hrs. under an argon atmosphere. The reaction mixture was concentrated under reduced pressure and ethanol was added to the concentrated residue. The insoluble material was filtered off and the filtrate was concentrated to give 3-ethylbenzonitrile as a brown oil (1.07 g, 76%).

(Step 2)

The title compound was obtained as a pale-green oil from 3-ethylbenzonitrile obtained in Step 1 of Reference Example 127 by a method similar to that of Reference Example 85 (400 mg, 39%).

$^1$H-NMR (200 MHz, DMSO-d$_6$) δ: 1.18 (3H, t, J=7.6 Hz), 2.58 (2H, q, J=7.6 Hz), 3.20-3.35 (4H, m), 6.99-7.66 (4H, m).

Reference Example 128

1,1-dimethylethyl {[3-(methylthio)phenyl]methyl}carbamate

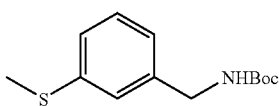 [SMILES: CSc1cccc(CNC(=O)OC(C)(C)C)c1]

To a solution of [3-(methylthio)phenyl]acetic acid (6.81 g, 37.4 mmol) in toluene (120 mL) were added triethylamine (3.97 g, 39.2 mmol) and diphenylphosphoryl azide (10.8 g, 39.2 mmol), and the mixture was stirred at room temperature for 1 hr. and then with heating at 90° C. for 1 hr. 2-Methyl-2-propanol (71.5 mL, 747 mmol) was added to the reaction mixture and the mixture was stirred with heating at 90° C. 3 days. The reaction mixture was concentrated under reduced pressure and the concentrated residue was purified by silica gel column chromatography (14%-17% ethyl acetate/hexane) to give the title compound as a pale-yellow oil (5.00 g, 53%).

$^1$H-NMR (200 MHz, CDCl$_3$) δ: 1.46 (9H, s), 2.48 (3H, s), 4.28 (1H, d, J=5.8 Hz), 4.82 (1H, bs), 7.02-7.28 (4H, m).

Reference Example 129

1-[3-(methylthio)phenyl]methanamine hydrochloride

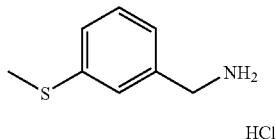

To a solution of 1,1-dimethylethyl {[3-(methylthio)phenyl]methyl}carbamate (4.90 g, 19.3 mmol) obtained in Reference Example 128 in ethyl acetate (25 mL) was added 4N hydrogen chloride-ethyl acetate solution (19.3 mL, 77.4 mmol), and the mixture was stirred at room temperature for 15 hrs. Diethyl ether (50 mL) was added and the precipitated solid was collected by filtration and washed with diethyl ether to give the title compound as a white powder (3.33 g, 91%).
$^1$H-NMR (300 MHz, DMSO-$d_6$) δ: 2.50 (3H, s), 3.99 (2H, s), 7.27-7.23 (2H, m), 7.31-7.37 (1H, m), 7.44 (1H, s), 8.45 (3H, bs).

Reference Example 130

3-[(methyloxy)methyl]benzonitrile

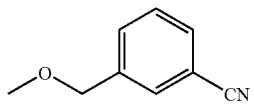

To a suspension of sodium methylate (3.03 g, 56.1 mmol) in methanol (20 mL) was added a solution of 3-(bromomethyl)benzonitrile (10.0 g, 51.0 mmol) in THF (100 mL) at 0° C., and the mixture was stirred at room temperature for 2 hrs. DMF (30 mL) and sodium methylate (1.21 g, 22.4 mmol) were added, and the mixture was stirred again at room temperature for 8 hrs. THF and methanol were evaporated under reduced pressure and the concentrated residue was partitioned between ethyl acetate and water. The organic layer was washed with water (3 times) and saturated brine, and dried over anhydrous sodium sulfate. The solvent was evaporated under reduced pressure to give the title compound as a pale-yellow oil (7.04 g, 94%).
$^1$H-NMR (200MHz, CDCl$_3$) δ: 3.42 (3H, s), 4.48 (2H, s), 7.41-7.49 (1H, m), 7.54-7.64 (3H, m).

Reference Example 131

1-{3-[(methyloxy)methyl]phenyl}methanamine

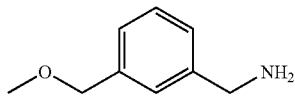

To a suspension of aluminum lithium hydride (2.90 g, 61.2 mmol) in diethyl ether (70 mL) was added dropwise a solution of 3-[(methyloxy)methyl]benzonitrile (6.00 g, 40.8 mmol) obtained in Reference Example 130 in diethyl ether (50 mL) at room temperature, and the mixture was stirred at room temperature for 2 hrs. and then heated under reflux for 1 hr. Aluminum lithium hydride (1.00 g, 21.1 mmol) was added again, and the mixture was heated under reflux for 1 hr. After cooling to 0° C., water (60 mL) and 4N aqueous sodium hydroxide solution (80 mL) were added dropwise. The insoluble material was filtered off through celite and the filtrate was extracted 3 times with ethyl acetate. The organic layers were combined, washed with saturated brine and dried over anhydrous sodium sulfate. The solvent was evaporated under reduced pressure to give the title compound as a yellow oil (4.43 g, 72%).
$^1$H-NMR (300 MHz, CDCl$_3$) δ: 3.40 (3H, s), 3.88 (2H, s), 4.46 (2H, s), 7.19-7.36 (4H, m).

Reference Example 132

Phenylmethyl {[3-(methylthio)phenyl]methyl}carbamate

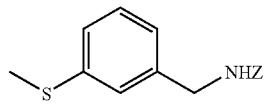

To a solution of [3-(methylthio)phenyl]acetic acid (1.00 g, 5.49 mmol) in toluene (20 mL) were added triethylamine (0.583 g, 5.76 mmol) and diphenylphosphoryl azide (1.76 g, 5.76 mmol), and the mixture was stirred at room temperature stirred for 1 hr. and then with heating at 90° C. for 1 hr. Benzyl alcohol (0.653 g, 6.04 mmol) was added to the reaction mixture, and the mixture was stirred with heating at 90° C. for 4 hrs. The reaction mixture was concentrated under reduced pressure and the concentrated residue was purified by silica gel column chromatography (25% ethyl acetate/hexane) to give the title compound as a pale-yellow oil (1.33 g, 80%).
$^1$H-NMR (200 MHz, DMSO-$d_6$) δ: 2.46 (3H, s), 4.34-4.40 (2H, m), 5.14 (2H, s), 7.16-7.39 (9H, m).

Reference Example 133

Phenylmethyl {[3-(methylsulfonyl)phenyl]methyl}carbamate

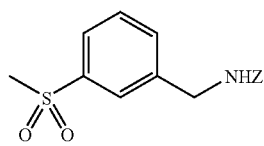

To a solution of phenylmethyl {[3-(methylthio)phenyl]methyl}carbamate (0.710 g, 2.47 mmol) obtained in Reference Example 132 in chloroform (10 mL) was added 3-chloroperbenzoic acid (1.24 g, 4.94 mmol) at room temperature, and the mixture was stirred at room temperature for 2 hrs. The reaction mixture was concentrated under reduced pressure and the concentrated residue was partitioned between ethyl acetate and water. The organic layer was washed with saturated aqueous sodium hydrogen carbonate, water and saturated brine, and dried over anhydrous sodium sulfate. The solvent was evaporated under reduced pressure, and the concentrated residue was purified by silica gel column chromatography (50% ethyl acetate/hexane) to give the title compound as a pale-yellow oil (0.540 g, 68%);
$^1$H-NMR (200 MHz, CDCl$_3$) δ: 3.03 (3H, s), 4.47 (2H, d, J=6.0 Hz), 5.14 (2H, s), 5.30 (1H, m), 7.30-7.38 (5H, m), 7.52-7.57 (2H, m), 7.82-7.86 (2H, m).

Reference Example 134

1-[3-(methylsulfonyl)phenyl]methanamine

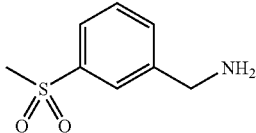

To a solution of phenylmethyl {[3-(methylsulfonyl)phenyl]methyl}carbamate (0.490 g, 1.53 mmol) obtained in Reference Example 133 in MeOH (10 mL) was added 10% Pd—C (200 mg), and the mixture was stirred under a hydrogen atmosphere (1 atm) at room temperature for 1.5 hrs. The insoluble material was filtered off and the filtrate was concentrated to give the title compound as a colorless oil (251 mg, 88%).
$^1$H-NMR (300MHz, CDCl$_3$) δ: 3.06 (3H, s), 4.00 (2H, s), 7.54 (1H, t, J=7.5 Hz), 7.64 (1H, d, J=7.5 Hz), 7.83 (1H, d, J=7.5 Hz), 7.93 (1H, s).

Reference Example 135

3-[(methylthio)methyl]benzonitrile

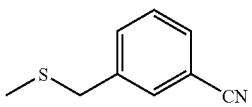

To a suspension of sodium methanethiolate (3.75 g, 53.6 mmol) in DMF (50 mL) was added 3-(bromomethyl)benzonitrile (10.0 g, 51.0 mmol) at 0° C., and the mixture was stirred at room temperature for 15 hrs. The reaction mixture was partitioned between ethyl acetate and water, and the organic layer was washed with water (3 times) and saturated brine and dried over anhydrous sodium sulfate. The solvent was evaporated under reduced pressure to give the title compound as a pale-yellow oil (8.16 g, 98%).
$^1$H-NMR (300MHz, CDCl$_3$) δ: 2.00 (3H, s), 3.68 (2H, s), 7.43 (1H, t, J=7.8 Hz), 7.54-56 (2H, m), 7.61 (1H, s).

Reference Example 136

1-{3-[(methylthio)methyl]phenyl}methanamine

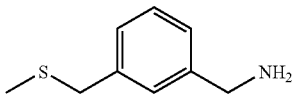

The title compound was obtained as a yellow oil (3.35 g, 82%) from 3-[(methylthio)methyl]benzonitrile obtained in Reference Example 135 by a method similar to that of Reference Example 131.
$^1$H-NMR (300MHz, CDCl$_3$) δ: 2.01 (3H, s), 3.68 (2H, s), 3.87 (2H, s), 7.17-7.33 (4H, m).

Reference Example 137

1-(3-propylphenyl)methanamine

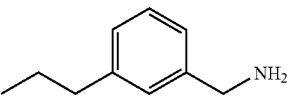

(Step 1)

A suspension of 3-(bromomethyl)benzonitrile (1.25 g, 6.38 mmol), tetraethyltin (3.00 g, 12.8 mmol) and tetrakis(triphenylphosphine)palladium (148 mg, 0.128 mmol) in HMPA (6 mL) was stirred at 60° C. for 15 hrs. The reaction mixture was partitioned between diethyl ether and water. The organic layer was washed with water and saturated brine, and dried over anhydrous sodium sulfate. The solvent was evaporated under reduced pressure, and the concentrated residue was purified by silica gel column chromatography (20% ethyl acetate/hexane) to give 3-propylbenzonitrile as a pale-yellow oil (1.25 g, crude).

(Step 2)

The title compound was obtained as a yellow oil (0.560 g, 59% by 2 steps) from 3-propylbenzonitrile by a method similar to that of Reference Example 131.
$^1$H-NMR (300MHz, CDCl$_3$) δ: 0.95 (3H, t, J=7.2 Hz), 1.60-1.68 (2H, m), 2.58 (2H, t, J=7.5 Hz), 3.84 (2H, s), 7.04-7.12 (3H, m), 7.21-7.26 (1H, m).

Reference Example 138

1-(3-ethyl-4-fluorophenyl)methanamine

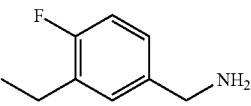

(Step 1)

A suspension of 3-bromo-4-fluorobenzonitrile (0.851 g, 4.26 mmol), tetraethyltin (2.00 g, 8.51 mmol) and tetrakis(triphenylphosphine)palladium (98.4 mg, 0.0851 mmol) in HMPA (4 mL) was stirred at 60° C. for 15 hrs. The reaction mixture was partitioned between ethyl acetate and water. The organic layer was washed with water and saturated brine, and dried over anhydrous sodium sulfate. The solvent was evaporated under reduced pressure, and the concentrated residue was purified by silica gel column chromatography (20% ethyl acetate/hexane) to give 3-ethyl-4-fluorobenzonitrile as a pale-yellow oil (1.25 g, crude).

(Step 2)

The title compound was obtained as a yellow oil (0.354 g, 54% by 2 steps) from 3-ethyl-4-fluorobenzonitrile by a method similar to that of Reference Example 131.

$^1$H-NMR (300MHz, CDCl$_3$) δ: 1.23 (3H, t, J=7.5 Hz), 2.66 (2H, q, J=7.5 Hz), 3.82 (2H, s), 6.91-6.99 (1H, m), 7.07-7.16 (2H, m).

Reference Example 139

N-(3-cyanophenyl)-2,2,2-trifluoroacetamide

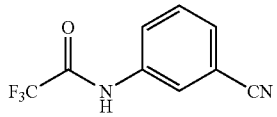 [SMILES: N#Cc1cccc(NC(=O)C(F)(F)F)c1]

To a solution of 3-aminobenzonitrile (10.0 g, 84.6 mmol) and triethylamine (23.6 mL, 169 mmol) in THF (150 mL) was added dropwise trifluoroacetic acid anhydride (18.7 g, 88.9 mmol) at 0° C., and the mixture was stirred at room temperature for 3 hrs. The reaction mixture was concentrated under reduced pressure. The concentrated residue was partitioned between ethyl acetate and water. The organic layer was washed with 0.1N hydrochloric acid, water, saturated aqueous sodium hydrogen carbonate and saturated brine, and dried over anhydrous sodium sulfate. The solvent was evaporated under reduced pressure, and hexane was added to the concentrated residue. The precipitated solid was collected by filtration to give the title compound as a brown powder (16.8 g, 93%).

$^1$H-NMR (300 MHz, DMSO-d$_6$) δ: 6.43 (1H, t, J=8.1 Hz), 7.72 (1H, dt, J=8.1, 1.5 Hz), 7.96 (1H, ddd, J=1.5, 2.1, 8.1 Hz), 8.10 (1H, t, J=1.5 Hz), 11.58 (1H, bs).

Reference Example 140

N-(3-cyanophenyl)-2,2,2-trifluoro-N-methylacetamide

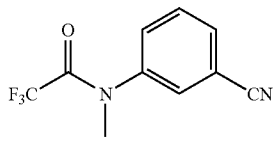 [SMILES: CN(C(=O)C(F)(F)F)c1cccc(C#N)c1]

To a solution of N-(3-cyanophenyl)-2,2,2-trifluoroacetamide (5.00 g, 23.3 mmol) obtained in Reference Example 139 and iodomethane (4.97 g, 35.0 mmol) in DMF (50 mL) was added potassium carbonate (6.45 g, 46.7 mmol) at room temperature, and the mixture was stirred at room temperature for 3 hrs. The reaction mixture was partitioned between ethyl acetate and 1N hydrochloric acid. The organic layer was washed with water and saturated brine, and dried over anhydrous sodium sulfate. The solvent was evaporated under reduced pressure, and hexane-diisopropyl ether was added to the concentrated residue. The precipitated solid was collected by filtration to give the title compound as a pale-brown powder (4.70 g, 88%).

$^1$H-NMR (300 MHz, DMSO-d$_6$) δ: 3.30 (3H, s), 7.72 (1H, t, J=8.1 Hz), 7.86 (1H, d, J=7.5 Hz), 7.96 (1H, d, J=7.2 Hz), 8.10 (1H, s).

Reference Example 141

N-[3-(aminomethyl)phenyl]-2,2,2-trifluoro-N-methylacetamide hydrochloride

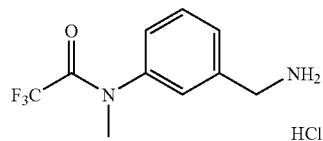 [SMILES: CN(C(=O)C(F)(F)F)c1cccc(CN)c1 ; Cl]

To a solution of N-(3-cyanophenyl)-2,2,2-trifluoro-N-methylacetamide (2.00 g, 8.77 mmol) obtained in Reference Example 140 and acetic acid (0.502 mL, 8.77 mmol) in THF (20 mL)-MeOH (20 mL) was added 10% Pd—C (2.00 g), and the mixture was stirred under a hydrogen atmosphere (1 atm) at room temperature for 2 hrs. The insoluble material was filtered off, and the filtrate was concentrated and dissolved again in ethyl acetate. 4N Hydrogen chloride-ethyl acetate solution (3.5 mL) and diethyl ether were added dropwise and the precipitated solid was collected by filtration to give the title compound as a white powder (800 mg, 34%).

$^1$H-NMR (300 MHz, DMSO-d$_6$) δ: 3.29 (3H, s), 4.06 (2H, q, J=5.4 Hz), 7.44-7.60 (4H, m), 8.46 (3H, bs).

Reference Example 142 ethyl 5-methyl-4-oxo-3,4-dihydrothieno[3,4-d]pyrimidine-2-carboxylate

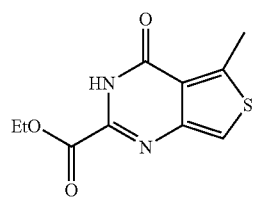 [SMILES: CCOC(=O)c1nc2csc(C)c2c(=O)[nH]1]

The title compound was obtained as a blue powder (1.48 g, 68%) from methyl 4-amino-2-methylthiophene-3-carboxylate hydrochloride (synthesized by the method described in Synth. Commun., 2002, 32(16), 2565) by a method similar to that of Reference Example 22, Step 2.

$^1$H-NMR (300 MHz, DMSO-d$_6$) δ: 1.33 (3H, d, J=7.2 Hz), 2.88 (3H, s), 4.34 (2H, q, J=7.2 Hz)-, 7.79 (1H, s), 11.72 (1H, bs).

Reference Example 143 ethyl 6-methyl-4-oxo-4,7-dihydro-3H-pyrrolo[2,3-d]pyrimidine-2-carboxylate

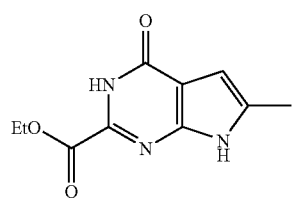

The title compound was obtained as a white powder (650 mg, 50%) from ethyl 2-amino-5-methyl-1H-pyrrole-3-carboxylate (synthesized by a method described in *J. Heterocyclic. Chem.*, 1986, 23, 1555.) by a method similar to that of Reference Example 22, Step 2.

$^1$H-NMR (300 MHz, DMSO-d$_6$) δ: 1.33 (3H, t, J=7.2 Hz), 2.31 (3H, s), 4.33 (2H, q, J=7.2 Hz), 6.26 (1H, s), 11.97 (1H, bs), 12.12 (1H, bs).

Reference Example 144 ethyl 6,7-dimethyl-4-oxo-4,7-dihydro-3H-pyrrolo[2,3-d]pyrimidine-2-carboxylate

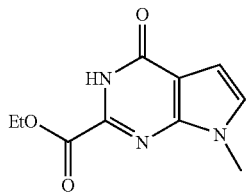 [SMILES: CCOC(=O)c1nc2c(ccn2C)c(=O)[nH]1]

The title compound was obtained as a white powder (180 mg, 26%) from ethyl 2-amino-1,5-dimethyl-1H-pyrrole-3-carboxylate (synthesized by the method described in *J. Heterocyclic. Chem.*, 1986, 23, 1555) by a method similar to that of Reference Example 22, Step 2.

$^1$H-NMR (300 MHz, DMSO-d$_6$) δ: 1.34 (3H, t, J=6.9 Hz), 2.36 (3H, s), 3.66 (3H, s), 4.36 (2H, q, J=7.2 Hz), 6.37 (1H, s), 12.06 (1H, bs).

Reference Example 145

2-amino-4,5-dimethylfuran-3-carboxamide

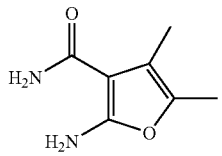

2-Amino-4,5-dimethylfuran-3-carbonitrile synthesized by a method described in *Bull. Chem. Soc. Jpn.*, 1970, 43, 3290. (4.50 g, 33.1 mmol) was added to concentrated sulfuric acid (20 mL) and the reaction mixture was stirred with heating at 60° C. for 30 min. The reaction mixture was cooled to 0° C., pulverized ice (40 g) was added carefully, and 28% aqueous ammonia (45 mL) was added dropwise to adjust the mixture to pH 9. The precipitated solid was collected by filtration, washed with water and ethanol and dried under reduced pressure to give the title compound as a brown powder (3.71 g, 73%).

$^1$H-NMR (200 MHz, DMSO-d$_6$) δ: 1.98 (3H, s), 2.03 (3H, s), 6.30 (2H, bs), 6.51 (2H, bs).

Reference Example 146

5,6-dimethyl-4-oxo-3,4-dihydrofuro[2,3-d]pyrimidine-2-carboxylic acid

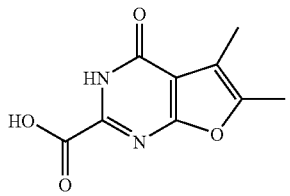

To a suspension of 2-amino-4,5-dimethylfuran-3-carboxamide (1.50 g, 10.7 mmol) obtained in Reference Example 145 and diethyl oxalate (6.26 g, 42.8 mmol) in ethanol (70 mL) was added sodium ethylate (18.2 g, 53.5 mmol) at 0° C., and the mixture was heated under reflux for 5 hrs. Sodium ethylate (9.10 g, 26.7 mmol) was added again, and the mixture was heated under reflux for 15 hrs. The reaction mixture was allowed to cool to room temperature, and poured into 1N hydrochloric acid cooled to 0° C. Ethanol was evaporated under reduced pressure, and the precipitated solid was collected by filtration, washed with water and dried to give the title compound as a brown powder (1.67 g, 75%).

$^1$H-NMR (300 MHz, DMSO-d$_6$) δ: 2.07 (3H, s), 2.15 (3H, s), 11.21 (1H, bs), 12.67 (1H, bs).

Reference Example 147

Ethyl {[3-(aminocarbonyl)-4,5-dimethylfuran-2-yl]amino}(oxo)acetate

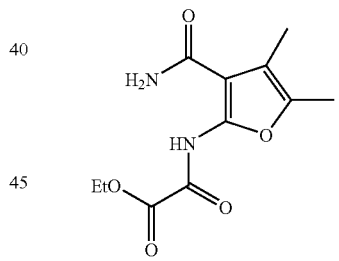

To a suspension of 5,6-dimethyl-4-oxo-3,4-dihydrofuro[2,3-d]pyrimidine-2-carboxylic acid (500 mg, 2.40 mmol) obtained in Reference Example 146 and DMF (0.1 mL) in THF (10 mL) was added dropwise oxalyl chloride (457 mg, 3.60 mmol) at 0° C., and the mixture was stirred at room temperature for 3 hrs. The reaction mixture was concentrated under reduced pressure and ethanol (5 mL) and THF (5 mL) were added to the concentrated residue. Pyridine (0.291 mL, 3.60 mmol) was further added dropwise. The mixture was stirred at room temperature for 2 hrs. and then with heating at 50° C. for 15 hrs. The reaction mixture was concentrated under reduced pressure and the concentrated residue was partitioned between ethyl acetate and water. The organic layer was washed with saturated brine and dried over anhydrous sodium sulfate. The solvent was evaporated under reduced pressure, diethyl ether-ethanol was added to the concentrated residue. The precipitated solid was collected by filtration to give the title compound as a yellow powder (297 mg, 49%).

$^1$H-NMR (300 MHz, DMSO-$d_6$) δ: 1.29 (3H, t, J=6.9 Hz), 2.02 (3H, s), 2.16 (3H, s), 4.28 (2H, q, J=6.9 Hz), 6.85-7.38 (2H, m), 11.17 (1H, bs).

Reference Example 148 ethyl 5,6-dimethyl-4-oxo-3,4-dihydrofuro[2,3-d]pyrimidine-2-carboxylate

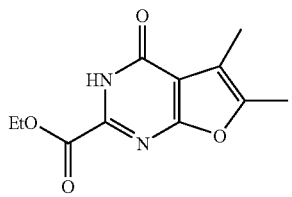 [SMILES: CCOC(=O)c1nc2oc(C)c(C)c2c(=O)[nH]1]

To a suspension of ethyl {[3-(aminocarbonyl)-4,5-dimethylfuran-2-yl]amino}(oxo)acetate (280 mg, 1.10 mmol) obtained in Reference Example 147 in toluene (20 mL) were added p-toluene sulfonic acid monohydrate (105 mg, 0.550 mmol), and the mixture was heated under reflux for 4 hrs. The reaction mixture was partitioned between ethyl acetate and water. The organic layer was washed with saturated brine, dried over sodium sulfate and concentrated under reduced pressure. The solvent was evaporated under reduced pressure and the obtained concentrated residue was crystallized from ethanol to give the title compound as a pale-yellow powder (150 mg, 58%).

$^1$H-NMR (300 MHz, DMSO-$d_6$) δ: 1.33 (3H, t, J=7.2 Hz), 2.19 (3H, s), 2.34 (3H, s), 4.35 (2H, q, J=7.2 Hz), 12.81 (1H, bs).

Reference Example 149 ethyl 1,3-dimethyl-4-oxo-4,5-dihydro-1H-pyrazolo[3,4-d]pyrimidine-6-carboxylate

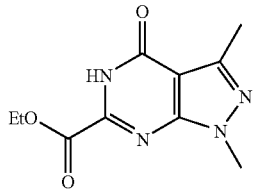 [SMILES: CCOC(=O)c1nc2c(c(C)nn2C)c(=O)[nH]1]

To a solution of 5-amino-1,3-dimethyl-1H-pyrazole-4-carboxamide (3.00 g, 19.5 mmol) synthesized by the method described in *J. Org. Chem.*, 1956, 21, 1240 and diethyl oxalate (11.4 g, 77.8 mmol) in ethanol (500 mL) was added sodium ethylate (33.1 g, 97.3 mmol) at 0° C., and the mixture was heated under reflux for 18 hrs. The reaction mixture was allowed to cool to room temperature and poured into 1N hydrochloric acid (about 100 mL) cooled to 0° C. Ethanol was evaporated under reduced pressure, and the precipitated solid was collected by filtration and washed with water and ethanol to give the title compound as a pale-yellow powder (2.52 g, 55%).

$^1$H-NMR (300 MHz, DMSO-$d_6$) δ: 1.35 (3H, t, J=7.2 Hz), 2.44 (3H, s), 3.86 (3H, s), 4.38 (2H, q, J=7.2 Hz), 12.40 (1H, bs).

Reference Example 150

2-ethyl 5-methyl 4-oxo-3,4-dihydrothieno[3,4-d]pyrimidine-2,5-dicarboxylate

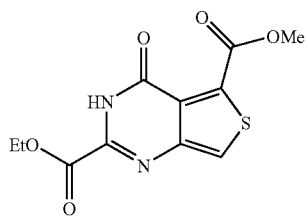 [SMILES: CCOC(=O)c1nc2csc(C(=O)OC)c2c(=O)[nH]1]

The title compound was obtained as a white powder (707 mg, 54%) from dimethyl 4-aminothiophene-2,3-dicarboxylate hydrochloride (synthesized by a method described in *Synth. Commun.*, 2002, 32(16), 2565) by a method similar to that of Reference Example 22, Step 2.

$^1$H-NMR (300 MHz, DMSO-$d_6$) δ: 1.34 (3H, t, J=7.2 Hz), 3.88 (3H, s), 4.37 (2H, q, J=7.2 Hz), 8.41 (1H, s).

Reference Example 151 ethyl 5-{[({4-[(ethyloxy)carbonyl]phenyl}methyl)oxy]methyl}-4-oxo-3,4-dihydroquinazoline-2-carboxylate

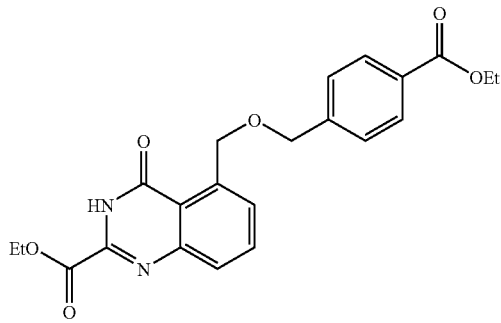 [SMILES: CCOC(=O)c1ccc(COCc2cccc3nc(C(=O)OCC)[nH]c(=O)c23)cc1]

(Step 1)
To a solution of ethyl 5-(bromomethyl)-4-oxo-3-({[2-(trimethylsilyl)ethyl]oxy}methyl)-3,4-dihydroquinazoline-2-carboxylate (1.00 g, 2.26 mmol) obtained in Reference Example 124, Step 2 and ethyl 4-(hydroxymethyl)benzoate (408 mg, 2.26 mmol) in THF (20 mL) was added a suspension of 60% sodium hydride (99.4 mg, 2.49 mmol) in THF (10 mL) at 0° C., and the mixture was stirred at 0° C. for 1 hr. and at room temperature for 2 hrs. Saturated ammonium chloride was added to the reaction mixture, and the mixture was extracted with ethyl acetate. The organic layer was washed with water and saturated brine and dried over anhydrous sodium sulfate. The solvent was evaporated under reduced pressure, and the concentrated residue was purified by silica gel column chromatography (11% ethyl acetate/hexane) to give ethyl 5-{[({4-[(ethyloxy)carbonyl]phenyl}methyl)oxy]methyl}-4-oxo-3-({[2-(trimethylsilyl)ethyl]oxy}methyl)-3,4-dihydroquinazoline-2-carboxylate as a colorless oil (310 mg, 25%).

(Step 2)
To a solution of ethyl 5-{[({4-[(ethyloxy)carbonyl]phenyl}methyl)oky]methyl}-4-oxo-3-({[2-(trimethylsilyl)

ethyl]oxy}methyl)-3,4-dihydroquinazoline-2carboxylate (310 mg, 0.573 mmol) in dichloromethane (8 mL) was added trifluoroacetic acid (2 mL) at 0° C., and the mixture was stirred at room temperature for 1 hr. The solvent was evaporated under reduced pressure from the reaction mixture, and the concentrated residue was crystallized from diethyl ether to give the title compound as a white powder (211 mg, 90%).

$^1$H-NMR (300 MHz, DMSO-$d_6$) δ: 1.30-1.38 (6H, m), 4.28-4.42 (4H, m), 4.81 (2H, s), 5.23 (2H, s), 7.57 (2H, d, J=7.8 Hz), 7.72-7.74 (1H, m), 7.86-7.89 (2H, m), 7.98 (2H, d, J=8.1 Hz), 12.55 (1H, bs).

Reference Example 152

1,1-dimethylethyl (4-chloro-3-fluorophenyl)carbamate

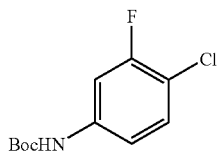 [SMILES: CC(C)(C)OC(=O)Nc1ccc(Cl)c(F)c1]

A solution of 4-chloro-3-fluoroaniline (9.90 g, 68.0 mmol) and bis(1,1-dimethylethyl) dicarbonate (16.3 g, 74.8 mmol) in THF (100 mL) was stirred with heating at 60° C. for 15 hrs. Bis(1,1-dimethylethyl) bicarbonate (4.75 g, 21.8 mmol) was added again, and the mixture was further stirred at 60° C. for 3 days. The reaction mixture was concentrated under reduced pressure and crystallized from hexane to give the title compound as a white powder (11.8 g, 71%).

$^1$H-NMR (300 MHz, DMSO-$d_6$) δ: 1.48 (9H, s), 7.24 (1H, ddd, J=8.9, 2.4, 0.9 Hz), 7.45 (1H, t, J=8.8 Hz), 7.56 (1H, dd, J=12.2, 2.3 Hz), 9.73 (1H, s).

Reference Example 153 ethyl 6-amino-3-chloro-2-fluorobenzoate hydrochloride

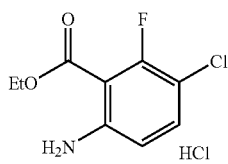 [SMILES: CCOC(=O)c1c(N)ccc(Cl)c1F ; Cl]

(Step 1)
To a solution of 1,1-dimethylethyl (4-chloro-3-fluorophenyl)carbamate (10.0 g, 40.7 mmol) obtained in Reference Example 152 in THF (150 mL) was added dropwise n-butyllithium (1.6 M hexane solution, 56 mL, 89.5 mmol) at −78° C., and the mixture was stirred at −78° C. for 4 hrs. Ethyl chlorocarbonate (4.64 g, 42.7 mmol) was added to the reaction mixture and the mixture was stirred at −78° C. for 1 hr. Saturated aqueous ammonium chloride solution (150 mL) was added, and the mixture was partitioned between ethyl acetate and water. The organic layer was washed with saturated brine, dried over sodium sulfate and concentrated under reduced pressure to give ethyl 3-chloro-6-({[(1,1-dimethylethyl)oxy]carbonyl}amino)-2-fluorobenzoate as a pale-yellow powder (12.8 g).

$^1$H-NMR (300MHz, DMSO-$d_6$) δ: 1.29 (3H, t, J=7.2 Hz), 1.45 (9H, s), 4.27 (2H, q, J=7.2 Hz), 7.35 (1H, dd, J=9.0, 1.5 Hz), 7.64-7.72 (1H, m), 9.58 (1H, s).

(Step 2)
Ethyl 3-chloro-6-({[(1,1-dimethylethyl)oxy]carbonyl}amino)-2-fluorobenzoate (12.8 g) was dissolved in ethyl acetate (20 mL), 4N hydrogen chloride-ethyl acetate solution (70 mL) was added, and the mixture was stirred at room temperature for 4 hrs. Diethyl ether (70 mL) was added to the reaction mixture, and the precipitated solid was collected by filtration. The solid was washed with diethyl ether to give the title compound as a pale-yellow powder (8.40 g, 81% by 2 steps).

$^1$H-NMR (300 MHz, DMSO-$d_6$) δ: 1.29 (3H, t, J=7.2 Hz), 4.30 (2H, q, J=7.1 Hz), 6.48 (3H, s), 6.63 (1H, dd, J=9.1, 1.6 Hz), 7.34 (1H, dd, J=9.0, 8.1 Hz).

Reference Example 154 ethyl 6-chloro-5-fluoro-4-oxo-3,4-dihydroquinazoline-2-carboxylate

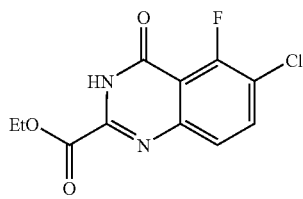 [SMILES: CCOC(=O)c1nc2ccc(Cl)c(F)c2c(=O)[nH]1]

Ethyl 6-amino-3-chloro-2-fluorobenzoate hydrochloride (5.00 g, 19.7 mmol) obtained in Reference Example 153 was suspended in 1N hydrogen chloride-acetic acid solution (100 mL), ethyl cyanoformate (2.92 g, 29.5 mmol) was added, and the mixture was stirred with heating at 80° C. for 4 hrs. The mixture was allowed to cool to room temperature, diethyl ether (50 mL) was added, and the precipitated solid was collected by filtration. The solid was washed with ethanol and diethyl ether to give the title compound as a white powder (4.81 g, 90%).

$^1$H-NMR (300 MHz, DMSO-$d_6$) δ: 1.35 (3H, t, J=7.2 Hz), 4.38 (2H, q, J=7.2 Hz), 7.67 (1H, dd, J=8.9, 1.5 Hz), 8.03 (1H, dd, J=8.9, 7.5 Hz), 12.86 (1H, s).

Reference Example 155 ethyl 5-({[(4-cyanophenyl)methyl]oxy}methyl)-4-oxo-3,4-dihydrothieno[2,3-d]pyrimidine-2-carboxylate

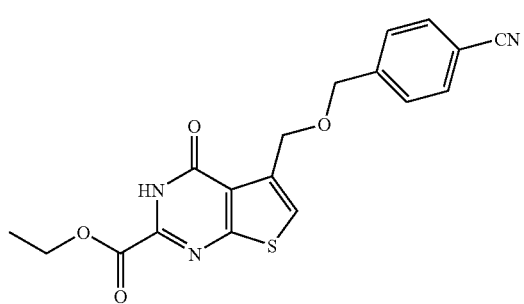 [SMILES: CCOC(=O)c1nc2scc(COCc3ccc(C#N)cc3)c2c(=O)[nH]1]

To a solution (10 mL) of 4-(hydroxymethyl)benzonitrile (176 mg, 1.32 mmol) in THF was added sodium hydride (60% in oil dispersion, 102 mg, 2.65 mmol) by small portions, and the mixture was stirred at room temperature for 10 min. Ethyl 5-(bromomethyl)-4-oxo-3,4-dihydrothieno[2,3-d]pyrimidine-2-carboxylate (400 mg, 1.26 mmol) obtained in Example 216, Step 1, was added to the reaction mixture and the mixture was further stirred for 1 hr. The reaction mixture was concentrated under reduced pressure, and ethyl acetate was added to the obtained residue. The organic-layer was washed with 1N hydrochloric acid and saturated brine, dried over anhydrous sodium sulfate and concentrated under reduced pressure. Diethyl ether was added to the concentrated residue and the precipitated solid was collected by filtration. To a mixture of the obtained solid, 1-ethyl-3-(3-dimethylaminopropyl)carbodiimide hydrochloride (363 mg, 1.89 mmol), 4-dimethylaminopyridine (15.4 mg, 0.126 mmol) and THF (5 mL) was added ethanol (0.735 mL, 12.6 mmol), and the mixture was stirred at room temperature for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (244 mg, 52%).

melting point: 236-237° C.

$^1$H NMR (300 MHz, DMSO-$d_6$) δ 1.34 (3 H, t, J=7.1 Hz), 4.37 (2 H, q, J=7.1 Hz), 4.76 (2 H, s), 4.90 (2 H, d, J=1.1 Hz), 7.59 (2 H, d, J=8.5 Hz), 7.71 (1 H, t, J=1.1 Hz), 7.77-7.89 (2 H, m), 12.87 (1 H, s).

Reference Example 156 ethyl 5-({[(4-fluorophenyl)methyl]oxy}methyl)-4-oxo-3,4-dihydrothieno[2,3-d]pyrimidine-2-carboxylate

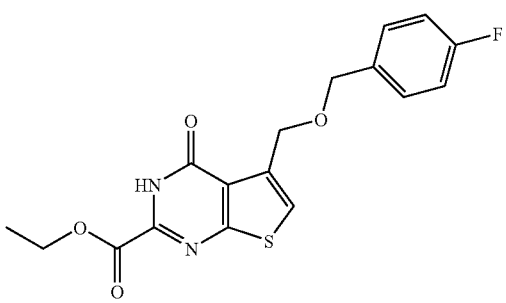 [SMILES: CCOC(=O)c1nc2scc(COCc3ccc(F)cc3)c2c(=O)[nH]1]

To a solution of (4-fluorophenyl)methanol (0.181 mL, 1.66 mmol) in THF (10 mL) was added sodium hydride (60% oil dispersion, 127 mg, 3.31 mmol) by small portions, and the mixture was stirred at room temperature for 10 min. Ethyl 5-(bromomethyl)-4-oxo-3,4-dihydrothieno[2,3-d]pyrimidine-2-carboxylate (500 mg, 1.58 mmol) obtained in Example 216, Step 1 was added to the reaction mixture, and the mixture was further stirred for 1 hr. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. Diethyl ether was added to the concentrated residue, and the precipitated solid was collected by filtration.

To a mixture of the obtained solid, 1-ethyl-3-(3-dimethylaminopropyl)carbodiimide hydrochloride (453 mg, 2.36 mmol), 4-dimethylaminopyridine (19.3 mg, 0.158 mmol) and THF (5 mL) was added ethanol (0.919 mL, 15.8 mmol), and the mixture was stirred at room temperature for 12 hrs. The reaction mixture was concentrated under reduced pressure, and ethyl acetate was added to the obtained residue. The organic layer was washed with 1N hydrochloric acid and saturated brine, dried over anhydrous sodium sulfate and concentrated under reduced pressure. The concentrated residue was crystallized from ethyl acetate to give the title compound as a white powder (105 mg, 8%).

melting point: 195-196° C.

$^1$H NMR (300 MHz, DMSO-$d_6$) δ 1.34 (3 H, t, J=7.1 Hz), 4.37 (2 H, q, J=7.0 Hz), 4.64 (2 H, s), 4.85 (2 H, d, J=1.3 Hz), 7.18 (2 H, t, J=8.9 Hz), 7.44 (2 H, dd, J=8.7, 5.7 Hz), 7.66 (1 H, t, J=1.2 Hz), 12.85 (1 H, s).

Reference Example 157

5-({[(4-carboxyphenyl)methyl]oxy}methyl)-4-oxo-3,4-dihydrothieno[2,3-d]pyrimidine-2-carboxylic acid

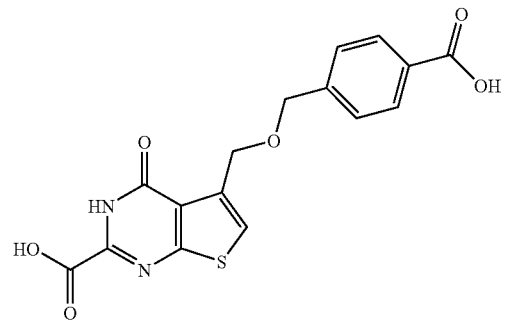 [SMILES: O=C(O)c1ccc(COCc2csc3nc(C(=O)O)[nH]c(=O)c23)cc1]

To a mixture of sodium hydride (60%-in-oil dispersion, 1.39 g, 36.4 mmol) and THF (43 mL) was added dropwise a solution of ethyl 5-(bromomethyl)-4-oxo-3,4-dihydrothieno[2,3-d]pyrimidine-2-carboxylate (5.49 g, 17.3 mmol) obtained in Example 216, Step 1 and ethyl 4-(hydroxymethyl)benzoate (3.27 g, 18.2 mmol) obtained by the method described in J. Am. Chem. Soc. (2004), 126 (23), 7186-7187 and the like in THF (72 mL) at 0° C. After stirring for 1 hr., the reaction mixture was added dropwise to a mixture of 2N hydrochloric acid (210 mL), ethyl acetate (70 mL) and dry ice. After dropwise addition, the mixture was added to ethyl acetate (700 mL) and washed with saturated brine, dried over anhydrous sodium sulfate, and concentrated under reduced pressure. Diethyl ether was added to the concentrated residue and the precipitated solid was collected by filtration. To a solution (58 mL) of the obtained solid in THF were added oxalyl chloride (1.51 mL, 17.3 mmol) and DMF (1 drop), and the mixture was stirred at room temperature for 20 min. The reaction mixture was concentrated under reduced pressure. THF (30 mL), ethanol (30 mL) and pyridine (3.50 mL, 43.3 mmol) were added to the concentrated residue, and the mixture was stirred at room temperature for 30 min. The reaction mixture was concentrated under reduced pressure. Diethyl ether and 1N hydrochloric acid were added to the concentrated residue and the precipitated solid was collected by filtration, washed 3 times with 1N hydrochloric acid, 4 times with water and 3 times with diethyl ether and dried to give a pale-yellow powder (5.17 g). A suspension of the obtained solid (3.52 g) and 4N aqueous sodium hydroxide solution (10.6 mL, 42.3 mmol) in water (45 mL), methanol (45 mL) and THF (45 mL) was stirred at 90° C. for 1 hr. The reaction mixture was concentrated under reduced pressure, and the concentrated residue was acidified with 1N hydrochloric acid (10.6 mL) and extracted with THF (1000 mL). The organic layer was washed with 1N hydrochloric acid and saturated brine, dried over anhydrous sodium sulfate and concentrated under reduced pressure. Crystallization from methanol-THF mixed solvent gave the title compound as a pale-yellow powder (2.88 g, 46%).

melting point: 248° C.

$^1$H NMR (300 MHz, DMSO-$d_6$) δ 4.74 (2 H, s), 4.89 (2 H, d, J=0.9 Hz), 7.51 (2 H, d, J=8.3 Hz), 7.67 (1 H, s), 7.94 (2 H, d, J=8.1 Hz), 12.61 (1 H, s), 12.94 (1 H, s).

Reference Example 158 ethyl 5-{[({4-[(ethyloxy)carbonyl]phenyl}methyl)oxy]methyl}-4-oxo-3,4-dihydrothieno[2,3-d]pyrimidine-2-carboxylate

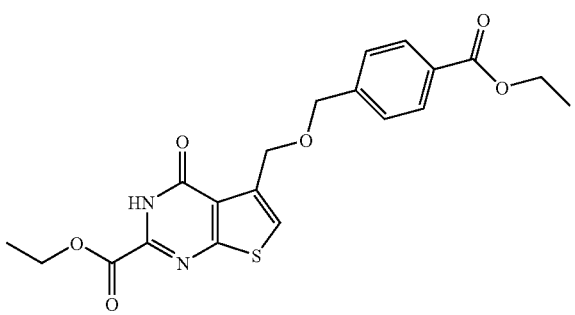 [SMILES: CCOC(=O)c1ccc(COCc2csc3nc(C(=O)OCC)[nH]c(=O)c23)cc1]

To a mixture of 5-({[(4-carboxyphenyl)methyl]oxy}methyl)-4-oxo-3,4-dihydrothieno[2,3-d]pyrimidine-2-carboxylic acid (2.88 g, 7.99 mmol) obtained in Reference Example 157 and THF (30 mL) was added oxalyl chloride (4.60 mL, 52.7 mmol) and DMF (1 drop), and the mixture was stirred at room temperature for 1 hr. The reaction mixture was concentrated, and THF (15 mL) and ethanol (15 mL) were added to the concentrated residue. Pyridine (5.69 mL, 70.3 mmol) was added to the mixture, and the mixture was stirred at room temperature for 12 hrs. The reaction mixture was concentrated under reduced pressure and ethyl acetate and 1N hydrochloric acid were added to the concentrated residue. The precipitated solid was collected by filtration and washed twice with 1N hydrochloric acid, 4 times with water and once with diethyl ether. The obtained crude crystals were recrystallized from THF-ethyl acetate to give the title compound as a white powder (1.87 g, 56%).

melting point: 181° C.

$^1$H NMR (300 MHz, DMSO-$d_6$) δ 1.34 (6 H, q, J=7.1 Hz), 4.25-4.44 (4 H, m), 4.76 (2 H, s), 4.90 (2 H, s), 7.54 (2 H, d, J=8.1 Hz), 7.70 (1 H, s), 7.89-8.01 (2 H, m), 12.87 (1 H, s).

Reference Example 159 ethyl 5-[({[4-(hydroxymethyl)phenyl]carbonyl}oxy)methyl]-4-oxo-3,4-dihydrothieno[2,3-d]pyrimidine-2-carboxylate

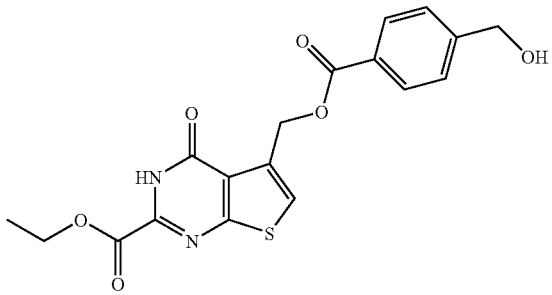 [SMILES: CCOC(=O)c1nc2scc(COC(=O)c3ccc(CO)cc3)c2c(=O)[nH]1]

A mixture of ethyl 5-(bromomethyl)-4-oxo-3,4-dihydrothieno[2,3-d]pyrimidine-2-carboxylate (1000 mg, 3.15 mmol) obtained in Example 216, Step 1, 4-(hydroxymethyl)benzoic acid (504 mg, 3.31 mmol) and DMA (20 mL) was added dropwise to a mixture of sodium hydride (60% oil dispersion, 363 mg, 9.46 mmol) and DMA (10 mL) at 0° C. The reaction mixture was stirred for 1 hr. 45 min. and added dropwise to a mixture of 2N hydrochloric acid (100 mL) and dry ice. After dropwise addition, the mixture was added to ethyl acetate, washed with 1N hydrochloric acid and saturated brine, dried over anhydrous sodium sulfate and concentrated under reduced pressure. The obtained concentrated residue was crystallized from ethyl acetate-diethyl ether to give the title compound as a pale-yellow powder (347 mg, 28%).

melting point: 196° C.

$^1$H NMR (300 MHz, DMSO-$d_6$) δ 1.35 (3 H, t, J=7.1 Hz), 4.38 (2 H, q, J=7.1 Hz), 4.59 (2 H, d, J=5.7 Hz), 5.38 (1 H, t, J=5.7 Hz), 5.62 (2 H, s), 7.47 (2 H, d, J=8.3 Hz), 7.86 (1 H, s), 7.99 (2 H, d, J=8.3 Hz), 12.95 (1 H, s).

Reference Example 160 ethyl 5-{[methyl(phenylmethyl)amino]methyl}-4-oxo-3,4-dihydrothieno[2,3-d]pyrimidine-2-carboxylate

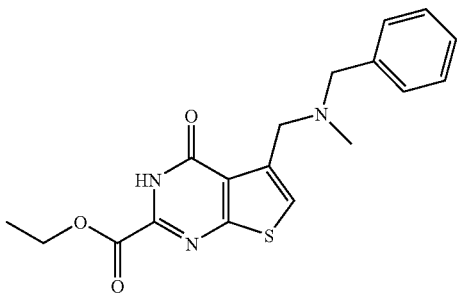 [SMILES: CCOC(=O)c1nc2scc(CN(C)Cc3ccccc3)c2c(=O)[nH]1]

To a mixture of ethyl 5-(bromomethyl)-4-oxo-3,4-dihydrothieno[2,3-d]pyrimidine-2-carboxylate (600 mg, 1.89 mmol) obtained in Example 216, Step 1 and THF (12 mL) were added N-methyl-1-phenylmethanamine (0.269 mL, 2.08 mmol) and triethylamine (0.527 mL, 3.78 mmol) at room temperature and the mixture was stirred for 1 hr. The reaction mixture was concentrated under reduced pressure and ethyl acetate was added to the residue. The mixture was washed with saturated brine, dried over anhydrous sodium sulfate and concentrated under reduced pressure. The concentrated residue was purified by silica gel column chromatography (1-8% methanol/ethyl acetate). The obtained crude crystals were crystallized from ethyl acetate/hexane mixed solvent to give the title compound as a white powder (351 mg, 52%).

melting point: 129° C.

$^1$H NMR (300 MHz, DMSO-d$_6$) δ 1.33 (3 H, t, J=7.2 Hz), 2.32 (3 H, s), 4.15 (4 H, s), 4.32 (2 H, q, J=7.0 Hz), 7.28-7.51 (5 H, m), 7.64 (1 H, s).

Reference Example 161 ethyl 4-oxo-5-{[(phenylmethyl)thio]methyl}-3,4-dihydrothieno[2,3-d]pyrimidine-2-carboxylate

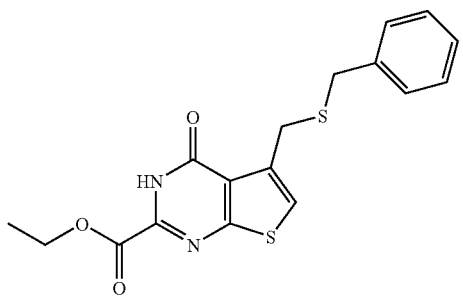 [SMILES: CCOC(=O)c1nc2scc(CSCc3ccccc3)c2c(=O)[nH]1]

To a mixture of ethyl 5-(bromomethyl)-4-oxo-3,4-dihydrothieno[2,3-d]pyrimidine-2-carboxylate (600 mg, 1.89 mmol) obtained in Example 216, Step 1 and DMA (12 mL) were added phenylmethanethiol (0.244 mL, 2.08 mmol) and triethylamine (0.527 mL, 3.78 mmol) at room temperature and the mixture was stirred for 1 hr. The reaction mixture was concentrated under reduced pressure, and ethyl acetate was added to the obtained residue. The mixture was washed with 1N hydrochloric acid and saturated brine, dried over anhydrous sodium sulfate and concentrated under reduced pressure. The concentrated residue was purified by silica gel column chromatography (5-50% ethyl acetate/hexane). The obtained crude crystals were recrystallized from a mixed solvent of ethyl acetate/hexane to give the title compound as a white powder (207 mg, 30%).

melting point: 170-171° C.

$^1$H NMR (300 MHz, DMSO-d$_6$) δ 1.35 (3 H, t, J=7.2 Hz), 3.73 (2 H, s), 3.99 (2 H, s), 4.37 (2 H, q, J=7.1 Hz), 7.15-7.34 (5 H, m), 7.57 (1 H, s), 12.82 (1 H, s).

Reference Example 162 ethyl 5-(cyanomethyl)-4-oxo-3,4-dihydrothieno[2,3-d]pyrimidine-2-carboxylate

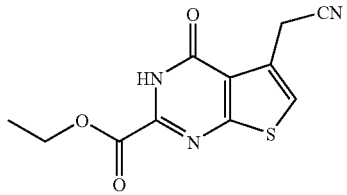 [SMILES: CCOC(=O)c1nc2scc(CC#N)c2c(=O)[nH]1]

To a mixture of ethyl 5-(bromomethyl)-4-oxo-3,4-dihydrothieno[2,3-d]pyrimidine-2-carboxylate (2000 mg, 6.31 mmol) obtained in Example 216, step 1 and DMF (10 mL) was added sodium cyanide (649 mg, 13.2 mmol) at room temperature, and the mixture was stirred for 12 hrs. The reaction mixture was acidified with 1N hydrochloric acid, and extracted with ethyl acetate. The organic layer was washed with water and saturated brine, dried over anhydrous sodium sulfate and concentrated under reduced pressure. The concentrated residue was crystallized from ethyl acetate to give the title compound as a pale-brown powder (300 mg, 18%).

melting point: 183° C.

$^1$H NMR (300 MHz, DMSO-d$_6$) δ 1.35 (3 H, t, J=7.2 Hz), 4.27 (2 H, d, J=1.1 Hz), 4.37 (2 H, q, J=7.0 Hz), 7.75 (1 H, s), 13.00 (1 H, s).

Reference Example 163 ethyl 5,6-dibromo-4-oxo-3,4-dihydrothieno[2,3-d]pyrimidine-2-carboxylate

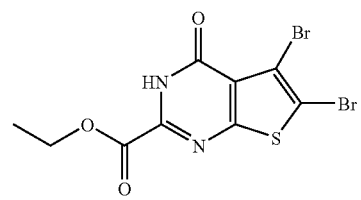

To a mixture of ethyl 4-oxo-3,4-dihydrothieno[2,3-d]pyrimidine-2-carboxylate (1000 mg, 4.46 mmol) obtained in Reference Example 26 and acetic acid (20 mL) was added bromine (6.90 mL, 134 mmol), and the mixture was stirred at room temperature for 12 hrs. Bromine (6.90 mL, 134 mmol) was further added, and the mixture was stirred at room temperature for 12 hrs. 1N Sodium hydrogen carbonate was added until the color of bromine disappeared, and the precipitated solid was collected by filtration, washed 3 times with water and once with diethyl ether and dried to give the title compound as a gray powder (1.20 g, 70%).

melting point: 269-270° C.

$^1$H NMR (300 MHz, DMSO-d$_6$) δ 1.34 (3 H, t, J=7.2 Hz), 4.37 (2 H, q, J=7.0 Hz), 13.17 (1 H, s).

Reference Example 164 ethyl 6-bromo-4-oxo-3,4-dihydrothieno[2,3-d]pyrimidine-2-carboxylate

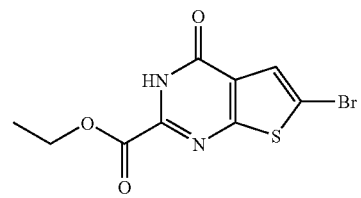 [SMILES: CCOC(=O)c1nc2sc(Br)cc2c(=O)[nH]1]

A mixture of ethyl 4-oxo-3,4-dihydrothieno[2,3-d]pyrimidine-2-carboxylate (1000 mg, 4.46 mmol) obtained in Reference Example 26, bromine (1.37 mL, 26.8 mmol) and acetic acid (20 mL) was stirred at room temperature for 6 hrs. The reaction mixture was concentrated under reduced pressure, and ethyl acetate was added to the obtained residue. The organic layer was washed with water and saturated brine, dried over anhydrous sodium sulfate and concentrated under reduced pressure. The concentrated residue was crystallized from ethyl acetate to give the title compound as a pale-gray powder (1.25 g, 93%).

melting point: 252-253° C.
$^1$H NMR (300 MHz, DMSO-$d_6$) δ 1.34 (3 H, t, J=7.2 Hz), 4.36 (2 H, q, J=7.0 Hz), 7.67 (1 H, s), 13.06 (1 H, s).

Reference Example 165 ethyl 6-bromo-5-nitro-4-oxo-3,4-dihydrothieno[2,3-d]pyrimidine-2-carboxylate

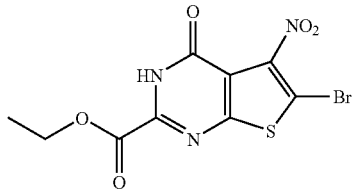 [SMILES: CCOC(=O)c1nc2sc(Br)c([N+](=O)[O-])c2c(=O)[nH]1]

To a mixture of ethyl 6-bromo-4-oxo-3,4-dihydrothieno[2,3-d]pyrimidine-2-carboxylate (800 mg, 2.64 mmol) obtained in Reference Example 164 and concentrated sulfuric acid (13 mL) was added sodium nitrate (269 mg, 3.17 mmol) at 0° C. After stirring for 30 min., the reaction mixture was added to a mixed solution of ice water (200 mL) and diethyl ether (100 mL) to remove the aqueous layer. The insoluble material in the upper layer was collected by filtration, washed 4 times with water and twice with diethyl ether, and dried to give the title compound as pale-yellow crystal (734 mg, 80%).

melting point: 284° C.
$^1$H NMR (300 MHz, DMSO-$d_6$) δ 1.34 (3 H, t, J=7.1 Hz), 4.38 (2 H, q, J=7.2 Hz), 13.54 (1 H, s).

Reference Example 166 ethyl 5-amino-4-oxo-3,4-dihydrothieno[2,3-d]pyrimidine-2-carboxylate hydrobromide

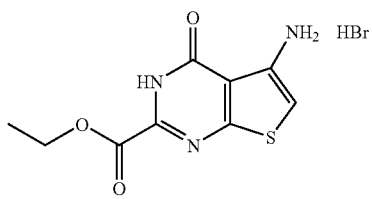 [SMILES: CCOC(=O)c1nc2scc(N)c2c(=O)[nH]1 ; Br]

A mixture of ethyl 6-bromo-5-nitro-4-oxo-3,4-dihydrothieno[2,3-d]pyrimidine-2-carboxylate (600 mg, 1.72 mmol) obtained in Reference Example 165, 10% palladium carbon (50% wet, 240 mg), ethanol (15 mL) and THF (15 mL) was stirred under a hydrogen atmosphere (1 atm) at room temperature for 12 hrs. The catalyst was filtered off, and the filtrate was concentrated under reduced pressure. The obtained concentrated residue was crystallized from ethanol. The obtained crude crystals were dissolved in methanol and an insoluble material was filtered off and the filtrate was concentrated under reduced pressure. The obtained concentrated residue was crystallized from ethanol to give the title compound as a brown powder (198 mg, 36%).

melting point: 201° C.
$^1$H NMR (300 MHz, DMSO-$d_6$) δ 1.34 (3 H, t, J=7.2 Hz), 4.36 (2 H, q, J=7.2 Hz), 6.67 (1 H, s), 12.88 (1 H, s).

Reference Example 167 ethyl 4-oxo-5-[(phenylacetyl)amino]-3,4-dihydrothieno[2,3-d]pyrimidine-2-carboxylate

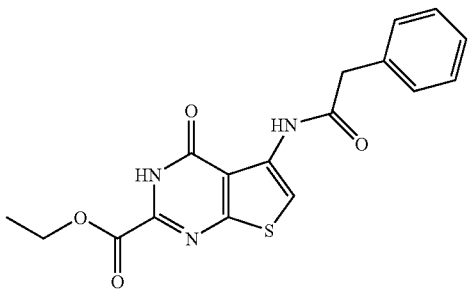 [SMILES: CCOC(=O)c1nc2scc(NC(=O)Cc3ccccc3)c2c(=O)[nH]1]

To a mixture of ethyl 5-amino-4-oxo-3,4-dihydrothieno[2,3-d]pyrimidine-2-carboxylate hydrobromide (160 mg, 0.500 mmol) obtained in Reference Example 166 and THF (2 mL) were added phenylacetyl chloride (0.0727 mL, 0.550 mmol) and triethylamine (0.146 mL, 1.05 mmol) at room temperature. The mixture was stirred for 1 hr at room temperature and concentrated under reduced pressure. Ethyl acetate was added to the obtained residue, and the organic layer was washed with 1N hydrochloric acid, water and saturated brine, dried over anhydrous sodium sulfate and concentrated under reduced pressure. The concentrated residue was crystallized from ethyl acetate to give the title compound as a pale-purple powder (138 mg, 77%).

melting point: 237° C.
$^1$H NMR (300 MHz, DMSO-$d_6$) δ 1.33 (3 H, t, J=7.1 Hz), 3.81 (2 H, s), 4.36 (2 H, q, J=7.2 Hz), 7.22-7.41 (5 H, m), 7.92 (1 H, s), 9.89 (1 H, s), 13.13 (1 H, s).

Reference Example 168 ethyl 5-(3-bromophenyl)-4-oxo-3,4-dihydrothieno[2,3-d]pyrimidine-2-carboxylate

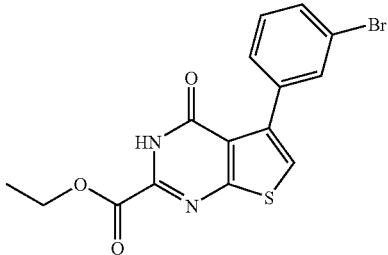 [SMILES: CCOC(=O)c1nc2scc(-c3cccc(Br)c3)c2c(=O)[nH]1]

A mixture of 2-amino-4-(3-bromophenyl)thiophene-3-carboxylic acid (1.00 g, 3.20 mmol), ethyl cyanoformate (0.348 ml, 3.52 mmol) and a 1N solution (10.0 ml) of hydrogen chloride in acetic acid was stirred at 90° C. for 1.5 hrs. The reaction mixture was concentrated under reduced pressure, and ethyl acetate was added to the obtained residue. The organic layer was washed with water and saturated brine, dried over anhydrous sodium sulfate and concentrated under reduced pressure. The concentrated residue was crystallized from ethyl acetate to give the title compound as a pale-yellow powder (1.05 g, 86.4%).

melting point: 190° C.

$^1$H NMR (300 MHz, DMSO-$d_6$) δ 1.36 (3 H, t, J=7.1 Hz), 4.39 (2 H, q, J=7.2 Hz), 7.38 (1 H, t, J=7.9 Hz), 7.53-7.60 (2 H, m), 7.75 (1 H, t, J=1.8 Hz), 7.86 (1 H, s), 12.88 (1 H, s).

Reference Example 169

Diethyl 5-methyl-4-oxo-3,4-dihydrothieno[2,3-d]pyrimidine-2,6-dicarboxylate

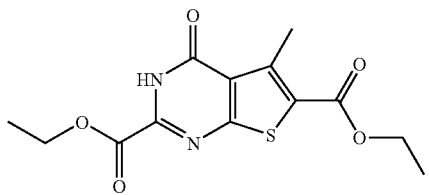 [SMILES: CCOC(=O)c1nc2sc(C(=O)OCC)c(C)c2c(=O)[nH]1]

A mixture of diethyl 5-amino-3-methylthiophene-2,4-dicarboxylate (5.00 g, 19.4 mmol), ethyl cyanoformate (2.11 ml, 21.4 mmol) and a 1N solution (50.0 ml) of hydrogen chloride in acetic acid was stirred at 90° C. for 2 hrs. The reaction mixture was concentrated under reduced pressure and the concentrated residue was crystallized from diethyl ether to give the title compound as a white powder (4.98 g, 82.6%).

melting point: 237-238° C.

$^1$H NMR (300 MHz, DMSO-$d_6$) δ 1.33 (6 H, q, J=7.2 Hz), 2.85 (3 H, s), 4.29-4.41 (4 H, m), 13.06 (1 H, s).

Reference Example 170 ethyl 5-(azidomethyl)-4-oxo-3,4-dihydrothieno[2,3-d]pyrimidine-2-carboxylate

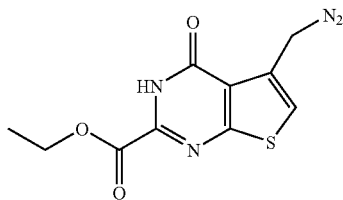

To a mixture of ethyl 5-(bromomethyl)-4-oxo-3,4-dihydrothieno[2,3-d]pyrimidine-2-carboxylate (2000 mg, 6.31 mmol) obtained in Example 216, Step 1 and DMF (20 mL) was added sodium azide (861 mg, 13.2 mmol), and the mixture was stirred at room temperature for 12 hrs. 1N Hydrochloric acid was added to the reaction mixture, and the mixture was extracted with ethyl acetate. The organic layer was washed 5 times with water and once with saturated brine, dried over anhydrous sodium sulfate and concentrated under reduced pressure. The concentrated residue was crystallized from ethyl acetate to give the title compound as a white powder (1330 mg, 76%).

melting point: 192° C.

$^1$H NMR (300 MHz, DMSO-$d_6$) δ 1.35 (3H, t, J=7.2 Hz), 4.37 (2 H, q, J=7.2 Hz), 4.76 (2 H, s), 7.81 (1 H, s), 12.97 (1 H, s).

Reference Example 171 ethyl 5-(aminomethyl)-4-oxo-3,4-dihydrothieno[2,3-d]pyrimidine-2-carboxylate hydrochloride

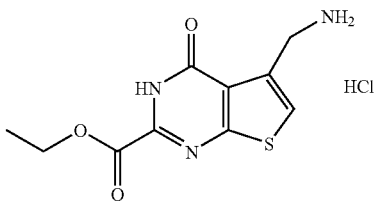 [SMILES: CCOC(=O)c1nc2scc(CN)c2c(=O)[nH]1 ; Cl]

A mixture of ethyl 5-(azidomethyl)-4-oxo-3,4-dihydrothieno[2,3-d]pyrimidine-2-carboxylate (100 mg, 0.358 mmol) obtained in Reference Example 170, 2N hydrogen chloride ethanol solution (0.268 ml, 1.07 mmol), 10% palladium carbon (50% wet) (25.0 mg), ethanol (1 mL) and THF (1 mL) was stirred at room temperature under a hydrogen atmosphere (1 atm) for 1 hr. The catalyst was filtered off and the filtrate was concentrated under reduced pressure. The obtained concentrated residue was crystallized from ethyl acetate to give the title compound as a white powder (104 mg, 94%).

melting point: 262-263° C.

$^1$H NMR (300 MHz, DMSO-$d_6$) δ 1.35 (3 H, t, J=7.1 Hz), 4.05-4.64 (4 H, m), 7.87 (1 H, s), 8.34 (3 H, s), 13.23 (1H, s).

Reference Example 172 ethyl 4-oxo-5-{[(phenylcarbonyl)amino]methyl}-3,4-dihydrothieno[2,3-d]pyrimidine-2-carboxylate

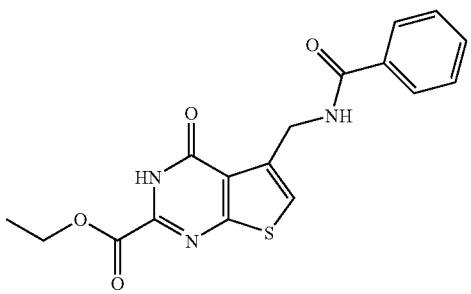 [SMILES: CCOC(=O)c1nc2scc(CNC(=O)c3ccccc3)c2c(=O)[nH]1]

To a mixture of ethyl 5-(aminomethyl)-4-oxo-3,4-dihydrothieno[2,3-d]pyrimidine-2-carboxylate hydrochloride (250 mg, 0.863 mmol) obtained in Reference Example 171 and THF (3.0 ml) were added benzoyl chloride (0.110 ml, 0.949 mmol) and triethylamine (0.253 ml, 1.81 mmol), and the mixture was stirred at room temperature for 1 hr. The reaction mixture was concentrated under reduced pressure, and ethyl acetate was added to the obtained residue. The organic layer was washed with saturated aqueous sodium hydrogen carbonate solution, saturated brine, 1N hydrochloric acid and saturated brine, dried over anhydrous sodium sulfate and concentrated under reduced pressure. The concentrated residue was crystallized from ethyl acetate to give the title compound as a white powder (223 mg, 72%).

melting point: 204° C.

$^1$H NMR (300 MHz, DMSO-$d_6$) δ 1.35 (3 H, t, J=7.1 Hz), 4.38 (2 H, q, J=7.0 Hz), 4.80 (2 H, d, J=4.9 Hz), 7.43-7.60 (4 H, m), 7.86-7.94 (2 H, m), 9.03 (1 H, t, J=5.7 Hz), 12.93 (1 H, s).

Reference Example 173 ethyl 5-{[({4-[(methyloxy)carbonyl]phenyl}carbonyl)amino]methyl}-4-oxo-3,4-dihydrothieno[2,3-d]pyrimidine-2-carboxylate

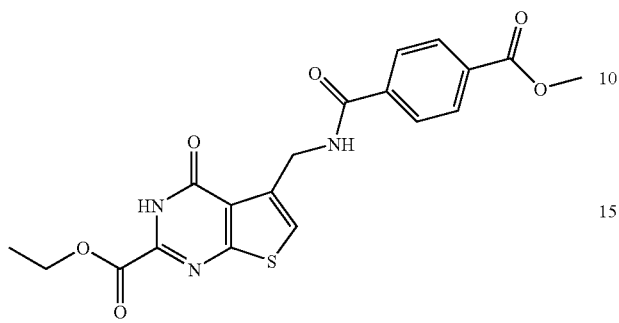

To a mixture of 4-[(methyloxy)carbonyl]benzoic acid (373 mg, 2.07 mmol) and THF (5.0 ml) were added oxalyl chloride (0.450 ml, 5.18 mmol) and DMF (1 drop), and the mixture was stirred at room temperature for 1 hr. The reaction mixture was concentrated under reduced pressure, and THF (5.0 mL) was added to the concentrated residue. To this mixture were added ethyl 5-(aminomethyl)-4-oxo-3,4-dihydrothieno[2,3-d]pyrimidine-2-carboxylate hydrochloride (500 mg, 1.73 mmol) obtained in Reference Example 171 and triethylamine (0.960 ml, 6.90 mmol), and the mixture was stirred at room temperature for 1 hr. The reaction mixture was concentrated under reduced pressure, and ethyl acetate was added to the obtained residue. The organic layer was washed with saturated aqueous sodium hydrogen carbonate solution, saturated brine, 1N hydrochloric acid and saturated brine, dried over anhydrous sodium sulfate and concentrated under reduced pressure. The concentrated residue was crystallized from ethyl acetate to give the title compound as a white powder (558 mg, 82%).

melting point: 236° C.
$^1$H NMR (300 MHz, DMSO-$d_6$) δ 1.35 (3 H, t, J=7.2 Hz), 3.89 (3 H, s), 4.37 (2 H, q, J=7.2 Hz), 4.82 (2 H, d, J=5.5 Hz), 7.52 (1 H, s), 7.77-8.22 (4 H, m), 9.23 (1 H, s), 12.93 (1 H, s).

Reference Example 174 ethyl 5-(dibromomethyl)-4-oxo-3,4-dihydrothieno[2,3-d]pyrimidine-2-carboxylate

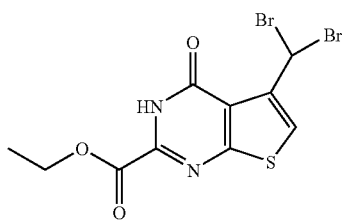 [SMILES: CCOC(=O)c1nc2scc(C(Br)Br)c2c(=O)[nH]1]

A mixture of ethyl 5-methyl-4-oxo-3,4-dihydrothieno[2,3-d]pyrimidine-2-carboxylate (3000 mg, 12.6 mmol) obtained by the method described in U.S. Pat. No. 4,054,656 and the like, N-bromosuccinimide (5.15 g, 29.0 mmol) and 2,2'-azobis(isobutyronitrile) (207 mg, 1.26 mmol) was stirred in carbon tetrachloride (60 mL) at 80° C. for 1.5 hrs. The reaction mixture was concentrated under reduced pressure, and ethyl acetate and water were added to the obtained residue. The organic layer was washed with water and saturated brine, dried over anhydrous sodium sulfate and concentrated under reduced pressure. The concentrated residue was crystallized from diethyl ether to give the title compound as a white powder (4.62 g, 93%).

melting point: 214-215° C.
$^1$H NMR (300 MHz, DMSO-$d_6$) δ 1.35 (3 H, t, J=7.2 Hz), 4.38 (2 H, q, J=7.0 Hz), 7.57 (1 H, d, J=0.6 Hz), 8.26 (1 H, s), 13.15 (1 H, s).

Reference Example 175 ethyl 5-formyl-4-oxo-3,4-dihydrothieno[2,3-d]pyrimidine-2-carboxylate

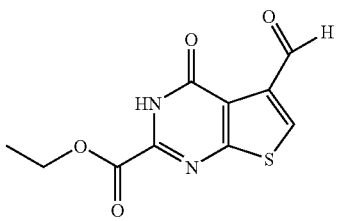 [SMILES: CCOC(=O)c1nc2scc(C=O)c2c(=O)[nH]1]

A mixture of ethyl 5-(dibromomethyl)-4-oxo-3,4-dihydrothieno[2,3-d]pyrimidine-2-carboxylate (4.00 g, 10.1 mmol) obtained in Reference Example 174 and 1N hydrochloric acid (51.0 mL, 50.5 mmol) was stirred in a mixed solvent of THF (40 mL) and MeOH (40 mL) at 60° C. for 1.5 hrs. The reaction mixture was concentrated under reduced pressure, and ethyl acetate was added to the obtained residue. The organic layer was washed with water and saturated brine, dried over anhydrous sodium sulfate and concentrated under reduced pressure. The concentrated residue was crystallized from ethyl acetate to give the title compound as a pale-yellow powder (2.26 g, 89%).

melting point: 213-214° C.
$^1$H NMR (300 MHz, DMSO-$d_6$) δ 1.36 (3 H, t, J=7.2 Hz), 4.39 (2 H, q, J=7.2 Hz), 8.61 (1 H, s), 10.51 (1 H, s), 13.29 (1 H, s).

Reference Example 176

2-[(ethyloxy)carbonyl]-4-oxo-3,4-dihydrothieno[2,3-d]pyrimidine-5-carboxylic acid

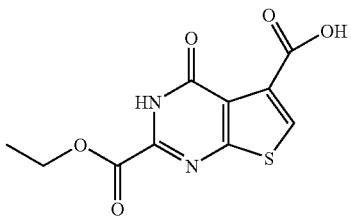 [SMILES: CCOC(=O)c1nc2scc(C(=O)O)c2c(=O)[nH]1]

To a mixture of ethyl 5-formyl-4-oxo-3,4-dihydrothieno[2,3-d]pyrimidine-2-carboxylate (1.70 g, 6.74 mmol) obtained in Reference Example 175, acetonitrile (20 mL) and water (20 mL) was added sodium chlorite (2.43 g, 27.0 mmol) and the mixture was stirred at room temperature for 12 hrs. The reaction mixture was concentrated under reduced pressure, and the obtained residue was acidified with 1N hydrochloric acid. Ethyl acetate and THF were added and the organic layer was washed with 1N hydrochloric acid and saturated brine, dried over anhydrous sodium sulfate and concentrated under reduced pressure. The concentrated residue was crystallized from ethyl acetate to give the title compound as a white powder (1.33 g, 73%).

melting point: 258° C.

$^1$H NMR (300 MHz, DMSO-d$_6$) δ 1.36 (3 H, t, J=7.1 Hz), 4.41 (2 H, q, J=7.0 Hz), 8.68 (1 H, s).

Reference Example 177 ethyl 4-oxo-5-{[(phenylmethyl)amino]carbonyl}-3,4-dihydrothieno[2,3-d]pyrimidine-2-carboxylate

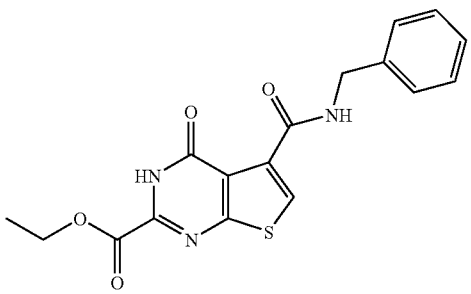 [SMILES: CCOC(=O)c1nc2scc(C(=O)NCc3ccccc3)c2c(=O)[nH]1]

To a mixture of 2-[(ethyloxy)carbonyl]-4-oxo-3,4-dihydrothieno[2,3-d]pyrimidine-5-carboxylic acid (400 mg, 1.49 mmol) obtained in Reference Example 176 and THF (10 mL) were added oxalyl chloride (0.390 mL, 4.47 mmol) and DMF (0.0500 mL, 0.646 mmol), and the mixture was stirred at room temperature for 1 hr. The reaction mixture was concentrated under reduced pressure. To a suspension of the concentrated residue in THF (10 mL) were added benzylamine (0.326 mL, 2.98 mmol) and triethylamine (0.415 mL, 2.98 mmol) and the mixture was stirred at room temperature for 12 hrs. The reaction mixture was concentrated under reduced pressure and ethyl acetate was added to the obtained residue. The organic layer was washed with 1N hydrochloric acid, saturated aqueous sodium hydrogen carbonate solution, 1N hydrochloric acid and saturated brine, dried over anhydrous sodium sulfate and concentrated under reduced pressure. The concentrated residue was crystallized from ethyl acetate to give the title compound as a white powder (373 mg, 70%).

melting point: 215-216° C.
$^1$H NMR (300 MHz, DMSO-d$_6$) δ 1.35 (3 H, t, J=7.2 Hz), 4.39 (2 H, q, J=7.1 Hz), 4.56 (2 H, d, J=5.5 Hz), 7.13-7.53 (5 H, m), 8.56 (1 H, s), 11.24 (1 H, s), 13.52 (1 H, s).

Reference Example 178 ethyl 5-{[({4-[(ethyloxy)carbonyl]phenyl}methyl)amino]carbonyl}-4-oxo-3,4-dihydrothieno[2,3-d]pyrimidine-2-carboxylate

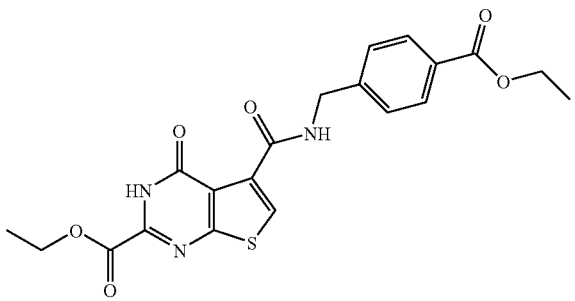 [SMILES: CCOC(=O)c1ccc(CNC(=O)c2csc3nc(C(=O)OCC)[nH]c(=O)c23)cc1]

To a mixture of 2-[(ethyloxy)carbonyl]-4-oxo-3,4-dihydrothieno[2,3-d]pyrimidine-5-carboxylic acid (600 mg, 2.24 mmol) obtained in Reference Example 176 and THF (6 mL) were added oxalyl chloride (0.590 mL, 6.72 mmol) and DMF (0.0500 mL, 0.650 mmol) and the mixture was stirred at room temperature for 1 hr. The reaction mixture was concentrated under reduced pressure. To a suspension of the concentrated residue in THF (6 mL) were added ethyl 4-(aminomethyl)benzoate hydrochloride (966 mg, 4.48 mmol) and triethylamine (1.20 mL, 8.96 mmol), and the mixture was stirred at room temperature for 12 hrs. The reaction mixture was concentrated under reduced pressure and ethyl acetate was added to the obtained residue. The organic layer was washed with 1N hydrochloric acid, saturated aqueous sodium hydrogen carbonate solution, 1N hydrochloric acid and saturated brine, dried over anhydrous sodium sulfate and concentrated under reduced pressure. The concentrated residue was crystallized from ethyl acetate to give the title compound as a white powder (771 mg, 80%).

melting point: 227-228° C.
$^1$H NMR (300 MHz, DMSQ-d$_6$) δ 1.31 (3 H, t, J=6.2 Hz), 1.36 (3 H, t, J=6.2 Hz), 4.31 (2 H, q, J=7.1 Hz), 4.40 (2 H, q, J=7.1 Hz), 4.65 (2 H, d, J=5.5 Hz), 7.50 (2 H, d, J=8.5 Hz), 7.93 (2 H, d, J=8.5 Hz), 8.57 (1 H, s), 11.27 (1 H, s), 13.53 (1 H, s).

Formulation Example 1

| | | |
|---|---|---|
| (1) Compound of Example 1 | | 50 mg |
| (2) Lactose | | 34 mg |
| (3) Cornstarch | | 10.6 mg |
| (4) Cornstarch (paste) | | 5 mg |
| (5) Magnesium stearate | | 0.4 mg |
| (6) Carboxymethylcellulose calcium | | 20 mg |

The above-mentioned (1)-(6) were mixed by a conventional method and compressed by a tableting machine to give tablets.

Formulation Example 2

| | | |
|---|---|---|
| (1) Compound of Example 2 | | 10.0 mg |
| (2) Lactose | | 60.0 mg |
| (3) Cornstarch | | 35.0 mg |
| (4) Gelatin | | 5 mg |
| (5) Magnesium stearate | | 2.0 mg |

A mixture of the compound of Example 2 (10.0 mg) and lactose (60.0 mg) and cornstarch (35.0 mg) was granulated using 10% aqueous gelatin solution (0.03 ml, 3.0 mg as gelatin) and passing through a 1 mm mesh sieve, dried at 40° C. and passed through a sieve again. The granules thus obtained are mixed with magnesium stearate (2.0 mg) and compressed. The obtained core tablet is sugar-coated with an aqueous suspension of sucrose, titanium dioxide, talc and gum arabic. The coated tablet is polished with bee wax to give a coated tablet.

Formulation Example 3

| | | |
|---|---|---|
| (1) Compound of Example 3 | | 10.0 mg |
| (2) Lactose | | 70.0 mg |

-continued

| | |
|---|---|
| (3) Cornstarch | 50.0 mg |
| (4) Soluble starch | 7.0 mg |
| (5) Magnesium stearate | 3.0 mg |

The compound of Example 3 (10.0 mg) and magnesium stearate (3.0 mg) are granulated with an aqueous solution (0.07 ml) of soluble starch (7.0 mg as soluble starch), dried and mixed with lactose (70.0 mg) and cornstarch (50.0 mg). The mixture is compressed to give tablets.

Experimental Example 1

MMP-13 Inhibitory Activity

[Method]
To 10 μg of MMP-13 precursor (GenzymeTechne) was added 1 ml of assay buffer (50 mM Tris-HCl (pH 7.5), 10 nM $CaCl_2$, 150 mM NaCl, 0.05% Brij-35), and 4-aminophenylmercuric acid (Sigma) was added to the final concentration of 1 mM. The MMP-13 precursor was activated by incubating at 37° C. for 2 hrs.

In a 96 well black plate (Corning), to 6.3 ng/ml of MMP-13 solution (49 μl) diluted with assay buffer was added the test compound (1 μl) diluted with dimethyl sulfoxide (DMSO) and 620 nM Cy3-PLGLK(Cy5Q)AR-$NH_2$ (50 μl, synthesized by Amersham Biosciences) in assay buffer was added to start the enzyme reaction. After incubation at 37° C. for 40 min, 500 mM EDTA solution (6 μl) was added to stop the reaction. For measurement, Farcyte (Amersham Biosciences) was used to measure at excitation wavelength 535 nm and measurement wavelength 595 nm. The enzyme inhibitory activity was calculated in inhibitory rate (% inhibition) by the following formula:

% inhibition=100−(X−C)/(T−C)×100

T: value of well with addition of DMSO instead of test compound
C: value of well with addition of DMSO instead of test compound and addition of EDTA solution before addition of substrate solution
X: value of well with addition of test compound

[Results]
The MMP-13 activity inhibitory rates of the compound (1 μM) are described below.

| Example Compound | MMP-13 activity inhibitory rate (%) |
|---|---|
| 1 | 91 |
| 179 | 99 |
| 209 | 94 |
| 217 | 100 |
| 286 | 97 |
| 287 | 98 |
| 339 | 96 |
| 341 | 98 |
| 366 | 93 |
| 383 | 91 |
| 384 | 91 |
| 385 | 96 |
| 386 | 94 |

INDUSTRIAL APPLICABILITY

Since compound [I], a salt thereof and a prodrug thereof of the present invention have a superior MMP inhibitory action, particularly an MMP-13 inhibitory action, they are useful as safe drugs for the prophylaxis or treatment of all MMP associated diseases, such as joint disease (e.g., osteoarthritis, rheumatoid arthritis and the like), osteoporosis, cancer, periodontal disease, cornea ulcer, chronic ulcer, pathologic bone resorption (Paget's disease and the like), nephritis, angiogenesis, aneurysm, arteriosclerosis, emphysema, chronic obstructive pulmonary disease (COPD), liver cirrhosis, autoimmune disease (Crohn's disease, Sjogren's disease and the like), infiltration or metastasis of cancer and the like, or as contraceptives.

This application is based on a patent application No. 2004-135596 filed in Japan, the contents of which are hereby incorporated by reference.

The invention claimed is:
1. 4-[2-({6-fluoro-2-[({[3-(methoxy)phenyl]methyl}amino)carbonyl]-4-oxo-3,4-dihydroquinazolin-5-yl}oxy)ethyl]benzoic acid, or a salt thereof.
2. A pharmaceutical agent comprising the compound of claim 1 or a salt thereof and a pharmaceutically acceptable carrier.

* * * * *